United States Patent
Brittingham et al.

(10) Patent No.: US 12,071,466 B2
(45) Date of Patent: Aug. 27, 2024

(54) ANTI-HUMAN KALLIKREIN-2 (HK2) CHIMERIC ANTIGEN RECEPTOR (CAR) AND METHODS OF USE THEREOF

(71) Applicant: Janssen Biotech, Inc., Horsham, PA (US)

(72) Inventors: Raymond Brittingham, Spring House, PA (US); Rajkumar Ganesan, Blue Bell, PA (US); Sherry La Porte, Horsham, PA (US); John T. Lee, North Wales, PA (US); Jinquan Luo, Malvern, PA (US); Theresa McDevitt, Warminster, PA (US); Fei Shen, Collegeville, PA (US); Sanjaya Singh, Blue Bell, PA (US); Degang Song, Wynnewood, PA (US); Sathyadevi Venkataramani, Blue Bell, PA (US); Fang Yi, Collegeville, PA (US); Yonghong Zhao, Trooper, PA (US)

(73) Assignee: Janssen Biotech, Inc., Horsham, PA (US)

( * ) Notice: Subject to any disclaimer, the term of this patent is extended or adjusted under 35 U.S.C. 154(b) by 454 days.

(21) Appl. No.: 16/936,719

(22) Filed: Jul. 23, 2020

(65) Prior Publication Data

US 2022/0064254 A1    Mar. 3, 2022

Related U.S. Application Data

(60) Provisional application No. 63/030,522, filed on May 27, 2020, provisional application No. 62/910,645, filed on Oct. 4, 2019, provisional application No. 62/898,635, filed on Sep. 11, 2019, provisional application No. 62/878,958, filed on Jul. 26, 2019.

(51) Int. Cl.
| | |
|---|---|
| *A61K 35/17* | (2015.01) |
| *A61K 38/00* | (2006.01) |
| *C07K 14/705* | (2006.01) |
| *C07K 14/725* | (2006.01) |
| *C07K 16/40* | (2006.01) |

(52) U.S. Cl.
CPC .......... *C07K 14/7051* (2013.01); *A61K 35/17* (2013.01); *C07K 14/70517* (2013.01); *C07K 14/70596* (2013.01); *C07K 16/40* (2013.01); *A61K 38/00* (2013.01); *C07K 2317/53* (2013.01); *C07K 2317/565* (2013.01); *C07K 2317/622* (2013.01); *C07K 2319/02* (2013.01); *C07K 2319/03* (2013.01)

(58) Field of Classification Search
CPC .......... C07K 14/7051; C07K 14/70517; C07K 14/70596; C07K 16/40; C07K 2317/53; C07K 2317/565; C07K 2317/622; C07K 2319/02; C07K 2319/03; A61K 35/17; A61K 38/00
See application file for complete search history.

(56) References Cited

U.S. PATENT DOCUMENTS

| | | |
|---|---|---|
| 3,832,253 A | 8/1974 | Palma et al. |
| 3,854,480 A | 12/1974 | Zaffaroni |
| 4,452,774 A | 6/1984 | Kent |
| 4,667,014 A | 5/1987 | Nestor, Jr. et al. |
| 4,748,034 A | 5/1988 | de Rham |
| 5,075,109 A | 12/1991 | Tice et al. |
| 5,225,539 A | 7/1993 | Winter |
| 5,239,660 A | 8/1993 | Ooi |
| 5,545,806 A | 8/1996 | Lonberg et al. |
| 5,569,825 A | 10/1996 | Lonberg et al. |
| 5,585,089 A | 12/1996 | Queen et al. |
| 5,639,641 A | 6/1997 | Pedersen et al. |
| 5,693,761 A | 12/1997 | Queen et al. |
| 5,714,352 A | 2/1998 | Jakobovits |
| 6,265,150 B1 | 7/2001 | Terstappen et al. |
| 9,345,782 B2 | 5/2016 | Strand et al. |
| 10,100,125 B2 | 10/2018 | Timmermand et al. |
| 2002/0197266 A1 | 2/2002 | Debinski |
| 2007/0004909 A1 | 1/2007 | Johnson et al. |
| 2009/0060910 A1 | 3/2009 | Johnson et al. |

FOREIGN PATENT DOCUMENTS

| | | |
|---|---|---|
| EP | 0 239 400 B1 | 8/1994 |
| GB | 2 188 638 B | 5/1990 |
| GB | 2 520 353 A | 5/2015 |
| WO | WO 2003/076610 A2 | 9/2003 |
| WO | WO 2009/085462 A1 | 7/2009 |
| WO | WO 2011/123708 A2 | 10/2011 |
| WO | WO 2011/123708 A3 | 10/2011 |
| WO | WO 2014/093908 A2 | 6/2014 |
| WO | WO 2015/075445 A1 | 5/2015 |
| WO | WO 2018/005556 A1 | 1/2018 |
| WO | WO 2018/005559 A1 | 1/2018 |
| WO | WO 2018/052828 A1 | 3/2018 |
| WO | WO 2019/018402 A2 | 1/2019 |
| WO | WO 2019/018402 A3 | 1/2019 |
| WO | WO 2019/118475 A1 | 6/2019 |
| WO | WO 2019/138354 A1 | 7/2019 |
| WO | WO 2021/019386 A1 | 2/2021 |

OTHER PUBLICATIONS

Bird, R.E., et al., "Single-Chain Antigen-Binding Proteins", (1988), Science, vol. 242, pp. 423-426.
Chothia, C., et al., "Canonical Structures for the Hypervariable Regions of Immunoglobulins", (1987), J.Mol.Biol., vol. 196, pp. 901-917.
Haskard, D.O., et al., The Production of Human Monoclonal Autoantibodies from Patients with Rheumatoid Arthritis by the EBV-Hybridoma Technique, (1984), Journal of Immunological Methods, vol. 74, pp. 361-367.
Hudecz, F., "Synthesis of Peptide Bioconjugates", (2005), Methods of Molecular Biology, vol. 298, pp. 209-223.

(Continued)

*Primary Examiner* — Robert S Landsman

(57) ABSTRACT

The present disclosure provides for chimeric antigen receptors (CARs) that specifically target a human Kallikrein-2 (hK2), and immunoresponsive cells comprising such CARs, for the treatment of cancer.

35 Claims, 40 Drawing Sheets

Specification includes a Sequence Listing.

(56) References Cited

OTHER PUBLICATIONS

Huse, W.D., et al., "Generation of a Large Combinatorial Library of the Immunoglobulin Repertoire in Phage Lambda", (1989), Science, vol. 246, pp. 1275-1281.
Huston, J.S., et al., "Protein engineering of antibody binding sites: Recovery of specific activity in an anti-digoxin single-chain Fv analogue produced in *Escherichia coli*", (1988), Proc. Natl. Acad. Sci, USA, vol. 85, pp. 5879-5883.
Kirin, S.I., et al., "Amino Acid and Peptide Bioconjugates of Cooper(II) and Zinc(II) Complexes with a Modified N,N-Bis(2-picolyl)amine Ligand", (2005), Inorganic Chemistry, vol. 44, No. 15, pp. 5405-5415.
Knappik, A., et al., "Fully Synthetic Human Combinatorial Antibody Libraries (HuCAL) Based on Modular Consensus Frameworks and CDRs Randomized with Trinucleotides", (2000), J. Mol. Biol., vol. 296, pp. 57-86.
Kohler, G., et al., "Derivation of specific antibody-producing tissue culture and tumor lines by cell fusion", (1976), Eur. J. Immunol., vol. 6, pp. 511-519.
Lefranc, M.P., et al., "IMGT unique numbering for immunoglobulin and T cell receptor variable domains and Ig superfamily V-like domains", (2003), Developmental and Comparative Immunology, vol. 27, pp. 55-77.
Pedersen, J.T., et al., "Comparison of Surface Accessible Residues in Human and Murine Immunoglobulin Fv Domains", (1994), J. Mol. Biol., vol. 235, pp. 959-973.
Roder, J.C., et al., "The EBV-Hybridoma Technique", (1986), The Methods of Enzymology, vol. 121, pp. 140-167.
Rosenberg, S.A., et al., "Use of Tumor-Infiltrating Lymphocytes and Interleukin-2 in the Immunotherapy of patients with Metastatic Melanoma", (1988), The New England Journal of Medicine, vol. 319, No. 25, pp. 1676-1680.
Shi, L., et al., "De Novo Selection of High-Affinity Antibodies from Synthetic Fab Libraries Displayed on Phage as pIX Fusion Proteins", (2010), J. Mol. Biol., vol. 397, pp. 385-396.
Singh, S., et al., "Selective targeting of the IL23 pathway: Generation and characterization of a novel high-affinity humanized anti-IL23A antibody", (2015), mAbs, vol. 7, No. 4, pp. 778-791.
Tatusova, T.A., et al., "BLAST 2 Sequences, a new tool for comparing protein and nucleotide sequences", (1999), FEMS Microbiology Letters, vol. 174, pp. 247-250.
Väisänen, V., et al., "Development of Sensitive Immunoassays for Free and Total Human Glandular Kallikrein 2", (2004) Clinical Chemistry, vol. 50, No. 9, pp. 1607-1617.
Finlay, J.A., et al., "Development of a Dual Monoclonal Antibody Immunoassay for Total Human Kallikrein 2", (2001), Clinical Chemistry, vol. 47, No. 7, pp. 1218-1224.
Fisher, T.L., et al., "Generation of Monoclonal Antibodies Specific for Human Kallikrein 2 (hK2) Using hK2-Expressing Tumors", (2002), The Prostate, vol. 51, pp. 153-165.
Piironen, T., et al., "Determination and analysis of antigenic epitopes of prostate specific antigen (PSA) and human glandular kallikrein 2 (hK2) using synthetic peptides and computer modeling", (1998), Protein Science, vol. 7, No. 2, pp. 259-269.
Yu, H., et al., "CART cell therapy for prostate cancer: status and promise", (2019), OncoTargets and Therapy, vol. 12, pp. 391-395.
International Search Report from PCT/IB2020/056966 dated Oct. 5, 2020.

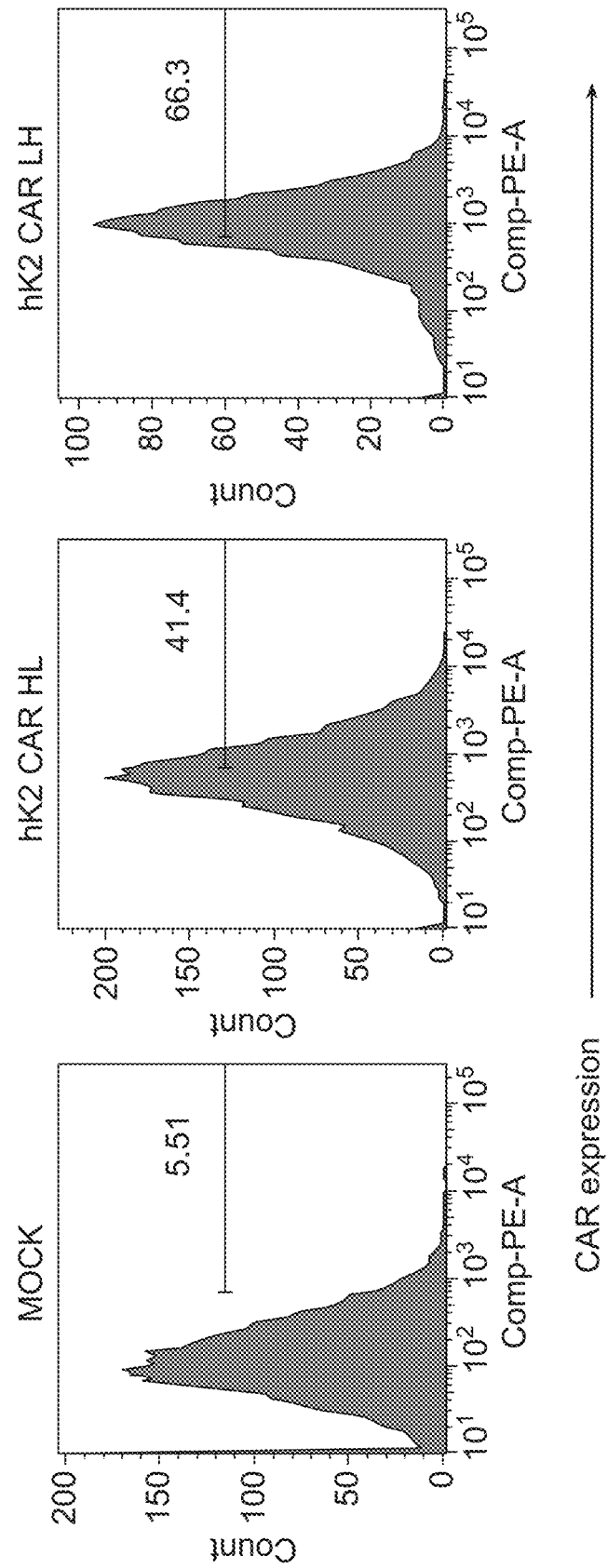

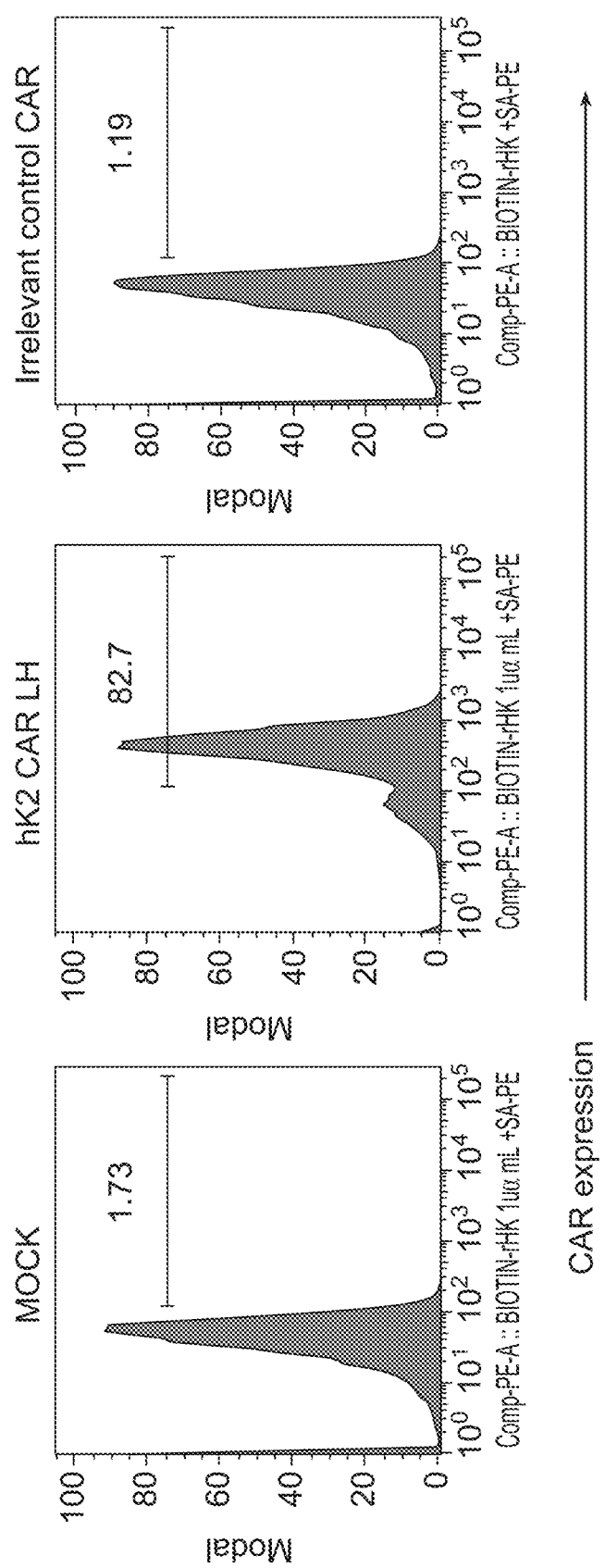

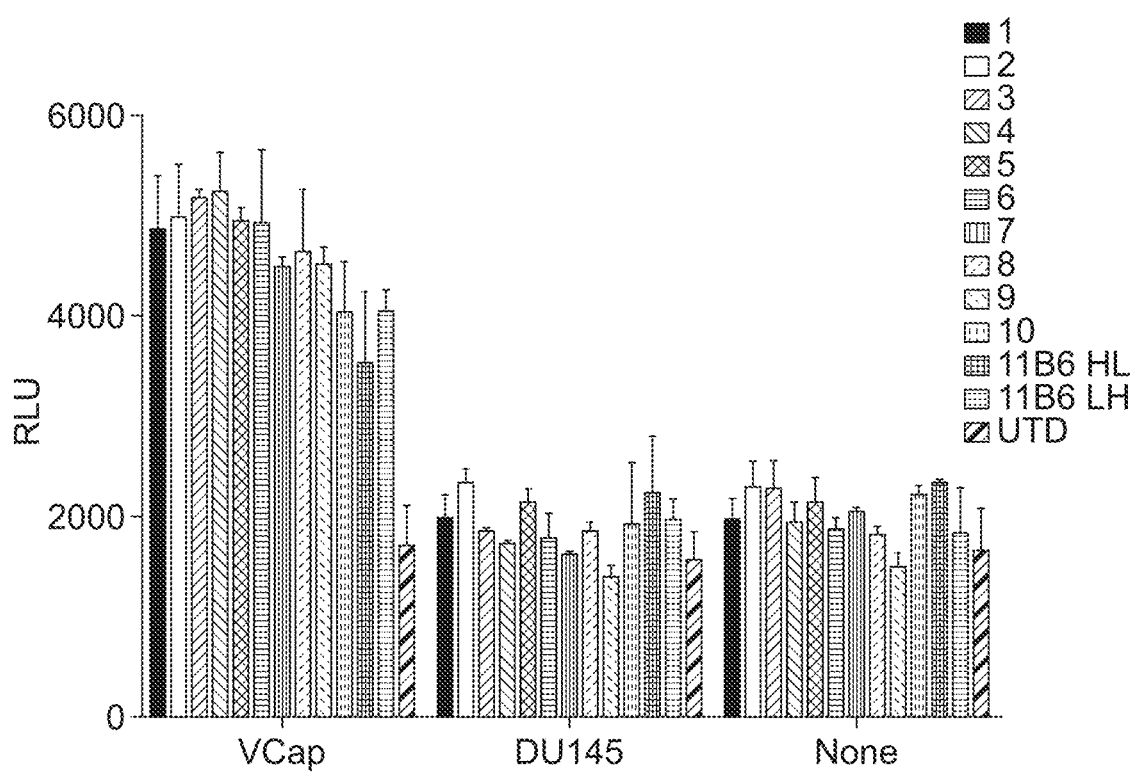

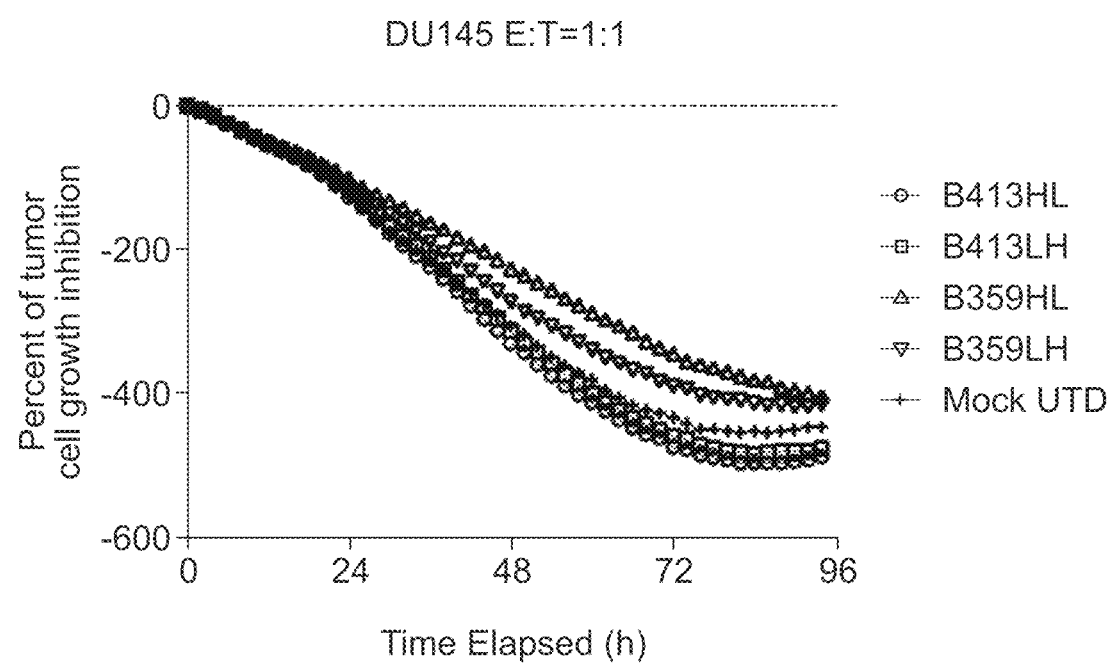

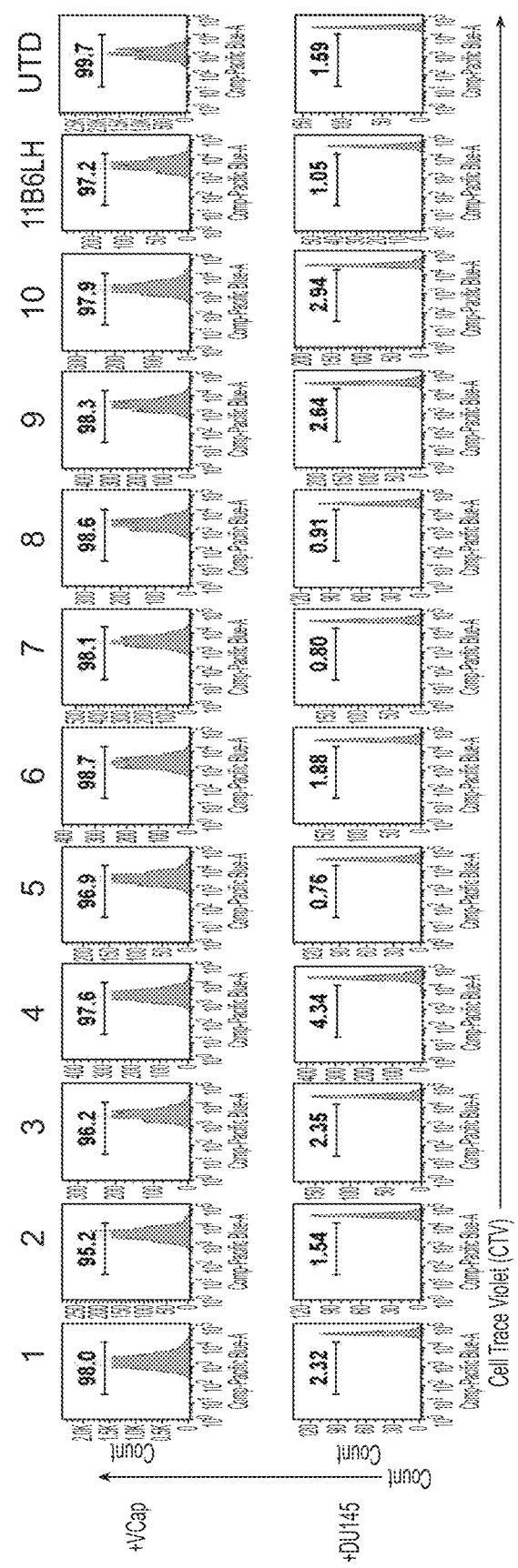

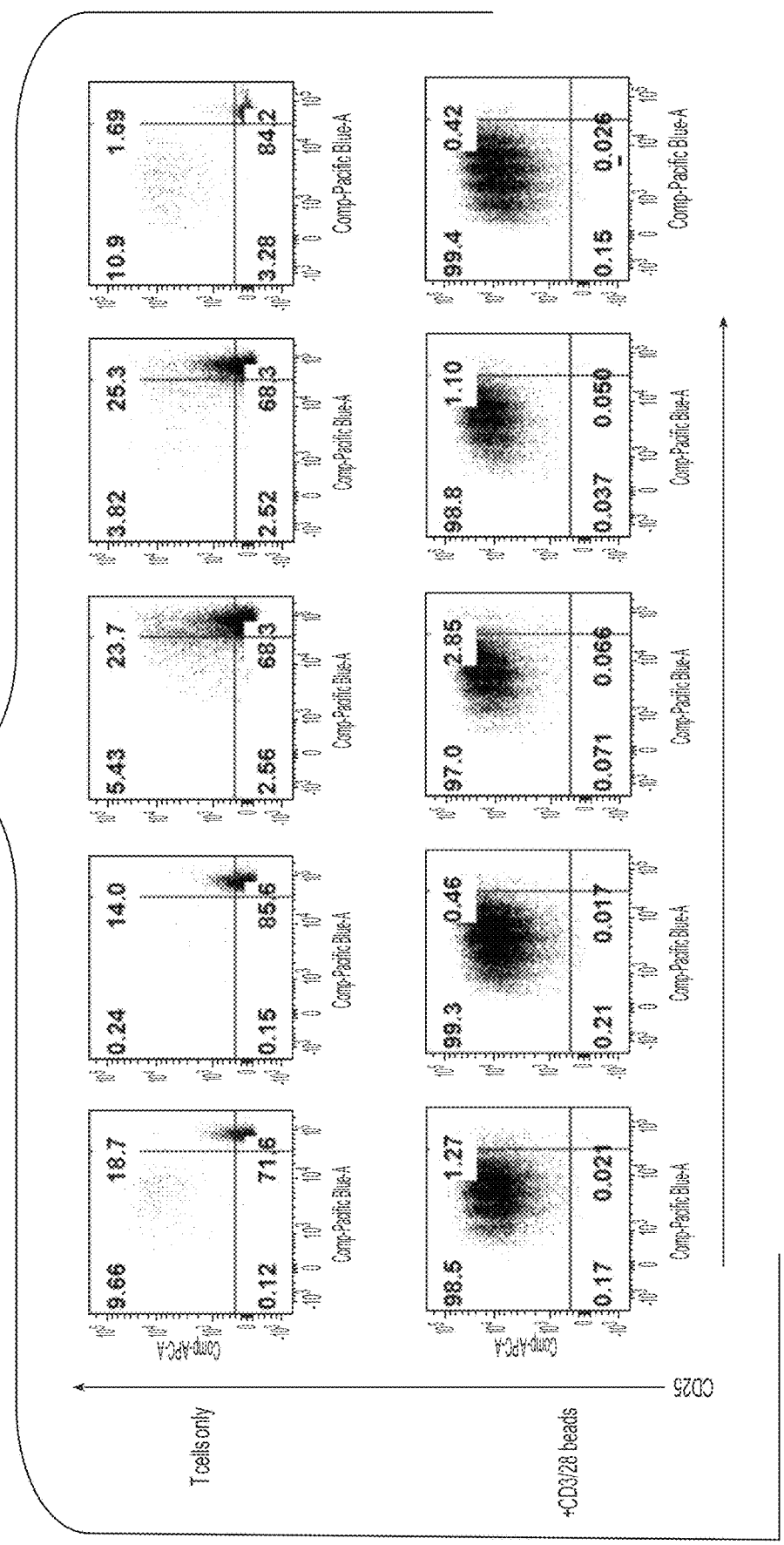

FIG. 17A

```
              1                                             45
mu1lB6_VH  DVQLQESGPGLVKPSQSLSLTCTVTGNSITSDYAWNWIRQFPGNR
hu1lB6_VH  QVQLQESGPGLVKPSDTLSLTCAVSGNSITSDYAWNWIRQPPGKG
KL2B357_VH QVQLQESGPGLVKPSQTLSLTCTVSGNSITSDYAWNWIRQFPGKG
KL2B358_VH QVQLQESGPGLVKPSQTLSLTCTVSGNSITSDYAWNWIRQPPGKG
KL2B359_VH QVQLQESGPGLVKPSQTLSLTCTVSGNSITSDYAWNWIRQFPGKR
KL2B360_VH QVQLQESGPGLVKPSQTLSLTCTVSGNSITSDYAWNWIRQFPGKG
      HCF3 QVQLQESGPGLVKPSDTLSLTCAVSGNSITSDYAWNWIRQFPGKG
      HCG5 QVQLQESGPGLVKPSDTLSLTCAVSGNSITSDYAWNWIRQFPGKG
       Aln :************:;*****:*:*************** **:

46                                            90
mu1lB6_VH  LEWMGYISYSGSTTYSPSLKSRFSITRDTSKNQFFLQLNSVTPED
hu1lB6_VH  LEWIGYISYSGSTTYNPSLKSRVTMSRDTSKNQFSLKLSSVTAVD
KL2B357_VH LEWIGYISYSGSTTYNPSLKSRVTISRDTSKNQFSLKLSSVTAAD
KL2B358_VH LEWIGYISYSGSTTYNPSLKSRVTISRDTSKNQFSLKLSSVTAAD
KL2B359_VH LEWIGYISYSGSTTYNPSLKSRVTISRDTSKNQFSLKLSSVTAAD
KL2B360_VH LEWIGYISYSGSTTYNPSLKSRVTISRDTSKNQFSLKLSSVTAAD
      HCF3 LEWIGYISYSGSTTYNPSLKSRVTISRDTSKNQFSLKLSSVTPVD
      HCG5 LEWMGYISYSGSTTYNPSLKSRVTISRDTSKNQFSLKLSSVTPVD
       Aln ***:***********.******.::;********* *:*.***. *

91                    117
mu1lB6_VH  TATYFCATGYYYGSGFWGQGTLVTVSS
hu1lB6_VH  TAVYYCATGYYYGSGFWGQGTLVTVSS
KL2B357_VH TAVYYCATGYYYGSGFWGQGTLVTVSS
KL2B358_VH TAVYYCATGYYYGSGFWGQGTLVTVSS
KL2B359_VH TAVYYCATGYYYGSGFWGQGTLVTVSS
KL2B360_VH TAVYYCATGYYYGSGFWGQGTLVTVSS
      HCF3 TAVYYCATGYYYGSGFWGQGTLVTVSS
      HCG5 TAVYYCATGYYYGSGFWGQGTLVTVSS
       Aln **.*:**********************
```

VH consensus sequence        SEQ ID NO: 345
QVQLQESGPGLVKPSX$_1$TLSLTCX$_2$VSGNSITSDYAWNWIRQX$_3$PGKGLEWX$_4$GYISYSGSTTY
NPSLKSRVTMSRDTSKNQFSLKLSSVTX$_5$X$_6$DTAVYYCATGYYYGSGFWGQGTLVTVSS X1 is D or Q;
X2 is A or T;
X3 is P or F;
X4 is I or M;
X5 is A or P; or
X6 is V or A.

FIG. 17B

```
             1                                                    50
h11B6        VPLIEGRIVGGWECEKHSQPWQVAVYSHGWAHCGGVLVHPQWVLTAAHCL
KL2B494      VPLIEGRIVGGWECEKHSQPWQVAVYSHGWAHCGGVLVHPQWVLTAAHCL
KL2B467      VPLIEGRIVGGWECEKHSQPWQVAVYSHGWAHCGGVLVHPQWVLTAAHCL
KL2B30       VPLIEGRIVGGWECEKHSQPWQVAVYSHGWAHCGGVLVHPQWVLTAAHCL
KL2B413      VPLIEGRIVGGWECEKHSQPWQVAVYSHGWAHCGGVLVHPQWVLTAAHCL
KL2B53       VPLIEGRIVGGWECEKHSQPWQVAVYSHGWAHCGGVLVHPQWVLTAAHCL 51                                                   100
h11B6        KKNSQVWLGRHNLFEPEDTGQRVPVSHSFPHPLYNMSLLKHQSLRPDEDS
KL2B494      KKNSQVWLGRHNLFEPEDTGQRVPVSHSFPHPLYNMSLLKHQSLRPDEDS
KL2B467      KKNSQVWLGRHNLFEPEDTGQRVPVSHSFPHPLYNMSLLKHQSLRPDEDS
KL2B30       KKNSQVWLGRHNLFEPEDTGQRVPVSHSFPHPLYNMSLLKHQSLRPDEDS
KL2B413      KKNSQVWLGRHNLFEPEDTGQRVPVSHSFPHPLYNMSLLKHQSLRPDEDS
KL2B53       KKNSQVWLGRHNLFEPEDTGQRVPVSHSFPHPLYNMSLLKHQSLRPDEDS 101                                                  150
h11B6        SHDLMLLRLSEPAKITDVVKVLGLPTQEPALGTTCYASGWGSIEPEEFLR
KL2B494      SHDLMLLRLSEPAKITDVVKVLGLPTQEPALGTTCYASGWGSIEPEEFLR
KL2B467      SHDLMLLRLSEPAKITDVVKVLGLPTQEPALGTTCYASGWGSIEPEEFLR
KL2B30       SHDLMLLRLSEPAKITDVVKVLGLPTQEPALGTTCYASGWGSIEPEEFLR
KL2B413      SHDLMLLRLSEPAKITDVVKVLGLPTQEPALGTTCYASGWGSIEPEEFLR
KL2B53       SHDLMLLRLSEPAKITDVVKVLGLPTQEPALGTTCYASGWGSIEPEEFLR 151                                                  200
h11B6        PRSLQCVSLHLLSNDMCARAYSEKVTEFMLCAGLWTGGKDTCGGDSGGPL
KL2B494      PRSLQCVSLHLLSNDMCARAYSEKVTEFMLCAGLWTGGKDTCGGDSGGPL
KL2B467      PRSLQCVSLHLLSNDMCARAYSEKVTEFMLCAGLWTGGKDTCGGDSGGPL
KL2B30       PRSLQCVSLHLLSNDMCARAYSEKVTEFMLCAGLWTGGKDTCGGDSGGPL
KL2B413      PRSLQCVSLHLLSNDMCARAYSEKVTEFMLCAGLWTGGKDTCGGDSGGPL
KL2B53       PRSLQCVSLHLLSNDMCARAYSEKVTEFMLCAGLWTGGKDTCGGDSGGPL 201                                         244
H11B6        VCNGVLQGITSWGPEPCALPEKPAVYTKVVHYRKWIKDTIAANP
KL2B494      VCNGVLQGITSWGPEPCALPEKPAVYTKVVHYRKWIKDTIAANP
KL2B467      VCNGVLQGITSWGPEPCALPEKPAVYTKVVHYRKWIKDTIAANP
KL2B30       VCNGVLQGITSWGPEPCALPEKPAVYTKVVHYRKWIKDTIAANP
KL2B413      VCNGVLQGITSWGPEPCALPEKPAVYTKVVHYRKWIKDTIAANP
KL2B53       VCNGVLQGITSWGPEPCALPEKPAVYTKVVHYRKWIKDTIAANP
```

ANTI-HUMAN KALLIKREIN-2 (HK2) CHIMERIC ANTIGEN RECEPTOR (CAR) AND METHODS OF USE THEREOF

CROSS-REFERENCE TO RELATED APPLICATIONS

This application claims the benefit of U.S. Provisional Application Ser. No. 62/878,958, filed 26 Jul. 2019, U.S. Provisional Application Ser. No. 62/898,635, filed 11 Sep. 2019, U.S. Provisional Application Ser. No. 62/910,645, filed 4 Oct. 2019, and U.S. Provisional Application Ser. No. 63/030,522, filed 27 May 2020 The entire content of the aforementioned applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 30, 2020, is named JBI6124USNP1_SL.txt and is 554,082 bytes in size.

TECHNICAL FIELD

The invention relates to hK2-targeting chimeric antigen receptors (CARs) comprising hK2-targeting single-chain variable fragments and engineered hK2-targeting immune cells expressing the CARs. Also provided are nucleic acids and expression vectors encoding the CARs, recombinant cells containing the vectors, and compositions comprising the engineered immune cells expressing the hK2-targeting CARs. Methods of making the CARs, and engineered immune cells, and methods of using the engineered immune cells to treat conditions including cancer are also provided.

BACKGROUND

Prostate cancer is the second most frequently diagnosed cancer and the sixth leading cause of cancer death in males, accounting for 14% (903,500) of the total new cancer cases and 6% (258,400) of the total cancer deaths in males worldwide. The course of prostate cancer from diagnosis to death is best categorized as a series of clinical stages based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate stage. Although surgery, radiation, or a combination of both can be curative for patients with localized disease, a significant proportion of these patients have recurrent disease as evidenced by a rising level of PSA, which can lead to the development of metastases, especially in the high-risk group—a transition to the lethal stage of the disease.

Androgen depletion therapy (ADT) is the standard treatment with a generally predictable outcome: decline in PSA, a period of stability in which the tumor does not proliferate, followed by rising PSA and regrowth as castration-resistant disease. Historically, ADT has been the standard of care for patients with metastatic prostate cancer.

Kallikrein related peptidase 2 (hK2, HK2) is a trypsin-like enzyme with androgen receptor (AR)-driven expression specific to prostate tissue and prostate cancer. hK2 is activated by Transmembrane Protease, Serine 2 (TMPRSS2) and secreted into the ducts of the prostate, where it initiates a cascade that cleaves semenogelin, the extracellular matrix in ejaculate, to enhance sperm motility. hK2 expression is restricted to the prostate and prostate cancer tissue, however it has recently been demonstrated that hK2 was detectable in breast cancer lines and primary patient samples after appropriate activation of the AR-pathway by steroid hormones (U.S. Pat. Publ. No. 2018/0326102). Similar to PSA, retrograde release of catalytically inactive hK2 into the blood occurs when the highly structured organization of the prostate is compromised upon hypertrophy or malignant transformation.

T cell therapy utilizes isolated T cells that have been genetically modified to enhance their specificity for a specific tumor associated antigen. Genetic modification may involve the expression of a chimeric antigen receptor (CAR) or an exogenous T cell receptor to provide new antigen specificity onto the T cell. T cells expressing chimeric antigen receptors (CAR-T cells) can induce tumor immunoreactivity. There is a need for better cancer therapies utilizing CAR-T cells.

SUMMARY

Disclosed herein are chimeric antigen receptors (CARs), e.g., CARs that target a human Kallikrein-2 (hK2), cells comprising the CARs, vectors encoding the CARs, e.g., recombinant expression vectors, and nucleic acid molecules encoding the CARs, methods of making the CARs, compositions, polypeptides, proteins, nucleic acids, host cells, populations of cells and methods of treating disorders, e.g., cancer, using the disclosed CARs.

In one aspect is provided a chimeric antigen receptor (CAR) comprising:
  (a) an extracellular domain comprising an scFv that specifically binds to the human Kallikrein-2 (hK2) antigen,
  (b) a transmembrane domain, and
  (c) an intracellular signaling domain optionally comprising at least one co-stimulatory domain.

In some embodiments, the CAR further comprises
  (d) a CD8a-hinge region,
  wherein the transmembrane domain comprises a CD8a transmembrane region (CD8a-TM) polypeptide; and
  wherein the intracellular signaling domain comprises a co-stimulatory domain comprising a TNF receptor superfamily member 9 (CD137) component and a primary signaling domain comprising a T-cell surface glycoprotein CD3 zeta chain (CD3z) component.

In some embodiments, the CD8a-hinge region comprises an amino acid sequence that is at least 90% identical to SEQ ID NO: 25, 269, 270, 271, or 272;
  the transmembrane domain comprises an amino acid sequence that is at least 90% identical to SEQ ID NO: 26; and/or
  the intracellular signaling domain comprises a co-stimulatory domain having an amino acid sequence that is at least 90% identical to SEQ ID NO: 27, and a primary signaling domain having an amino acid sequence that is at least 90% identical to SEQ ID NO: 28.

In another aspect is provided a chimeric antigen receptor (CAR) comprising an extracellular antigen-binding domain, a transmembrane domain and an intracellular signaling domain, where the extracellular antigen-binding domain comprises:
  a heavy chain complementarity determining region 1 (CDR1) having the amino acid sequence of SEQ ID NO: 63, a heavy chain CDR2 having the amino acid sequence of SEQ ID NO: 64, and a heavy chain CDR3 having the amino acid sequence of SEQ ID NO: 66;

a heavy chain complementarity determining region 1 (CDR1) having the amino acid sequence of SEQ ID NO: 314, a heavy chain CDR2 having the amino acid sequence of SEQ ID NO: 315, and a heavy chain CDR3 having the amino acid sequence of SEQ ID NO: 311;

a heavy chain complementarity determining region 1 (CDR1) having the amino acid sequence of SEQ ID NO: 309, a heavy chain CDR2 having the amino acid sequence of SEQ ID NO: 310, and a heavy chain CDR3 having the amino acid sequence of SEQ ID NO: 311;

a heavy chain complementarity determining region 1 (CDR1) having the amino acid sequence of SEQ ID NO: 63, a heavy chain CDR2 having the amino acid sequence of SEQ ID NO: 65, and a heavy chain CDR3 having the amino acid sequence of SEQ ID NO: 66;

a heavy chain complementarity determining region 1 (CDR1) having the amino acid sequence of SEQ ID NO: 72, a heavy chain CDR2 having the amino acid sequence of SEQ ID NO: 73, and a heavy chain CDR3 having the amino acid sequence of SEQ ID NO: 66;

a heavy chain complementarity determining region 1 (CDR1) having the amino acid sequence of SEQ ID NO: 86, a heavy chain CDR2 having the amino acid sequence of SEQ ID NO: 87, and a heavy chain CDR3 having the amino acid sequence of SEQ ID NO: 88;

a heavy chain complementarity determining region 1 (CDR1) having the amino acid sequence of SEQ ID NO: 92, a heavy chain CDR2 having the amino acid sequence of SEQ ID NO: 93, and a heavy chain CDR3 having the amino acid sequence of SEQ ID NO: 94;

a heavy chain complementarity determining region 1 (CDR1) having the amino acid sequence of SEQ ID NO: 102, a heavy chain CDR2 having the amino acid sequence of SEQ ID NO: 103, and a heavy chain CDR3 having the amino acid sequence of SEQ ID NO: 104;

a heavy chain complementarity determining region 1 (CDR1) having the amino acid sequence of SEQ ID NO: 105, a heavy chain CDR2 having the amino acid sequence of SEQ ID NO: 106, and a heavy chain CDR3 having the amino acid sequence of SEQ ID NO: 104;

a heavy chain complementarity determining region 1 (CDR1) having the amino acid sequence of SEQ ID NO: 107, a heavy chain CDR2 having the amino acid sequence of SEQ ID NO: 108, and a heavy chain CDR3 having the amino acid sequence of SEQ ID NO: 109;

a heavy chain complementarity determining region 1 (CDR1) having the amino acid sequence of SEQ ID NO: 110, a heavy chain CDR2 having the amino acid sequence of SEQ ID NO: 111, and a heavy chain CDR3 having the amino acid sequence of SEQ ID NO: 109;

a heavy chain complementarity determining region 1 (CDR1) having the amino acid sequence of SEQ ID NO: 102, a heavy chain CDR2 having the amino acid sequence of SEQ ID NO: 112, and a heavy chain CDR3 having the amino acid sequence of SEQ ID NO: 113;

a heavy chain complementarity determining region 1 (CDR1) having the amino acid sequence of SEQ ID NO: 105, a heavy chain CDR2 having the amino acid sequence of SEQ ID NO: 114, and a heavy chain CDR3 having the amino acid sequence of SEQ ID NO: 113;

a heavy chain complementarity determining region 1 (CDR1) having the amino acid sequence of SEQ ID NO: 115, a heavy chain CDR2 having the amino acid sequence of SEQ ID NO: 116, and a heavy chain CDR3 having the amino acid sequence of SEQ ID NO: 117;

a heavy chain complementarity determining region 1 (CDR1) having the amino acid sequence of SEQ ID NO: 118, a heavy chain CDR2 having the amino acid sequence of SEQ ID NO: 119, and a heavy chain CDR3 having the amino acid sequence of SEQ ID NO: 117;

a heavy chain complementarity determining region 1 (CDR1) having the amino acid sequence of SEQ ID NO: 120, a heavy chain CDR2 having the amino acid sequence of SEQ ID NO: 121, and a heavy chain CDR3 having the amino acid sequence of SEQ ID NO: 122; or a heavy chain complementarity determining region 1 (CDR1) having the amino acid sequence of SEQ ID NO: 123, a heavy chain CDR2 having the amino acid sequence of SEQ ID NO: 124, and a heavy chain CDR3 having the amino acid sequence of SEQ ID NO: 122, where the extracellular antigen-binding domain binds the hK2 antigen.

In another aspect is provided a chimeric antigen receptor (CAR) comprising an extracellular antigen-binding domain, a transmembrane domain and an intracellular signaling domain, where the extracellular antigen-binding domain comprises:

a light chain complementarity determining region 1 (CDR1) having the amino acid sequence of SEQ ID NO: 67, a light chain CDR2 having the amino acid sequence of SEQ ID NO: 69, and a light chain CDR3 having the amino acid sequence of SEQ ID NO: 71;

a light chain complementarity determining region 1 (CDR1) having the amino acid sequence of SEQ ID NO: 68, a light chain CDR2 having the amino acid sequence of SEQ ID NO: 70, and a light chain CDR3 having the amino acid sequence of SEQ ID NO: 71;

a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91;

a light chain complementarity determining region 1 (CDR1) having the amino acid sequence of SEQ ID NO: 95, a light chain CDR2 having the amino acid sequence of SEQ ID NO: 96, and a light chain CDR3 having the amino acid sequence of SEQ ID NO: 71;

a light chain complementarity determining region 1 (CDR1) having the amino acid sequence of SEQ ID NO: 312, a light chain CDR2 having the amino acid sequence of SEQ ID NO: 313, and a light chain CDR3 having the amino acid sequence of SEQ ID NO: 91;

a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91;

a light chain complementarity determining region 1 (CDR1) having the amino acid sequence of SEQ ID NO: 67, a light chain CDR2 having the amino acid sequence of SEQ ID NO: 126, and a light chain CDR3 having the amino acid sequence of SEQ ID NO: 71;

a light chain complementarity determining region 1 (CDR1) having the amino acid sequence of SEQ ID NO: 128, a light chain CDR2 having the amino acid sequence of SEQ ID NO: 129, and a light chain CDR3 having the amino acid sequence of SEQ ID NO: 130;

a light chain complementarity determining region 1 (CDR1) having the amino acid sequence of SEQ ID NO: 125, a light chain CDR2 having the amino acid sequence of SEQ ID NO: 131, and a light chain CDR3 having the amino acid sequence of SEQ ID NO: 132;
a light chain complementarity determining region 1 (CDR1) having the amino acid sequence of SEQ ID NO: 133, a light chain CDR2 having the amino acid sequence of SEQ ID NO: 134, and a light chain CDR3 having the amino acid sequence of SEQ ID NO: 135;
a light chain complementarity determining region 1 (CDR1) having the amino acid sequence of SEQ ID NO: 136, a light chain CDR2 having the amino acid sequence of SEQ ID NO: 137, and a light chain CDR3 having the amino acid sequence of SEQ ID NO: 138; or
a light chain complementarity determining region 1 (CDR1) having the amino acid sequence of SEQ ID NO: 97, a light chain CDR2 having the amino acid sequence of SEQ ID NO: 127, and a light chain CDR3 having the amino acid sequence of SEQ ID NO: 139, where the extracellular antigen-binding domain binds the hK2 antigen.

In some embodiments, the extracellular antigen-binding domain further comprises:
a light chain complementarity determining region 1 (CDR1) having the amino acid sequence of SEQ ID NO: 67, a light chain CDR2 having the amino acid sequence of SEQ ID NO: 69, and a light chain CDR3 having the amino acid sequence of SEQ ID NO: 71; or
a light chain complementarity determining region 1 (CDR1) having the amino acid sequence of SEQ ID NO: 68, a light chain CDR2 having the amino acid sequence of SEQ ID NO: 70, and a light chain CDR3 having the amino acid sequence of SEQ ID NO: 71;
a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91;
a light chain complementarity determining region 1 (CDR1) having the amino acid sequence of SEQ ID NO: 95, a light chain CDR2 having the amino acid sequence of SEQ ID NO: 96, and a light chain CDR3 having the amino acid sequence of SEQ ID NO: 71;
a light chain complementarity determining region 1 (CDR1) having the amino acid sequence of SEQ ID NO: 312, a light chain CDR2 having the amino acid sequence of SEQ ID NO: 313, and a light chain CDR3 having the amino acid sequence of SEQ ID NO: 91;
a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91;
a light chain complementarity determining region 1 (CDR1) having the amino acid sequence of SEQ ID NO: 67, a light chain CDR2 having the amino acid sequence of SEQ ID NO: 126, and a light chain CDR3 having the amino acid sequence of SEQ ID NO: 71;
a light chain complementarity determining region 1 (CDR1) having the amino acid sequence of SEQ ID NO: 128, a light chain CDR2 having the amino acid sequence of SEQ ID NO: 129, and a light chain CDR3 having the amino acid sequence of SEQ ID NO: 130;
a light chain complementarity determining region 1 (CDR1) having the amino acid sequence of SEQ ID NO: 125, a light chain CDR2 having the amino acid sequence of SEQ ID NO: 131, and a light chain CDR3 having the amino acid sequence of SEQ ID NO: 132;
a light chain complementarity determining region 1 (CDR1) having the amino acid sequence of SEQ ID NO: 133, a light chain CDR2 having the amino acid sequence of SEQ ID NO: 134, and a light chain CDR3 having the amino acid sequence of SEQ ID NO: 135;
a light chain complementarity determining region 1 (CDR1) having the amino acid sequence of SEQ ID NO: 136, a light chain CDR2 having the amino acid sequence of SEQ ID NO: 137, and a light chain CDR3 having the amino acid sequence of SEQ ID NO: 138; or
a light chain complementarity determining region 1 (CDR1) having the amino acid sequence of SEQ ID NO: 97, a light chain CDR2 having the amino acid sequence of SEQ ID NO: 127, and a light chain CDR3 having the amino acid sequence of SEQ ID NO: 139.

In another aspect is provided a chimeric antigen receptor (CAR), comprising an extracellular antigen-binding domain, a transmembrane domain and an intracellular signaling domain, wherein the extracellular antigen-binding domain comprises:
a light chain variable domain (VL) comprising an amino acid sequence selected from SEQ ID NOS: 1, 2, 3, 74, 75, 147, 148, 149, 150, 151, 152 and 318; and/or
a heavy chain variable domain (VH) comprising an amino acid sequence selected from SEQ ID NOS: 4, 5, 6, 76, 77, 140, 141, 142, 143, 144, 145, 146 and 317;
wherein the extracellular antigen-binding domain binds the human Kallikrein-2 (hK2) antigen.

In some embodiments, the extracellular antigen-binding domain comprises:
a light chain variable region comprising an amino acid sequence of SEQ ID NO: 1 and a heavy chain variable region comprising an amino acid sequence of SEQ ID NO: 4;
a light chain variable region comprising an amino acid sequence of SEQ ID NO: 2 and a heavy chain variable region comprising an amino acid sequence of SEQ ID NO: 4;
a light chain variable region comprising an amino acid sequence of SEQ ID NO: 3 and a heavy chain variable region comprising an amino acid sequence of SEQ ID NO: 6;
a light chain variable region comprising an amino acid sequence of SEQ ID NO: 3 and a heavy chain variable region comprising an amino acid sequence of SEQ ID NO: 4;
a light chain variable region comprising an amino acid sequence of SEQ ID NO: 2 and a heavy chain variable region comprising an amino acid sequence of SEQ ID NO: 6;
a light chain variable region comprising an amino acid sequence of SEQ ID NO: 3 and a heavy chain variable region comprising an amino acid sequence of SEQ ID NO: 4;
a light chain variable region comprising an amino acid sequence of SEQ ID NO: 1 and a heavy chain variable region comprising an amino acid sequence of SEQ ID NO: 6;
a light chain variable region comprising an amino acid sequence of SEQ ID NO: 3 and a heavy chain variable region comprising an amino acid sequence of SEQ ID NO: 5;
a light chain variable region comprising an amino acid sequence of SEQ ID NO: 1 and a heavy chain variable region comprising an amino acid sequence of SEQ ID NO: 5;

a light chain variable region comprising an amino acid sequence of SEQ ID NO: 2 and a heavy chain variable region comprising an amino acid sequence of SEQ ID NO: 5;

a light chain variable region comprising an amino acid sequence of SEQ ID NO: 3 and a heavy chain variable region comprising an amino acid sequence of SEQ ID NO: 5;

a light chain variable region comprising an amino acid sequence of SEQ ID NO: 74 and a heavy chain variable region comprising an amino acid sequence of SEQ ID NO: 76;

a light chain variable region comprising an amino acid sequence of SEQ ID NO: 75 and a heavy chain variable region comprising an amino acid sequence of SEQ ID NO: 77;

a light chain variable region comprising an amino acid sequence of SEQ ID NO: 147 and a heavy chain variable region comprising an amino acid sequence of SEQ ID NO: 140;

a light chain variable region comprising an amino acid sequence of SEQ ID NO: 75 and a heavy chain variable region comprising an amino acid sequence of SEQ ID NO: 141;

a light chain variable region comprising an amino acid sequence of SEQ ID NO: 75 and a heavy chain variable region comprising an amino acid sequence of SEQ ID NO: 140;

a light chain variable region comprising an amino acid sequence of SEQ ID NO: 148 and a heavy chain variable region comprising an amino acid sequence of SEQ ID NO: 142;

a light chain variable region comprising an amino acid sequence of SEQ ID NO: 149 and a heavy chain variable region comprising an amino acid sequence of SEQ ID NO: 143;

a light chain variable region comprising an amino acid sequence of SEQ ID NO: 150 and a heavy chain variable region comprising an amino acid sequence of SEQ ID NO: 144;

a light chain variable region comprising an amino acid sequence of SEQ ID NO: 151 and a heavy chain variable region comprising an amino acid sequence of SEQ ID NO: 145;

a light chain variable region comprising an amino acid sequence of SEQ ID NO: 152 and a heavy chain variable region comprising an amino acid sequence of SEQ ID NO: 146;

a light chain variable region comprising an amino acid sequence of SEQ ID NO: 318 and a heavy chain variable region comprising an amino acid sequence of SEQ ID NO: 317.

In some embodiments, the extracellular antigen-binding domain comprises a single-chain variable fragment (scFv). In some embodiments, the scFv comprises a linker polypeptide between the light chain variable region (VL) and the heavy chain variable region (VH). In some embodiments, the linker polypeptide comprises an amino acid sequence of SEQ ID NO: 7. In some embodiments, the scFv comprises an amino acid sequence selected from the group consisting of SEQ ID NOS: 8-23, 169-184 and 340-343. In some embodiments, the extracellular antigen-binding domain comprises a signal polypeptide. In some embodiments, the signal polypeptide comprises an amino acid sequence of SEQ ID NO: 24.

In some embodiments, the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member component, and a combination thereof. In some embodiments, the CD137 component comprises an amino acid sequence of SEQ ID NO: 27. In some embodiments, the CD3z component comprises an amino acid sequence of SEQ ID NO: 28. In some embodiments, the intracellular signaling domain comprises an amino acid sequence of SEQ ID NO: 45. In some embodiments, the transmembrane domain comprises a CD8a transmembrane region (CD8a-TM) polypeptide. In some embodiments, the CD8a-TM polypeptide comprises an amino acid sequence of SEQ ID NO: 26.

In various embodiments, the CAR further comprises a hinge region linking the transmembrane domain to the extracellular antigen-binding domain. In some embodiments, the hinge region is a CD8a-hinge region. In some embodiments, the CD8a-hinge region comprises an amino acid sequence of SEQ ID NO: 25, 269, 270, 271, or 272. In some embodiments, the extracellular antigen-binding domain comprises an amino acid sequence selected from the group consisting of SEQ ID NOS: 29-44, 78-81, 221-236, and 273-308. In some embodiments, the CAR comprises an amino acid sequence selected from the group consisting of SEQ ID NOS: 46-61, 82-85 and 205-220.

In another aspect is provided an isolated lymphocyte expressing any of the above-described CARs. In some embodiments, the lymphocyte is a T lymphocyte. In some embodiments, the lymphocyte is a natural killer (NK) cell.

Also provided is an isolated nucleic acid molecule encoding any of the above-described CARs. Also provided is a vector comprising the nucleic acid molecule. In addition, a cell expressing the nucleic acid molecule is also provided.

Further provided is a pharmaceutical composition comprising an effective amount of any of the above lymphocytes, and a pharmaceutically acceptable excipient.

In one aspect, the present disclosure provides a CAR according to the present disclosure for use in a method of therapy.

In one aspect, the present disclosure provides a lymphocyte according to the present disclosure for use in a method of therapy.

In one aspect, the present disclosure provides a composition, e.g. a pharmaceutical composition, according to the present disclosure for use in a method of therapy.

In one aspect, the present disclosure provides a CAR according to the present disclosure for use in a method of treating cancer.

In one aspect, the present disclosure provides a lymphocyte according to the present disclosure for use in a method of treating cancer.

In one aspect, the present disclosure provides a composition, e.g. a pharmaceutical composition, according to the present disclosure for use in a method of treating cancer.

In one embodiment, the cancer is prostate cancer.

In one embodiment, the cancer is androgen receptor (AR) expressing breast cancer.

In another aspect is provided a method of treating a subject having cancer. The method comprises administering a therapeutically effective amount of any of the above lymphocytes to a subject in need thereof, whereby the lymphocyte induces killing of cancer cells in the subject. In some embodiments, the cancer is prostate cancer. In some embodiments, the cancer is androgen receptor (AR) expressing breast cancer.

In another aspect is provided a method of targeted killing of a cancer cell, the method comprising contacting the cancer cell with any of the above lymphocytes, whereby the lymphocyte induces killing of the cancer cell. In some embodiments, the cancer cell is a prostate cancer cell. In some embodiments, the cancer is androgen receptor (AR) expressing breast cancer.

In another aspect is provided a method of detecting the presence of cancer in a subject, comprising:
(a) contacting a cell sample obtained from the subject with any of the above CARs, thereby forming a CAR-cell complex, and
(b) detecting the complex, wherein detection of the complex is indicative of the presence of cancer in the subject.

BRIEF DESCRIPTION OF THE DRAWINGS

The foregoing will be apparent from the following more particular description of example embodiments, as illustrated in the accompanying drawings.

This patent application file contains at least one drawing executed in color. Copies of this patent application with color drawing(s) will be provided by the Office upon request and payment of the necessary fee.

FIGS. 1A-1C show the construction and expression of hK2 CAR on human T cells. FIG. 1A shows a schematic illustration of the construct for the hK2 CARs; TM: transmembrane. FIGS. 1B and 1C show hK2 CAR expression on T cells-surface. Primary human T cells were electroporated with no mRNA (MOCK) or 10 µg of mRNA expressing either an hK2 scFv CAR or irrelevant control CAR. 24 hours post-electroporation CAR surface expression was measured by flow cytometry following staining with 2 µg/ml biotinylated L-protein and streptavidin-conjugated PE (FIG. 1B) or biotinylated hK2 (1 µg/ml) and streptavidin-conjugated PE (FIG. 1C).

FIGS. 5A-5B show that 11B6 thermally stabilized scFvs CAR clones were evaluated in the JNL reporter assay for antigen-dependent activity. FIG. 5A shows Jurkat cells containing the luciferase gene driven by the signaling-responsive NFAT promoter (termed JNL cells), were transduced with the various hK2 CAR constructs. Expression was determined by biotinylated hK2 followed by streptavidin-conjugated PE. FIG. 5B shows binding between the CAR construct and its cognate cellular antigen (hK2 on target cells) leads to luciferase expression in the JNL cells. JNL cells containing the indicated CAR clones and un-transduced JNL cells (UTD) were co-cultured with target cells lines (VCap or DU145 cells) and luciferase activity was measured as luminescence intensity. Clones were considered active when the luminescence intensity exceeded 1.5-fold the level of UTD cells in the presence of antigen-expressing cells.

FIG. 7F shows percent tumor cell growth inhibition of hK2 negative DU145 cells by CAR-T cells transduced with CAR17 (B413HL in the FIG), CAR18 (B413LH in the FIG), CAR19 (B359HL in the FIG) and CAR20 (B359LH in the FIG) in the real-time IncuCyte killing assay assessing antigen-dependent cytotoxicity. Tumor cell growth inhibition (%)=(Initial Viable Target Cell Number-Current Viable Target Cell Number)/Initial Viable Cell Number*100(%).

FIGS. 10A-10E show the results from an hK2 CAR-T cells proliferation assay. (FIGS. 10A, 10C) hK2 CAR and un-transduced (UTD) T cells were labelled with CellTrace Violet (CTV; 5 µM) and co-cultured with hK2 (+) VCap and hK2 (−) DU145 cells. Five days post co-culture, cells were harvested and stained with CD3, CD25, NearIR live/dead Dye and hK2 CAR. Flow cytometric analysis was performed on a Fortessa flow cytometer with Flowjo software. Lymphocytes were identified by live CD3, and the frequencies of CAR+T cells with CTV dye dilution and activation marker CD25 were determined. (FIGS. 10B, 10D) CD3/28 beads stimulated T cells and T cells only were used as positive and negative controls, respectively. The data in FIG. 10E shows that hK2 CAR+ T cells proliferate more robustly than CD3/28 beads positive control after 5 days of coculture with VCap cells. Different CAR constructs engineered T cells have different proliferation activity and displayed different CAR+ T cells counts. The CAR+ T cells counts based on mean absolute cell count+/−SEM from three technical replicates.

FIG. 11A is a schematic illustration of the construct for the hK2 CARs; TM: transmembrane. In FIG. 11B, primary human T cells were transduced with novel hK2 scFvs based KL2B413 HL&LH and rehumanized 11B6 KL2B359 HL&LH CARS lentivirus (MOI 3) and CAR expression was determined by biotinylated hK2 (1 ug/ml) followed by streptavidin-conjugated PE 14 day post transduction. FIG. 11B provides a summary of the percentage of hK2 CAR+T cells (% positive) detected by novel KL2B413 HL&LH and rehumanized 11B6 KL2B359 HL&LH CARS analyzed. As shown, different clones have different CAR expression level, ranges from 45.1% to 59.9%. All CAR T cells were normalized to the equal CAR+ T cells for subsequent functional assays.

In FIG. 12A, Jurkat cells containing the luciferase gene driven by the signaling-responsive NFAT promoter (termed JNL cells), were transduced with the various hK2 CAR constructs. Expression was determined by biotinylated hK2 followed by streptavidin-conjugated PE. CAR expression in transduced JNL cells was confirmed for the selected clones with 46-50% of cells expression on rehumanized 11B6 KL2B359 CARs and 73.7-96% of cells on KL2B413 CARs. The data shown in FIG. 12B indicates that binding between the hK2 CAR construct and its cognate cellular antigen (hK2 on target cells) leads to luciferase expression in the JNL cells. JNL cells containing the indicated CAR clones and JNL cells (UTD) were co-cultured with target cells lines (VCap, LNCap/Hk2, LNCap, C4-2B, 22Rv1 or DU145 cells) and luciferase activity was measured as luminescence intensity. Clones were considered active when the luminescence intensity exceeded 1.5-fold the level of UTD cells in the presence of antigen-expressing cells. No antigen-dependent activation was found for the novel KL2B413 and rehumanized 11B6 HL&LH CARs.

FIGS. 16A-16F show the results of a hK2 CAR T cell proliferation assay. hK2 CAR and untransduced (UTD) T cells were labelled with CellTrace Violet (CTV; 5 uM) and co-cultured with HK2 (+) VCap and HK2 (−) DU145 cells. Five days post co-culture, cells were harvested and stained with CD3, CD25, NearIR live/dead Dye and hK2 CAR. Flow cytometric analysis was performed on a Fortessa flow cytometer with Flowjo software. Lymphocytes were identified by live CD3, and the frequencies of CAR+T cells with CTV dye dilution and activation marker CD25 were determined. By gating on CD3+ T cells, as shown in FIGS. 16A-16C, the hK2(+) Vcap cells but not hK2(−) DU145 cells promoted the all CAR constructs engineered T cells proliferation and upregulation of activation marker CD25, as shown in FIGS. 16D-16F. CD3/28 beads stimulated T cells and T cells only were used as positive and negative controls, respectively. T cells only without any stimulation do not proliferate, and CD3/28 beads stimulated T cells displayed equivalent proliferation pattern. As shown, hK2 CAR+ T cells proliferate more robustly than CD3/28 beads positive control after 5 days of coculture with VCap cells. Different CAR constructs engineered T cells have different proliferation activity and displayed different CAR+ T cells counts. The summary of percentage of proliferating T cells and CD25 expressing T cells based on mean absolute cell count+/−SEM from duplicate is shown in FIGS. 16C and 16F.

FIG. 17A shows the sequence alignment of the VH domains of mu11B6, hu11B6, KL2B357, KL2B358, KL2B359, KL2B360, HCF3 and HCG5. FIG. 17A discloses SEQ ID NOS 317, 5, 140, 141, 77, 140, 6, 4 and 345, respectively, in order of appearance. FIG. 17B shows the protected segments mapped onto the sequence of hK2 antigen to visualize the binding epitopes of hK2 antibodies identified through HDX-MS. FIG. 17B discloses SEQ ID NOS 351, 351, 351, 351, 351 and 351, respectively, in order of appearance.

DETAILED DESCRIPTION

Figure 1A:
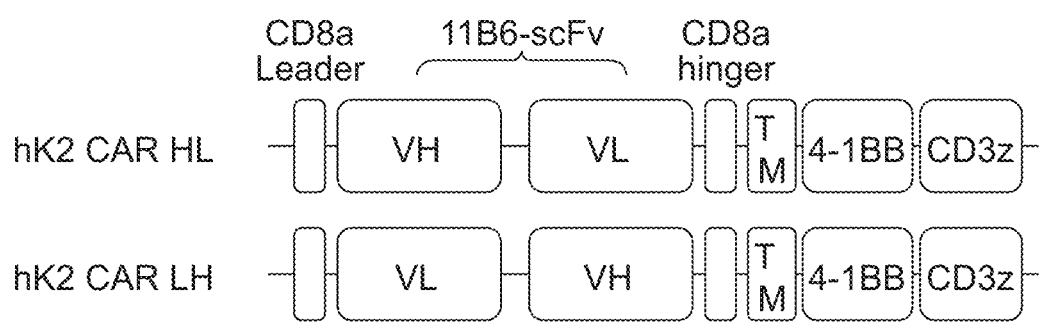

A description of example embodiments follows.

The present disclosure provides for chimeric antigen receptors (CARs) that target human Kallikrein-2 (hK2), cells comprising such CARs, and methods of treating cancer (e.g., prostate cancer or AR-expressing breast cancer) using the CARs described herein.

The CARs of the invention have antigen specificity for hK2. The phrases "have antigen specificity" and "elicit antigen-specific response" as used herein mean that the CAR can specifically bind to and immunologically recognize an antigen, such that binding of the CAR to the hK2 antigen elicits an immune response. Methods of testing the CARs for antigen specificity and for the ability to recognize target cells are known in the art.

The disclosure also provides related nucleic acids, recombinant expression vectors, host cells, populations of cells, antibodies, or antigen binding portions thereof, and pharmaceutical compositions relating to the CARs of the invention.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly-used dictionaries, should be interpreted as having a meaning that is consistent with their meaning in the context of the relevant art and/or as otherwise defined herein.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Definitions

As used in this specification and the appended claims, the singular forms "a," "an," and "the" include plural referents unless the content clearly dictates otherwise. Thus, for example, reference to "a cell" includes a combination of two or more cells, and the like.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

"Activation" or "stimulation" or "activated" or "stimulated" refers to induction of a change in the biologic state of a cell resulting in expression of activation markers, cytokine production, proliferation or mediating cytotoxicity of target cells. Cells may be activated by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to T cell and/or NK cell proliferation and/or upregulation or downregulation of key molecules.

"Antigen binding fragment" or "antigen binding domain" refers to a portion of the protein that binds an antigen. Antigen binding fragments may be synthetic, enzymatically obtainable or genetically engineered polypeptides and include portions of an immunoglobulin that bind an antigen, such as the VH, the VL, the VH and the VL, Fab, Fab', F(ab')$_2$, Fd and Fv fragments, domain antibodies (dAb) consisting of one VH domain or one VL domain, shark variable IgNAR domains, camelized VH domains, VHH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3, alternative scaffolds that bind an antigen, and multispecific proteins comprising the antigen binding fragments. Antigen binding fragments (such as VH and VL) may be linked together via a synthetic linker to form various types of single antibody designs where the VH/VL domains may pair intramolecularly, or intermolecularly in those cases when the VH and VL domains are expressed by separate single chains, to form a monovalent antigen binding domain, such as single chain Fv (scFv) or diabody. Antigen binding fragments may also be conjugated to other antibodies, proteins, antigen binding fragments or alternative scaffolds which may be monospecific or multispecific to engineer bispecific and multispecific proteins.

"Cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor.

"Full length antibody" is comprised of two heavy chains (HC) and two light chains (LC) inter-connected by disulfide bonds as well as multimers thereof (e.g. IgM). Each heavy chain is comprised of a heavy chain variable domain (VH) and a heavy chain constant domain, the heavy chain constant domain comprised of subdomains CH1, hinge, CH2 and CH3. Each light chain is comprised of a light chain variable domain (VL) and a light chain constant domain (CL). The VH and the VL may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or a synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody".

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Modulate" refers to either enhanced or decreased ability of a test molecule to mediate an enhanced or a reduced response (i.e., downstream effect) when compared to the response mediated by a control or a vehicle.

"Natural killer cell" and "NK cell" are used interchangeably and synonymously herein. NK cell refers to a differentiated lymphocyte with a CD16$^+$ CD56$^+$ and/or CD57$^+$ TCR$^-$ phenotype. NK cells are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

"Specifically binds," "specific binding," "specifically binding" or "binds" refer to a proteinaceous molecule binding to an antigen or an epitope within the antigen with greater affinity than for other antigens. Typically, the proteinaceous molecule binds to the antigen or the epitope within the antigen with an equilibrium dissociation constant ($K_D$) of about $1\times10^{-7}$ M or less, for example about $5\times10^{-8}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, typically with the $K_D$ that is at least one hundred fold less than its $K_D$ for binding to a non-specific antigen (e.g., BSA, casein). In the context of the prostate neoantigens described here, "specific binding" refers to binding of the proteinaceous molecule to the prostate neoantigen without detectable binding to a wild-type protein the neoantigen is a variant of.

"Tumor cell" or a "cancer cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid, uptake of exogenous nucleic acid or it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo.

The term "chimeric antigen receptor" or "CAR" as used herein is defined as a cell-surface receptor comprising an extracellular target-binding domain, a transmembrane domain and an intracellular signaling domain, all in a combination that is not naturally found together on a single protein. This particularly includes receptors wherein the extracellular domain and the intracellular signaling domain are not naturally found together on a single receptor protein. The chimeric antigen receptors of the present invention are intended primarily for use with lymphocyte such as T cells and natural killer (NK) cells.

The terms "T cell" and "T lymphocyte" are interchangeable and used synonymously herein. As used herein, T cell includes thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD8+ T cell), CD4+CD8+ T cell, or any other subset of T cells. Other illustrative populations of T cells suitable for use in particular embodiments include naive T cells and memory T cells. Also included are "NKT cells", which refer to a specialized population of T cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (T6 T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation, and were found to be an important source of IL-17 and to induce robust CD8+ cytotoxic T cell response. Also included are "regulatory T cells" or "Tregs", which refer to T cells that suppress an abnormal or excessive immune response and play a role in immune tolerance. Tregs are typically transcription factor Foxp3-positive CD4+T cells and can also include transcription factor Foxp3-negative regulatory T cells that are IL-10-producing CD4+T cells.

The terms "natural killer cell" and "NK cell" are interchangeable and used synonymously herein. As used herein, NK cell refers to a differentiated lymphocyte with a CD 16+ CD56+ and/or CD57+ TCR− phenotype. NK cells are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

As used herein, the term "antigen" refers to any agent (e.g., protein, peptide, polysaccharide, glycoprotein, glycolipid, nucleic acid, portions thereof, or combinations thereof) molecule capable of being bound by a T-cell receptor. An antigen is also able to provoke an immune response. An example of an immune response may involve, without limitation, antibody production, or the activation of specific immunologically competent cells, or both. A skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components, organisms, subunits of proteins/ antigens, killed or inactivated whole cells or lysates.

The terms "antibody" and "antibodies" refer to monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), intrabodies, minibodies, diabodies and anti-idiotypic (anti-Id) antibodies (including, e.g., anti-Id antibodies to antigen-specific TCR), and epitope-binding fragments of any of the above. The terms "antibody" and "antibodies" also refer to covalent diabodies such as those disclosed in U.S. Pat. Appl. Pub. 2007/ 0004909 and Ig-DARTS such as those disclosed in U.S. Pat. Appl. Pub. 2009/0060910. Antibodies useful as a TCR-binding molecule include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgM1, IgM2, IgA1 and IgA2) or subclass.

The term "host cell" means any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5α, JM109, and KCB, SURE® Competent Cells, and SOLOPACK Gold Cells, can be used as host cells for vector replication and/or expression. Additionally, bacterial cells such as E. coli LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, CHO, Saos, and PC12.

Host cells of the present disclosure include T cells and natural killer cells that contain DNA or RNA sequences encoding the CAR and that express the CAR on the cell surface. Host cells may be used for enhancing T cell activity, natural killer cell activity, treatment of cancer, and treatment of autoimmune disease.

"Activation" or "stimulation" means to induce a change in the cells' biologic state by which the cells (e.g., T cells and NK cells) express activation markers, produce cytokines, proliferate and/or become cytotoxic to target cells. All these changes can be produced by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to T cell and/or NK cell proliferation and/or upregulation or downregulation of key molecules.

The term "proliferation" refers to an increase in cell division, either symmetric or asymmetric division of cells. The term "expansion" refers to the outcome of cell division and cell death.

The term "differentiation" refers to a method of decreasing the potency or proliferation of a cell or moving the cell to a more developmentally restricted state.

The terms "express" and "expression" mean allowing or causing the information in a gene or DNA sequence to become produced, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or transmembrane.

The term "transfection" means the introduction of a "foreign" (i.e., extrinsic or extracellular) nucleic acid into a cell using recombinant DNA technology. The term "genetic modification" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences operably linked to polynucleotide encoding the chimeric antigen receptor, such as start, stop, promoter, signal, secretion, or other sequences used by a cell's genetic machinery. The gene or sequence may include nonfunctional sequences or sequences with no known function. A host cell that receives and expresses introduced DNA or RNA has been "genetically engineered." The DNA or RNA introduced to a host cell can come from any source, including cells of the same genus or species as the host cell, or from a different genus or species.

The term "transduction" means the introduction of a foreign nucleic acid into a cell using a viral vector.

The term "regulatory element" refers to any cis-acting genetic element that controls some aspect of the expression of nucleic acid sequences. In some embodiments, the term "promoter" comprises essentially the minimal sequences required to initiate transcription. In some embodiments, the term "promoter" includes the sequences to start transcription, and in addition, also include sequences that can upregulate or downregulate transcription, commonly termed "enhancer elements" and "repressor elements", respectively.

As used herein, the term "operatively linked," and similar phrases, when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

By "enhance" or "promote," or "increase" or "expand" or "improve" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, effector function, persistence, and/or an increase in cancer cell death killing ability, among others apparent from the understanding in the art and the description herein. In certain embodiments, an "increased" or "enhanced" amount can be a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. In certain embodiments, a "decrease" or "reduced" amount can be a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "protein" is used herein encompasses all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "nucleic acid", "nucleotide", and "polynucleotide" encompass both DNA and RNA unless specified otherwise. By a "nucleic acid sequence" or "nucleotide sequence" is meant the nucleic acid sequence encoding an amino acid; these terms may also refer to the nucleic acid sequence including the portion coding for any amino acids added as an artifact of cloning, including any amino acids coded for by linkers.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

"Kallikrein related peptidase 2", "hK2", or "klk2" refers to a known protein which is also called kallikrein-2, glandular kallikrein 2, or HK2. hK2 is produced as a preproprotein and cleaved during proteolysis to generate active protease. All hK2 isoforms and variants are encompassed in "hK2". The amino acid sequences of the various isoforms are retrievable from GenBank accession numbers NP_005542.1, NP 001002231.1 and NP_001243009. The amino acid sequence of a full length hK2 is shown in SEQ ID NO: 62. The sequence includes the signal peptide (residues 1-18) and the pro-peptide region (residues 19-24).

The terminology used herein is for the purpose of describing particular embodiments only and is not intended to be limiting. As used herein, the indefinite articles "a", "an" and "the" should be understood to include plural reference unless the context clearly indicates otherwise.

Chimeric Antigen Receptors

The present invention relates generally to the use of T cells genetically modified to stably express a desired chimeric antigen receptor. A chimeric antigen receptor (CAR) is an artificially constructed hybrid protein or polypeptide containing the antigen binding domains of an antibody (scFv) linked to T-cell signaling domains. Characteristics of CARs can include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigens independent of antigen processing, thus bypassing a major mechanism of tumor evasion. Moreover, when expressed in T-cells, CARs advantageously do not dimerize with endogenous T cell receptor (TCR) alpha and beta chains.

The CARs described herein provide recombinant polypeptide constructs comprising at least an extracellular antigen binding domain, a transmembrane domain and an intracellular signaling domain (also referred to herein as "a cytoplasmic signaling domain") comprising a functional signaling domain derived from a stimulatory molecule as defined below. T cells expressing a CAR are referred to herein as CAR T cells, CAR-T cells or CAR modified T cells, and these terms are used interchangeably herein. The cell can be genetically modified to stably express an antibody binding domain on its surface, conferring novel antigen specificity that is MHC independent.

In some instances, the T cell is genetically modified to stably express a CAR that combines an antigen recognition domain of a specific antibody with an intracellular domain of the CD3-zeta chain or FcγRI protein into a single chimeric protein. In one embodiment, the stimulatory molecule is the zeta chain associated with the T cell receptor complex.

An "intracellular signaling domain," or a "cytoplasmic signaling domain", as used herein, refers to an intracellular portion of a molecule. It is the functional portion of the protein which acts by transmitting information within the cell to regulate cellular activity via defined signaling pathways by generating second messengers or functioning as effectors by responding to such messengers. The intracellular signaling domain generates a signal that promotes an immune effector function of the CAR containing cell, e.g., a CAR-T cell. Examples of immune effector function, e.g., in a CAR-T cell, include cytolytic activity and helper activity, including the secretion of cytokines.

In an embodiment, the intracellular signaling domain can comprise a primary intracellular signaling domain. Example primary intracellular signaling domains include those derived from the molecules responsible for primary stimulation, or antigen dependent simulation. In an embodiment, the intracellular signaling domain can comprise a co-stimulatory intracellular domain. Example co-stimulatory intracellular signaling domains include those derived from molecules responsible for co-stimulatory signals, or antigen independent stimulation. For example, in the case of a CAR-T, a primary intracellular signaling domain can comprise a cytoplasmic sequence of a T cell receptor, and a co-stimulatory intracellular signaling domain can comprise cytoplasmic sequence from co-receptor or co-stimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3-zeta, FcR gamma, FcR beta, CD3 gamma, CD3 delta, CD3 epsilon, CD5, CD22, CD79a, CD79b, and CD66d DAP10 and DAP12.

The term "zeta" or alternatively "zeta chain", "CD3-zeta" or "TCR-zeta" is defined as the protein provided as Gen-Bank Acc. No. BAG36664.1, or the equivalent residues from a nonhuman species, e.g., murine, rabbit, primate, mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. At times, e.g. in or the aspects and/or embodiments of the disclosure, the "zeta stimulatory domain" or a "CD3-zeta stimulatory domain" is also referred to as "primary signaling domain". In one aspect, the cytoplasmic domain of CD3-zeta stimulatory domain comprises residues 52 through 164 of GenBank Acc. No. BAG36664.1 or the equivalent residues from a non-human species, e.g., mouse, rodent, monkey, ape and the like, that are functional orthologs thereof. In a preferred embodiment, the intracellular signaling domain comprises a CD3-zeta stimulatory domain. In one aspect, the "zeta stimulatory domain" or a "CD3-zeta stimulatory domain" is the sequence provided as SEQ ID NO: 28, or a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 28.

The term "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules are cell surface molecules other than antigen receptors or their ligands that are required for an efficient immune response. Co-stimulatory molecules include, but are not limited to an MHC class 1 molecule, BTLA and a Toll ligand receptor, as well as OX40, CD2, CD27, CD28, CDS, ICAM-1, LFA-1 (CD11a/CD18) and 4-1BB (CD137).

A co-stimulatory intracellular signaling domain can be the intracellular portion of a co-stimulatory molecule. A co-stimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, MyD88, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment thereof.

The term "4-1BB" or alternatively "CD137" refers to a member of the TNFR superfamily with an amino acid sequence provided as GenBank Acc. No. AAA62478.2, or the equivalent residues from a nonhuman species, e.g., mouse, rodent, monkey, ape and the like; and a "4-1BB co-stimulatory domain" is defined as amino acid residues 214-255 of GenBank accession no. AAA62478.2, or the equivalent residues from a non-human species, e.g., mouse, rodent, monkey, ape and the like. At times, e.g. in aspects and/or embodiments of the disclosure, the "4-1BB co-stimulatory domain" is also referred to as "co-stimulatory domain".

In a preferred embodiment, the intracellular signaling domain comprises a costimulatory intracellular signaling domain, wherein the costimulatory intracellular signaling domain is a 4-1BB costimulatory domain or "CD137 costimulatory domain". In one aspect, the "4-1BB co-stimulatory domain" or "CD137 co-stimulatory domain" is the sequence provided as SEQ ID NO: 27 or the equivalent residues from a non-human species, e.g., mouse, rodent, monkey, ape and the like, or a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 27. In a preferred embodiment the 4-1BB costimulatory domain is the sequence provided as SEQ ID No:27.

In one embodiment, a transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In one example embodiment, the transmembrane domain comprises the CD8α hinge domain. In one embodiment, the CAR comprises a CD8α hinge domain and a CD8α transmembrane domain.

In some embodiments, the cytoplasmic signaling domain further comprises one or more functional signaling domains derived from at least one co-stimulatory molecule as defined herein. In one embodiment, the co-stimulatory molecule is chosen from 4-1BB (i.e., CD137), CD27, CD3-zeta and/or CD28. CD28 is a T cell marker important in T cell co-stimulation. CD27 is a member of the tumor necrosis factor receptor superfamily and acts as a co-stimulatory immune checkpoint molecule. 4-1BB transmits a potent co-stimulatory signal to T cells, promoting differentiation and enhancing long-term survival of T lymphocytes. CD3-zeta associates with TCRs to produce a signal and contains immunoreceptor tyrosine-based activation motifs (ITAMs). In another embodiment, the co-stimulatory molecule is MyD88 or CD40.

In one embodiment, the CAR comprises an intracellular hinge domain comprising CD8 and an intracellular T cell receptor signaling domain comprising CD28, 4-1BB, and CD3-zeta. In another embodiment, the CAR comprises an intracellular hinge domain and an intracellular T cell receptor signaling domain comprising CD28, 4-1BB, and CD3-zeta, wherein the hinge domain comprises all or part of the extracellular region of CD8, CD4 or CD28; all or part of an antibody constant region; all or part of the FcγRIIIa receptor, an IgG hinge, an IgM hinge, an IgA hinge, an IgD hinge, an IgE hinge, or an Ig hinge. The IgG hinge may be from IgG1, IgG2, IgG3, IgG4, IgM1, IgM2, IgA1, IgA2, IgD, IgE, or a chimera thereof.

CARs described herein provide recombinant polypeptide constructs comprising at least an extracellular antigen binding domain, a transmembrane domain and an intracellular signaling domain (also referred to herein as "a cytoplasmic signaling domain") comprising, e.g., a functional signaling domain derived from a stimulatory molecule as defined below In one embodiment, the CAR comprises a chimeric fusion protein comprising an extracellular antigen recognition domain, a transmembrane domain and an intracellular signaling domain comprising a functional signaling domain derived from a stimulatory molecule. In one embodiment, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one embodiment, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule.

The CARs of the invention can be designed to comprise the CD28 and/or 4-1BB signaling domain by itself or be combined with any other desired cytoplasmic domain(s) useful in the context of the CARs of the invention. In one embodiment, the cytoplasmic domain of the CAR can further comprise the signaling domain of CD3-zeta. For example, the cytoplasmic domain of the CAR can include but is not limited to CD3-zeta, 4-1BB and CD28 signaling modules and combinations thereof.

In one embodiment, the CAR comprises a hinge domain comprising a CD8α hinge domain, a CD8α transmembrane domain. and an intracellular signaling domain comprising 4-1BB, and CD3-zeta. In one embodiment, the CAR comprises a hinge domain comprising a CD8α hinge domain, a CD8α transmembrane domain. and an intracellular signaling domain comprising CD28, 4-1BB, and CD3-zeta.

In another embodiment, the CAR comprises a CD8α hinge domain, a CD8α transmembrane domain, and an intracellular signaling domain comprising the signaling domain of CD3-zeta and a 4-1BB costimulatory domain.

In another embodiment, the CAR comprises a CD8a-hinge region comprising the amino acid sequence of SEQ ID NO: 25; a transmembrane domain comprising the amino acid sequence of SEQ ID NO: 26; and an intracellular signaling domain comprising a co-stimulatory domain comprising an amino acid sequence of SEQ ID NO: 27, and a primary signaling domain comprising an amino acid sequence of SEQ ID NO: 28.

Accordingly, the invention provides CAR T cells and methods of their use for adoptive therapy.

The disclosure further provides variants, e.g., functional variants, of the CARs, nucleic acids, polypeptides, and proteins described herein. "Variant" refers to a polypeptide or a polynucleotide that differs from a reference polypeptide or a reference polynucleotide by one or more modifications for example, substitutions, insertions or deletions. The term "functional variant" as used herein refers to a CAR, polypeptide, or protein having substantial or significant sequence identity or similarity to a parent CAR, polypeptide, or protein, which functional variant retains the biological activity of the CAR, polypeptide, or protein for which it is a variant. Functional variants encompass, e.g., those variants of the CAR, polypeptide, or protein described herein (the parent CAR, polypeptide, or protein) that retain the ability to recognize target cells to a similar extent, the same extent, or to a higher extent, as the parent CAR, polypeptide, or protein. In reference to the parent CAR, polypeptide, or protein, the functional variant can, for example, be at least about 30%, about 40%, about 50%, about 60%, about 75%, about 80%, about 85%, about 90%, about 91%, about 92%, about 93%, about 94%, about 95%, about 96%, about 97%, about 98%, about 99% or more identical in amino acid sequence to the parent CAR, polypeptide, or protein.

Herein, the structure of polypeptides is in places defined on the basis of % sequence identity with a recited reference sequence (with a given SEQ ID NO). In this context, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. Typically, the comparison window with correspond to the full length of the sequence being compared. For example, it is possible to use the BLAST program, "BLAST 2 sequences" (Tatusova et al, "Blast 2 sequences—a new tool for comparing protein and nucleotide sequences", FEMS Microbiol Lett. 174:247-250) available on the site http://www.ncbi.nlm.nih.gov/gorf/bl2.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program. Determining sequence identity of a query sequence to a reference sequence is within the ability of the skilled person and can be performed using commercially available analysis software such as BLAST™.

A functional variant can, for example, comprise the amino acid sequence of the parent CAR, polypeptide, or protein with at least one conservative amino acid substitution. In another embodiment, the functional variants can comprise the amino acid sequence of the parent CAR, polypeptide, or protein with at least one non-conservative amino acid substitution. In this case, the non-conservative amino acid substitution may not interfere with or inhibit the biological activity of the functional variant. The non-conservative amino acid substitution may enhance the biological activity of the functional variant such that the biological activity of the functional variant is increased as compared to the parent CAR, polypeptide, or protein.

Amino acid substitutions of the inventive CARs may be conservative amino acid substitutions. Conservative amino acid substitutions are known in the art, and include amino acid substitutions in which one amino acid having certain physical and/or chemical properties is exchanged for another amino acid that has the same or similar chemical or physical properties. For example, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The CAR, polypeptide, or protein can consist essentially of the specified amino acid sequence or sequences described herein, such that other components e.g., other amino acids, do not materially change the biological activity of the functional variant.

The CARs, polypeptides, and proteins of embodiments of the disclosure (including functional portions and functional variants) can be of any length, i.e., can comprise any number of amino acids, provided that the CARs, polypeptides, or proteins (or functional portions or functional variants thereof) retain their biological activity, e.g., the ability to specifically bind to an antigen, detect diseased cells (e.g., cancer cells) in a host, or treat or prevent disease in a host, etc. For example, the polypeptide can be about 50 to about 5000 amino acids long, such as about 50, about 70, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000 or more amino acids in length. The polypeptides of the invention also include oligopeptides.

The CARs, polypeptides, and proteins of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, α-(2-amino-2-norbornane)-carboxylic acid, α,γ-diaminobutyric acid, α,β-diaminopropionic acid, homophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, indoline-2-carboxylic acid, 1,2,3,4-tetrahydroisoquinoline-3-carboxylic acid, aminomalonic acid, aminomalonic acid monoamide, and α-tert-butylglycine.

The CARs, polypeptides, and proteins of embodiments of the invention (including functional portions and functional variants) can be subject to post-translational modifications. They can be glycosylated, esterified, N-acylated, amidated, carboxylated, phosphorylated, esterified, cyclized via, e.g., a disulfide bridge, or converted into an acid addition salt. In some embodiments, they are dimerized or polymerized, or conjugated.

The CARs, polypeptides, and/or proteins of embodiments of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; and *Epitope Mapping*, ed. Westwood et al., Oxford University Press, Oxford, United Kingdom, 2001. Also, polypeptides and proteins can be recombinantly produced using the nucleic acids described herein using standard recombinant methods. See, for instance, Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994. Further, some of the CARs, polypeptides, and proteins of the invention (including functional portions and functional variants thereof) can be isolated and/or purified from a source, such as a plant, a bacterium, an insect, a mammal, etc. Methods of isolation and purification are known in the art. Alternatively, the CARs, polypeptides, and/or proteins described herein (including functional portions and functional variants thereof) can be commercially synthesized. In this respect, the CARs, polypeptides, and proteins can be synthetic, recombinant, isolated, and/or purified.

Examples of modified nucleotides that can be used to generate the recombinant nucleic acids utilized to produce the polypeptides described herein include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, carboxymethylaminomethyl-2-thiouridine, 5-carboxymethylaminomethyluracil, dihydrouracil, $N^6$-substituted adenine, 7-methylguanine, 5-methylaminomethyluracil, 5-methoxyaminomethyl-2-thiouracil, beta-D-mannosylqueosine, 5"-methoxycarboxymethyluracil, 5-methoxyuracil, 2-methylthio-$N^6$-isopentenyladenine, uracil-5-oxyacetic acid (v), wybutoxosine, pseudouracil, queuosine, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

The nucleic acid can comprise any isolated or purified nucleotide sequence which encodes any of the CARs, polypeptides, or proteins, or functional portions or functional variants thereof. Alternatively, the nucleotide sequence can comprise a nucleotide sequence which is degenerate to any of the sequences or a combination of degenerate sequences.

Some embodiments of the invention also provide an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein. The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-12 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the CARs described herein. It is generally appreciated that conditions can be rendered more stringent by the addition of increasing amounts of formamide.

In an embodiment, the nucleic acids of the invention can be incorporated into a recombinant expression vector. The present disclosure provides recombinant expression vectors comprising any of the nucleic acids of the invention. As used herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors described herein are not naturally-occurring as a whole; however, parts of the vectors can be naturally-occurring. The described recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. The non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λEMBL4, and λNM1149, λZapII (Stratagene) can be used. Examples of plant expression vectors include pBI01, pBI01.2, pBI121, pBI101.3, and pBIN19 (Clontech). Examples of animal expression vectors include pEUK-Cl, pMAM, and pMAM-neo (Clontech). The recombinant expression vector may be a viral vector, e.g., a retroviral vector, e.g., a gamma retroviral vector.

In an embodiment, the recombinant expression vectors of the invention are prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, SV40, 2µ plasmid, λ, bovine papilloma virus, and the like.

The recombinant expression vector may comprise regulatory sequences, such as transcription and translation initiation and termination codons, which are specific to the type of host (e.g., bacterium, plant, fungus, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the described expression vectors include, for instance, neomycin/G418 resistance genes, histidinol x resistance genes, histidinol resistance genes, tetracycline resistance genes, and ampicillin resistance genes.

The recombinant expression vector can comprise a native or normative promoter operably linked to the nucleotide sequence encoding the CAR, polypeptide, or protein (including functional portions and functional variants thereof), or to the nucleotide sequence which is complementary to or which hybridizes to the nucleotide sequence encoding the CAR, polypeptide, or protein. The selection of promoters, e.g., strong, weak, tissue-specific, inducible and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an RSV promoter, an SV40 promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, and nitroreductase.

Included in the scope of the invention are conjugates, e.g., bioconjugates, comprising any of the CARs, polypeptides, or proteins (including any of the functional portions or variants thereof), host cells, nucleic acids, recombinant expression vectors, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

An embodiment of the invention further provides an antibody, or antigen binding portion thereof, which binds, e.g., specifically binds, to an epitope of the CARs of the invention. The antibody can be any type of immunoglobulin that is known in the art. Immunoglobulins may be assigned to five major classes, IgA, IgD, IgE, IgG and IgM. IgA and IgG are further classified as the isotypes IgA1, IgA2, IgG1, IgG2, IgG3 and IgG4. Antibody light chains of vertebrate species can be assigned to one of two types, kappa (κ) and lambda (λ), based on the amino acid sequences of their constant domains. The antibody can be of any class or isotype.

The antibodies include immunoglobulin molecules including monoclonal antibodies including murine, human, humanized and chimeric monoclonal antibodies, polyclonal, antigen-binding fragments, bispecific or multispecific antibodies, monomeric, dimeric, tetrameric or multimeric antibodies, single chain antibodies, domain antibodies and any other modified configuration of the immunoglobulin molecule that comprises an antigen binding site of the required specificity. The antibody can be a naturally-occurring antibody, e.g., an antibody isolated and/or purified from a mammal, e.g., a murine, primate, mouse, rabbit, goat, horse, chicken, hamster, human, etc. Alternatively, the antibody can be an engineered (e.g., genetically-engineered) antibody.

Humanized antibodies have antigen binding sites derived from non-human species and the variable region frameworks are derived from human immunoglobulin sequences. Human antibodies have heavy and light chain variable regions in which both the framework and the antigen binding site are derived from sequences of human origin.

Also, the antibody can have any level of affinity or avidity for the functional portion of the CAR. In some embodiments, the antibody may bind the hK2 antigen with a range of affinities ($K_D$). In one embodiment according to the invention, and in some embodiments of each and every one of the numbered embodiments listed below, the antibody binds to the hK2 antigen with high affinity, for example, with a $K_D$ equal to or less than about $10^{-7}$ M, such as but not limited to, 1-9.9 (or any range or value therein, such as 1, 2, 3, 4, 5, 6, 7, 8, or 9)×$10^{-8}$M, $10^{-9}$ M, $10^{-10}$ M, $10^{-11}$ M, $10^{-12}$ M, $10^{-13}$ M, $10^{-14}$ M, $10^{-15}$ M or any range or value therein, as determined by surface plasmon resonance or the Kinexa method, as practiced by those of skill in the art. One example affinity is equal to or less than 1×$10^{-8}$ M. Another example affinity is equal to or less than 1×$10^{-9}$ M.

Methods of testing antibodies for the ability to bind to any functional portion of the CARs are known in the art and include any antibody-antigen binding assay, such as, for example, radioimmunoassay (RIA), Western blot, enzyme-linked immunosorbent assay (ELISA), immunoprecipitation, and competitive inhibition assays.

Suitable methods of making antibodies are known in the art. For instance, standard hybridoma methods are described in, e.g., Kohler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5th Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 127581 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display can also be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen (i.e., hK2), and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are known in the art and are described in, for example, Janeway et al., supra, U.S. Pat. Nos. 5,225,539, 5,585,089 and 5,693,761, European Patent No. 0239400 Bi, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994). Antibodies, as utilized herein, can be multiple or single chain, or intact immunoglobulins, and may be derived from natural sources or from recombinant sources. Antibodies can be tetramers of immunoglobulin molecules.

The term "antibody fragment" refers to at least one portion of an intact antibody, or recombinant variants thereof, that retains the antigen binding properties of the parental full length antibody. It refers to, for example, the antigen binding domain, e.g., an antigenic determining variable region of an intact antibody, that is sufficient to confer recognition and binding, e.g., specific binding of the antibody fragment to a target, such as an antigen. "Antigen-binding fragment" refers to a portion of an immunoglobulin molecule. Examples of antibody fragments include, but are not limited to, Fab, Fab', F(ab')$_2$, and Fv fragments, single chain antibodies (scFv), linear antibodies, single domain antibodies such as sdAb (either VL or VH), camelid VHH domains, and multi-specific antibodies formed from antibody fragments.

The term "scFv" refers to a protein comprising at least one antibody fragment comprising a variable region of a light chain and at least one antibody fragment comprising a variable region of a heavy chain. In some embodiments, the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

An embodiment of the invention also provides antigen binding portions of any of the antibodies described herein. The antigen binding portion can be any portion that has at least one antigen binding site, such as Fab, F(ab')2, dsFv, sFv, diabodies, and triabodies. In some embodiments, antigen-binding fragments are heavy chain complementarity determining regions (HCDR) 1, 2 and/or 3, light chain complementarity determining regions (LCDR) 1, 2 and/or 3, a heavy chain variable region (VH), or a light chain variable region (VL), Fab, F(ab')$_2$, Fd and Fv fragments and domain antibodies (dAb) comprising (e.g., consisting of) either one VH domain or one VL domain. VH and VL domains may be linked together via a linker, e.g., a synthetic linker.

"Complementarity determining regions (CDR)" are antigen binding sites in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk, Mol Biol 196:901-17, 1987). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Also provided by the present disclosure is a nucleic acid comprising a nucleotide sequence encoding any of the CARs, polypeptides, or proteins described herein (including functional portions and functional variants thereof).

The portion of the CAR comprising an antibody or antibody fragment thereof may exist in a variety of forms where the antigen binding domain is expressed as part of a contiguous polypeptide chain including, for example, a single domain antibody fragment (sdAb), a scFv and a human chimeric or humanized antibody (Harlow et al., 1999, *In: Using Antibodies: A Laboratory Manual*, Cold Spring Harbor Laboratory Press, N.Y.; Harlow et al., 1989, *In: Antibodies: A Laboratory Manual*, Cold Spring Harbor, N.Y.; Houston et al., 1988, *Proc. Natl. Acad. Sci. USA* 85:5879-5883; Bird et al., 1988, *Science* 242:423-426). In one aspect, the antigen binding domain of a CAR composition of the invention comprises an antibody fragment. In one aspect, the CAR comprises an antibody fragment that comprises a scFv.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and known in the art.

The term "antigen" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene.

It is apparent that the present disclosure includes, but is not limited to, the use of partial nucleotide sequences of more than one gene and that these nucleotide sequences are arranged in various combinations to encode polypeptides that elicit the desired immune response.

In one aspect, the disclosure provides a CAR, comprising an extracellular antigen-binding domain, a transmembrane domain and an intracellular signaling domain, wherein the extracellular antigen-binding domain binds the hK2 antigen.

In one aspect, the disclosure provides a CAR, comprising an extracellular antigen-binding domain, a transmembrane domain and an intracellular signaling domain, wherein the extracellular antigen-binding domain comprises:
- light chain CDR1, CDR2, and CDR3 from a variable region comprising an amino acid sequence of SEQ ID NO: 1, and heavy chain CDR1, CDR2, and CDR3 from a variable region comprising an amino acid sequence of SEQ ID NO: 4;
- light chain CDR1, CDR2, and CDR3 from a variable region comprising an amino acid sequence of SEQ ID NO: 2, and heavy chain CDR1, CDR2, and CDR3 from a variable region comprising an amino acid sequence of SEQ ID NO: 4;
- light chain CDR1, CDR2, and CDR3 from a variable region comprising an amino acid sequence of SEQ ID NO: 3, and heavy chain CDR1, CDR2, and CDR3 from a variable region comprising an amino acid sequence of SEQ ID NO: 6;
- light chain CDR1, CDR2, and CDR3 from a variable region comprising an amino acid sequence of SEQ ID NO: 3, and heavy chain CDR1, CDR2, and CDR3 from a variable region comprising an amino acid sequence of SEQ ID NO: 4;
- light chain CDR1, CDR2, and CDR3 from a variable region comprising an amino acid sequence of SEQ ID NO: 2, and heavy chain CDR1, CDR2, and CDR3 from a variable region comprising an amino acid sequence of SEQ ID NO: 6;
- light chain CDR1, CDR2, and CDR3 from a variable region comprising an amino acid sequence of SEQ ID NO: 1, and heavy chain CDR1, CDR2, and CDR3 from a variable region comprising an amino acid sequence of SEQ ID NO: 6;
- light chain CDR1, CDR2, and CDR3 from a variable region comprising an amino acid sequence of SEQ ID NO: 3, and heavy chain CDR1, CDR2, and CDR3 from a variable region comprising an amino acid sequence of SEQ ID NO: 5;
- light chain CDR1, CDR2, and CDR3 from a variable region comprising an amino acid sequence of SEQ ID NO: 1, and heavy chain CDR1, CDR2, and CDR3 from a variable region comprising an amino acid sequence of SEQ ID NO: 5;
- light chain CDR1, CDR2, and CDR3 from a variable region comprising an amino acid sequence of SEQ ID NO: 2, and heavy chain CDR1, CDR2, and CDR3 from a variable region comprising an amino acid sequence of SEQ ID NO: 5;
- light chain CDR1, CDR2, and CDR3 from a variable region comprising an amino acid sequence of SEQ ID NO: 74, and heavy chain CDR1, CDR2, and CDR3 from a variable region comprising an amino acid sequence of SEQ ID NO: 76;
- light chain CDR1, CDR2, and CDR3 from a variable region comprising an amino acid sequence of SEQ ID NO: 75, and heavy chain CDR1, CDR2, and CDR3 from a variable region comprising an amino acid sequence of SEQ ID NO: 77;
- light chain CDR1, CDR2, and CDR3 from a variable region comprising an amino acid sequence of SEQ ID NO: 147, and heavy chain CDR1, CDR2, and CDR3 from a variable region comprising an amino acid sequence of SEQ ID NO: 140;
- light chain CDR1, CDR2, and CDR3 from a variable region comprising an amino acid sequence of SEQ ID NO: 75, and heavy chain CDR1, CDR2, and CDR3 from a variable region comprising an amino acid sequence of SEQ ID NO: 141;
- light chain CDR1, CDR2, and CDR3 from a variable region comprising an amino acid sequence of SEQ ID NO: 75, and heavy chain CDR1, CDR2, and CDR3 from a variable region comprising an amino acid sequence of SEQ ID NO: 140;
- light chain CDR1, CDR2, and CDR3 from a variable region comprising an amino acid sequence of SEQ ID NO: 148, and heavy chain CDR1, CDR2, and CDR3 from a variable region comprising an amino acid sequence of SEQ ID NO: 142;
- light chain CDR1, CDR2, and CDR3 from a variable region comprising an amino acid sequence of SEQ ID NO: 149, and heavy chain CDR1, CDR2, and CDR3 from a variable region comprising an amino acid sequence of SEQ ID NO: 143;
light chain CDR1, CDR2, and CDR3 from a variable region comprising an amino acid sequence of SEQ ID NO: 150, and heavy chain CDR1, CDR2, and CDR3 from a variable region comprising an amino acid sequence of SEQ ID NO: 144;
light chain CDR1, CDR2, and CDR3 from a variable region comprising an amino acid sequence of SEQ ID NO: 151, and heavy chain CDR1, CDR2, and CDR3 from a variable region comprising an amino acid sequence of SEQ ID NO: 145;
light chain CDR1, CDR2, and CDR3 from a variable region comprising an amino acid sequence of SEQ ID NO: 152, and heavy chain CDR1, CDR2, and CDR3 from a variable region comprising an amino acid sequence of SEQ ID NO: 146;
a light chain CDR1, CDR2, and CDR3 from a variable region comprising an amino acid sequence of SEQ ID NO: 318 and a heavy chain CDR1, CDR2, and CDR3 from a variable region comprising an amino acid sequence of SEQ ID NO: 317;
wherein the extracellular antigen-binding domain binds the hK2 antigen.

In one embodiment the extracellular antigen-binding domain comprises light chain CDR1, CDR2, and CDR3 from a variable region comprising an amino acid sequence of SEQ ID NO: 1, and heavy chain CDR1, CDR2, and CDR3 from a variable region comprising an amino acid sequence of SEQ ID NO: 4.

In one embodiment the extracellular antigen-binding domain comprises light chain CDR1, CDR2, and CDR3 from a variable region comprising an amino acid sequence of SEQ ID NO: 2, and heavy chain CDR1, CDR2, and CDR3 from a variable region comprising an amino acid sequence of SEQ ID NO: 4.

In one embodiment the extracellular antigen-binding domain comprises light chain CDR1, CDR2, and CDR3 from a variable region comprising an amino acid sequence of SEQ ID NO: 3, and heavy chain CDR1, CDR2, and CDR3 from a variable region comprising an amino acid sequence of SEQ ID NO: 6.

In one embodiment the extracellular antigen-binding domain comprises light chain CDR1, CDR2, and CDR3 from a variable region comprising an amino acid sequence of SEQ ID NO: 3, and heavy chain CDR1, CDR2, and CDR3 from a variable region comprising an amino acid sequence of SEQ ID NO: 4.

In one embodiment the extracellular antigen-binding domain comprises light chain CDR1, CDR2, and CDR3 from a variable region comprising an amino acid sequence of SEQ ID NO: 2, and heavy chain CDR1, CDR2, and CDR3 from a variable region comprising an amino acid sequence of SEQ ID NO: 6.

In one embodiment the extracellular antigen-binding domain comprises light chain CDR1, CDR2, and CDR3 from a variable region comprising an amino acid sequence of SEQ ID NO: 1, and heavy chain CDR1, CDR2, and CDR3 from a variable region comprising an amino acid sequence of SEQ ID NO: 6.

In one embodiment the extracellular antigen-binding domain comprises light chain CDR1, CDR2, and CDR3 from a variable region comprising an amino acid sequence of SEQ ID NO: 3, and heavy chain CDR1, CDR2, and CDR3 from a variable region comprising an amino acid sequence of SEQ ID NO: 5.

In one embodiment the extracellular antigen-binding domain comprises light chain CDR1, CDR2, and CDR3 from a variable region comprising an amino acid sequence of SEQ ID NO: 1, and heavy chain CDR1, CDR2, and CDR3 from a variable region comprising an amino acid sequence of SEQ ID NO: 5.

In one embodiment the extracellular antigen-binding domain comprises light chain CDR1, CDR2, and CDR3 from a variable region comprising an amino acid sequence of SEQ ID NO: 2, and heavy chain CDR1, CDR2, and CDR3 from a variable region comprising an amino acid sequence of SEQ ID NO: 5.

In one embodiment the extracellular antigen-binding domain comprises light chain CDR1, CDR2, and CDR3 from a variable region comprising an amino acid sequence of SEQ ID NO: 74, and heavy chain CDR1, CDR2, and CDR3 from a variable region comprising an amino acid sequence of SEQ ID NO: 76.

In one embodiment the extracellular antigen-binding domain comprises light chain CDR1, CDR2, and CDR3 from a variable region comprising an amino acid sequence of SEQ ID NO: 75, and heavy chain CDR1, CDR2, and CDR3 from a variable region comprising an amino acid sequence of SEQ ID NO: 77.

In one embodiment the extracellular antigen-binding domain comprises light chain CDR1, CDR2, and CDR3 from a variable region comprising an amino acid sequence of SEQ ID NO: 147, and heavy chain CDR1, CDR2, and CDR3 from a variable region comprising an amino acid sequence of SEQ ID NO: 140.

In one embodiment the extracellular antigen-binding domain comprises light chain CDR1, CDR2, and CDR3 from a variable region comprising an amino acid sequence of SEQ ID NO: 75, and heavy chain CDR1, CDR2, and CDR3 from a variable region comprising an amino acid sequence of SEQ ID NO: 141.

In one embodiment the extracellular antigen-binding domain comprises light chain CDR1, CDR2, and CDR3 from a variable region comprising an amino acid sequence of SEQ ID NO: 75, and heavy chain CDR1, CDR2, and CDR3 from a variable region comprising an amino acid sequence of SEQ ID NO: 140.

In one embodiment the extracellular antigen-binding domain comprises light chain CDR1, CDR2, and CDR3 from a variable region comprising an amino acid sequence of SEQ ID NO: 148, and heavy chain CDR1, CDR2, and CDR3 from a variable region comprising an amino acid sequence of SEQ ID NO: 142 In one embodiment the extracellular antigen-binding domain comprises light chain CDR1, CDR2, and CDR3 from a variable region comprising an amino acid sequence of SEQ ID NO: 149, and heavy chain CDR1, CDR2, and CDR3 from a variable region comprising an amino acid sequence of SEQ ID NO: 143.

In one embodiment the extracellular antigen-binding domain comprises light chain CDR1, CDR2, and CDR3 from a variable region comprising an amino acid sequence of SEQ ID NO: 150, and heavy chain CDR1, CDR2, and CDR3 from a variable region comprising an amino acid sequence of SEQ ID NO: 144.

In one embodiment the extracellular antigen-binding domain comprises light chain CDR1, CDR2, and CDR3 from a variable region comprising an amino acid sequence of SEQ ID NO: 151, and heavy chain CDR1, CDR2, and CDR3 from a variable region comprising an amino acid sequence of SEQ ID NO: 145.

In one embodiment the extracellular antigen-binding domain comprises light chain CDR1, CDR2, and CDR3 from a variable region comprising an amino acid sequence of SEQ ID NO: 152, and heavy chain CDR1, CDR2, and CDR3 from a variable region comprising an amino acid sequence of SEQ ID NO: 146.

In one embodiment the extracellular antigen-binding domain comprises a light chain CDR1, CDR2, and CDR3 from a variable region comprising an amino acid sequence of SEQ ID NO: 318 and a heavy chain CDR1, CDR2, and CDR3 from a variable region comprising an amino acid sequence of SEQ ID NO: 317.

In one aspect, the disclosure provides a CAR, comprising an extracellular antigen-binding domain, a transmembrane domain and an intracellular signaling domain, wherein the extracellular antigen-binding domain comprises:

a heavy chain CDR1 having an amino acid sequence selected from the group consisting of SEQ ID NO: 63, SEQ ID NO: 72, SEQ ID NO: 86, SEQ ID NO: 92, SEQ ID NO: 102, SEQ ID NO: 105, SEQ ID NO: 107, SEQ ID NO: 110, SEQ ID NO: 115, SEQ ID NO: 118, SEQ ID NO: 120, SEQ ID NO: 123, SEQ ID NO: 309, and SEQ ID NO: 314, and conservative modifications thereof, wherein the extracellular antigen-binding domain binds the hK2 antigen.

In one aspect, the disclosure provides a CAR, comprising an extracellular antigen-binding domain, a transmembrane domain and an intracellular signaling domain, wherein the extracellular antigen-binding domain comprises:

a heavy chain CDR2 having an amino acid sequence selected from the group consisting of SEQ ID NO: 64, SEQ ID NO: 65, SEQ ID NO: 73, SEQ ID NO: 87, SEQ ID NO: 93, SEQ ID NO: 103, SEQ ID NO: 106, SEQ ID NO: 108, SEQ ID NO: 111, SEQ ID NO: 112, SEQ ID NO: 114, SEQ ID NO: 116, SEQ ID NO: 119, SEQ ID NO: 121, SEQ ID NO: 124, SEQ ID NO: 310, and SEQ ID NO: 315, and conservative modifications thereof, wherein the extracellular antigen-binding domain binds the hK2 antigen.

In one aspect, the disclosure provides a CAR, comprising an extracellular antigen-binding domain, a transmembrane domain and an intracellular signaling domain, wherein the extracellular antigen-binding domain comprises:

a heavy chain CDR3 having an amino acid sequence selected from the group consisting of SEQ ID NO: 66, SEQ ID NO: 88, SEQ ID NO: 94, SEQ ID NO: 104, SEQ ID NO: 109, SEQ ID NO: 113, SEQ ID NO: 117, SEQ ID NO: 122, and SEQ ID NO: 311, and conservative modifications thereof, wherein the extracellular antigen-binding domain binds the hK2 antigen.

In one aspect, the disclosure provides a CAR, comprising an extracellular antigen-binding domain, a transmembrane domain and an intracellular signaling domain, wherein the extracellular antigen-binding domain comprises:

a heavy chain complementarity determining region 1 (CDR1) having the amino acid sequence of SEQ ID NO: 63, a heavy chain CDR2 having the amino acid sequence of SEQ ID NO: 64, and a heavy chain CDR3 having the amino acid sequence of SEQ ID NO: 66;

a heavy chain complementarity determining region 1 (CDR1) having the amino acid sequence of SEQ ID NO: 314, a heavy chain CDR2 having the amino acid sequence of SEQ ID NO: 315, and a heavy chain CDR3 having the amino acid sequence of SEQ ID NO: 311;

a heavy chain complementarity determining region 1 (CDR1) having the amino acid sequence of SEQ ID NO: 309, a heavy chain CDR2 having the amino acid sequence of SEQ ID NO: 310, and a heavy chain CDR3 having the amino acid sequence of SEQ ID NO: 311;

a heavy chain complementarity determining region 1 (CDR1) having the amino acid sequence of SEQ ID NO: 63, a heavy chain CDR2 having the amino acid sequence of SEQ ID NO: 65, and a heavy chain CDR3 having the amino acid sequence of SEQ ID NO: 66;

a heavy chain complementarity determining region 1 (CDR1) having the amino acid sequence of SEQ ID NO: 72, a heavy chain CDR2 having the amino acid sequence of SEQ ID NO: 73, and a heavy chain CDR3 having the amino acid sequence of SEQ ID NO: 66; or a heavy chain complementarity determining region 1 (CDR1) having the amino acid sequence of SEQ ID NO: 86, a heavy chain CDR2 having the amino acid sequence of SEQ ID NO: 87, and a heavy chain CDR3 having the amino acid sequence of SEQ ID NO: 88;

a heavy chain complementarity determining region 1 (CDR1) having the amino acid sequence of SEQ ID NO: 92, a heavy chain CDR2 having the amino acid sequence of SEQ ID NO: 93, and a heavy chain CDR3 having the amino acid sequence of SEQ ID NO: 94;

a heavy chain complementarity determining region 1 (CDR1) having the amino acid sequence of SEQ ID NO: 102, a heavy chain CDR2 having the amino acid sequence of SEQ ID NO: 103, and a heavy chain CDR3 having the amino acid sequence of SEQ ID NO: 104;

a heavy chain complementarity determining region 1 (CDR1) having the amino acid sequence of SEQ ID NO: 105, a heavy chain CDR2 having the amino acid sequence of SEQ ID NO: 106, and a heavy chain CDR3 having the amino acid sequence of SEQ ID NO: 104;

a heavy chain complementarity determining region 1 (CDR1) having the amino acid sequence of SEQ ID NO: 107, a heavy chain CDR2 having the amino acid sequence of SEQ ID NO: 108, and a heavy chain CDR3 having the amino acid sequence of SEQ ID NO: 109;

a heavy chain complementarity determining region 1 (CDR1) having the amino acid sequence of SEQ ID NO: 110, a heavy chain CDR2 having the amino acid sequence of SEQ ID NO: 111, and a heavy chain CDR3 having the amino acid sequence of SEQ ID NO: 109;

a heavy chain complementarity determining region 1 (CDR1) having the amino acid sequence of SEQ ID NO: 102, a heavy chain CDR2 having the amino acid sequence of SEQ ID NO: 112, and a heavy chain CDR3 having the amino acid sequence of SEQ ID NO: 113;

a heavy chain complementarity determining region 1 (CDR1) having the amino acid sequence of SEQ ID NO: 105, a heavy chain CDR2 having the amino acid sequence of SEQ ID NO: 114, and a heavy chain CDR3 having the amino acid sequence of SEQ ID NO: 113;

a heavy chain complementarity determining region 1 (CDR1) having the amino acid sequence of SEQ ID NO: 115, a heavy chain CDR2 having the amino acid sequence of SEQ ID NO: 116, and a heavy chain CDR3 having the amino acid sequence of SEQ ID NO: 117;

a heavy chain complementarity determining region 1 (CDR1) having the amino acid sequence of SEQ ID NO: 118, a heavy chain CDR2 having the amino acid sequence of SEQ ID NO: 119, and a heavy chain CDR3 having the amino acid sequence of SEQ ID NO: 117;

a heavy chain complementarity determining region 1 (CDR1) having the amino acid sequence of SEQ ID NO: 120, a heavy chain CDR2 having the amino acid sequence of SEQ ID NO: 121, and a heavy chain CDR3 having the amino acid sequence of SEQ ID NO: 122; or a heavy chain complementarity determining region 1 (CDR1) having the amino acid sequence of SEQ ID NO: 123, a heavy chain CDR2 having the amino acid sequence of SEQ ID NO: 124, and a heavy chain CDR3 having the amino acid sequence of SEQ ID NO: 122, wherein the extracellular antigen-binding domain binds the hK2 antigen.

In one embodiment the extracellular antigen-binding domain comprises a heavy chain complementarity determining region 1 (CDR1) having the amino acid sequence of SEQ ID NO: 63, a heavy chain CDR2 having the amino acid sequence of SEQ ID NO: 64, and a heavy chain CDR3 having the amino acid sequence of SEQ ID NO: 66.

In one embodiment the extracellular antigen-binding domain comprises a heavy chain complementarity determining region 1 (CDR1) having the amino acid sequence of SEQ ID NO: 314, a heavy chain CDR2 having the amino acid sequence of SEQ ID NO: 315, and a heavy chain CDR3 having the amino acid sequence of SEQ ID NO: 311.

In one embodiment the extracellular antigen-binding domain comprises a heavy chain complementarity determining region 1 (CDR1) having the amino acid sequence of SEQ ID NO: 309, a heavy chain CDR2 having the amino acid sequence of SEQ ID NO: 310, and a heavy chain CDR3 having the amino acid sequence of SEQ ID NO: 311.

In one embodiment the extracellular antigen-binding domain comprises a heavy chain complementarity determining region 1 (CDR1) having the amino acid sequence of SEQ ID NO: 63, a heavy chain CDR2 having the amino acid sequence of SEQ ID NO: 65, and a heavy chain CDR3 having the amino acid sequence of SEQ ID NO: 66.

In one embodiment the extracellular antigen-binding domain comprises a heavy chain complementarity determining region 1 (CDR1) having the amino acid sequence of SEQ ID NO: 72, a heavy chain CDR2 having the amino acid sequence of SEQ ID NO: 73, and a heavy chain CDR3 having the amino acid sequence of SEQ ID NO: 66;

In one embodiment the extracellular antigen-binding domain comprises a heavy chain complementarity determining region 1 (CDR1) having the amino acid sequence of SEQ ID NO: 86, a heavy chain CDR2 having the amino acid sequence of SEQ ID NO: 87, and a heavy chain CDR3 having the amino acid sequence of SEQ ID NO: 88.

In one embodiment the extracellular antigen-binding domain comprises a heavy chain complementarity determining region 1 (CDR1) having the amino acid sequence of SEQ ID NO: 92, a heavy chain CDR2 having the amino acid sequence of SEQ ID NO: 93, and a heavy chain CDR3 having the amino acid sequence of SEQ ID NO: 94.

In one embodiment the extracellular antigen-binding domain comprises a heavy chain complementarity determining region 1 (CDR1) having the amino acid sequence of SEQ ID NO: 102, a heavy chain CDR2 having the amino acid sequence of SEQ ID NO: 103, and a heavy chain CDR3 having the amino acid sequence of SEQ ID NO: 104.

In one embodiment the extracellular antigen-binding domain comprises a heavy chain complementarity determining region 1 (CDR1) having the amino acid sequence of SEQ ID NO: 105, a heavy chain CDR2 having the amino acid sequence of SEQ ID NO: 106, and a heavy chain CDR3 having the amino acid sequence of SEQ ID NO: 104.

In one embodiment the extracellular antigen-binding domain comprises a heavy chain complementarity determining region 1 (CDR1) having the amino acid sequence of SEQ ID NO: 107, a heavy chain CDR2 having the amino acid sequence of SEQ ID NO: 108, and a heavy chain CDR3 having the amino acid sequence of SEQ ID NO: 109.

In one embodiment the extracellular antigen-binding domain comprises a heavy chain complementarity determining region 1 (CDR1) having the amino acid sequence of SEQ ID NO: 110, a heavy chain CDR2 having the amino acid sequence of SEQ ID NO: 111, and a heavy chain CDR3 having the amino acid sequence of SEQ ID NO: 109.

In one embodiment the extracellular antigen-binding domain comprises a heavy chain complementarity determining region 1 (CDR1) having the amino acid sequence of SEQ ID NO: 102, a heavy chain CDR2 having the amino acid sequence of SEQ ID NO: 112, and a heavy chain CDR3 having the amino acid sequence of SEQ ID NO: 113.

In one embodiment the extracellular antigen-binding domain comprises a heavy chain complementarity determining region 1 (CDR1) having the amino acid sequence of SEQ ID NO: 105, a heavy chain CDR2 having the amino acid sequence of SEQ ID NO: 114, and a heavy chain CDR3 having the amino acid sequence of SEQ ID NO: 113.

In one embodiment the extracellular antigen-binding domain comprises a heavy chain complementarity determining region 1 (CDR1) having the amino acid sequence of SEQ ID NO: 115, a heavy chain CDR2 having the amino acid sequence of SEQ ID NO: 116, and a heavy chain CDR3 having the amino acid sequence of SEQ ID NO: 117.

In one embodiment the extracellular antigen-binding domain comprises a heavy chain complementarity determining region 1 (CDR1) having the amino acid sequence of SEQ ID NO: 118, a heavy chain CDR2 having the amino acid sequence of SEQ ID NO: 119, and a heavy chain CDR3 having the amino acid sequence of SEQ ID NO: 117.

In one embodiment the extracellular antigen-binding domain comprises a heavy chain complementarity determining region 1 (CDR1) having the amino acid sequence of SEQ ID NO: 120, a heavy chain CDR2 having the amino acid sequence of SEQ ID NO: 121, and a heavy chain CDR3 having the amino acid sequence of SEQ ID NO: 122.

In one embodiment the extracellular antigen-binding domain comprises a heavy chain complementarity determining region 1 (CDR1) having the amino acid sequence of SEQ ID NO: 123, a heavy chain CDR2 having the amino acid sequence of SEQ ID NO: 124, and a heavy chain CDR3 having the amino acid sequence of SEQ ID NO: 122.

In one aspect, the disclosure provides a CAR, comprising an extracellular antigen-binding domain, a transmembrane domain and an intracellular signaling domain, wherein the extracellular antigen-binding domain comprises:
  a light chain CDR1 having an amino acid sequence selected from the group consisting of SEQ ID NO: 67, SEQ ID NO: 68, SEQ ID NO: 89, SEQ ID NO: 95, SEQ ID NO: 97, SEQ ID NO: 125, SEQ ID NO: 128, SEQ ID NO: 133, SEQ ID NO: 136, and SEQ ID NO: 312, and conservative modifications thereof, wherein the extracellular antigen-binding domain binds the hK2 antigen.

In one aspect, the disclosure provides a CAR, comprising an extracellular antigen-binding domain, a transmembrane domain and an intracellular signaling domain, wherein the extracellular antigen-binding domain comprises:
  a light chain CDR2 having an amino acid sequence selected from the group consisting of SEQ ID NO: 69, SEQ ID NO: 70, SEQ ID NO: 90, SEQ ID NO: 96, SEQ ID NO: 126, SEQ ID NO: 137, SEQ ID NO: 129, SEQ ID NO: 131, SEQ ID NO: 134, SEQ ID NO: 137, and SEQ ID NO: 313, and conservative modifications thereof, wherein the extracellular antigen-binding domain binds the hK2 antigen.

In one aspect, the disclosure provides a CAR, comprising an extracellular antigen-binding domain, a transmembrane domain and an intracellular signaling domain, wherein the extracellular antigen-binding domain comprises:

a light chain CDR3 having an amino acid sequence selected from the group consisting of SEQ ID NO: 71, SEQ ID NO: 91, SEQ ID NO: 130, SEQ ID NO: 132, SEQ ID NO: 135, SEQ ID NO: 138, and SEQ ID NO: 139, and conservative modifications thereof, wherein the extracellular antigen-binding domain binds the hK2 antigen.

In one aspect, the disclosure provides a CAR, comprising an extracellular antigen-binding domain, a transmembrane domain and an intracellular signaling domain, wherein the extracellular antigen-binding domain comprises:

a light chain complementarity determining region 1 (CDR1) having the amino acid sequence of SEQ ID NO: 67, a light chain CDR2 having the amino acid sequence of SEQ ID NO: 69, and a light chain CDR3 having the amino acid sequence of SEQ ID NO: 71;

a light chain complementarity determining region 1 (CDR1) having the amino acid sequence of SEQ ID NO: 68, a light chain CDR2 having the amino acid sequence of SEQ ID NO: 70, and a light chain CDR3 having the amino acid sequence of SEQ ID NO: 71;

a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91;

a light chain complementarity determining region 1 (CDR1) having the amino acid sequence of SEQ ID NO: 95, a light chain CDR2 having the amino acid sequence of SEQ ID NO: 96, and a light chain CDR3 having the amino acid sequence of SEQ ID NO: 71;

a light chain complementarity determining region 1 (CDR1) having the amino acid sequence of SEQ ID NO: 312, a light chain CDR2 having the amino acid sequence of SEQ ID NO: 313, and a light chain CDR3 having the amino acid sequence of SEQ ID NO: 91;

a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91;

a light chain complementarity determining region 1 (CDR1) having the amino acid sequence of SEQ ID NO: 67, a light chain CDR2 having the amino acid sequence of SEQ ID NO: 126, and a light chain CDR3 having the amino acid sequence of SEQ ID NO: 71;

a light chain complementarity determining region 1 (CDR1) having the amino acid sequence of SEQ ID NO: 128, a light chain CDR2 having the amino acid sequence of SEQ ID NO: 129, and a light chain CDR3 having the amino acid sequence of SEQ ID NO: 130;

a light chain complementarity determining region 1 (CDR1) having the amino acid sequence of SEQ ID NO: 125, a light chain CDR2 having the amino acid sequence of SEQ ID NO: 131, and a light chain CDR3 having the amino acid sequence of SEQ ID NO: 132;

a light chain complementarity determining region 1 (CDR1) having the amino acid sequence of SEQ ID NO: 133, a light chain CDR2 having the amino acid sequence of SEQ ID NO: 134, and a light chain CDR3 having the amino acid sequence of SEQ ID NO: 135;

a light chain complementarity determining region 1 (CDR1) having the amino acid sequence of SEQ ID NO: 136, a light chain CDR2 having the amino acid sequence of SEQ ID NO: 137, and a light chain CDR3 having the amino acid sequence of SEQ ID NO: 138; or a light chain complementarity determining region 1 (CDR1) having the amino acid sequence of SEQ ID NO: 97, a light chain CDR2 having the amino acid sequence of SEQ ID NO: 127, and a light chain CDR3 having the amino acid sequence of SEQ ID NO: 139, wherein the extracellular antigen-binding domain binds the hK2 antigen.

In one embodiment the extracellular antigen-binding domain comprises a light chain complementarity determining region 1 (CDR1) having the amino acid sequence of SEQ ID NO: 67, a light chain CDR2 having the amino acid sequence of SEQ ID NO: 69, and a light chain CDR3 having the amino acid sequence of SEQ ID NO: 71.

In one embodiment the extracellular antigen-binding domain comprises a light chain complementarity determining region 1 (CDR1) having the amino acid sequence of SEQ ID NO: 68, a light chain CDR2 having the amino acid sequence of SEQ ID NO: 70, and a light chain CDR3 having the amino acid sequence of SEQ ID NO: 71

In one embodiment the extracellular antigen-binding domain comprises a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91.

In one embodiment the extracellular antigen-binding domain comprises a light chain complementarity determining region 1 (CDR1) having the amino acid sequence of SEQ ID NO: 95, a light chain CDR2 having the amino acid sequence of SEQ ID NO: 96, and a light chain CDR3 having the amino acid sequence of SEQ ID NO: 71.

In one embodiment the extracellular antigen-binding domain comprises a light chain complementarity determining region 1 (CDR1) having the amino acid sequence of SEQ ID NO: 312, a light chain CDR2 having the amino acid sequence of SEQ ID NO: 313, and a light chain CDR3 having the amino acid sequence of SEQ ID NO: 91.

In one embodiment the extracellular antigen-binding domain comprises a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91.

In one embodiment the extracellular antigen-binding domain comprises a light chain complementarity determining region 1 (CDR1) having the amino acid sequence of SEQ ID NO: 67, a light chain CDR2 having the amino acid sequence of SEQ ID NO: 126, and a light chain CDR3 having the amino acid sequence of SEQ ID NO: 71.

In one embodiment the extracellular antigen-binding domain comprises a light chain complementarity determining region 1 (CDR1) having the amino acid sequence of SEQ ID NO: 128, a light chain CDR2 having the amino acid sequence of SEQ ID NO: 129, and a light chain CDR3 having the amino acid sequence of SEQ ID NO: 130.

In one embodiment the extracellular antigen-binding domain comprises a light chain complementarity determining region 1 (CDR1) having the amino acid sequence of SEQ ID NO: 125, a light chain CDR2 having the amino acid sequence of SEQ ID NO: 131, and a light chain CDR3 having the amino acid sequence of SEQ ID NO: 132.

In one embodiment the extracellular antigen-binding domain comprises a light chain complementarity determining region 1 (CDR1) having the amino acid sequence of SEQ ID NO: 133, a light chain CDR2 having the amino acid sequence of SEQ ID NO: 134, and a light chain CDR3 having the amino acid sequence of SEQ ID NO: 135.

In one embodiment the extracellular antigen-binding domain comprises a light chain complementarity determining region 1 (CDR1) having the amino acid sequence of SEQ ID NO: 136, a light chain CDR2 having the amino acid sequence of SEQ ID NO: 137, and a light chain CDR3 having the amino acid sequence of SEQ ID NO: 138.

In one embodiment the extracellular antigen-binding domain comprises a light chain complementarity determining region 1 (CDR1) having the amino acid sequence of SEQ ID NO: 97, a light chain CDR2 having the amino acid sequence of SEQ ID NO: 127, and a light chain CDR3 having the amino acid sequence of SEQ ID NO: 139.

In one aspect, the disclosure provides a CAR, comprising an extracellular antigen-binding domain, a transmembrane domain and an intracellular signaling domain, wherein the extracellular antigen-binding domain comprises:
a heavy chain complementarity determining region 1 (CDR1) having the amino acid sequence of SEQ ID NO: 63, a heavy chain CDR2 having the amino acid sequence of SEQ ID NO: 64, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71;
a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 68, a light chain CDR2 having the amino acid sequence of SEQ ID NO: 70, a light chain CDR3 having the amino acid sequence of SEQ ID NO: 71;
a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71;
a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71;
a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71;
a heavy chain complementarity determining region 1 (CDR1) having the amino acid sequence of SEQ ID NO: 314, a heavy chain CDR2 having the amino acid sequence of SEQ ID NO: 315, a heavy chain CDR3 having the amino acid sequence of SEQ ID NO: 311, and a light chain complementarity determining region 1 (CDR1) having the amino acid sequence of SEQ ID NO: 312, a light chain CDR2 having the amino acid sequence of SEQ ID NO: 313, a light chain CDR3 having the amino acid sequence of SEQ ID NO: 91;
a heavy chain complementarity determining region 1 (CDR1) having the amino acid sequence of SEQ ID NO: 102, a heavy chain CDR2 having the amino acid sequence of SEQ ID NO: 103, a heavy chain CDR3 having the amino acid sequence of SEQ ID NO: 104, and a light chain complementarity determining region 1 (CDR1) having the amino acid sequence of SEQ ID NO: 128, a light chain CDR2 having the amino acid sequence of SEQ ID NO: 129, a light chain CDR3 having the amino acid sequence of SEQ ID NO: 130;
a heavy chain complementarity determining region 1 (CDR1) having the amino acid sequence of SEQ ID NO: 107, a heavy chain CDR2 having the amino acid sequence of SEQ ID NO: 108, a heavy chain CDR3 having the amino acid sequence of SEQ ID NO: 109, and a light chain complementarity determining region 1 (CDR1) having the amino acid sequence of SEQ ID NO: 125, a light chain CDR2 having the amino acid sequence of SEQ ID NO: 131, a light chain CDR3 having the amino acid sequence of SEQ ID NO: 132;
a heavy chain complementarity determining region 1 (CDR1) having the amino acid sequence of SEQ ID NO: 102, a heavy chain CDR2 having the amino acid sequence of SEQ ID NO: 112, a heavy chain CDR3 having the amino acid sequence of SEQ ID NO: 113, and a light chain complementarity determining region 1 (CDR1) having the amino acid sequence of SEQ ID NO: 133, a light chain CDR2 having the amino acid sequence of SEQ ID NO: 134, a light chain CDR3 having the amino acid sequence of SEQ ID NO: 135;
a heavy chain complementarity determining region 1 (CDR1) having the amino acid sequence of SEQ ID NO: 115, a heavy chain CDR2 having the amino acid sequence of SEQ ID NO: 116, a heavy chain CDR3 having the amino acid sequence of SEQ ID NO: 117, and a light chain complementarity determining region 1 (CDR1) having the amino acid sequence of SEQ ID NO: 136, a light chain CDR2 having the amino acid sequence of SEQ ID NO: 137, a light chain CDR3 having the amino acid sequence of SEQ ID NO: 138; or
a heavy chain complementarity determining region 1 (CDR1) having the amino acid sequence of SEQ ID NO: 120, a heavy chain CDR2 having the amino acid sequence of SEQ ID NO: 121, a heavy chain CDR3 having the amino acid sequence of SEQ ID NO: 122, and a light chain complementarity determining region 1 (CDR1) having the amino acid sequence of SEQ ID NO: 97, a light chain CDR2 having the amino acid sequence of SEQ ID NO: 127, a light chain CDR3 having the amino acid sequence of SEQ ID NO: 138;
wherein the extracellular antigen-binding domain binds the hK2 antigen.

In one aspect, the disclosure provides a CAR, comprising an extracellular antigen-binding domain, a transmembrane domain and an intracellular signaling domain, wherein the extracellular antigen-binding domain comprises:
a heavy chain complementarity determining region 1 (CDR1) having the amino acid sequence of SEQ ID NO: 63, a heavy chain CDR2 having the amino acid sequence of SEQ ID NO: 64, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 68, a light chain CDR2 having the amino acid sequence of SEQ ID NO: 70, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71;

a heavy chain complementarity determining region 1 (CDR1) having the amino acid sequence of SEQ ID NO: 314, a heavy chain CDR2 having the amino acid sequence of SEQ ID NO: 315, a heavy chain CDR3 having the amino acid sequence of SEQ ID NO: 311, and a light chain complementarity determining region 1 (CDR1) having the amino acid sequence of SEQ ID NO: 312, a light chain CDR2 having the amino acid sequence of SEQ ID NO: 313, a light chain CDR3 having the amino acid sequence of SEQ ID NO: 91;

a heavy chain complementarity determining region 1 (CDR1) having the amino acid sequence of SEQ ID NO: 102, a heavy chain CDR2 having the amino acid sequence of SEQ ID NO: 103, a heavy chain CDR3 having the amino acid sequence of SEQ ID NO: 104, and a light chain complementarity determining region 1 (CDR1) having the amino acid sequence of SEQ ID NO: 128, a light chain CDR2 having the amino acid sequence of SEQ ID NO: 129, a light chain CDR3 having the amino acid sequence of SEQ ID NO: 130;

a heavy chain complementarity determining region 1 (CDR1) having the amino acid sequence of SEQ ID NO: 107, a heavy chain CDR2 having the amino acid sequence of SEQ ID NO: 108, a heavy chain CDR3 having the amino acid sequence of SEQ ID NO: 109, and a light chain complementarity determining region 1 (CDR1) having the amino acid sequence of SEQ ID NO: 125, a light chain CDR2 having the amino acid sequence of SEQ ID NO: 131, a light chain CDR3 having the amino acid sequence of SEQ ID NO: 132;

a heavy chain complementarity determining region 1 (CDR1) having the amino acid sequence of SEQ ID NO: 102, a heavy chain CDR2 having the amino acid sequence of SEQ ID NO: 112, a heavy chain CDR3 having the amino acid sequence of SEQ ID NO: 113, and a light chain complementarity determining region 1 (CDR1) having the amino acid sequence of SEQ ID NO: 133, a light chain CDR2 having the amino acid sequence of SEQ ID NO: 134, a light chain CDR3 having the amino acid sequence of SEQ ID NO: 135;

a heavy chain complementarity determining region 1 (CDR1) having the amino acid sequence of SEQ ID NO: 115, a heavy chain CDR2 having the amino acid sequence of SEQ ID NO: 116, a heavy chain CDR3 having the amino acid sequence of SEQ ID NO: 117, and a light chain complementarity determining region 1 (CDR1) having the amino acid sequence of SEQ ID NO: 136, a light chain CDR2 having the amino acid sequence of SEQ ID NO: 137, a light chain CDR3 having the amino acid sequence of SEQ ID NO: 138;

a heavy chain complementarity determining region 1 (CDR1) having the amino acid sequence of SEQ ID NO: 120, a heavy chain CDR2 having the amino acid sequence of SEQ ID NO: 121, a heavy chain CDR3 having the amino acid sequence of SEQ ID NO: 122, and a light chain complementarity determining region 1 (CDR1) having the amino acid sequence of SEQ ID NO: 97, a light chain CDR2 having the amino acid sequence of SEQ ID NO: 127, a light chain CDR3 having the amino acid sequence of SEQ ID NO: 138;

a heavy chain complementarity determining region 1 (CDR1) having the amino acid sequence of SEQ ID NO: 72, a heavy chain CDR2 having the amino acid sequence of SEQ ID NO: 73, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71;

a heavy chain complementarity determining region 1 (CDR1) having the amino acid sequence of SEQ ID NO: 72, a heavy chain CDR2 having the amino acid sequence of SEQ ID NO: 73, a heavy chain CDR3 having the amino acid sequence of SEQ ID NO: 66, and a light chain complementarity determining region 1 (CDR1) having the amino acid sequence of SEQ ID NO: 68, a light chain CDR2 having the amino acid sequence of SEQ ID NO: 70, a light chain CDR3 having the amino acid sequence of SEQ ID NO: 71;

a heavy chain complementarity determining region 1 (CDR1) having the amino acid sequence of SEQ ID NO: 72, a heavy chain CDR2 having the amino acid sequence of SEQ ID NO: 73, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71;

a heavy chain complementarity determining region 1 (CDR1) having the amino acid sequence of SEQ ID NO: 72, a heavy chain CDR2 having the amino acid sequence of SEQ ID NO: 73, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71;

a heavy chain complementarity determining region 1 (CDR1) having the amino acid sequence of SEQ ID NO: 72, a heavy chain CDR2 having the amino acid sequence of SEQ ID NO: 73, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71;

a heavy chain complementarity determining region 1 (CDR1) having the amino acid sequence of SEQ ID NO: 309, a heavy chain CDR2 having the amino acid sequence of SEQ ID NO: 310, a heavy chain CDR3 having the amino acid sequence of SEQ ID NO: 311, and a light chain complementarity determining region 1 (CDR1) having the amino acid sequence of SEQ ID NO: 312, a light chain CDR2 having the amino acid sequence of SEQ ID NO: 313, a light chain CDR3 having the amino acid sequence of SEQ ID NO: 91;

a heavy chain complementarity determining region 1 (CDR1) having the amino acid sequence of SEQ ID NO: 105, a heavy chain CDR2 having the amino acid sequence of SEQ ID NO: 106, a heavy chain CDR3 having the amino acid sequence of SEQ ID NO: 104, and a light chain complementarity determining region 1 (CDR1) having the amino acid sequence of SEQ ID NO: 128, a light chain CDR2 having the amino acid sequence of SEQ ID NO: 129, a light chain CDR3 having the amino acid sequence of SEQ ID NO: 130;

a heavy chain complementarity determining region 1 (CDR1) having the amino acid sequence of SEQ ID NO: 110, a heavy chain CDR2 having the amino acid sequence of SEQ ID NO: 111, a heavy chain CDR3 having the amino acid sequence of SEQ ID NO: 109, and a light chain complementarity determining region 1 (CDR1) having the amino acid sequence of SEQ ID NO: 125, a light chain CDR2 having the amino acid sequence of SEQ ID NO: 131, a light chain CDR3 having the amino acid sequence of SEQ ID NO: 132;

a heavy chain complementarity determining region 1 (CDR1) having the amino acid sequence of SEQ ID NO: 105, a heavy chain CDR2 having the amino acid sequence of SEQ ID NO: 114, a heavy chain CDR3 having the amino acid sequence of SEQ ID NO: 113, and a light chain complementarity determining region 1 (CDR1) having the amino acid sequence of SEQ ID NO: 133, a light chain CDR2 having the amino acid sequence of SEQ ID NO: 134, a light chain CDR3 having the amino acid sequence of SEQ ID NO: 135;

a heavy chain complementarity determining region 1 (CDR1) having the amino acid sequence of SEQ ID NO: 118, a heavy chain CDR2 having the amino acid sequence of SEQ ID NO: 119, a heavy chain CDR3 having the amino acid sequence of SEQ ID NO: 117, and a light chain complementarity determining region 1 (CDR1) having the amino acid sequence of SEQ ID NO: 136, a light chain CDR2 having the amino acid sequence of SEQ ID NO: 137, a light chain CDR3 having the amino acid sequence of SEQ ID NO: 138;

a heavy chain complementarity determining region 1 (CDR1) having the amino acid sequence of SEQ ID NO: 123, a heavy chain CDR2 having the amino acid sequence of SEQ ID NO: 124, a heavy chain CDR3 having the amino acid sequence of SEQ ID NO: 122, and a light chain complementarity determining region 1 (CDR1) having the amino acid sequence of SEQ ID NO: 97, a light chain CDR2 having the amino acid sequence of SEQ ID NO: 127, a light chain CDR3 having the amino acid sequence of SEQ ID NO: 139;

a heavy chain complementarity determining region 1 (CDR1) having the amino acid sequence of SEQ ID NO: 120, a heavy chain CDR2 having the amino acid sequence of SEQ ID NO: 121, a heavy chain CDR3 having the amino acid sequence of SEQ ID NO: 122, and a light chain complementarity determining region 1 (CDR1) having the amino acid sequence of SEQ ID NO: 97, a light chain CDR2 having the amino acid sequence of SEQ ID NO: 127, a light chain CDR3 having the amino acid sequence of SEQ ID NO: 139; or a heavy chain complementarity determining region 1 (CDR1) having the amino acid sequence of SEQ ID NO: 86, a heavy chain CDR2 having the amino acid sequence of SEQ ID NO: 87, a heavy chain CDR3 having the amino acid sequence of SEQ ID NO: 88, and a light chain complementarity determining region 1 (CDR1) having the amino acid sequence of SEQ ID NO: 89, a light chain CDR2 having the amino acid sequence of SEQ ID NO: 90, a light chain CDR3 having the amino acid sequence of SEQ ID NO: 91;

wherein the extracellular antigen-binding domain binds the hK2 antigen.

In one embodiment, the extracellular antigen-binding domain comprises:

a heavy chain complementarity determining region 1 (CDR1) having the amino acid sequence of SEQ ID NO: 63, a heavy chain CDR2 having the amino acid sequence of SEQ ID NO: 64, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71.

In one embodiment, the extracellular antigen-binding domain comprises:

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 68, a light chain CDR2 having the amino acid sequence of SEQ ID NO: 70, a light chain CDR3 having the amino acid sequence of SEQ ID NO: 71.

In one embodiment, the extracellular antigen-binding domain comprises:

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71.

In one embodiment, the extracellular antigen-binding domain comprises:

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71.

In one embodiment, the extracellular antigen-binding domain comprises:
a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71.

In one embodiment, the extracellular antigen-binding domain comprises:
a heavy chain complementarity determining region 1 (CDR1) having the amino acid sequence of SEQ ID NO: 314, a heavy chain CDR2 having the amino acid sequence of SEQ ID NO: 315, a heavy chain CDR3 having the amino acid sequence of SEQ ID NO: 311, and a light chain complementarity determining region 1 (CDR1) having the amino acid sequence of SEQ ID NO: 312, a light chain CDR2 having the amino acid sequence of SEQ ID NO: 313, a light chain CDR3 having the amino acid sequence of SEQ ID NO: 91.

In one embodiment, the extracellular antigen-binding domain comprises:
a heavy chain complementarity determining region 1 (CDR1) having the amino acid sequence of SEQ ID NO: 102, a heavy chain CDR2 having the amino acid sequence of SEQ ID NO: 103, a heavy chain CDR3 having the amino acid sequence of SEQ ID NO: 104, and a light chain complementarity determining region 1 (CDR1) having the amino acid sequence of SEQ ID NO: 128, a light chain CDR2 having the amino acid sequence of SEQ ID NO: 129, a light chain CDR3 having the amino acid sequence of SEQ ID NO: 130.

In one embodiment, the extracellular antigen-binding domain comprises:
a heavy chain complementarity determining region 1 (CDR1) having the amino acid sequence of SEQ ID NO: 107, a heavy chain CDR2 having the amino acid sequence of SEQ ID NO: 108, a heavy chain CDR3 having the amino acid sequence of SEQ ID NO: 109, and a light chain complementarity determining region 1 (CDR1) having the amino acid sequence of SEQ ID NO: 125, a light chain CDR2 having the amino acid sequence of SEQ ID NO: 131, a light chain CDR3 having the amino acid sequence of SEQ ID NO: 132.

In one embodiment, the extracellular antigen-binding domain comprises:
a heavy chain complementarity determining region 1 (CDR1) having the amino acid sequence of SEQ ID NO: 102, a heavy chain CDR2 having the amino acid sequence of SEQ ID NO: 112, a heavy chain CDR3 having the amino acid sequence of SEQ ID NO: 113, and a light chain complementarity determining region 1 (CDR1) having the amino acid sequence of SEQ ID NO: 133, a light chain CDR2 having the amino acid sequence of SEQ ID NO: 134, a light chain CDR3 having the amino acid sequence of SEQ ID NO: 135.

In one embodiment, the extracellular antigen-binding domain comprises:
a heavy chain complementarity determining region 1 (CDR1) having the amino acid sequence of SEQ ID NO: 115, a heavy chain CDR2 having the amino acid sequence of SEQ ID NO: 116, a heavy chain CDR3 having the amino acid sequence of SEQ ID NO: 117, and a light chain complementarity determining region 1 (CDR1) having the amino acid sequence of SEQ ID NO: 136, a light chain CDR2 having the amino acid sequence of SEQ ID NO: 137, a light chain CDR3 having the amino acid sequence of SEQ ID NO: 138.

In one embodiment, the extracellular antigen-binding domain comprises:
a heavy chain complementarity determining region 1 (CDR1) having the amino acid sequence of SEQ ID NO: 120, a heavy chain CDR2 having the amino acid sequence of SEQ ID NO: 121, a heavy chain CDR3 having the amino acid sequence of SEQ ID NO: 122, and a light chain complementarity determining region 1 (CDR1) having the amino acid sequence of SEQ ID NO: 97, a light chain CDR2 having the amino acid sequence of SEQ ID NO: 127, a light chain CDR3 having the amino acid sequence of SEQ ID NO: 138.

In one embodiment, the extracellular antigen-binding domain comprises:
a heavy chain complementarity determining region 1 (CDR1) having the amino acid sequence of SEQ ID NO: 72, a heavy chain CDR2 having the amino acid sequence of SEQ ID NO: 73, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71.

In one embodiment, the extracellular antigen-binding domain comprises:
a heavy chain complementarity determining region 1 (CDR1) having the amino acid sequence of SEQ ID NO: 72, a heavy chain CDR2 having the amino acid sequence of SEQ ID NO: 73, a heavy chain CDR3 having the amino acid sequence of SEQ ID NO: 66, and a light chain complementarity determining region 1 (CDR1) having the amino acid sequence of SEQ ID NO: 68, a light chain CDR2 having the amino acid sequence of SEQ ID NO: 70, a light chain CDR3 having the amino acid sequence of SEQ ID NO: 71.

In one embodiment, the extracellular antigen-binding domain comprises:
a heavy chain complementarity determining region 1 (CDR1) having the amino acid sequence of SEQ ID NO: 72, a heavy chain CDR2 having the amino acid sequence of SEQ ID NO: 73, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71.

In one embodiment, the extracellular antigen-binding domain comprises:
a heavy chain complementarity determining region 1 (CDR1) having the amino acid sequence of SEQ ID NO: 72, a heavy chain CDR2 having the amino acid sequence of SEQ ID NO: 73, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71.

In one embodiment, the extracellular antigen-binding domain comprises:

a heavy chain complementarity determining region 1 (CDR1) having the amino acid sequence of SEQ ID NO: 72, a heavy chain CDR2 having the amino acid sequence of SEQ ID NO: 73, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71.

In one embodiment, the extracellular antigen-binding domain comprises:
a heavy chain complementarity determining region 1 (CDR1) having the amino acid sequence of SEQ ID NO: 309, a heavy chain CDR2 having the amino acid sequence of SEQ ID NO: 310, a heavy chain CDR3 having the amino acid sequence of SEQ ID NO: 311, and a light chain complementarity determining region 1 (CDR1) having the amino acid sequence of SEQ ID NO: 312, a light chain CDR2 having the amino acid sequence of SEQ ID NO: 313, a light chain CDR3 having the amino acid sequence of SEQ ID NO: 91.

In one embodiment, the extracellular antigen-binding domain comprises:
a heavy chain complementarity determining region 1 (CDR1) having the amino acid sequence of SEQ ID NO: 105, a heavy chain CDR2 having the amino acid sequence of SEQ ID NO: 106, a heavy chain CDR3 having the amino acid sequence of SEQ ID NO: 104, and a light chain complementarity determining region 1 (CDR1) having the amino acid sequence of SEQ ID NO: 128, a light chain CDR2 having the amino acid sequence of SEQ ID NO: 129, a light chain CDR3 having the amino acid sequence of SEQ ID NO: 130.

In one embodiment, the extracellular antigen-binding domain comprises:
a heavy chain complementarity determining region 1 (CDR1) having the amino acid sequence of SEQ ID NO: 110, a heavy chain CDR2 having the amino acid sequence of SEQ ID NO: 111, a heavy chain CDR3 having the amino acid sequence of SEQ ID NO: 109, and a light chain complementarity determining region 1 (CDR1) having the amino acid sequence of SEQ ID NO: 125, a light chain CDR2 having the amino acid sequence of SEQ ID NO: 131, a light chain CDR3 having the amino acid sequence of SEQ ID NO: 132.

In one embodiment, the extracellular antigen-binding domain comprises:
a heavy chain complementarity determining region 1 (CDR1) having the amino acid sequence of SEQ ID NO: 105, a heavy chain CDR2 having the amino acid sequence of SEQ ID NO: 114, a heavy chain CDR3 having the amino acid sequence of SEQ ID NO: 113, and a light chain complementarity determining region 1 (CDR1) having the amino acid sequence of SEQ ID NO: 133, a light chain CDR2 having the amino acid sequence of SEQ ID NO: 134, a light chain CDR3 having the amino acid sequence of SEQ ID NO: 135.

In one embodiment, the extracellular antigen-binding domain comprises:
a heavy chain complementarity determining region 1 (CDR1) having the amino acid sequence of SEQ ID NO: 118, a heavy chain CDR2 having the amino acid sequence of SEQ ID NO: 119, a heavy chain CDR3 having the amino acid sequence of SEQ ID NO: 117, and a light chain complementarity determining region 1 (CDR1) having the amino acid sequence of SEQ ID NO: 136, a light chain CDR2 having the amino acid sequence of SEQ ID NO: 137, a light chain CDR3 having the amino acid sequence of SEQ ID NO: 138.

In one embodiment, the extracellular antigen-binding domain comprises:
a heavy chain complementarity determining region 1 (CDR1) having the amino acid sequence of SEQ ID NO: 123, a heavy chain CDR2 having the amino acid sequence of SEQ ID NO: 124, a heavy chain CDR3 having the amino acid sequence of SEQ ID NO: 122, and a light chain complementarity determining region 1 (CDR1) having the amino acid sequence of SEQ ID NO: 97, a light chain CDR2 having the amino acid sequence of SEQ ID NO: 127, a light chain CDR3 having the amino acid sequence of SEQ ID NO: 139.

In one embodiment, the extracellular antigen-binding domain comprises:
a heavy chain complementarity determining region 1 (CDR1) having the amino acid sequence of SEQ ID NO: 120, a heavy chain CDR2 having the amino acid sequence of SEQ ID NO: 121, a heavy chain CDR3 having the amino acid sequence of SEQ ID NO: 122, and a light chain complementarity determining region 1 (CDR1) having the amino acid sequence of SEQ ID NO: 97, a light chain CDR2 having the amino acid sequence of SEQ ID NO: 127, a light chain CDR3 having the amino acid sequence of SEQ ID NO: 139.

In one embodiment, the extracellular antigen-binding domain comprises:
a heavy chain complementarity determining region 1 (CDR1) having the amino acid sequence of SEQ ID NO: 86, a heavy chain CDR2 having the amino acid sequence of SEQ ID NO: 87, a heavy chain CDR3 having the amino acid sequence of SEQ ID NO: 88, and a light chain complementarity determining region 1 (CDR1) having the amino acid sequence of SEQ ID NO: 89, a light chain CDR2 having the amino acid sequence of SEQ ID NO: 90, a light chain CDR3 having the amino acid sequence of SEQ ID NO: 91.

In one aspect, the disclosure provides a CAR, comprising an extracellular antigen-binding domain, a transmembrane domain and an intracellular signaling domain, wherein the extracellular antigen-binding domain comprises:
a light chain variable region (LCVR) comprising an amino acid sequence selected from the group consisting of SEQ ID NOS: 1-3, or a heavy chain variable region (HCVR) comprising an amino acid sequence selected from the group consisting of SEQ ID NOS: 4-6, or a combination of a LCVR comprising an amino acid sequence selected from the group consisting of SEQ ID NOS: 1-3, and a HCVR comprising an amino acid sequence selected from the group consisting of SEQ ID NOS: 4-6, wherein the extracellular antigen-binding domain binds the hK2 antigen.

In one embodiment, the extracellular antigen-binding domain comprises:
- a light chain variable region comprising an amino acid sequence of SEQ ID NO: 1 and a heavy chain variable region comprising an amino acid sequence of SEQ ID NO: 4;
- a light chain variable region comprising an amino acid sequence of SEQ ID NO: 2 and a heavy chain variable region comprising an amino acid sequence of SEQ ID NO: 4;
- a light chain variable region comprising an amino acid sequence of SEQ ID NO: 3 and a heavy chain variable region comprising an amino acid sequence of SEQ ID NO: 6;

a light chain variable region comprising an amino acid sequence of SEQ ID NO: 3 and a heavy chain variable region comprising an amino acid sequence of SEQ ID NO: 4;
a light chain variable region comprising an amino acid sequence of SEQ ID NO: 2 and a heavy chain variable region comprising an amino acid sequence of SEQ ID NO: 6;
a light chain variable region comprising an amino acid sequence of SEQ ID NO: 1 and a heavy chain variable region comprising an amino acid sequence of SEQ ID NO: 6;
a light chain variable region comprising an amino acid sequence of SEQ ID NO: 1 and a heavy chain variable region comprising an amino acid sequence of SEQ ID NO: 5;
a light chain variable region comprising an amino acid sequence of SEQ ID NO: 2 and a heavy chain variable region comprising an amino acid sequence of SEQ ID NO: 5;
a light chain variable region comprising an amino acid sequence of SEQ ID NO: 3 and a heavy chain variable region comprising an amino acid sequence of SEQ ID NO: 5;
a light chain variable region comprising an amino acid sequence of SEQ ID NO: 74 and a heavy chain variable region comprising an amino acid sequence of SEQ ID NO: 76; a light chain variable region comprising an amino acid sequence of SEQ ID NO: 75 and a heavy chain variable region comprising an amino acid sequence of SEQ ID NO: 77;
a light chain variable region comprising an amino acid sequence of SEQ ID NO: 147 and a heavy chain variable region comprising an amino acid sequence of SEQ ID NO: 140;
a light chain variable region comprising an amino acid sequence of SEQ ID NO: 75 and a heavy chain variable region comprising an amino acid sequence of SEQ ID NO: 141;
a light chain variable region comprising an amino acid sequence of SEQ ID NO: 75 and a heavy chain variable region comprising an amino acid sequence of SEQ ID NO: 140;
a light chain variable region comprising an amino acid sequence of SEQ ID NO: 148 and a heavy chain variable region comprising an amino acid sequence of SEQ ID NO: 142;
a light chain variable region comprising an amino acid sequence of SEQ ID NO: 149 and a heavy chain variable region comprising an amino acid sequence of SEQ ID NO: 143;
a light chain variable region comprising an amino acid sequence of SEQ ID NO: 150 and a heavy chain variable region comprising an amino acid sequence of SEQ ID NO: 144;
a light chain variable region comprising an amino acid sequence of SEQ ID NO: 151 and a heavy chain variable region comprising an amino acid sequence of SEQ ID NO: 145;
a light chain variable region comprising an amino acid sequence of SEQ ID NO: 152 and a heavy chain variable region comprising an amino acid sequence of SEQ ID NO: 146;
a light chain variable region comprising an amino acid sequence of SEQ ID NO: 318 and a heavy chain variable region comprising an amino acid sequence of SEQ ID NO: 317.

In one embodiment, the extracellular antigen-binding domain comprises a light chain variable region comprising an amino acid sequence of SEQ ID NO: 1 and a heavy chain variable region comprising an amino acid sequence of SEQ ID NO: 4.

In one embodiment, the extracellular antigen-binding domain comprises a light chain variable region comprising an amino acid sequence of SEQ ID NO: 2 and a heavy chain variable region comprising an amino acid sequence of SEQ ID NO: 4.

In one embodiment, the extracellular antigen-binding domain comprises a light chain variable region comprising an amino acid sequence of SEQ ID NO: 3 and a heavy chain variable region comprising an amino acid sequence of SEQ ID NO: 6.

In one embodiment, the extracellular antigen-binding domain comprises a light chain variable region comprising an amino acid sequence of SEQ ID NO: 3 and a heavy chain variable region comprising an amino acid sequence of SEQ ID NO: 4.

In one embodiment, the extracellular antigen-binding domain comprises a light chain variable region comprising an amino acid sequence of SEQ ID NO: 2 and a heavy chain variable region comprising an amino acid sequence of SEQ ID NO: 6.

In one embodiment, the extracellular antigen-binding domain comprises a light chain variable region comprising an amino acid sequence of SEQ ID NO: 1 and a heavy chain variable region comprising an amino acid sequence of SEQ ID NO: 6.

In one embodiment, the extracellular antigen-binding domain comprises a light chain variable region comprising an amino acid sequence of SEQ ID NO: 1 and a heavy chain variable region comprising an amino acid sequence of SEQ ID NO: 5.

In one embodiment, the extracellular antigen-binding domain comprises a light chain variable region comprising an amino acid sequence of SEQ ID NO: 2 and a heavy chain variable region comprising an amino acid sequence of SEQ ID NO: 5.

In one embodiment, the extracellular antigen-binding domain comprises a light chain variable region comprising an amino acid sequence of SEQ ID NO: 3 and a heavy chain variable region comprising an amino acid sequence of SEQ ID NO: 5.

In one embodiment, the extracellular antigen-binding domain comprises a light chain variable region comprising an amino acid sequence of SEQ ID NO: 74 and a heavy chain variable region comprising an amino acid sequence of SEQ ID NO: 76.

In one embodiment, the extracellular antigen-binding domain comprises a light chain variable region comprising an amino acid sequence of SEQ ID NO: 75 and a heavy chain variable region comprising an amino acid sequence of SEQ ID NO: 77.

In one embodiment, the extracellular antigen-binding domain comprises a light chain variable region comprising an amino acid sequence of SEQ ID NO: 147 and a heavy chain variable region comprising an amino acid sequence of SEQ ID NO: 140.

In one embodiment, the extracellular antigen-binding domain comprises a light chain variable region comprising an amino acid sequence of SEQ ID NO: 75 and a heavy chain variable region comprising an amino acid sequence of SEQ ID NO: 141.

In one embodiment, the extracellular antigen-binding domain comprises a light chain variable region comprising an amino acid sequence of SEQ ID NO: 75 and a heavy chain variable region comprising an amino acid sequence of SEQ ID NO: 140.

In one embodiment, the extracellular antigen-binding domain comprises a light chain variable region comprising an amino acid sequence of SEQ ID NO: 148 and a heavy chain variable region comprising an amino acid sequence of SEQ ID NO: 142.

In one embodiment, the extracellular antigen-binding domain comprises a light chain variable region comprising an amino acid sequence of SEQ ID NO: 149 and a heavy chain variable region comprising an amino acid sequence of SEQ ID NO: 143.

In one embodiment, the extracellular antigen-binding domain comprises a light chain variable region comprising an amino acid sequence of SEQ ID NO: 150 and a heavy chain variable region comprising an amino acid sequence of SEQ ID NO: 144.

In one embodiment, the extracellular antigen-binding domain comprises a light chain variable region comprising an amino acid sequence of SEQ ID NO: 151 and a heavy chain variable region comprising an amino acid sequence of SEQ ID NO: 145.

In one embodiment, the extracellular antigen-binding domain comprises a light chain variable region comprising an amino acid sequence of SEQ ID NO: 152 and a heavy chain variable region comprising an amino acid sequence of SEQ ID NO: 146.

In one embodiment, the extracellular antigen-binding domain comprises a light chain variable region comprising an amino acid sequence of SEQ ID NO: 318 and a heavy chain variable region comprising an amino acid sequence of SEQ ID NO: 317.

In one embodiment, the extracellular antigen-binding domain comprises:
- a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 1 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 4;
- a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 2 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 4;
- a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 3 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 6;
- a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 3 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 4;
- a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 2 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 6;
- a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 3 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 4;
- a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 1 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 6;
- a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 3 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 5;
- a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 1 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 5;
a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 2 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 5;
a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 74 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 76;
a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 75 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 77;
a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 147 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 140;
a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 75 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 141;
a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 75 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 140;
a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 148 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 142;
a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 149 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 143;
a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 150 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 144;
a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 151 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 145;
a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 152 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 146;

a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 318 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 317.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 1 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 4.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 2 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 4.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 3 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 6.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 2 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 6.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 3 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 4.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 1 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 6.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 3 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 5.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 1 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 5.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 2 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 5.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 74 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 76.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 75 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 77.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 147 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 140.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 75 and a heavy chain variable region comprising an amino acid sequence having at least 50, at least 55, at least 60, at least 65, at least 70, at least 92, at least 93, at least 94, at least 95, at least 96, at least 97, at least 98 or at least 99%, sequence identity with SEQ ID NO: 141.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 75 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 140.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 148 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 142.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 149 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 143.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 150 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 144.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 151 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 145.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 152 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 146.

In one embodiment, the extracellular antigen-binding domain comprises a light chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 318 and a heavy chain variable region comprising an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 317.

In one embodiment, the extracellular antigen-binding domain comprises a scFv. In some embodiments, the scFv comprises a linker polypeptide between the light chain variable region and the heavy chain variable region. In certain embodiments, the extracellular antigen-binding domain is a scFv which comprises an amino acid sequence selected from the group consisting of SEQ ID NOS: 8-23, 169-184 and 340-343, and specifically binds to a hK2 polypeptide (e.g., a human hK2 polypeptide having the amino acid sequence of SEQ ID NO: 62, or fragments thereof).

In recombinant expression systems, the linker is a peptide linker and may include any naturally occurring amino acid. Exemplary amino acids that may be included into the linker are Gly, Ser Pro, Thr, Glu, Lys, Arg, Ile, Leu, His and The. The linker should have a length that is adequate to link the VH and the VL in such a way that they form the correct conformation relative to one another so that they retain the desired activity, such as binding to hK2.

The linker may be about 5-50 amino acids long. In some embodiments, the linker is about 10-40 amino acids long. In some embodiments, the linker is about 10-35 amino acids long. In some embodiments, the linker is about 10-30 amino acids long. In some embodiments, the linker is about 10-25 amino acids long. In some embodiments, the linker is about 10-20 amino acids long. In some embodiments, the linker is about 15-20 amino acids long. In some embodiments, the linker is 6 amino acids long. In some embodiments, the linker is 7 amino acids long. In some embodiments, the linker is 8 amino acids long. In some embodiments, the linker is 9 amino acids long. In some embodiments, the linker is 10 amino acids long. In some embodiments, the linker is 11 amino acids long. In some embodiments, the linker is 12 amino acids long. In some embodiments, the linker is 13 amino acids long. In some embodiments, the linker is 14 amino acids long. In some embodiments, the linker is 15 amino acids long. In some embodiments, the linker is 16 amino acids long. In some embodiments, the linker is 17 amino acids long. In some embodiments, the linker is 18 amino acids long. In some embodiments, the linker is 19 amino acids long. In some embodiments, the linker is 20 amino acids long. In some embodiments, the linker is 21 amino acids long. In some embodiments, the linker is 22 amino acids long. In some embodiments, the linker is 23 amino acids long. In some embodiments, the linker is 24 amino acids long. In some embodiments, the linker is 25 amino acids long. In some embodiments, the linker is 26 amino acids long. In some embodiments, the linker is 27 amino acids long. In some embodiments, the linker is 28 amino acids long. In some embodiments, the linker is 29 amino acids long. In some embodiments, the linker is 30 amino acids long. In some embodiments, the linker is 31 amino acids long. In some embodiments, the linker is 32 amino acids long. In some embodiments, the linker is 33 amino acids long. In some embodiments, the linker is 34 amino acids long. In some embodiments, the linker is 35 amino acids long. In some embodiments, the linker is 36 amino acids long. In some embodiments, the linker is 37 amino acids long. In some embodiments, the linker is 38 amino acids long. In some embodiments, the linker is 39 amino acids long. In some embodiments, the linker is 40 amino acids long. Exemplary linkers that may be used are Gly rich linkers, Gly and Ser containing linkers, Gly and Ala containing linkers, Ala and Ser containing linkers, and other flexible linkers.

In one embodiment, the linker polypeptide comprises an amino acid sequence of SEQ ID NO: 7. In one embodiment, the linker polypeptide comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 7. In one embodiment, the linker polypeptide comprises an amino acid sequence of any one of SEQ ID NOS: 237-268. In one embodiment, the linker polypeptide comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with any one of SEQ ID NOS: 237-268.

In one embodiment, the scFv comprises an amino acid sequence selected from the group consisting of SEQ ID NOS: 8-23, 169-184 and 340-343. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 8, or the sequence of SEQ ID NO:8. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 9, or the sequence of SEQ ID NO:9. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 10, or the sequence of SEQ ID NO:10. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 11, or the sequence of SEQ ID NO:11. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 12, or the sequence of SEQ ID NO:12. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 13, or the sequence of SEQ ID NO:13. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 14, or the sequence of SEQ ID NO:14. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 15, or the sequence of SEQ ID NO:15. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 16, or the sequence of SEQ ID NO:16. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 17, or the sequence of SEQ ID NO:17. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 18, or the sequence of SEQ ID NO:18. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 19, or the sequence of SEQ ID NO:19. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 20, or the sequence of SEQ ID NO:20. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 21, or the sequence of SEQ ID NO:21. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 22, or the sequence of SEQ ID NO:22. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 23, or the sequence of SEQ ID NO:23. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 169, or the sequence of SEQ ID NO:169. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 170, or the sequence of SEQ ID NO:170. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 171, or the sequence of SEQ ID NO:171. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 172, or the sequence of SEQ ID NO:172. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 173, or the sequence of SEQ ID NO:173. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 174, or the sequence of SEQ ID NO:174. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 175, or the sequence of SEQ ID NO:175. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 176, or the sequence of SEQ ID NO:176. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 177, or the sequence of SEQ ID NO:177. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 178, or the sequence of SEQ ID NO:178. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 179, or the sequence of SEQ ID NO:179. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 180, or the sequence of SEQ ID NO:180. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 181, or the sequence of SEQ ID NO:181. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 182, or the sequence of SEQ ID NO:182. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 183, or the sequence of SEQ ID NO:183. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 184, or the sequence of SEQ ID NO:184. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 340, or the sequence of SEQ ID NO:340. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 341, or the sequence of SEQ ID NO:341. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 342, or the sequence of SEQ ID NO:342. In one embodiment, the scFv comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 343, or the sequence of SEQ ID NO:343.

In one embodiment, the extracellular antigen-binding domain comprises a signal polypeptide. The signal polypeptide may be positioned at the N-terminus of the extracellular antigen binding domain that binds hK2. The signal polypeptide may be optionally cleaved from the extracellular antigen binding domain during cellular processing and localization of the CAR to the cellular membrane. Any of various signal polypeptides known to one of skill in the art may be used as the signal polypeptide. Non-limiting examples of peptides from which the signal polypeptides may be derived include FcεR, human immunoglobulin (IgG) heavy chain (HC) variable region, CD8α, or any of various other proteins secreted by T cells. In various embodiments, the signal polypeptide is compatible with the secretory pathway of a T cell. In some embodiments, the signal polypeptide comprises an amino acid sequence of SEQ ID NO: 24. In one embodiment, the signal polypeptide comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 24.

In one aspect, the disclosure provides a CAR, comprising an extracellular antigen-binding domain, a transmembrane domain and an intracellular signaling domain, wherein the extracellular antigen-binding domain comprises an amino acid sequence selected from the group consisting of SEQ ID NOS: 29-44, 78-81, 221-236, and 273-308. Another feature of the CAR having an extracellular antigen-binding domain comprising an amino acid sequence selected from the group consisting of SEQ ID NOS: 29-44, 78-81, 221-236, and 273-308 is that the extracellular antigen-binding domain binds the hK2 antigen.

In one embodiment, the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member (such as, e.g., CD28 or inducible T-cell co-stimulator (ICOS)) component, and a combination thereof.

In one embodiment, the CD137 component comprises an amino acid sequence of SEQ ID NO: 27. In one embodiment, the CD137 component comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 27.

In one embodiment, the CD3z component comprises an amino acid sequence of SEQ ID NO: 28. In one embodiment, the CD3z component comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 28.

In one embodiment, the intracellular signaling domain comprises an amino acid sequence of SEQ ID NO: 45. In one embodiment, the intracellular signaling domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 45.

In one embodiment, the transmembrane domain comprises a CD8a transmembrane region (CD8a-TM) polypeptide. In some embodiments, the CD8a-TM polypeptide comprises an amino acid sequence of SEQ ID NO: 26. In some embodiments, the CD8a-TM polypeptide comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 26.

In one embodiment, the transmembrane domain comprises at least the transmembrane region(s) of) the α, β or ζ chain of the T-cell receptor, CD28, CD3 epsilon, CD45, CD4, CD5, CD8, CD8α, CD9, CD16, CD22, CD33, CD37, CD40, CD64, CD80, CD86, CD134, CD137, CD154. In another embodiment, the transmembrane domain comprises at least the transmembrane domain of ζ, η or FcεR1γ and -β, MB1 (Igα.), B29 or CD3-γ, ζ, or η. In another embodiment, the transmembrane domain is synthetic, e.g., comprising predominantly hydrophobic residues such as leucine and valine, a triplet of phenylalanine, or tryptophan.

In one embodiment, the CAR further comprises a hinge region linking the transmembrane domain to the extracellular antigen-binding domain. In some embodiments, the hinge region is a CD8a-hinge region. In some embodiments, CD8a-hinge region comprises an amino acid sequence of SEQ ID NO: 25. In some embodiments, the CD8a-hinge region comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 25. In some embodiments, the hinge region comprises the sequence EPKSCDKTHTCPPCP (SEQ ID NO: 269), or comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with EPKSCDKTHTCPPCP (SEQ ID NO: 269). In some embodiments, the hinge region comprises the sequence ERKCCVECPPCP (SEQ ID NO: 270), or comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with ERKCCVECPPCP (SEQ ID NO: 270). In some embodiments, the hinge region comprises the sequence ELKTPLGDTTHTCPRCP(EPKSCDTPPPCPRCP)₃ (SEQ ID NO: 271), or comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with ELKTPLGDTTHTCPRCP(EPKSCDTPPPCPRCP)₃ (SEQ ID NO: 271). In some embodiments, the hinge region comprises the sequence ESKYGPPCPSCP (SEQ ID NO: 272), or comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with ESKYGPPCPSCP (SEQ ID NO: 272).

In one embodiment, the CAR comprises an extracellular antigen-binding domain, a hinge region, a transmembrane domain and an intracellular signaling domain. In one such embodiment, the hinge region is a CD8α hinge region, the transmembrane domain is a CD8α-TM domain, and the intracellular signaling domain comprises a CD3-zeta domain and a 4-1BB/CD137 domain.

In one such embodiment, the hinge region is a CD8α hinge region comprising the amino acid sequence of SEQ ID No: 25, the transmembrane domain is a CD8α-TM domain comprising the amino acid sequence of SEQ ID NO: 26, and the intracellular signaling domain comprises a CD3-zeta domain and a 4-1BB/CD137 domain comprising an amino acid sequence of SEQ ID NO: 45.

In another embodiment, the hinge region is a CD8α hinge region comprising the amino acid sequence of SEQ ID No: 25, the transmembrane domain is a CD8α-TM domain comprising the amino acid sequence of SEQ ID NO: 26, and the intracellular signaling domain comprises a 4-1BB/CD137 domain comprising the amino acid sequence of SEQ ID NO 27, and a CD3-zeta domain comprising the amino acid sequence of SEQ ID NO: 28.

In one embodiment, the extracellular antigen-binding domain comprises an amino acid sequence selected from the group consisting of SEQ ID NOS: 29-44, 78-81, 221-236, and 273-308. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 29, or the sequence of SEQ ID NO:29. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 30, or the sequence of SEQ ID NO:30. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 31, or the sequence of SEQ ID NO:31. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 32, or the sequence of SEQ ID NO:32. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 33, or the sequence of SEQ ID NO:33. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 34, or the sequence of SEQ ID NO:34. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 35, or the sequence of SEQ ID NO:35. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 36, or the sequence of SEQ ID NO:36. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 37, or the sequence of SEQ ID NO:37. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 38, or the sequence of SEQ ID NO:38. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 39, or the sequence of SEQ ID NO:39. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 40, or the sequence of SEQ ID NO:40. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 41, or the sequence of SEQ ID NO:41. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 42, or the sequence of SEQ ID NO:42. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 43, or the sequence of SEQ ID NO:43. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 44, or the sequence of SEQ ID NO:44. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 78, or the sequence of SEQ ID NO:78. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 79, or the sequence of SEQ ID NO:79. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 80, or the sequence of SEQ ID NO:80. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 81, or the sequence of SEQ ID NO:81. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 221, or the sequence of SEQ ID NO:221. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 222, or the sequence of SEQ ID NO:222. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 223, or the sequence of SEQ ID NO:223. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 224, or the sequence of SEQ ID NO:224. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 225, or the sequence of SEQ ID NO:225. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 226, or the sequence of SEQ ID NO:226. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 227, or the sequence of SEQ ID NO:227. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 228, or the sequence of SEQ ID NO:228. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 229, or the sequence of SEQ ID NO:229. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 230, or the sequence of SEQ ID NO:230. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 231, or the sequence of SEQ ID NO:231. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 232, or the sequence of SEQ ID NO:232. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 233, or the sequence of SEQ ID NO:233. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 234, or the sequence of SEQ ID NO:234. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 235, or the sequence of SEQ ID NO:235. In one embodiment, the extracellular antigen-binding domain comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 236, or the sequence of SEQ ID NO:236.

CAR Constructs and Immunoresponsive Cells Expressing CARs

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

In one embodiment, the present disclosure provides a cell expressing the nucleic acid molecule encoding for a CAR. In one embodiment, the CAR of the present disclosure comprises an amino acid sequence selected from the group consisting of SEQ ID NOS: 46-61, 82-85 and 205-220. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 46, or the sequence of SEQ ID NO: 46. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 47, or the sequence of SEQ ID NO: 47. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 48, or the sequence of SEQ ID NO: 48. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 49, or the sequence of SEQ ID NO: 49. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 50, or the sequence of SEQ ID NO: 50. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 51, or the sequence of SEQ ID NO: 51. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 52, or the sequence of SEQ ID NO: 52. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 53, or the sequence of SEQ ID NO: 53. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 54, or the sequence of SEQ ID NO: 54. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 55, or the sequence of SEQ ID NO: 55. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 56, or the sequence of SEQ ID NO: 56. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 57, or the sequence of SEQ ID NO: 57. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 58, or the sequence of SEQ ID NO: 58. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 59, or the sequence of SEQ ID NO: 59. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 60, or the sequence of SEQ ID NO: 60. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 61, or the sequence of SEQ ID NO: 61. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 82, or the sequence of SEQ ID NO: 82. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 83, or the sequence of SEQ ID NO: 83. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 84, or the sequence of SEQ ID NO: 84. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 85, or the sequence of SEQ ID NO: 85. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 205, or the sequence of SEQ ID NO: 205. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 206, or the sequence of SEQ ID NO: 206. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 207, or the sequence of SEQ ID NO: 207. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 208, or the sequence of SEQ ID NO: 208. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 209, or the sequence of SEQ ID NO: 209. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 210, or the sequence of SEQ ID NO: 210. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 211, or the sequence of SEQ ID NO: 211. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 212, or the sequence of SEQ ID NO: 212. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 213, or the sequence of SEQ ID NO: 213. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 214, or the sequence of SEQ ID NO: 214. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 215, or the sequence of SEQ ID NO: 215. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 216, or the sequence of SEQ ID NO: 216. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 217, or the sequence of SEQ ID NO: 217. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 218, or the sequence of SEQ ID NO: 218. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 219, or the sequence of SEQ ID NO: 219. In some embodiments, the CAR of the present disclosure comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 220, or the sequence of SEQ ID NO: 220.

In certain embodiments, the CAR may comprise a signal polypeptide. In certain embodiments the signal peptide is at the N-terminus of the CAR sequence. In certain embodiments the signal peptide is at the C-terminus of the CAR sequence. In certain embodiments, the signal peptide comprises or consists of the amino acid sequence of SEQ ID No: 24.

Herein, the structure of nucleic acid molecules is in places defined in the basis of % sequence identity with a recited reference sequence (with a given SEQ ID NO). In this context, % sequence identity regarding nucleic acid molecules refers to the similarity between at least two different nucleic acid sequences. When a position in both of the two compared sequences is occupied by the same base e.g., if a position in each of two DNA molecules is occupied by adenine, then the molecules are identical at that position, The percent of identity between two sequences is a function of the number of matching or homologous positions shared by the two sequences divided by the number of positions compared and multiplied by 100. For example, if 6 of 10 of the positions in two sequences are matched or homologous then the two sequences are 60% identical (or homologous). By way of example, the DNA sequences ATTGCC and TATGGC share 50% identity (or homology). Generally, a comparison is made when two sequences are aligned to give maximum homology. The respective percent identity can be determined by standard alignment algorithms, for example, the Basic Local Alignment Search Tool (BLAST) described by Altshul et al. ((1990) J. MoI. Biol. 215:403-10); the algorithm of Needleman et al. ((1970) J. MoI. Biol. 48:444-53); or the algorithm of Meyers et al. ((1988) Comput. Appl. Biosci. 4:11-17). A set of parameters may be the Blosum 62 scoring matrix with a gap penalty of 12, a gap extend penalty of 4, and a frameshift gap penalty of 5. The percent identity between two nucleotide sequences can also be determined using the algorithm of Meyers and Miller ((1989) CABIOS 4:11-17), which has been incorporated into the ALIGN program (version 2.0), using a PAM120 weight residue table, a gap length penalty of 12, and a gap penalty of 4. The percent identity is usually calculated by comparing sequences of similar length.

In various embodiments, the nucleic acid molecule encoding for a CAR comprises a nucleic acid sequence of any one of SEQ ID NOS: 153-160. In various embodiments, the nucleic acid molecule encoding for a CAR comprises a nucleic acid sequence comprises a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with any one of SEQ ID NOS: 153-160.

In various embodiments, the nucleic acid molecule encoding for a CAR comprises a nucleic acid sequence of any one of SEQ ID NOS: 161-168. In various embodiments, the nucleic acid molecule encoding for a CAR comprises a nucleic acid sequence comprises a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with any one of SEQ ID NOS: 161-168.

In various embodiments, the nucleic acid molecule encoding for a CAR comprises a nucleic acid sequence of any one of SEQ ID NOS: 195-204. In various embodiments, the nucleic acid molecule encoding for a CAR comprises a nucleic acid sequence comprises a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with any one of SEQ ID NOS: 195-204.

In various embodiments, the nucleic acid molecule encoding for a CAR comprises a nucleic acid sequence of any one of SEQ ID NOS: 320-325. In various embodiments, the nucleic acid molecule encoding for a CAR comprises a nucleic acid sequence comprises a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with any one of SEQ ID NOS: 320-325.

In various embodiments, the nucleic acid molecule encoding for a CAR comprises a nucleic acid sequence of any one of SEQ ID NOS: 326-331. In various embodiments, the nucleic acid molecule encoding for a CAR comprises a nucleic acid sequence comprises a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with any one of SEQ ID NOS: 326-331.

In various embodiments, the nucleic acid molecule encoding for a CAR comprises a nucleic acid sequence of any one of SEQ ID NOS: 336-339. In various embodiments, the nucleic acid molecule encoding for a CAR comprises a nucleic acid sequence comprises a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with any one of SEQ ID NOS: 336-339.

In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 153, or the sequence of SEQ ID No:153. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 154, or the sequence of SEQ ID No:154. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 155, or the sequence of SEQ ID No:155. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 156, or the sequence of SEQ ID No:156. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 157, or the sequence of SEQ ID No:157. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 158, or the sequence of SEQ ID No:158. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 159, or the sequence of SEQ ID No:159. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 160, or the sequence of SEQ ID No:160. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 161, or the sequence of SEQ ID No:161. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 162, or the sequence of SEQ ID No:162. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 163, or the sequence of SEQ ID No:163. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 164, or the sequence of SEQ ID No:164. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 165, or the sequence of SEQ ID No:165. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 166, or the sequence of SEQ ID No:166. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 167, or the sequence of SEQ ID No:167. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 168, or the sequence of SEQ ID No:168. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 195, or the sequence of SEQ ID No:195. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 196, or the sequence of SEQ ID No:196. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 197, or the sequence of SEQ ID No:197. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 198, or the sequence of SEQ ID No:198. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 199, or the sequence of SEQ ID No:199. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 200, or the sequence of SEQ ID No:200. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 201, or the sequence of SEQ ID No:201. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 202, or the sequence of SEQ ID No:202. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 203, or the sequence of SEQ ID No:203. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 204, or the sequence of SEQ ID No:204. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 320, or the sequence of SEQ ID No:320. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 321, or the sequence of SEQ ID No:321. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 322, or the sequence of SEQ ID No:322. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 323, or the sequence of SEQ ID No:323. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 324, or the sequence of SEQ ID No:324. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 325, or the sequence of SEQ ID No:325. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 326, or the sequence of SEQ ID No:326. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 327, or the sequence of SEQ ID No:327. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 328, or the sequence of SEQ ID No:328. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 329, or the sequence of SEQ ID No:329. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 330, or the sequence of SEQ ID No:330. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 331, or the sequence of SEQ ID No:331. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 336, or the sequence of SEQ ID No:336. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 337, or the sequence of SEQ ID No:337. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 338, or the sequence of SEQ ID No:338. In an embodiment, the nucleic acid molecule encoding for a CAR comprises a nucleic acid sequence comprising a sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NOS: 339, or the sequence of SEQ ID No:339.

In one aspect, the present disclosure provides isolated immunoresponsive cells comprising the CARs described herein. In some embodiments, the isolated immunoresponsive cell is transduced with the CAR, for example, the CAR is constitutively expressed on the surface of the immunoresponsive cell. In certain embodiments, the isolated immunoresponsive cell is further transduced with at least one co-stimulatory ligand such that the immunoresponsive cell expresses the at least one co-stimulatory ligand. In certain embodiments, the at least one co-stimulatory ligand is selected from the group consisting of 4-1BBL, CD48, CD70, CD80, CD86, OX40L, TNFRSF14, and combinations thereof. In certain embodiments, the isolated immunoresponsive cell is further transduced with at least one cytokine such that the immunoresponsive cell secretes the at least one cytokine. In certain embodiments, the at least cytokine is selected from the group consisting of IL-2, IL-3, IL-6, IL-7, IL-11, IL-12, IL-15, IL-17, IL-21, and combinations thereof. In some embodiments, the isolated immunoresponsive cell is selected from the group consisting of a T lymphocyte (T cell), a Natural Killer (NK) cell, a cytotoxic T lymphocyte (CTL), a regulatory T cell, a human embryonic stem cell, a lymphoid progenitor cell, a T cell-precursor cell, and a pluripotent stem cell from which lymphoid cells may be differentiated.

In one embodiment, the CAR T cells of the disclosure can be generated by introducing a lentiviral vector comprising a desired CAR, for example, a CAR comprising anti-hK2, CD8α hinge and transmembrane domain, and human 4-1BB and CD3-zeta signaling domains, into the cells. The CAR T cells of the invention are able to replicate in vivo resulting in long-term persistence that can lead to sustained tumor control.

Embodiments of the invention further provide host cells comprising any of the recombinant expression vectors described herein. As used herein, the term "host cell" refers to any type of cell that can contain the recombinant expression vector. The host cell can be a eukaryotic cell, e.g., plant, animal, or algae, fungi, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, polypeptide, or protein, the host cell may be a mammalian cell. The host cell may be a human cell. While the host cell can be of any cell type, can originate from any type of tissue, and can be of any developmental stage, the host cell may be a peripheral blood lymphocyte (PBL). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to bone marrow, blood, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD8$^+$ T cells (e.g., cytotoxic T cells), CD4$^+$ helper T cells, e.g., Th$_1$ and Th$_2$ cells, peripheral blood mononuclear cells (PBMCs), peripheral blood leukocytes (PBLs), tumor infiltrating cells, memory T cells, naïve T cells, and the like. The T cell may be a CD8$^+$ T cell or a CD4$^+$ T cell.

Also provided are a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, an erythrocyte, a neutrophil, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment, the population of cells is a clonal population comprising host cells comprising a recombinant expression vector as described herein.

Pharmaceutical Compositions/Administration

In embodiments of the present disclosure, the CAR-expressing cells may be provided in compositions, e.g., suitable pharmaceutical composition(s) comprising the CAR-expressing cells and a pharmaceutically acceptable carrier. In one aspect, the present disclosure provides pharmaceutical compositions comprising an effective amount of a lymphocyte expressing one or more of the CARs described and a pharmaceutically acceptable excipient. Pharmaceutical compositions of the present disclosure may comprise a CAR-expressing cell, e.g., a plurality of CAR-expressing cells, as described herein, in combination with one or more pharmaceutically or physiologically acceptable carriers, excipients or diluents. As used herein, the term "in combination with" means that two or more therapeutic agents are be administered to a subject together in a mixture, concurrently as single agents or sequentially as single agents in any order.

A pharmaceutically acceptable carrier can be an ingredient in a pharmaceutical composition, other than an active ingredient, which is nontoxic to the subject.

A pharmaceutically acceptable carrier can include, but is not limited to, a buffer, excipient, stabilizer, or preservative. Examples of pharmaceutically acceptable carriers are solvents, dispersion media, coatings, antibacterial and antifungal agents, isotonic and absorption delaying agents, and the like that are physiologically compatible, such as salts, buffers, antioxidants, saccharides, aqueous or non-aqueous carriers, preservatives, wetting agents, surfactants or emulsifying agents, or combinations thereof. The amounts of pharmaceutically acceptable carrier(s) in the pharmaceutical compositions may be determined experimentally based on the activities of the carrier(s) and the desired characteristics of the formulation, such as stability and/or minimal oxidation.

Such compositions may comprise buffers such as acetic acid, citric acid, formic acid, succinic acid, phosphoric acid, carbonic acid, malic acid, aspartic acid, histidine, boric acid, Tris buffers, HEPPSO, HEPES, neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); antibacterial and antifungal agents; and preservatives.

Compositions of the present disclosure can be formulated for a variety of means of parenteral or non-parenteral administration. In one embodiment, the compositions can be formulated for infusion or intravenous administration. Compositions disclosed herein can be provided, for example, as sterile liquid preparations, e.g., isotonic aqueous solutions, emulsions, suspensions, dispersions, or viscous compositions, which may be buffered to a desirable pH. Formulations suitable for oral administration can include liquid solutions, capsules, sachets, tablets, lozenges, and troches, powders liquid suspensions in an appropriate liquid and emulsions.

The term "pharmaceutically acceptable," as used herein with regard to pharmaceutical compositions, means approved by a regulatory agency of the Federal or a state government or listed in the U.S. Pharmacopeia or other generally recognized pharmacopeia for use in animals and/ or in humans.

In one aspect, the disclosure relates to administering a genetically modified T cell expressing a CAR for the treatment of a subject having cancer or at risk of having cancer using lymphocyte infusion. In at least one embodiment, autologous lymphocyte infusion is used in the treatment. Autologous PBMCs are collected from a subject in need of treatment and T cells are activated and expanded using the methods described herein and known in the art and then infused back into the subject.

In one aspect, the disclosure relates generally to the treatment of a subject at risk of developing cancer. The invention also includes treating a malignancy or an autoimmune disease in which chemotherapy and/or immunotherapy in a subject results in significant immunosuppression, thereby increasing the risk of the subject developing cancer. In one aspect, the present disclosure provides methods of preventing cancer, the methods comprising administering an amount of a lymphocyte expressing one or more of the CARs described to a subject in need thereof.

In one aspect, the present disclosure provides methods of treating a subject having cancer, the methods comprising administering a therapeutically effective amount of a lymphocyte expressing one or more of the CARs described to a subject in need thereof, whereby the lymphocyte induces or modulates killing of cancer cells in the subject.

In another aspect, the present disclosure provides methods of reducing tumor burden in a subject having cancer, the methods comprising administering a therapeutically effective amount of a lymphocyte expressing one or more of the CARs described herein to a subject in need thereof, whereby the lymphocyte induces killing of cancer cells in the subject. In another aspect, the present disclosure provides methods of increasing survival of a subject having cancer, the methods comprising administering a therapeutically effective amount of a lymphocyte expressing one or more of the CARs described to a subject in need thereof, whereby the survival of the subject is lengthened. Generally, the lymphocytes expressing the CAR(s) induce killing of cancer cells in the subject and result in reduction or eradication of the tumors/cancer cells in the subject. A non-limiting list of cancers, inclusive of metastatic lesions, that can be targeted, includes prostate cancer and prostate-derived cancer. In one embodiment, the cancer being treated in a subject is prostate cancer. In some embodiments, the cancer is an androgen receptor (AR) expressing breast cancer.

In one aspect, the methods described herein are applicable to treatment of noncancerous conditions that are at risk of developing into a cancerous condition, such as, e.g., enlarged prostate, benign prostate hyperplasia (BPH), and high PSA levels in absence of diagnosed prostate cancer.

In one aspect, methods of treating a subject having cancer are provided that comprise administering a therapeutically effective amount of a lymphocyte expressing a CAR, the CAR having an extracellular antigen-binding domain that binds the hK2 antigen, to a subject in need thereof, whereby the lymphocyte induces killing of cancer cells in the subject. In some embodiments, the at least one of the CARs comprises an amino acid sequence selected from the group consisting of SEQ ID NOS: 46-61, 82-85 and 205-220. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 46, or the sequence of SEQ ID NO: 46. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 47, or the sequence of SEQ ID NO: 47. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 48, or the sequence of SEQ ID NO: 48. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 49, or the sequence of SEQ ID NO: 49. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 50, or the sequence of SEQ ID NO: 50. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 51, or the sequence of SEQ ID NO: 51. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 52, or the sequence of SEQ ID NO: 52. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 53, or the sequence of SEQ ID NO: 53. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 54, or the sequence of SEQ ID NO: 54. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 55, or the sequence of SEQ ID NO: 55. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 56, or the sequence of SEQ ID NO: 56. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 57, or the sequence of SEQ ID NO: 57. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 58, or the sequence of SEQ ID NO: 58. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 59, or the sequence of SEQ ID NO: 59. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 60, or the sequence of SEQ ID NO: 60. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 61, or the sequence of SEQ ID NO: 61. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 82, or the sequence of SEQ ID NO: 82. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 83, or the sequence of SEQ ID NO: 83. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 84, or the sequence of SEQ ID NO: 84. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 85, or the sequence of SEQ ID NO: 85. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 205, or the sequence of SEQ ID NO: 205. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 206, or the sequence of SEQ ID NO: 206. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 207, or the sequence of SEQ ID NO: 207. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 208, or the sequence of SEQ ID NO: 208. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 209, or the sequence of SEQ ID NO: 209. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 210, or the sequence of SEQ ID NO: 210. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 211, or the sequence of SEQ ID NO: 211. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 212, or the sequence of SEQ ID NO: 212. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 213, or the sequence of SEQ ID NO: 213. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 214, or the sequence of SEQ ID NO: 214. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 215, or the sequence of SEQ ID NO: 215. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 216, or the sequence of SEQ ID NO: 216. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 217, or the sequence of SEQ ID NO: 217. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 218, or the sequence of SEQ ID NO: 218. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 219, or the sequence of SEQ ID NO: 219. In some embodiments, the CAR comprises an amino acid sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 220, or the sequence of SEQ ID NO: 220.

In one aspect, a method of targeted killing of a cancer cell is disclosed, the method comprising contacting the cancer cell with a lymphocyte expressing one or more of the CARs described, whereby the lymphocyte induces killing of the cancer cell. A non-limiting list of cancer cells, inclusive of metastatic cancer cells, that can be targeted include prostate cancer, and combinations thereof. In one embodiment, the cancer cell is a prostate cancer cell.

Pharmaceutical compositions of the present disclosure may be administered in a manner appropriate to the disease to be treated (or prevented). The quantity and frequency of administration will be determined by such factors as the condition of the subject, and the type and severity of the subject's disease, although appropriate dosages may be determined by clinical trials.

The terms "treat" or "treatment" refer to therapeutic treatment wherein the object is to slow down (lessen) an undesired physiological change or disease, or provide a beneficial or desired clinical outcome during treatment. Beneficial or desired clinical outcomes include alleviation of symptoms, diminishment of extent of disease, stabilized (i.e., not worsening) state of disease, delay or slowing of disease progression, amelioration or palliation of the disease state, and/or remission (whether partial or total), whether detectable or undetectable. "Treatment" can also mean prolonging survival as compared to expected survival if a subject was not receiving treatment. Those in need of treatment include those subjects already with the undesired physiological change or disease as well as those subjects prone to have the physiological change or disease.

"Prevent," "preventing," "prevention," or "prophylaxis" of a disease or disorder means preventing that a disorder occurs in a subject. A "therapeutically effective amount" or "effective amount", used interchangeably herein, refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Example indicators of an effective therapeutic or combination of therapeutics that include, for example, improved wellbeing of the patient, reduction of a tumor burden, arrested or slowed growth of a tumor, and/or absence of metastasis of cancer cells to other locations in the body.

As used herein, the term "subject" refers to an animal. The terms "subject" and "patient" may be used interchangeably herein in reference to a subject. As such, a "subject" includes a human that is being treated for a disease, or prevention of a disease, as a patient. The methods described herein may be used to treat an animal subject belonging to any classification. Examples of such animals include mammals. Mammals, include, but are not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). In one embodiment, the mammal is a human.

When a therapeutically effective amount is indicated, the precise amount of the compositions of the present disclosure to be administered can be determined by a physician with consideration of individual differences in age, weight, tumor size, extent of infection or metastasis, and condition of the subject. It can generally be stated that a pharmaceutical composition comprising the T cells described herein may be administered at a dosage of about $10^4$ to about $10^{10}$ cells/kg body weight, in some instances about $10^5$ to about $10^6$ cells/kg body weight, including all integer values within those ranges. In some embodiments, a pharmaceutical composition comprising the T cells described herein may be administered at a dosage of about $10^6$ cells/kg body weight. T cell compositions may also be administered multiple times at these dosages. The cells can be administered by using infusion techniques that are commonly known in immunotherapy (see, e.g., Rosenberg et al., *New Eng. J. of Med.* 319:1676, 1988).

Delivery systems useful in the context of embodiments of the invention may include time-released, delayed release, and sustained release delivery systems such that the delivery of the T cell compositions occurs prior to, and with sufficient time to cause, sensitization of the site to be treated. The composition can be used in conjunction with other therapeutic agents or therapies. Such systems can avoid repeated administrations of the composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polyesteramides, polyorthoesters, polycaprolactones, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; sylastic systems; peptide based systems; hydrogel release systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775; 4,667,014; 4,748,034; and 5,239,660 and (b) diffusional systems in which an active component permeates at a controlled rate from a polymer such as described in U.S. Pat. Nos. 3,854,480 and 3,832,253. In addition, pump-based hardware delivery systems can be used, some of which are adapted for implantation.

In certain aspects, it may be desirable to administer activated T cells to a subject and then subsequently redraw blood (or have an apheresis performed), activate the T cells according to the present disclosure, and reinfuse the subject with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

The administration of the CAR-T cells and compositions may be carried out in any manner, e.g., by parenteral or nonparenteral administration, including by aerosol inhalation, injection, infusions, ingestion, transfusion, implantation or transplantation. For example, the CAR-T cells and compositions described herein may be administered to a patient trans-arterially, intradermally, subcutaneously, intratumorally, intramedullary, intranodally, intramuscularly, by intravenous (i.v.) injection, or intraperitoneally. In one aspect, the compositions of the present disclosure are administered by i.v. injection. In one aspect, the compositions of the present disclosure are administered to a subject by intradermal or subcutaneous injection. The compositions of T cells may be injected, for instance, directly into a tumor, lymph node, tissue, organ, or site of infection.

Administration can be autologous or non-autologous. For example, immunoresponsive cells expressing a human Kallikrein-2 (e.g., hK2)-specific CAR can be obtained from one subject, and administered to the same subject or a different, compatible subject. Peripheral blood derived T cells of the present disclosure, or expanded T cells (e.g., in vivo, ex vivo or in vitro derived) can be administered via, e.g., intravenous injection, localized injection, systemic injection, catheter administration, or parenteral administration.

In particular embodiments, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the present disclosure may be introduced, thereby creating a CAR-T cell. Subjects in need thereof may subsequently undergo standard treatment with high dose chemotherapy followed by peripheral blood stem cell transplantation. In certain aspects, following or concurrent with the transplant, subjects receive an infusion of the expanded CAR-T cells. In one aspect, expanded cells are administered before or following surgery.

The dosage administered to a patient having a malignancy is sufficient to alleviate or at least partially arrest the disease being treated ("therapeutically effective amount"). The dosage of the above treatments to be administered to a subject will vary with the precise nature of the condition being treated and the recipient of the treatment. The scaling of dosages for human administration can be performed according to practices generally accepted in the art.

The CAR T cells of the invention can undergo in vivo T cell expansion and can establish hK2-specific memory cells that persist at high levels for an extended amount of time in blood and bone marrow. In some instances, the CAR T cells of the invention infused into a subject can eliminate cancer cells, e.g., prostate cancer cells or AR-expressing breast cancer, in vivo in subjects with advanced chemotherapy-resistant cancer.

In one embodiment, a CAR of the present disclosure is introduced into T cells, e.g., using in vitro transcription, and the subject (e.g., human) receives an initial administration of CAR-T cells of the disclosure, and one or more subsequent administrations of the CAR-T cells, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR-T cells are administered to the subject (e.g., human) per week, e.g., 2, 3, or 4 administrations of the CAR-T cells are administered per week. In one embodiment, the subject receives more than one administration of the CAR-T cells per week (e.g., 2, 3 or 4 administrations per week) (also referred to herein as a cycle), followed by a week of no CAR-T cell administrations, and then one or more additional administration of the CAR-T cells (e.g., more than one administration of the CAR-T cells per week) is administered to the subject. In another embodiment, the subject receives more than one cycle of CAR-T cells, and the time between each cycle is less than 10, 9, 8, 7, 6, 5, 4, or 3 days. In one embodiment, the CAR-T cells are administered every other day for 3 administrations per week. In one embodiment, the CAR-T cells are administered for at least two, three, four, five, six, seven, eight or more weeks.

In one embodiment, administration may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

The CAR-T cells may be administered in the methods of the invention by maintenance therapy, such as, e.g., once a week for a period of 6 months or more.

In one embodiment, CAR-T cells are generated using lentiviral viral vectors, such as lentivirus. CAR-T cells generated with such viral vectors will generally have stable CAR expression.

In one embodiment, CAR-T cells transiently express CAR vectors for 4, 5, 6, 7, 8, 9, 10, 11, 12, 13, 14, 15 days after transduction. Transient expression of CARs can be affected by RNA CAR vector delivery. In one embodiment, the CAR RNA is transduced into the T cell by electroporation.

If a patient is at high risk of generating an anti-CAR antibody response during the course of transient CAR therapy (such as those generated by RNA transductions), CAR-T infusion breaks should not last more than ten to fourteen days.

A CAR-expressing cell described herein may be used in combination with other known agents and therapies. Administered "in combination", as used herein, means that two (or more) different treatments are delivered to the subject during the course of the subject's treatment e.g., the two or more treatments are delivered after the subject has been diagnosed with the cancer and before the cancer has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In one embodiment, other therapeutic agents such as factors may be administered before, after, or at the same time (simultaneous with) as the CAR-T cells, including, but not limited to, interleukins, as well as colony stimulating factors, such as G-, M- and GM-CSF, and interferons.

The CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

In further embodiments, the CAR-expressing cells described herein may be used in a treatment regimen in combination with surgery, radiation, chemotherapy, immunosuppressive agents, antibodies, or other immunoablative agents. In another embodiment, the CAR-expressing cell described herein can be used in combination with an anti-androgen treatment. In one embodiment, the subject can be administered an agent which enhances the activity of a CAR-expressing cell. For example, in one embodiment, the agent can be an agent which inhibits an inhibitory molecule.

A description of example embodiments follows.

1. A chimeric antigen receptor (CAR) comprising:
    (a) an extracellular domain comprising an scFv that specifically binds to the human Kallikrein-2 (hK2) antigen,
    (b) a transmembrane domain, and
    (c) an intracellular signaling domain optionally comprising at least one co-stimulatory domain.
2. The CAR of embodiment 1, further comprising
    (d) a CD8a-hinge region,
    wherein the transmembrane domain comprises a CD8a transmembrane region (CD8a-TM) polypeptide; and
    wherein the intracellular signaling domain comprises a co-stimulatory domain comprising a TNF receptor superfamily member 9 (CD137) component and a primary signaling domain comprising a T-cell surface glycoprotein CD3 zeta chain (CD3z) component.
3. The CAR of embodiment 2, wherein
    (b) the CD8a-hinge region comprises an amino acid sequence that is at least 90% identical to SEQ ID NO: 25, 269, 270, 271, or 272;
    (c) the transmembrane domain comprises an amino acid sequence that is at least 90% identical to SEQ ID NO: 26; and/or
    (d) the intracellular signaling domain comprises a co-stimulatory domain having an amino acid sequence that is at least 90% identical to SEQ ID NO: 27, and a primary signaling domain having an amino acid sequence that is at least 90% identical to SEQ ID NO: 28.
4. A chimeric antigen receptor (CAR), comprising an extracellular antigen-binding domain, a transmembrane domain and an intracellular signaling domain, wherein the extracellular antigen-binding domain comprises:
    a heavy chain complementarity determining region 1 (CDR1) having the amino acid sequence of SEQ ID NO: 63, a heavy chain CDR2 having the amino acid sequence of SEQ ID NO: 64, and a heavy chain CDR3 having the amino acid sequence of SEQ ID NO: 66;
    a heavy chain complementarity determining region 1 (CDR1) having the amino acid sequence of SEQ ID NO: 314, a heavy chain CDR2 having the amino acid sequence of SEQ ID NO: 315, and a heavy chain CDR3 having the amino acid sequence of SEQ ID NO: 311;

a heavy chain complementarity determining region 1 (CDR1) having the amino acid sequence of SEQ ID NO: 309, a heavy chain CDR2 having the amino acid sequence of SEQ ID NO: 310, and a heavy chain CDR3 having the amino acid sequence of SEQ ID NO: 311;

a heavy chain complementarity determining region 1 (CDR1) having the amino acid sequence of SEQ ID NO: 63, a heavy chain CDR2 having the amino acid sequence of SEQ ID NO: 65, and a heavy chain CDR3 having the amino acid sequence of SEQ ID NO: 66; or a heavy chain complementarity determining region 1 (CDR1) having the amino acid sequence of SEQ ID NO: 72, a heavy chain CDR2 having the amino acid sequence of SEQ ID NO: 73, and a heavy chain CDR3 having the amino acid sequence of SEQ ID NO: 66;

a heavy chain complementarity determining region 1 (CDR1) having the amino acid sequence of SEQ ID NO: 86, a heavy chain CDR2 having the amino acid sequence of SEQ ID NO: 87, and a heavy chain CDR3 having the amino acid sequence of SEQ ID NO: 88;

a heavy chain complementarity determining region 1 (CDR1) having the amino acid sequence of SEQ ID NO: 92, a heavy chain CDR2 having the amino acid sequence of SEQ ID NO: 93, and a heavy chain CDR3 having the amino acid sequence of SEQ ID NO: 94 a heavy chain complementarity determining region 1 (CDR1) having the amino acid sequence of SEQ ID NO: 102, a heavy chain CDR2 having the amino acid sequence of SEQ ID NO: 103, and a heavy chain CDR3 having the amino acid sequence of SEQ ID NO: 104;

a heavy chain complementarity determining region 1 (CDR1) having the amino acid sequence of SEQ ID NO: 105, a heavy chain CDR2 having the amino acid sequence of SEQ ID NO: 106, and a heavy chain CDR3 having the amino acid sequence of SEQ ID NO: 104;

a heavy chain complementarity determining region 1 (CDR1) having the amino acid sequence of SEQ ID NO: 107, a heavy chain CDR2 having the amino acid sequence of SEQ ID NO: 108, and a heavy chain CDR3 having the amino acid sequence of SEQ ID NO: 109;

a heavy chain complementarity determining region 1 (CDR1) having the amino acid sequence of SEQ ID NO: 110, a heavy chain CDR2 having the amino acid sequence of SEQ ID NO: 111, and a heavy chain CDR3 having the amino acid sequence of SEQ ID NO: 109;

a heavy chain complementarity determining region 1 (CDR1) having the amino acid sequence of SEQ ID NO: 102, a heavy chain CDR2 having the amino acid sequence of SEQ ID NO: 112, and a heavy chain CDR3 having the amino acid sequence of SEQ ID NO: 113;

a heavy chain complementarity determining region 1 (CDR1) having the amino acid sequence of SEQ ID NO: 105, a heavy chain CDR2 having the amino acid sequence of SEQ ID NO: 114, and a heavy chain CDR3 having the amino acid sequence of SEQ ID NO: 113;

a heavy chain complementarity determining region 1 (CDR1) having the amino acid sequence of SEQ ID NO: 115, a heavy chain CDR2 having the amino acid sequence of SEQ ID NO: 116, and a heavy chain CDR3 having the amino acid sequence of SEQ ID NO: 117;

a heavy chain complementarity determining region 1 (CDR1) having the amino acid sequence of SEQ ID NO: 118, a heavy chain CDR2 having the amino acid sequence of SEQ ID NO: 119, and a heavy chain CDR3 having the amino acid sequence of SEQ ID NO: 117;

a heavy chain complementarity determining region 1 (CDR1) having the amino acid sequence of SEQ ID NO: 120, a heavy chain CDR2 having the amino acid sequence of SEQ ID NO: 121, and a heavy chain CDR3 having the amino acid sequence of SEQ ID NO: 122; or a heavy chain complementarity determining region 1 (CDR1) having the amino acid sequence of SEQ ID NO: 123, a heavy chain CDR2 having the amino acid sequence of SEQ ID NO: 124, and a heavy chain CDR3 having the amino acid sequence of SEQ ID NO: 122;

wherein the extracellular antigen-binding domain binds the hK2 antigen.

5. A chimeric antigen receptor (CAR), comprising an extracellular antigen-binding domain, a transmembrane domain and an intracellular signaling domain, wherein the extracellular antigen-binding domain comprises:

a light chain complementarity determining region 1 (CDR1) having the amino acid sequence of SEQ ID NO: 67, a light chain CDR2 having the amino acid sequence of SEQ ID NO: 69, and a light chain CDR3 having the amino acid sequence of SEQ ID NO: 71;

a light chain complementarity determining region 1 (CDR1) having the amino acid sequence of SEQ ID NO: 68, a light chain CDR2 having the amino acid sequence of SEQ ID NO: 70, and a light chain CDR3 having the amino acid sequence of SEQ ID NO: 71;

a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91;

a light chain complementarity determining region 1 (CDR1) having the amino acid sequence of SEQ ID NO: 95, a light chain CDR2 having the amino acid sequence of SEQ ID NO: 96, and a light chain CDR3 having the amino acid sequence of SEQ ID NO: 71;

a light chain complementarity determining region 1 (CDR1) having the amino acid sequence of SEQ ID NO: 312, a light chain CDR2 having the amino acid sequence of SEQ ID NO: 313, and a light chain CDR3 having the amino acid sequence of SEQ ID NO: 91;

a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91;

a light chain complementarity determining region 1 (CDR1) having the amino acid sequence of SEQ ID NO: 67, a light chain CDR2 having the amino acid sequence of SEQ ID NO: 126, and a light chain CDR3 having the amino acid sequence of SEQ ID NO: 71;

a light chain complementarity determining region 1 (CDR1) having the amino acid sequence of SEQ ID NO: 128, a light chain CDR2 having the amino acid sequence of SEQ ID NO: 129, and a light chain CDR3 having the amino acid sequence of SEQ ID NO: 130;

a light chain complementarity determining region 1 (CDR1) having the amino acid sequence of SEQ ID NO: 125, a light chain CDR2 having the amino acid sequence of SEQ ID NO: 131, and a light chain CDR3 having the amino acid sequence of SEQ ID NO: 132;

a light chain complementarity determining region 1 (CDR1) having the amino acid sequence of SEQ ID NO: 133, a light chain CDR2 having the amino acid sequence of SEQ ID NO: 134, and a light chain CDR3 having the amino acid sequence of SEQ ID NO: 135;

a light chain complementarity determining region 1 (CDR1) having the amino acid sequence of SEQ ID NO: 136, a light chain CDR2 having the amino acid sequence of SEQ ID NO: 137, and a light chain CDR3 having the amino acid sequence of SEQ ID NO: 138; or a light chain complementarity determining region 1 (CDR1) having the amino acid sequence of SEQ ID NO: 97, a light chain CDR2 having the amino acid sequence of SEQ ID NO: 127, and a light chain CDR3 having the amino acid sequence of SEQ ID NO: 139, wherein the extracellular antigen-binding domain binds the hK2 antigen.

6. The CAR according to embodiment 4, wherein the extracellular antigen-binding domain further comprises:

a light chain complementarity determining region 1 (CDR1) having the amino acid sequence of SEQ ID NO: 67, a light chain CDR2 having the amino acid sequence of SEQ ID NO: 69, and a light chain CDR3 having the amino acid sequence of SEQ ID NO: 71;

a light chain complementarity determining region 1 (CDR1) having the amino acid sequence of SEQ ID NO: 68, a light chain CDR2 having the amino acid sequence of SEQ ID NO: 70, and a light chain CDR3 having the amino acid sequence of SEQ ID NO: 71;

a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91;

a light chain complementarity determining region 1 (CDR1) having the amino acid sequence of SEQ ID NO: 95, a light chain CDR2 having the amino acid sequence of SEQ ID NO: 96, and a light chain CDR3 having the amino acid sequence of SEQ ID NO: 71;

a light chain complementarity determining region 1 (CDR1) having the amino acid sequence of SEQ ID NO: 312, a light chain CDR2 having the amino acid sequence of SEQ ID NO: 313, and a light chain CDR3 having the amino acid sequence of SEQ ID NO: 91;

a light chain complementarity determining region 1 (CDR1) having the amino acid sequence of SEQ ID NO: 89, a light chain CDR2 having the amino acid sequence of SEQ ID NO: 90, and a light chain CDR3 having the amino acid sequence of SEQ ID NO: 91;

a light chain complementarity determining region 1 (CDR1) having the amino acid sequence of SEQ ID NO: 67, a light chain CDR2 having the amino acid sequence of SEQ ID NO: 126, and a light chain CDR3 having the amino acid sequence of SEQ ID NO: 71;

a light chain complementarity determining region 1 (CDR1) having the amino acid sequence of SEQ ID NO: 128, a light chain CDR2 having the amino acid sequence of SEQ ID NO: 129, and a light chain CDR3 having the amino acid sequence of SEQ ID NO: 130;

a light chain complementarity determining region 1 (CDR1) having the amino acid sequence of SEQ ID NO: 125, a light chain CDR2 having the amino acid sequence of SEQ ID NO: 131, and a light chain CDR3 having the amino acid sequence of SEQ ID NO: 132;

a light chain complementarity determining region 1 (CDR1) having the amino acid sequence of SEQ ID NO: 133, a light chain CDR2 having the amino acid sequence of SEQ ID NO: 134, and a light chain CDR3 having the amino acid sequence of SEQ ID NO: 135;

a light chain complementarity determining region 1 (CDR1) having the amino acid sequence of SEQ ID NO: 136, a light chain CDR2 having the amino acid sequence of SEQ ID NO: 137, and a light chain CDR3 having the amino acid sequence of SEQ ID NO: 138; or a light chain complementarity determining region 1 (CDR1) having the amino acid sequence of SEQ ID NO: 97, a light chain CDR2 having the amino acid sequence of SEQ ID NO: 127, and a light chain CDR3 having the amino acid sequence of SEQ ID NO: 139.

7. The CAR according to embodiment 6, wherein the extracellular antigen-binding domain comprises:

a heavy chain complementarity determining region 1 (CDR1) having the amino acid sequence of SEQ ID NO: 63, a heavy chain CDR2 having the amino acid sequence of SEQ ID NO: 64, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 68, a light chain CDR2 having the amino acid sequence of SEQ ID NO: 70, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71;

a heavy chain complementarity determining region 1 (CDR1) having the amino acid sequence of SEQ ID NO: 314, a heavy chain CDR2 having the amino acid sequence of SEQ ID NO: 315, a heavy chain CDR3 having the amino acid sequence of SEQ ID NO: 311, and a light chain complementarity determining region 1 (CDR1) having the amino acid sequence of SEQ ID NO: 312, a light chain CDR2 having the amino acid sequence of SEQ ID NO: 313, a light chain CDR3 having the amino acid sequence of SEQ ID NO: 91;

a heavy chain complementarity determining region 1 (CDR1) having the amino acid sequence of SEQ ID NO: 102, a heavy chain CDR2 having the amino acid sequence of SEQ ID NO: 103, a heavy chain CDR3 having the amino acid sequence of SEQ ID NO: 104, and a light chain complementarity determining region 1 (CDR1) having the amino acid sequence of SEQ ID NO: 128, a light chain CDR2 having the amino acid sequence of SEQ ID NO: 129, a light chain CDR3 having the amino acid sequence of SEQ ID NO: 130;

a heavy chain complementarity determining region 1 (CDR1) having the amino acid sequence of SEQ ID NO: 107, a heavy chain CDR2 having the amino acid sequence of SEQ ID NO: 108, a heavy chain CDR3 having the amino acid sequence of SEQ ID NO: 109, and a light chain complementarity determining region 1 (CDR1) having the amino acid sequence of SEQ ID NO: 125, a light chain CDR2 having the amino acid sequence of SEQ ID NO: 131, a light chain CDR3 having the amino acid sequence of SEQ ID NO: 132;

a heavy chain complementarity determining region 1 (CDR1) having the amino acid sequence of SEQ ID NO: 102, a heavy chain CDR2 having the amino acid sequence of SEQ ID NO: 112, a heavy chain CDR3 having the amino acid sequence of SEQ ID NO: 113, and a light chain complementarity determining region 1 (CDR1) having the amino acid sequence of SEQ ID NO: 133, a light chain CDR2 having the amino acid sequence of SEQ ID NO: 134, a light chain CDR3 having the amino acid sequence of SEQ ID NO: 135;

a heavy chain complementarity determining region 1 (CDR1) having the amino acid sequence of SEQ ID NO: 115, a heavy chain CDR2 having the amino acid sequence of SEQ ID NO: 116, a heavy chain CDR3 having the amino acid sequence of SEQ ID NO: 117, and a light chain complementarity determining region 1 (CDR1) having the amino acid sequence of SEQ ID NO: 136, a light chain CDR2 having the amino acid sequence of SEQ ID NO: 137, a light chain CDR3 having the amino acid sequence of SEQ ID NO: 138; or a heavy chain complementarity determining region 1 (CDR1) having the amino acid sequence of SEQ ID NO: 120, a heavy chain CDR2 having the amino acid sequence of SEQ ID NO: 121, a heavy chain CDR3 having the amino acid sequence of SEQ ID NO: 122, and a light chain complementarity determining region 1 (CDR1) having the amino acid sequence of SEQ ID NO: 97, a light chain CDR2 having the amino acid sequence of SEQ ID NO: 127, a light chain CDR3 having the amino acid sequence of SEQ ID NO: 138.

8. The CAR according to embodiment 6, wherein the extracellular antigen-binding domain comprises: a heavy chain complementarity determining region 1 (CDR1) having the amino acid sequence of SEQ ID NO: 86, a heavy chain CDR2 having the amino acid sequence of SEQ ID NO: 87, a heavy chain CDR3 having the amino acid sequence of SEQ ID NO: 88, and a light chain complementarity determining region 1 (CDR1) having the amino acid sequence of SEQ ID NO: 89, a light chain CDR2 having the amino acid sequence of SEQ ID NO: 90, a light chain CDR3 having the amino acid sequence of SEQ ID NO: 91.

9. A chimeric antigen receptor (CAR), comprising an extracellular antigen-binding domain, a transmembrane domain and an intracellular signaling domain, wherein the extracellular antigen-binding domain comprises:

a light chain variable domain (VL) comprising an amino acid sequence selected from SEQ ID NOS: 1, 2, 3, 74, 75, 147, 148, 149, 150, 151, 152 and 318; and/or a heavy chain variable domain (VH) comprising an amino acid sequence selected from SEQ ID NOS: 4, 5, 6, 76, 77, 140, 141, 142, 143, 144, 145, 146 and 317;

wherein the extracellular antigen-binding domain binds the human Kallikrein-2 (hK2) antigen.

10. The CAR of embodiment 9, wherein the extracellular antigen-binding domain comprises:

a light chain variable region comprising an amino acid sequence of SEQ ID NO: 1 and a heavy chain variable region comprising an amino acid sequence of SEQ ID NO: 4;

a light chain variable region comprising an amino acid sequence of SEQ ID NO: 2 and a heavy chain variable region comprising an amino acid sequence of SEQ ID NO: 4;

a light chain variable region comprising an amino acid sequence of SEQ ID NO: 3 and a heavy chain variable region comprising an amino acid sequence of SEQ ID NO: 6;

a light chain variable region comprising an amino acid sequence of SEQ ID NO: 3 and a heavy chain variable region comprising an amino acid sequence of SEQ ID NO: 4;

a light chain variable region comprising an amino acid sequence of SEQ ID NO: 2 and a heavy chain variable region comprising an amino acid sequence of SEQ ID NO: 6;

a light chain variable region comprising an amino acid sequence of SEQ ID NO: 1 and a heavy chain variable region comprising an amino acid sequence of SEQ ID NO: 6;

a light chain variable region comprising an amino acid sequence of SEQ ID NO: 3 and a heavy chain variable region comprising an amino acid sequence of SEQ ID NO: 5;

a light chain variable region comprising an amino acid sequence of SEQ ID NO: 2 and a heavy chain variable region comprising an amino acid sequence of SEQ ID NO: 5; or a light chain variable region comprising an amino acid sequence of SEQ ID NO: 1 and a heavy chain variable region comprising an amino acid sequence of SEQ ID NO: 5;

a light chain variable region comprising an amino acid sequence of SEQ ID NO: 74 and a heavy chain variable region comprising an amino acid sequence of SEQ ID NO: 76;

a light chain variable region comprising an amino acid sequence of SEQ ID NO: 75 and a heavy chain variable region comprising an amino acid sequence of SEQ ID NO: 77;

a light chain variable region comprising an amino acid sequence of SEQ ID NO: 147 and a heavy chain variable region comprising an amino acid sequence of SEQ ID NO: 140;

a light chain variable region comprising an amino acid sequence of SEQ ID NO: 75 and a heavy chain variable region comprising an amino acid sequence of SEQ ID NO: 141;

a light chain variable region comprising an amino acid sequence of SEQ ID NO: 75 and a heavy chain variable region comprising an amino acid sequence of SEQ ID NO: 140;

a light chain variable region comprising an amino acid sequence of SEQ ID NO: 148 and a heavy chain variable region comprising an amino acid sequence of SEQ ID NO: 142;

a light chain variable region comprising an amino acid sequence of SEQ ID NO: 149 and a heavy chain variable region comprising an amino acid sequence of SEQ ID NO: 143;

a light chain variable region comprising an amino acid sequence of SEQ ID NO: 150 and a heavy chain variable region comprising an amino acid sequence of SEQ ID NO: 144;

a light chain variable region comprising an amino acid sequence of SEQ ID NO: 151 and a heavy chain variable region comprising an amino acid sequence of SEQ ID NO: 145;

a light chain variable region comprising an amino acid sequence of SEQ ID NO: 152 and a heavy chain variable region comprising an amino acid sequence of SEQ ID NO: 146;

a light chain variable region comprising an amino acid sequence of SEQ ID NO: 318 and a heavy chain variable region comprising an amino acid sequence of SEQ ID NO: 317.

11. The CAR of any of embodiments 1-10, wherein the extracellular antigen-binding domain comprises a single-chain variable fragment (scFv).

12. The CAR of embodiment 11, wherein the scFv comprises a linker polypeptide between the light chain variable region (VL) and the heavy chain variable region (VH).

13. The CAR of embodiment 12, wherein the linker polypeptide comprises an amino acid sequence of SEQ ID NO: 7.

14. The CAR of any of embodiments 11-12, wherein the scFv comprises an amino acid sequence selected from the group consisting of SEQ ID NOS: 8-23, 169-184 and 340-343.

15. The CAR of any of embodiments 1-14, wherein the extracellular antigen-binding domain comprises a signal polypeptide.

16. The CAR of embodiment 15, wherein the signal polypeptide comprises an amino acid sequence of SEQ ID NO: 24.

17. The CAR of any of embodiments 4-16, wherein the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member component, and a combination thereof.

18. The CAR of embodiment 17, wherein the CD137 component comprises an amino acid sequence of SEQ ID NO: 27.

19. The CAR of embodiment 17 or embodiment 18, wherein the CD3z component comprises an amino acid sequence of SEQ ID NO: 28.

20. The CAR of any one of embodiments 17-19, wherein the intracellular signaling domain comprises an amino acid sequence of SEQ ID NO: 45.

21. The CAR of any of embodiments 2-20, wherein the transmembrane domain comprises a CD8a transmembrane region (CD8a-TM) polypeptide.

22. The CAR of embodiment 21, wherein the CD8a-TM polypeptide comprises an amino acid sequence of SEQ ID NO: 26.

23. The CAR of any of embodiments 4-22, further comprising a hinge region linking the transmembrane domain to the extracellular antigen-binding domain.

24. The CAR of embodiment 23, wherein the hinge region is a CD8a-hinge region.

25. The CAR of embodiment 24, wherein the CD8a-hinge region comprises an amino acid sequence of SEQ ID NO: 25, 279, 280, 281, or 282.

26. The CAR of any of embodiments 1-25, wherein the extracellular antigen-binding domain comprises an amino acid sequence selected from the group consisting of SEQ ID NOS: 29-44, 78-81, 221-236, and 273-308.

27. The CAR of any of embodiments 1-26, wherein the CAR comprises an amino acid sequence selected from the group consisting of SEQ ID NOS: 46-61, 82-85 and 205-220.

28. An isolated lymphocyte expressing the CAR of any of claims 1-27.

29. The isolated lymphocyte of embodiment 28, wherein the lymphocyte is a T lymphocyte.

30. The isolated lymphocyte of embodiment 28, wherein the lymphocyte is a natural killer (NK) cell.

31. An isolated nucleic acid molecule encoding the CAR of any of embodiments 1-30.

32. A vector comprising the nucleic acid molecule of embodiment 31.

33. A cell expressing the nucleic acid molecule of embodiment 31.

34. A pharmaceutical composition, comprising an effective amount of the lymphocyte of any of embodiments 28-30.

35. A pharmaceutical composition, comprising an effective amount of the lymphocyte of any of embodiments 28-30 and a pharmaceutically acceptable excipient.

36. The CAR of any of embodiments 1-27 or the pharmaceutical composition of embodiments 34 or 35 for use in therapy.

37. The CAR of any of embodiments 1-27 or the pharmaceutical composition of embodiments 34 or 35 for use in a method of treating a subject having cancer.

38. A method of treating a subject having cancer, the method comprising:
   administering a therapeutically effective amount of the lymphocyte of any of embodiments 28-30 to a subject in need thereof, whereby the lymphocyte induces killing of cancer cells in the subject.

39. The method of embodiment 38, or the CAR or the pharmaceutical composition for use in a method of embodiment 37, wherein the cancer is prostate cancer or androgen receptor-expressing breast cancer.

40. The method of embodiment 38, or the CAR or the pharmaceutical composition for use in a method of embodiment 37, wherein the cancer is prostate cancer.

41. The method of embodiment 38, or the CAR or the pharmaceutical composition for use in a method of embodiment 37, wherein the cancer is androgen receptor-expressing breast cancer.

42. A method of targeted killing of a cancer cell, the method comprising:
   contacting the cancer cell with the lymphocyte of any of embodiments 28-30, whereby the lymphocyte induces killing of the cancer cell.

43. The method of embodiment 42, wherein the cancer cell is a prostate cancer cell or androgen receptor-expressing breast cancer cell.

44. A method of detecting the presence of cancer in a subject, comprising:

(c) contacting a cell sample obtained from the subject with the CAR of any one of embodiments 1-27, thereby forming a CAR-cell complex, and (d) detecting the complex, wherein detection of the complex is indicative of the presence of cancer in the subject.

Preferably the embodiment is performed in vitro.

45. The CAR of embodiment 1, wherein the transmembrane domain comprises a CD8a-TM polypeptide comprising an amino acid sequence of SEQ ID NO: 26.

46. The CAR of embodiment 2, wherein the transmembrane domain comprises a CD8a-TM polypeptide comprising an amino acid sequence of SEQ ID NO: 26.

47. The CAR of embodiment 2 or 46, wherein the wherein the CD8a hinge region comprises an amino acid sequence of SEQ ID NO: 25.

48. The CAR of embodiment 2 or 47, wherein the CD137 component comprises an amino acid sequence of SEQ ID NO: 27.

49. The CAR of embodiment 2, 47 or 48, wherein the CD3z component comprises an amino acid sequence of SEQ ID NO: 28.

50. The CAR of embodiment 3, wherein
    (b) the CD8a-hinge region comprises an amino acid sequence that is at least
    90, 91, 92, 93, 94, 95, 96, 97, 98 or 99% identical to SEQ ID NO: 25, 269, 270, 271, or 272, preferably wherein the CD8a-hinge region comprises an amino acid sequence that is at least 90, 91, 92, 93, 94, 95, 96, 97, 98 or 99% identical to SEQ ID NO: 25;
    (c) the transmembrane domain comprises an amino acid sequence that is at least 90, 91, 92, 93, 94, 95, 96, 97, 98 or 99% identical to SEQ ID NO: 26; and/or
    (d) the intracellular signaling domain comprises a co-stimulatory domain having an amino acid sequence that is at least 90, 91, 92, 93, 94, 95, 96, 97, 98 or 99% identical to SEQ ID NO: 27, and a primary signaling domain having an amino acid sequence that is at least 90, 91, 92, 93, 94, 95, 96, 97, 98 or 99% identical to SEQ ID NO: 28.

51. The CAR of embodiment 3, wherein the CD8a hinge region comprises an amino acid sequence of SEQ ID NO: 25.

52. The CAR of embodiment 3, wherein the CD8a-TM polypeptide comprises an amino acid sequence of SEQ ID NO: 26.

53. The CAR of embodiment 3, wherein the CD137 component comprises an amino acid sequence of SEQ ID NO: 27.

54. The CAR of embodiment 3, wherein the CD3z component comprises an amino acid sequence of SEQ ID NO: 28.

55. The CAR of embodiment 3, wherein
    (b) the CD8a-hinge region comprises the amino acid sequence of SEQ ID NO: 25;
    (c) the transmembrane domain comprises the amino acid sequence of SEQ ID NO: 26; and
    (d) the intracellular signaling domain comprises a co-stimulatory domain comprising an amino acid sequence of SEQ ID NO: 27, and a primary signaling domain comprising an amino acid sequence of SEQ ID NO: 28.

56. The CAR of embodiments 45-55, wherein the extracellular antigen-binding domain comprises an amino acid sequence selected from the group consisting of SEQ ID NOS: 29-44, 78-81, 221-236, and 273-308.

57. The CAR of any of embodiments 45-55, wherein the CAR comprises an amino acid sequence selected from the group consisting of SEQ ID NOS: 46-61, 82-85 and 205-220.

58. An isolated lymphocyte expressing the CAR of any of claims 45-55.

59. The isolated lymphocyte of embodiment 58, wherein the lymphocyte is a T lymphocyte.

60. The isolated lymphocyte of embodiment 58, wherein the lymphocyte is a natural killer (NK) cell.

61. An isolated nucleic acid molecule encoding the CAR of any of embodiments 45-55.

62. A vector comprising the nucleic acid molecule of embodiment 61.

63. A cell expressing the nucleic acid molecule of embodiment 61.

64. A pharmaceutical composition, comprising an effective amount of the lymphocyte of any of embodiments 58-60.

65. A pharmaceutical composition, comprising an effective amount of the lymphocyte of any of embodiments 58-60 and a pharmaceutically acceptable excipient.

66. The CAR of any of embodiments 45-55 or the pharmaceutical composition of embodiments 64 or 65 for use in therapy.

67. The CAR of any of embodiments 45-55 or the pharmaceutical composition of embodiments 64 or 65 for use in a method of treating a subject having cancer.

68. A method of treating a subject having cancer, the method comprising:
    administering a therapeutically effective amount of the lymphocyte of any of embodiments 58-60 to a subject in need thereof, whereby the lymphocyte induces killing of cancer cells in the subject.

69. The method of embodiment 68, or the CAR or the pharmaceutical composition for use in a method of embodiment 67, wherein the cancer is prostate cancer or androgen receptor-expressing breast cancer.

70. The method of embodiment 68, or the CAR or the pharmaceutical composition for use in a method of embodiment 67, wherein the cancer is prostate cancer.

71. The method of embodiment 68, or the CAR or the pharmaceutical composition for use in a method of embodiment 67, wherein the cancer is androgen receptor-expressing breast cancer.

72. A method of targeted killing of a cancer cell, the method comprising: contacting the cancer cell with the lymphocyte of any of embodiments 58-60, whereby the lymphocyte induces killing of the cancer cell.

73. The method of embodiment 72, wherein the cancer cell is a prostate cancer cell or androgen receptor-expressing breast cancer cell.

74. A method of detecting the presence of cancer in a subject, comprising:
    (a) contacting a cell sample obtained from the subject with the CAR of any one of embodiments 45-55, thereby forming a CAR-cell complex, and
    (b) detecting the complex, wherein detection of the complex is indicative of the presence of cancer in the subject.

Preferably the embodiment is performed in vitro.

EXAMPLES

The following examples are provided to further describe some of the embodiments disclosed herein. The examples are intended to illustrate, not to limit, the disclosed embodiments.

Example 1: Construction and Expression of hK2 scFv CARs with 11B6 scFv hK2 CAR constructs comprising an scFv derived from the hK2-targeting antibody 11B6 were constructed as illustrated in FIG. 1A. Dynabeads Human T-Expander CD3/CD28 stimulated T cells were subjected to electroporation, then washed three times with OPTI-MEM (Invitrogen), and resuspended in OPTI-MEM at the final concentration of 50E6/ml. Subsequently, 0.1 ml of the cells (5E6) was mixed with 10 ug of IVT CAR encoding RNA and electroporated in a 2-mm Gap cuvette (Harvard Apparatus BTX, Holliston, Mass., USA) using BTX ECM830 (Harvard Apparatus BTX, Holliston, Mass., USA) by pressing the "pulse" button one time. (Settings: 500 Volts, 750 μsec Pulse Length and single(1) pulse, 100 mSec interval.) Post electroporation, the T cells were transferred to a 6-well plate and immediately put back into a 37° C. incubator. Primary human T cells were electroporated with no mRNA (MOCK) or 10 μg of mRNA expressing either an hK2 scFv CAR or irrelevant control CAR. 24 hours post-electroporation CAR surface expression was measured by flow cytometry following staining with 2 μg/ml biotinylated L-protein and streptavidin-conjugated PE (FIG. 1B) or biotinylated hK2 (1 μg/ml) and streptavidin-conjugated PE (FIG. 1C).

Twenty-four hours post electroporation, the T cells were counted. 1E5 T cells were collected for each. The cells were washed with FACS buffer twice using 200 μL/well of FACS buffer for microtiter plates, with the supernatant discarded. All wells were stained with 100 μl staining buffer containing Protein L (Genscript, Cat. No. M000971:500; 2 ug/ml), incubated for at least 30 minutes at 4° C. while being protected from light. The cells were washed by adding FACS Buffer twice, using 150 μL/well for microtiter plates with FACS buffer. Centrifugation at 400×g was performed for 4 minutes at room temperature. The supernatant was then discarded. All wells were stained with 1001 Streptavidin-R-Phycoerythrin (SA-PE;1:250) and Live/dead Fixable Near-IR Dead Cell Stain dye (1:1000), incubated for at least 30 minutes at 4° C. while being protected from light. The cells were then ready for flow cytometry analysis.

As shown in FIG. 1B, protein L staining was observed on both HK2 HL & LH CARs (41.4% and 66.3%, respectively), whereas only the background staining (~5.5%) was seen in the control T cells that were T cells without mRNA electroporation. As shown in FIG. 1C, CAR expression on primary human T cells also could be detected via J&J internal biotin-labeled recombinant HK2 protein (Biotin-Hk2 protein, Lot:20180810, CBIS ID:KL2W12.CB.003, 2.4 mg/ml, 1 mM Benzamidine) followed by SA-PE. As shown, T cells can efficiently express HK2 LH CAR (82.7%) as measured by flow cytometry, whereas only the background staining (~1.73% or 1.19%) was seen in the control T cells that were T cells without mRNA electroporation or undisclosed control CAR (non-HK2 specific). Results are shown for representative donor T cells and were reproducible in multiple donors (at least n=3). +Biotin label (EZ-Link™ Sulfo-NHS-LC-Biotin, Thermo Fisher Scientific cat #:21327)

Example 2: Tumor Cell Killing by hK2 CAR-T Cells

Co-culture for CellTrace Violet (CTV, Thermo Fisher Scientific Catalog number: C34557) based cytotoxicity assay using flow cytometer was performed as follows.

T cells were prepared as follows. Twenty-four hours post EP, T cells were counted and resuspended at the concentration needed for the most concentrated/desired E:T. The T cells were added at 100 μl/well of assay (2×10$^6$ cells/ml; plated 100 μl in a 10:1 E:T ratio, i.e., 2E5 T cells per 2E4 target cells). A stock of the 10:1 E:T concentration was made, with two-fold serial dilutions made with complete T cell media (Optimizer w/CTS, 5% Human Serum, 1% GlutaMax) to 0.3125:1. The T cells were plated (1001/well) in triplicate using a 96 well round bottom tissue culture treated plate.

CTV labeled target cells were prepared as follows. 20 μL DMSO was added to a vial of CTV staining solution. This stock solution was diluted into 20 mL of PBS (warmed to 37° C.) for a 5 μM staining solution. 10E6 tumor cells were collected, washed with PBS twice and resuspended in 4E6/ml (2.5 ml). An equal volume (2.5 ml) of CTV staining solution was added. The cells were incubated for 20 minutes in a 37° C. incubator. 40 ml PRMI+20% FBS was added to the cells to absorb any unbound dye. The cells were incubated for 5 minutes. The cells were centrifuged for 5 minutes at 400×g. The cell pellet was resuspended in pre-warmed RPMI+10% FBS medium. In the meantime, T cells were seeded at the desired E/T ratio described above. The tumor cell lines Vcap (HK2+) and DU145(HK2−) were recounted, and then the cells were resuspended in 2E5/ml and 1001 in duplicate. The cells were co-incubated with labelled tumor cell lines in a flat-bottom 96-well plate.

A cytotoxicity assay was performed as follows using a flow cytometer. After 20 hours of co-culture, all of the cells were transferred to a U-bottom 96-well plate and washed. After 20 hours of co-culture all of the cells were collected from a flat-bottom 96-well plate and transferred to a U-bottom 96-well plate, and then washed. 30 μl of 0.25% trypsin was added to all the wells and incubated for 5 minutes in a 37° C. incubator. After 5 minutes, all of the tumor cells were collected to a U-bottom 96-well plate. The cells were centrifuged and washed for 5 minutes at 400×g twice. The cell pellet was then resuspended in diluted (1:1000) LIVE/DEAD™ Fixable Near-IR staining dye (100 μl). The cells were incubated for 30 mins at 4° C., and washed with FACS buffer twice by centrifuging the cells for 5 minutes at 400×g. After washing, all of the cells were fixed for 10 minutes using 100 μl of BD Cytofix™ Fixation Buffer (50 μl FACS buffer+50 μl Fixation Buffer). The cells were centrifuged and washed for 5 minutes at 400×g once. The cell pellet was resuspended in FACS buffer. Stained samples were analyzed by multicolor flow cytometry after the end of the incubation period.

The percentage of cytotoxic activity was calculated using the following equation:

% specific death=% Near IR+CTV+(dead)cells−% spontaneous Near IR+CTV+/(100%−% spontaneous Near IR+CTV+(dead)cells)×100%.

Twenty-four hours after transient transfection, target cells (Vcap and DU145) were labeled with Cell Trace Violet (CTV) fluorescent dye and then co-cultured with hK2 CAR-T cells. Mock T cells served as negative effector controls. Cells were co-cultured for 20 hours at the indicated effector-to-target cell (E/T) ratio shown in FIG. 2. Percent killing is the ratio of the absolute number of live (viability dye negative) target (CTV positive) cells remaining in the co-culture relative to the number of live targets cultured without CAR-T cells. As shown, hK2 CAR LH T cells specifically and efficiently lysed the hK2(+) human prostate cancer cell lines VCap cells, but not K2 (−) DU145 cells E/T ratios of 10:1 to 0.3125:1, whereas only the background cytotoxicity was seen in the T cells that were Mock or hK2 HL CAR.

hK2-specific CAR-T cells were also tested for real-time cytotoxicity using xCELLigence as a real-time cell analysis system as a potency assay for immune cell-mediated cytolysis of target cells.

50 μL of target cancer cell culturing media was added to each well of the 96-well E-Plates (ACEA Biosciences), and the background impedance was measured and displayed as a Cell Index. Then, adherent target cells VCap and DU145 were dissociated and seeded at a density of 5E4 (VCap), 5E3 (DU145) cells/well of the E-Plate in a volume of 100 μL, and allowed to passively adhere on the electrode surface. Post seeding, the E-Plate was kept at ambient temperature inside a laminar flow hood for 30 minutes and then transferred to the RTCA MP instrument inside a cell culture incubator. Data recording was initiated immediately at 15-minute intervals for the entire duration (96 hours) of the experiment.

At the time treatment was applied (24 hours post cancer cells seeding), data acquisition was paused, 50 μL of media was removed from each well, and effector CART cells were added at different effector to target (E:T) ratios in a volume of 50 μL. HK2 CAR+ and undisclosed control CAR (non-HK2 specific) T cells were resuspended. Two-fold dilutions were then performed in duplicate in a 96-well plate (from 5:1 to 0.156:1 E/T ratio). Target plus Mock effector controls (no RNA electroporation T cells) were also added to the target cells.

Figure 3A:
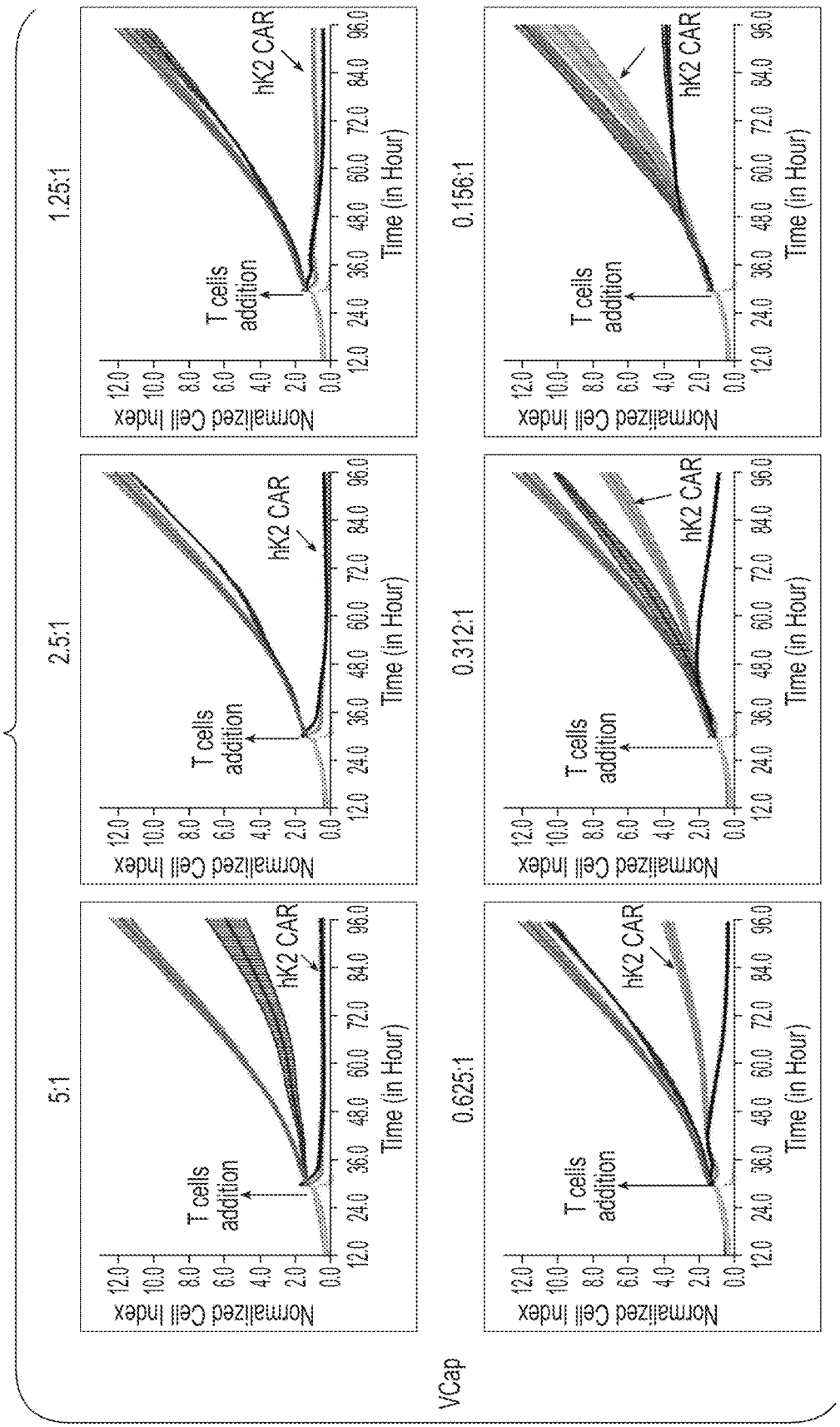
FIGS. 3A-3B show real-time hK2-specific CAR-T cell-mediated cytotoxicity. Normalized cell index (CI) plot for target cells (FIG. 3A) VCap (5E4) and (FIG. 3B) DU145 (5E3) incubated with Mock, 10 µg mRNA electroporated (24 hours post transfection) hK211B6 CAR LH or control CAR-T cells at different E:T ratios for approximately 72 hours. When seeded alone, target cells adhere to the plate and proliferate, increasing the CI readout. When T cells were added to target cells, hK2 CAR- and control CAR-T cells caused hK2 (+) VCap cell cytolysis and subsequent progressive decrease in CI at an E/T ratio from 5:1 to 0.156:1. The reduction in CI value after addition of effector cells reflects the loss of viability of target cells. A parallel experiment using hK2(−) DU145 target cells was also performed, as shown in (FIG. 3B); at the E:T ratios tested in this experiment, hK2 and control CAR T cells did not reduce CI after addition which displayed no cytolytic activity. The Y-axis is the normalized CI generated by the RTCA software and displayed in real time. X-axis is the time of cell culture and treatment time in hour. Mean values of the CI were plotted±standard deviation.
Figure 3B:
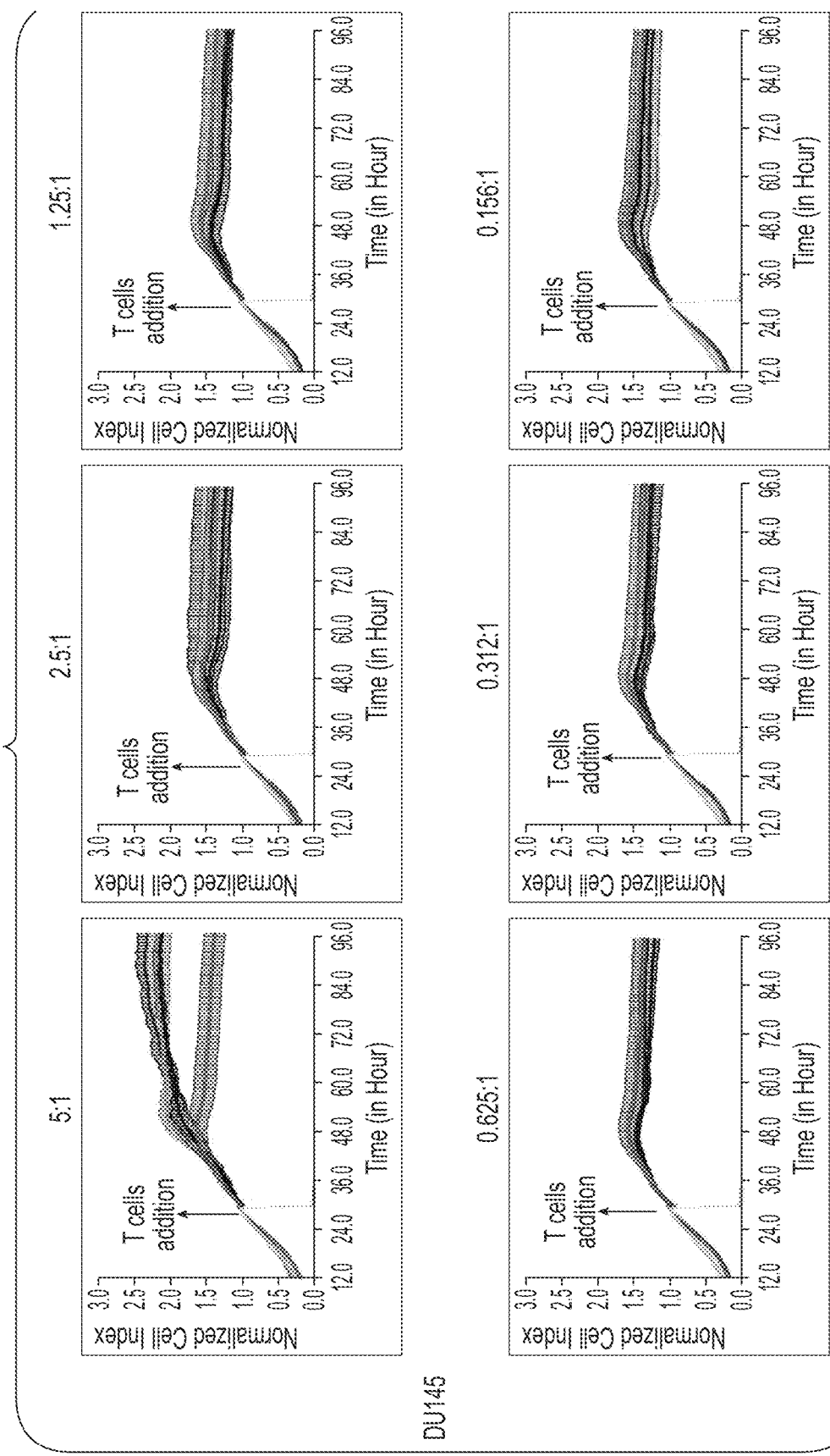

Target cells VCap (5E4) and DU145 (5E3) incubated with Mock, 10 μg mRNA electroporated (24 hours post transfection) hK211B6 CAR LH or control CAR-T cells at different E/T ratios for approximately 72 hours. Normalized cell index (CI) plots for VCap and DU145 are shown in FIG. 3A and FIG. 3B, respectively. When seeded alone, target cells adhere to the plate and proliferate, increasing the CI readout. When T cells were added to target cells, hK2 CAR- and control CAR-T cells cause cell cytolysis and subsequent progressive decrease in CI.

Example 3: Cytokine Production of hK2 CAR-T Cells

Without wishing to be bound by theory, IFN-γ produced by cytotoxic T cells could allow for exertion of immune surveillance of tumors, which can directly inhibit proliferation and induce apoptosis of some malignancies in vivo and in vitro. To determine whether hK2 CAR-modified human T cells were able to recognize and be activated by hK2 (+) tumor cells, the supernatant was collected from xCELLigence-based killing assay, as described in Example 2 and FIGS. 3A-3B. After about 70 hours co-culture, the supernatant was collected and assayed by ELISA according to the directions provided with the ELISA kit (Human IFN-γ ELISA MAX™ Deluxe, BioLegend, Cat #:430106).

Figure 4:
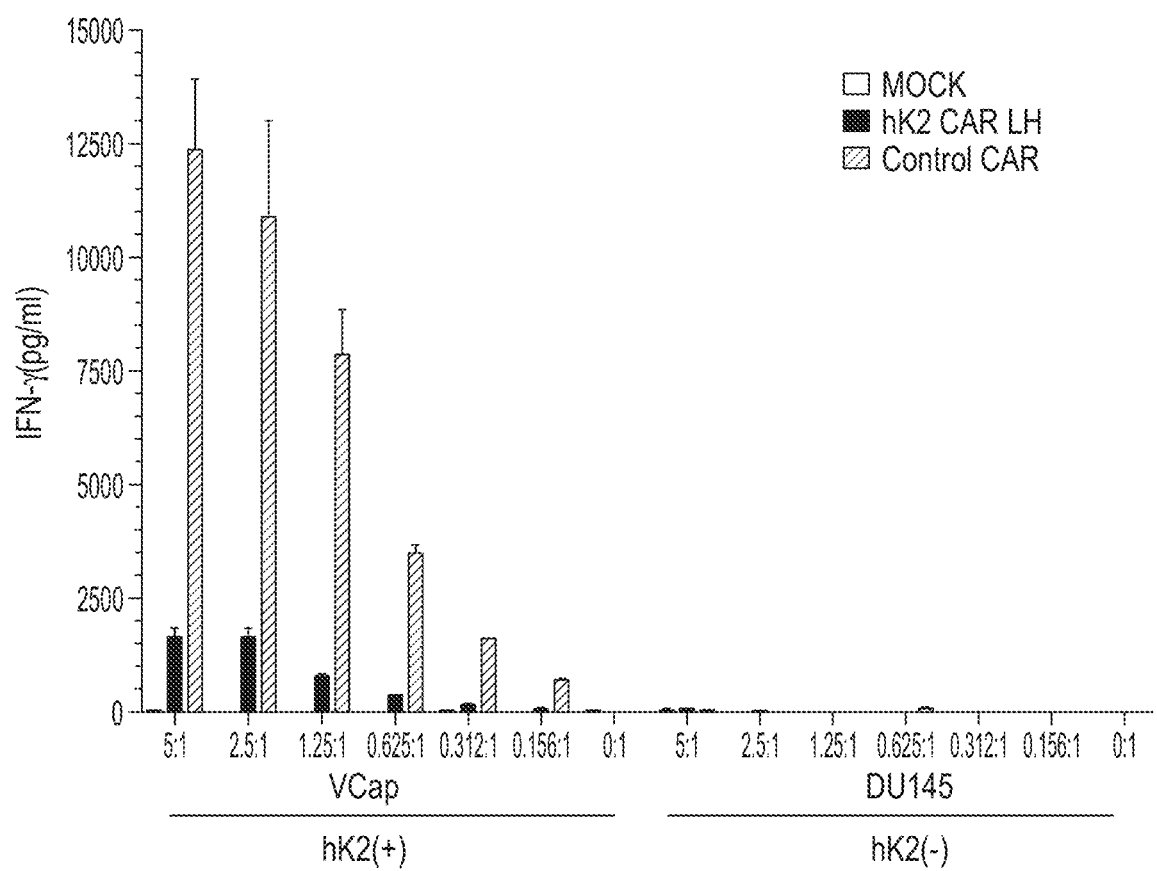
FIG. 4 shows Th1 cytokine interferon-γ (IFN-γ) production of antigen-stimulated CAR-T cells. Supernatant was collected from xCELLigence based killing assay (see FIGS. 3A-3B) approximately 70 hours co-culture (VCap #5E4, DU145 #5E3). hK2 CAR LH- and Control CAR modified T cells secrete IFN-γ during co-culture with hK2-expressing VCap cells, but not hK2-negative DU145 cells. Mean IFN-γ concentration±standard deviation (pg/ml) from duplicate cultures is shown.

Th1 cytokine interferon-γ (IFN-γ) production of antigen-stimulated CAR-T cells is shown in FIG. 4. hK2 CAR LH- and control CAR modified T cells secrete IFN-γ during co-culture with hK2-expressing VCap cells in a E:T ratio-dependent manner, but not hK2-negative DU145 cells. Undisclosed control CAR secreted much higher amount of IFN-γ due to the much higher antigen expression level than hK2. Mean IFN-γ concentration SD (pg/ml) from duplicate cultures is shown.

Example 4: Generation and Characterization of Thermally Stabilized scFvs CAR Constructs The anti-HK2 antibody clone 11B6 was identified by immunization of BALB/c mice with recombinant HK2 by Vaisanen et al (Clinical Chemistry 50:9, 1607-1617 (2004). Humanization of the murine-derived clone 11B6 was performed by the method described in Singh et al., MAbs. 2015; 7(4):778-91. Because the exodomain of wild-type 11B6 as scFv did not retain binding at elevated temperature (55° C.), humanization was performed as scFv and the *E. coli*-expressed supernatants from the humanized variants were incubated at 60° C. for 15 minutes, followed by screening for binding to recombinant HK2 using ELISA. Ten hK2-targeting CARs containing a thermally stabilized scFv derived from the antibody 11B6 were generated.

Description and SEQ ID NOS of the ten CAR constructs containing thermally stabilized scFvs are provided in Table 1.

TABLE 1

CAR constructs with 11B6 thermally stabilized scFvs

| # of construct | Description | SEQ ID NO |
|---|---|---|
| 1 | HL_HCG5_LCD6_20AA | 46 |
| 2 | HL_HCG5_LCHumanized_20AA | 47 |
| 3 | HL_HCF3_LCB7_20AA | 48 |
| 4 | HL_HCG5_LCB7_20AA | 49 |
| 5 | LH_LCD6_HCG5_20AA | 50 |
| 6 | LH_LCHumanized_HCF3_20AA | 51 |
| 7 | LH_LCHumanized_HCG5_20AA | 52 |
| 8 | LH_LCB7_HCF3_20AA | 53 |
| 9 | LH_LCB7_HCG5_20AA | 54 |
| 10 | LH_LCD6_HCF3_20AA | 55 |

To identify different scFv based CAR with antigen independent activation via Jurkat-Lucia™ NFAT Cells (JNLs). Nuclear factor of activated T-cells (NFAT) is a family of transcription factors first identified as a regulator of immune cells. T cell activation leads to calcium influx, activating calcineurin that dephosphorylates serine rich nuclear localization signal at the N-terminus of NFAT, leading to nuclear import of NFAT. Without wishing to be bound by theory, tonic signaling due to scFv clustering could be subsequently detected by Firefly luciferase driven by NFAT promoter in JNL reporter cell line.

JNL cells, i.e., Jurkat cells containing the luciferase gene driven by the signaling-responsive NFAT promoter, were transduced with the various CAR constructs. Binding between the CAR construct and its cognate cellular antigen (hK2 on target cells) leads to luciferase expression in the JNL cells.

Lentiviral transduction was performed as follows. JNL cells were harvested and resuspended to 1E6/ml. 500 μl of JNL cells and lentiviral virus were added at a MOI of 3, and mixed by pipetting up and down. The mixture was incubate in a 37° C. incubator for 24 hours. 500 μl JNL media was added to each well, with culturing continued in a 37° C. incubator. The cells were transferred to a T25 flask on day 4. At days 5-6, transduction validation was performed. 150 μl of cells was harvested to examine CAR expression via appropriate detection reagent for the specific CAR you are using (e.g. biotin-hk2 Protein is used to detect hk2 CAR). The JNL cells were maintained at 5×10$^5$/ml until enough cells were obtained to either freeze down or use in the assay.

The thermally stabilized scFvs CARs were evaluated in a JNL reporter assay for antigen-dependent activity. Jurkat cells containing the luciferase gene driven by the signaling-responsive NFAT promoter (termed JNL cells) were transduced with the various hK2 CAR constructs. The assay was performed as follows. Coculturing with target cell lines was performed at an effector to target ratio of 2:1. The JNL cells were spun down to remove any secreted luciferase in the medium; the JNL cells were then resuspend in fresh media at 4×10⁵/ml. The cells were harvested. Then, both antigen-positive and antigen-negative target cell lines were prepared at 2E5/ml. 100 μl JNL was added to 100 μl target cells. For the JNL-only control, 100 μl media was added instead of target cells. For positive control, JNL cells only or CAR JNL cells were added to 1× Cell Stimulation Cocktail and incubate in a 37° C. incubator for 24 hours. 150 μl of the supernatant was harvested into a 96-well plate and centrifuged to remove cells. 100 μl of supernatant was transferred from the plate to a solid bottom black plate. Then, 100 μl QUANTI-luc lucia detection reagent was added. The mixture was incubated at room temperature for 5 minutes before reading with Envision multiplate reader.

Figure 5A:
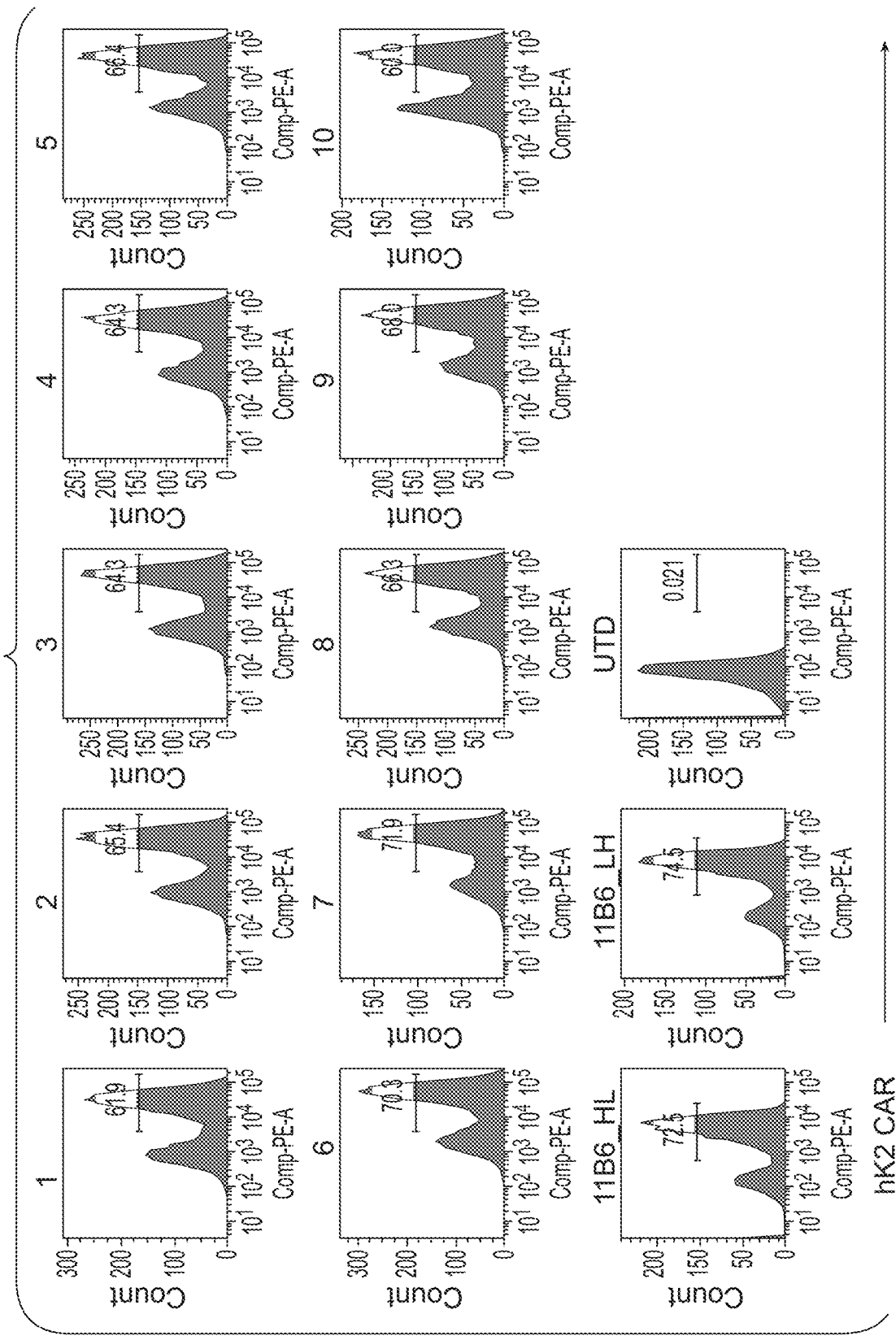

CAR expression was determined by biotinylated hK2 followed by streptavidin-conjugated PE, with the results shown in FIG. 5A. CAR expression in transduced JNL cells was confirmed for all of the selected clones with 60-75% of cells showing detectable expression across the different clones and parental 11B6 CARs. JNL cells containing the indicated CAR clones and un-transduced JNL cells (UTD) were co-cultured with target cells lines (VCap or DU145 cells) and luciferase activity was measured as luminescence intensity. Clones were considered active when the luminescence intensity exceeded 1.5-fold the level of UTD cells in the presence of antigen-expressing cells.

The binding between the CAR construct and its cognate cellular antigen (hK2 on target cells) leads to luciferase expression in the JNL cells (FIG. 5B). JNL cells containing the indicated CAR clones and JNL cells (untransduced, hereinafter "UTD") were co-cultured with target cells lines (VCap or DU145 cells) and luciferase activity was measured as luminescence intensity. Clones were considered active when the luminescence intensity exceeded 1.5-fold the level of UTD cells in the presence of antigen-expressing cells. No antigen-dependent activation was found for all the 10 clones and parental 11B6 CAR HL and LH.

Example 5: Expression of Thermally Stabilized scFvs CARs on T Cells

To evaluate the function of thermally stabilized 11B6 CARs T cells and pick top candidate construct, 11B6 thermally stabilized and parental scFvs based CAR T cells were generated using lentiviral transduction. Primary human T cells were transduced with 11B6 thermally stabilized and parental scFvs based CAR lentivirus with a multiplicity of infection (MOI) of 3. CAR expression was determined by biotinylated hK2 (1 μg/ml) followed by streptavidin-conjugated PE 14 days post transduction.

The experimental protocol is as follows.

Lentiviral packaging was undertaken. 14E6 Lenti-X™ 293T cells were seeded per 150 mm² round-bottomed Corning™ BioCoat™ Collagen I coated culture dish, and incubated at 37° C. overnight using DMEM+10% FBS medium.

With Lenti-X™ 293T cells at the ideal confluency of 80-85%, the following was prepared. Culture media was replaced with 21 ml 293T growth media. Lipofectamine 2000 was diluted at room temperature and equilibrated OptiMEM. Diluted Lipofectamine 2000 was added to mixed plasmids drop-wise, and mixed well. The mixture was incubated at room temperature for 25 minutes. The transfection mixture was added to Lenti-X 293T cells dropwise, with the plate gently swirled to mix. The mixture was incubated in a 37° C. incubator. Lentivirus was harvested 24 and 48 hours post transfection. The above reagents are summarized in the Table 2.

TABLE 2

| Reagent | Amount per 15 cm dish |
|---|---|
| pMDLg/p | 18 μg |
| pRSV.Rev | 18 μg |
| pMD2.G | 7 μg |
| Transfer (CAR) plasmid | 15 μg |
| OptiMEM | 1500 μl |

Lentiviral concentration was performed as follows. Lentivirus-containing supernatants were harvested and centrifuged at 500×g for 10 min if excessive 293T cells are floating around before filtering through 0.45 μm cellulose acetate filters. Supernatant was transferred to a sterile container, combined with 1/3 volume of Lenti-X Concentrator (Clontech, Cat. #631232), and mixed by gentle inversion. The mixture was incubated at 4° C. overnight. The sample was centrifuged at 1,500×g for 45 minutes at 4° C., with a white pellet visible after centrifugation. The supernatant was carefully removed without disturbing the pellet. Residual supernatants were removed with a pipette after a brief centrifugation at 1,500×g. The pellet was gently resuspended in 1/10 of the original volume using cold T cell growth. The virus was aliquoted in 200 μl and immediately stored at −80° C.

Viral titering was performed as follows. Log-phase SupT1 was grown in complete RPMI. 100 μl 20,000 SupT1 cells/ml were seeded per well in a flat 96-well plate. Virus titration was then performed in 96-well round bottom plates). 100 μl media was added to all the wells in the plate. A virus aliquot was thawed from −80° C. freezer with one's hands. The aliquot was pipetted up and down to mix well, with 50 μl virus added to the first well, followed by thorough mixing. A serial 1:3 dilution was performed by pipetting 50 μl virus to the next well. Then, 50 μl media was added to primary Ab only, secondary Ab only, and un-transduced controls. 50 μl of each was transferred from the titration plate to 100 μl SupT1 cells in the assay plate with a multi-channel pipette, and incubated at 37° C. overnight. 100 μl of pre-warmed media was added to each sample, and incubated another two days. The transduction efficiency was determined by flow cytometry. Samples were transferred to a round bottom 96 well plate and spun at 1400 RPM for 3 minutes. The supernatant was discarded quickly, followed by blotting to remove excessive media in the hood. The wash was repeated with 150 μl FACS buffer. A staining protocol appropriate for CAR constructs was then undertaken. Samples were resuspended in 150 μl FACS buffer before flow cytometry analysis.

Viral titer calculation: Titer=(% CAR positive/100)× 2×10⁴×20×dilution factor

To exclude multiple copy integrations, titers with the closest transduction to 20% is used. T-cell activation, transduction and expansion was performed as follows. A vial of naïve T cells was thawed in a water bath and added dropwise to a 15 ml conical tube containing 9 ml of pre-warmed T-cell media (TCM CTS OpTmizer T Cell Expansion SFM+ 5% human serum+IL-2100 IU/ml). The cryovial was washed with 1 ml of media to recover maximum number, and spun at 300×g for 8 minutes at room temperature. The pellet was resuspended in fresh 10 ml TCM, counted, and resuspended to 1E6 cells per milliner. 5E5 cells were added per well in 24-well plate. 1.5×10⁶ CD3/CD28 beads were added per well in 500 µl volume such that the total volume was 1 ml per well. Twenty-four hours post activation, virus was thawed at room temperature. Virus was added at a multiplicity of infection (MOI) of 3, gently swirled to mix, and returned to the plate at the incubator. (The lentiviral functional titer was previously determined with SupT1 titer assay.) One well was reserved for Untransduced (UTD) in which is no virus added.

Twenty four hours post-transduction, 1 ml TCM was added to each well. Penicillin-Streptomycin was added from this point onward (Day 2). On days 3-5, 4 ml TCM was added for each 2 ml of cells and transferred to a T25 tissue culture treated flask. The flasks were placed horizontally in the incubator (Day 3). Equal volume of TCM was added for T-cell culture (Day 4). On days 5-14, the cells were checked every other day, with the viability, size and total cell count recorded. The cell density was adjusted to one million cells per mL. The ideal time of harvest is donor dependent and determined by the cell size and the fold of expansion. Cells were generally frozen when the cell size was less than 8 m based on the MOXI flow cell counter with the 100 to 200-fold of expansion.

Lentiviral transduction efficiency was checked on harvest day as follows. Cultures were mixed well. 100 µl of T-cells was harvested to a corresponding well in 96-well plate with 1001 µl FACS Buffer, mixed, and spun at 1300 RPM for 3 minutes at room temperature. The cells were resuspended in 2001 µl FACS buffer and centrifugation repeated at 4° C. The cells were resuspended in 100 µl of Biotin labeled hK2 (1 µg/ml diluted in FACS buffer) and incubated on ice for 30 minutes. 100 µl of FACS buffer was added, and spun washed at 4° C. The spin wash was repeated after adding another 200 µl FACS buffer. Staining with 100 µl of master solution containing secondary antibody SA-PE (1:250), live dead fixable stain (1:500), αCD3, αCD4 and αCD8 antibodies was performed on ice for 30 minutes. 100 µl FACS buffer was added and spun wash at 4° C., discarded and resuspended in 200 µl FACS buffer before spin washing at 4° C. The samples were resuspended in 100 µl FACS Buffer before analyzing by flow cytometry.

Figure 6:
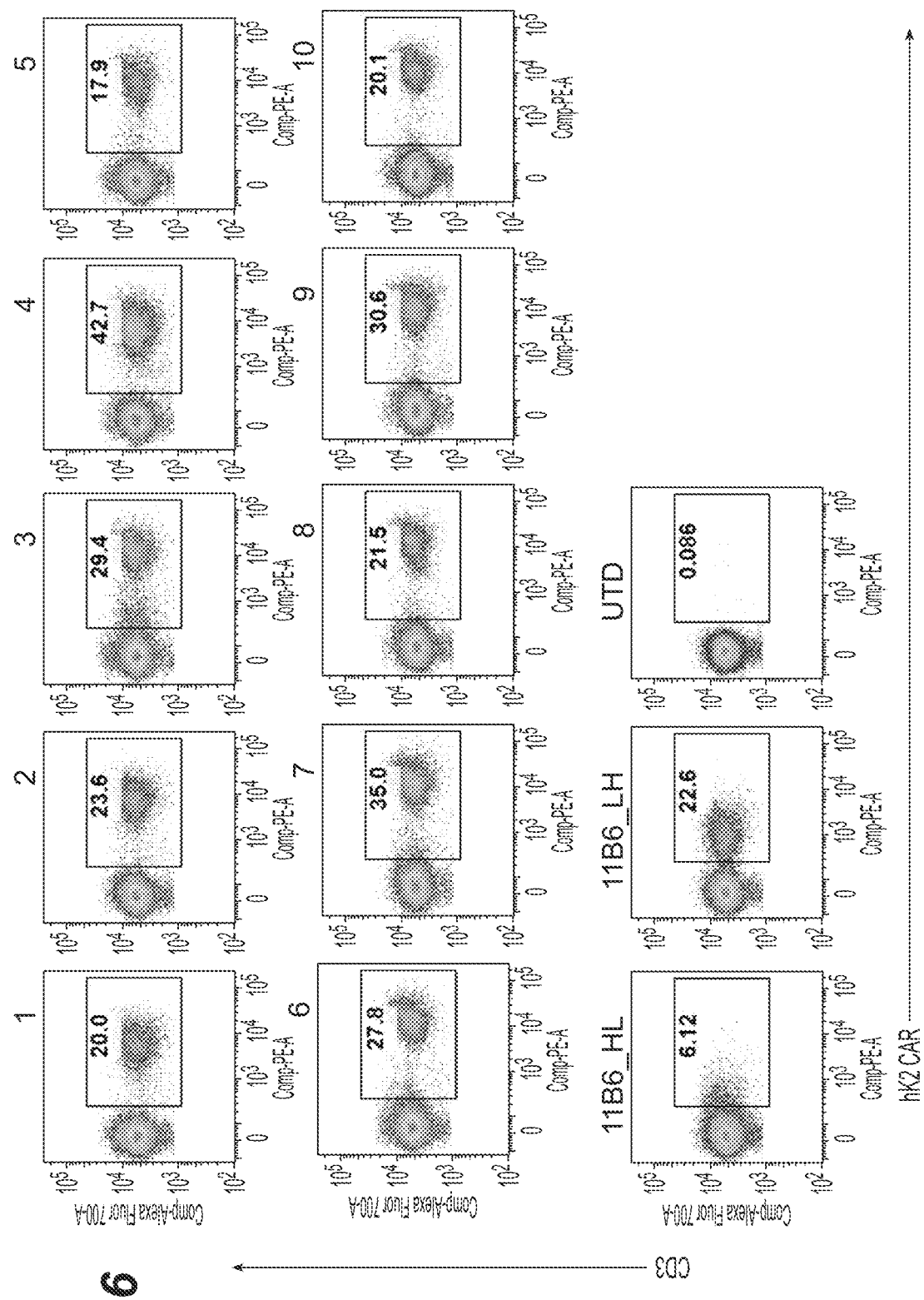
FIG. 6 shows hK2 CAR expression on T cells-surface. Primary human T cells were transduced with 11B6 thermally stabilized and parental scFvs based CAR lentivirus (multiplicity of infection (MOI): 3) and CAR expression was determined by biotinylated hK2 (1 µg/ml) followed by streptavidin-conjugated PE 14 days post transduction.

Cell harvest and freezing was performed as follows. The final cell count was determined. The culture was harvested and centrifuged at 300×g for 10 minutes at room temperature. The culture was resuspended in a smaller volume of media to fit in a 50 ml conical tube. The tubes were placed in magnets at 4° C. for 10 minutes to "de-bead". The cells were gently transferred from the tube to minimize disturbing the beads/magnet, and the exact volume recorded. Counting was repeated. Centrifugation was performed at 300×g for 10 minutes, with the supernatant discarded. Cells were frozen in CS-10 CryoStor® cell cryopreservation media in a cooling container. The containers were immediately transferred to −80° C. for 24-48 hours before permanent storage in liquid Nitrogen. The results are shown in FIG. 6, and confirm hK2 CAR expression on the surface of the transduced T cells. Summary of the percentage of hK2 CAR+ T cells (% positive) detected by each of the 10 thermally stabilized clones and parental 11B6 HL & LH analyzed is provided. As shown, different clones have different CAR expression level, ranges from 17.9% to 42.7%. All CAR T cells were normalized to the equal CAR+ T cells for subsequent functional assays.

Example 6: Tumor Cell Killing by 11B6 Thermally Stabilized scFv CAR-T Cells

Figure 7A:
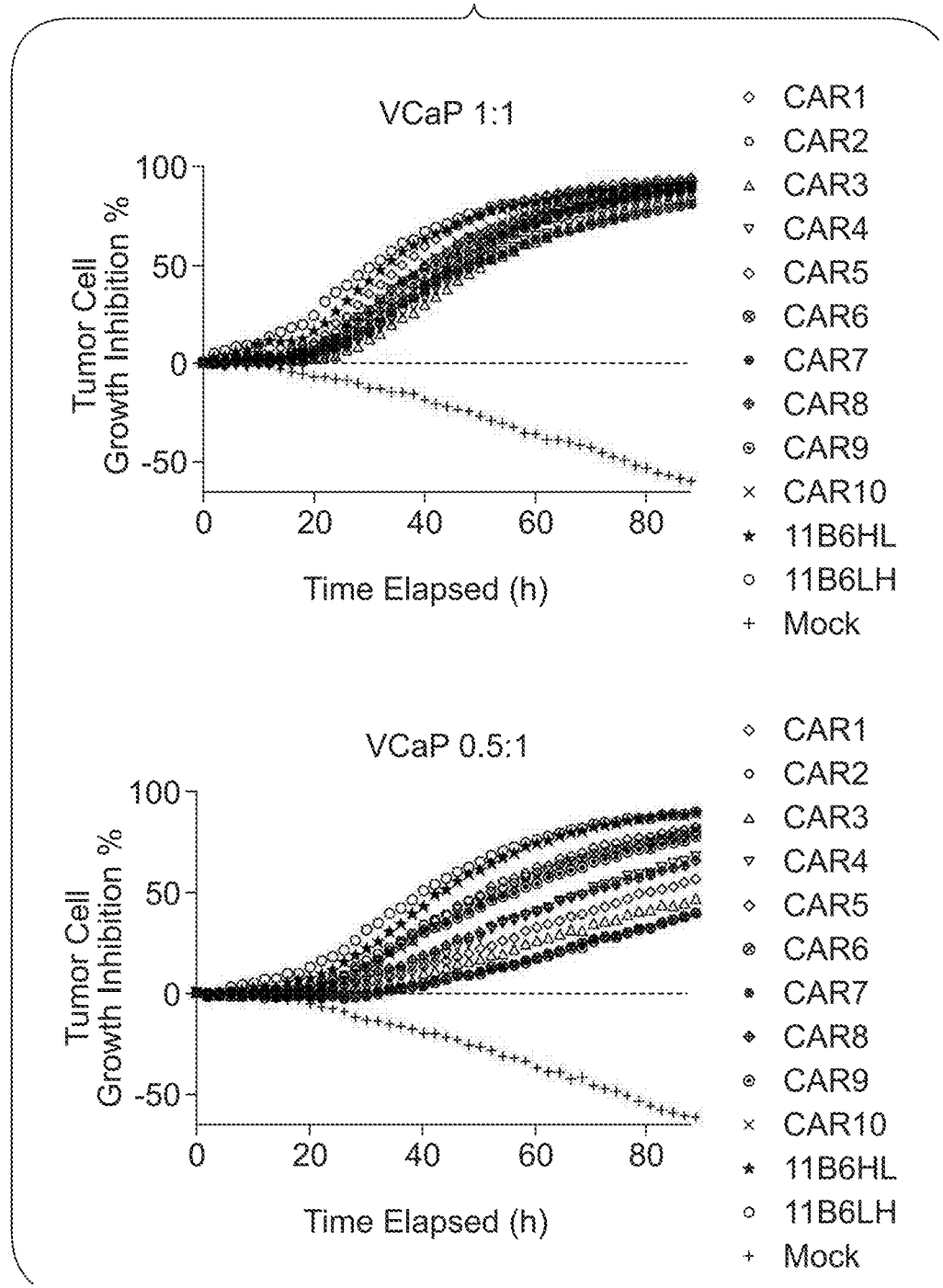
FIGS. 7A-7B show that 11B6 thermally stabilized scFv CAR-T cells were evaluated in the real-time IncuCyte killing assay for antigen-dependent cytotoxicity. Thermally stabilized hK2 CAR-T cells and parental 11B6 CAR-Ts were co-incubated with VCaP cells (FIG. 7A) and PC3 cells (FIG. 7B) for 88 hours. Effector-to-target (E/T) ratio was calculated based on CAR expression data (see FIG. 6). Target cells were stably expressing a red nuclear dye which was measured by IncuCyte imaging system in a real-time fashion. Tumor cell growth inhibition (%)=(Initial Viable Target Cell Number-Current Viable Target Cell Number)/Initial Viable Cell Number*100(%).
Figure 7B:
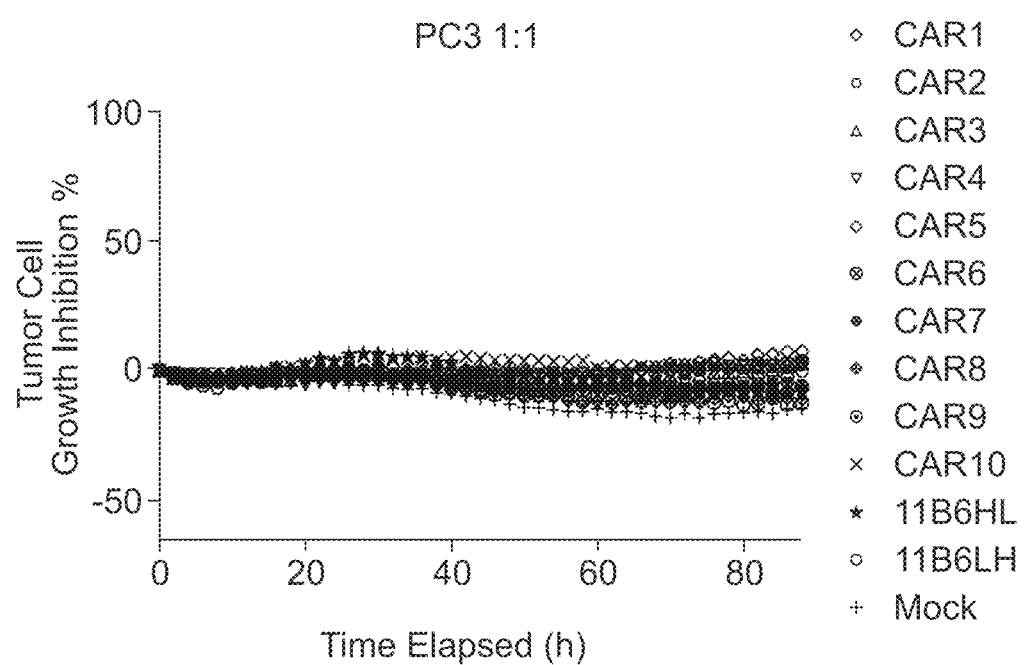
Figure 7C:
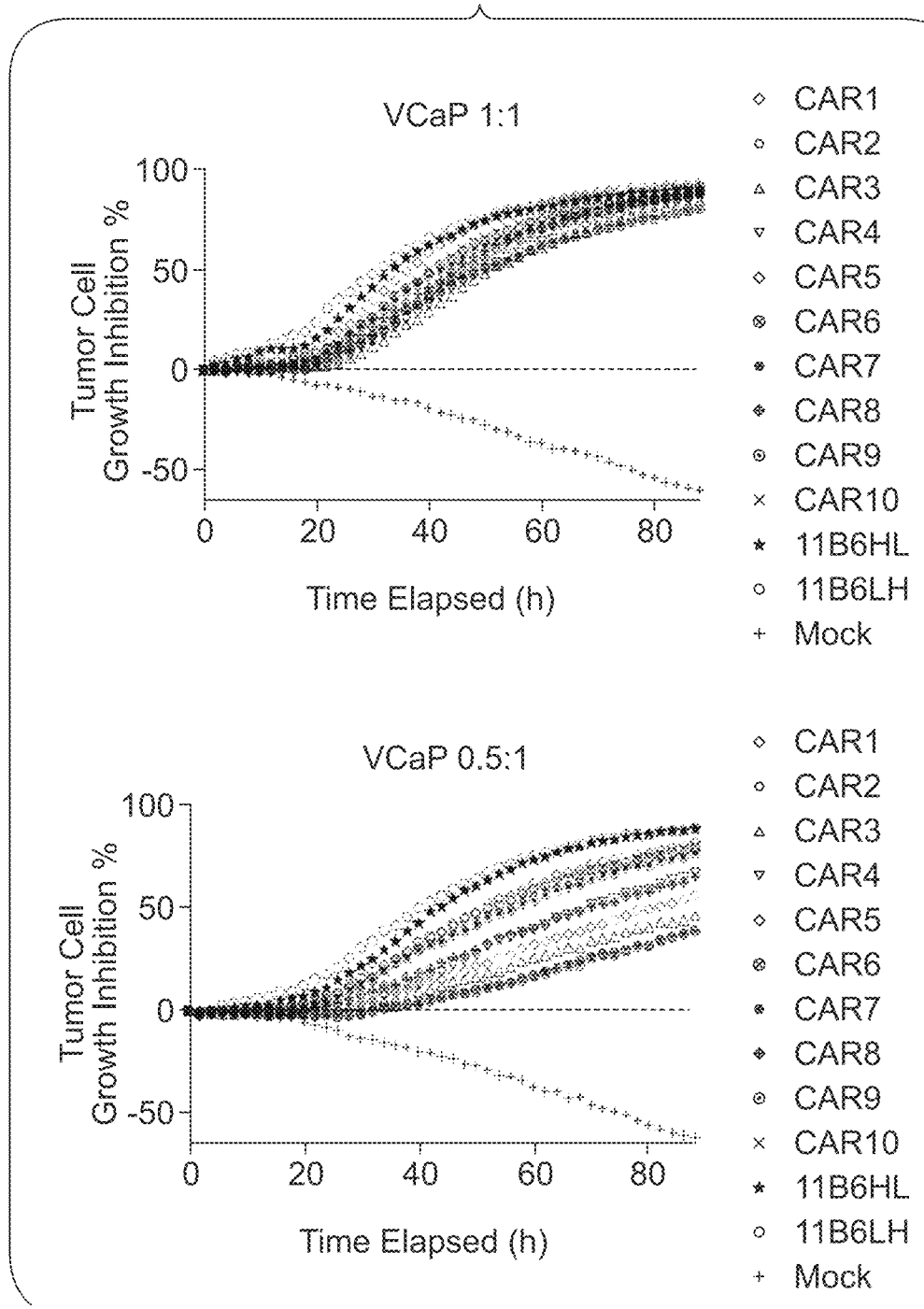
FIG. 7C shows percent tumor cell growth inhibition of hK2 positive VCaP cells at effector:target ratio of 1:1 or 0.5:1 by T cells transduced with CAR1-10 or the parental 11B6_HL or 11B6_LH. in the real-time IncuCyte killing assay assessing antigen-dependent cytotoxicity. Tumor cell growth inhibition (%)=(Initial Viable Target Cell Number-Current Viable Target Cell Number)/Initial Viable Cell Number*100(%).
Figure 7D:
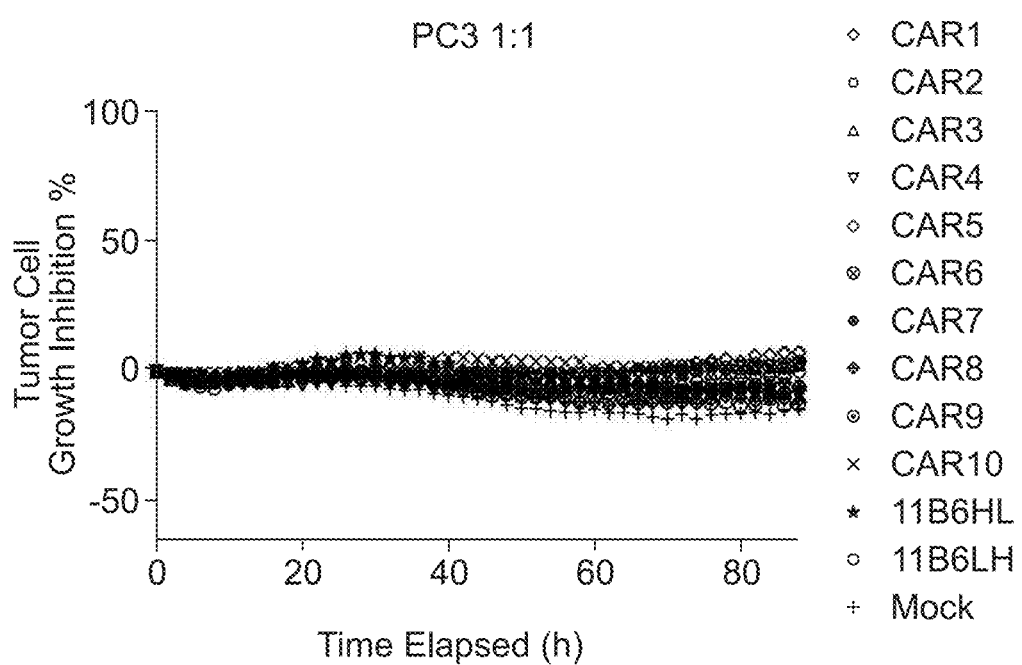
FIG. 7D shows percent tumor cell growth inhibition of PC3 cells at effector:target ratio of 1:1 by T cells transduced with CAR1-10 or the parental 11B6_HL or 11B6_LH. in the real-time IncuCyte killing assay assessing antigen-dependent cytotoxicity. Tumor cell growth inhibition (%)=(Initial Viable Target Cell Number-Current Viable Target Cell Number)/Initial Viable Cell Number*100(%).
Figure 7E:
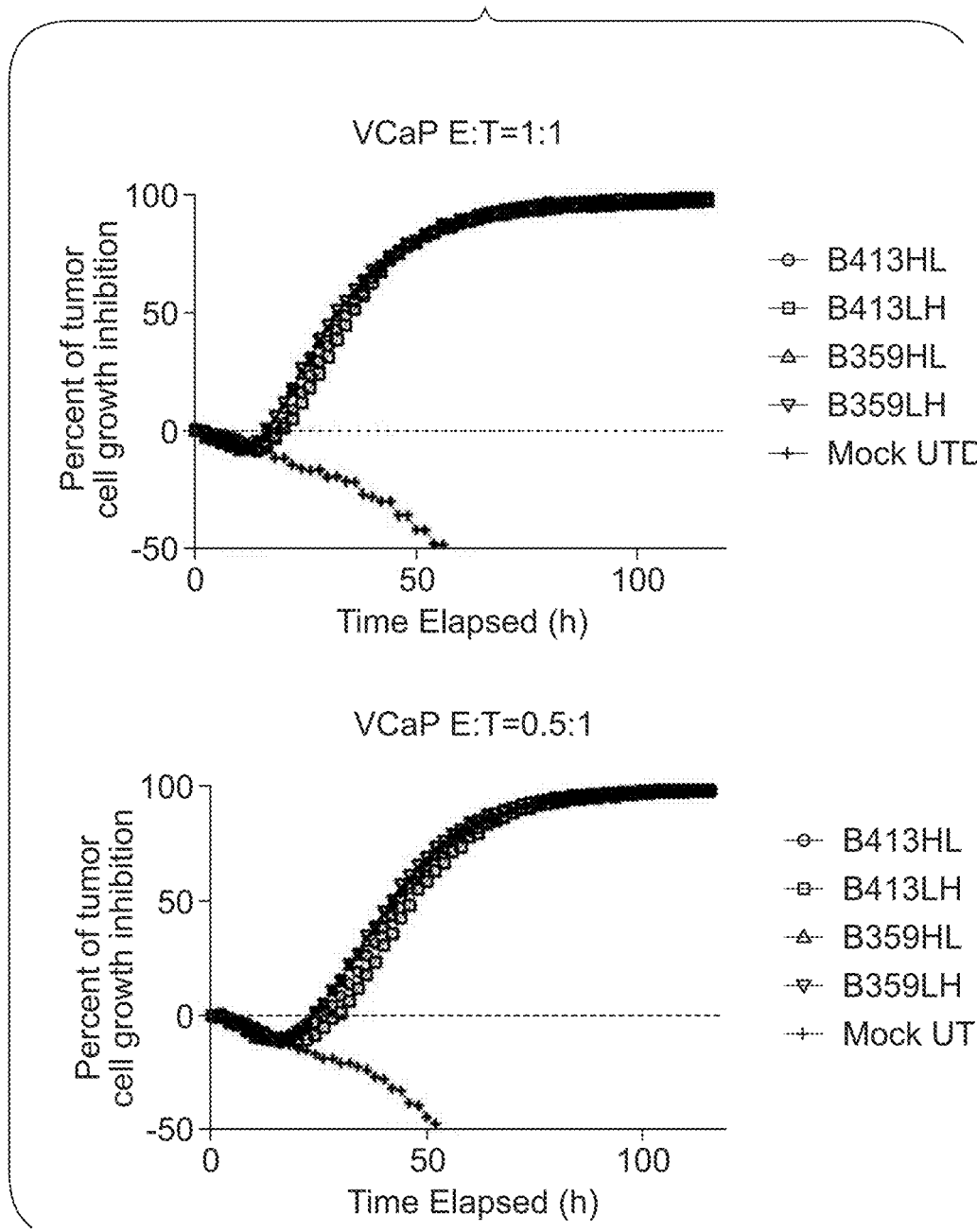
FIG. 7E shows percent tumor cell growth inhibition of hK2 positive VCaP cells by CAR T cells transduced with CAR17 (B413HL in the FIG), CAR18 (B413LH in the FIG), CAR19 (B359HL in the FIG) and CAR20 (B359LH in the FIG) in the real-time IncuCyte killing assay assessing antigen-dependent cytotoxicity. Tumor cell growth inhibition (%)=(Initial Viable Target Cell Number-Current Viable Target Cell Number)/Initial Viable Cell Number*100(%).

11B6 thermally stabilized scFv CAR-T cells were evaluated in the real-time IncuCyte killing assay for antigen-dependent cytotoxicity. Thermally stabilized hK2 CAR-T cells and parental 11B6 CAR-T cells were co-incubated with VCaP cells (FIG. 7A) and PC3 cells (FIG. 7B) for 88 hours. Effector-to-target (E/T) ratio was calculated based on CAR expression data (FIG. 6). Target cells were stably expressing a red nuclear dye which was measured by IncuCyte imaging system in a real-time fashion. Tumor cell growth inhibition (%)=(Initial Viable Target Cell Number-Current Viable Target Cell Number)/Initial Viable Cell Number*100(%).

scFv CAR-T cells also were evaluated in the real-time IncuCyte tumor killing assay for antigen-dependent cytotoxicity. Thermally stabilized hK2 CAR-T cells and parental 11B6 CAR-T cells were co-incubated with VCaP cells (FIG. 7C) or PC3 cells (FIG. 7D) for 88 hours at effector:target ratio of 1:1 or 0.5:1 which was calculated based on CAR expression data. CAR-T cells transduced with CAR17, CAR18, CAR19 and CAR20 were co-incubated with hK2 positive VCaP cells and hK2 negative DU145 cells for 96 hours at effector-to-target (ET) ratio of 1:1 or 0.5:1 which was calculated based on CAR expression on T cells. The percent tumor cell growth inhibition over time of CAR-T cells transduced with CAR17, CAR18, CAR19 and CAR20 is shown in FIG. 7E for VCap cells and in FIG. 7F for DU145 cells. Target cells were stably expressing a red nuclear dye which was measured by IncuCyte imaging system in a real-time fashion. Tumor cell growth inhibition (%)=(Initial Viable Target Cell Number-Current Viable Target Cell Number)/Initial Viable Cell Number*100(%). Tested CAR-T cells achieved approximately 100% TGI whereas the untransduced control did not demonstrate any TGI. No TGI was observed with the tested CAR-T cells in hK2 negative DU145 cells.

Example 7: Cytokine Production of 11B6 Thermally Stabilized scFv CAR-T Cells

Figure 8:
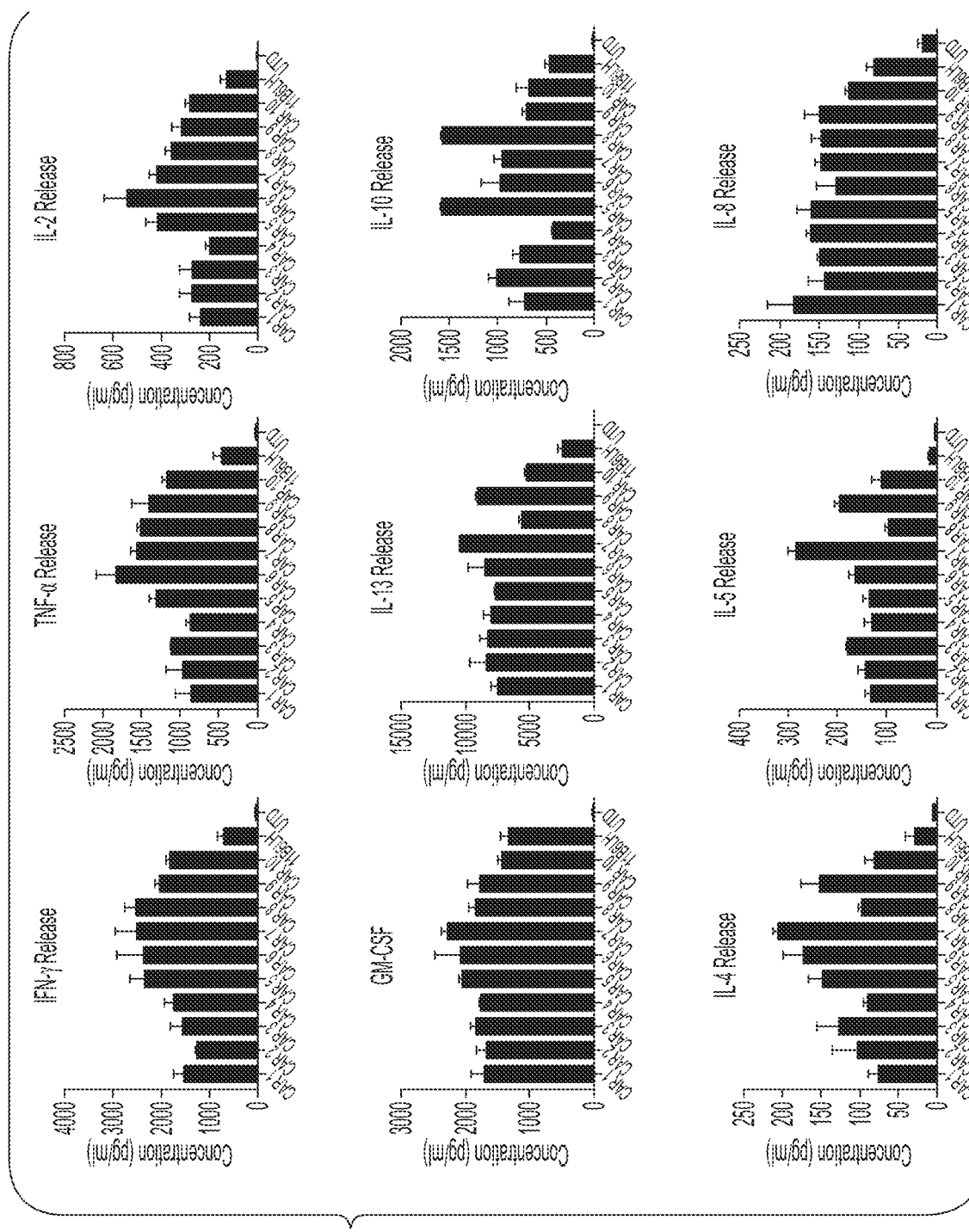
FIG. 8 shows cytokine release by hK2 lenti-CAR-T cells. Supernatant collected from overnight (approximately 20 hours) co-culture of hK2 CAR-T cells with VCap cells at 1:1 of E/T ratio was analyzed using 13-plex Milliplex Human High Sensitivity T cell kit (HSTCMAG28SPMX13). hK2 CAR modified T cells secrete cytokines during co-culture with hK2-expressing VCap cells, but minimal for un-transduced T cells (UTD). Mean cytokine concentration± standard deviation (pg/ml) from duplicate cultures is shown.

Supernatant was collected from overnight (approximately 20 hours) co-culture of hK2 CAR-T cells with VCap cells at 1:1 of E/T ratio and was analyzed using 13-plex Milliplex Human High Sensitivity T cell kit (HSTCMAG28SPMX-13). hK2 CAR modified T cells secrete cytokines during co-culture with hK2-expressing VCap cells, but minimal for un-transduced T cells (UTD). The results of cytokine release by hK2 lenti-CAR-T cells are shown in FIG. 8.

Figure 9:
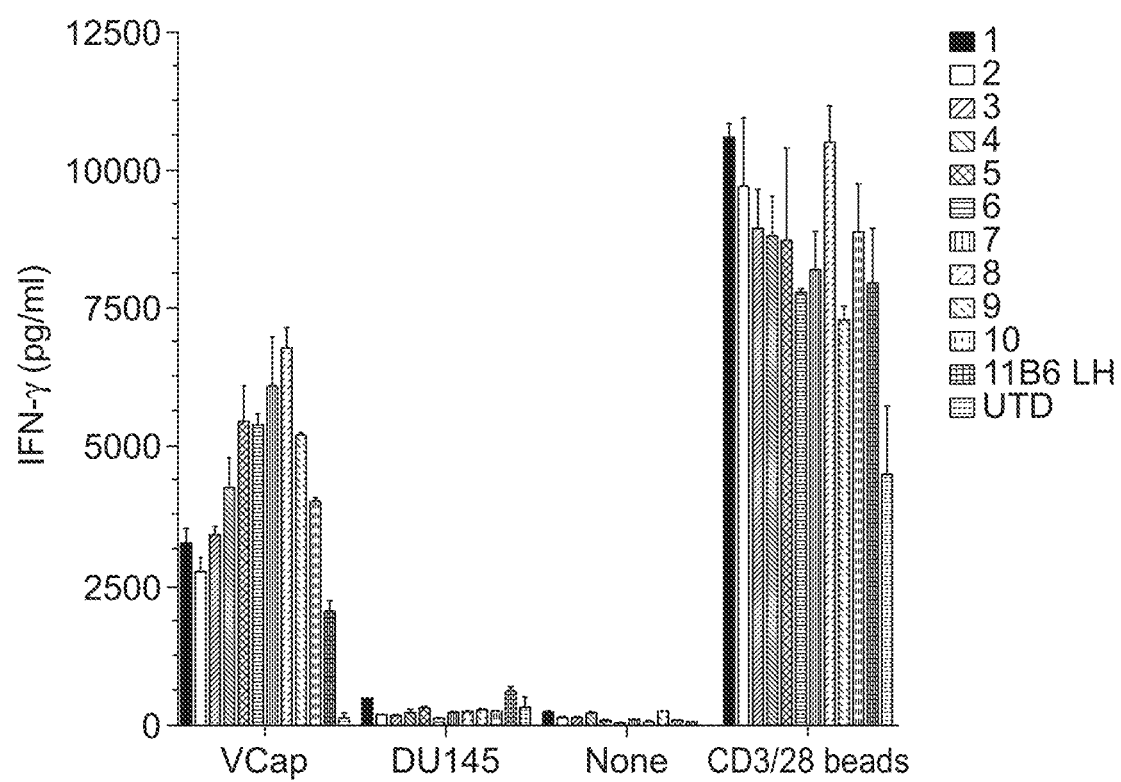
FIG. 9 shows IFN-γ release by hK2 lenti-CAR-T cells. Supernatant collected from overnight (approximately 20 hours) co-culture of hK2 CAR-T cells with VCap, DU145 (5E4 cells) cells at 1:1 of E/T ratio. hK2 CAR modified T cells secrete IFN-γ during co-culture with hK2-expressing VCap cells, but not hK2-negative DU145 cells. Mean IFN-γ concentration±standard deviation (pg/ml) from duplicate cultures is shown. CD3/28 beads stimulated T cells and T cells only were used as positive and negative controls, respectively.

Supernatant was collected from overnight (approximately 20 hours) co-culture of hK2 CAR-T cells with VCap, DU145 (5E4 cells) cells at 1:1 of E/T ratio. hK2 CAR modified T cells secrete IFN-γ during co-culture with hK2-expressing VCap cells, but not hK2-negative DU145 cells. CD3/28 beads stimulated T cells and T cells only were used as positive and negative controls, respectively. IFN-γ release by hK2 lenti-CAR-T cells is shown in FIG. 9. (The protocol of Example 3 was used.) Mean IFN-γ concentration±SD (pg/ml) from duplicate cultures is shown. CD3/28 beads stimulated T cells and T cells only were used as positive and negative controls, respectively. As shown, different thermally stabilized CAR T cells produce different amount of IFN-gamma when co-culture with hK2 (+) VCap cells, which is associated with cytotoxic activity during cell-mediated immune response.

Figure 10A:
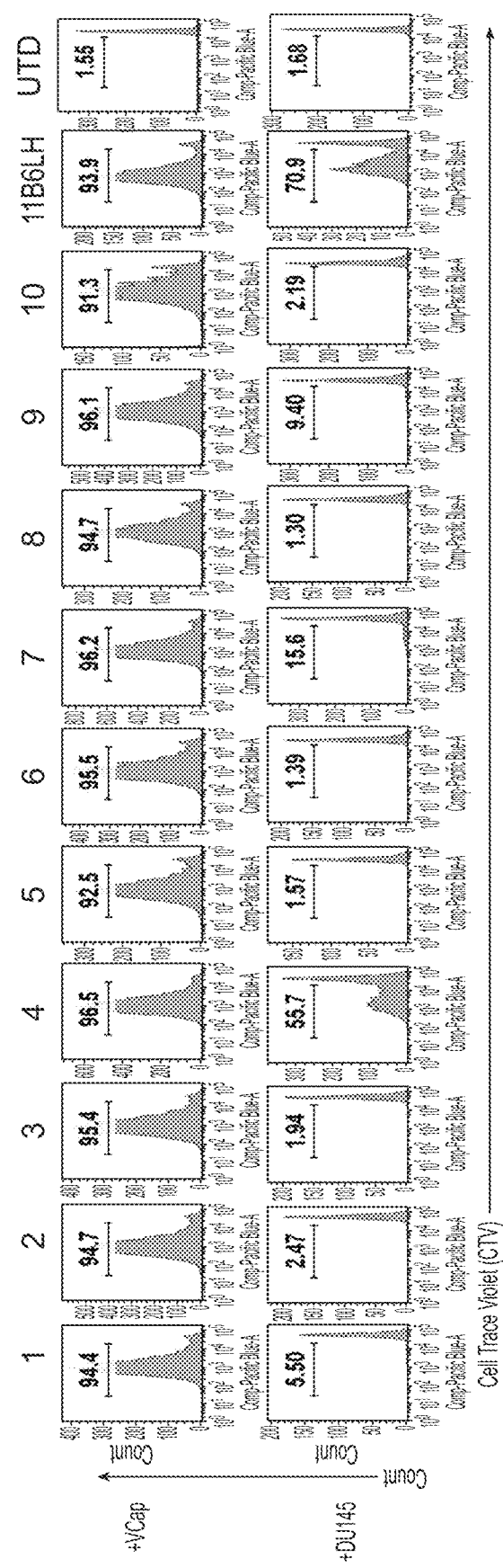
Figure 10C:
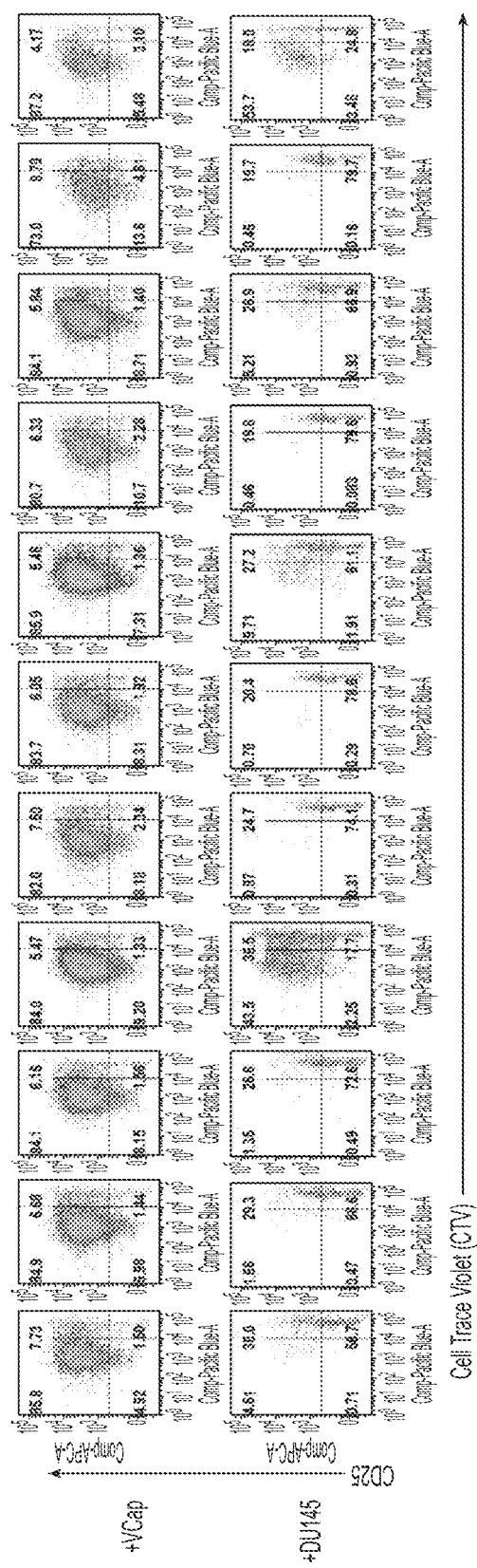
Figure 10D:
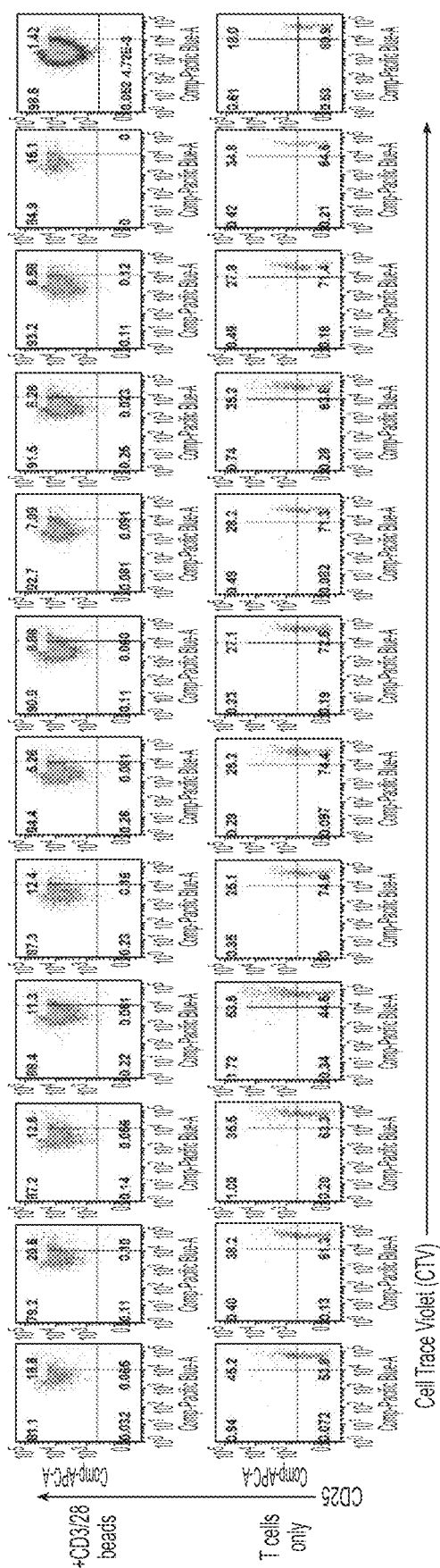
Figure 10E:
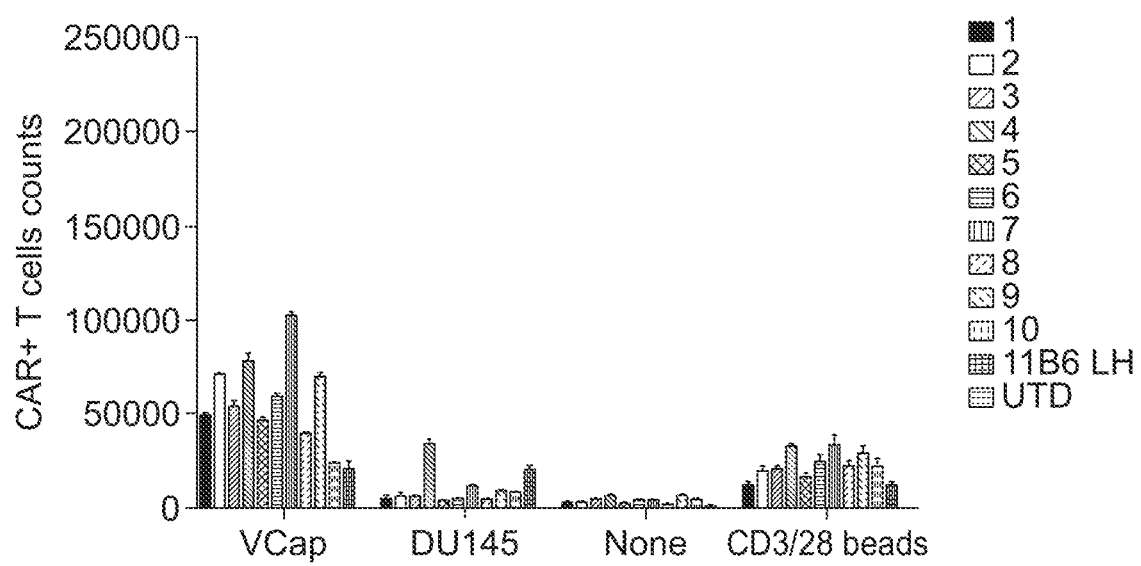

Example 8: Proliferation of hK2 CAR-T Cells hK2 CAR-T cells were evaluated in a proliferation assay. T-cell proliferation is an important in vitro parameter of in vivo immune function. To further evaluate the function of thermally stabilized 11B6 CARs T cells and pick top candidate construct, 11B6 thermally stabilized and parental scFvs based CAR T cells were labeled with CTV to assess T cell proliferation.

hK2 CAR and un-transduced (UTD) T cells were labelled with CellTrace Violet (CTV; 5 µM) and co-cultured with hK2 (+) VCap and hK2 (−) DU145 cells. Five days post co-culture, cells were harvested and stained with CD3, CD25, NearIR live/dead Dye and hK2 CAR. Flow cytometric analysis was performed on a Fortessa flow cytometer with Flowjo software. Lymphocytes were identified by live CD3, and the frequencies of CAR-T cells with CTV dye dilution and activation marker CD25 were determined. By gating on hK2 CAR+ T cells, as shown, the hK2(+) Vcap cells but not hK2(−) DU145 cells promoted the all CAR constructs engineered T cells proliferation and upregulation of activation marker CD25 (FIGS. 10A, 10C). CD3/28 beads stimulated T cells and T cells only were used as positive and negative controls, respectively. T cells only without any stimulation do not proliferate and CD3/28 beads stimulated T cells displayed equivalent proliferation pattern (FIGS. 10B, 10D). As shown in FIG. 10E, hK2 CAR+ T cells proliferate more robustly than CD3/28 beads positive control after 5 days of coculture with VCap cells. Different CAR constructs engineered T cells have different proliferation activity and displayed different CAR+ T cells counts. The CAR+ T cells counts based on mean absolute cell count+/−SEM from three technical replicates.

The protocol is as follows. The tumor cells Vcap and DU145 were collected, washed twice with PBS, and resuspended in 10E6/ml in PBS containing 100 ug/ml Mitomycin C (MMC) for 1.5 hours in a 37° C. incubator so as to block tumor cells proliferation. 20 µL of DMSO was added to a vial of CTV staining solution. 5 µl of the solution was diluted into 5 mL (1:1000) PBS (warmed to 37° C.) to provide a 5 µM staining solution. The 2E6 T cells were counted, collected, washed with PBS twice, and resuspended in 4E6/ml (0.5 ml). An equal volume (0.5 ml) of CTV staining solution was added. The cells were incubated for 20 minutes at 37° C. Then, 4 ml PRMI+20% FBS was added to the cells to absorb any unbound dye. The cells were incubated for 5 minutes, and centrifuged for 5 minutes at 400×g. The cell pellet was resuspended in pre-warmed RPMI+10% FBS medium. The T cells were counted, and 1E5 cells (100 µl) were seeded in 96-wells flat bottom-plate.

In the meantime, MMC-treated tumor cells hK2(+) VCap and HK2(−) DU145 were collected and counted after 1.5 hours, and then resuspended at 1E6/ml. 1E5 of the cells (100 µl) were cocultured with T cells in a 96-well plate. T cells alone, and T cells added 3:1 CD3/28 beads to cells ratio, were used as negative and positive controls, respectively.

After 5 days of co-culture, all of the cells were collected from each well. The cells were centrifuged and washed for 5 minutes at 400×g twice, then stained hK2CAR, CD3, CD8 and CD25, live/dead (Near-IR) in 96-well U bottom plate. After washing, all cells were fixed for 10 minutes using 100 µl BD Cytofix™ Fixation Buffer (501 FACS buffer+50 µl Fixation Buffer). The stained samples were analyzed by multicolor flow cytometry after the end of the incubation period.

Data analysis was performed as follows. A CTV histogram was prepared. The CTV undiluted gate was set to encompass the far-right peak (CTV bright) of T cells cultured alone, and the CTV diluted gate to capture the rest of the population. This was applied to all samples.

Figure 11A:
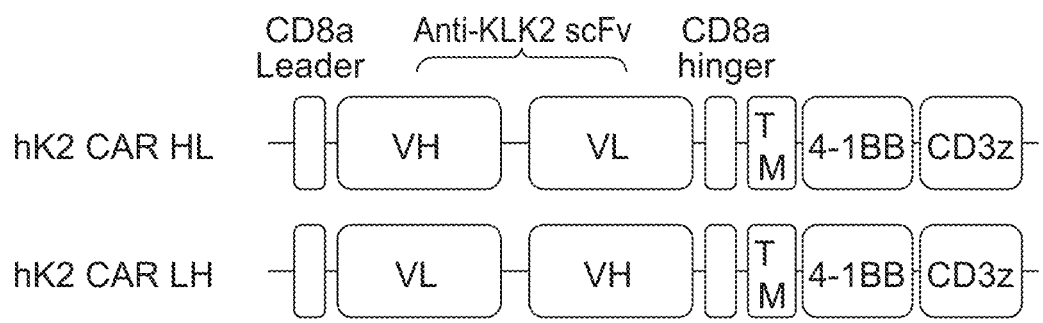
FIGS. 11A-11B show the results of assays to determine the level of expression of hK2 CARs on primary T cells using biotin-labeled hK2 protein.

Example 9: Construction and Expression of hK2 scFv CARs with Anti-HK2 scFv hK2 CAR constructs comprising an scFv derived from the novel anti-HK2 scFv were constructed as illustrated in FIG. 11A.

To evaluate the function of these novel anti-HK2 scFv CARs T cells and to pick a top candidate construct, hK2 HL and \LH CAR-T cells were generated using lentiviral transduction. Primary human T cells were transduced with hK2 CAR HL and LH, novel scFvs based CAR lentivirus with a multiplicity of infection (MOI) of 3. CAR expression was determined by biotinylated hK2 (1 µg/ml) followed by streptavidin-conjugated PE 14 days post transduction.

The experimental protocol is as follows.

Lentiviral packaging was undertaken. 14E6 Lenti-X™ 293T cells were seeded per 150 mm$^2$ round-bottomed Corning™ BioCoat™ Collagen I coated culture dish, and incubated at 37° C. overnight using DMEM+10% FBS medium.

With Lenti-X™ 293T cells at the ideal confluency of 80-85%, the following was prepared. Culture media was replaced with 21 ml 293T growth media. Lipofectamine 2000 was diluted at room temperature and equilibrated OptiMEM. Diluted Lipofectamine 2000 was added to mixed plasmids drop-wise, and mixed well. The mixture was incubated at room temperature for 25 minutes. The transfection mixture was added to Lenti-X 293T cells dropwise, with the plate gently swirled to mix. The mixture was incubated in a 37° C. incubator. Lentivirus was harvested 24 and 48 hours post transfection. The above reagents are summarized in the Table 3.

TABLE 3

| Reagent | Amount per 15 cm dish |
|---|---|
| pMDLg/p | 18 µg |
| pRSV.Rev | 18 µg |
| pMD2.G | 7 µg |
| Transfer (CAR) plasmid | 15 µg |
| OptiMEM | 1500 µl |

Lentiviral concentration was performed as follows. Lentivirus-containing supernatants were harvested and centrifuged at 500×g for 10 min if excessive 293T cells are floating around before filtering through 0.45 µm cellulose acetate filters. Supernatant was transferred to a sterile container, combined with 1/3 volume of Lenti-X Concentrator (Clontech, Cat. #631232), and mixed by gentle inversion. The mixture was incubated at 4° C. overnight. The sample was centrifuged at 1,500×g for 45 minutes at 4° C., with a white pellet visible after centrifugation. The supernatant was carefully removed without disturbing the pellet. Residual supernatants were removed with a pipette after a brief centrifugation at 1,500×g. The pellet was gently resuspended in 1/10 of the original volume using cold T cell growth. The virus was aliquoted in 200 µl and immediately stored at −80° C.

Viral titering was performed as follows. Log-phase SupT1 was grown in complete RPMI. 100 µl 20,000 SupT1 cells/ml were seeded per well in a flat 96-well plate. Virus titration was then performed in 96-well round bottom plates). 100 µl media was added to all the wells in the plate. A virus aliquot was thawed from −80° C. freezer with one's hands. The aliquot was pipetted up and down to mix well, with 50 µl virus added to the first well, followed by thorough mixing. A serial 1:3 dilution was performed by pipetting 50 µl virus to the next well. Then, 50 µl media was added to primary Ab only, secondary Ab only, and un-transduced controls. 50 µl of each was transferred from the titration plate to 100 µl SupT1 cells in the assay plate with a multi-channel pipette, and incubated at 37° C. overnight. 100 µl of pre-warmed media was added to each sample, and incubated another two days. The transduction efficiency was determined by flow cytometry. Samples were transferred to a round bottom 96 well plate and spun at 1400 RPM for 3 minutes. The supernatant was discarded quickly, followed by blotting to remove excessive media in the hood. The wash was repeated with 150 µl FACS buffer. A staining protocol appropriate for CAR constructs was then undertaken. Samples were resuspended in 150 µl FACS buffer before flow cytometry analysis.

Viral titer calculation: Titer=(% CAR positive/100)× $2\times10^4\times20\times$dilution factor To exclude multiple copy integrations, titers with the closest transduction to 20% is used. T-cell activation, transduction and expansion was performed as follows. A vial of naïve T cells was thawed in a water bath and added dropwise to a 15 ml conical tube containing 9 ml of pre-warmed T-cell media (TCM CTS OpTmizer T Cell Expansion SFM+ 5% human serum+IL-2100 IU/ml). The cryovial was washed with 1 ml of media to recover maximum number, and spun at 300×g for 8 minutes at room temperature. The pellet was resuspended in fresh 10 ml TCM, counted, and resuspended to 1E6 cells per milliner. 5E5 cells were added per well in 24-well plate. $1.5\times10^6$ CD3/CD28 beads were added per well in 500 µl volume such that the total volume was 1 ml per well. Twenty-four hours post activation, virus was thawed at room temperature. Virus was added at a multiplicity of infection (MOI) of 3, gently swirled to mix, and returned to the plate at the incubator. (The lentiviral functional titer was previously determined with SupT1 titer assay.) One well was reserved for Untransduced (UTD) in which is no virus added.

Twenty four hours post-transduction, 1 ml TCM was added to each well. Penicillin-Streptomycin was added from this point onward (Day 2). On days 3-5, 4 ml TCM was added for each 2 ml of cells and transferred to a T25 tissue culture treated flask. The flasks were placed horizontally in the incubator (Day 3). Equal volume of TCM was added for T-cell culture (Day 4). On days 5-14, the cells were checked every other day, with the viability, size and total cell count recorded. The cell density was adjusted to one million cells per mL. The ideal time of harvest is donor dependent and determined by the cell size and the fold of expansion. Cells were generally frozen when the cell size was less than 8 m based on the MOXI flow cell counter with the 100 to 200-fold of expansion.

Lentiviral transduction efficiency was checked on harvest day as follows. Cultures were mixed well. 100 µl of T-cells was harvested to a corresponding well in 96-well plate with 1001 µl FACS Buffer, mixed, and spun at 1300 RPM for 3 minutes at room temperature. The cells were resuspended in 2001 µl FACS buffer and centrifugation repeated at 4° C. The cells were resuspended in 100 µl of Biotin labeled hK2 (1 µg/ml diluted in FACS buffer) and incubated on ice for 30 minutes. 100 µl of FACS buffer was added, and spun washed at 4° C. The spin wash was repeated after adding another 200 µl FACS buffer. Staining with 100 µl of master solution containing secondary antibody SA-PE (1:250), live dead fixable stain (1:500), αCD3, αCD4 and αCD8 antibodies was performed on ice for 30 minutes. 100 µl FACS buffer was added and spun wash at 4° C., discarded and resuspended in 200 µl FACS buffer before spin washing at 4° C. The samples were resuspended in 100 µl FACS Buffer before analyzing by flow cytometry.

Figure 11B:
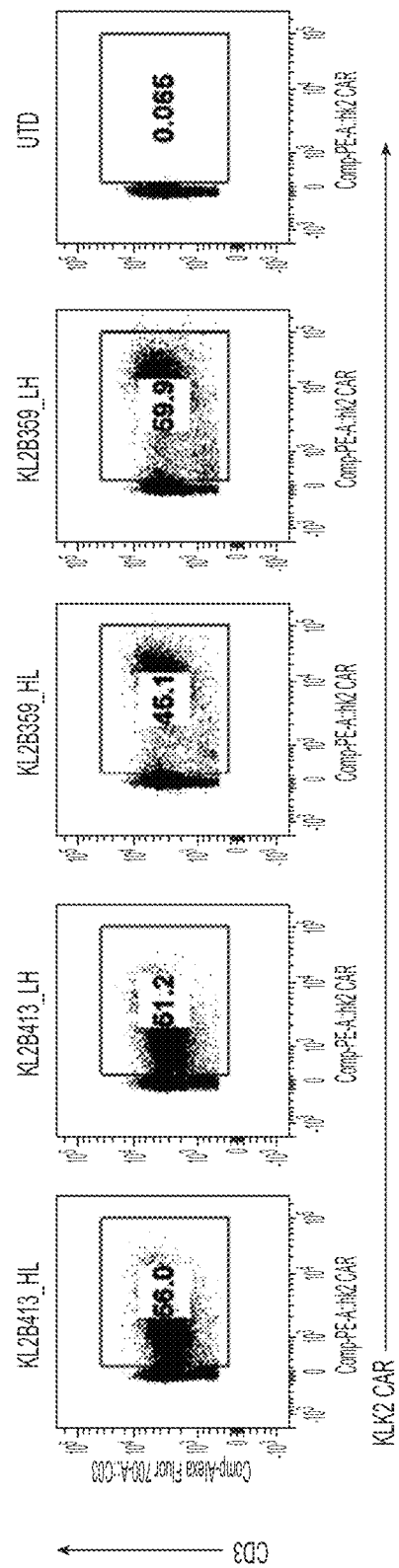

Cell harvest and freezing was performed as follows. The final cell count was determined. The culture was harvested and centrifuged at 300×g for 10 minutes at room temperature. The culture was resuspended in a smaller volume of media to fit in a 50 ml conical tube. The tubes were placed in magnets at 4° C. for 10 minutes to "de-bead". The cells were gently transferred from the tube to minimize disturbing the beads/magnet, and the exact volume recorded. Counting was repeated. Centrifugation was performed at 300×g for 10 minutes, with the supernatant discarded. Cells were frozen in CS-10 CryoStor® cell cryopreservation media in a cooling container. The containers were immediately transferred to −80° C. for 24-48 hours before permanent storage in liquid Nitrogen. The results are shown in FIG. 11B, and confirm hK2 CAR expression on the surface of the transduced T cells. A summary of the percentage of hK2 CAR+ T cells (% positive) detected by novel KL2B413 HL&LH and rehumanized 11B6 KL2B359 HL&LH CARS analyzed is provided. As shown, different clones have different CAR expression level, ranges from 45.1% to 59.9%. All CAR T cells were normalized to the equal CAR+ T cells for subsequent functional assays.

Example 10: Generation of Anti-hK2 Antibodies and scFvs

Antibody Generation from Humanization of Parental m11B6 Antibody.

A parental mouse anti-HK2 antibody, m11B6 has been described in Vaisanen et al (Clinical Chemistry 50:9, 1607-1617 (2004)). Humanized 11B6 (referred herein to as hu11B6) has been generated and described in U.S. Pat. Nos. 9,345,782 and 10,100,125.

Engineering of hu11B6 were initiated to generate additional anti-HK2 antibodies with improved properties, such as improved thermostability. Residue positions were identified in hu11B6 frameworks which could potentially be altered to improve thermostability of hu11B6 using modeling. The positions identified were residues P41, 149, M70, and A88 in the VH and 580, L82, A88 and Y91 in the VL (residue numbering according to the amino acid sequences of hu11B6_VH of SEQ ID NO: 5 and hu11B6_VL of SEQ ID NO: 2).

Binary combinatorial scFv libraries were generated in the orientation VH-linker-VL in which one of the variable regions represented the combinatorial library and the second one being the parental hu11B6 VH or VL. Linker sequence of GGSEGKSSGSGSESKSTGGS (SEQ ID NO: 7) was used to conjugate the VH/VL regions. The engineered scFvs were expressed in *E. coli* and the produced scFvs in the supernatants were tested for binding to human hK2 by ELISA and compared to the binding of hu11B6. Any new variants exhibiting binding comparable to hu11B6 were consolidated and further tested for binding to human hK2 after incubation of the supernatants at 55° C., 60° C., and 65° C. for 10 minutes. The molecules which retained comparable binding to hu11B6 after incubation at 55° C., 60° C., and 65° C. and improved thermostability were matrixed in both orientations (VH-linker-VL; VL-linker-VH) and converted to mammalian scFvs for further characterization. The matrixed scFvs were also incorporated into CAR constructs and further characterized as further described in Example 11.

In addition, another humanization of parental mouse 11B6 was performed following the approach outlined by Singh et al (MAbs. 2015; 7(4):778-91). with extensive germ line variation and careful screening of the variants for enhanced thermal stability. Based on sequence conservation, the human heavy chain germline IGHV4-30 and the light chain germline IGKV3D-11, were chosen for framework adaption. A binary scFv library was constructed with residues comprising a select set of somatic hypermutation sites and mouse/human germline variations. The variants were cloned and expressed in E. coli as described above. The supernatants were screened at different temperatures in single point ELISA for enhanced thermal stability. A mouse/human chimeric 11B6 scFv was used as parental control. Clone KL2B359 which maintained binding activity similar to murine 11B6 and a Tm value of 67° C. was converted to scFv-Fc and CAR-T for additional profiling. The measured affinity ($K_D$) of KL2B359 to hK2 by SPR was ~0.7-1 nM. HCF3-LCD6, HCG5-LCB7, KL2B357, KL2B358 and KL2B360 also resulted from this campaign and were further characterized for functionality.

Antibody Generation Using Transgenic Mice (Ablexis®) and Transgenic Rats (OmniRat®) Expressing Human Immunoglobulin Loci.

The OmniRat® contains a chimeric human/rat IgH locus (comprising 22 human VHS, all human D and $J_H$ segments in natural configuration linked to the rat $C_H$ locus) together with fully human IgL loci (12 Vκs linked to Jκ-Cκ and 16 Vλs linked to Jλ-Cλ). (see e.g., Osborn, et al. (2013) J Immunol 190(4): 1481-1490). Accordingly, the rats exhibit reduced expression of rat immunoglobulin, and in response to immunization, the introduced human heavy and light chain transgenes undergo class switching and somatic mutation to generate high affinity chimeric human/rat IgG monoclonal antibodies with fully human variable regions. The preparation and use of OmniRat®, and the genomic modifications carried by such rats, is described in WO14/093908.

Ablexis® mice generate antibodies having human variable domains linked to human CH1 and CL domains, chimeric human/mouse hinge region, and mouse Fc regions. Ablexis Kappa Mouse and Lambda Mouse strains are distinguished by which of their heavy chains are human or mouse as noted below. Antibodies produced by the Kappa Mouse lack sequence derived from mouse $V_H$, $D_H$ and $J_H$ exons and mouse Vκ, Jκ and Cκ exons. The endogenous mouse Igλ is active in the Kappa Mouse. The human Igκ chains comprise approximately 90-95% of the naïve repertoire and mouse Igλ chains comprise approximately 5-10% of the naïve repertoire in this strain. Antibodies produced by the Lambda Mouse lack sequence derived from mouse $V_H$, $D_H$ and $J_H$ exons and mouse Vλ, Jλ and Cλ exons. The endogenous mouse Igκ is active in the Lambda Mouse. The human Igλ chains comprise approximately 40% of the naïve repertoire and mouse Igκ chains comprise approximately 60% of the naïve repertoire. The preparation and use of Ablexis®, and the genomic modifications carried by such mice, is described in WO11/123708.

Ablexis mice and OmniRats rats were immunized with soluble full length KLK2 protein (human Kallikrein-26-His protein).

human Kallikrein-2 6-His protein
(SEQ ID NO: 319)
VPLIEGRIVGGWECEKHSQPWQVAVYSHGWAHCGGVLVHPQWVLTAAHC

LKKNSQVWLGRHNLFEPEDTGQRVPVSHSFPHPLYNMSLLKHQSLRPDE

DSSHDLMLLRLSEPAKITDVVKVLGLPTQEPALGTTCYASGWGSIEPEE

FLRPRSLQCVSLHYSEKVTEFMLCAGLWTGGKDTCGGDSGGPLVCNGVL

QGITSWGPEPCALPEKPAVYTKVVHYRKWIKDTIAANPHHHHHH

Lymphocytes from Ablexis mice and OniRats rats were extracted from lymph nodes and fusions performed by cohorts. Cells were combined and sorted for CD138 expression. Hybridoma screening was performed in high throughput miniaturized MSD format using soluble hK2 antigen. Approximately >300 samples were identified to be hK2 binders. The binding of >300 anti-hKLK2 supernatant samples to human KLK2 protein was measured by single cycle kinetics method by Biacore 8K SPR. Additionally the supernatant samples were tested for binding to human KLK3 protein as well. In parallel, supernatants were also tested for binding to KLK2 expressing cell lines VCap and negative cell line DU145 by Flow Cytometry. Selected cell binders were moved forward to scFv conversion in both VH-VL and VL/VH orientation and thermal stability tests as described above. KL2B413, KL2B30, KL2B53 and KL2B242 resulted from the Ablexis mice immunization campaign. KL2B467 and KL2B494 resulted from the OmniRat immunization campaign.

Antibodies generated through the various immunization and humanization campaigns described above were expressed in a fab format, a mAb format, a scFv format in the VH-linker-VL orientation or a scFv format in VL-linker-VH orientation and were further analyzed as described below. The linker sequence of SEQ ID NO: 7 described above was used to conjugate the VH/VL regions.

Example 11. Structural Characterization of Anti KLK2 Antibodies

Sequences of antibody variable domains and scFv antibody fragments which showed highest performance in intracellular assay are provided herein. Variable domains were expressed in a Fab format, a scFv format in the VH-linker-VL orientation or a scFv format in VL-linker-VH orientation.

Variable Domains VH, VL and CDRs

Table 4 shows the VH and VL amino acid sequences of selected anti-hK2 antibodies. Table 5 shows the Kabat HCDR1, HCDR2 and HCDR3 of selected anti-hK2 selected antibodies. Table 6 shows the Kabat LCDR1, LCDR2 and LCDR3 of the selected anti-hK2 antibodies. Table 7 shows the AbM HCDR1, HCDR2 and HCDR3 of selected anti-hK2 antibodies. Table 8 shows the AbM LCDR1, LCDR2 and LCDR3 of the anti-hK2. Table 9 summarizes the variable domain sequence and SEQ ID NO of selected hK2 antibodies. Table 10 shows the protein and DNA SEQ ID NOs for the VH and VL regions.

TABLE 4

VH and VL amino acid sequences of selected anti-hK2 antibodies.

| mAb name | VH name | VH amino acid Sequence | VH SEQ ID NO: | VL name | VL amino acid sequence | VL SEQ ID NO: |
|---|---|---|---|---|---|---|
| m11B6 | m11B6_VH | DVQLQESGPGLVKPSQSLSLTCTVTGNSITSDYAWNWIRQFPGNRLEWMGYISYSGSTTYSPSLKSRFSITRDTSKNQFFLQLNSVTPEDTATYFCATGYYYGSGFWGQGTLVTVSS | 317 | m11B6_VL | DIVLTQSPASLAVSLGQRATISCRASESVEYFGTSLMHWYRQKPGQPPKLLIYAASNVESGVPARFSGSGSGTDFSLNIQPVEEDDFSMYFCQQTRKVPYTFGGGTKLEIK | 318 |
| h11B6 | hu11B6_VH | QVQLQESGPGLVKPSDTLSLTCAVSGNSITSDYAWNWIRQPPGKGLEWIGYISYSGSTTYNPSLKSRVTMSRDTSKNQFSLKLSSVTAVDTAVYYCATGYYYGSGFWGQGTLVTVSS | 5 | hu11B6_VL | DIVLTQSPDSLAVSLGERATINCKASESVEYFGTSLMHWYQQKPGQPPKLLIYAASNRESGVPDRFSGSGSGTDFTLTISSLQAEDVAVYYCQQTRKVPYTFGQGTKLEIK | 2 |
| HCF3-LCD6 | HCF3_HV | QVQLQESGPGLVKPSDTLSLTCAVSGNSITSDYAWNWIRQPPGKGLEWIGYISYSGSTTYNPSLKSRVTISRDTSKNQFSLKLSSVTPVDTAVYYCATGYYYGSGFWGQGTLVTVSS | 6 | LCD6_VL | DIVLTQSPDSLAVSLGERATINCKASESVEYFGTSLMHWYQQKPGQPPKLLIYAASNRESGVPDRFSGSGSGTDFTLTIQSVQAEDVSVYFCQQTRKVPYTFGQGTKLEIK | 1 |
| HCG5-LCB7 | HCG5_VH | QVQLQESGPGLVKPSDTLSLTCAVSGNSITSDYAWNWIRQPPGKGLEWMGYISYSGSTTYNPSLKSRVTISRDTSKNQFSLKLSSVTPVDTAVYYCATGYYYGSGFWGQGTLVTVSS | 4 | LCB7_VL | DIVLTQSPDSLAVSLGERATINCKASESVEYFGTSLMHWYQQKPGQPPKLLIYAASNRESGVPDRFSGSGSGTDFTLTISSVQAEDVAVYYCQQTRKVPYTFGQGTKLEIK | 3 |
| KL2B357 | KL2B357_VH | QVQLQESGPGLVKPSQTLSLTCTVSGNSITSDYAWNWIRQFPGKGLEWIGYISYSGSTTYNPSLKSRVTISRDTSKNQFSLKLSSVTAADTAVYYCATGYYYGSGFWGQGTLVTVSS | 140 | KL2B357_VL | DIVLTQSPDSLAVSLGERATINCRASESVEYFGTSLMHWYQQKPGQPPKLLIYAASNVESGVPDRFSGSGSGTDFTLTISSLQAEDVAVYFCQQTRKVPYTFGGGTKVEIK | 147 |
| KL2B358 | KL2B358_VH | QVQLQESGPGLVKPSQTLSLTCTVSGNSITSDYAWNWIRQPPGKGLEWIGYISYSGSTTYNPSLKSRVTISRDTSKNQFSLKLSSVTAADTAVYYCATGYYYGSGFWGQGTLVTVSS | 141 | KL2B358_VL | EIVLTQSPATLSLSPGERATLSCRASESVEYFGTSLMHWYQQKPGQPPRLLIYAASNVESGIPARFSGSGSGTDFTLTISSVEPEDFAVYFCQQTRKVPYTFGGGTKVEIK | 75 |

TABLE 4-continued

VH and VL amino acid sequences of selected anti-hK2 antibodies.

| mAb name | VH name | VH amino acid Sequence | VH SEQ ID NO: | VL name | VL amino acid sequence | VL SEQ ID NO: |
|---|---|---|---|---|---|---|
| KL2B359 | KL2B359_VH | QVQLQESGPGL VKPSQTLSLTCT VSGNSITSDYAW NWIRQFPGKRLE WIGYISYSGSTT YNPSLKSRVTIS RDTSKNQFSLKL SSVTAADTAVY YCATGYYYGSG FWGQGTLVTVS S | 77 | KL2B359_VL | EIVLTQSPATLSLS PGERATLSCRASE SVEYFGTSLMHW YQQKPGQPPRLLI YAASNVESGIPAR FSGSGSGTDFTLTI SSVEPEDFAVYFC QQTRKVPYTFGGG TKVEIK | 75 |
| KL2B360 | KL2B360_VH | QVQLQESGPGL VKPSQTLSLTCT VSGNSITSDYAW NWIRQFPGKGLE WIGYISYSGSTT YNPSLKSRVTIS RDTSKNQFSLKL SSVTAADTAVY YCATGYYYGSG FWGQGTLVTVS S | 140 | KL2B360_VL | EIVLTQSPATLSLS PGERATLSCRASE SVEYFGTSLMHW YQQKPGQPPRLLI YAASNVESGIPAR FSGSGSGTDFTLTI SSVEPEDFAVYFC QQTRKVPYTFGGG TKVEIK | 75 |
| KL2B413 | KL2B413_VH | EVQLVESGGGL VQPGGSLRLSCA ASGFTFSSYWM TWVRQAPGKGL EWVANIKQDGS ERYYVDSVKGR FTISRDNAKNSL YLQMNSLRAED TAVYYCARDQN YDILTGHYGMD VWGQGTTVTVS S | 76 | KL2B413_VL | EIVLTQSPSFLSAS VGDRVTITCRASQ GISSYLSWYQQKP GKAPKLLIYATST LQSGVPSRFSGSGS GTEFTLTISSLQPE DFATYCQQLNSY PRTFGQGTKVEIK | 74 |
| KL2B30 | KL2B30_VH | QVQLQESGPGL VKPSETLSLTCT VSGGSISSYYWS WIRQPPGKGLE WIGYIYYSGSTN YNPSLKSRVTIS VDTSKNQFSLKL SSVTAADTAVY YCAGTTIFGWT PNFYYGMDVW GQGTTVTVSS | 142 | KL2B30_VL | DIQMTQSPSFLSAS VGDRVTITCRASQ GISSYLAWYQQKP GKAPKFLIYAAST LQSGVPSRFSGSGS GTEFTLTISSLQPE DFATYYCQQLNSY PLTFGGGTKVEIK | 148 |
| KL2B53 | KL2B53_VH | EVQLVESGGGV VQPGRSLRLSCV ASGFTFSSYDIH WVRQAPGKGLE WVAIISYDGSKK DYTDSVKGRFTI SRDNSKNTLYL QMDSERVEDSA VYSCARESGWS HYYYYGMDVW GQGTMVTVSS | 143 | KL2B53_VL | DIVMTQSPSSLSAS VGDRVTITCRASQ DISNYLAWYQQKP GKVPKFLIYAAST LHSGVPSRFSGSGS GTDFTLTISSLQPE DVATYYCQKYNS APYTFGQGTRLEI K | 149 |
| KL2B242 | KL2B242_VH | QVQLQESGPGL VKPSETLSLTCT VSGGSISSYYWS WLRQPAGSGLE WIGRLYVSGFTN YNPSLKSRVTLS LDPSRNQLSLKL SSVTAADTAVY YCAGDSGNYW GWFDPWGQGTL VTVSS | 144 | KL2B242_VL | SYELTQPPSVSVSP GETASITCSGDQL GENYACWYQQKP GQSPVLVIYQDSK RPSGIPERFSGSNS GNTATLTISGTQA LDEADYYCQAWD NSIVVFGGGTKLT VL | 150 |

TABLE 4-continued

VH and VL amino acid sequences of selected anti-hK2 antibodies.

| mAb name | VH name | VH amino acid Sequence | VH SEQ ID NO: | VL name | VL amino acid sequence | VL SEQ ID NO: |
|---|---|---|---|---|---|---|
| KL2B467 | KL2B467_VH | QVQLVESGGGVVQPGRSLRLSCAASGFTFSYYGMHWVRQAPGKGLEWVAFISYDGSNKYYADSVKGRFTISRDNSKNTLYLQMNSLRAEDTAVYYCAHLPYSGSYWAFDYWGQGTQVTVSS | 145 | KL2B467_VL | QSVLTQPPSVSVAPGQTASITCGGDNIGSKSVHWYQQKPGQAPVLVVYDNSDRPSGIPERFSGSNSGTTATLTISRVEAGDEADYYCQVWDSSSDHPVVFGGGTKVTV | 151 |
| KL2B494 | KL2B494_VH | QVQLVESGGGLVQPGGSLRLSCAASGFTFSHYAMSWVRQAPGKGLEWVSTIGGSGGSTYYADSVKGRFTISRDNSKNTLYLQMNSLRAEDTAVYYCAKPHIVMVTALLYDGMDVWGQGTMVTVSS | 146 | KL2B494_VL | SSELTQPPSVSVAPGQTARITCGGNNIGSKSVHWYQQKPGQAPVLVVYDDSDRPSGIPERFSGSNSGNTATLTISRVEAGDEADYYCQVWDSSSDHVVFGGGTKLTVL | 152 |

TABLE 5

Kabat HCDR1, HCDR2 and HCDR3 amino acid sequences of selected anti-KLK2 antibodies.

| | Kabat HCDR1 | | Kabat HCDR2 | | Kabat HCDR3 | |
|---|---|---|---|---|---|---|
| mAb name | Sequence | SEQ ID NO: | Sequence | SEQ ID NO: | Sequence | SEQ ID NO: |
| m11B6 | SDYAWN | 63 | YISYSGSTTYSPSLKS | 64 | GYYYGSGF | 66 |
| hu11B6 | SDYAWN | 63 | YISYSGSTTYNPSLKS | 65 | GYYYGSGF | 66 |
| HCF3-LCD6 | SDYAWN | 63 | YISYSGSTTYNPSLKS | 65 | GYYYGSGF | 66 |
| HCG5-LCB7 | SDYAWN | 63 | YISYSGSTTYNPSLKS | 65 | GYYYGSGF | 66 |
| KL2B357 | SDYAWN | 63 | YISYSGSTTYNPSLKS | 65 | GYYYGSGF | 66 |
| KL2B358 | SDYAWN | 63 | YISYSGSTTYNPSLKS | 65 | GYYYGSGF | 66 |
| KL2B359 | SDYAWN | 63 | YISYSGSTTYNPSLKS | 65 | GYYYGSGF | 66 |
| KL2B360 | SDYAWN | 63 | YISYSGSTTYNPSLKS | 65 | GYYYGSGF | 66 |
| KL2B413 | SYWMT | 314 | NIKQDGSERYYVDSVKG | 315 | DQNYDILTGHYGMDV | 311 |
| KL2B30 | SYYWS | 102 | YIYYSGSTNYNPSLKS | 103 | TTIFGVVTPNFYYGMDV | 104 |
| KL2B53 | SYDIH | 107 | IISYDGSKKDYTDSVKG | 108 | ESGWSHYYYGMDV | 109 |
| KL2B242 | SYYWS | 102 | RLYVSGFTNYNPSLKS | 112 | DSGNYWGWFDP | 113 |

TABLE 5-continued

Kabat HCDR1, HCDR2 and HCDR3 amino acid sequences of selected anti-KLK2 antibodies.

| mAb name | Kabat HCDR1 Sequence | SEQ ID NO: | Kabat HCDR2 Sequence | SEQ ID NO: | Kabat HCDR3 Sequence | SEQ ID NO: |
|---|---|---|---|---|---|---|
| KL2B467 | YYGMH | 115 | FISYDGSNKYYADSVKG | 116 | LPYSGSYWAFDY | 117 |
| KL2B494 | HYAMS | 120 | TIGGSGGSTYYADSVKG | 121 | PHIVMVTALLYDGMDV | 122 |

TABLE 6

Kabat LCDR1, LCDR2 and LCDR3 amino acid sequences of selected anti-hK2 antibodies.

| mAb name | Kabat LCDR1 Sequence | SEQ ID NO | Kabat LCDR2 Sequence | SEQ ID NO | Kabat LCDR3 Sequence | SEQ ID NO |
|---|---|---|---|---|---|---|
| m11B6 | RASESVEYFGTSLMH | 67 | AASNVES | 69 | QQTRKVPYT | 71 |
| hu11B6 | KASESVEYFGTSLMH | 68 | AASNRES | 70 | QQTRKVPYT | 71 |
| HCF3-LCD6 | KASESVEYFGTSLMH | 68 | AASNRES | 70 | QQTRKVPYT | 71 |
| HCG5-LCB7 | KASESVEYFGTSLMH | 68 | AASNRES | 70 | QQTRKVPYT | 71 |
| KL2B357 | RASESVEYFGTSLMH | 67 | AASNVES | 126 | QQTRKVPYT | 71 |
| KL2B358 | RASESVEYFGTSLMH | 67 | AASNVES | 126 | QQTRKVPYT | 71 |
| KL2B359 | RASESVEYFGTSLMH | 67 | AASNVES | 69 | QQTRKVPYT | 71 |
| KL2B360 | RASESVEYFGTSLMH | 67 | AASNVES | 126 | QQTRKVPYT | 71 |
| KL2B413 | RASQGISSYLS | 312 | ATSTLQS | 313 | QQLNSYPRT | 91 |
| KL2B30 | RASQGISSYLA | 128 | AASTLQS | 129 | QQLNSYPLT | 130 |
| KL2B53 | RASQDISNYLA | 125 | AASTLHS | 131 | QKYNSAPYT | 132 |
| KL2B242 | SGDQLGENYAC | 133 | QDSKRPS | 134 | QAWDNSIVV | 135 |
| KL2B467 | GGDNIGSKSVH | 136 | DNSDRPS | 137 | QVWDSSSDHPVV | 138 |
| KL2B494 | GGNNIGSKSVH | 97 | DDSDRPS | 127 | QVWDSSSDHW | 139 |

TABLE 7

AbM HCDR1, HCDR2 and HCDR3 amino acid sequences of selected anti-hK2 antibodies.

| | AbM HCDR1 | | AbM HCDR2 | | AbM HCDR3 | |
|---|---|---|---|---|---|---|
| mAb name | Sequence | SEQ ID NO: | Sequence | SEQ ID NO | Sequence | SEQ ID NO: |
| m11B6 | GNSITSDYAWN | 72 | YISYSGSTT | 73 | GYYYGSF | 66 |
| hu11B6 | GNSITSDYAWN | 72 | YISYSGSTT | 73 | GYYYGSF | 66 |
| HCF3-LCD6 | GNSITSDYAWN | 72 | YISYSGSTT | 73 | GYYYGSF | 66 |
| HCG5-LCB7 | GNSITSDYAWN | 72 | YISYSGSTT | 73 | GYYYGSF | 66 |
| KL2B357 | GNSITSDYAWN | 72 | YISYSGSTT | 73 | GYYYGSF | 66 |
| KL2B358 | GNSITSDYAWN | 72 | YISYSGSTT | 73 | GYYYGSF | 66 |
| KL2B359 | GNSITSDYAWN | 72 | YISYSGSTT | 73 | GYYYGSF | 66 |
| KL2B360 | GNSITSDYAWN | 72 | YISYSGSTT | 73 | GYYYGSF | 66 |
| KL2B413 | GFTFSSYWMT | 309 | NIKQDGSER | 310 | DQNYDILTGHYGMDV | 311 |
| KL2B30 | GGSISSYYWS | 105 | YIYYSGSTN | 106 | TTIFGVVTPNFYYGMDV | 104 |
| KL2B53 | GFTFSSYDIH | 110 | IISYDGSKKD | 111 | ESGWSHYYYYGMDV | 109 |
| KL2B242 | GGSISSYYWS | 105 | RLYVSGFTN | 114 | DSGNYWGWFDP | 113 |
| KL2B467 | GFTFSYY | 118 | FISYDGSNK | 119 | LPYSGSYWAFD | 117 |
| KL2B494 | GFTFSHYAMS | 123 | TIGGSGGSTYY | 124 | PHIVMVTALLYDGMDV | 122 |

TABLE 8

AbM LCDR1, LCDR2 and LCDR3 amino acid sequences of selected anti-hK2 antibodies.

| | AbM LCDR1 | | AbM LCDR2 | | AbM LCDR3 | |
|---|---|---|---|---|---|---|
| mAb name | Sequence | SEQ ID NO: | Sequence | SEQ ID NO | Sequence | SEQ ID NO: |
| m11B6 | RASESVEYFGTSLMH | 67 | AASNVES | 69 | QQTRKVPYT | 71 |
| hu11B6 | KASESVEYFGTSLMH | 68 | AASNRES | 70 | QQTRKVPYT | 71 |
| HCF3-LCD6 | KASESVEYFGTSLMH | 68 | AASNRES | 70 | QQTRKVPYT | 71 |
| HCG5-LCB7 | KASESVEYFGTSLMH | 68 | AASNRES | 70 | QQTRKVPYT | 71 |
| KL2B357 | RASESVEYFGTSLMH | 67 | AASNVES | 126 | QQTRKVPYT | 71 |
| KL2B358 | RASESVEYFGTSLMH | 67 | AASNVES | 126 | QQTRKVPYT | 71 |

TABLE 8-continued

AbM LCDR1, LCDR2 and LCDR3 amino acid sequences of selected anti-hK2 antibodies.

| | AbM LCDR1 | | AbM LCDR2 | | AbM LCDR3 | |
|---|---|---|---|---|---|---|
| mAb name | Sequence | SEQ ID NO: | Sequence | SEQ ID NO | Sequence | SEQ ID NO: |
| KL2B359 | RASESVEYFGTSLMH | 67 | AASNVES | 69 | QQTRKVPYT | 71 |
| KL2B360 | RASESVEYFGTSLMH | 67 | AASNVES | 126 | QQTRKVPYT | 71 |
| KL2B413 | RASQGISSYLS | 312 | ATSTLQS | 313 | QQLNSYPRT | 91 |
| KL2B30 | RASQGISSYLA | 128 | AASTLQS | 129 | QQLNSYPLT | 130 |
| KL2B53 | RASQDISNYLA | 125 | AASTLHS | 131 | QKYNSAPYT | 132 |
| KL2B242 | SGDQLGENYAC | 133 | QDSKRPS | 134 | QAWDNSIVV | 135 |
| KL2B467 | GGDNIGSKSVH | 136 | DNSDRPS | 137 | QVWDSSSDHPW | 138 |
| KL2B494 | GGNNIGSKSVH | 97 | DDSDRPS | 127 | QVWDSSSDHVV | 139 |

TABLE 9

Amino acid sequences and SEQ ID NO summary of the variable domains of selected anti-hK2 antibodies

| Antibody | Region | Amino acid sequence | SEQ ID NO: |
|---|---|---|---|
| m11B6 | HCDR1 | SDYAWN | 63 |
| | HCDR2 | YISYSGSTTYSPSLKS | 64 |
| | HCDR3 | GYYYGSGF | 66 |
| | LICDR1 | RASESVEYFGTSLMH | 67 |
| | LCDR2 | AASNVES | 69 |
| | LCDR3 | QQTRKVPYT | 71 |
| | VH (m11B6_VH) | DVQLQESGPGLVKPSQSLSLTCTVTGNSITSDYAWNWIRQFPGNRLEWMGYISYSGSTTYSPSLKSRFSITRDTSKNQFFLQLNSVTPEDTATYFCATGYYYGSGFWGQGTLVTVSS | 317 |
| | VL (m11B6_VL) | DIVLTQSPASLAVSLGQRATISCRASESVEYFGTSLMHWYRQKPGQPPKLLIYAASNVESGVPARFSGSGSGTDFSLNIQPVEEDDFSMYFCQQTRKVPYTFGGGTKLEIK | 318 |
| h11B6 | HCDR1 | SDYAWN | 63 |
| | HCDR2 | YISYSGSTTYNPSLKS | 65 |
| | HCDR3 | GYYYGSGF | 66 |
| | LICDR1 | KASESVEYFGTSLMH | 68 |
| | LCDR2 | AASNRES | 70 |
| | LCDR3 | QQTRKVPYT | 71 |
| | VH (hu11B6_VH) | QVQLQESGPGLVKPSDTLSLTCAVSGNSITSDYAWNWIRQPPGKGLEWIGYISYSGSTTYNPSLKSRVTMSRDTSKNQFSLKLSSVTAVDTAVYYCATGYYYGSGFWGQGTLVTVSS | 5 |
| | VL (hu11B6_VL) | DIVLTQSPDSLAVSLGERATINCKASESVEYFGTSLMHWYQQKPGQPPKLLIYAASNRESGVPDRFSGSGSGTDFTLTISSLQAEDVAVYYCQQTRKVPYTFGQGTKLEIK | 2 |
| HCF3-LCD6 | HCDR1 | SDYAWN | 63 |
| | HCDR2 | YISYSGSTTYNPSLKS | 65 |
| | HCDR3 | GYYYGSGF | 66 |
| | LICDR1 | KASESVEYFGTSLMH | 68 |
| | LCDR2 | AASNRES | 70 |
| | LCDR3 | QQTRKVPYT | 71 |

TABLE 9-continued

Amino acid sequences and SEQ ID NO summary of the variable domains of selected anti-hK2 antibodies

| Antibody | Region | Amino acid sequence | SEQ ID NO: |
|---|---|---|---|
| | VH (HCF3_VH) | QVQLQESGPGLVKPSDTLSLTCAVSGNSITSDYAWNWIRQFPGKGLEWIGYISYSGSTTYNPSLKSRVTISRDTSKNQFSLKLSSVTPVDTAVYYCATGYYYGSGFWGQGTLVTVSS | 6 |
| | VL (LCD6_VL) | DIVLTQSPDSLAVSLGERATINCKASESVEYFGTSLMHWYQQKPGQPPKLLIYAASNRESGVPDRFSGSGSGTDFTLTIQSVQAEDVSVYFCQQTRKVPYTFGQGTKLEIK | 1 |
| HCG5-LCB7 | HCDR1 | SDYAWN | 63 |
| | HCDR2 | YISYSGSTTYNPSLKS | 65 |
| | HCDR3 | GYYYGSGF | 66 |
| | LICDR1 | KASESVEYFGTSLMH | 68 |
| | LCDR2 | AASNRES | 70 |
| | LCDR3 | QQTRKVPYT | 71 |
| | VH (HCG5_VH) | QVQLQESGPGLVKPSDTLSLTCAVSGNSITSDYAWNWIRQFPGKGLEWMGYISYSGSTTYNPSLKSRVTISRDTSKNQFSLKLSSVTPVDTAVYYCATGYYYGSGFWGQGTLVTVSS | 4 |
| | VL (LCB7_VL) | DIVLTQSPDSLAVSLGERATINCKASESVEYFGTSLMHWYQQKPGQPPKLLIYAASNRESGVPDRFSGSGSGTDFTLTISSVQAEDVAVYYCQQTRKVPYTFGQGTKLEIK | 3 |
| KL2B357 | HCDR1 | SDYAWN | 63 |
| | HCDR2 | YISYSGSTTYNPSLKS | 100 or 65 |
| | HCDR3 | GYYYGSGF | 66 |
| | LICDR1 | RASESVEYFGTSLMH | 67 |
| | LCDR2 | AASNVES | 126 |
| | LCDR3 | QQTRKVPYT | 71 |
| | VH (KL2B357_VH) | QVQLQESGPGLVKPSQTLSLTCTVSGNSITSDYAWNWIRQFPGKGLEWIGYISYSGSTTYNPSLKSRVTISRDTSKNQFSLKLSSVTAADTAVYYCATGYYYGSGFWGQGTLVTVSS | 140 |
| | VL (KL2B_357_VL) | DIVLTQSPDSLAVSLGERATINCRASESVEYFGTSLMHWYQQKPGQPPKLLIYAASNVESGVPDRFSGSGSGTDFTLTISSLQAEDVAVYFCQQTRKVPYTFGGGTKVEIK | 147 |
| KL2B358 | HCDR1 | SDYAWN | 63 |
| | HCDR2 | YISYSGSTTYNPSLKS | 65 |
| | HCDR3 | GYYYGSGF | 66 |
| | LICDR1 | RASESVEYFGTSLMH | 67 |
| | LCDR2 | AASNVES | 126 |
| | LCDR3 | QQTRKVPYT | 71 |
| | VH (KL2B358_VH) | QVQLQESGPGLVKPSQTLSLTCTVSGNSITSDYAWNWIRQPPGKGLEWIGYISYSGSTTYNPSLKSRVTISRDTSKNQFSLKLSSVTAADTAVYYCATGYYYGSGFWGQGTLVTVSS | 141 |
| | VL (KL2B_358_VL) | EIVLTQSPATLSLSPGERATLSCRASESVEYFGTSLMHWYQQKPGQPPRLLIYAASNVESGIPARFSGSGSGTDFTLTISSVEPEDFAVYFCQQTRKVPYTFGGGTKVEIK | 75 |
| KL2B359 | HCDR1 | SDYAWN | 63 |
| | HCDR2 | YISYSGSTTYNPSLKS | 65 |
| | HCDR3 | GYYYGSGF | 66 |
| | LICDR1 | RASESVEYFGTSLMH | 67 |
| | LCDR2 | AASNVES | 69 |
| | LCDR3 | QQTRKVPYT | 71 |
| | VH (KL2B359_VH) | QVQLQESGPGLVKPSQTLSLTCTVSGNSITSDYAWNWIRQFPGKRLEWIGYISYSGSTTYNPSLKSRVTISRDTSKNQFSLKLSSVTAADTAVYYCATGYYYGSGFWGQGTLVTVSS | 77 |
| | VL (KL2B_359_VL) | EIVLTQSPATLSLSPGERATLSCRASESVEYFGTSLMHWYQQKPGQPPRLLIYAASNVESGIPARFSGSGSGTDFTLTISSVEPEDFAVYFCQQTRKVPYTFGGGTKVEIK | 75 |
| KL2B360 | HCDR1 | SDYAWN | 63 |
| | HCDR2 | YISYSGSTTYNPSLKS | 65 |
| | HCDR3 | GYYYGSGF | 66 |
| | LICDR1 | RASESVEYFGTSLMH | 67 |
| | LCDR2 | AASNVES | 69 |

TABLE 9-continued

Amino acid sequences and SEQ ID NO summary of the variable domains of selected anti-hK2 antibodies

| Antibody | Region | Amino acid sequence | SEQ ID NO: |
|---|---|---|---|
| | LCDR3 | QQTRKVPYT | 71 |
| | VH (KL2B360_VH) | QVQLQESGPGLVKPSQTLSLTCTVSGNSITSDY AWNWIRQFPGKGLEWIGYISYSGSTTYNPSLK SRVTISRDTSKNQFSLKLSSVTAADTAVYYCA TGYYYGSGFWGQGTLVTVSS | 140 |
| | VL (KL2B_360_VL) | EIVLTQSPATLSLSPGERATLSCRASESVEYFG TSLMHWYQQKPGQPPRLLIYAASNVESGIPAR FSGSGSGTDFTLTISSVEPEDFAVYFCQQTRKV PYTFGGGTKVEIK | 75 |
| KL2B413 | HCDR1 | SYWMT | 314 |
| | HCDR2 | NIKQDGSERYYVDSVKG | 315 |
| | HCDR3 | DQNYDILTGHYGMDV | 311 |
| | LICDR1 | RASQGISSYLS | 312 |
| | LCDR2 | ATSTLQS | 313 |
| | LCDR3 | QQLNSYPRT | 91 |
| | VH (KL2B413_VH) | EVQLVESGGGLVQPGGSLRLSCAASGFTFSSY WMTWVRQAPGKGLEWVANIKQDGSERYYV DSVKGRFTISRDNAKNSLYLQMNSLRAEDTA VYYCARDQNYDILTGHYGMDVWGQGTTVTV SS | 76 |
| | VL (KL2B_413_VL) | EIVLTQSPSFLSASVGDRVTITCRASQGISSYLS WYQQKPGKAPKLLIYATSTLQSGVPSRFSGSG SGTEFTLTISSLQPEDFATYYCQQLNSYPRTFG QGTKVEIK | 74 |
| KL2B30 | HCDR1 | SYYWS | 102 |
| | HCDR2 | YIYYSGSTNYNPSLKS | 103 |
| | HCDR3 | TTIFGVVTPNFYYGMDV | 104 |
| | LICDR1 | RASQGISSYLA | 128 |
| | LCDR2 | AASTLQS | 129 |
| | LCDR3 | QQLNSYPLT | 130 |
| | VH (KL2B30_VH) | QVQLQESGPGLVKPSETLSLTCTVSGGSISSYY WSWIRQPPGKGLEWIGYIYYSGSTNYNPSLKS RVTISVDTSKNQFSLKLSSVTAADTAVYYCAG TTIFGVVTPNFYYGMDVWGQGTTVTVSS | 142 |
| | VL (KL2B30_VL) | DIQMTQSPSFLSASVGDRVTITCRASQGISSYL AWYQQKPGKAPKFLIYAASTLQSGVPSRFSGS GSGTEFTLTISSLQPEDFATYYCQQLNSYPLTF GGGTKVEIK | 148 |
| KL2B53 | HCDR1 | SYDIH | 107 |
| | HCDR2 | IISYDGSKKDYTDSVKG | 108 |
| | HCDR3 | ESGWSHYYYYGMDV | 109 |
| | LICDR1 | RASQDISNYLA | 125 |
| | LCDR2 | AASTLHS | 131 |
| | LCDR3 | QKYNSAPYT | 132 |
| | VH (KL2B53_VH) | EVQLVESGGGVVQPGRSLRLSCVASGFTFSSY DIHWVRQAPGKGLEWVAIISYDGSKKDYTDS VKGRFTISRDNSKNTLYLQMDSLRVEDSAVY SCARESGWSHYYYYGMDVWGQGTMVTVSS | 143 |
| | VL (KL2B53_VL) | DIVMTQSPSSLSASVGDRVTITCRASQDISNYL AWYQQKPGKVPKFLIYAASTLHSGVPSRFSGS GSGTDFTLTISSLQPEDVATYYCQKYNSAPYT FGQGTRLEIK | 149 |
| KL2B242 | HCDR1 | SYYWS | 102 |
| | HCDR2 | RLYVSGFTNYNPSLKS | 112 |
| | HCDR3 | DSGNYWGWFDP | 113 |
| | LICDR1 | SGDQLGENYAC | 133 |
| | LCDR2 | QDSKRPS | 134 |
| | LCDR3 | QAWDNSIVV | 135 |
| | VH (KL2B242_VH) | QVQLQESGPGLVKPSETLSLTCTVSGGSISSYY WSWLRQPAGSGLEWIGRLYVSGFTNYNPSLK SRVTLSLDPSRNQLSLKLSSVTAADTAVYYCA GDSGNYWGWFDPWGQGTLVTVSS | 144 |
| | VL (KL2B242_VL) | SYELTQPPSVSVSPGETASITCSGDQLGENYAC WYQQKPGQSPVLVIYQDSKRPSGIPERFSGSN SGNTATLTISGTQALDEADWCQAWDNSIVVF GGGTKLTVL | 150 |
| KL2B467 | HCDR1 | WGMH | 115 |
| | HCDR2 | FISYDGSNKYYADSVKG | 116 |
| | HCDR3 | LPYSGSYWAFDY | 117 |

TABLE 9-continued

Amino acid sequences and SEQ ID NO summary of the variable domains of selected anti-hK2 antibodies

| Antibody | Region | Amino acid sequence | SEQ ID NO: |
|---|---|---|---|
|  | L1CDR1 | GGDNIGSKSVH | 136 |
|  | LCDR2 | DNSDRPS | 137 |
|  | LCDR3 | QVWDSSSDHPVV | 138 |
|  | VH (KL2B467_VH) | QVQLVESGGGVVQPGRSLRLSCAASGFTFSYYGMHWVRQAPGKGLEWVAFISYDGSNKYYADSVKGRFTISRDNSKNTLYLQMNSLRAEDTAVYYCAHLPYSGSYWAFDYWGQGTQVTVSS | 145 |
|  | VL (KL2B467_VL) | QSVLTQPPSVSVAPGQTASITCGGDNIGSKSVHWYQQKPGQAPVLVVYDNSDRPSGIPERFSGSNSGTTATLTISRVEAGDEADYYCQVWDSSSDHPVVFGGGTKVTV | 151 |
| KL2B494 | HCDR1 | HYAMS | 120 |
|  | HCDR2 | TIGGSGGSTYYADSVKG | 121 |
|  | HCDR3 | PHIVMVTALLYDGMDV | 122 |
|  | L1CDR1 | GGNNIGSKSVH | 97 |
|  | LCDR2 | DDSDRPS | 127 |
|  | LCDR3 | QVWDSSSDHVV | 139 |
|  | VH (KL2B494_VH) | QVQLVESGGGLVQPGGSLRLSCAASGFTFSHYAMSWVRQAPGKGLEWVSTIGGSGGSTYYADSVKGRFTISRDNSKNTLYLQMNSLRAEDTAVYYCAKPHIVMVTALLYDGMDVWGQGTMVTVSS | 146 |
|  | VL (KL2B494_VL) | SSELTQPPSVSVAPGQTARITCGGNNIGSKSVHWYQQKPGQAPVLVVYDDSDRPSGIPERFSGSNSGNTATLTISRVEAGDEADYYCQVWDSSSDHVVFGGGTKLTVL | 152 |

TABLE 10

SEQ ID NO: DNA sequences of the VH and VL domains of selected hK2 antibodies.

| Antibody | VH Protein SEQ ID NO: | VL Protein SEQ ID NO | VH cDNA SEQ ID NO: | VL cDNA SEQ ID NO: |
|---|---|---|---|---|
| m11B6 | 317 | 318 | 320 | 326 |
| hu11B6 | 5 | 2 | 321 | 327 |
| HCF3-LCD6 | 6 | 1 | 322 | 328 |
| HCG5-LCB7 | 4 | 3 | 323 | 329 |
| KL2B357 | 140 | 147 | 153 | 161 |
| KL2B358 | 141 | 75 | 154 | 162 |
| KL2B359 | 77 | 75 | 324 | 330 |
| KL2B360 | 140 | 75 | 155 | 163 |
| KL2B413 | 76 | 74 | 325 | 331 |
| KL2B30 | 142 | 148 | 156 | 164 |
| KL2B53 | 143 | 149 | 157 | 165 |
| KL2B242 | 144 | 150 | 158 | 166 |
| KL2B467 | 145 | 151 | 159 | 167 |
| KL2B494 | 146 | 152 | 160 | 168 |

Consensus VH and VL Sequences

Figure 2:
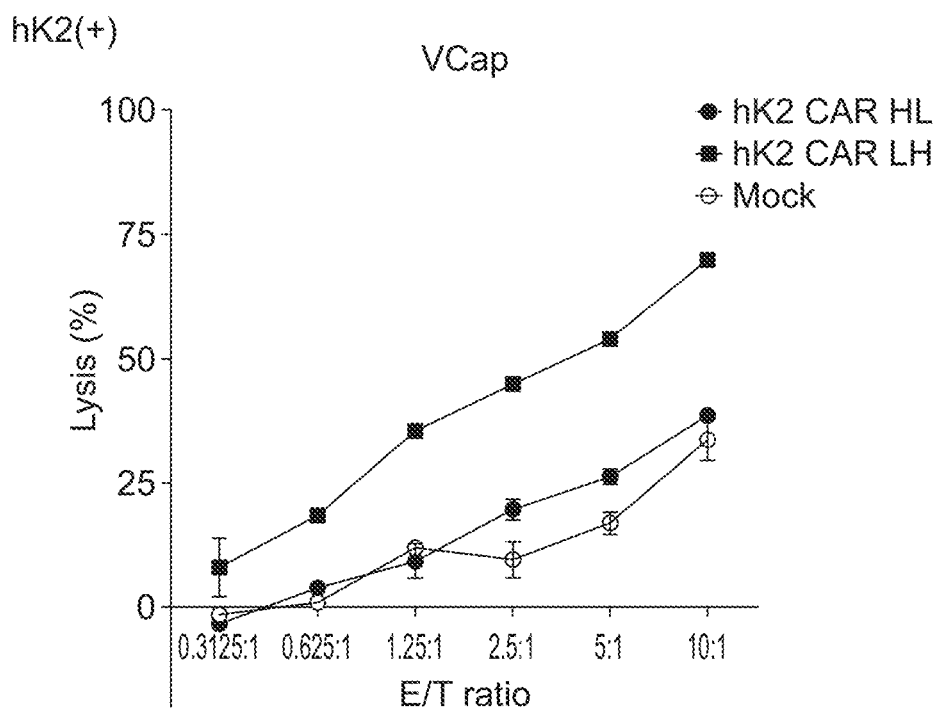
FIG. 2 shows cytotoxicity of hK2-expressing tumor cells by CAR-T cells in 20-hour flow based assay at the indicated effector-to-target cell (E/T) ratio. 24 hours after transient transfection, target cells (Vcap and DU145) were labeled with Cell Trace Violet (CTV) fluorescent dye and then co-cultured with hK2 CAR-T cells. Mock T cells served as negative effector controls. Percent killing is the ratio of the absolute number of live (viability dye negative) target (CTV positive) cells remaining in the co-culture relative to the number of live targets cultured without CAR-T cells.
Figure 2:
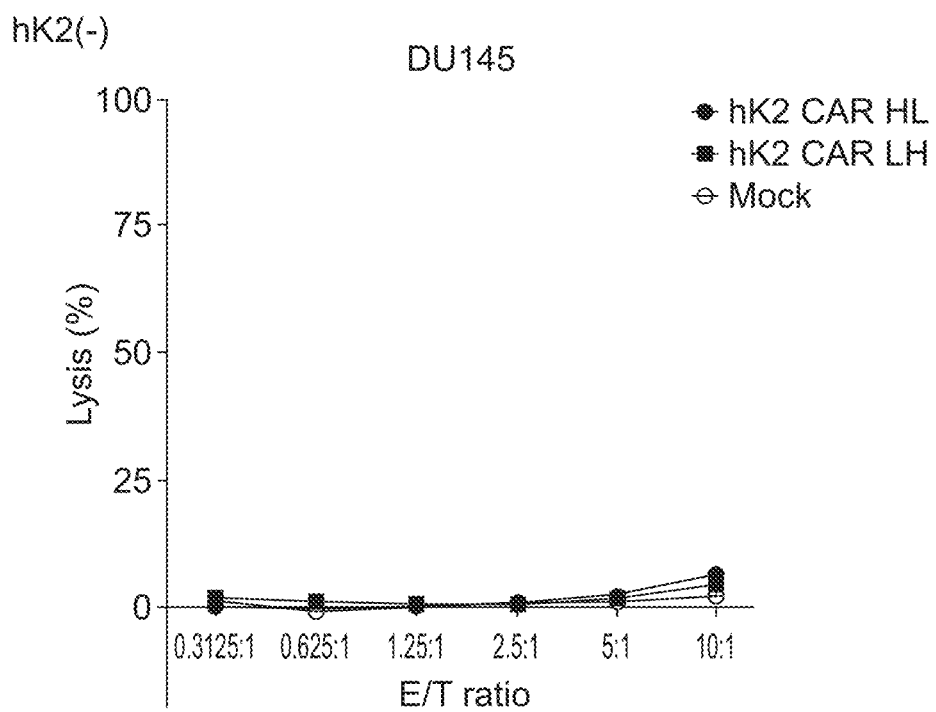

FIG. 17A shows the sequence alignment of the VH domains of mu11B6, hu11B6, KL2B357, KL2B358, KL2B359, KL2B360, HCF3 and HCG5. FIG. 2 shows the sequence alignment of the VL domains of mu11B6, hu11B6, KL2B357, KL2B358, KL2B359, KL2B360, LDC6 and LCB7. Consensus amino acid sequence of SEQ ID NO: 344 and SEQ ID NO:345 were determined for the VH and VL domains, respectively. HCDR and LCDR residues are underlined.

SEQ ID NO: 344
QVQLQESGPGLVKPSX$_1$TLSLTCX$_2$VSGNSITSDYAWNWIRQX$_3$PGKGLEWX$_4$GYISYSGSTTYNPSLKSRVTMSRDTSKNQFSLKLSSVTX$_5$X$_6$DTAVYYCATGYYYGSGFWGQGTLVTVSS

Where,
X1 is D or Q;
X2 is A or T;
X3 is P or F;
X4 is I or M;
X5 is A or P; or
X6 is V or A;

SEQ ID NO: 345
X$_1$IVLTQSPX$_2$X$_3$LX$_4$X$_5$SX$_6$GERATX$_6$X$_8$CX$_9$ASESVEYFGTSLMHWYQQKPGQPPX$_{10}$LLIYAASNX$_{11}$ESGX$_{12}$PX$_{13}$RFSGSGSGTDFTLTIX$_{14}$SLQX$_{15}$EDX$_{16}$AVYX$_{17}$CQQTRKVPYTFGX$_{18}$GTKX$_{19}$EIK

X1 is D or E;
X2 is D or A;
X3 is S or T;
X4 is A or S;
X5 is V or L;
X6 is L or P;
X7 is I or L;
X8 is N or S;
X9 is R or K;
X10 is K or R;
X11 is V or R;
X12 is V or I;
X13 is A or D;
X14 is Q or S;
X15 is P or A;
X16 is F or V;
X17 is Y or F;
X18 is Q or G; and
X19 is L or V;

Fab-Fc and scFvs

The hK2 specific VH/VL regions were engineered as VH-CH1-linker CH2-CH3 and VL-CL and expressed as IgG2 or IgG4 or were engineered as scFvs in either the VH-Linker-VL or VL-linker-VH orientations. The linker that is used in the scFv was the linker of SEQ ID NO: 7 described above. The scFv were used to generate bispecific antibodies as described in Example 7 or to generated CAR as described in Example 11.

Table 11 shows the HC amino acid sequences of selected anti-hK2 antibodies in the mAb format. Table 12 shows the LC amino acid sequences of selected anti-hK2 antibodies in a mAb. Table 13 summaries the HC and LC DNA SEQ ID NOs of selected anti-hK2 antibodies in the mAb format. Table 14 shows the amino acid sequences of selected scFvs in VH-linker-VL or VL-linker-VH orientation.

TABLE 11

Amino acid sequence of the HC (VH-CH1-linker CH2-CH) of selected anti-hK2antibodies in a mAb format.

| KLK2 HEAVY CHAIN | HC PROTEIN SEQ ID NO: | HC AMINO ACID SEQUENCE |
|---|---|---|
| m11B6_HC | 332 | DVQLQESGPGLVKPSQSLSLTCTVTGNSITSDYAWNWIR QFPGNRLEWMGYISYSGSTTYSPSLKSRFSITRDTSKNQF FLQLNSVTPEDTATYFCATGYYYGSGFWGQGTLVTVSS AKTTAPSVYPLAPVCGDTTGSSVTLGCLVKGYFPEPVTL TWNSGSLSSGVHTFPAVLQSDLYTLSSSVTVTSSTWPSQ SITCNVAHPASSTKVDKKIEPRGPTIKPCPPCKCPAPNLL GGPSVFIFPPKIKDVLMISLSPIVTCVVVDVSEDDPDVQIS WFVNNVEVHTAQTQTHREDYNSTLRVVSALPIQHQDW MSGKEFKCKVNNKDLPAPIERTISKPKGSVRAPQVYVLP PPEEEMTKKQVTLTCMVTDFMPEDIYVEWTNNGKTELN YKNTEPVLDSDGSYFMYSKLRVEKKNWVERNSYSCSV VHEGLHNHHTTKSFSRTPGK |
| h11B6_HC | 334 | QVQLQESGPGLVKPSDTLSLTCAVSGNSITSDYAWNWIR QPPGKGLEWIGYISYSGSTTYNPSLKSRVTMSRDTSKNQ FSLKLSSVTAVDTAVYYCATGYYYGSGFWGQGTLVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTVL HQDWLNGKEYKCKVSNKALPAPIEKTISKAKGQPREPQ VYTLPPSREEMTKNQVSLTCLVKGFYPSDIAVEWESNG QPENNYKTTPPVLDSDGSFFLYSKLTVDKSRWQQGNVF SCSVMHEALHNHYTQKSLSLSPGK |
| KL2B30_HC | 185 | QVQLQESGPGLVKPSETLSLTCTVSGGSISSYYWSWIRQ PPGKGLEWIGYIYYSGSTNYNPSLKSRVTISVDTSKNQFS LKLSSVTAADTAVYYCAGTTIFGVVTPNFYYGMDVWG QGTTVTVSSASTKGPSVFPLAPCSRSTSESTAALGCLVK DYFPEPVTVSWNSGALTSGVHTFPAVLQSSGLYSLSSVV TVPSSSLGTKTYTCNVDHKPSNTKVDKRVESKYGPPCPP CPAPEAAGGPSVFLFPPKPKDTLMISRTPEVTCVVVDVS QEDPEVQFNWYVDGVEVHNAKTKPREEQFNSTYRVVS VLTVLHQDWLNGKEYKCKVSNKGLPSSIEKTISKAKGQ PREPQVYTLPPSQEEMTKNQVSLTCLVKGFYPSDIAVEW ESNGQPENNYKTTPPVLDSDGSFFLYSRLTVDKSRWQE GNVFSCSVMHEALHNHYTQKSLSLSLGK |
| K2B53_HC | 187 | EVQLVESGGGVVQPGRSLRLSCVASGFTFSSYDIHWVR QAPGKGLEWVAIISYDGSKKDYTDSVKGRFTISRDNSKN TLYLQMDSLRVEDSAVYSCARESGWSHYYYGMDVW GQGTMVTVSSASTKGPSVFPLAPCSRSTSESTAALGCLV KDYFPEPVTVSWNSGALTSGVHTFPAVLQSSGLYSLSSV VTVPSSSLGTKTYTCNVDHKPSNTKVDKRVESKYGPPCP PCPAPEAAGGPSVFLFPPKPKDTLMISRTPEVTCVVVDVS QEDPEVQFNWYVDGVEVHNAKTKPREEQFNSTYRVVS VLTVLHQDWLNGKEYKCKVSNKGLPSSIEKTISKAKGQ PREPQVYTLPPSQEEMTKNQVSLTCLVKGFYPSDIAVEW ESNGQPENNYKTTPPVLDSDGSFFLYSRLTVDKSRWQE GNVFSCSVMHEALHNHYTQKSLSLSLGK |
| KL2B242_HC | 189 | QVQLQESGPGLVKPSETLSLTCTVSGGSISSYYWSWLRQ PAGSGLEWIGRLYVSGFTNYNPSLKSRVTLSLDPSRNQL SLKLSSVTAADTAVYYCAGDSGNYWGWFDPWGQGTL VTVSSASTKGPSVFPLAPCSRSTSESTAALGCLVKDYFPE PVTVSWNSGALTSGVHTFPAVLQSSGLYSLSSVVTVPSS SLGTKTYTCNVDHKPSNTKVDKRVESKYGPPCPPCPAPE AAGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ |

TABLE 11-continued

Amino acid sequence of the HC (VH-CH1-linker CH2-CH) of selected anti-hK2 antibodies in a mAb format.

| KLK2 HEAVY CHAIN | HC PROTEIN SEQ ID NO: | HC AMINO ACID SEQUENCE |
|---|---|---|
| | | VYTLPPSQEEMTKNQVSLTCLVKGFYPSDIAVEWESNG QPENNYKTTPPVLDSDGSFFLYSRLTVDKSRWQEGNVFS CSVMHEALHNHYTQKSLSLSLGK |
| KL2B467_HC | 191 | QVQLVESGGGVVQPGRSLRLSCAASGFTFSYYGMHWV RQAPGKGLEWVAFISYDGSNKYYADSVKGRFTISRDNS KNTLYLQMNSLRAEDTAVYYCAHLPYSGSYWAFDYW GQGTQVTVSSASTKGPSVFPLAPSSKSTSGGTAALGCLV KDYFPEPVTVSWNSGALTSGVHTFPAVLQSSGLYSLSSV VTVPSSSLGTQTYICNVNHKPSNTKVDKKVEPKSCDKTH TCPPCPAPEAAGGPSVFLFPPKPKDTLMISRTPEVTCVVV SVSHEDPEVKFNWYVDGVEVHNAKTKPREEQYNSTYR VVSVLTVLHQDWLNGKEYKCKVSNKALPAPIEKTISKA KGQPREPQVYTLPPSREEMTKNQVSLTCLVKGFYPSDIA VEWESNGQPENNYKTTPPVLDSDGSFFLYSKLTVDKSR WQQGNVFSCSVMHEALHNHYTQKSLSLSPGK |
| KL2B494_HC | 193 | QVQLVESGGGLVQPGGSLRLSCAASGFTFSHYAMSWVR QAPGKGLEWVSTIGGSGGSTYYADSVKGRFTISRDNSK NTLYLQMNSLRAEDTAVYYCAKPHIVMVTALLYDGMD VWGQGTMVTVSSASTKGPSVFPLAPSSKSTSGGTAALG CLVKDYFPEPVTVSWNSGALTSGVHTFPAVLQSSGLYSL SSVVTVPSSSLGTQTYICNVNHKPSNTKVDKKVEPKSCD KTHTCPPCPAPEAAGGPSVFLFPPKPKDTLMISRTPEVTC VVVSVSHEDPEVKFNWYVDGVEVHNAKTKPREEQYNS TYRVVSVLTVLHQDWLNGKEYKCKVSNKALPAPIEKTI SKAKGQPREPQVYTLPPSREEMTKNQVSLTCLVKGFYPS DIAVEWESNGQPENNYKTTPPVLDSDGSFFLYSKLTVDK SRWQQGNVFSCSVMHEALHNHYTQKSLSLSPGK |

TABLE 12

Amino acid sequences of the LC (VL-CL) of selected anti-hK2 antibodies in a mAb (Fab-Fc) format.

| KLK2 LIGHT CHAIN | LC PROTEIN SEQ ID NO: | LC AMINO ACID SEQUENCE |
|---|---|---|
| m11B6_LC | 333 | DIVLTQSPASLAVSLGQRATISCRASESVEYFGTSLMHW YRQKPGQPPKLLIYAASNVESGVPARFSGSGSGTDFSLNI QPVEEDDFSMYFCQQTRKVPYTFGGGTKLEIKRADAAP TVSIFPPSSEQLTSGGASVVCFLNNFYPKDINVKWKIDGS ERQNGVLNSWTDQDSKDSTYSMSSTLTLTKDEYERHNS YTCEATHKTSTSPIVKSFNRNEC |
| h11B6_LC | 335 | DIVLTQSPDSLAVSLGERATINCKASESVEYFGTSLMHW YQQKPGQPPKLLIYAASNRESGVPDRFSGSGSGTDFTLTI SSLQAEDVAVYYCQQTRKVPYTFGQGTKLEIKRTVAAP SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC |
| KL2B30_LC | 186 | DIQMTQSPSFLSASVGDRVTITCRASQGISSYLAWYQQK PGKAPKFLIYAASTLQSGVPSRFSGSGSGTEFTLTISSLQP EDFATYYCQQLNSYPLTFGGGTKVEIKRTVAAPSVFIFPP SDEQLKSGTASVVCLLNNFYPREAKVQWKVDNALQSG NSQESVTEQDSKDSTYSLSSTLTLSKADYEKHKVYACEV THQGLSSPVTKSFNRGEC |
| KL2B53_LC | 188 | DIVMTQSPSSLSASVGDRVTITCRASQDISNYLAWYQQK PGKVPKFLIYAASTLHSGVPSRFSGSGSGTDFTLTISSLQP EDVATYYCQKYNSAPYTFGQGTRLEIKRTVAAPSVFIFP PSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| KL2B242_LC | 190 | SYELTQPPSVSVSPGETASITCSGDQLGENYACWYQQKP GQSPVLVIYQDSKRPSGIPERFSGSNSGNTATLTISGTQA |

TABLE 12-continued

Amino acid sequences of the LC (VL-CL) of selected anti-hK2 antibodies in a mAb (Fab-Fc) format.

| KLK2 LIGHT CHAIN | LC PROTEIN SEQ ID NO: | LC AMINO ACID SEQUENCE |
|---|---|---|
| | | LDEADYYCQAWDNSIVVFGGGTKLTVLGQPKAAPSVTL FPPSSEELQANKATLVCLISDFYPGAVTVAWKADSSPVK AGVETTTPSKQSNNKYAASSYLSLTPEQWKSHRSYSCQ VTHEGSTVEKTVAPTECS |
| KL2B467_LC | 192 | QSVLTQPPSVSVAPGQTASITCGGDNIGSKSVHWYQQKP GQAPVLVVYDNSDRPSGIPERFSGSNSGTTATLTISRVEA GDEADYYCQVWDSSSDHPVVFGGGTKVTVLGQPKAAP SVTLFPPSSEELQANKATLVCLISDFYPGAVTVAWKADS SPVKAGVETTTPSKQSNNKYAASSYLSLTPEQWKSHRS YSCQVTHEGSTVEKTVAPTECS |
| KL2B494_LC | 194 | SSELTQPPSVSVAPGQTARITCGGNNIGSKSVHWYQQKP GQAPVLVVYDDSDRPSGIPERFSGSNSGNTATLTISRVEA GDEADYYCQVWDSSSDHVVFGGGTKLTVLGQPKAAPS VTLFPPSSEELQANKATLVCLISDFYPGAVTVAWKADSS PVKAGVETTTPSKQSNNKYAASSYLSLTPEQWKSHRSY SCQVTHEGSTVEKTVAPTECS |

TABLE 13

SEQ ID Nos of the cDNA sequences of HC and LC of selected hK2 antibodies

| Antibody | HC Protein SEQ ID NO: | LC Protein SEQ ID NO: | HC cDNA SEQ ID NO: | LC cDNA SEQ ID NO: |
|---|---|---|---|---|
| m11B6 | 332 | 333 | 336 | 337 |
| hu11B6 | 334 | 335 | 338 | 339 |
| KL2B30 | 185 | 186 | 195 | 196 |
| KL2B53 | 187 | 188 | 197 | 198 |
| KL2B242 | 189 | 190 | 199 | 200 |
| KL2B467 | 191 | 192 | 201 | 202 |
| KL2B494 | 193 | 194 | 203 | 204 |

TABLE 14

Amino acid sequences of the variable domain of selected anti-hK2 scFvs antibodies in VH-linker-VL (HL) or in VL-linker-VH (LH) format.

| scFv name | Acronym | Amino acid sequence of scFv | SEQ ID NO: |
|---|---|---|---|
| scFv1 | HCG5_LDC6_HL | QVQLQESGPGLVKPSDTLSLTCAVSGNSITSD YAWNWIRQFPGKGLEWMGYISYSGSTTYNP SLKSRVTISRDTSKNQFSLKLSSVTPVDTAVY YCATGYYYGSGFWGQGTLVTVSSGGSEGKS SGSGSESKSTGGSDIVLTQSPDSLAVSLGERA TINCKASESVEYFGTSLMHWYQQKPGQPPKL LIYAASNRESGVPDRFSGSGSGTDFTLTIQSV QAEDVSVYFCQQTRKVPYTFGQGTKLEIK | 8 |
| scFv2 | HCG5_hu11B6_ HL | QVQLQESGPGLVKPSDTLSLTCAVSGNSITSD YAWNWIRQFPGKGLEWMGYISYSGSTTYNP SLKSRVTISRDTSKNQFSLKLSSVTPVDTAVY YCATGYYYGSGFWGQGTLVTVSSGGSEGKS SGSGSESKSTGGSDIVLTQSPDSLAVSLGERA TINCKASESVEYFGTSLMHWYQQKPGQPPKL LIYAASNRESGVPDRFSGSGSGTDFTLTISSLQ AEDVAVYYCQQTRKVPYTFGQGTKLEIK | 9 |
| scFv3 | HCF3_hu11B6_HL | QVQLQESGPGLVKPSDTLSLTCAVSGNSITSD YAWNWIRQFPGKGLEWIGYISYSGSTTYNPS LKSRVTISRDTSKNQFSLKLSSVTPVDTAVYY CATGYYYGSGFWGQGTLVTVSSGGSEGKSS GSGSESKSTGGSDIVLTQSPDSLAVSLGERATI NCKASESVEYFGTSLMHWYQQKPGQPPKLLI YAASNRESGVPDRFSGSGSGTDFTLTISSVQA EDVAVYYCQQTRKVPYTFGQGTKLEIK | 10 |

TABLE 14-continued

Amino acid sequences of the variable domain of selected anti-hK2 scFvs antibodies in VH-linker-VL (HL) or in VL-linker-VH (LH) format.

| scFv name | Acronym | Amino acid sequence of scFv | SEQ ID NO: |
|---|---|---|---|
| scFv4 | HCG5_LCB7_HL | QVQLQESGPGLVKPSDTLSLTCAVSGNSITSD YAWNWIRQFPGKGLEWMGYISYSGSTTYNP SLKSRVTISRDTSKNQFSLKLSSVTPVDTAVY YCATGYYYGSGFWGQGTLVTVSSGGSEGKS SGSGSESKSTGGSDIVLTQSPDSLAVSLGERA TINCKASESVEYFGTSLMHWYQQKPGQPPKL LIYAASNRESGVPDRFSGSGSGTDFTLTISSVQ AEDVAVYYCQQTRKVPYTFGQGTKLEIK | 11 |
| scFv5 | LCD6_HCG5_LH | DIVLTQSPDSLAVSLGERATINCKASESVEYF GTSLMHWYQQKPGQPPKLLIYAASNRESGVP DRFSGSGSGTDFTLTIQSVQAEDVSVYFCQQT RKVPYTFGQGTKLEIKGGSEGKSSGSGSESKS TGGSQVQLQESGPGLVKPSDTLSLTCAVSGN SITSDYAWNWIRQFPGKGLEWMGYISYSGST TYNPSLKSRVTISRDTSKNQFSLKLSSVTPVD TAVYYCATGYYYGSGFWGQGTLVTVSS | 12 |
| scFv6 | hu11B6_HCF3_LH | DIVLTQSPDSLAVSLGERATINCKASESVEYF GTSLMHWYQQKPGQPPKLLIYAASNRESGVP DRFSGSGSGTDFTLTISSLQAEDVAVYYCQQT RKVPYTFGQGTKLEIKGGSEGKSSGSGSESKS TGGSQVQLQESGPGLVKPSDTLSLTCAVSGN SITSDYAWNWIRQFPGKGLEWIGYISYSGSTT YNPSLKSRVTISRDTSKNQFSLKLSSVTPVDT AVYYCATGYYYGSGFWGQGTLVTVSS | 13 |
| scFv7 | hu11B6_HCG5_LH | DIVLTQSPDSLAVSLGERATINCKASESVEYF GTSLMHWYQQKPGQPPKLLIYAASNRESGVP DRFSGSGSGTDFTLTISSLQAEDVAVYYCQQT RKVPYTFGQGTKLEIKGGSEGKSSGSGSESKS TGGSQVQLQESGPGLVKPSDTLSLTCAVSGN SITSDYAWNWIRQFPGKGLEWMGYISYSGST TYNPSLKSRVTISRDTSKNQFSLKLSSVTPVD TAVYYCATGYYYGSGFWGQGTLVTVSS | 14 |
| scFv8 | LCB7_HCF3_LH | DIVLTQSPDSLAVSLGERATINCKASESVEYF GTSLMHWYQQKPGQPPKLLIYAASNRESGVP DRFSGSGSGTDFTLTISSVQAEDVAVYYCQQ TRKVPYTFGQGTKLEIKGGSEGKSSGSGSESK STGGSQVQLQESGPGLVKPSDTLSLTCAVSG NSITSDYAWNWIRQFPGKGLEWIGYISYSGST TYNPSLKSRVTISRDTSKNQFSLKLSSVTPVD TAVYYCATGYYYGSGFWGQGTLVTVSS | 15 |
| scFv9 | LCB7_HCG5_LH | DIVLTQSPDSLAVSLGERATINCKASESVEYF GTSLMHWYQQKPGQPPKLLIYAASNRESGVP DRFSGSGSGTDFTLTISSVQAEDVAVYYCQQ TRKVPYTFGQGTKLEIKGGSEGKSSGSGSESK STGGSQVQLQESGPGLVKPSDTLSLTCAVSG NSITSDYAWNWIRQFPGKGLEWMGYISYSGS TTYNPSLKSRVTISRDTSKNQFSLKLSSVTPV DTAVYYCATGYYYGSGFWGQGTLVTVSS | 16 |
| scFv10 | LCD6_HCF3_LH | DIVLTQSPDSLAVSLGERATINCKASESVEYF GTSLMHWYQQKPGQPPKLLIYAASNRESGVP DRFSGSGSGTDFTLTIQSVQAEDVSVYFCQQT RKVPYTFGQGTKLEIKGGSEGKSSGSGSESKS TGGSQVQLQESGPGLVKPSDTLSLTCAVSGN SITSDYAWNWIRQFPGKGLEWIGYISYSGSTT YNPSLKSRVTISRDTSKNQFSLKLSSVTPVDT AVYYCATGYYYGSGFWGQGTLVTVSS | 17 |
| scFv11 | hu11B6_LCB7_HL | QVQLQESGPGLVKPSDTLSLTCAVSGNSITSD YAWNWIRQPPGKGLEWIGYISYSGSTTYNPS LKSRVTMSRDTSKNQFSLKLSSVTAVDTAVY YCATGYYYGSGFWGQGTLVTVSSGGSEGKS SGSGSESKSTGGSDIVLTQSPDSLAVSLGERA TINCKASESVEYFGTSLMHWYQQKPGQPPKL LIYAASNRESGVPDRFSGSGSGTDFTLTISSVQ AEDVAVYYCQQTRKVPYTFGQGTKLEIK | 18 |

TABLE 14-continued

Amino acid sequences of the variable domain of selected anti-hK2 scFvs antibodies in VH-linker-VL (HL) or in VL-linker-VH (LH) format.

| scFv name | Acronym | Amino acid sequence of scFv | SEQ ID NO: |
|---|---|---|---|
| scFv12 | hu11B6_LCD6_HL | QVQLQESGPGLVKPSDTLSLTCAVSGNSITSD YAWNWIRQPPGKGLEWIGYISYSGSTTYNPS LKSRVTMSRDTSKNQFSLKLSSVTAVDTAVY YCATGYYYGSGFWGQGTLVTVSSGGSEGKS SGSGSESKSTGGSDIVLTQSPDSLAVSLGERA TINCKASESVEYFGTSLMHWYQQKPGQPPKL LIYAASNRESGVPDRFSGSGSGTDFTLTIQSV QAEDVSVYFCQQTRKVPYTFGQGTKLEIK | 19 |
| scFv13 | hu11B6_HL | QVQLQESGPGLVKPSDTLSLTCAVSGNSITSD YAWNWIRQPPGKGLEWIGYISYSGSTTYNPS LKSRVTMSRDTSKNQFSLKLSSVTAVDTAVY YCATGYYYGSGFWGQGTLVTVSSGGSEGKS SGSGSESKSTGGSDIVLTQSPDSLAVSLGERA TINCKASESVEYFGTSLMHWYQQKPGQPPKL LIYAASNRESGVPDRFSGSGSGTDFTLTISSLQ AEDVAVYYCQQTRKVPYTFGQGTKLEIK | 20 |
| scFv14 | LCD6_hu11B6_LH | DIVLTQSPDSLAVSLGERATINCKASESVEYF GTSLMHWYQQKPGQPPKLLIYAASNRESGVP DRFSGSGSGTDFTLTIQSVQAEDVSVYFCQQT RKVPYTFGQGTKLEIKGGSEGKSSGSGSESKS TGGSQVQLQESGPGLVKPSDTLSLTCAVSGN SITSDYAWNWIRQPPGKGLEWIGYISYSGSTT YNPSLKSRVTMSRDTSKNQFSLKLSSVTAVD TAVYYCATGYYYGSGFWGQGTLVTVSS | 21 |
| scFv15 | hu11B6_LH | DIVLTQSPDSLAVSLGERATINCKASESVEYF GTSLMHWYQQKPGQPPKLLIYAASNRESGVP DRFSGSGSGTDFTLTISSLQAEDVAVYYCQQT RKVPYTFGQGTKLEIKGGSEGKSSGSGSESKS TGGSQVQLQESGPGLVKPSDTLSLTCAVSGN SITSDYAWNWIRQPPGKGLEWIGYISYSGSTT YNPSLKSRVTMSRDTSKNQFSLKLSSVTAVD TAVYYCATGYYYGSGFWGQGTLVTVSS | 22 |
| scFv16 | LCB7_hu11B6_LH | DIVLTQSPDSLAVSLGERATINCKASESVEYF GTSLMHWYQQKPGQPPKLLIYAASNRESGVP DRFSGSGSGTDFTLTISSVQAEDVAVYYCQQ TRKVPYTFGQGTKLEIKGGSEGKSSGSGSESK STGGSQVQLQESGPGLVKPSDTLSLTCAVSG NSITSDYAWNWIRQPPGKGLEWIGYISYSGST TYNPSLKSRVTMSRDTSKNQFSLKLSSVTAV DTAVYYCATGYYYGSGFWGQGTLVTVSS | 23 |
| scFv17 | KL2B413_HL | EVQLVESGGGLVQPGGSLRLSCAASGFTFSS YWMTWVRQAPGKGLEWVANIKQDGSERYY VDSVKGRFTISRDNAKNSLYLQMNSLRAEDT AVYYCARDQNYDILTGHYGMDVWGQGTTV TVSSGGSEGKSSGSGSESKSTGGSEIVLTQSPS FLSASVGDRVTITCRASQGISSYLSWYQQKPG KAPKLLIYATSTLQSGVPSRFSGSGSGTEFTLT ISSLQPEDFATYYCQQLNSYPRTFGQGTKVEI K | 340 |
| scFv18 | KL2B413_LH | EIVLTQSPSFLSASVGDRVTITCRASQGISSYL SWYQQKPGKAPKLLIYATSTLQSGVPSRFSGS GSGTEFTLTISSLQPEDFATYYCQQLNSYPRT FGQGTKVEIKGGSEGKSSGSGSESKSTGGSEV QLVESGGGLVQPGGSLRLSCAASGFTFSSYW MTWVRQAPGKGLEWVANIKQDGSERYYVD SVKGRFTISRDNAKNSLYLQMNSLRAEDTAV YYCARDQNYDILTGHYGMDVWGQGTTVTV SS | 341 |
| scFv19 | KL2B359_HL | QVQLQESGPGLVKPSQTLSLTCTVSGNSITSD YAWNWIRQFPGKRLEWIGYISYSGSTTYNPS LKSRVTISRDTSKNQFSLKLSSVTAADTAVYY CATGYYYGSGFWGQGTLVTVSSGGSEGKSS GSGSESKSTGGSEIVLTQSPATLSLSPGERATL SCRASESVEYFGTSLMHWYQQKPGQPPRLLI YAASNVESGIPARFSGSGSGTDFTLTISSVEPE DFAVYFCQQTRKVPYTFGGGTKVEIK | 342 |

TABLE 14-continued

Amino acid sequences of the variable domain of selected anti-hK2 scFvs antibodies in VH-linker-VL (HL) or in VL-linker-VH (LH) format.

| scFv name | Acronym | Amino acid sequence of scFv | SEQ ID NO: |
|---|---|---|---|
| scFv20 | KL2B359_LH | EIVLTQSPATLSLSPGERATLSCRASESVEYFGTSLMHWYQQKPGQPPRLLIYAASNVESGIPARFSGSGSGTDFTLTISSVEPEDFAVYFCQQTRKVPYTFGGGTKVEIKGGSEGKSSGSGSESKSTGGSQVQLQESGPGLVKPSQTLSLTCTVSGNSITSDYAWNWIRQFPGKRLEWIGYISYSGSTTYNPSLKSRVTISRDTSKNQFSLKLSSVTAADTAVYYCATGYYYGSGFWGQGTLVTVSS | 343 |
| scFv21 | KL2B357_HL | QVQLQESGPGLVKPSQTLSLTCTVSGNSITSDYAWNWIRQFPGKGLEWIGYISYSGSTTYNPSLKSRVTISRDTSKNQFSLKLSSVTAADTAVYYCATGYYYGSGFWGQGTLVTVSSGGSEGKSSGSGSESKSTGGSDIVLTQSPDSLAVSLGERATINCRASESVEYFGTSLMHWYQQKPGQPPKLLIYAASNVESGVPDRFSGSGSGTDFTLTISSLQAEDVAVYFCQQTRKVPYTFGGGTKVEIK | 169 |
| scFv22 | KL2B357_LH | DIVLTQSPDSLAVSLGERATINCRASESVEYFGTSLMHWYQQKPGQPPKLLIYAASNVESGVPDRFSGSGSGTDFTLTISSLQAEDVAVYFCQQTRKVPYTFGGGTKVEIKGGSEGKSSGSGSESKSTGGSQVQLQESGPGLVKPSQTLSLTCTVSGNSITSDYAWNWIRQFPGKGLEWIGYISYSGSTTYNPSLKSRVTISRDTSKNQFSLKLSSVTAADTAVYYCATGYYYGSGFWGQGTLVTVSS | 170 |
| scFv23 | KL2B358_HL | QVQLQESGPGLVKPSQTLSLTCTVSGNSITSDYAWNWIRQPPGKGLEWIGYISYSGSTTYNPSLKSRVTISRDTSKNQFSLKLSSVTAADTAVYYCATGYYYGSGFWGQGTLVTVSSGGSEGKSSGSGSESKSTGGSEIVLTQSPATLSLSPGERATLSCRASESVEYFGTSLMHWYQQKPGQPPRLLIYAASNVESGIPARFSGSGSGTDFTLTISSVEPEDFAVYFCQQTRKVPYTFGGGTKVEIK | 171 |
| scFv24 | KL2B358_LH | EIVLTQSPATLSLSPGERATLSCRASESVEYFGTSLMHWYQQKPGQPPRLLIYAASNVESGIPARFSGSGSGTDFTLTISSVEPEDFAVYFCQQTRKVPYTFGGGTKVEIKGGSEGKSSGSGSESKSTGGSQVQLQESGPGLVKPSQTLSLTCTVSGNSITSDYAWNWIRQPPGKGLEWIGYISYSGSTTYNPSLKSRVTISRDTSKNQFSLKLSSVTAADTAVYYCATGYYYGSGFWGQGTLVTVSS | 172 |
| scFv25 | KL2B360_HL | QVQLQESGPGLVKPSQTLSLTCTVSGNSITSDYAWNWIRQFPGKGLEWIGYISYSGSTTYNPSLKSRVTISRDTSKNQFSLKLSSVTAADTAVYYCATGYYYGSGFWGQGTLVTVSSGGSEGKSSGSGSESKSTGGSEIVLTQSPATLSLSPGERATLSCRASESVEYFGTSLMHWYQQKPGQPPRLLIYAASNVESGIPARFSGSGSGTDFTLTISSVEPEDFAVYFCQQTRKVPYTFGGGTKVEIK | 173 |
| scFv26 | KL2B360_LH | EIVLTQSPATLSLSPGERATLSCRASESVEYFGTSLMHWYQQKPGQPPRLLIYAASNVESGIPARFSGSGSGTDFTLTISSVEPEDFAVYFCQQTRKVPYTFGGGTKVEIKGGSEGKSSGSGSESKSTGGSQVQLQESGPGLVKPSQTLSLTCTVSGNSITSDYAWNWIRQFPGKGLEWIGYISYSGSTTYNPSLKSRVTISRDTSKNQFSLKLSSVTAADTAVYYCATGYYYGSGFWGQGTLVTVSS | 174 |
| scFv27 | KL2B30_HL | QVQLQESGPGLVKPSETLSLTCTVSGGSISSYYWSWIRQPPGKGLEWIGYIYYSGSTNYNPSLKSRVTISVDTSKNQFSLKLSSVTAADTAVYYCAGTTIFGVVTPNFYYGMDVWGQGTTVTVSSGGSEGKSSGSGSESKSTGGSDIQMTQSPSFLSASVGDRVTITCRASQGISSYLAWYQQKPGKAPKFLIYAASTLQSGVPSRFSGSGSGTEFTLTISSLQPEDFATYYCQQLNSYPLTFGGGTKVEIK | 175 |

TABLE 14-continued

Amino acid sequences of the variable domain of selected anti-hK2 scFvs antibodies in VH-linker-VL (HL) or in VL-linker-VH (LH) format.

| scFv name | Acronym | Amino acid sequence of scFv | SEQ ID NO: |
|---|---|---|---|
| scFv28 | KL2B30_LH | DIQMTQSPSFLSASVGDRVTITCRASQGISSYL AWYQQKPGKAPKFLIYAASTLQSGVPSRFSG SGSGTEFTLTISSLQPEDFATYYCQQLNSYPLT FGGGTKVEIKGGSEGKSSGSGSESKSTGGSQV QLQESGPGLVKPSETLSLTCTVSGGSISSYYW SWIRQPPGKGLEWIGYIYYSGSTNYNPSLKSR VTISVDTSKNQFSLKLSSVTAADTAVYYCAG TTIFGVVTPNFYYGMDVWGQGTTVTVSS | 176 |
| scFv29 | KL2B53_HL | EVQLVESGGGVVQPGRSLRLSCVASGFTFSS YDIHWVRQAPGKGLEWVAIISYDGSKKDYT DSVKGRFTISRDNSKNTLYLQMDSLRVEDSA VYSCARESGWSHYYYGMDVWGQGTMVT VSSGGSEGKSSGSGSESKSTGGSDIVMTQSPS SLSASVGDRVTITCRASQDISNYLAWYQQKP GKVPKFLIYAASTLHSGVPSRFSGSGSGTDFT LTISSLQPEDVATYYCQKYNSAPYTFGQGTR LEIK | 177 |
| scFv30 | KL2B53_LH | DIVMTQSPSSLSASVGDRVTITCRASQDISNY LAWYQQKPGKVPKFLIYAASTLHSGVPSRFS GSGSGTDFTLTISSLQPEDVATYYCQKYNSAP YTFGQGTRLEIKGGSEGKSSGSGSESKSTGGS EVQLVESGGGVVQPGRSLRLSCVASGFTFSS YDIHWVRQAPGKGLEWVAIISYDGSKKDYT DSVKGRFTISRDNSKNTLYLQMDSLRVEDSA VYSCARESGWSHYYYGMDVWGQGTMVT VSS | 178 |
| scFv31 | KL2B242_HL | QVQLQESGPGLVKPSETLSLTCTVSGGSISSY YWSWLRQPAGSGLEWIGRLYVSGFTNYNPS LKSRVTLSLDPSRNQLSLKLSSVTAADTAVY YCAGDSGNYWGWFDPWGQGTLVTVSSGGS EGKSSGSGSESKSTGGSSYELTQPPSVSVSPG ETASITCSGDQLGENYACWYQQKPGQSPVLV IYQDSKRPSGIPERFSGSNSGNTATLTISGTQA LDEADYYCQAWDNSIVVFGGGTKLTVL | 179 |
| scFv32 | KL2B242_LH | SYELTQPPSVSVSPGETASITCSGDQLGENYA CWYQQKPGQSPVLVIYQDSKRPSGIPERFSGS NSGNTATLTISGTQALDEADYYCQAWDNSIV VFGGGTKLTVLGGSEGKSSGSGSESKSTGGS QVQLQESGPGLVKPSETLSLTCTVSGGSISSY YWSWLRQPAGSGLEWIGRLYVSGFTNYNPS LKSRVTLSLDPSRNQLSLKLSSVTAADTAVY YCAGDSGNYWGWFDPWGQGTLVTVSS | 180 |
| scFv33 | KL2B467_HL | QVQLVESGGGVVQPGRSLRLSCAASGFTFSY YGMHWVRQAPGKGLEWVAFISYDGSNKYY ADSVKGRFTISRDNSKNTLYLQMNSLRAEDT AVYYCAHLPYSGSYWAFDYWGQGTQVTVS SGGSEGKSSGSGSESKSTGGSQSVLTQPPSVS VAPGQTASITCGGDNIGSKSVHWYQQKPGQ APVLVVYDNSDRPSGIPERFSGSNSGTTATLTI SRVEAGDEADYYCQVWDSSSDHPVVFGGGT KVTV | 181 |
| scFv34 | KL2B467_LH | QSVLTQPPSVSVAPGQTASITCGGDNIGSKSV HWYQQKPGQAPVLVVYDNSDRPSGIPERFSG SNSGTTATLTISRVEAGDEADYYCQVWDSSS DHPVVFGGGTKVTVGGSEGKSSGSGSESKST GGSQVQLVESGGGVVQPGRSLRLSCAASGFT FSYYGMHWVRQAPGKGLEWVAFISYDGSNK YYADSVKGRFTISRDNSKNTLYLQMNSLRAE DTAVYYCAHLPYSGSYWAFDYWGQGTQVT VSS | 182 |
| scFv35 | KL2B494_HL | QVQLVESGGGLVQPGGSLRLSCAASGFTFSH YAMSWVRQAPGKGLEWVSTIGGSGGSTYYA DSVKGRFTISRDNSKNTLYLQMNSLRAEDTA VYYCAKPHIVMVTALLYDGMDVWGQGTMV TVSS GGSEGKSSGSGSESKSTGGSSSELTQPPSVSV APGQTARITCGGNNIGSKSVHWYQQKPGQAP | 183 |

TABLE 14-continued

Amino acid sequences of the variable domain of selected anti-hK2 scFvs antibodies in VH-linker-VL (HL) or in VL-linker-VH (LH) format.

| scFv name | Acronym | Amino acid sequence of scFv | SEQ ID NO: |
|---|---|---|---|
| | | VLVVYDDSDRPSGIPERFSGSNSGNTATLTIS RVEAGDEADYYCQVWDSSSDHVVFGGGTKL TVL | |
| scFv36 | KL2B494_LH | SSELTQPPSVSVAPGQTARITCGGNNIGSKSV HWYQQKPGQAPVLVVYDDSDRPSGIPERFSG SNSGNTATLTISRVEAGDEADYYCQVWDSSS DHVVFGGGTKLTVLGGSEGKSSGSGSESKST GGSQVQLVESGGGLVQPGGSLRLSCAASGFT FSHYAMSWVRQAPGKGLEWVSTIGGSGGST YYADSVKGRFTISRDNSKNTLYLQMNSLRAE DTAVYYCAKPHIVMVTALLYDGMDVWGQG TMVTVSS | 184 |

Example 12. Biophysical Characterization of Anti-hK2 Antibodies

Affinity and Thermal Stability of Anti-hK2 Antibodies.

Affinity of selected hK2 antibodies for soluble hK2 was measured by surface plasmon resonance (SPR). SPR is a label-free technique to study the strength of an interaction between two binding partners by measuring the change in mass upon complex formation and dissociation. Antibodies were captured on a sensor chip coated with an anti-Fc antibody followed by injection of soluble hK2 at various concentrations and specified association and dissociation times. Post dissociation, the surface was regenerated with an appropriate solution to prepare for the next interaction. Kinetic information (on-rate and off-rate constants) were extracted by fitting sensorgrams to the 1:1 Langmuir model. Binding affinity ($K_D$) are reported as the ratio of rate constants ($k_{off}/k_{on}$). $K_D$ values of selected hK2 antibodies are listed in Table 15.

Thermal stability was determined by Differential Scanning Fluorimetry (NanoDSF) using an automated Prometheus instrument. NanoDSF was used to measure $T_m$ of molecules at a concentration of 0.5 mg/mL in Phosphate Buffered Saline, pH 7.4. Measurements were made by loading samples into 24 well capillary from a 384 well sample plate. Duplicate runs were performed for each sample. The thermal scans span from 20° C. to 95° C. at a rate of 1.0° C./minute. Intrinsic tryptophan and tyrosine fluorescence were monitored at the emission wavelengths of 330 nm and 350 nm, and the F350/F330 nm ratio were plotted against temperature to generate unfolding curves. Measured Tm values are listed in Table 15.

TABLE 15

$K_D$ and $T_m$ of selected molecules

| Molecule | $K_D$ (nM) | Tm (° C.) |
|---|---|---|
| KL2B413 (scFv) | 34.3 | 67 |
| KL2B359 (scFv) | 0.7-1 | 67 |
| KL2B30 (Fab) | 0.460 | >70 |
| KL2B242 (Fab) | 0.040 | >70 |
| KL2B53 (Fab) | 0.080 | >70 |
| KL2B467 (Fab) | 0.078 | >70 |
| KL2B494 (Fab) | 0.053 | >70 |

KL2B413 scFv generated from the Ablexis immunization campaign had a thermal stability (Tm) of 67° C. as measured by Nano DSF and a binding affinity ($K_D$) to human hK2 of about 34 nM. Clone KL2B359 obtained for the re-humanization campaign and which had maintained a binding affinity similar to murine 11B6 was converted to scFv-Fc and CAR-T for additional profiling. KL2B359 scFv shows a Tm of 67° C. and a binding affinity ($K_D$) to hK2 of ~0.7-1 nM. KL2B30, KL2B242, KL2B53, KL2B467 and KL2B494 Fab showed binding affinities below 0.5 nM and Tm values above 70° C.

Epitope Mapping

The epitope on selected KL2B antibodies was determined by hydrogen-deuterium exchange mass spectrometry (HDX-MS). Human KLK2 antigen was used for epitope mapping experiment.

Briefly, purified the KLK2 antigen was incubated with and without anti-KLK2 antibodies in deuterium oxide labeling buffer. The hydrogen-deuterium exchange (HDX) mixture was quenched at different time point by the addition of 8 M urea, 1M TCEP, pH 3.0. The quenched sample was passed over an immobilized pepsin/FPXIII column at 600 µL/min equilibrated with buffer A (1% acetonitrile, 0.1% FA in H2O) at room temperature. Peptic fragments were loaded onto a reverse phase trap column at 600 µL/min with buffer A and desalted for 1 min (600 µL buffer A). The desalted fragments were separated by a C18 column with a linear gradient of 8% to 35% buffer B (95% acetonitrile, 5% H2O, 0.0025% TFA) at 100 µL/min over 20 min and analyzed by mass spectrometry. Mass spectrometric analyses were carried out using an LTQ™ Orbitrap Fusion Lumos mass spectrometer (Thermo Fisher Scientific) with the capillary temperature at 275° C., resolution 150,000, and mass range (m/z) 300-1,800. BioPharma Finder 3.0 (Thermo Fisher Scientific) was used for the peptide identification of non-deuterated samples prior to the HDX experiments. HDExaminer version 2.5 (Sierra Analytics, Modesto, Calif.) was used to extract centroid values from the MS raw data files for the HDX experiments.

Incubation of hK2 antibodies, hu11B6, KL2B494, KL2B467, KL2B30, KL2B413 and KL2B53 with soluble hK2 protein resulted in different patterns of hydrogen exchange and overall protection. The protected segments were mapped onto the sequence of hK2 antigen to visualize the binding epitopes (FIG. 17B). KL2B494, KL2B467 and KL2B30 bound to a common sequence consisting of residues 173-178 (SEQ ID NO: 346, KVTEF) and residue 230-234 (SEQ ID NO: 347, HYRKW). KL2B53 showed a different pattern of protection and bound to a sequence consisting of residues 27-32 (Seq ID NO: 348, SHGWAH), 60-75 (SEQ ID NO: 349, RHNLFEPEDTGQRVP) and 138-147 (SEQ ID NO: 350, GWGSIEPEE).

Example 13. Generation and Characterization of Additional scFvs CAR Constructs

The ectodomain of 11B6 cloned as scFv did not retain binding at elevated temperature (55° C.) and hence additional campaigns were initiated to generate new humanized antibodies from the parental 11B6.

hK2 CARs containing thermally stabilized scFvs derived from the antibody 11B6 were generated. The description and SEQ ID NOs: of the CAR constructs containing thermally stabilized scFvs are provided in Table 16. The names in the description refer back to the VH or the VL chains identified above, 2AA refers to the 20 amino acid long linker between the VH/VL pairs in the scFv. The scFv in the CARs were cloned in either VH-L-VL or VL-L-VH orientation.

The generated scFvs KL2B413_HL, KL2B413_LH, KL2B359_HL and KL2B359_LH were also incorporated into CAR constructs and further characterized. Table 16 shows the generated CAR constructs and their SEQ ID NOs. The signal sequence used was MAWVWTLLFLMAAAQ-SIQA (SEQ ID NO: 24)

TABLE 16

| Name of CAR construct | Description of scFv in the CAR | SEQ ID NO: of scFv amino acid sequence I the CAR | SEQ ID NO: of full ECD domain of CAR (including signal sequence) | SEQ ID NO: of CAR amino acid sequence |
|---|---|---|---|---|
| CAR1 | HL_HCG5_LCD6_20AA (scFv1) | 8 | 273 | 46 |
| CAR2 | HL_HCG5_LCh11B6_20AA (scFv2) | 9 | 274 | 47 |
| CAR3 | HL_HCF3_LCB7_20AA (scFv3) | 10 | 275 | 48 |
| CAR4 | HL_HCG5_LCB7_20AA (scFv4) | 11 | 276 | 49 |
| CAR5 | LH_LCD6_HCG5_20AA (scFv5) | 12 | 277 | 50 |
| CAR6 | LH_LCHumanized_HCF3_20AA (scFv6) | 13 | 278 | 51 |
| CAR7 | LH_LCHumanized_HCG5_20AA (scFv7) | 14 | 279 | 52 |
| CAR8 | LH_LCB7_HCF3_20AA (scFv8) | 15 | 280 | 53 |
| CAR9 | LH_LCB7_HCG5_20AA (scFv9) | 16 | 281 | 54 |
| CAR10 | LH_LCD6_HCF3_20AA (scFv10) | 17 | 282 | 55 |
| CAR11 | HL_HCHumanized_LCB7_20AA (scFv11) | 18 | 283 | 56 |
| CAR12 | HL_HCHumanized_LCD6_20AA (scFv12) | 19 | 284 | 57 |
| CARB | HL_HCHumanized_LCHumanized_20AA (scFv13) | 20 | 285 | 58 |
| CAR14 | LH_LCD6_HCHumanized_20AA (scFv14) | 21 | 286 | 59 |
| CAR15 | LH_LCHumanized_HCHumanized_20AA (scFv15) | 22 | 287 | 60 |
| CAR16 | LH_LCB7_HCHumanized_20AA (scFv16) | 23 | 288 | 61 |
| CAR17 | KL2B413_HL (scFv17) | 340 | 289 | 82 |
| CAR18 | KL2B413_LH(scFv18) | 341 | 290 | 83 |
| CAR19 | KL2B359_HL (scFv19) | 342 | 291 | 84 |
| CAR20 | KL2B359_LH (scFv20) | 343 | 292 | 85 |
| CAR21 | KL2B357 HL (scFv21) | 169 | 319 | 205 |
| CAR22 | KL2B357 LH (scFv22) | 170 | 320 | 206 |
| CAR23 | KL2B358 HL (scFv23) | 171 | 321 | 207 |
| CAR24 | KL2B358 LH (scFv24) | 172 | 322 | 208 |
| CAR25 | KL2B360 HL (scFv25) | 173 | 323 | 209 |
| CAR26 | KL2B360 LH (scFv26) | 174 | 324 | 210 |
| CAR27 | KL2B30 HL (scFv27) | 175 | 325 | 211 |
| CAR28 | KL2B30 LH (scFv28) | 176 | 326 | 212 |
| CAR29 | KL2B53 HL (scFv29) | 177 | 327 | 213 |
| CAR30 | KL2B53 LH (scFv30) | 178 | 328 | 214 |
| CAR31 | KL2B242 HL (scFv31) | 179 | 329 | 215 |
| CAR32 | KL2B242 LH (scFv32) | 180 | 330 | 216 |
| CAR33 | KL2B467 HL (scFv33) | 181 | 331 | 217 |
| CAR34 | KL2B467 LH (scFv34) | 182 | 332 | 218 |
| CAR35 | KL2B494 HL (scFv35) | 183 | 333 | 219 |
| CAR36 | KL2B494 LH (scFv36) | 184 | 334 | 220 |

LCHumanized refers to hu11B6_VL.
HCHumanized refers to hu11B6_VH

Example 14: Identification of Different scFv-Based CAR with Antigen-Independent Activation Via Jurkat-Lucia™ NFAT Cells Nuclear factor of activated T-cells (NEAT) is a family of transcription factors first identified as a regulator of immune cells. Without wishing to be bound by theory, T cell activation leads to calcium influx, which activates calcineurin that dephosphorylates serine rich nuclear localization signal at the N-terminus of NEAT, leading to nuclear import of NEAT. Tonic signaling due to scFv clustering could be subsequently detected by Firefly luciferase driven by NEAT promoter in JNL reporter cell line.

Jurkat cells containing the luciferase gene driven by the signaling-responsive NFAT promoter (termed JNL cells), were transduced with the various CAR constructs. Binding between the CAR construct and its cognate cellular antigen (hK2 on target cells) leads to luciferase expression in the JNL cells. Novel hK2 KL2B413 and rehumanized 11B6 CAR clones were evaluated in the JNL reporter assay for antigen-dependent activity according to the following protocol.

Lentiviral transduction was performed as follows. JNL cells were harvested and resuspended to 1E6/ml. 500 µl JNL cells and lentiviral virus at MOI of 3 were added, and mixed by pipetting up and down. The mixture was placed in the 37° C. incubator for 24 hours. Then, 500 µl of JNL media was added to each well. Culturing was continued in the 37° C. incubator. The cells were transferred to a T25 flask on day 4. At day 5-6, transduction validation was performed. 150 µl of cells was harvested to examine CAR expression via appropriate detection reagent for the specific CAR of interest (e.g. biotin-hK2 Protein is used to detect hK2 CAR). The JNL cells were maintained at $5 \times 10^5$/ml until there were enough cells to freeze down or use for the JNL assay described below.

A JNL assay was performed as follows. Co-culture with target cell lines was undertaken at the effector to target ratio of 2:1. JNL cells were spun down to remove any secreted luciferase in the medium, and resuspended in fresh media at $4 \times 10^5$/ml. The JNL cells were harvested. Both antigen positive and antigen negative target cell lines were prepared at 2E5/ml. Then, 100 µl JNL was added to 100 µl target cells. For the JNL only control, 100 µl of media was added instead of target cells. For the positive control, JNL cells only or CAR JNL cells were added to 1× Cell Stimulation Cocktail, and incubated in a 37° C. incubator for 24 hours. 150 µl of supernatant was harvested into a 96-well plate and centrifuged to remove cells. 100 µl of supernatant was transferred from the plate to a solid bottom black plate, followed by addition of 100 µl QUANTI-luc lucia detection reagent and incubation at room temperature for 5 minutes before reading with Envision multiplate reader.

Figure 12A:
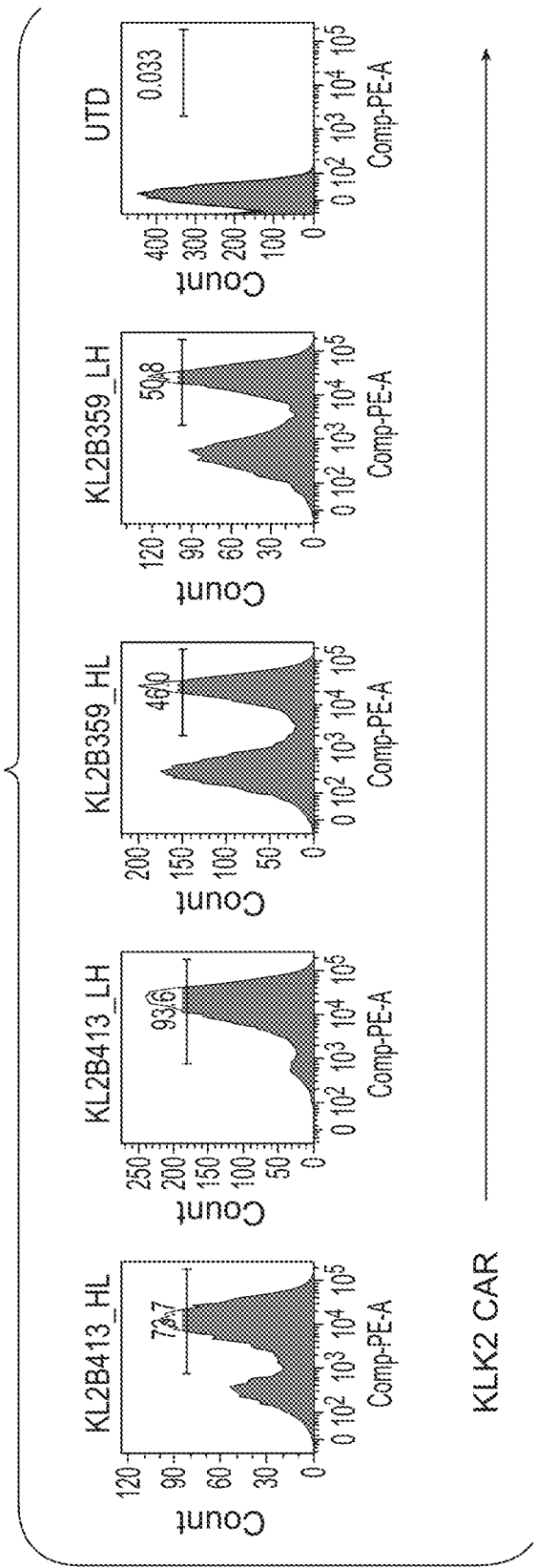
FIGS. 12A-12B show the results of evaluation of novel hK2 KL2B413 and rehumanized 11B6 CAR clones in the JNL reporter assay for antigen-dependent activity.

Jurkat cells containing the luciferase gene driven by the signaling-responsive NFAT promoter (termed JNL cells) were transduced with various hK2 CAR constructs. Expression was determined by biotinylated hK2 followed by streptavidin-conjugated PE. The data are shown in FIG. 12A. CAR expression in transduced JNL cells was confirmed for the selected clones, with 46-50% of cells expression on rehumanized 11B6 KL2B359 CARs and 73.7-96% of cells on KL2B413 CARs.

Figure 12B:
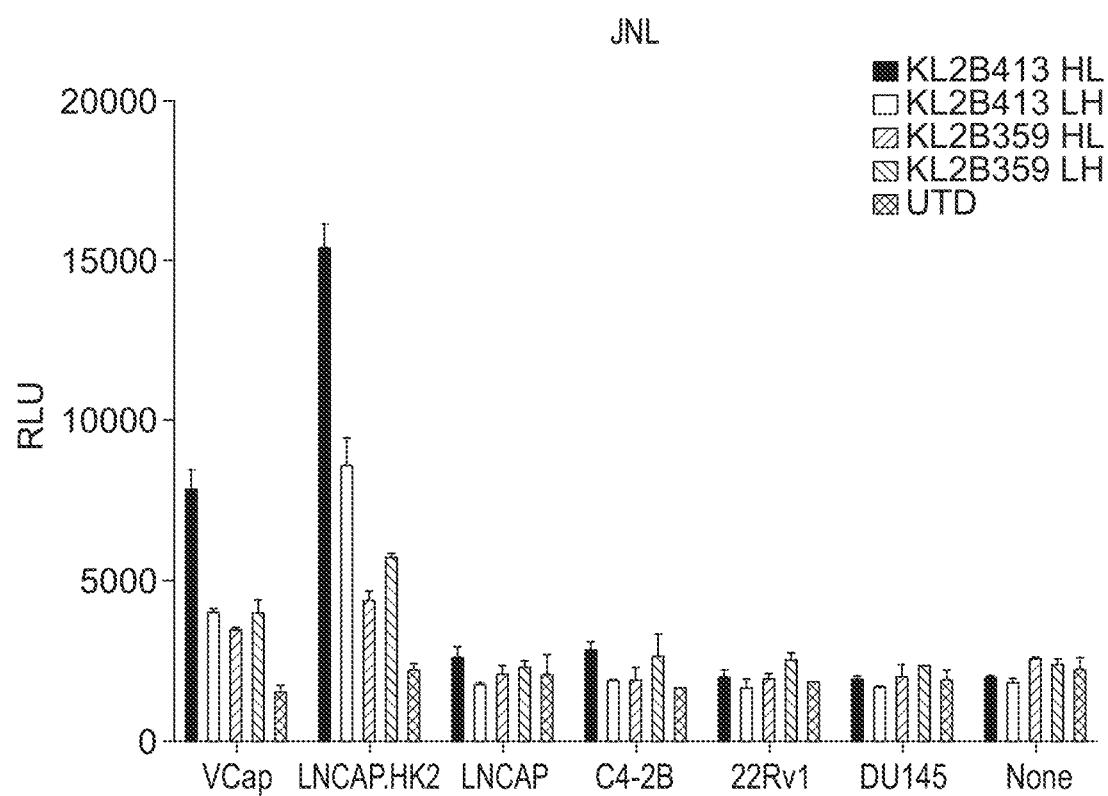

The data in FIG. 12B shows that binding between the hK2 CAR construct and its cognate cellular antigen (hK2 on target cells) leads to luciferase expression in the JNL cells. JNL cells containing the indicated CAR clones and JNL cells (UTD) were co-cultured with target cells lines (VCap, LNCap/Hk2, LNCap, C4-2B, 22Rv1 or DU145 cells) and luciferase activity was measured as luminescence intensity. Clones were considered active when the luminescence intensity exceeded 1.5-fold the level of UTD cells in the presence of antigen-expressing cells. No antigen-dependent activation was found for the novel KL2B413 and rehumanized 11B6 HL&LH CARs.

Figure 13A:
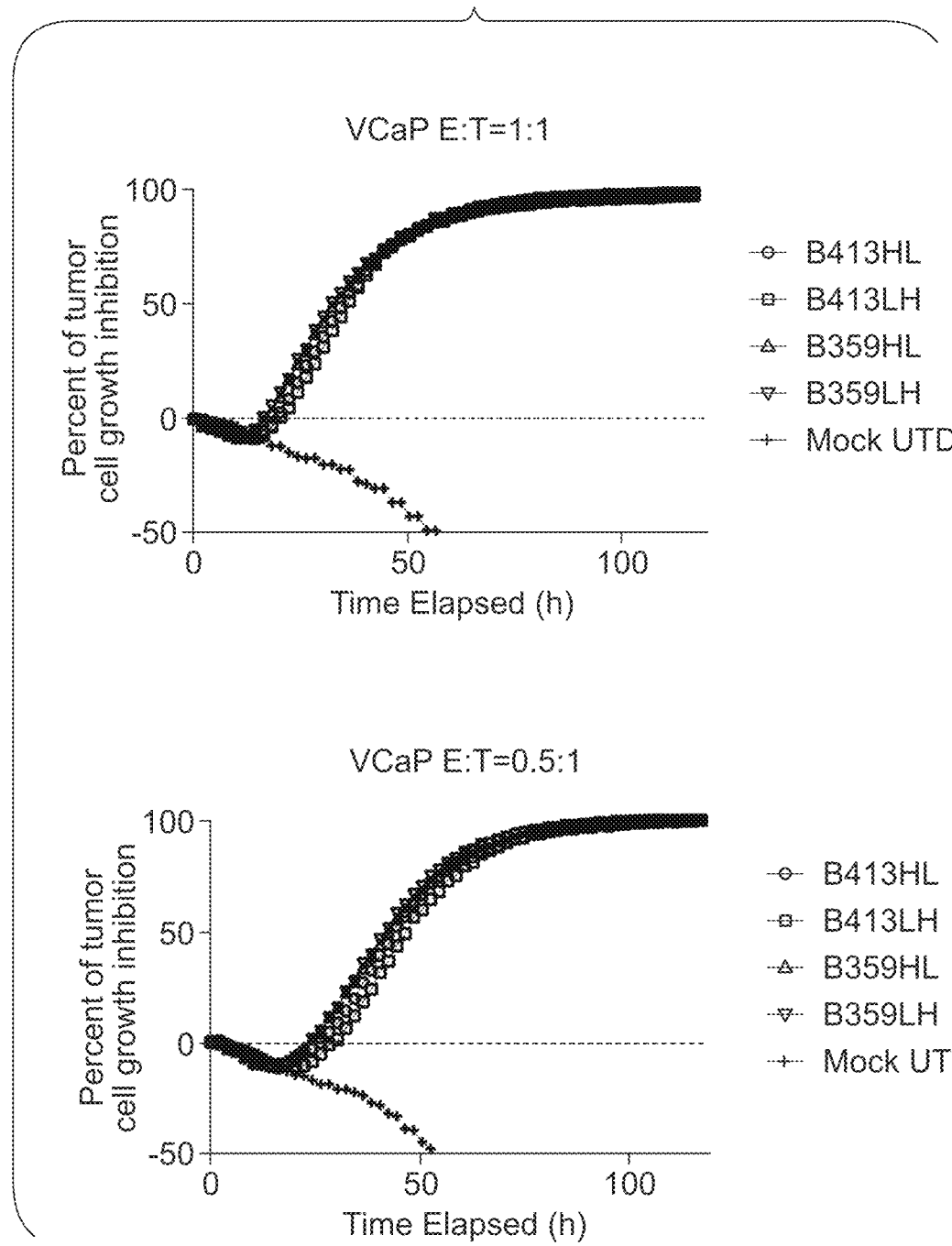
FIGS. 13A-13B show the results of an evaluation of HK2 CAR-T cells in the real-time IncuCyte killing assay for antigen-dependent cytotoxicity. HK2 CAR-T cells were co-incubated with HK2+ VCaP cells (FIG. 13A) and HK2- DU145 cells (FIG. 13B) for 96 hours. The Effector-to-Target (ET) ratio was calculated based on CAR expression data (FIG. 11B). Target cells were stably expressing a red nuclear dye which was measured by IncuCyte imaging system in a real-time fashion. Tumor cell growth inhibition (%)=(Initial Viable Target Cell Number-Current Viable Target Cell Number)/Initial Viable Cell Number*100(%)
Figure 13B:
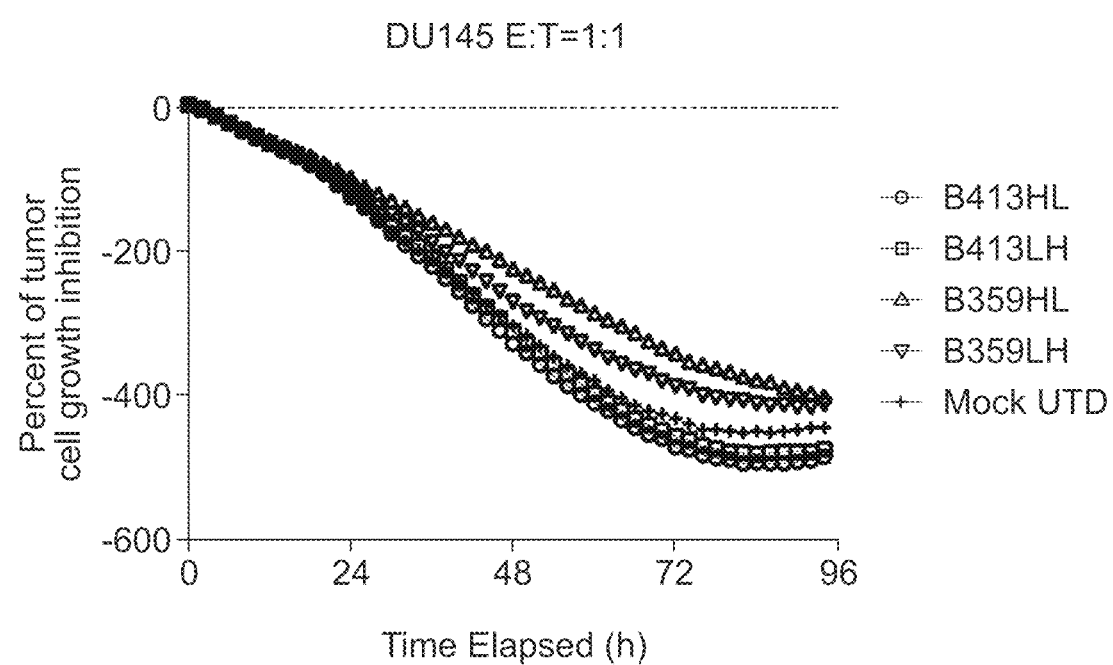

Example 15: HK2 CAR-T Cells were Evaluated in the Real-Time IncuCyte Killing Assay for Antigen-Dependent Cytotoxicity HK2 CAR-T cells were co-incubated with HK2+ VCaP cells and HK2-DU145 cells for 96 hours. The effector-to-target (ET) ratio was calculated based on CAR expression data shown in FIGS. 11A-11B. Target cells were stably expressing a red nuclear dye, which was measured by IncuCyte imaging system in a real-time fashion. The data is shown in FIG. 13A for HK2 CAR-T cells co-incubated with HK2+ VCaP cells, and in FIG. 13B for HK2 CAR-T cells co-incubated with HK2-DU145 cells. In these FIGS., tumor cell growth inhibition (%)=(Initial Viable Target Cell Number-Current Viable Target Cell Number)/Initial Viable Cell Number*100(%).

Example 16. Characterization of CAR-T Cells Transduced with KL2B413 HL, KL2B413 LH, KL2B359 HL or KL2B359 LH Activation of CAR-T Cells is Antigen-Dependent The generated CAR-T cells were evaluated in the JNL reporter assay for antigen-dependent activity as described in Example 4. Briefly, Jurkat cells containing the luciferase gene driven by the signaling-responsive NFAT promoter (termed JNL cells) were transduced with CAR17 (KL2B413_HL), CAR18 (KL2B413_LH), CAR19 (KL2B359_HL) or CAR20 (KL2B359_LH) constructs. Expression of each CAR was determined by biotinylated hK2 followed by streptavidin-conjugated PE. CAR expression in transduced JNL cells was confirmed for the selected clones with 46-50% of cells expressing KL2B359-based CARs and 73.7-96% of cells expressing KL2B413-based CARs as shown in FIG. 6. The percent JNL cells expressing each CAR was following: KL2B413_HL: 73.7%, KL2B413_LH: 93.6%, KL2B359_HL: 46%, KL2B359_LH: 50.8%.

Binding between the hK2 CAR construct and its cognate cellular antigen (hK2 on target cells) leads to luciferase expression in the JNL cells. To that end, JNL cells transduced with the test CAR constructs or untransduced JNL cells (UTD) were co-cultured with target cells lines (VCap, LNCap/hK2 (LNCaP cells recombinantly expressing hK2), LNCaP, C4-2B, 22Rv1 or DU145 cells) and luciferase activity was measured as luminescence intensity. Constructs were considered active when the luminescence intensity exceeded 1.5-fold the level of UTD cells in the presence of antigen-expressing cells. No antigen-dependent activation was found for the tested CAR constructs. FIG. 13A shows the RLU (relative light units) resulting from binding of CAR-T cells to test target cells ad indicated in the FIG.

CAR-T Cells Produce Cytokines Upon Antigen Stimulation

Figure 14:
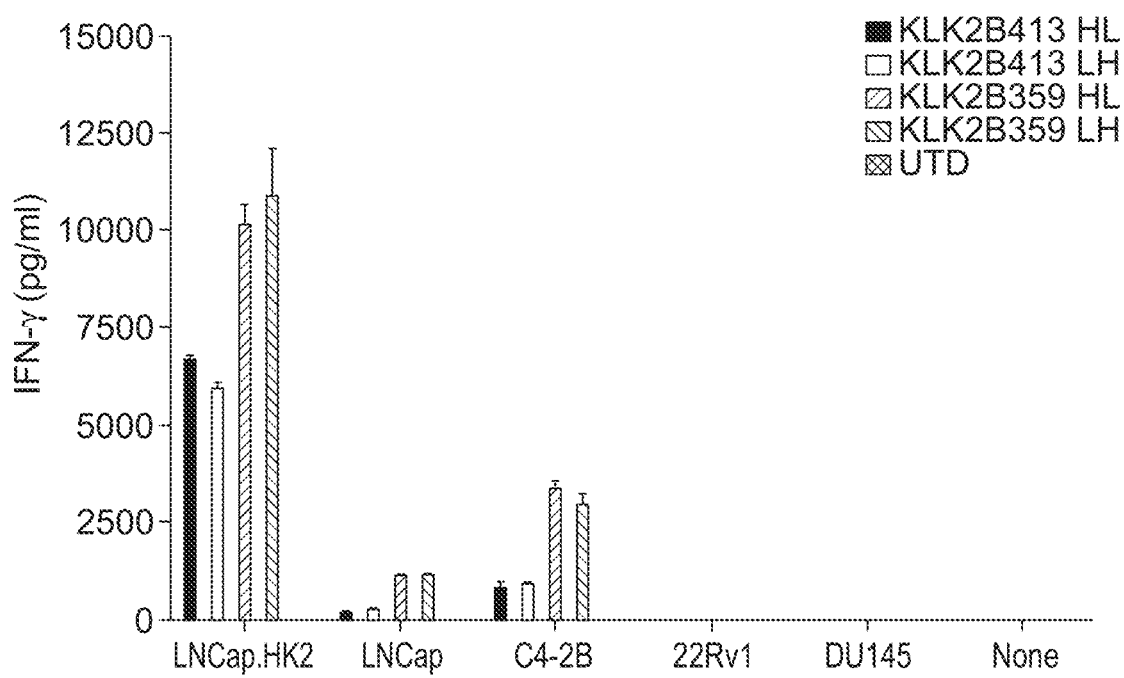
FIG. 14 illustrates data showing Th1 cytokine IFN-gamma production of antigen-stimulated CAR-T Cells. IFN-γ produced by cytotoxic T cells is critical for exerting immune surveillance of tumors, which can directly inhibit proliferation and induce apoptosis of some malignancies in vivo and in vitro. To determine whether hK2 CAR-modified human T cells were able to recognize and activated by hK2 (+) tumor cells, primary T cells containing the indicated CAR clones and control untransduced T cells (UTD) were co-cultured with target cells lines (LNCap/Hk2, LNCap, C4-2B, 22Rv1 or DU145 cells) and supernatant were collected for IFN-g concentration measurement. As shown, hK2 CAR modified T cells secrete IFN-gamma during co-culture with hK2-expressing LNCap/hK2 cells, even very low Hk2 expressing C4-2B and LNCap cells but not hK2-negative DU145 cells. Undisclosed control CAR secreted much higher amount of IFN-γ due to the much higher antigen expression level than hK2. Mean IFN-γ concentration±SD (pg/ml) from duplicate cultures is shown.

IFN-γ produced by cytotoxic T cells is critical for exerting immune surveillance of tumors, which can directly inhibit proliferation and induce apoptosis of some malignancies in vivo and in vitro. To determine whether hK2 CAR-modified human T cells were able to recognize and become activated by hK2 positive tumor cells, primary T cells transduced with indicated CAR clones and control untransduced T cells (UTD) were co-cultured with target cells lines (LNCaP/hK2, LNCaP, C4-2B, 22Rv1 or DU145 cells) and supernatant were collected for IFN-γ concentration measurement. As shown in FIG. 14, CAR-T cells transduced with hK2 CARs cells secreted IFN-γ during co-culture with LNCaP cells recombinantly expressing hK2 (LNCap/hK2) cells and also during co-culture with very low hK2-expressing C4-2B and LNCap cells but not hK2-negative DU145 cells. Mean IFN-γ concentration±SD (pg/ml) from duplicate cultures is shown in FIG. 14.

CAR-T Cells Proliferate in Antigen-Dependent Manner

CAR-T cells were evaluated for their proliferation using T-cell proliferation assay protocol described in Example 4.

hK2 CAR-T and untransduced (UTD) T cells were labelled with CellTrace Violet (CTV; 5 μM) and co-cultured with hK2 positive VCap and hK2 negative DU145 cells. Five days post co-culture, cells were harvested and stained with CD3, CD25, NearIR live/dead Dye and hK2 CAR. Flow cytometric analysis was performed on a Fortessa flow cytometer with Flowjo software. Lymphocytes were identified by live CD3, and the frequencies of CAR-T cells with CTV dye dilution and activation marker CD25 were determined. By gating on CD3+ T cells, the hK2 positive Vcap cells but not hK2 negative DU145 cells promoted proliferation of each tested CAR-T cell line, as shown in FIGS. 10C, 10D, and 10E, and upregulation of activation marker CD25 as shown in FIG. 11B and FIG. 12A. T cells only without any stimulation did not proliferate and CD3/28 beads stimulated T cells displayed equivalent proliferation pattern. hK2 CAR+ T cells proliferated more robustly than CD3/28 beads positive control after 5 days of coculture with VCap cells. Different tested CAR-T cells had different proliferation activity and displayed different CAR-T cells counts. The percentage of proliferating T cells and CD25 expressing T cells was based on mean absolute cell count+/−SEM from duplicate.

Example 17: Th1 Cytokine IFN-Gamma Production of Antigen-Stimulated CAR-T Cells

Without wishing to be bound by theory, IFN-γ produced by cytotoxic T cells is critical for exerting immune surveillance of tumors, which can directly inhibit proliferation and induce apoptosis of some malignancies in vivo and in vitro.

To determine whether hK2 CAR-modified human T cells were able to recognize and activated by hK2 (+) tumor cells, primary T cells containing the indicated CAR clones and control untransduced T cells (UTD) were co-cultured with target cells lines (LNCap/Hk2, LNCap, C4-2B, 22Rv1 or DU145 cells) and supernatant were collected for IFN-g concentration measurement. The data are shown in FIG. 14 as the mean IFN-γ concentration±SD (pg/ml) from duplicate cultures. As shown, hK2 CAR modified T cells secrete IFN-gamma during co-culture with hK2-expressing LNCap/hK2 cells, even very low Hk2 expressing C4-2B and LNCap cells but not hK2-negative DU145 cells. Undisclosed control CAR secreted a much higher amount of IFN-γ due to the much higher antigen expression level than hK2.

Example 18: CD107a Degranulation Assay to Evaluate hK2 CAR T Cells' Antitumor Activity Without wishing to be bound by theory, tumor cells can be recognized and killed by cytotoxic lymphocytes, such as CD8+ T lymphocytes and natural killer (NK) cells, mainly through the immune secretion of lytic granules that kill target cells. This process involves the fusion of the granule membrane with the cytoplasmic membrane of the immune effector cell, resulting in surface exposure of lysosomal-associated proteins that are typically present on the lipid bilayer surrounding lytic granules, such as CD107a. Therefore, membrane expression of CD107a constitutes a marker of immune cell activation and cytotoxic degranulation.

Figure 15A:
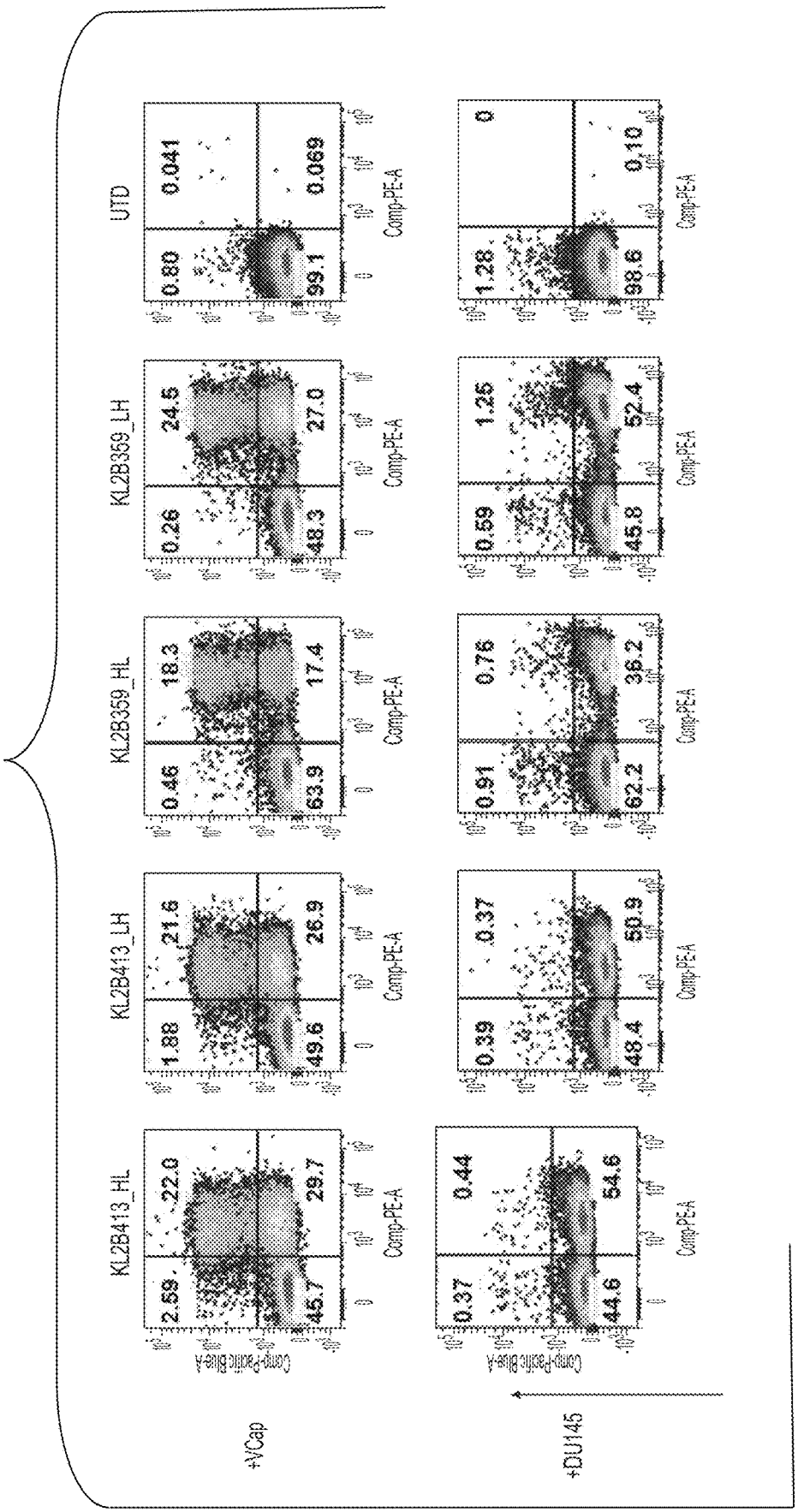
FIGS. 15A-15B shows the results of a CD107a degranulation assay to evaluate hK2 CAR T cells' antitumor activity. Target cells ($5 \times 10^4$) were cocultured with an equal number of effector cells in 0.1 ml per well in a 96-well plate. Control wells contained T cells alone. Anti-CD107a (5 per well) was added in addition to 1l/sample of monensin (BD Biosciences) and incubated for 4 hours at 37° C. Cells were washed two times with PBS, stained for expression of the hK2 CAR, CD3, and CD8 and analyzed on a flow cytometer BD Fortessa. As shown, the presence of hK2 antigen on Vcap cells leads to an increase in CD107A+hK2 CAR(+) T cells, but not in hK2 CAR(−) and UTD T cells measured by flow cytometry, whereas only the background staining (<2%) was seen in the CAR T cells only without tumor cells stimulation. Phorbol 12-myristate 13-acetate (PMA) in combination with ionomycin (eBioscience™ Cell Stimulation Cocktail; 500×) was a consistent inducer of CD107a cell surface expression in this 4-hour cell culture model, which was used as a positive control. Results are shown for representative donor T cells and are reproducible in multiple donors.
Figure 15B:
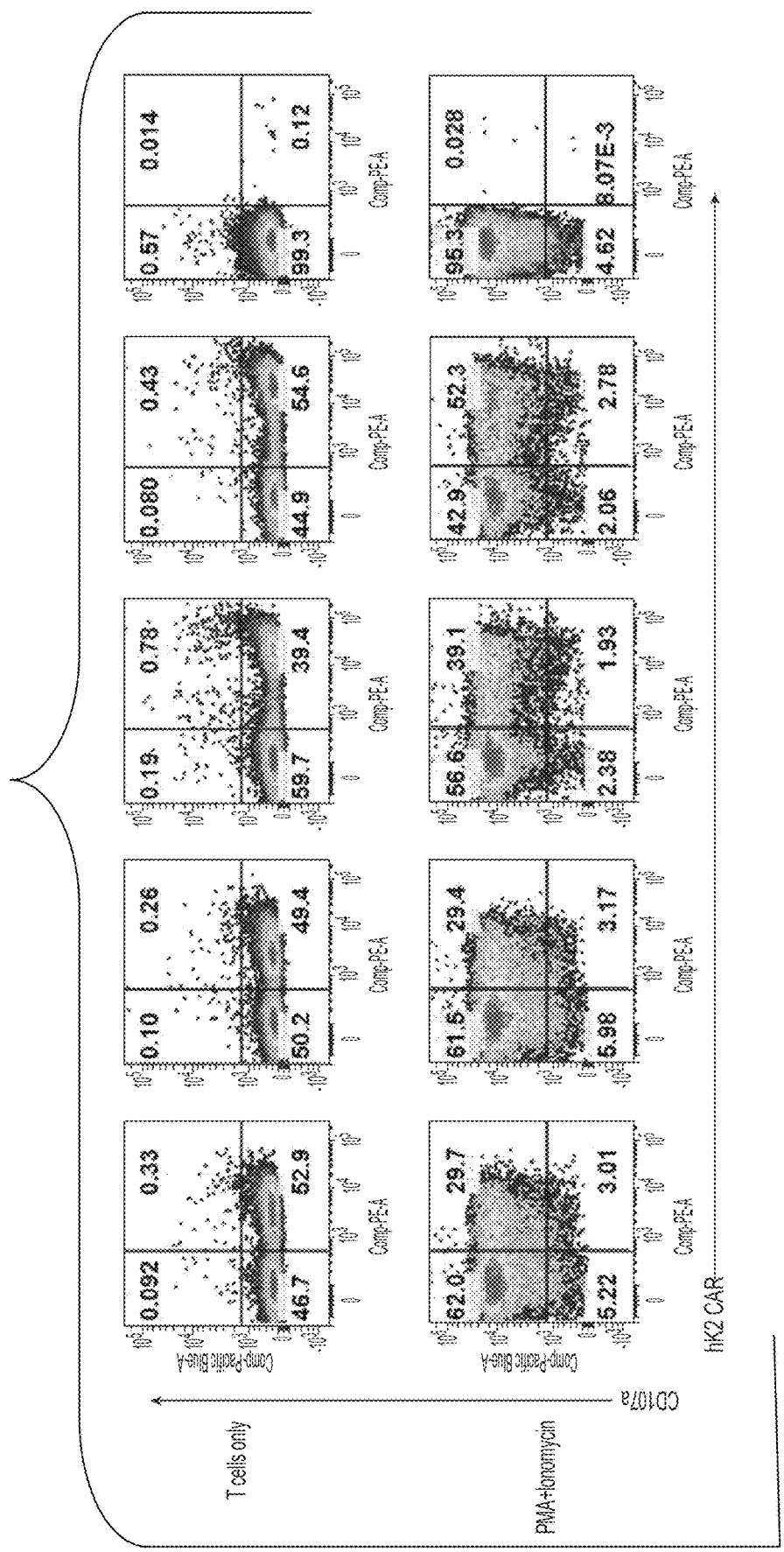

The degranulation assay was performed as follows. Target cells ($5 \times 10^4$) were cocultured with an equal number of effector cells in 0.1 ml per well in a 96-well plate. Control wells contained T cells alone. Anti-CD107a (5 μl per well) was added in addition to 1l/sample of monensin (BD Biosciences), followed by incubation for 4 hours at 37° C. Cells were washed two times with PBS, stained for expression of the hK2 CAR, CD3, and CD8 and analyzed on a flow cytometer BD Fortessa. The data are shown in FIG. 15.

As shown, the presence of hK2 antigen on Vcap cells leads to an increase in CD107A+ hK2 CAR(+) T cells, but not in hK2 CAR(−) and UTD T cells measured by flow cytometry. Only the background staining (<2%) was seen in the CAR T cells without tumor cell stimulation. Phorbol 12-myristate 13-acetate (PMA) in combination with ionomycin (eBioscience™ Cell Stimulation Cocktail; 500×) was a consistent inducer of CD107a cell surface expression in this 4-hour cell culture model, which was used as a positive control. The results shown in FIG. 15 are for representative donor T cells and are reproducible in multiple donors.

Example 19: T-Cell Proliferation is an Important In Vitro Parameter of In Vivo Immune Function To further evaluate the function of novel KL2B413 and rehumanized 11B6 (KL2B359) CAR T cells and to assist in picking the top candidate construct, CAR T cells were labeled with CellTrace™ Violet (CTV; 5 uM) for the T cells proliferation assay. The following protocol was followed, with the results shown in FIGS. 16A-16F.

Tumor cells Vcap and DU145 were collected and washed twice with PBS. The cells were resuspended in 10E6/ml in PBS containing 100 ug/ml Mitomycin C (MMC) for 1.5 hours in a 37° C. incubator to block proliferation of tumor cells. 20 μL DMSO was added to a vial of CTV staining solution. Then, 5 μl of solution was diluted into 5 mL (1:1000) of PBS (warmed to 37° C.) to yield a 5 μM staining solution. 2E6 T cells were counted and collected, washed with PBS twice, and then resuspended in 4E6/ml (0.5 ml). An equal volume (0.5 ml) of CTV staining solution was added. The cells were incubated for 20 minutes at 37° C. After 20 minutes, 4 ml PRMI+20% FBS was added to the cells to absorb any unbound dye, and the cells were incubated for 5 minutes. The cells were centrifuged for 5 minutes at 400×g, followed by resuspension of the cell pellet in pre-warmed RPMI+10% FBS medium. The T cells were counted, and 1E5 cells (100 μl) were seeded in a 96-well flat bottom-plate.

In the meantime, MMC treated tumor cells hK2(+) VCap and HK2(−) DU145 were collected and counted post 1.5 hours, and then resuspended in 1E6/ml. 1E5 cells (100 μl) were co-cultured with T cells in 96-well plate. T cells alone and T cells added in a 3:1 CD3/28 beads to cells ratio were used as negative and positive controls, respectively. After five days of co-culture, all the cells were collected from each well. The cells were centrifuged and washed for 5 minutes at 400×g twice, and stained with hK2CAR, CD3, CD8 and CD25, live/dead (Near-IR) in 96-well U bottom plate. After washing, all cells were fixed for 10 minutes using BD Cytofix™ Fixation Buffer (501 FACS buffer+50 μl Fixation Buffer) in 100 μl. Stained samples were analyzed by multicolor flow cytometry after the end of the incubation period.

Flow cytometric analysis was performed on a Fortessa flow cytometer with Flowjo software. Lymphocytes were identified by live CD3, and the frequencies of CAR+ T cells with CTV dye dilution and activation marker CD25 were determined.

To prepare a CTV histogram, the CTV undiluted gate was set to encompass the far-right peak (CTV bright) of T cells cultured alone, and the CTV diluted gate to capture the rest of the population. This setting was applied to all samples. A statistic was added to include absolute # of cells in the CTV diluted population. A table was created with this statistic, followed by export of data (cell counts) to Excel for reformatting before transferring to Prism.

Figure 16A:
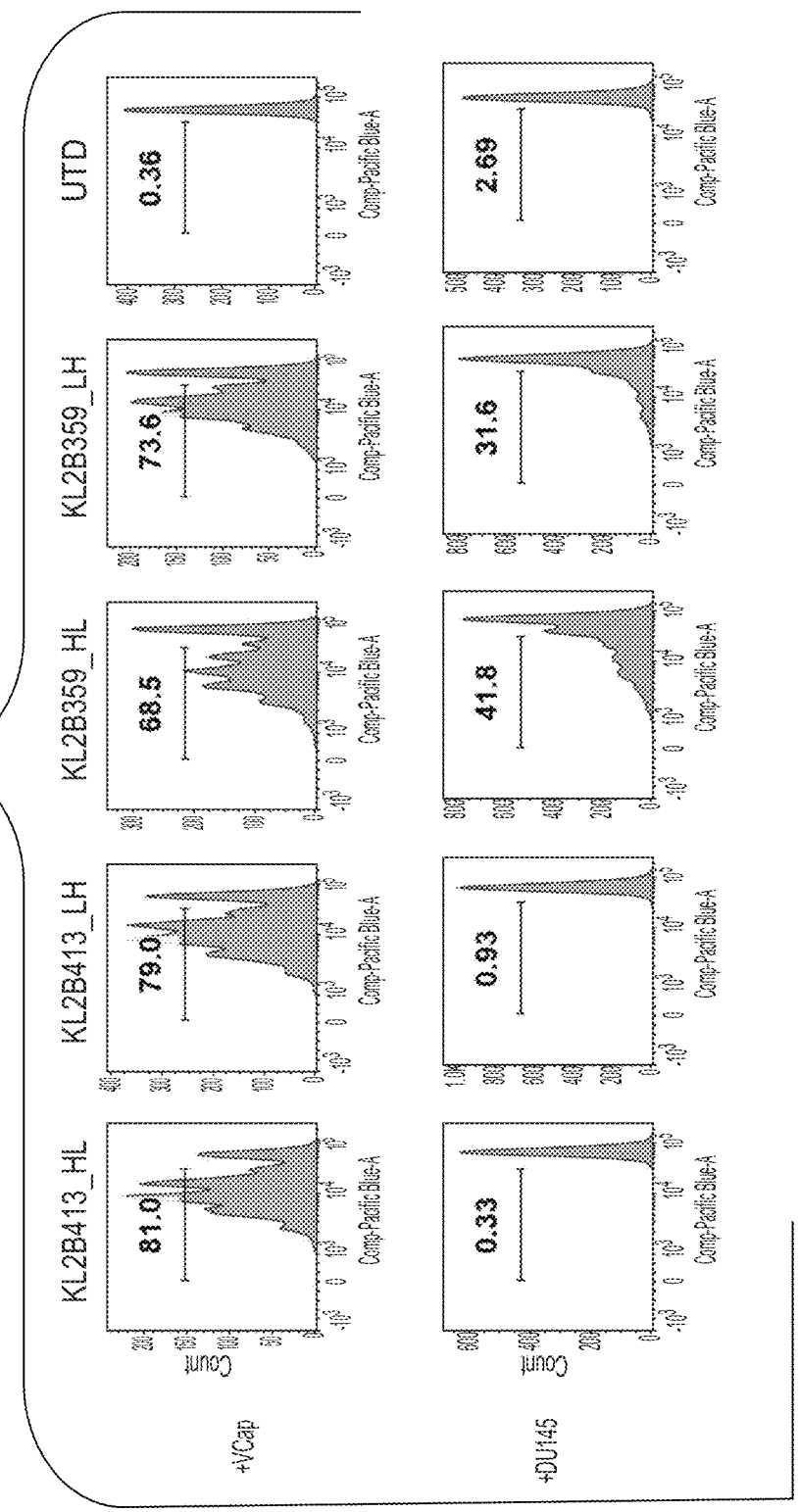
Figure 16B:
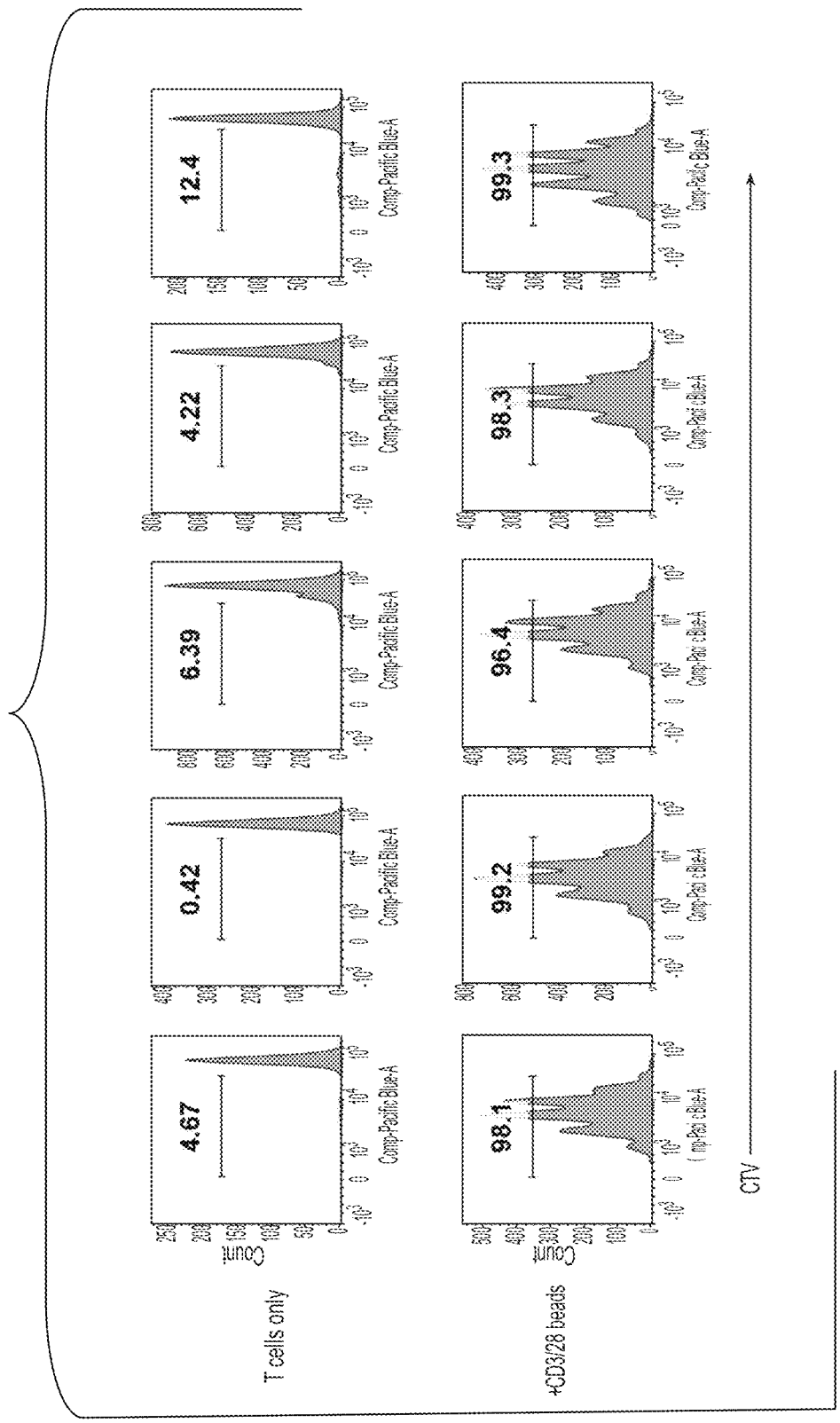
Figure 16C:
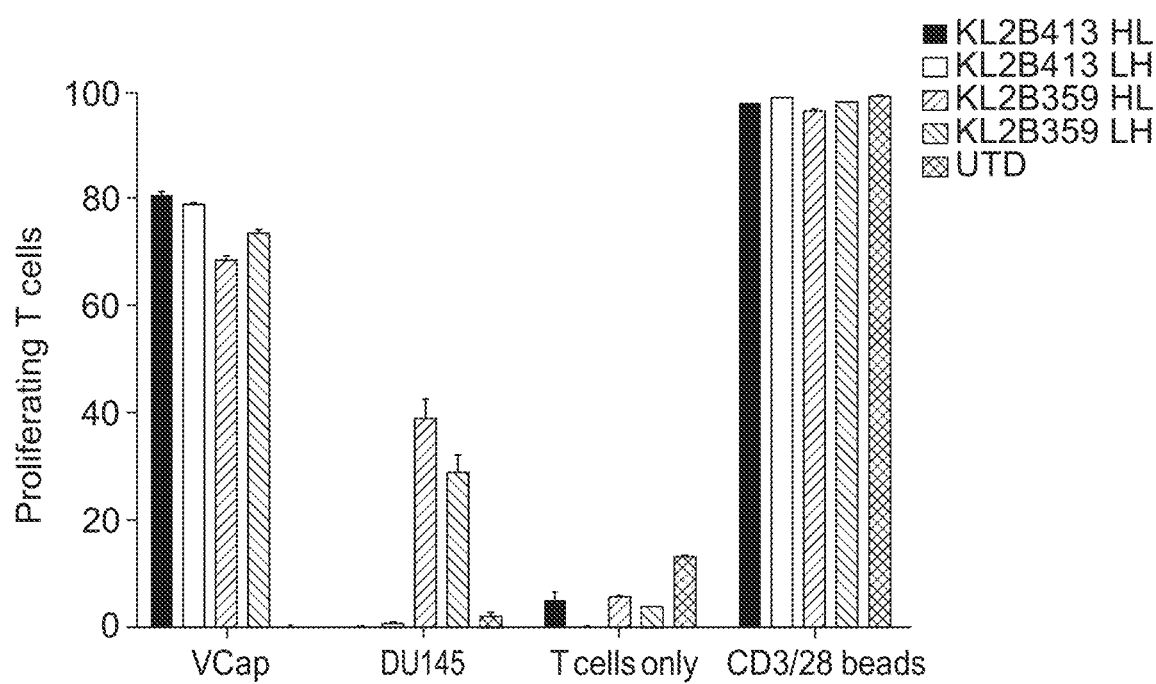
Figure 16D:
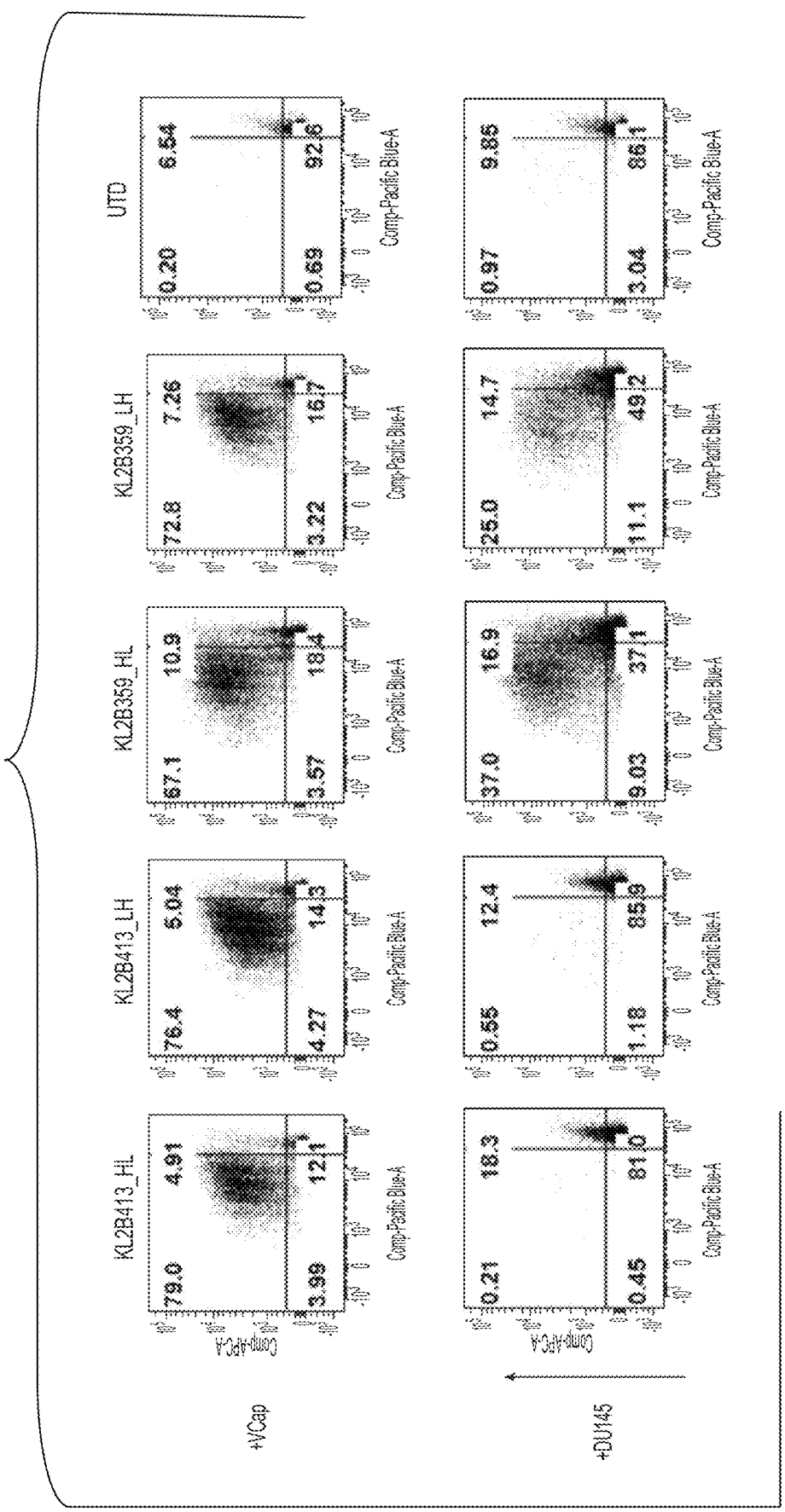
Figure 16F:
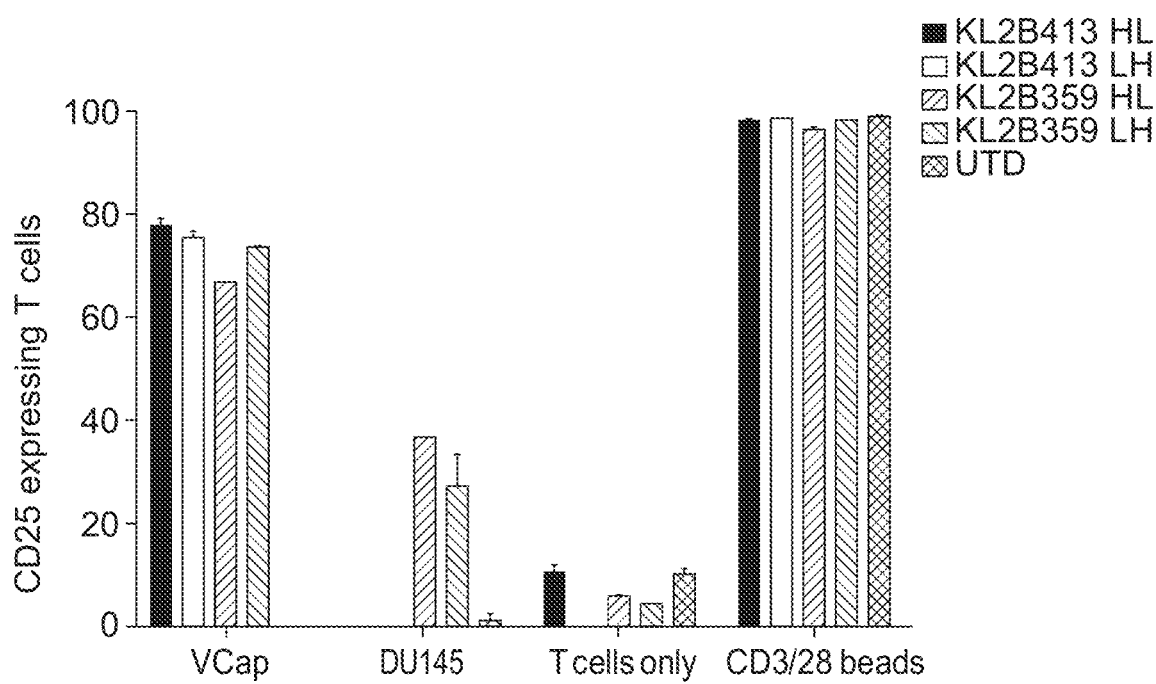

FIGS. 16A-16F show the results of a hK2 CAR T cell proliferation assay. By gating on CD3+ T cells, as shown in FIGS. 16A-16C, the hK2(+) Vcap cells but not hK2(−) DU145 cells promoted the proliferation of all CAR constructs engineered T cells and upregulation of activation marker CD25, as shown in FIGS. 16D-16F. CD3/28 beads stimulated T cells were used as positive controls, and T cells only were used as negative controls. T cells only without any stimulation do not proliferate and CD3/28 beads stimulated T cells displayed equivalent proliferation pattern. As shown, hK2 CAR+ T cells proliferate more robustly than the CD3/28 beads positive control after 5 days of coculture with VCap cells. Different CAR construct-engineered T cells have different proliferation activity and displayed different CAR+ T cells counts. The summary of percentage of proliferating T cells and CD25 expressing T cells based on mean absolute cell count+/−SEM from duplicate is shown in FIGS. 16C and 16F.

Example 20: Construction and Expression of hK2 scFv CARs hK2 CAR constructs comprising the following scFv sequences are constructed:

```
KL2B357 HL:
QVQLQESGPGLVKPSQTLSLTCTVSGNSITSDYAWNWIRQFPGKGLEWIGYISYSGSTTY
NPSLKSRVTISRDTSKNQFSLKLSSVTAADTAVYYCATGYYYGSGFWGQGTLVTVSSGG
SEGKSSGSGSESKSTGGSDIVLTQSPDSLAVSLGERATINCRASESVEYFGTSLMHWYQQ
KPGQPPKLLIYAASNVESGVPDRFSGSGSGTDFTLTISSLQAEDVAVYFCQQTRKVPYTF
GGGTKVEIK
(SEQ ID NO: 221)

KL2B357 LH:
DIVLTQSPDSLAVSLGERATINCRASESVEYFGTSLMHWYQQKPGQPPKLLIYAASNVES
GVPDRFSGSGSGTDFTLTISSLQAEDVAVYFCQQTRKVPYTFGGGTKVEIKGGSEGKSSG
SGSESKSTGGSQVQLQESGPGLVKPSQTLSLTCTVSGNSITSDYAWNWIRQFPGKGLEWI
GYISYSGSTTYNPSLKSRVTISRDTSKNQFSLKLSSVTAADTAVYYCATGYYYGSGFWGQ
GTLVTVSS
(SEQ ID NO: 222)

KL2B358 HL:
QVQLQESGPGLVKPSQTLSLTCTVSGNSITSDYAWNWIRQPPGKGLEWIGYISYSGSTTY
NPSLKSRVTISRDTSKNQFSLKLSSVTAADTAVYYCATGYYYGSGFWGQGTLVTVSSGG
SEGKSSGSGSESKSTGGSEIVLTQSPATLSLSPGERATLSCRASESVEYFGTSLMHWYQQK
PGQPPRLLIYAASNVESGIPARFSGSGSGTDFTLTISSVEPEDFAVYFCQQTRKVPYTFGGG
TKVEIK
(SEQ ID NO: 223)

KL2B358 LH:
EIVLTQSPATLSLSPGERATLSCRASESVEYFGTSLMHWYQQKPGQPPRLLIYAASNVESG
IPARFSGSGSGTDFTLTISSVEPEDFAVYFCQQTRKVPYTFGGGTKVEIKGGSEGKSSGSG
SESKSTGGSQVQLQESGPGLVKPSQTLSLTCTVSGNSITSDYAWNWIRQPPGKGLEWIGY
ISYSGSTTYNPSLKSRVTISRDTSKNQFSLKLSSVTAADTAVYYCATGYYYGSGFWGQGT
LVTVSS
(SEQ ID NO: 224)

KL2B360 HL:
QVQLQESGPGLVKPSQTLSLTCTVSGNSITSDYAWNWIRQFPGKGLEWIGYISYSGSTTY
NPSLKSRVTISRDTSKNQFSLKLSSVTAADTAVYYCATGYYYGSGFWGQGTLVTVSSGG
SEGKSSGSGSESKSTGGSEIVLTQSPATLSLSPGERATLSCRASESVEYFGTSLMHWYQQK
PGQPPRLLIYAASNVESGIPARFSGSGSGTDFTLTISSVEPEDFAVYFCQQTRKVPYTFGGG
TKVEIK
(SEQ ID NO: 225)

KL2B360 LH:
EIVLTQSPATLSLSPGERATLSCRASESVEYFGTSLMHWYQQKPGQPPRLLIYAASNVESG
IPARFSGSGSGTDFTLTISSVEPEDFAVYFCQQTRKVPYTFGGGTKVEIKGGSEGKSSGSG
SESKSTGGSQVQLQESGPGLVKPSQTLSLTCTVSGNSITSDYAWNWIRQFPGKGLEWIGY
ISYSGSTTYNPSLKSRVTISRDTSKNQFSLKLSSVTAADTAVYYCATGYYYGSGFWGQGT
LVTVSS
(SEQ ID NO: 226)

KL2B30 HL:
QVQLQESGPGLVKPSETLSLTCTVSGGSISSYYWSWIRQPPGKGLEWIGYIYYSGSTNYN
PSLKSRVTISVDTSKNQFSLKLSSVTAADTAVYYCAGTTIFGVVTPNFYYGMDVWGQGT
TVTVSSGGSEGKSSGSGSESKSTGGSDIQMTQSPSFLSASVGDRVTITCRASQGISSYLAW
YQQKPGKAPKFLIYAASTLQSGVPSRFSGSGSGTEFTLTISSLQPEDFATYYCQQLNSYPL
TFGGGTKVEIK
(SEQ ID NO: 227)

KL2B30 LH:
DIQMTQSPSFLSASVGDRVTITCRASQGISSYLAWYQQKPGKAPKFLIYAASTLQSGVPSR
FSGSGSGTEFTLTISSLQPEDFATYYCQQLNSYPLTFGGGTKVEIKGGSEGKSSGSGSESK
STGGSQVQLQESGPGLVKPSETLSLTCTVSGGSISSYYWSWIRQPPGKGLEWIGYIYYSGS
TNYNPSLKSRVTISVDTSKNQFSLKLSSVTAADTAVYYCAGTTIFGVVTPNFYYGMDVW
GQGTTVTVSS
(SEQ ID NO: 228)
```

```
KL2B53 HL:
EVQLVESGGGVVQPGRSLRLSCVASGFTFSSYDIHWVRQAPGKGLEWVAIISYDGSKKD
YTDSVKGRFTISRDNSKNTLYLQMDSLRVEDSAVYSCARESGWSHYYYGMDVWGQG
TMVTVSSGGSEGKSSGSGSESKSTGGSDIVMTQSPSSLSASVGDRVTITCRASQDISNYLA
WYQQKPGKVPKFLIYAASTLHSGVPSRFSGSGSGTDFTLTISSLQPEDVATYYCQKYNSA
PYTFGQGTRLEIK
(SEQ ID NO: 229)

KL2B53 LH:
DIVMTQSPSSLSASVGDRVTITCRASQDISNYLAWYQQKPGKVPKFLIYAASTLHSGVPS
RFSGSGSGTDFTLTISSLQPEDVATYYCQKYNSAPYTFGQGTRLEIKGGSEGKSSGSGSES
KSTGGSEVQLVESGGGVVQPGRSLRLSCVASGFTFSSYDIHWVRQAPGKGLEWVAIISY
DGSKKDYTDSVKGRFTISRDNSKNTLYLQMDSLRVEDSAVYSCARESGWSHYYYGM
DVWGQGTMVTVSS
(SEQ ID NO: 230)

KL2B242 HL:
QVQLQESGPGLVKPSETLSLTCTVSGGSISSYYWSWLRQPAGSGLEWIGRLYVSGFTNYN
PSLKSRVTLSLDPSRNQLSLKLSSVTAADTAVYYCAGDSGNYWGWFDPWGQGTLVTVS
SGGSEGKSSGSGSESKSTGGSSYELTQPPSVSVSPGETASITCSGDQLGENYACWYQQKP
GQSPVLVIYQDSKRPSGIPERFSGSNSGNTATLTISGTQALDEADYYCQAWDNSIVVFGG
GTKLTVL
(SEQ ID NO: 231)

KL2B242 LH:
SYELTQPPSVSVSPGETASITCSGDQLGENYACWYQQKPGQSPVLVIYQDSKRPSGIPERF
SGSNSGNTATLTISGTQALDEADYYCQAWDNSIVVFGGGTKLTVLGGSEGKSSGSGSES
KSTGGSQVQLQESGPGLVKPSETLSLTCTVSGGSISSYYWSWLRQPAGSGLEWIGRLYVS
GFTNYNPSLKSRVTLSLDPSRNQLSLKLSSVTAADTAVYYCAGDSGNYWGWFDPWGQG
TLVTVSS
(SEQ ID NO: 232)

KL2B467 HL:
QVQLVESGGGVVQPGRSLRLSCAASGFTFSYYGMHWVRQAPGKGLEWVAFISYDGSNK
YYADSVKGRFTISRDNSKNTLYLQMNSLRAEDTAVYYCAHLPYSGSYWAFDYWGQGT
QVTVSSGGSEGKSSGSGSESKSTGGSQSVLTQPPSVSVAPGQTASITCGGDNIGSKSVHW
YQQKPGQAPVLVVYDNSDRPSGIPERFSGSNSGTTATLTISRVEAGDEADYYCQVWDSS
SDHPVVFGGGTKVTV
(SEQ ID NO: 233)

KL2B467 LH:
QSVLTQPPSVSVAPGQTASITCGGDNIGSKSVHWYQQKPGQAPVLVVYDNSDRPSGIPER
FSGSNSGTTATLTISRVEAGDEADYYCQVWDSSSDHPVVFGGGTKVTVGGSEGKSSGSG
SESKSTGGSQVQLVESGGGVVQPGRSLRLSCAASGFTFSYYGMHWVRQAPGKGLEWVA
FISYDGSNKYYADSVKGRFTISRDNSKNTLYLQMNSLRAEDTAVYYCAHLPYSGSYWAF
DYWGQGTQVTVSS
(SEQ ID NO: 234)

KL2B494 HL:
QVQLVESGGGLVQPGGSLRLSCAASGFTFSHYAMSWVRQAPGKGLEWVSTIGGSGGST
YYADSVKGRFTISRDNSKNTLYLQMNSLRAEDTAVYYCAKPHIVMVTALLYDGMDVW
GQGTMVTVSSGGSEGKSSGSGSESKSTGGSSSELTQPPSVSVAPGQTARITCGGNNIGSKS
VHWYQQKPGQAPVLVVYDDSDRPSGIPERFSGSNSGNTATLTISRVEAGDEADYYCQV
WDSSSDHVVFGGGTKLTVL
(SEQ ID NO: 235)

KL2B494 LH:
SSELTQPPSVSVAPGQTARITCGGNNIGSKSVHWYQQKPGQAPVLVVYDDSDRPSGIPER
FSGSNSGNTATLTISRVEAGDEADYYCQVWDSSSDHVVFGGGTKLTVLGGSEGKSSGSG
SESKSTGGSQVQLVESGGGLVQPGGSLRLSCAASGFTFSHYAMSWVRQAPGKGLEWVS
TIGGSGGSTYYADSVKGRFTISRDNSKNTLYLQMNSLRAEDTAVYYCAKPHIVMVTALL
YDGMDVWGQGTMVTVSS
(SEQ ID NO: 236)
```

The hK2 CAR constructs comprised the following sequences:

```
KL2B357 HL:
QVQLQESGPGLVKPSQTLSLTCTVSGNSITSDYAWNWIRQFPGKGLEWIGYISYSGSTTY
NPSLKSRVTISRDTSKNQFSLKLSSVTAADTAVYYCATGYYYGSGFWGQGTLVTVSSGG
SEGKSSGSGSESKSTGGSDIVLTQSPDSLAVSLGERATINCRASESVEYFGTSLMHWYQQ
KPGQPPKLLIYAASNVESGVPDRFSGSGSGTDFTLTISSLQAEDVAVYFCQQTRKVPYTF
GGGTKVEIKTSTPAPRPPTPAPTIASQPLSLRPEACRPAAGGAVHTRGLDFACDIYIWAPL
AGTCGVLLLSLVITLYCKRGRKKLLYIFKQPFMRPVQTTQEEDGCSCRFPEEEEGGCELR
```

```
VKFSRSADAPAYKQGQNQLYNELNLGRREEYDVLDKRRGRDPEMGGKPRRKNPQEGL
YNELQKDKMAEAYSEIGMKGERRRGKGHDGLYQGLSTATKDTYDALHMQALPPR
(SEQ ID NO: 205)

KL2B357 LH:
DIVLTQSPDSLAVSLGERATINCRASESVEYFGTSLMHWYQQKPGQPPKLLIYAASNVES
GVPDRFSGSGSGTDFTLTISSLQAEDVAVYFCQQTRKVPYTFGGGTKVEIKGGSEGKSSG
SGSESKSTGGSQVQLQESGPGLVKPSQTLSLTCTVSGNSITSDYAWNWIRQFPGKGLEWI
GYISYSGSTTYNPSLKSRVTISRDTSKNQFSLKLSSVTAADTAVYYCATGYYYGSGFWGQ
GTLVTVSSTSTPAPRPPTPAPTIASQPLSLRPEACRPAAGGAVHTRGLDFACDIYIWAPLA
GTCGVLLLSLVITLYCKRGRKKLLYIFKQPFMRPVQTTQEEDGCSCRFPEEEEGGCELRV
KFSRSADAPAYKQGQNQLYNELNLGRREEYDVLDKRRGRDPEMGGKPRRKNPQEGLY
NELQKDKMAEAYSEIGMKGERRRGKGHDGLYQGLSTATKDTYDALHMQALPPR
(SEQ ID NO: 206)

KL2B358 HL:
QVQLQESGPGLVKPSQTLSLTCTVSGNSITSDYAWNWIRQPPGKGLEWIGYISYSGSTTY
NPSLKSRVTISRDTSKNQFSLKLSSVTAADTAVYYCATGYYYGSGFWGQGTLVTVSSGG
SEGKSSGSGSESKSTGGSEIVLTQSPATLSLSPGERATLSCRASESVEYFGTSLMHWYQQK
PGQPPRLLIYAASNVESGIPARFSGSGSGTDFTLTISSVEPEDFAVYFCQQTRKVPYTFGGG
TKVEIKTSTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKF
SRSADAPAYKQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR
(SEQ ID NO: 207)

KL2B358 LH:
EIVLTQSPATLSLSPGERATLSCRASESVEYFGTSLMHWYQQKPGQPPRLLIYAASNVESG
IPARFSGSGSGTDFTLTISSVEPEDFAVYFCQQTRKVPYTFGGGTKVEIKGGSEGKSSGSG
SESKSTGGSQVQLQESGPGLVKPSQTLSLTCTVSGNSITSDYAWNWIRQPPGKGLEWIGY
ISYSGSTTYNPSLKSRVTISRDTSKNQFSLKLSSVTAADTAVYYCATGYYYGSGFWGQGT
LVTVSSTSTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKF
SRSADAPAYKQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR
(SEQ ID NO: 208)

KL2B360 HL:
QVQLQESGPGLVKPSQTLSLTCTVSGNSITSDYAWNWIRQFPGKGLEWIGYISYSGSTTY
NPSLKSRVTISRDTSKNQFSLKLSSVTAADTAVYYCATGYYYGSGFWGQGTLVTVSSGG
SEGKSSGSGSESKSTGGSEIVLTQSPATLSLSPGERATLSCRASESVEYFGTSLMHWYQQK
PGQPPRLLIYAASNVESGIPARFSGSGSGTDFTLTISSVEPEDFAVYFCQQTRKVPYTFGGG
TKVEIKTSTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKF
SRSADAPAYKQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR
(SEQ ID NO: 209)

KL2B360 LH:
EIVLTQSPATLSLSPGERATLSCRASESVEYFGTSLMHWYQQKPGQPPRLLIYAASNVESG
IPARFSGSGSGTDFTLTISSVEPEDFAVYFCQQTRKVPYTFGGGTKVEIKGGSEGKSSGSG
SESKSTGGSQVQLQESGPGLVKPSQTLSLTCTVSGNSITSDYAWNWIRQFPGKGLEWIGY
ISYSGSTTYNPSLKSRVTISRDTSKNQFSLKLSSVTAADTAVYYCATGYYYGSGFWGQGT
LVTVSSTSTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKF
SRSADAPAYKQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR
(SEQ ID NO: 210)

KL2B30 HL:
QVQLQESGPGLVKPSETLSLTCTVSGGSISSYYWSWIRQPPGKGLEWIGYIYYSGSTNYN
PSLKSRVTISVDTSKNQFSLKLSSVTAADTAVYYCAGTTIFGVVTPNFYYGMDVWGQGT
TVTVSSGGSEGKSSGSGSESKSTGGSDIQMTQSPSFLSASVGDRVTITCRASQGISSYLAW
YQQKPGKAPKFLIYAASTLQSGVPSRFSGSGSGTEFTLTISSLQPEDFATYYCQQLNSYPL
TFGGGTKVEIKTSTPAPRPPTPAPTIASQPLSLRPEACRPAAGGAVHTRGLDFACDIYIWA
PLAGTCGVLLLSLVITLYCKRGRKKLLYIFKQPFMRPVQTTQEEDGCSCRFPEEEEGGCE
LRVKFSRSADAPAYKQGQNQLYNELNLGRREEYDVLDKRRGRDPEMGGKPRRKNPQE
GLYNELQKDKMAEAYSEIGMKGERRRGKGHDGLYQGLSTATKDTYDALHMQALPPR
(SEQ ID NO: 211)

KL2B30 LH:
DIQMTQSPSFLSASVGDRVTITCRASQGISSYLAWYQQKPGKAPKFLIYAASTLQSGVPSR
FSGSGSGTEFTLTISSLQPEDFATYYCQQLNSYPLTFGGGTKVEIKGGSEGKSSGSGSESK
STGGSQVQLQESGPGLVKPSETLSLTCTVSGGSISSYYWSWIRQPPGKGLEWIGYIYYSGS
TNYNPSLKSRVTISVDTSKNQFSLKLSSVTAADTAVYYCAGTTIFGVVTPNFYYGMDVW
GQGTTVTVSSTSTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCEL
```

RVKFSRSADAPAYKQGQNQLYNELNLGRREEYDVLDKRRGRDPEMGGKPRRKNPQEG
LYNELQKDKMAEAYSEIGMKGERRRGKGHDGLYQGLSTATKDTYDALHMQALPPR
(SEQ ID NO: 212)

KL2B53 HL:
EVQLVESGGGVVQPGRSLRLSCVASGFTFSSYDIHWVRQAPGKGLEWVAIISYDGSKKD
YTDSVKGRFTISRDNSKNTLYLQMDSLRVEDSAVYSCARESGWSHYYYGMDVWGQG
TMVTVSSGGSEGKSSGSGSESKSTGGSDIVMTQSPSSLSASVGDRVTITCRASQDISNYLA
WYQQKPGKVPKFLIYAASTLHSGVPSRFSGSGSGTDFTLTISSLQPEDVATYYCQKYNSA
PYTFGQGTRLEIKTSTPAPRPPTPAPTIASQPLSLRPEACRPAAGGAVHTRGLDFACDIYIW
APLAGTCGVLLLSLVITLYCKRGRKKLLYIFKQPFMRPVQTTQEEDGCSCRFPEEEEGGC
ELRVKFSRSADAPAYKQGQNQLYNELNLGRREEYDVLDKRRGRDPEMGGKPRRKNPQ
EGLYNELQKDKMAEAYSEIGMKGERRRGKGHDGLYQGLSTATKDTYDALHMQALPPR
(SEQ ID NO: 213)

KL2B53 LH:
DIVMTQSPSSLSASVGDRVTITCRASQDISNYLAWYQQKPGKVPKFLIYAASTLHSGVPS
RFSGSGSGTDFTLTISSLQPEDVATYYCQKYNSAPYTFGQGTRLEIKGGSEGKSSGSGSES
KSTGGSEVQLVESGGGVVQPGRSLRLSCVASGFTFSSYDIHWVRQAPGKGLEWVAIISY
DGSKKDYTDSVKGRFTISRDNSKNTLYLQMDSLRVEDSAVYSCARESGWSHYYYGM
DVWGQGTMVTVSSTSTPAPRPPTPAPTIASQPLSLRPEACRPAAGGAVHTRGLDFACDIY
IWAPLAGTCGVLLLSLVITLYCKRGRKKLLYIFKQPFMRPVQTTQEEDGCSCRFPEEEEG
GCELRVKFSRSADAPAYKQGQNQLYNELNLGRREEYDVLDKRRGRDPEMGGKPRRKN
PQEGLYNELQKDKMAEAYSEIGMKGERRRGKGHDGLYQGLSTATKDTYDALHMQALP
PR
(SEQ ID NO: 214)

KL2B242 HL:
QVQLQESGPGLVKPSETLSLTCTVSGGSISSYYWSWLRQPAGSGLEWIGRLYVSGFTNYN
PSLKSRVTLSLDPSRNQLSLKLSSVTAADTAVYYCAGDSGNYWGWFDPWGQGTLVTVS
SGGSEGKSSGSGSESKSTGGSSYELTQPPSVSVSPGETASITCSGDQLGENYACWYQQKP
GQSPVLVIYQDSKRPSGIPERFSGSNSGNTATLTISGTQALDEADYYCQAWDNSIVVFGG
GTKLTVLTSTPAPRPPTPAPTIASQPLSLRPEACRPAAGGAVHTRGLDFACDIYIWAPLAG
TCGVLLLSLVITLYCKRGRKKLLYIFKQPFMRPVQTTQEEDGCSCRFPEEEEGGCELRVK
FSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR
(SEQ ID NO: 215)

KL2B242 LH:
SYELTQPPSVSVSPGETASITCSGDQLGENYACWYQQKPGQSPVLVIYQDSKRPSGIPERF
SGSNSGNTATLTISGTQALDEADYYCQAWDNSIVVFGGGTKLTVLGGSEGKSSGSGSES
KSTGGSQVQLQESGPGLVKPSETLSLTCTVSGGSISSYYWSWLRQPAGSGLEWIGRLYVS
GFTNYNPSLKSRVTLSLDPSRNQLSLKLSSVTAADTAVYYCAGDSGNYWGWFDPWGQG
TLVTVSSTSTPAPRPPTPAPTIASQPLSLRPEACRPAAGGAVHTRGLDFACDIYIWAPLAG
TCGVLLLSLVITLYCKRGRKKLLYIFKQPFMRPVQTTQEEDGCSCRFPEEEEGGCELRVK
FSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR
(SEQ ID NO: 216)

KL2B467 HL:
QVQLVESGGGVVQPGRSLRLSCAASGFTFSYYGMHWVRQAPGKGLEWVAFISYDGSNK
YYADSVKGRFTISRDNSKNTLYLQMNSLRAEDTAVYYCAHLPYSGSYWAFDYWGQGT
QVTVSSGGSEGKSSGSGSESKSTGGSQSVLTQPPSVSVAPGQTASITCGGDNIGSKSVHW
YQQKPGQAPVLVVYDNSDRPSGIPERFSGSNSGTTATLTISRVEAGDEADYYCQVWDSS
SDHPVVFGGGTKVTVSTSTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSCRFPEEEE
GGCELRVKFSRSADAPAYKQGQNQLYNELNLGRREEYDVLDKRRGRDPEMGGKPRRK
NPQEGLYNELQKDKMAEAYSEIGMKGERRRGKGHDGLYQGLSTATKDTYDALHMQAL
PPR
(SEQ ID NO: 217)

KL2B467 LH:
QSVLTQPPSVSVAPGQTASITCGGDNIGSKSVHWYQQKPGQAPVLVVYDNSDRPSGIPER
FSGSNSGTTATLTISRVEAGDEADYYCQVWDSSSDHPVVFGGGTKVTVGGSEGKSSGSG
SESKSTGGSQVQLVESGGGVVQPGRSLRLSCAASGFTFSYYGMHWVRQAPGKGLEWVA
FISYDGSNKYYADSVKGRFTISRDNSKNTLYLQMNSLRAEDTAVYYCAHLPYSGSYWAF
DYWGQGTQVTVSSTSTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDGCSCRFPEEEEGG
CELRVKFSRSADAPAYKQGQNQLYNELNLGRREEYDVLDKRRGRDPEMGGKPRRKNP
QEGLYNELQKDKMAEAYSEIGMKGERRRGKGHDGLYQGLSTATKDTYDALHMQALPP
R
(SEQ ID NO: 218)

KL2B494 HL:
QVQLVESGGGLVQPGGSLRLSCAASGFTFSHYAMSWVRQAPGKGLEWVSTIGGSGGST
YYADSVKGRFTISRDNSKNTLYLQMNSLRAEDTAVYYCAKPHIVMVTALLYDGMDVW
GQGTMVTVSSGGSEGKSSGSGSESKSTGGSSSELTQPPSVSVAPGQTARITCGGNNIGSKS
VHWYQQKPGQAPVLVVYDDSDRPSGIPERFSGSNSGNTATLTISRVEAGDEADYYCQV
WDSSSDHVVFGGGTKLTVLTSTPAPRPPTPAPTIASQPLSLRPEACRPAAGGAVHTRGLD

-continued

```
FACDIYIWAPLAGTCGVLLLSLVITLYCKRGRKKLLYIFKQPFMRPVQTTQEEDGCSCRFP
EEEEGGCELRVKFSRSADAPAYKQGQNQLYNELNLGRREEYDVLDKRRGRDPEMGGKP
RRKNPQEGLYNELQKDKMAEAYSEIGMKGERRRGKGHDGLYQGLSTATKDTYDALHM
QALPPR
(SEQ ID NO: 219)

KL2B494 LH:
SSELTQPPSVSVAPGQTARITCGGNNIGSKSVHWYQQKPGQAPVLVVYDDSDRPSGIPER
FSGSNSGNTATLTISRVEAGDEADYYCQVWDSSSDHVVFGGGTKLTVLGGSEGKSSGSG
SESKSTGGSQVQLVESGGGLVQPGGSLRLSCAASGFTFSHYAMSWVRQAPGKGLEWVS
TIGGSGGSTYYADSVKGRFTISRDNSKNTLYLQMNSLRAEDTAVYYCAKPHIVMVTALL
YDGMDVWGQGTMVTVSSTSTPAPRPPTPAPTIASQPLSLRPEACRPAAGGAVHTRGLDF
ACDIYIWAPLAGTCGVLLLSLVITLYCKRGRKKLLYIFKQPFMRPVQTTQEEDGCSCRFP
EEEEGGCELRVKFSRSADAPAYKQGQNQLYNELNLGRREEYDVLDKRRGRDPEMGGKP
RRKNPQEGLYNELQKDKMAEAYSEIGMKGERRRGKGHDGLYQGLSTATKDTYDALHM
QALPPR
(SEQ ID NO: 220)
```

Dynabeads Human T-Expander CD3/CD28 stimulated T cells are subjected to electroporation, then washed three times with OPTI-MEM (Invitrogen), and resuspended in OPTI-MEM at the final concentration of 50E6/ml. Subsequently, 0.1 ml of the cells (5E6) are mixed with 10 ug of IVT CAR encoding RNA and electroporated in a 2-mm Gap cuvette (Harvard Apparatus BTX, Holliston, Mass., USA) using BTX ECM830 (Harvard Apparatus BTX, Holliston, Mass., USA) by pressing the "pulse" button one time. (Settings: 500 Volts, 750 μsec Pulse Length and single(1) pulse, 100 mSec interval.) Post electroporation, the T cells are transferred to a 6-well plate and immediately put back into a 37° C. incubator. Primary human T cells are electroporated with no mRNA (MOCK) or 10 g of mRNA expressing either the hK2 scFv CAR or irrelevant control CAR. 24 hours post-electroporation CAR surface expression is measured by flow cytometry following staining with 2 μg/ml biotinylated L-protein and streptavidin-conjugated PE, or biotinylated hK2 (1 μg/ml) and streptavidin-conjugated PE.

Twenty-four hours post electroporation, the T cells are counted. 1E5 T cells are collected for each. The cells are washed with FACS buffer twice using 200 μL/well of FACS buffer for microtiter plates, with the supernatant discarded. All wells are stained with 100 μl staining buffer containing Protein L (Genscript, Cat. No. M000971:500; 2 ug/ml), and incubated for at least 30 minutes at 4° C. while being protected from light. The cells are washed by adding FACS Buffer twice, using 150 μL/well for microtiter plates with FACS buffer. Centrifugation at 400×g is performed for 4 minutes at room temperature. The supernatant is then discarded. All wells are stained with 100 μl Streptavidin-R-Phycoerythrin (SA-PE;1:250) and Live/dead Fixable Near-IR Dead Cell Stain dye (1:1000), incubated for at least 30 minutes at 4° C. while being protected from light. The cells are then ready for flow cytometry analysis.

Observation of protein L staining is seen for the hK2 CARs, whereas only the background staining (~5.5%) is seen in the control T cells that were T cells without mRNA electroporation. CAR expression on primary human T cells also can be detected via J&J internal biotin-labeled recombinant KLK2 protein followed by SA-PE. As shown, T cells efficiently express hK2 CARs as measured by flow cytometry, whereas only the background staining is seen in the control T cells that are T cells without mRNA electroporation or undisclosed control CAR (non-hK2 specific).

Example 21: Tumor Cell Killing by hK2 CAR-T Cells

Co-culture for CellTrace Violet (CTV, Thermo Fisher Scientific Catalog number: C34557) based cytotoxicity assay using flow cytometer is performed as follows.

The T cells are prepared as follows. Twenty-four hours post EP, T cells are counted and resuspended at the concentration needed for the most concentrated/desired E:T. The T cells are added at 100 μl/well of assay (2×10⁶ cells/ml; plated 100 μl in a 10:1 E:T ratio, i.e., 2E5 T cells per 2E4 target cells). A stock of the 10:1 E:T concentration is made, with two-fold serial dilutions made with complete T cell media (Optimizer w/CTS, 5% Human Serum, 1% Gluta-Max) to 0.3125:1. The T cells are plated (100 ul/well) in triplicate using a 96 well round bottom tissue culture treated plate.

CTV labeled target cells are prepared as follows. 20 μL DMSO is added to a vial of CTV staining solution. This stock solution is diluted into 20 mL of PBS (warmed to 37° C.) for a 5 μM staining solution. 10E6 tumor cells are collected, washed with PBS twice and resuspended in 4E6/ml (2.5 ml). An equal volume (2.5 ml) of CTV staining solution is added. The cells are incubated for 20 minutes in a 37° C. incubator. 40 ml PRMI+20% FBS are added to the cells to absorb any unbound dye. The cells are incubated for 5 minutes. The cells are centrifuged for 5 minutes at 400×g. The cell pellet is resuspended in pre-warmed RPMI+10% FBS medium. In the meantime, T cells are seeded at the desired E/T ratio described above. hK2+ tumor cell lines and a hK2-tumor cell line are recounted, and then the cells are resuspended in 2E5/ml and 100 ul in duplicate. The cells are co-incubated with labelled tumor cell lines in a flat-bottom 96-well plate.

A cytotoxicity assay is performed as follows using a flow cytometer. After 20 hours of co-culture, all of the cells are transferred to a U-bottom 96-well plate and washed. After 20 hours of co-culture all of the cells are collected from a flat-bottom 96-well plate and transferred to a U-bottom 96-well plate, and then washed. 30 μl of 0.25% trypsin is added to all the wells and incubated for 5 minutes in a 37° C. incubator. After 5 minutes, all of the tumor cells are collected to a U-bottom 96-well plate. The cells are centrifuged and washed for 5 minutes at 400×g twice. The cell pellet is then resuspended in diluted (1:1000) LIVE/DEAD™ Fixable Near-IR staining dye (100 μl). The cells are incubated for 30 mins at 4° C., and washed with FACS buffer twice by centrifuging the cells for 5 minutes at 400×g. After washing, all of the cells are fixed for 10 minutes using 100 µl of BD Cytofix™ Fixation Buffer (50 ul FACS buffer+50 ul Fixation Buffer). The cells are centrifuged and washed for 5 minutes at 400×g once. The cell pellet is resuspended in FACS buffer.

Stained samples are analyzed by multicolor flow cytometry after the end of the incubation period. The percentage of cytotoxic activity is calculated using the following equation:

% specific death=% Near IR+CTV+(dead)cells−% spontaneous Near IR+CTV+/(100%−% spontaneous Near IR+CTV+(dead)cells)×100%.

Twenty-four hours after transient transfection, target cells (hK2positive Vcap and hK2 negative DU145 cells) are labeled with Cell Trace Violet (CTV) fluorescent dye and then co-cultured with hK2 CAR-T cells. Mock T cells serve as negative effector controls. Cells are co-cultured for 20 hours at the effector-to-target cell (E/T) ratios ranging from 0.3125:1 to 10:1. The percent killing is measured as the ratio of the absolute number of live (viability dye negative) target (CTV positive) cells remaining in the co-culture relative to the number of live target cells cultured without CAR-T cells. As shown, hK2 CAR T cells specifically and efficiently lyse the hK2(+) human cancer cell lines, but not hK2(−) cells at E/T ratios of 10:1 to 0.3125:1, whereas only the background cytotoxicity is seen in the T cells that were Mock or hK2 CAR.

hK2 CAR-T cells are also tested for real-time cytotoxicity using xCELLigence as a real-time cell analysis system as a potency assay for immune cell-mediated cytolysis of target cells.

50 µL of target cancer cell culturing media is added to each well of the 96-well E-Plates (ACEA Biosciences), and the background impedance is measured and displayed as a Cell Index. Then, adherent target cells hK2(+) and hK2(−) are dissociated and seeded at a density of 5E4 (VCap), 5E3 cells/well of the E-Plate in a volume of 100 µL, and allowed to passively adhere on the electrode surface. Post seeding, the E-Plate is kept at ambient temperature inside a laminar flow hood for 30 minutes and then transferred to the RTCA MP instrument inside a cell culture incubator. Data recording is initiated immediately at 15-minute intervals for the entire duration (96 hours) of the experiment.

At the time treatment is applied (24 hours post cancer cells seeding), data acquisition is paused, 50 µL of media is removed from each well, and effector CAR-T cells are added at different effector to target (E:T) ratios in a volume of 50 µL. hK2(+) CAR-T and undisclosed control CAR (non-hK2 specific) T cells are resuspended. Two-fold dilutions are then performed in duplicate in a 96-well plate (from 5:1 to 0.156:1 E/T ratio). Target plus Mock effector controls (no RNA electroporation T cells) are also added to the target cells.

Target cells hK2(+) and hK2(−) are incubated with Mock, 10 µg mRNA electroporated (24 hours post transfection) into hK2(+) and hK2(−) CAR-T cells at different E/T ratios for approximately 72 hours. Normalized cell index (CI) plots for hK2(+) and hK2(−) are generated. When seeded alone, target cells adhered to the plate and proliferated, increasing the CI readout.

Example 22: Cytokine Production by hK2 CAR-T Cells

IFN-γ produced by cytotoxic T cells allows for exertion of immune surveillance of tumors, which can directly inhibit proliferation and induce apoptosis of some malignancies in vivo and in vitro. To determine whether hK2 CAR-T cells are able to recognize and be activated by hK2 (+) tumor cells, the supernatant was collected from xCELLigence-based killing assay, as described in Example 21. After about 70 hours co-culture, the supernatant was collected and assayed by ELISA according to the directions provided with the ELISA kit (Human IFN-γ ELISA MAX™ Deluxe, BioLegend, Cat #:430106).

IFN-γ production of antigen-stimulated CAR-T cells occurs. hK2 CAR and control CAR-T cells secreted IFN-γ during co-culture with hK2-expressing cells in an E:T ratio-dependent manner, but not during co-culture with hK2-negative cells. Undisclosed control CAR secreted much higher amount of IFN-γ due to the much higher antigen expression level than hK2.

Example 21: Tumor Cell Killing by hK2 CAR-T Cells hK2 CAR-T cells are evaluated in the real-time IncuCyte tumor killing assay for antigen-dependent cytotoxicity. hK2 CAR-T cells are co-incubated with target cells for 88 hours at effector:target ratio of 1:1 or 0.5:1 which was calculated based on CAR expression data. Target cells are identified that are stably expressing a red nuclear dye as measured by IncuCyte imaging system in a real-time fashion. The following calculation is performed: Tumor cell growth inhibition (%)=(Initial Viable Target Cell Number-Current Viable Target Cell Number)/Initial Viable Cell Number*100(%).

Example 22: Cytokine Production by hK2 CAR-T Cells

Supernatant is collected from overnight (approximately 20 hours) co-culture of hK2CAR-T cells with cells at 1:1 of E/T ratio and was analyzed using 13-plex Milliplex Human High Sensitivity T cell kit (HSTCMAG28SPMX13). hK2 CAR modified T cells secreted cytokines during co-culture with hK2-expressing cells, but minimal for un-transduced T cells (UTD). The results of cytokine release by hK2 CAR-T cells.

Supernatant was collected from overnight (approximately 20 hours) co-culture of hK2 CAR-T cells with cells at 1:1 of E/T ratio. hK2 CAR-T cells secreted IFN-γ during co-culture with hK2-expressing cells, but not during co-culture with hK2-negative cells. CD3/28 beads stimulated T cells and T cells only were used as positive and negative controls, respectively. IFN-γ release by hK2 CAR-T cells. Mean IFN-γ concentration SD (pg/ml) from duplicate cultures is shown. Different thermally stabilized CAR-T cells produced different amount of IFN-γ when co-culture with hK2 (+) cells.

Example 23: Proliferation of hK2 CAR-T Cells hK2 CAR-T cells are evaluated in a proliferation assay. T-cell proliferation is an important in vitro parameter of in vivo immune function. To further evaluate the function of hK2 CAR-T cells, the hK2 CAR-T cells are labeled with CTV to assess T cells proliferation.

hK2 CAR-T and un-transduced (UTD) T cells are labelled with CellTrace Violet (CTV; 5 µM) and co-cultured with hK2(+) and hK2(−) cells. Five days post co-culture, cells are harvested and stained with CD3, CD25, NearIR live/dead Dye and hK2 CAR. Flow cytometric analysis is performed on a Fortessa flow cytometer with Flowjo software. Lymphocytes are identified by live CD3, and the frequencies of CAR-T cells with CTV dye dilution and activation marker CD25 are determined. By gating on hK2 CAR+ T cells, as shown, the hK2 (+) cells but not hK2 (−) cells promote the all CAR constructs. CD3/28 beads stimulated T cells and T cells only are used as positive and negative controls, respectively. T cells only without any stimulation do not proliferate and CD3/28 beads stimulated T cells displayed equivalent proliferation pattern. hK2CAR-T cells proliferated more robustly than CD3/28 beads positive control after 5 days of co-culture with cells. Different CAR constructs engineered T cells have different proliferation activity and displayed different CAR-T cells counts. The CAR-T cells counts are based on mean absolute cell count+/−SEM from three technical replicates.

The protocol is performed as follows. The tumor cells are collected, washed twice with PBS, and resuspended in 10E6/ml in PBS containing 100 ug/ml Mitomycin C (MMC) for 1.5 hours in a 37° C. incubator so as to block tumor cells proliferation. 20 μL of DMSO is added to a vial of CTV staining solution. 5 μl of the solution is diluted into 5 mL (1:1000) PBS (warmed to 37° C.) to provide a 5 μM staining solution. The 2E6 T cells are counted, collected, washed with PBS twice, and resuspended in 4E6/ml (0.5 ml). An equal volume (0.5 ml) of CTV staining solution is added. The cells are incubated for 20 minutes at 37° C. Then, 4 ml PRMI+20% FBS is added to the cells to absorb any unbound dye. The cells are incubated for 5 minutes, and centrifuged for 5 minutes at 400×g. The cell pellet is resuspended in pre-warmed RPMI+10% FBS medium. The T cells are counted, and 1E5 cells (100 ul) are seeded in 96-wells flat bottom-plate.

In the meantime, MMC-treated tumor cells are collected and counted after 1.5 hours, and then resuspended at 1E6/ml. 1E5 of the cells (100 μl) are cocultured with T cells in a 96-well plate. T cells alone, and T cells added 3:1 CD3/28 beads to cells ratio, are used as negative and positive controls, respectively.

After 5 days of co-culture, all of the cells are collected from each well. The cells are centrifuged and washed for 5 minutes at 400×g twice, then stained hK2 CAR, CD3, CD8 and CD25, live/dead (Near-IR) in 96-well U bottom plate. After washing, all cells are fixed for 10 minutes using 100 μl BD Cytofix™ Fixation Buffer (50 ul FACS buffer+50 ul Fixation Buffer). The stained samples are analyzed by multicolor flow cytometry after the end of the incubation period.

Data analysis is performed as follows. A CTV histogram is prepared. The CTV undiluted gate is set to encompass the far-right peak (CTV bright) of T cells cultured alone, and the CTV diluted gate to capture the rest of the population. This is applied to all samples.

Example 24: Characterization of CAR-T Cells Transduced with Various Constructs Described Herein The generated CAR-T cells are evaluated in the JNL reporter assay for antigen-dependent activity. Briefly, Jurkat cells containing the luciferase gene driven by the signaling-responsive NFAT promoter (termed JNL cells) are transduced with any construct comprising one or more nucleic acid sequences of SEQ ID NOS: 153-160, 161-168, 195-204, 320-325, 326-331, and 336-339.

Alternatively, the construct may comprise a nucleic acid sequence encoding:

a light chain variable region comprising an amino acid sequence of SEQ ID NO: 1 and a heavy chain variable region comprising an amino acid sequence of SEQ ID NO: 4;

a light chain variable region comprising an amino acid sequence of SEQ ID NO: 2 and a heavy chain variable region comprising an amino acid sequence of SEQ ID NO: 4;

a light chain variable region comprising an amino acid sequence of SEQ ID NO: 3 and a heavy chain variable region comprising an amino acid sequence of SEQ ID NO: 6;

a light chain variable region comprising an amino acid sequence of SEQ ID NO: 3 and a heavy chain variable region comprising an amino acid sequence of SEQ ID NO: 4;

a light chain variable region comprising an amino acid sequence of SEQ ID NO: 2 and a heavy chain variable region comprising an amino acid sequence of SEQ ID NO: 6;

a light chain variable region comprising an amino acid sequence of SEQ ID NO: 3 and a heavy chain variable region comprising an amino acid sequence of SEQ ID NO: 4;

a light chain variable region comprising an amino acid sequence of SEQ ID NO: 1 and a heavy chain variable region comprising an amino acid sequence of SEQ ID NO: 6;

a light chain variable region comprising an amino acid sequence of SEQ ID NO: 3 and a heavy chain variable region comprising an amino acid sequence of SEQ ID NO: 5;

a light chain variable region comprising an amino acid sequence of SEQ ID NO: 1 and a heavy chain variable region comprising an amino acid sequence of SEQ ID NO: 5;

a light chain variable region comprising an amino acid sequence of SEQ ID NO: 2 and a heavy chain variable region comprising an amino acid sequence of SEQ ID NO: 5;

a light chain variable region comprising an amino acid sequence of SEQ ID NO: 3 and a heavy chain variable region comprising an amino acid sequence of SEQ ID NO: 5;

a light chain variable region comprising an amino acid sequence of SEQ ID NO: 74 and a heavy chain variable region comprising an amino acid sequence of SEQ ID NO: 76;

a light chain variable region comprising an amino acid sequence of SEQ ID NO: 75 and a heavy chain variable region comprising an amino acid sequence of SEQ ID NO: 77;

a light chain variable region comprising an amino acid sequence of SEQ ID NO: 147 and a heavy chain variable region comprising an amino acid sequence of SEQ ID NO: 140;

a light chain variable region comprising an amino acid sequence of SEQ ID NO: 75 and a heavy chain variable region comprising an amino acid sequence of SEQ ID NO: 141;

a light chain variable region comprising an amino acid sequence of SEQ ID NO: 75 and a heavy chain variable region comprising an amino acid sequence of SEQ ID NO: 140;

a light chain variable region comprising an amino acid sequence of SEQ ID NO: 148 and a heavy chain variable region comprising an amino acid sequence of SEQ ID NO: 142;

a light chain variable region comprising an amino acid sequence of SEQ ID NO: 149 and a heavy chain variable region comprising an amino acid sequence of SEQ ID NO: 143;

a light chain variable region comprising an amino acid sequence of SEQ ID NO: 150 and a heavy chain variable region comprising an amino acid sequence of SEQ ID NO: 144;

a light chain variable region comprising an amino acid sequence of SEQ ID NO: 151 and a heavy chain variable region comprising an amino acid sequence of SEQ ID NO: 145;

a light chain variable region comprising an amino acid sequence of SEQ ID NO: 152 and a heavy chain variable region comprising an amino acid sequence of SEQ ID NO: 146;

a light chain variable region comprising an amino acid sequence of SEQ ID NO: 318 and a heavy chain variable region comprising an amino acid sequence of SEQ ID NO: 317.

Expression of each CAR is determined by biotinylated hK2 followed by streptavidin-conjugated PE.

Binding between the hK2 CAR construct and its cognate cellular antigen (hK2 on target cells) leads to luciferase expression in the JNL cells. To that end, JNL cells transduced with the test CAR constructs or untransduced JNL cells (UTD) are co-cultured with target tumor cell lines and luciferase activity was measured as luminescence intensity. Constructs are considered active when the luminescence intensity exceeded 1.5-fold the level of UTD cells in the presence of antigen-expressing cells.

CAR-T Cells Mediate Tumor Cell Killing in Antigen-Dependent Manner

CAR-T cells are transduced with CAR17, CAR18, CAR19 and CAR20 are co-incubated with hK2 positive cells and hK2 negative cells for 96 hours at effector-to-target (ET) ratio of 1:1 or 0.5:1 which was calculated based on CAR expression on T cells. Target cells stably express a red nuclear dye, which is measured by IncuCyte imaging system in a real-time fashion. Tumor cell growth inhibition (TGI) (%)=(Initial Viable Target Cell Number-Current Viable Target Cell Number)/Initial Viable Cell Number*100(%). Tested CAR-T cells may achieve approximately 100% TGI whereas the untransduced control may not demonstrate any TGI. No TGI may be observed with the tested CAR-T cells in hK2 negative cells.

CAR-T Cells Produce Cytokines Upon Antigen Stimulation

IFN-γ produced by cytotoxic T cells is critical for exerting immune surveillance of tumors, which can directly inhibit proliferation and induce apoptosis of some malignancies in vivo and in vitro. To determine whether hK2 CAR-modified human T cells are able to recognize and become activated by hK2 positive tumor cells, primary T cells are transduced with indicated CAR clones and control untransduced T cells (UTD) were co-cultured with target cells lines and supernatant were collected for IFN-γ concentration measurement. CAR-T cells transduced with hK2 CARs cells secrete IFN-γ during co-culture with LNCaP cells recombinantly express hK2 cells and also during co-culture with very low hK2-expressing cells but not hK2-negative cells.

CAR-T Cells are Activated and Upregulate Markers of Degranulation in Antigen-Dependent Manner Tumor cells can be recognized and killed by cytotoxic lymphocytes, such as CD8+T lymphocytes and natural killer (NK) cells mainly through the immune secretion of lytic granules that kill the target tumor cells. This process involves the fusion of the granule membrane with the cytoplasmic membrane of the immune effector cell, resulting in surface exposure of lysosomal-associated proteins that are typically present on the lipid bilayer surrounding lytic granules, such as CD107a. Therefore, membrane expression of CD107a constitutes a marker of immune cell activation and cytotoxic degranulation.

The degranulation assay is performed as described below. Target cells ($5\times10^4$) are co-cultured with an equal number of effector cells in 0.1 ml per well in a 96-well plate. Control wells contained T cells alone. Anti-CD107a (51 per well) are added in addition to 1 μl/sample of monensin (BD Biosciences) and incubated for 4 hours at 37° C. Cells are washed two times with PBS, stained for expression of the hK2 CAR, CD3, and CD8 and analyzed on a flow cytometer BD Fortessa.

hK2 CAR-T Cells Proliferate in Antigen-Dependent Manner

CAR-T cells are evaluated for their proliferation using T-cell proliferation assay protocol described in Example 23. hK2 CAR-T and untransduced (UTD) T cells are labelled with CellTrace Violet (CTV; 5 μM) and co-cultured with hK2 positive and hK2 negative cells. Five days post co-culture, cells are harvested and stained with CD3, CD25, NearIR live/dead Dye and hK2 CAR. Flow cytometric analysis is performed on a Fortessa flow cytometer with Flowjo software. Lymphocytes are identified by live CD3, and the frequencies of CAR-T cells with CTV dye dilution and activation marker CD25 were determined. The percentage of proliferating T cells and CD25 expressing T cells is based on mean absolute cell count+/−SEM from duplicate.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

```
SEQ ID NO: 1-VL 1 (LCD6)
DIVLTQSPDSLAVSLGERATINCKASESVEYFGTSLMHWYQQKPGQPPKLLIYAAS
NRESGVPDRFSGSGSGTDFTLTIQSVQAEDVSVYFCQQTRKVPYTFGQGTKLEIK

SEQ ID NO: 2-VL 2 (LCHumanized)
DIVLTQSPDSLAVSLGERATINCKASESVEYFGTSLMHWYQQKPGQPPKLLIYAAS
NRESGVPDRFSGSGSGTDFTLTISSLQAEDVAVYYCQQTRKVPYTFGQGTKLEIK SEQ ID NO: 3-VL 3 (LCB7)
DIVLTQSPDSLAVSLGERATINCKASESVEYFGTSLMHWYQQKPGQPPKLLIYAAS
NRESGVPDRFSGSGSGTDFTLTISSVQAEDVAVYYCQQTRKVPYTFGQGTKLEIK
```

SEQ ID NO: 4-VH 1 (HCG5)
QVQLQESGPGLVKPSDTLSLTCAVSGNSITSDYAWNWIRQFPGKGLEWMGYISYS
GSTTYNPSLKSRVTISRDTSKNQFSLKLSSVTPVDTAVYYCATGYYYGSGFWGQG
TLVTVSS

SEQ ID NO: 5-VH 2 (HCHumanized)
QVQLQESGPGLVKPSDTLSLTCAVSGNSITSDYAWNWIRQPPGKGLEWIGYISYSG
STTYNPSLKSRVTMSRDTSKNQFSLKLSSVTAVDTAVYYCATGYYYGSGFWGQG
TLVTVSS SEQ ID NO: 6-VH 3 (HCF3)
QVQLQESGPGLVKPSDTLSLTCAVSGNSITSDYAWNWIRQFPGKGLEWIGYISYSG
STTYNPSLKSRVTISRDTSKNQFSLKLSSVTPVDTAVYYCATGYYYGSGFWGQGT
LVTVSS SEQ ID NO: 7-Linker sequence
GGSEGKSSGSGSESKSTGGS SEQ ID NO: 8-scFV 1 (HL_HCG5_LCD6_20AA)
QVQLQESGPGLVKPSDTLSLTCAVSGNSITSDYAWNWIRQFPGKGLEWMGYISYS
GSTTYNPSLKSRVTISRDTSKNQFSLKLSSVTPVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTIQSVQAED
VSVYFCQQTRKVPYTFGQGTKLEIK SEQ ID NO: 9-scFV 2 (HL_HCG5_LCHumanized_20AA)
QVQLQESGPGLVKPSDTLSLTCAVSGNSITSDYAWNWIRQFPGKGLEWMGYISYS
GSTTYNPSLKSRVTISRDTSKNQFSLKLSSVTPVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSLQAED
VAVYYCQQTRKVPYTFGQGTKLEIK SEQ ID NO: 10-scFV 3 (HL_HCF3_LCB7_20AA)
QVQLQESGPGLVKPSDTLSLTCAVSGNSITSDYAWNWIRQFPGKGLEWIGYISYSG
STTYNPSLKSRVTISRDTSKNQFSLKLSSVTPVDTAVYYCATGYYYGSGFWGQGT
LVTVSSGGSEGKSSGSGSESKSTGGSDIVLTQSPDSLAVSLGERATINCKASESVEY
FGTSLMHWYQQKPGQPPKLLIYAASNRESGVPDRFSGSGSGTDFTLTISSVQAEDV
AVYYCQQTRKVPYTFGQGTKLEIK SEQ ID NO: 11-scFV 4 (HL_HCG5_LCB7_20AA)
QVQLQESGPGLVKPSDTLSLTCAVSGNSITSDYAWNWIRQFPGKGLEWMGYISYS
GSTTYNPSLKSRVTISRDTSKNQFSLKLSSVTPVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSVQAED
VAVYYCQQTRKVPYTFGQGTKLEIK SEQ ID NO: 12-scFV 5 (LH_LCD6_HCG5_20AA)
DIVLTQSPDSLAVSLGERATINCKASESVEYFGTSLMHWYQQKPGQPPKLLIYAAS
NRESGVPDRFSGSGSGTDFTLTIQSVQAEDVSVYFCQQTRKVPYTFGQGTKLEIKG
GSEGKSSGSGSESKSTGGSQVQLQESGPGLVKPSDTLSLTCAVSGNSITSDYAWNW
IRQFPGKGLEWMGYISYSGSTTYNPSLKSRVTISRDTSKNQFSLKLSSVTPVDTAVY
YCATGYYYGSGFWGQGTLVTVSS SEQ ID NO: 13-scFV 6 (LH_LCHumanized_HCF3_20AA)
DIVLTQSPDSLAVSLGERATINCKASESVEYFGTSLMHWYQQKPGQPPKLLIYAAS
NRESGVPDRFSGSGSGTDFTLTISSLQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWIGYISYSGSTTYNPSLKSRVTISRDTSKNQFSLKLSSVTPVDTAVY
YCATGYYYGSGFWGQGTLVTVSS SEQ ID NO: 14-scFV 7 (LH_LCHumanized_HCG5_20AA)
DIVLTQSPDSLAVSLGERATINCKASESVEYFGTSLMHWYQQKPGQPPKLLIYAAS
NRESGVPDRFSGSGSGTDFTLTISSLQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWMGYISYSGSTTYNPSLKSRVTISRDTSKNQFSLKLSSVTPVDTAVY
YCATGYYYGSGFWGQGTLVTVSS SEQ ID NO: 15-scFV 8 (LH_LCB7_HCF3_20AA)
DIVLTQSPDSLAVSLGERATINCKASESVEYFGTSLMHWYQQKPGQPPKLLIYAAS
NRESGVPDRFSGSGSGTDFTLTISSVQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWIGYISYSGSTTYNPSLKSRVTISRDTSKNQFSLKLSSVTPVDTAVY
YCATGYYYGSGFWGQGTLVTVSS SEQ ID NO: 16-scFV 9 (LH_LCB7_HCG5_20AA)
DIVLTQSPDSLAVSLGERATINCKASESVEYFGTSLMHWYQQKPGQPPKLLIYAAS
NRESGVPDRFSGSGSGTDFTLTISSVQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWMGYISYSGSTTYNPSLKSRVTISRDTSKNQFSLKLSSVTPVDTAVY
YCATGYYYGSFWGQGTLVTVSS SEQ ID NO: 17-scFV 10 (LH_LCD6_HCF3_20AA)
DIVLTQSPDSLAVSLGERATINCKASESVEYFGTSLMHWYQQKPGQPPKLLIYAAS
NRESGVPDRFSGSGSGTDFTLTIQSVQAEDVSVYFCQQTRKVPYTFGQGTKLEIKG
GSEGKSSGSGSESKSTGGSQVQLQESGPGLVKPSDTLSLTCAVSGNSITSDYAWNW
IRQFPGKGLEWIGYISYSGSTTYNPSLKSRVTISRDTSKNQFSLKLSSVTPVDTAVY
YCATGYYYGSFWGQGTLVTVSS SEQ ID NO: 18-scFV 11 (HL_HCHumanized_LCB7_20AA)
QVQLQESGPGLVKPSDTLSLTCAVSGNSITSDYAWNWIRQPPGKGLEWIGYISYSG
STTYNPSLKSRVTMSRDTSKNQFSLKLSSVTAVDTAVYYCATGYYYGSFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSVQAED
VAVYYCQQTRKVPYTFGQGTKLEIK SEQ ID NO: 19-scFV 12 (HL_HCHumanized_LCD6_20AA)
QVQLQESGPGLVKPSDTLSLTCAVSGNSITSDYAWNWIRQPPGKGLEWIGYISYSG
STTYNPSLKSRVTMSRDTSKNQFSLKLSSVTAVDTAVYYCATGYYYGSFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTIQSVQAED
VSVYFCQQTRKVPYTFGQGTKLEIK SEQ ID NO: 20-scFV 13 (HL_HCHumanized_LCHumanized_20AA)
QVQLQESGPGLVKPSDTLSLTCAVSGNSITSDYAWNWIRQPPGKGLEWIGYISYSG
STTYNPSLKSRVTMSRDTSKNQFSLKLSSVTAVDTAVYYCATGYYYGSFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSLQAED
VAVYYCQQTRKVPYTFGQGTKLEIK SEQ ID NO: 21-scFV 14 (LH_LCD6_HCHumanized_20AA)
DIVLTQSPDSLAVSLGERATINCKASESVEYFGTSLMHWYQQKPGQPPKLLIYAAS
NRESGVPDRFSGSGSGTDFTLTIQSVQAEDVSVYFCQQTRKVPYTFGQGTKLEIKG
GSEGKSSGSGSESKSTGGSQVQLQESGPGLVKPSDTLSLTCAVSGNSITSDYAWNW
IRQPPGKGLEWIGYISYSGSTTYNPSLKSRVTMSRDTSKNQFSLKLSSVTAVDTAV
YYCATGYYYGSFWGQGTLVTVSS SEQ ID NO: 22-scFV 15 (LH_LCHumanized_HCHumanized_20AA)
DIVLTQSPDSLAVSLGERATINCKASESVEYFGTSLMHWYQQKPGQPPKLLIYAAS
NRESGVPDRFSGSGSGTDFTLTISSLQAEDVAVYYCQQTRKVPYTFGQGTKLEIKG
GSEGKSSGSGSESKSTGGSQVQLQESGPGLVKPSDTLSLTCAVSGNSITSDYAWNW
IRQPPGKGLEWIGYISYSGSTTYNPSLKSRVTMSRDTSKNQFSLKLSSVTAVDTAV
YYCATGYYYGSFWGQGTLVTVSS SEQ ID NO: 23-scFV 16 (LH_LCB7_HCHumanized_20AA)
DIVLTQSPDSLAVSLGERATINCKASESVEYFGTSLMHWYQQKPGQPPKLLIYAAS
NRESGVPDRFSGSGSGTDFTLTISSVQAEDVAVYYCQQTRKVPYTFGQGTKLEIKG
GSEGKSSGSGSESKSTGGSQVQLQESGPGLVKPSDTLSLTCAVSGNSITSDYAWNW
IRQPPGKGLEWIGYISYSGSTTYNPSLKSRVTMSRDTSKNQFSLKLSSVTAVDTAV
YYCATGYYYGSFWGQGTLVTVSS SEQ ID NO: 24-Signal sequence
MAWVWTLLFLMAAAQSIQA SEQ ID NO: 25-CD8a-hinge
TSTPAPRPPTPAPTIASQPLSLRPEACRPAAGGAVHTRGLDFACD SEQ ID NO: 26-CD8a-TM
IYIWAPLAGTCGVLLLSLVITLYC

SEP ID NO: 27-CD137
KRGRKKLLYIFKQPFMRPVQTTQEEDGCSCRFPEEEEGGCEL

SEP ID NO: 28-CD3zeta
RVKFSRSADAPAYKQGQNQLYNELNLGRREEYDVLDKRRGRDPEMGGKPRRKN
PQEGLYNELQKDKMAEAYSEIGMKGERRRGKGHDGLYQGLSTATKDTYDALHM
QALPPR SEQ ID NO: 29-Extracellular antigen-binding domain 1 (HL_HCG5_LCD6_20AA)
QVQLQESGPGLVKPSDTLSLTCAVSGNSITSDYAWNWIRQFPGKGLEWMGYISYS
GSTTYNPSLKSRVTISRDTSKNQFSLKLSSVTPVDTAVYYCATGYYYGSFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTIQSVQAED
VSVYFCQQTRKVPYTFGQGTKLEIK SEQ ID NO: 30-Extracellular antigen-binding domain 2
(HL_HCG5_LCHumanized_20AA)
QVQLQESGPGLVKPSDTLSLTCAVSGNSITSDYAWNWIRQFPGKGLEWMGYISYS
GSTTYNPSLKSRVTISRDTSKNQFSLKLSSVTPVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSLQAED
VAVYYCQQTRKVPYTFGQGTKLEIK SEQ ID NO: 31-Extracellular antigen-binding domain 3 (HL_HCF3_LCB7_20AA)
QVQLQESGPGLVKPSDTLSLTCAVSGNSITSDYAWNWIRQFPGKGLEWIGYISYSG
STTYNPSLKSRVTISRDTSKNQFSLKLSSVTPVDTAVYYCATGYYYGSGFWGQGT
LVTVSSGGSEGKSSGSGSESKSTGGSDIVLTQSPDSLAVSLGERATINCKASESVEY
FGTSLMHWYQQKPGQPPKLLIYAASNRESGVPDRFSGSGSGTDFTLTISSVQAEDV
AVYYCQQTRKVPYTFGQGTKLEIK SEQ ID NO: 32-Extracellular antigen-binding domain 4 (HL_HCG5_LCB7_20AA)
QVQLQESGPGLVKPSDTLSLTCAVSGNSITSDYAWNWIRQFPGKGLEWMGYISYS
GSTTYNPSLKSRVTISRDTSKNQFSLKLSSVTPVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSVQAED
VAVYYCQQTRKVPYTFGQGTKLEIK SEQ ID NO: 33-Extracellular antigen-binding domain 5 (LH_LCD6_HCG5_20AA)
DIVLTQSPDSLAVSLGERATINCKASESVEYFGTSLMHWYQQKPGQPPKLLIYAAS
NRESGVPDRFSGSGSGTDFTLTIQSVQAEDVSVYFCQQTRKVPYTFGQGTKLEIKG
GSEGKSSGSGSESKSTGGSQVQLQESGPGLVKPSDTLSLTCAVSGNSITSDYAWNW
IRQFPGKGLEWMGYISYSGSTTYNPSLKSRVTISRDTSKNQFSLKLSSVTPVDTAVY
YCATGYYYGSGFWGQGTLVTVSS SEQ ID NO: 34-Extracellular antigen-binding domain 6
(LH_LCHumanized_HCF3_20AA)
DIVLTQSPDSLAVSLGERATINCKASESVEYFGTSLMHWYQQKPGQPPKLLIYAAS
NRESGVPDRFSGSGSGTDFTLTISSLQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWIGYISYSGSTTYNPSLKSRVTISRDTSKNQFSLKLSSVTPVDTAVY
YCATGYYYGSGFWGQGTLVTVSS SEQ ID NO: 35-Extracellular antigen-binding domain 7
(LH_LCHumanized_HCG5_20AA)
DIVLTQSPDSLAVSLGERATINCKASESVEYFGTSLMHWYQQKPGQPPKLLIYAAS
NRESGVPDRFSGSGSGTDFTLTISSLQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWMGYISYSGSTTYNPSLKSRVTISRDTSKNQFSLKLSSVTPVDTAVY
YCATGYYYGSGFWGQGTLVTVSS SEQ ID NO: 36-Extracellular antigen-binding domain 8 (LH_LCB7_HCF3_20AA)
DIVLTQSPDSLAVSLGERATINCKASESVEYFGTSLMHWYQQKPGQPPKLLIYAAS
NRESGVPDRFSGSGSGTDFTLTISSVQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWIGYISYSGSTTYNPSLKSRVTISRDTSKNQFSLKLSSVTPVDTAVY
YCATGYYYGSGFWGQGTLVTVSS SEQ ID NO: 37-Extracellular antigen-binding domain 9 (LH_LCB7_HCG5_20AA)
DIVLTQSPDSLAVSLGERATINCKASESVEYFGTSLMHWYQQKPGQPPKLLIYAAS
NRESGVPDRFSGSGSGTDFTLTISSVQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWMGYISYSGSTTYNPSLKSRVTISRDTSKNQFSLKLSSVTPVDTAVY
YCATGYYYGSGFWGQGTLVTVSS SEQ ID NO: 38-Extracellular antigen-binding domain 10 (LH_LCD6_HCF3_20AA)
DIVLTQSPDSLAVSLGERATINCKASESVEYFGTSLMHWYQQKPGQPPKLLIYAAS
NRESGVPDRFSGSGSGTDFTLTIQSVQAEDVSVYFCQQTRKVPYTFGQGTKLEIKG
GSEGKSSGSGSESKSTGGSQVQLQESGPGLVKPSDTLSLTCAVSGNSITSDYAWNW
IRQFPGKGLEWIGYISYSGSTTYNPSLKSRVTISRDTSKNQFSLKLSSVTPVDTAVY
YCATGYYYGSGFWGQGTLVTVSS SEQ ID NO: 39-Extracellular antigen-binding domain 11
(HL_HCHumanized_LCB7_20AA)
QVQLQESGPGLVKPSDTLSLTCAVSGNSITSDYAWNWIRQPPGKGLEWIGYISYSG
STTYNPSLKSRVTMSRDTSKNQFSLKLSSVTAVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSVQAED
VAVYYCQQTRKVPYTFGQGTKLEIK SEQ ID NO: 40-Extracellular antigen-binding domain 12
(HL_HCHumanized_LCD6_20AA)
QVQLQESGPGLVKPSDTLSLTCAVSGNSITSDYAWNWIRQPPGKGLEWIGYISYSG
STTYNPSLKSRVTMSRDTSKNQFSLKLSSVTAVDTAVYYCATGYYYGSGFWGQG -continued TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTIQSVQAED
VSVYFCQQTRKVPYTFGQGTKLEIK SEQ ID NO: 41-Extracellular antigen-binding domain 13
(HL_HCHumanized_LCHumanized_20AA)
QVQLQESGPGLVKPSDTLSLTCAVSGNSITSDYAWNWIRQPPGKGLEWIGYISYSG
STTYNPSLKSRVTMSRDTSKNQFSLKLSSVTAVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSLQAED
VAVYYCQQTRKVPYTFGQGTKLEIK SEQ ID NO: 42-Extracellular antigen-binding domain 14
(LH_LCD6_HCHumanized_20AA)
DIVLTQSPDSLAVSLGERATINCKASESVEYFGTSLMHWYQQKPGQPPKLLIYAAS
NRESGVPDRFSGSGSGTDFTLTIQSVQAEDVSVYFCQQTRKVPYTFGQGTKLEIKG
GSEGKSSGSGSESKSTGGSQVQLQESGPGLVKPSDTLSLTCAVSGNSITSDYAWNW
IRQPPGKGLEWIGYISYSGSTTYNPSLKSRVTMSRDTSKNQFSLKLSSVTAVDTAV
YYCATGYYYGSGFWGQGTLVTVSS SEQ ID NO: 43-Extracellular antigen-binding domain 15
(LH_LCHumanized_HCHumanized_20AA)
DIVLTQSPDSLAVSLGERATINCKASESVEYFGTSLMHWYQQKPGQPPKLLIYAAS
NRESGVPDRFSGSGSGTDFTLTISSLQAEDVAVYYCQQTRKVPYTFGQGTKLEIKG
GSEGKSSGSGSESKSTGGSQVQLQESGPGLVKPSDTLSLTCAVSGNSITSDYAWNW
IRQPPGKGLEWIGYISYSGSTTYNPSLKSRVTMSRDTSKNQFSLKLSSVTAVDTAV
YYCATGYYYGSGFWGQGTLVTVSS SEQ ID NO: 44-Extracellular antigen-binding domain 16
(LH_LCB7_HCHumanized_20AA)
DIVLTQSPDSLAVSLGERATINCKASESVEYFGTSLMHWYQQKPGQPPKLLIYAAS
NRESGVPDRFSGSGSGTDFTLTISSVQAEDVAVYYCQQTRKVPYTFGQGTKLEIKG
GSEGKSSGSGSESKSTGGSQVQLQESGPGLVKPSDTLSLTCAVSGNSITSDYAWNW
IRQPPGKGLEWIGYISYSGSTTYNPSLKSRVTMSRDTSKNQFSLKLSSVTAVDTAV
YYCATGYYYGSGFWGQGTLVTVSS SEQ ID NO: 45-Intracellular signaling domain
KRGRKKLLYIFKQPFMRPVQTTQEEDGCSCRFPEEEEGGCELRVKFSRSADAPAYK
QGQNQLYNELNLGRREEYDVLDKRRGRDPEMGGKPRRKNPQEGLYNELNLQKDKM
AEAYSEIGMKGERRRGKGHDGLYQGLSTATKDTYDALHMQALPPR SEQ ID NO: 46-CAR 1 (HL_HCG5_LCD6_20AA; pDR000083431)
QVQLQESGPGLVKPSDTLSLTCAVSGNSITSDYAWNWIRQFPGKGLEWMGYISYS
GSTTYNPSLKSRVTISRDTSKNQFSLKLSSVTPVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTIQSVQAED
VSVYFCQQTRKVPYTFGQGTKLEIKTSTPAPRPPTPAPTIASQPLSLRPEACRPAAG
GAVHTRGLDFACDIYIWAPLAGTCGVLLLSLVITLYCKRGRKKLLYIFKQPFMRPV
QTTQEEDGCSCRFPEEEEGGCELRVKFSRSADAPAYKQGQNQLYNELNLGRREEY
DVLDKRRGRDPEMGGKPRRKNPQEGLYNELQKDKMAEAYSEIGMKGERRRGKG
HDGLYQGLSTATKDTYDALHMQALPPR SEQ ID NO: 47-CAR 2 (HL_HCG5_LCHumanized_20AA; pDR000083432)
QVQLQESGPGLVKPSDTLSLTCAVSGNSITSDYAWNWIRQFPGKGLEWMGYISYS
GSTTYNPSLKSRVTISRDTSKNQFSLKLSSVTPVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSLQAED
VAVYYCQQTRKVPYTFGQGTKLEIKTSTPAPRPPTPAPTIASQPLSLRPEACRPAAG
GAVHTRGLDFACDIYIWAPLAGTCGVLLLSLVITLYCKRGRKKLLYIFKQPFMRPV
QTTQEEDGCSCRFPEEEEGGCELRVKFSRSADAPAYKQGQNQLYNELNLGRREEY
DVLDKRRGRDPEMGGKPRRKNPQEGLYNELQKDKMAEAYSEIGMKGERRRGKG
HDGLYQGLSTATKDTYDALHMQALPPR SEQ ID NO: 48-CAR 3 (HL_HCF3_LCB7_20AA; pDR000083436)
QVQLQESGPGLVKPSDTLSLTCAVSGNSITSDYAWNWIRQFPGKGLEWIGYISYSG
STTYNPSLKSRVTISRDTSKNQFSLKLSSVTPVDTAVYYCATGYYYGSGFWGQGT
LVTVSSGGSEGKSSGSGSESKSTGGSDIVLTQSPDSLAVSLGERATINCKASESVEY
FGTSLMHWYQQKPGQPPKLLIYAASNRESGVPDRFSGSGSGTDFTLTISSVQAEDV
AVYYCQQTRKVPYTFGQGTKLEIKTSTPAPRPPTPAPTIASQPLSLRPEACRPAAGG
AVHTRGLDFACDIYIWAPLAGTCGVLLLSLVITLYCKRGRKKLLYIFKQPFMRPVQ
TTQEEDGCSCRFPEEEEGGCELRVKFSRSADAPAYKQGQNQLYNELNLGRREEYD
VLDKRRGRDPEMGGKPRRKNPQEGLYNELQKDKMAEAYSEIGMKGERRRGKGH
DGLYQGLSTATKDTYDALHMQALPPR SEQ ID NO: 49-CAR 4 (HL_HCG5_LCB7_20AA; DDR000083437)
QVQLQESGPGLVKPSDTLSLTCAVSGNSITSDYAWNWIRQFPGKGLEWMGYISYS
GSTTYNPSLKSRVTISRDTSKNQFSLKLSSVTPVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSVQAED

```
VAVYYCQQTRKVPYTFGQGTKLEIKTSTPAPRPPTPAPTIASQPLSLRPEACRPAAG
GAVHTRGLDFACDIYIWAPLAGTCGVLLLSLVITLYCKRGRKKLLYIFKQPFMRPV
QTTQEEDGCSCRFPEEEEGGCELRVKFSRSADAPAYKQGQNQLYNELNLGRREEY
DVLDKRRGRDPEMGGKPRRKNPQEGLYNELQKDKMAEAYSEIGMKGERRRGKG
HDGLYQGLSTATKDTYDALHMQALPPR

SEQ ID NO: 50-CAR 5 (LH_LCD6_HCG5_20AA; pDR000083438)
DIVLTQSPDSLAVSLGERATINCKASESVEYFGTSLMHWYQQKPGQPPKLLIYAAS
NRESGVPDRFSGSGSGTDFTLTIQSVQAEDVSVYFCQQTRKVPYTFGQGTKLEIKG
GSEGKSSGSGSESKSTGGSQVQLQESGPGLVKPSDTLSLTCAVSGNSITSDYAWNW
IRQFPGKGLEWMGYISYSGSTTYNPSLKSRVTISRDTSKNQFSLKLSSVTPVDTAVY
YCATGYYYGSGFWGQGTLVTVSSTSTPAPRPPTPAPTIASQPLSLRPEACRPAAGG
AVHTRGLDFACDIYIWAPLAGTCGVLLLSLVITLYCKRGRKKLLYIFKQPFMRPVQ
TTQEEDGCSCRFPEEEEGGCELRVKFSRSADAPAYKQGQNQLYNELNLGRREEYD
VLDKRRGRDPEMGGKPRRKNPQEGLYNELQKDKMAEAYSEIGMKGERRRGKGH
DGLYQGLSTATKDTYDALHMQALPPR

SEQ ID NO: 51-CAR 6 (LH_LCHumanized_HCF3_20AA; DDR000083440)
DIVLTQSPDSLAVSLGERATINCKASESVEYFGTSLMHWYQQKPGQPPKLLIYAAS
NRESGVPDRFSGSGSGTDFTLTISSLQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWIGYISYSGSTTYNPSLKSRVTISRDTSKNQFSLKLSSVTPVDTAVY
YCATGYYYGSGFWGQGTLVTVSSTSTPAPRPPTPAPTIASQPLSLRPEACRPAAGG
AVHTRGLDFACDIYIWAPLAGTCGVLLLSLVITLYCKRGRKKLLYIFKQPFMRPVQ
TTQEEDGCSCRFPEEEEGGCELRVKFSRSADAPAYKQGQNQLYNELNLGRREEYD
VLDKRRGRDPEMGGKPRRKNPQEGLYNELQKDKMAEAYSEIGMKGERRRGKGH
DGLYQGLSTATKDTYDALHMQALPPR SEQ ID NO: 52-CAR 7 (LH_LCHumanized_HCG5_20AA; DDR000083441)
DIVLTQSPDSLAVSLGERATINCKASESVEYFGTSLMHWYQQKPGQPPKLLIYAAS
NRESGVPDRFSGSGSGTDFTLTISSLQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWMGYISYSGSTTYNPSLKSRVTISRDTSKNQFSLKLSSVTPVDTAVY
YCATGYYYGSGFWGQGTLVTVSSTSTPAPRPPTPAPTIASQPLSLRPEACRPAAGG
AVHTRGLDFACDIYIWAPLAGTCGVLLLSLVITLYCKRGRKKLLYIFKQPFMRPVQ
TTQEEDGCSCRFPEEEEGGCELRVKFSRSADAPAYKQGQNQLYNELNLGRREEYD
VLDKRRGRDPEMGGKPRRKNPQEGLYNELQKDKMAEAYSEIGMKGERRRGKGH
DGLYQGLSTATKDTYDALHMQALPPR SEQ ID NO: 53-CAR 8 (LH_LCB7_HCF3_20AA; pDR000083443)
DIVLTQSPDSLAVSLGERATINCKASESVEYFGTSLMHWYQQKPGQPPKLLIYAAS
NRESGVPDRFSGSGSGTDFTLTISSVQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWIGYISYSGSTTYNPSLKSRVTISRDTSKNQFSLKLSSVTPVDTAVY
YCATGYYYGSGFWGQGTLVTVSSTSTPAPRPPTPAPTIASQPLSLRPEACRPAAGG
AVHTRGLDFACDIYIWAPLAGTCGVLLLSLVITLYCKRGRKKLLYIFKQPFMRPVQ
TTQEEDGCSCRFPEEEEGGCELRVKFSRSADAPAYKQGQNQLYNELNLGRREEYD
VLDKRRGRDPEMGGKPRRKNPQEGLYNELQKDKMAEAYSEIGMKGERRRGKGH
DGLYQGLSTATKDTYDALHMQALPPR SEQ ID NO: 54-CAR 9 (LH_LCB7_HCG5_20AA; DDR000083444)
DIVLTQSPDSLAVSLGERATINCKASESVEYFGTSLMHWYQQKPGQPPKLLIYAAS
NRESGVPDRFSGSGSGTDFTLTISSVQAEDVAVYYCQQTRKVPYTFGQGTKLEIKG
GSEGKSSGSGSESKSTGGSQVQLQESGPGLVKPSDTLSLTCAVSGNSITSDYAWNW
IRQFPGKGLEWMGYISYSGSTTYNPSLKSRVTISRDTSKNQFSLKLSSVTPVDTAVY
YCATGYYYGSGFWGQGTLVTVSSTSTPAPRPPTPAPTIASQPLSLRPEACRPAAGG
AVHTRGLDFACDIYIWAPLAGTCGVLLLSLVITLYCKRGRKKLLYIFKQPFMRPVQ
TTQEEDGCSCRFPEEEEGGCELRVKFSRSADAPAYKQGQNQLYNELNLGRREEYD
VLDKRRGRDPEMGGKPRRKNPQEGLYNELQKDKMAEAYSEIGMKGERRRGKGH
DGLYQGLSTATKDTYDALHMQALPPR SEQ ID NO: 55-CAR 10 (LH_LCD6_HCF3_20AA; pDR000083446)
DIVLTQSPDSLAVSLGERATINCKASESVEYFGTSLMHWYQQKPGQPPKLLIYAAS
NRESGVPDRFSGSGSGTDFTLTIQSVQAEDVSVYFCQQTRKVPYTFGQGTKLEIKG
GSEGKSSGSGSESKSTGGSQVQLQESGPGLVKPSDTLSLTCAVSGNSITSDYAWNW
IRQFPGKGLEWIGYISYSGSTTYNPSLKSRVTISRDTSKNQFSLKLSSVTPVDTAVY
YCATGYYYGSGFWGQGTLVTVSSTSTPAPRPPTPAPTIASQPLSLRPEACRPAAGG
AVHTRGLDFACDIYIWAPLAGTCGVLLLSLVITLYCKRGRKKLLYIFKQPFMRPVQ
TTQEEDGCSCRFPEEEEGGCELRVKFSRSADAPAYKQGQNQLYNELNLGRREEYD
VLDKRRGRDPEMGGKPRRKNPQEGLYNELQKDKMAEAYSEIGMKGERRRGKGH
DGLYQGLSTATKDTYDALHMQALPPR SEQ ID NO: 56-CAR 11 (HL_HCHumanized_LCB7_20AA; DDR000083433)
QVQLQESGPGLVKPSDTLSLTCAVSGNSITSDYAWNWIRQPPGKGLEWIGYISYSG
STTYNPSLKSRVTMSRDTSKNQFSLKLSSVTAVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSVQAED
VAVYYCQQTRKVPYTFGQGTKLEIKTSTPAPRPPTPAPTIASQPLSLRPEACRPAAG
GAVHTRGLDFACDIYIWAPLAGTCGVLLLSLVITLYCKRGRKKLLYIFKQPFMRPV
```

QTTQEEDGCSCRFPEEEEGGCELRVKFSRSADAPAYKQGQNQLYNELNLGRREEY
DVLDKRRGRDPEMGGKPRRKNPQEGLYNELQKDKMAEAYSEIGMKGERRRGKG
HDGLYQGLSTATKDTYDALHMQALPPR

SEQ ID NO: 57-CAR 12 (HL_HCHumanized_LCD6_20AA; DDR000083434)
QVQLQESGPGLVKPSDTLSLTCAVSGNSITSDYAWNWIRQPPGKGLEWIGYISYSG
STTYNPSLKSRVTMSRDTSKNQFSLKLSSVTAVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTIQSVQAED
VSVYFCQQTRKVPYTFGQGTKLEIKTSTPAPRPPTPAPTIASQPLSLRPEACRPAAG
GAVHTRGLDFACDIYIWAPLAGTCGVLLLSLVITLYCKRGRKKLLYIFKQPFMRPV
QTTQEEDGCSCRFPEEEEGGCELRVKFSRSADAPAYKQGQNQLYNELNLGRREEY
DVLDKRRGRDPEMGGKPRRKNPQEGLYNELQKDKMAEAYSEIGMKGERRRGKG
HDGLYQGLSTATKDTYDALHMQALPPR SEQ ID NO: 58-CAR 13 (HL_HCHumanized_LCHumanized_20AA;
pDR000083435)
QVQLQESGPGLVKPSDTLSLTCAVSGNSITSDYAWNWIRQPPGKGLEWIGYISYSG
STTYNPSLKSRVTMSRDTSKNQFSLKLSSVTAVDTAVYYCATGYYYGSGFWGQG
TLVTVSSGGSEGKSSGSGSESKSTGGSDIVLTQSPDSLAVSLGERATINCKASESVE
YFGTSLMHWYQQKPGQPPKLLIYAASNRESGVPDRFSGSGSGTDFTLTISSLQAED
VAVYYCQQTRKVPYTFGQGTKLEIKTSTPAPRPPTPAPTIASQPLSLRPEACRPAAG
GAVHTRGLDFACDIYIWAPLAGTCGVLLLSLVITLYCKRGRKKLLYIFKQPFMRPV
QTTQEEDGCSCRFPEEEEGGCELRVKFSRSADAPAYKQGQNQLYNELNLGRREEY
DVLDKRRGRDPEMGGKPRRKNPQEGLYNELQKDKMAEAYSEIGMKGERRRGKG
HDGLYQGLSTATKDTYDALHMQALPPR SEQ ID NO: 59-CAR 14 (LH_LCD6_HCHumanized_20AA; DDR000083439)
DIVLTQSPDSLAVSLGERATINCKASESVEYFGTSLMHWYQQKPGQPPKLLIYAAS
NRESGVPDRFSGSGSGTDFTLTIQSVQAEDVSVYFCQQTRKVPYTFGQGTKLEIKG
GSEGKSSGSGSESKSTGGSQVQLQESGPGLVKPSDTLSLTCAVSGNSITSDYAWNW
IRQPPGKGLEWIGYISYSGSTTYNPSLKSRVTMSRDTSKNQFSLKLSSVTAVDTAV
YYCATGYYYGSGFWGQGTLVTVSSTSTPAPRPPTPAPTIASQPLSLRPEACRPAAG
GAVHTRGLDFACDIYIWAPLAGTCGVLLLSLVITLYCKRGRKKLLYIFKQPFMRPV
QTTQEEDGCSCRFPEEEEGGCELRVKFSRSADAPAYKQGQNQLYNELNLGRREEY
DVLDKRRGRDPEMGGKPRRKNPQEGLYNELQKDKMAEAYSEIGMKGERRRGKG
HDGLYQGLSTATKDTYDALHMQALPPR SEQ ID NO: 60-CAR 15 (LH_LCHumanized_HCHumanized 20AA;
pDR000083442)
DIVLTQSPDSLAVSLGERATINCKASESVEYFGTSLMHWYQQKPGQPPKLLIYAAS
NRESGVPDRFSGSGSGTDFTLTISSLQAEDVAVYYCQQTRKVPYTFGQGTKLEIKG
GSEGKSSGSGSESKSTGGSQVQLQESGPGLVKPSDTLSLTCAVSGNSITSDYAWNW
IRQPPGKGLEWIGYISYSGSTTYNPSLKSRVTMSRDTSKNQFSLKLSSVTAVDTAV
YYCATGYYYGSGFWGQGTLVTVSSTSTPAPRPPTPAPTIASQPLSLRPEACRPAAG
GAVHTRGLDFACDIYIWAPLAGTCGVLLLSLVITLYCKRGRKKLLYIFKQPFMRPV
QTTQEEDGCSCRFPEEEEGGCELRVKFSRSADAPAYKQGQNQLYNELNLGRREEY
DVLDKRRGRDPEMGGKPRRKNPQEGLYNELQKDKMAEAYSEIGMKGERRRGKG
HDGLYQGLSTATKDTYDALHMQALPPR SEQ ID NO: 61-CAR 16 (LH_LCB7_HCHumanized_20AA; DDR000083445)
DIVLTQSPDSLAVSLGERATINCKASESVEYFGTSLMHWYQQKPGQPPKLLIYAAS
NRESGVPDRFSGSGSGTDFTLTISSVQAEDVAVYYCQQTRKVPYTFGQGTKLEIKG
GSEGKSSGSGSESKSTGGSQVQLQESGPGLVKPSDTLSLTCAVSGNSITSDYAWNW
IRQPPGKGLEWIGYISYSGSTTYNPSLKSRVTMSRDTSKNQFSLKLSSVTAVDTAV
YYCATGYYYGSGFWGQGTLVTVSSTSTPAPRPPTPAPTIASQPLSLRPEACRPAAG
GAVHTRGLDFACDIYIWAPLAGTCGVLLLSLVITLYCKRGRKKLLYIFKQPFMRPV
QTTQEEDGCSCRFPEEEEGGCELRVKFSRSADAPAYKQGQNQLYNELNLGRREEY
DVLDKRRGRDPEMGGKPRRKNPQEGLYNELQKDKMAEAYSEIGMKGERRRGKG
HDGLYQGLSTATKDTYDALHMQALPPR SEQ ID NO: 62-human Kallikrein-2 sequence (signal sequence: amino acids 1-18)
MWDLVLSIALSVGCTGAVPLIQSRIVGGWECEKHSQPWQVAVYSHGWAHCGGV
LVHPQWVLTAAHCLKKNSQVWLGRHNLFEPEDTGQRVPVSHSFPHPLYNMSLLK
HQSLRPDEDSSHDLMLLRLSEPAKITDVVKVLGLPTQEPALGTTCYASGWGSIEPE
EFLRPRSLQCVSLHLLSNDMCARAYSEKVTEFMLCAGLWTGGKDTCGGDSGGPL
VCNGVLQGITSWGPEPCALPEKPAVYTKVVHYRKWIKDTIAANP SEQ ID NO: 63-heavy chain CDR1 sequence
SDYAWN SEQ ID NO: 64-heavy chain CDR2 sequence
YISYSGSTTYSPSLKS SEQ ID NO: 65-heavy chain CDR2 sequence
YISYSGSTTYNPSLKS SEQ ID NO: 66-heavy chain CDR3 sequence
GYYYGSGF SEQ ID NO: 67-light chain CDR1 sequence
RASESVEYFGTSLMH SEQ ID NO: 68-light chain CDR1 sequence
KASESVEYFGTSLMH SEQ ID NO: 69-light chain CDR2 sequence
AASNVES SEQ ID NO: 70-light chain CDR2 sequence
AASNRES SEQ ID NO: 71-light chain CDR3 sequence
QQTRKVPYT SEQ ID NO: 72-heavy chain CDR1 sequence
GNSITSDYAWN SEQ ID NO: 73-heavy chain CDR1 sequence
YISYSGSTT SEQ ID NO: 74-VL 4 (KL2B413)
EIVLTQSPSFLSASVGDRVTITCRASQGISSYLSWYQQKPGKAPKLLIYATSTLQSG
VPSRFSGSGSGTEFTLTISSLQPEDFATYYCQQLNSYPRTFGQGTKVEIK SEQ ID NO: 75-VL 5 (KL2B359)
EIVLTQSPATLSLSPGERATLSCRASESVEYFGTSLMHWYQQKPGQPPRLLIYAASN
VESGIPARFSGSGSGTDFTLTISSVEPEDFAVYFCQQTRKVPYTFGGGTKVEIK SEQ ID NO: 76-VH 4 (KL2B413)
EVQLVESGGGLVQPGGSLRLSCAASGFTFSSYWMTWVRQAPGKGLEWVANIKQD
GSERYYVDSVKGRFTISRDNAKNSLYLQMNSLRAEDTAVYYCARDQNYDILTGH
YGMDVWGQGTTVTVSS SEQ ID NO: 77-VH 5 (KL2B359)
QVQLQESGPGLVKPSQTLSLTCTVSGNSITSDYAWNWIRQFPGKRLEWIGYISYSG
STTYNPSLKSRVTISRDTSKNQFSLKLSSVTAADTAVYYCATGYYYGSGFWGQGT
LVTVSS SEQ ID NO: 78-Extracellular antigen-binding domain 17 (KL2B413_HL)
EVQLVESGGGLVQPGGSLRLSCAASGFTFSSYWMTWVRQAPGKGLEWVANIKQD
GSERYYVDSVKGRFTISRDNAKNSLYLQMNSLRAEDTAVYYCARDQNYDILTGH
YGMDVWGQGTTVTVSSGGSEGKSSGSGSESKSTGGSEIVLTQSPSFLSASVGDRVT
ITCRASQGISSYLSWYQQKPGKAPKLLIYATSTLQSGVPSRFSGSGSGTEFTLTISSL
QPEDFATYYCQQLNSYPRTFGQGTKVEIK SEQ ID NO: 79-Extracellular antigen-binding domain 18 (KL2B413_LH)
EIVLTQSPSFLSASVGDRVTITCRASQGISSYLSWYQQKPGKAPKLLIYATSTLQSG
VPSRFSGSGSGTEFTLTISSLQPEDFATYYCQQLNSYPRTFGQGTKVEIKGGSEGKS
SGSGSESKSTGGSEVQLVESGGGLVQPGGSLRLSCAASGFTFSSYWMTWVRQAPG
KGLEWVANIKQDGSERYYVDSVKGRFTISRDNAKNSLYLQMNSLRAEDTAVYYC
ARDQNYDILTGHYGMDVWGQGTTVTVSS SEQ ID NO: 80-Extracellular antigen-binding domain 19 (KL2B359-HL)
QVQLQESGPGLVKPSQTLSLTCTVSGNSITSDYAWNWIRQFPGKRLEWIGYISYSG
STTYNPSLKSRVTISRDTSKNQFSLKLSSVTAADTAVYYCATGYYYGSGFWGQGT
LVTVSSGGSEGKSSGSGSESKSTGGSEIVLTQSPATLSLSPGERATLSCRASESVEYF
GTSLMHWYQQKPGQPPRLLIYAASNVESGIPARFSGSGSGTDFTLTISSVEPEDFAV
YFCQQTRKVPYTFGGGTKVEIK SEQ ID NO: 81-Extracellular antigen-binding domain 20 (KL2B359-LH)
EIVLTQSPATLSLSPGERATLSCRASESVEYFGTSLMHWYQQKPGQPPRLLIYAAS
NVESGIPARFSGSGSGTDFTLTISSVEPEDFAVYFCQQTRKVPYTFGGGTKVEIKGG
SEGKSSGSGSESKSTGGSQVQLQESGPGLVKPSQTLSLTCTVSGNSITSDYAWNWI
RQFPGKRLEWIGYISYSGSTTYNPSLKSRVTISRDTSKNQFSLKLSSVTAADTAVY
YCATGYYYGSGFWGQGTLVTVSS SEQ ID NO: 82-CAR 17 (KL2B413_HL; dBD000091628)
EVQLVESGGGLVQPGGSLRLSCAASGFTFSSYWMTWVRQAPGKGLEWVANIKQD
GSERYYVDSVKGRFTISRDNAKNSLYLQMNSLRAEDTAVYYCARDQNYDILTGH
YGMDVWGQGTTVTVSSGGSEGKSSGSGSESKSTGGSEIVLTQSPSFLSASVGDRVT
ITCRASQGISSYLSWYQQKPGKAPKLLIYATSTLQSGVPSRFSGSGSGTEFTLTISSL
QPEDFATYYCQQLNSYPRTFGQGTKVEIKTSPAPRPPTPAPTIASQPLSLRPEACRP
AAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYKQGQNQLYNELNLGR
REEYDVLDKRRGRDPEMGGKPRRKNPQEGLYNELQKDKMAEAYSEIGMKGERR
RGKGHDGLYQGLSTATKDTYDALHMQALPPR SEQ ID NO: 83-CAR 18 (KL2B413_LH; pBD000091623)
EIVLTQSPSFLSASVGDRVTITCRASQGISSYLSWYQQKPGKAPKLLIYATSTLQSG
VPSRFSGSGSGTEFTLTISSLQPEDFATYYCQQLNSYPRTFGQGTKVEIKGGSEGKS
SGSGSESKSTGGSEVQLVESGGGLVQPGGSLRLSCAASGFTFSSYWMTWVRQAPG
KGLEWVANIKQDGSERYYVDSVKGRFTISRDNAKNSLYLQMNSLRAEDTAVYYC
ARDQNYDILTGHYGMDVWGQGTTVTVSSTSTPAPRPPTPAPTIASQPLSLRPEACR
PAAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYKQGQNQLYNELNLGR
REEYDVLDKRRGRDPEMGGKPRRKNPQEGLYNELQKDKMAEAYSEIGMKGERR
RGKGHDGLYQGLSTATKDTYDALHMQALPPR SEQ ID NO: 84-CAR 19 (KL2B359-HL; dBD000091576)
QVQLQESGPGLVKPSQTLSLTCTVSGNSITSDYAWNWIRQFPGKRLEWIGYISYSG
STTYNPSLKSRVTISRDTSKNQFSLKLSSVTAADTAVYYCATGYYYGSGFWGQGT
LVTVSSGGSEGKSSGSGSESKSTGGSEIVLTQSPATLSLSPGERATLSCRASESVEYF
GTSLMHWYQQKPGQPPRLLIYAASNVESGIPARFSGSGSGTDFTLTISSVEPEDFAV
YFCQQTRKVPYTFGGGTKVEIKTSTPAPRPPTPAPTIASQPLSLRPEACRPAAGGAV
HTRGLDFACDIYIWAPLAGTCGVLLLSLVITLYCKRGRKKLLYIFKQPFMRPVQTT
QEEDGCSCRFPEEEEGGCELRVKFSRSADAPAYKQGQNQLYNELNLGRREEYDVL
DKRRGRDPEMGGKPRRKNPQEGLYNELQKDKMAEAYSEIGMKGERRRGKGHDG
LYQGLSTATKDTYDALHMQALPPR SEQ ID NO: 85-CAR 20 (KL2B359-LH; pBD000091577)
EIVLTQSPATLSLSPGERATLSCRASESVEYFGTSLMHWYQQKPGQPPRLLIYAASN
VESGIPARFSGSGSGTDFTLTISSVEPEDFAVYFCQQTRKVPYTFGGGTKVEIKGGS
EGKSSGSGSESKSTGGSQVQLQESGPGLVKPSQTLSLTCTVSGNSITSDYAWNWIR
QFPGKRLEWIGYISYSGSTTYNPSLKSRVTISRDTSKNQFSLKLSSVTAADTAVYYC
ATGYYYGSGFWGQGTLVTVSSTSTPAPRPPTPAPTIASQPLSLRPEACRPAAGGAV
HTRGLDFACDIYIWAPLAGTCGVLLLSLVITLYCKRGRKKLLYIFKQPFMRPVQTT
QEEDGCSCRFPEEEEGGCELRVKFSRSADAPAYKQGQNQLYNELNLGRREEYDVL
DKRRGRDPEMGGKPRRKNPQEGLYNELQKDKMAEAYSEIGMKGERRRGKGHDG
LYQGLSTATKDTYDALHMQALPPR SEQ ID NO: 86-heavy chain CDR1 sequence
GFTFSSYW SEQ ID NO: 87-heavy chain CDR2 sequence
IKQDGSER SEQ ID NO: 88-heavy chain CDR3 sequence
ARDQNYDILTGHYGMDV SEQ ID NO: 89-light chain CDR1 sequence
QGISSY SEQ ID NO: 90-light chain CDR2 sequence
ATS SEQ ID NO: 91-light chain CDR3 sequence
QQLNSYPRT SEQ ID NO: 92-heavy chain CDR1 sequence
GNSITSDYA SEQ ID NO: 93-heavy chain CDR2 sequence
ISYSGST SEQ ID NO: 94-heavy chain CDR3 sequence
ATGYYYGSGF SEQ ID NO: 95-light chain CDR1 sequence
ESVEYFGTSL SEQ ID NO: 96-light chain CDR2 sequence
AAS SEQ ID NO: 97-light chain CDR3 sequence
GGNNIGSKSVH SEQ ID NO: 98-Linker sequence
GTSGSSGSGSGGSGSGGG SEQ ID NO: 99-Linker sequence
GKPGSGKPGSGKPGSGKPGS SEQ ID NO: 100-heavy chain CDR2 sequence
YISYSGSTTYNPSLKS -continued SEQ ID NO: 101-heavy chain CDR1 sequence
GNSITSDYAWN SEQ ID NO: 102-heavy chain CDR1 sequence
SYYWS SEQ ID NO: 103-heavy chain CDR2 sequence
YIYYSGSTNYNPSLKS SEQ ID NO: 104-heavy chain CDR3 sequence
TTIFGVVTPNFYYGMDV SEQ ID NO: 105-heavy chain CDR1 sequence
GGSISSYYWS SEQ ID NO: 106-heavy chain CDR2 sequence
YIYYSGSTN SEQ ID NO: 107-heavy chain CDR1 sequence
SYDIH SEQ ID NO: 108-heavy chain CDR2 sequence
IISYDGSKKDYTDSVKG SEQ ID NO: 109-heavy chain CDR3 sequence
ESGWSHYYYYGMDV SEQ ID NO: 110-heavy chain CDR1 sequence
GFTFSSYDIH SEQ ID NO: 111-heavy chain CDR2 sequence
IISYDGSKKD SEQ ID NO: 112-heavy chain CDR2 sequence
RLYVSGFTNYNPSLKS SEQ ID NO: 113-heavy chain CDR3 sequence
DSGNYWGWFDP SEQ ID NO: 114-heavy chain CDR2 sequence
RLYVSGFTN SEQ ID NO: 115-heavy chain CDR1 sequence
YYGMH SEQ ID NO: 116-heavy chain CDR2 sequence
FISYDGSNKYYADSVKG SEQ ID NO: 117-heavy chain CDR3 sequence
LPYSGSYWAFDY SEQ ID NO: 118-heavy chain CDR1 sequence
GFTFSYY SEQ ID NO: 119-heavy chain CDR2 sequence
FISYDGSNKY SEQ ID NO: 120-heavy chain CDR1 sequence
HYAMS SEQ ID NO: 121-heavy chain CDR2 sequence
TIGGSGGSTYYADSVKG SEQ ID NO: 122-heavy chain CDR3 sequence
PHIVMVTALLYDGMDV SEQ ID NO: 123-heavy chain CDR1 sequence
GFTFSHYAMS SEQ ID NO: 124-heavy chain CDR3 sequence
TIGGSGGSTYY SEQ ID NO: 125-light chain CDR1 sequence
RASQDISNYLA SEQ ID NO: 126-light chain CDR2 sequence
AASNVES SEQ ID NO: 127-light chain CDR3 sequence
DDSDRPS SEQ ID NO: 128-light chain CDR1 sequence
RASQGISSYLA SEQ ID NO: 129-light chain CDR2 sequence
AASTLQS SEQ ID NO: 130-light chain CDR3 sequence
QQLNSYPLT SEQ ID NO: 131-light chain CDR2 sequence
AASTLHS SEQ ID NO: 132-light chain CDR3 sequence
QKYNSAPYT SEQ ID NO: 133-light chain CDR1 sequence
SGDQLGENYAC SEQ ID NO: 134-light chain CDR2 sequence
QDSKRPS SEQ ID NO: 135-light chain CDR3 sequence
QAWDNSIVV SEQ ID NO: 136-light chain CDR1 sequence
GGDNIGSKSVH SEQ ID NO: 137-light chain CDR2 sequence
DNSDRPS SEQ ID NO: 138-light chain CDR3 sequence
QVWDSSSDHPVV SEQ ID NO: 139-light chain CDR3 sequence
QVWDSSSDHVV SEQ ID NO: 140-VH (KL2B357, KL2B357 and KL2B360))
QVQLQESGPGLVKPSQTLSLTCTVSGNSITSDYAWNWIRQFPGKGLEWIGYISYSG
STTYNPSLKSRVTISRDTSKNQFSLKLSSVTAADTAVYYCATGYYYGSGFWGQGT
LVTVSS SEQ ID NO: 142-VH (KL2B30)
QVQLQESGPGLVKPSETLSLTCTVSGGSISSYYWSWIRQPPGKGLEWIGYIYYSGST
NYNPSLKSRVTISVDTSKNQFSLKLSSVTAADTAVYYCAGTTIFGVVTPNFYYGM
DVWGQGTTVTVSS SEQ ID NO: 143-VH (KL2B53)
EVQLVESGGGVVQPGRSLRLSCVASGFTFSSYDIHWVRQAPGKGLEWVAIISYDG
SKKDYTDSVKGRFTISRDNSKNTLYLQMDSLRVEDSAVYSCARESGWSHYYYYG
MDVWGQGTMVTVSS SEQ ID NO: 144-VH (KL2B242)
QVQLQESGPGLVKPSETLSLTCTVSGGSISSYYWSWLRQPAGSGLEWIGRLYVSGF
TNYNPSLKSRVTLSLDPSRNQLSLKLSSVTAADTAVYYCAGDSGNYWGWFDPWG
QGTLVTVSS SEQ ID NO: 145-VH (KL2B467)
QVQLVESGGGVVQPGRSLRLSCAASGFTFSYYGMHWVRQAPGKGLEWVAFISYD
GSNKYYADSVKGRFTISRDNSKNTLYLQMNSLRAEDTAVYYCAHLPYSGSYWAF
DYWGQGTQVTVSS SEQ ID NO: 146-VH (KL2B494)
QVQLVESGGGLVQPGGSLRLSCAASGFTFSHYAMSWVRQAPGKGLEWVSTIGGS
GGSTYYADSVKGRFTISRDNSKNTLYLQMNSLRAEDTAVYYCAKPHIVMVTALL
YDGMDVWGQGTMVTVSS SEQ ID NO: 147-VL (KL2B357)
DIVLTQSPDSLAVSLGERATINCRASESVEYFGTSLMHWYQQKPGQPPKLLIYAAS
NVESGVPDRFSGSGSGTDFTLTISSLQAEDVAVYFCQQTRKVPYTFGGGTKVEIK SEQ ID NO: 148-VL (KL2B30)
DIQMTQSPSFLSASVGDRVTITCRASQGISSYLAWYQQKPGKAPKFLIYAASTLQS
GVPSRFSGSGSGTEFTLTISSLQPEDFATYYCQQLNSYPLTFGGGTKVEIK SEQ ID NO: 149-VL (KL2B53)
DIVMTQSPSSLSASVGDRVTITCRASQDISNYLAWYQQKPGKVPKFLIYAASTLHS
GVPSRFSGSGSGTDFTLTISSLQPEDVATYYCQKYNSAPYTFGQGTRLEIK SEQ ID NO: 150-VL (KL2B242)
SYELTQPPSVSVSPGETASITCSGDQLGENYACWYQQKPGQSPVLVIYQDSKRPSGI
PERFSGSNSGNTATLTISGTQALDEADYYCQAWDNSIVVFGGGTKLTVL SEQ ID NO: 151-VL (KL2B467)
QSVLTQPPSVSVAPGQTASITCGGDNIGSKSVHWYQQKPGQAPVLVVYDNSDRPS
GIPERFSGSNSGTTATLTISRVEAGDEADYYCQVWDSSSDHPVVFGGGTKVTV SEQ ID NO: 152-VL (KL2B494)
SSELTQPPSVSVAPGQTARITCGGNNIGSKSVHWYQQKPGQAPVLVVYDDSDRPS
GIPERFSGSNSGNTATLTISRVEAGDEADYYCQVWDSSSDHVVFGGGTKLTVL SEQ ID NO: 153-VH (KL2B357)
CAGGTTCAGCTGCAAGAGTCTGGACCAGGCCTGGTCAAGCCCTCTCAGACCCT
GTCTCTGACCTGTACCGTGTCCGGCAACTCCATCACCTCTGACTACGCCTGGAA
CTGGATTCGGCAGTTCCCTGGCAAGGGCCTTGAGTGGATCGGCTACATCTCCT
ACTCCGGTTCCACCACCTACAACCCCAGCCTGAAGTCCCGGGTCACCATCTCCC
GCGACACCTCCAAGAACCAGTTCTCCCTGAAGCTGTCCTCCGTGACCGCTGCT
GATACCGCCGTGTACTACTGTGCCACCGGCTACTACTACGGCTCCGGCTTTTGG
GGACAGGGCACACTGGTTACCGTGTCTAGT SEQ ID NO: 154-VH (KL2B358)
CAGGTTCAGCTGCAAGAGTCTGGACCAGGCCTGGTCAAGCCCTCTCAGACCCT
GTCTCTGACCTGTACCGTGTCCGGCAACTCCATCACCTCTGACTACGCCTGGAA
CTGGATTCGGCAGCCACCTGGCAAGGGCCTTGAGTGGATCGGCTACATCTCCT
ACTCCGGTTCCACCACCTACAACCCCAGCCTGAAGTCCCGGGTCACCATCTCCC
GCGACACCTCCAAGAACCAGTTCTCCCTGAAGCTGTCCTCCGTGACCGCTGCT
GATACCGCCGTGTACTACTGTGCCACCGGCTACTACTACGGCTCCGGCTTTTGG
GGACAGGGCACACTGGTTACCGTGTCTAGT SEQ ID NO: 155-VH (KL2B360)
CAGGTTCAGCTGCAAGAGTCTGGACCAGGCCTGGTCAAGCCCTCTCAGACCCT
GTCTCTGACCTGTACCGTGTCCGGCAACTCCATCACCTCTGACTACGCCTGGAA
CTGGATTCGGCAGTTCCCTGGCAAGGGCCTTGAGTGGATCGGCTACATCTCCT
ACTCCGGTTCCACCACCTACAACCCCAGCCTGAAGTCCCGGGTCACCATCTCCC
GCGACACCTCCAAGAACCAGTTCTCCCTGAAGCTGTCCTCCGTGACCGCTGCT
GATACCGCCGTGTACTACTGTGCCACCGGCTACTACTACGGCTCCGGCTTTTGG
GGACAGGGCACACTGGTTACCGTGTCTAGT SEQ ID NO: 156-VH (KL2B30)
CAGGTGCAGCTGCAGGAGTCGGGCCCAGGACTGGTGAAGCCTTCGGAGACCCT
GTCCCTCACCTGCACTGTCTCTGGTGGCTCCATCAGTAGTTACTACTGGAGCTG
GATCCGGCAGCCCCCAGGGAAGGGACTGGAGTGGATTGGATATATCTATTACA
GTGGGAGCACCAACTACAACCCCTCCCTCAAGAGTCGAGTCACCATATCAGTA
GACACGTCCAAGAACCAGTTCTCCCTGAAGCTGAGCTCTGTGACCGCTGCGGA
CACGGCCGTGTATTACTGTGCGGGACTACGATTTTTGGAGTGGTTACCCCCA
ACTTCTACTACGGTATGGACGTCTGGGGCCAAGGGACCACGGTCACCGTCTCC
TCA SEQ ID NO: 157-VH (KL2B53)
GAGGTGCAGCTGGTGGAGTCTGGGGGAGGCGTGGTCCAGCCTGGGAGGTCCCT
GAGACTCTCCTGTGTAGCCTCTGGATTCACCTTCAGTAGTTATGACATACACTG
GGTCCGCCAGGCTCCAGGCAAGGGGCTGGAGTGGGTGGCAATTATTTCATATG
ATGGAAGTAAAAAAGACTATACAGACTCCGTGAAGGGCCGATTCACCATCTCC
AGAGACAATTCCAAGAACACGCTGTATCTGCAAATGGACAGCCTGAGAGTTGA
GGACTCGGCTGTGTATTCCTGTGCGAGAGAAAGTGGCTGGTCCCACTACTACT
ATTACGGTATGGACGTCTGGGGCCAAGGGACAATGGTCACCGTCTCTTCA SEQ ID NO: 158-VH (KL2B242)
CAGGTGCAGCTGCAGGAGTCGGGCCCAGGACTGGTGAAGCCTTCGGAGACCCT
GTCCCTCACCTGCACTGTCTCTGGTGGCTCCATCAGTAGTTACTATTGGAGCTG
GCTCCGGCAGCCCGCCGGGTCGGGACTGGAGTGGATTGGGCGTTTATATGTCA
GTGGGTTCACCAACTACAACCCCTCCCTCAAGAGTCGAGTCACCTTGTCACTA
GACCCGTCCAGGAACCAGTTGTCCCTGAAACTGAGTTCTGTGACCGCCGCGGA
CACGGCCGTATATTATTGTGCGGGAGATAGTGGGAACTACTGGGGTTGGTTCG
ACCCCTGGGGCCAGGGAACCCTGGTCACCGTCTCCTCA SEQ ID NO: 159-VH (KL2B467)
CAGGTGCAGCTGGTGGAGTCTGGGGGAGGCGTGGTCCAGCCTGGGAGGTCCCT
GAGACTCTCCTGTGCAGCCTCTGGATTCACCTTCAGTTACTATGGCATGCACTG
GGTCCGCCAGGCTCCAGGCAAGGGGCTGGAGTGGGTGGCATTTATATCATATG
ATGGAAGTAATAAATACTATGCAGACTCCGTGAAGGGCCGATTCACCATCTCC
AGAGACAATTCCAAGAACACGCTGTATCTGCAAATGAACAGCCTGAGAGCTG
AGGACACGGCTGTGTATTACTGTGCCCACCTCCCTTATAGTGGGAGCTACTGG
GCCTTTGACTACTGGGGCCAGGGAACCCAGGTCACCGTCTCTTCA SEQ ID NO: 160-VH (KL2B494)
CAGGTGCAGCTGGTGGAGTCTGGGGGAGGCTTGGTACAGCCTGGGGGGTCCCT
GAGACTCTCCTGTGCAGCCTCTGGATTCACCTTTAGTCATTATGCCATGAGCTG
GGTCCGCCAGGCTCCAGGGAAGGGGCTGGAGTGGGTCTCAACTATTGGTGGTA
GTGGTGGTAGCACATACTACGCAGACTCCGTGAAGGGCCGGTTCACCATCTCC
AGAGACAATTCCAAGAACACGCTGTATCTGCAAATGAACAGCCTGAGAGCCG
AGGACACGGCCGTATATTACTGTGCGAAACCTCATATTGTAATGGTGACTGCT
CTTCTCTACGACGGTATGGACGTCTGGGGCCAAGGGACAATGGTCACCGTCTC
CTCA SEQ ID NO: 161-VL (KL2B357)
GACATCGTGCTGACCCAGTCTCCAGACTCTCTGGCTGTGTCTCTGGGCGAGAG
AGCCACCATCAACTGCAGAGCCTCCGAGTCCGTGGAATACTTCGGCACCTCTC
TGATGCACTGGTACCAGCAGAAGCCCGGCCAGCCTCCTAAGCTGCTGATCTAC
GCCGCCTCCAACGTGGAATCTGGCGTGCCCGATAGATTTTCCGGCTCTGGCTCT
GGCACCGACTTTACCCTGACCATCAGCTCTCTGCAGGCCGAGGATGTGGCCGT
GTACTTCTGTCAGCAGACCCGGAAGGTGCCCTACACATTTGGCGGCGGAACAA
AGGTGGAAATCAAG SEQ ID NO: 162-VL (KL2B358)
GAGATCGTGCTGACCCAGTCTCCTGCCACACTGTCACTGTCTCCAGGCGAGAG
AGCCACCCTCTCTTGTAGAGCCTCCGAGTCCGTGGAATACTTCGGCACCTCTCT
GATGCACTGGTACCAGCAGAAGCCCGGCCAGCCTCCTAGACTGCTGATCTACG
CCGCCTCCAACGTCGAATCTGGCATCCCCGCTAGATTCTCCGGCTCTGGCTCTG
GCACAGACTTTACCCTGACCATCTCCTCCGTGGAACCCGAGGATTTCGCTGTGT
ACTTTTGCCAGCAGACCCGGAAGGTGCCCTACACATTTGGCGGCGGAACAAAG
GTGGAAATCAAG SEQ ID NO: 163-VL (KL2B360)
GAGATCGTGCTGACCCAGTCTCCTGCCACACTGTCACTGTCTCCAGGCGAGAG
AGCCACCCTCTCTTGTAGAGCCTCCGAGTCCGTGGAATACTTCGGCACCTCTCT
GATGCACTGGTACCAGCAGAAGCCCGGCCAGCCTCCTAGACTGCTGATCTACG
CCGCCTCCAACGTCGAATCTGGCATCCCCGCTAGATTCTCCGGCTCTGGCTCTG
GCACAGACTTTACCCTGACCATCTCCTCCGTGGAACCCGAGGATTTCGCTGTGT
ACTTTTGCCAGCAGACCCGGAAGGTGCCCTACACATTTGGCGGCGGAACAAAG
GTGGAAATCAAG SEQ ID NO: 164-VL (KL2B30)
GACATCCAGATGACCCAGTCTCCTTCCTTCCTGTCTGCATCTGTAGGAGACAGA
GTCACCATCACTTGCCGGGCCAGTCAGGGCATTAGCAGTTATTTAGCCTGGTAT
CAGCAAAAACCAGGGAAAGCCCCTAAGTTCCTGATCTATGCTGCATCCACTTT
GCAAAGTGGGGTCCCATCAAGGTTCAGCGGCAGTGGATCTGGGACAGAATTCA
CTCTCACAATCAGCAGCCTGCAGCCTGAAGATTTTGCAACTTATTACTGTCAAC
AGCTTAATAGTTACCCTCTCACTTTCGGCGGAGGGACCAAGGTGGAAATCAAA SEQ ID NO: 165-VL (KL2B53)
GACATCGTGATGACCCAGTCTCCATCCTCCCTGTCTGCATCTGTAGGAGACAG
AGTCACCATCACTTGCCGGGCAGTCAGGACATTAGCAATTATTTAGCCTGGT
ATCAGCAGAAACCAGGGAAAGTTCCTAAGTTCCTGATCTATGCTGCATCCACT
TTGCACTCTGGGGTCCCATCTCGGTTCAGTGGCAGTGGATCTGGGACAGATTTC
ACTCTCACCATCAGCAGCCTGCAGCCTGAAGATGTTGCAACTTATTACTGTCAA
AAGTATAACAGTGCCCCGTACACTTTTGGCCAAGGGACACGACTGGAGATTAA
A SEQ ID NO: 166-VL (KL2B242)
TCCTATGAGCTGACTCAGCCACCCTCAGTGTCCGTGTCCCCAGGAGAGACAGC
CAGCATCACCTGCTCTGGAGATCAATTGGGGGAAAATTATGCTTGCTGGTATC
AGCAGAAGCCAGGCCAGTCCCCTGTGTTGGTCATCTATCAAGATAGTAAGCGG
CCCTCAGGGATCCCTGAGCGATTCTCTGGCTCCAACTCTGGGAACACAGCCAC
TCTGACCATCAGCGGGACCCAGGCTCTGGATGAGGCTGACTATTACTGTCAGG
CGTGGGACAACAGTATTGTGGTATTCGGCGGAGGGACCAAGCTGACCGTCCTA SEQ ID NO: 167-VL (KL2B467)
CAGTCTGTGCTGACTCAGCCACCCTCGGTGTCAGTGGCCCCCGGGCAGACGGC
CAGTATTACCTGTGGGGGAGACAACATTGGAAGTAAAAGTGTGCACTGGTACC
AGCAGAAGCCAGGCCAGGCCCCTGTGCTGGTCGTCTATGATAATAGCGACCGG
CCCTCAGGGATCCCTGAGCGATTCTCTGGCTCCAACTCTGGGACCACGGCCAC
CCTGACCATCAGCAGGGTCGAAGCCGGGGATGAGGCCGACTATTACTGTCAGG
TGTGGGATAGTAGTAGTGATCATCCTGTGGTATTCGGCGGAGGGACCAAGGTC
ACCGTCCTA SEQ ID NO: 168-VL (KL2B494)
TCTTCTGAGCTGACTCAGCCACCCTCGGTGTCAGTGGCCCCAGGACAGACGGC
CAGGATTACCTGTGGGGGAAACAACATTGGAAGTAAAAGTGCACTGGTACC
AGCAGAAGCCAGGCCAGGCCCCTGTGCTGGTCGTCTATGATGATAGCGACCGG
CCCTCAGGGATCCCTGAGCGATTCTCTGGCTCCAACTCTGGGAACACGGCCAC

```
CCTGACCATCAGCAGGGTCGAAGCCGGGGATGAGGCCGACTATTACTGTCAGG
TGTGGGATAGTAGTAGTGATCATGTGGTATTCGGCGGAGGGACCAAGCTGACC
GTCCTA

SEQ ID NO: 169-KL2B357 ScFv-HL
QVQLQESGPGLVKPSQTLSLTCTVSGNSITSDYAWNWIRQFPGKGLEWIGYISYSG
STTYNPSLKSRVTISRDTSKNQFSLKLSSVTAADTAVYYCATGYYYGSGFWGQGT
LVTVSSGGSEGKSSGSGSESKSTGGSDIVLTQSPDSLAVSLGERATINCRASESVEY
FGTSLMHWYQQKPGQPPKLLIYAASNVESGVPDRFSGSGSGTDFTLTISSLQAEDV
AVYFCQQTRKVPYTFGGGTKVEIK

SEQ ID NO: 170-KL2B357 ScFv-LH
DIVLTQSPDSLAVSLGERATINCRASESVEYFGTSLMHWYQQKPGQPPKLLIYAAS
NVESGVPDRFSGSGSGTDFTLTISSLQAEDVAVYFCQQTRKVPYTFGGGTKVEIKG
GSEGKSSGSGSESKSTGGSQVQLQESGPGLVKPSQTLSLTCTVSGNSITSDYAWNW
IRQFPGKGLEWIGYISYSGSTTYNPSLKSRVTISRDTSKNQFSLKLSSVTAADTAVY
YCATGYYYGSGFWGQGTLVTVSS

SEQ ID NO: 171-KL2B358 ScFv-HL
QVQLQESGPGLVKPSQTLSLTCTVSGNSITSDYAWNWIRQPPGKGLEWIGYISYSG
STTYNPSLKSRVTISRDTSKNQFSLKLSSVTAADTAVYYCATGYYYGSGFWGQGT
LVTVSSGGSEGKSSGSGSESKSTGGSEIVLTQSPATLSLSPGERATLSCRASESVEYF
GTSLMHWYQQKPGQPPRLLIYAASNVESGIPARFSGSGSGTDFTLTISSVEPEDFAV
YFCQQTRKVPYTFGGGTKVEIK

SEQ ID NO: 172-KL2B358 ScFv-LH
EIVLTQSPATLSLSPGERATLSCRASESVEYFGTSLMHWYQQKPGQPPRLLIYAASN
VESGIPARFSGSGSGTDFTLTISSVEPEDFAVYFCQQTRKVPYTFGGGTKVEIKGGS
EGKSSGSGSESKSTGGSQVQLQESGPGLVKPSQTLSLTCTVSGNSITSDYAWNWIR
QPPGKGLEWIGYISYSGSTTYNPSLKSRVTISRDTSKNQFSLKLSSVTAADTAVYYC
ATGYYYGSGFWGQGTLVTVSS

SEQ ID NO: 173-KL2B360 ScFv-HL
QVQLQESGPGLVKPSQTLSLTCTVSGNSITSDYAWNWIRQFPGKGLEWIGYISYSG
STTYNPSLKSRVTISRDTSKNQFSLKLSSVTAADTAVYYCATGYYYGSGFWGQGT
LVTVSSGGSEGKSSGSGSESKSTGGSEIVLTQSPATLSLSPGERATLSCRASESVEYF
GTSLMHWYQQKPGQPPRLLIYAASNVESGIPARFSGSGSGTDFTLTISSVEPEDFAV
YFCQQTRKVPYTFGGGTKVEIK

SEQ ID NO: 174-KL2B360 ScFv-LH
EIVLTQSPATLSLSPGERATLSCRASESVEYFGTSLMHWYQQKPGQPPRLLIYAASN
VESGIPARFSGSGSGTDFTLTISSVEPEDFAVYFCQQTRKVPYTFGGGTKVEIKGGS
EGKSSGSGSESKSTGGSQVQLQESGPGLVKPSQTLSLTCTVSGNSITSDYAWNWIR
QFPGKGLEWIGYISYSGSTTYNPSLKSRVTISRDTSKNQFSLKLSSVTAADTAVYYC
ATGYYYGSGFWGQGTLVTVSS

SEQ ID NO: 175-KL2B30 ScFv-HL
QVQLQESGPGLVKPSETLSLTCTVSGGSISSYYWSWIRQPPGKGLEWIGYIYYSGST
NYNPSLKSRVTISVDTSKNQFSLKLSSVTAADTAVYYCAGTTIFGVVTPNFYYGM
DVWGQGTTVTVSSGGSEGKSSGSGSESKSTGGSDIQMTQSPSFLSASVGDRVTITC
RASQGISSYLAWYQQKPGKAPKFLIYAASTLQSGVPSRFSGSGSGTEFTLTISSLQP
EDFATYYCQQLNSYPLTFGGGTKVEIK

SEQ ID NO: 176-KL2B30 ScFv-LH
DIQMTQSPSFLSASVGDRVTITCRASQGISSYLAWYQQKPGKAPKFLIYAASTLQS
GVPSRFSGSGSGTEFTLTISSLQPEDFATYYCQQLNSYPLTFGGGTKVEIKGGSEGK
SSGSGSESKSTGGSQVQLQESGPGLVKPSETLSLTCTVSGGSISSYYWSWIRQPPGK
GLEWIGYIYYSGSTNYNPSLKSRVTISVDTSKNQFSLKLSSVTAADTAVYYCAGTTI
FGVVTPNFYYGMDVWGQGTTVTVSS

SEQ ID NO: 177-KL2B53 ScFv-HL
EVQLVESGGGVVQPGRSLRLSCVASGFTFSSYDIHWVRQAPGKGLEWVAIISYDG
SKKDYTDSVKGRFTISRDNSKNTLYLQMDSLRVEDSAVYSCARESGWSHYYYG
MDVWGQGTMVTVSSGGSEGKSSGSGSESKSTGGSDIVMTQSPSSLSASVGDRVTI
TCRASQDISNYLAWYQQKPGKVPKFLIYAASTLHSGVPSRFSGSGSGTDFTLTISSL
QPEDVATYYCQKYNSAPYTFGQGTRLEIK

SEQ ID NO: 178-KL2B53 ScFv-LH
DIVMTQSPSSLSASVGDRVTITCRASQDISNYLAWYQQKPGKVPKFLIYAASTLHS
GVPSRFSGSGSGTDFTLTISSLQPEDVATYYCQKYNSAPYTFGQGTRLEIKGGSEGK
SSGSGSESKSTGGSEVQLVESGGGVVQPGRSLRLSCVASGFTFSSYDIHWVRQAPG
KGLEWVAIISYDGSKKDYTDSVKGRFTISRDNSKNTLYLQMDSLRVEDSAVYSCA
RESGWSHYYYGMDVWGQGTMVTVSS
```

-continued

SEQ ID NO: 179-KL2B242 ScFv-HL
QVQLQESGPGLVKPSETLSLTCTVSGGSISSYYWSWLRQPAGSGLEWIGRLYVSGF
TNYNPSLKSRVTLSLDPSRNQLSLKLSSVTAADTAVYYCAGDSGNYWGWFDPWG
QGTLVTVSSGGSEGKSSGSGSESKSTGGSSYELTQPPSVSVSPGETASITCSGDQLG
ENYACWYQQKPGQSPVLVIYQDSKRPSGIPERFSGSNSGNTATLTISGTQALDEAD
YYCQAWDNSIVVFGGGTKLTVL

SEQ ID NO: 180-KL2B242 ScFv-LH
SYELTQPPSVSVSPGETASITCSGDQLGENYACWYQQKPGQSPVLVIYQDSKRPSGI
PERFSGSNSGNTATLTISGTQALDEADYYCQAWDNSIVVFGGGTKLTVLGGSEGK
SSGSGSESKSTGGSQVQLQESGPGLVKPSETLSLTCTVSGGSISSYYWSWLRQPAG
SGLEWIGRLYVSGFTNYNPSLKSRVTLSLDPSRNQLSLKLSSVTAADTAVYYCAG
DSGNYWGWFDPWGQGTLVTVSS

SEQ ID NO: 181-KL2B467 ScFv-HL
QVQLVESGGGVVQPGRSLRLSCAASGFTFSYYGMHWVRQAPGKGLEWVAFISYD
GSNKYYADSVKGRFTISRDNSKNTLYLQMNSLRAEDTAVYYCAHLPYSGSYWAF
DYWGQGTQVTVSSGGSEGKSSGSGSESKSTGGSQSVLTQPPSVSVAPGQTASITCG
GDNIGSKSVHWYQQKPGQAPVLVVYDNSDRPSGIPERFSGSNSGTTATLTISRVEA
GDEADYYCQVWDSSSDHPVVFGGGTKVTV

SEQ ID NO: 182-KL2B467 ScFv-LH
QSVLTQPPSVSVAPGQTASITCGGDNIGSKSVHWYQQKPGQAPVLVVYDNSDRPS
GIPERFSGSNSGTTATLTISRVEAGDEADYYCQVWDSSSDHPVVFGGGTKVTVGG
SEGKSSGSGSESKSTGGSQVQLVESGGGVVQPGRSLRLSCAASGFTFSYYGMHWV
RQAPGKGLEWVAFISYDGSNKYYADSVKGRFTISRDNSKNTLYLQMNSLRAEDT
AVYYCAHLPYSGSYWAFDYWGQGTQVTVSS

SEQ ID NO: 183-KL2B494 ScFv-HL
QVQLVESGGGLVQPGGSLRLSCAASGFTFSHYAMSWVRQAPGKGLEWVSTIGGS
GGSTYYADSVKGRFTISRDNSKNTLYLQMNSLRAEDTAVYYCAKPHIVMVTALL
YDGMDVWGQGTMVTVSSGGSEGKSSGSGSESKSTGGSSSELTQPPSVSVAPGQTA
RITCGGNNIGSKSVHWYQQKPGQAPVLVVYDDSDRPSGIPERFSGSNSGNTATLTI
SRVEAGDEADYYCQVWDSSSDHVVFGGGTKLTVL

SEQ ID NO: 184-KL2B494 ScFv-LH
SSELTQPPSVSVAPGQTARITCGGNNIGSKSVHWYQQKPGQAPVLVVYDDSDRPS
GIPERFSGSNSGNTATLTISRVEAGDEADYYCQVWDSSSDHVVFGGGTKLTVLGG
SEGKSSGSGSESKSTGGSQVQLVESGGGLVQPGGSLRLSCAASGFTFSHYAMSWV
RQAPGKGLEWVSTIGGSGGSTYYADSVKGRFTISRDNSKNTLYLQMNSLRAEDTA
VYYCAKPHIVMVTALLYDGMDVWGQGTMVTVSS

SEQ ID NO: 185-KL2B30 HC IgG4
QVQLQESGPGLVKPSETLSLTCTVSGGSISSYYWSWIRQPPGKGLEWIGYIYYSGST
NYNPSLKSRVTISVDTSKNQFSLKLSSVTAADTAVYYCAGTTIFGVVTPNFYYGM
DVWGQGTTVTVSSASTKGPSVFPLAPCSRSTSESTAALGCLVKDYFPEPVTVSWNS
GALTSGVHTFPAVLQSSGLYSLSSVVTVPSSSLGTKTYTCNVDHKPSNTKVDKRVE
SKYGPPCPPCPAPEAAGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLP
SSIEKTISKAKGQPREPQVYTLPPSQEEMTKNQVSLTCLVKGFYPSDIAVEWESNG
QPENNYKTTPPVLDSDGSFFLYSRLTVDKSRWQEGNVFSCSVMHEALHNHYTQKS
LSLSLGK

SEQ ID NO: 186-KL2B30 LC IgG4
DIQMTQSPSFLSASVGDRVTITCRASQGISSYLAWYQQKPGKAPKFLIYAASTLQS
GVPSRFSGSGSGTEFTLTISSLQPEDFATYYCQQLNSYPLTFGGGTKVEIKRTVAAP
SVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID NO: 187-KL2B53 HC IgG4
EVQLVESGGGVVQPGRSLRLSCVASGFTFSSYDIHWVRQAPGKGLEWVAIISYDG
SKKDYTDSVKGRFTISRDNSKNTLYLQMDSLRVEDSAVYSCARESGWSHYYYYG
MDVWGQGTMVTVSSASTKGPSVFPLAPCSRSTSESTAALGCLVKDYFPEPVTVSW
NSGALTSGVHTFPAVLQSSGLYSLSSVVTVPSSSLGTKTYTCNVDHKPSNTKVDKR
VESKYGPPCPPCPAPEAAGGPSVFLFPPKPKDTLMISRTPEVTCVVVDVSQEDPEV
QFNWYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSDIAVEWES
NGQPENNYKTTPPVLDSDGSFFLYSRLTVDKSRWQEGNVFSCSVMHEALHNHYT
QKSLSLSLGK

SEQ ID NO: 188-KL2B53 LC IgG4
DIVMTQSPSSLSASVGDRVTITCRASQDISNYLAWYQQKPGKVPKFLIYAASTLHS
GVPSRFSGSGSGTDFTLTISSLQPEDVATYYCQKYNSAPYTFGQGTRLEIKRTVAAP
SVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQ ID NO: 189-KL2B242 HC IgG4
QVQLQESGPGLVKPSETLSLTCTVSGGSISSYYWSWLRQPAGSGLEWIGRLYVSGF
TNYNPSLKSRVTLSLDPSRNQLSLKLSSVTAADTAVYYCAGDSGNYWGWFDPWG

-continued

QGTLVTVSSASTKGPSVFPLAPCSRSTSESTAALGCLVKDYFPEPVTVSWNSGALT
SGVHTFPAVLQSSGLYSLSSVVTVPSSSLGTKTYTCNVDHKPSNTKVDKRVESKY
GPPCPPCPAPEAAGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWESNGQPE
NNYKTTPPVLDSDGSFFLYSRLTVDKSRWQEGNVFSCSVMHEALHNHYTQKSLSL
SLGK

SEQ ID NO: 190-KL2B242 LC IgG4
SYELTQPPSVSVSPGETASITCSGDQLGENYACWYQQKPGQSPVLVIYQDSKRPSGI
PERFSGSNSGNTATLTISGTQALDEADYYCQAWDNSIVVFGGGTKLTVLGQPKAA
PSVTLFPPSSEELQANKATLVCLISDFYPGAVTVAWKADSSPVKAGVETTTPSKQS
NNKYAASSYLSLTPEQWKSHRSYSCQVTHEGSTVEKTVAPTECS

SEQ ID NO: 191-KL2B467 HC IgG4
QVQLVESGGGVVQPGRSLRLSCAASGFTFSYYGMHWVRQAPGKGLEWVAFISYD
GSNKYYADSVKGRFTISRDNSKNTLYLQMNSLRAEDTAVYYCAHLPYSGSYWAF
DYWGQGTQVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKV
EPKSCDKTHTCPPCPAPEAAGGPSVFLFPPKPKDTLMISRTPEVTCVVVSVSHEDPE
VKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHN
HYTQKSLSLSPGK

SEQ ID NO: 192-KL2B467 LC IgG4
QSVLTQPPSVSVAPGQTASITCGGDNIGSKSVHWYQQKPGQAPVLVVYDNSDRPS
GIPERFSGSNSGTTATLTISRVEAGDEADYYCQVWDSSSDHVVFGGGTKVTVLG
QPKAAPSVTLFPPSSEELQANKATLVCLISDFYPGAVTVAWKADSSPVKAGVETTT
PSKQSNNKYAASSYLSLTPEQWKSHRSYSCQVTHEGSTVEKTVAPTECS

SEQ ID NO: 193-KL2B494 HC IgG4
QVQLVESGGGLVQPGGSLRLSCAASGFTFSHYAMSWVRQAPGKGLEWVSTIGGS
GGSTYYADSVKGRFTISRDNSKNTLYLQMNSLRAEDTAVYYCAKPHIVMVTALL
YDGMDVWGQGTMVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTK
VDKKVEPKSCDKTHTCPPCPAPEAAGGPSVFLFPPKPKDTLMISRTPEVTCVVVSV
SHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHE
ALHNHYTQKSLSLSPGK

SEQ ID NO: 194-KL2B494 LC IgG4
SSELTQPPSVSVAPGQTARITCGGNNIGSKSVHWYQQKPGQAPVLVVYDDSDRPS
GIPERFSGSNSGNTATLTISRVEAGDEADYYCQVWDSSSDHVVFGGGTKLTVLGQ
PKAAPSVTLFPPSSEELQANKATLVCLISDFYPGAVTVAWKADSSPVKAGVETTTP
SKQSNNKYAASSYLSLTPEQWKSHRSYSCQVTHEGSTVEKTVAPTECS

SEQ ID NO: 195-KL2B30 HC DNA
CAGGTGCAGCTGCAGGAGTCGGGCCCAGGACTGGTGAAGCCTTCGGAGACCCT
GTCCCTCACCTGCACTGTCTCTGGTGGCTCCATCAGTAGTTACTACTGGAGCTG
GATCCGGCAGCCCCCAGGGAAGGGACTGGAGTGGATTGGATATATCTATTACA
GTGGGAGCACCAACTACAACCCCTCCCTCAAGAGTCGAGTCACCATATCAGTA
GACACGTCCAAGAACCAGTTCTCCCTGAAGCTGAGCTCTGTGACCGCTGCGGA
CACGGCCGTGTATTACTGTGCGGGGACTACGATTTTTGGAGTGGTTACCCCCA
ACTTCTACTACGGTATGGACGTCTGGGGCCAAGGGACCACGGTCACCGTCTCC
TCAGCTTCCACCAAGGGCCCATCCGTCTTCCCCCTGGCGCCCTGCTCCAGGAGC
ACCTCCGAGAGCACAGCCGCCCTGGGCTGCCTGGTCAAGGACTACTTCCCCGA
ACCGGTGACGGTGTCGTGGAACTCAGGCGCCCTGACCAGCGGCGTGCACACCT
TCCCGGCTGTCCTACAGTCCTCAGGACTCTACTCCCTCAGCAGCGTGGTGACCG
TGCCCTCCAGCAGCTTGGGCACGAAAACCTACACTTGCAACGTAGATCACAAG
CCCAGCAACACCAAGGTGGACAAGAGAGTTGAGTCCAAATATGGTCCCCCATG
CCCACCATGCCCAGCACCTGAGGCCGCCGGGGGACCATCAGTCTTCCTGTTCC
CCCCAAAACCCAAGGACACTCTCATGATCTCCCGGACCCCTGAGGTCACGTGC
GTGGTGGTGGACGTGAGCCAGGAAGACCCCGAGGTCCAGTTCAACTGGTACGT
GGATGGCGTGGAGGTGCATAATGCCAAGACAAAGCCGCGGGAGGAGCAGTTC
AACAGCACGTACCGTGTGGTCAGCGTCCTCACCGTCCTGCACCAGGACTGGCT
GAACGGCAAGGAGTACAAGTGCAAGGTCTCCAACAAAGGCCTCCCGTCCTCCA
TCGAGAAAACCATCTCCAAAGCCAAAGGGCAGCCCCGAGAGCCACAGGTGTA
CACCCTGCCCCCATCCCAGGAGGAGATGACCAAGAACCAGGTCAGCCTGACCT
GCCTGGTCAAAGGCTTCTACCCCAGCGACATCGCCGTGGAGTGGGAGAGCAAT
GGGCAGCCGGAGAACAACTACAAGACCACGCCTCCCGTGCTGGACTCCGACG
GCTCCTTCTTCCTCTACAGCAGGCTAACCGTGGACAAGAGCAGATGGCAGGAG
GGGAATGTCTTCTCATGCTCCGTGATGCATGAGGCTCTGCACAACCACTACAC
ACAGAAGAGCCTCTCCCTGTCTCTGGGTAAA

SEQ ID NO: 196-KL2B30 LC DNA
GACATCCAGATGACCCAGTCTCCTTCCTTCCTGTCTGCATCTGTAGGAGACAGA
GTCACCATCACTTGCCGGGCCAGTCAGGGCATTAGCAGTTATTTAGCCTGGTAT

CAGCAAAAACCAGGGAAAGCCCCTAAGTTCCTGATCTATGCTGCATCCACTTT
GCAAAGTGGGGTCCCATCAAGGTTCAGCGGCAGTGGATCTGGGACAGAATTCA
CTCTCACAATCAGCAGCCTGCAGCCTGAAGATTTTGCAACTTATTACTGTCAAC
AGCTTAATAGTTACCCTCTCACTTTCGGCGGAGGGACCAAGGTGGAAATCAAA
CGTACGGTGGCTGCACCATCTGTCTTCATCTTCCCGCCATCTGATGAGCAGTTG
AAATCTGGAACTGCCTCTGTTGTGTGCCTGCTGAATAACTTCTATCCCAGAGAG
GCCAAAGTACAGTGGAAGGTGGATAACGCCCTCCAATCGGGTAACTCCCAGG
AGAGTGTCACAGAGCAGGACAGCAAGGACAGCACCTACAGCCTCAGCAGCAC
CCTGACGCTGAGCAAAGCAGACTACGAGAAACACAAAGTCTACGCCTGCGAA
GTCACCCATCAGGGCCTGAGCTCGCCCGTCACAAAGAGCTTCAACAGGGGAGA
GTGT

SEQ ID NO: 197-KL2B53 HC DNA
GAGGTGCAGCTGGTGGAGTCTGGGGGAGGCGTGGTCCAGCCTGGGAGGTCCCT
GAGACTCTCCTGTGTAGCCTCTGGATTCACCTTCAGTAGTTATGACATACACTG
GGTCCGCCAGGCTCCAGGCAAGGGGCTGGAGTGGGTGGCAATTATTTCATATG
ATGGAAGTAAAAAAGACTATACAGACTCCGTGAAGGGCCGATTCACCATCTCC
AGAGACAATTCCAAGAACACGCTGTATCTGCAAATGGACAGCCTGAGAGTTGA
GGACTCGGCTGTGTATTCCTGTGCGAGAGAAAGTGGCTGGTCCCACTACTACT
ATTACGGTATGGACGTCTGGGGCCAAGGGACAATGGTCACCGTCTCTTCAGCT
TCCACCAAGGGCCCATCCGTCTTCCCCCTGGCGCCCTGCTCCAGGAGCACCTCC
GAGAGCACAGCCGCCCTGGGCTGCCTGGTCAAGGACTACTTCCCCGAACCGGT
GACGGTGTCGTGGAACTCAGGCGCCCTGACCAGCGGCGTGCACACCTTCCCGG
CTGTCCTACAGTCCTCAGGACTCTACTCCCTCAGCAGCGTGGTGACCGTGCCCT
CCAGCAGCTTGGGCACGAAAACCTACACTTGCAACGTAGATCACAAGCCCAGC
AACACCAAGGTGGACAAGAGAGTTGAGTCCAAATATGGTCCCCCATGCCCACC
ATGCCCAGCACCTGAGGCCGCCGGGGGACCATCAGTCTTCCTGTTCCCCCCAA
AACCCAAGGACACTCTCATGATCTCCCGGACCCCTGAGGTCACGTGCGTGGTG
GTGGACGTGAGCCAGGAAGACCCCGAGGTCCAGTTCAACTGGTACGTGGATG
GCGTGGAGGTGCATAATGCCAAGACAAAGCCGCGGGAGGAGCAGTTCAACAG
CACGTACCGTGTGGTCAGCGTCCTCACCGTCCTGCACCAGGACTGGCTGAACG
GCAAGGAGTACAAGTGCAAGGTCTCCAACAAAGGCCTCCCGTCCTCCATCGAG
AAAACCATCTCCAAAGCCAAAGGGCAGCCCCGAGAGCCACAGGTGTACACCC
TGCCCCCATCCCAGGAGGAGATGACCAAGAACCAGGTCAGCCTGACCTGCCTG
GTCAAAGGCTTCTACCCCAGCGACATCGCCGTGGAGTGGGAGAGCAATGGGC
AGCCGGAGAACAACTACAAGACCACGCCTCCCGTGCTGGACTCCGACGGCTCC
TTCTTCCTCTACAGCAGGCTAACCGTGGACAAGAGCAGATGGCAGGAGGGGA
ATGTCTTCTCATGCTCCGTGATGCATGAGGCTCTGCACAACCACTACACACAG
AAGAGCCTCTCCCTGTCTCTGGGTAAA

SEQ ID NO: 198-KL2B53 LC DNA
GACATCGTGATGACCCAGTCTCCATCCTCCCTGTCTGCATCTGTAGGAGACAG
AGTCACCATCACTTGCCGGGCGAGTCAGGACATTAGCAATTATTTAGCCTGGT
ATCAGCAGAAACCAGGGAAAGTTCCTAAGTTCCTGATCTATGCTGCATCCACT
TTGCACTCTGGGGTCCCATCTCGGTTCAGTGGCAGTGGATCTGGGACAGATTTC
ACTCTCACCATCAGCAGCCTGCAGCCTGAAGATGTTGCAACTTATTACTGTCAA
AAGTATAACAGTGCCCCGTACACTTTTGGCCAAGGGACACGACTGGAGATTAA
ACGTACGGTGGCTGCACCATCTGTCTTCATCTTCCCGCCATCTGATGAGCAGTT
GAAATCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCCAG
GAGAGTGTCACAGAGCAGGACAGCAAGGACAGCACCTACAGCCTCAGCAGCA
CCCTGACGCTGAGCAAAGCAGACTACGAGAAACACAAAGTCTACGCCTGCGA
AGTCACCCATCAGGGCCTGAGCTCGCCCGTCACAAAGAGCTTCAACAGGGGAG
AGTGT

SEQ ID NO: 199-KL2B242 HC DNA
CAGGTGCAGCTGCAGGAGTCGGGCCCAGGACTGGTGAAGCCTTCGGAGACCCT
GTCCCTCACCTGCACTGTCTCTGGTGGCTCCATCAGTAGTTACTATTGGAGCTG
GCTCCGGCAGCCCGCCGGGTCGGGACTGGAGTGGATTGGGCGTTTATATGTCA
GTGGGTTCACCAACTACAACCCCTCCCTCAAGAGTCGAGTCACCTTGTCACTA
GACCCGTCCAGGAACCAGTTGTCCCTGAAACTGAGTTCTGTGACCGCCGCGGA
CACGGCCGTATATTATTGTGCGGGAGATAGTGGGAACTACTGGGGTTGGTTCG
ACCCCTGGGGCCAGGGAACCCTGGTCACCGTCTCCTCAGCTTCCACCAAGGGC
CCATCCGTCTTCCCCCTGGCGCCCTGCTCCAGGAGCACCTCCGAGAGCACAGC
CGCCCTGGGCTGCCTGGTCAAGGACTACTTCCCCGAACCGGTGACGGTGTCGT
GGAACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAGCTTG
GGCACGAAAACCTACACTTGCAACGTAGATCACAAGCCCAGCAACACCAAGG
TGGACAAGAGAGTTGAGTCCAAATATGGTCCCCCATGCCCACCATGCCCAGCA
CCTGAGGCCGCCGGGGGACCATCAGTCTTCCTGTTCCCCCCAAAACCCAAGGA
CACTCTCATGATCTCCCGGACCCCTGAGGTCACGTGCGTGGTGGTGGACGTGA
GCCAGGAAGACCCCGAGGTCCAGTTCAACTGGTACGTGGATGGCGTGGAGGT
GCATAATGCCAAGACAAAGCCGCGGGAGGAGCAGTTCAACAGCACGTACCGT
GTGGTCAGCGTCCTCACCGTCCTGCACCAGGACTGGCTGAACGGCAAGGAGTA
CAAGTGCAAGGTCTCCAACAAAGGCCTCCCGTCCTCCATCGAGAAAACCATCT
CCAAAGCCAAAGGGCAGCCCCGAGAGCCACAGGTGTACACCCTGCCCCCATCC
CAGGAGGAGATGACCAAGAACCAGGTCAGCCTGACCTGCCTGGTCAAAGGCT
TCTACCCCAGCGACATCGCCGTGGAGTGGGAGAGCAATGGGCAGCCGGAGAA

CAACTACAAGACCACGCCTCCCGTGCTGGACTCCGACGGCTCCTTCTTCCTCTA
CAGCAGGCTAACCGTGGACAAGAGCAGATGGCAGGAGGGGAATGTCTTCTCA
TGCTCCGTGATGCATGAGGCTCTGCACAACCACTACACACAGAAGAGCCTCTC
CCTGTCTCTGGGTAAA

SEQ ID NO: 200-KL2B242 LC DNA
TCCTATGAGCTGACTCAGCCACCCTCAGTGTCCGTGTCCCCAGGAGAGACAGC
CAGCATCACCTGCTCTGGAGATCAATTGGGGGAAAATTATGCTTGCTGGTATC
AGCAGAAGCCAGGCCAGTCCCCTGTGTTGGTCATCTATCAAGATAGTAAGCGG
CCCTCAGGGATCCCTGAGCGATTCTCTGGCTCCAACTCTGGGAACACAGCCAC
TCTGACCATCAGCGGGACCCAGGCTCTGGATGAGGCTGACTATTACTGTCAGG
CGTGGGACAACAGTATTGTGGTATTCGGCGGAGGGACCAAGCTGACCGTCCTA
GGTCAGCCCAAGGCTGCACCCAGTGTCACTCTGTTCCCGCCCTCCTCTGAGGA
GCTTCAAGCCAACAAGGCCACACTGGTGTGTCTCATAAGTGACTTCTACCCGG
GAGCCGTGACAGTGGCCTGGAAGGCCGATAGCAGCCCCGTCAAGGCGGGAGT
GGAGACCACCACACCCTCCAAACAAAGCAACAACAAGTACGCGGCCAGCAGC
TATCTGAGCCTGACGCCTGAGCAGTGGAAGTCCCACAGAAGCTACAGCTGCCA
GGTCACGCATGAAGGGAGCACCGTGGAGAAGACAGTGGCCCCTACAGAATGT
TCA

SEQ ID NO: 201-KL2B467 HC DNA
CAGGTGCAGCTGGTGGAGTCTGGGGGAGGCGTGGTCCAGCCTGGGAGGTCCCT
GAGACTCTCCTGTGCAGCCTCTGGATTCACCTTCAGTTACTATGGCATGCACTG
GGTCCGCCAGGCTCCAGGCAAGGGGCTGGAGTGGGTGGCATTTATATCATATG
ATGGAAGTAATAAATACTATGCAGACTCCGTGAAGGGCCGATTCACCATCTCC
AGAGACAATTCCAAGAACACGCTGTATCTGCAAATGAACAGCCTGAGAGCTG
AGGACACGGCTGTGTATTACTGTGCCCACCTCCCTTATAGTGGGAGCTACTGG
GCCTTTGACTACTGGGGCCAGGGAACCCAGGTCACCGTCTCTTCAGCCTCCAC
CAAGGGCCCATCGGTCTTCCCCCTGGCACCCTCCTCCAAGAGCACCTCTGGGG
GCACAGCGGCCCTGGGCTGCCTGGTCAAGGACTACTTCCCCGAACCGGTGACG
GTGTCGTGGAACTCAGGCGCCCTGACCAGCGGCGTGCACACCTTCCCGGCTGT
CCTACAGTCCTCAGGACTCTACTCCCTCAGCAGCGTGGTGACCGTGCCCTCCAG
CAGCTTGGGCACCCAGACCTACATCTGCAACGTGAATCACAAGCCCAGCAACA
CCAAGGTGGACAAGAAAGTTGAGCCCAAATCTTGTGACAAAACTCACACATGC
CCACCGTGCCCAGCACCTGAAGCCGCCGGGGACCGTCAGTCTTCCTCTTCCC
CCCAAAACCCAAGGACACCCTCATGATCTCCCGGACCCCTGAGGTCACATGCG
TGGTGGTGAGCGTGAGCCACGAAGACCCTGAGGTCAAGTTCAACTGGTACGTG
GACGGCGTGGAGGTGCATAATGCCAAGACAAAGCCGCGGGAGGAGCAGTACA
ACAGCACGTACCGTGTGGTCAGCGTCCTCACCGTCCTGCACCAGGACTGGCTG
AATGGCAAGGAGTACAAGTGCAAGGTCTCCAACAAAGCCCTCCCAGCCCCCAT
CGAGAAAACCATCTCCAAAGCCAAAGGGCAGCCCCGAGAACCACAGGTGTAC
ACCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAATG
GGCAGCCGGAGAACAACTACAAGACCACGCCTCCCGTGCTGGACTCCGACGG
CTCCTTCTTCCTCTACAGCAAGCTCACCGTGGACAAGAGCAGATGGCAGCAGG
GGAACGTCTTCTCATGCTCCGTGATGCATGAGGCTCTGCACAACCACTACACG
CAGAAGAGCCTCTCCCTGTCTCCGGGTAAA

SEQ ID NO: 202-KL2B467 LC DNA
CAGTCTGTGCTGACTCAGCCACCCTCGGTGTCAGTGGCCCCCGGGCAGACGGC
CAGTATTACCTGTGGGGGAGACAACATTGGAAGTAAAAGTGTGCACTGGTACC
AGCAGAAGCCAGGCCAGGCCCCTGTGCTGGTCGTCTATGATAATAGCGACCGG
CCCTCAGGGATCCCTGAGCGATTCTCTGGCTCCAACTCTGGGACCACGGCCAC
CCTGACCATCAGCAGGGTCGAAGCCGGGGATGAGGCCGACTATTACTGTCAGG
TGTGGGATAGTAGTAGTGATCATCCTGTGGTATTCGGCGGAGGGACCAAGGTC
ACCGTCCTAGGTCAGCCCAAGGCTGCACCCAGTGTCACTCTGTTCCCGCCCTCC
TCTGAGGAGCTTCAAGCCAACAAGGCCACACTGGTGTGTCTCATAAGTGACTT
CTACCCGGGAGCCGTGACAGTGGCCTGGAAGGCCGATAGCAGCCCCGTCAAG
GCGGGAGTGGAGACCACCACACCCTCCAAACAAAGCAACAACAAGTACGCGG
CCAGCAGCTATCTGAGCCTGACGCCTGAGCAGTGGAAGTCCCACAGAAGCTAC
AGCTGCCAGGTCACGCATGAAGGGAGCACCGTGGAGAAGACAGTGGCCCCTA
CAGAATGTTCA

SEQ ID NO: 203-KL2B494 HC DNA
CAGGTGCAGCTGGTGGAGTCTGGGGGAGGCTTGGTACAGCCTGGGGGGTCCCT
GAGACTCTCCTGTGCAGCCTCTGGATTCACCTTTAGTCATTATGCCATGAGCTG
GGTCCGCCAGGCTCCAGGGAAGGGGCTGGAGTGGGTCTCAACTATTGGTGGTA
GTGGTGGTAGCACATACTACGCAGACTCCGTGAAGGGCCGGTTCACCATCTCC
AGAGACAATTCCAAGAACACGCTGTATCTGCAAATGAACAGCCTGAGAGCCG
AGGACACGGCCGTATATTACTGTGCGAAACCTCATATTGTAATGGTGACTGCT
CTTCTCTACGACGGTATGGACGTCTGGGGCCAAGGGACAATGGTCACCGTCTC
CTCAGCCTCCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCG
AACCGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTGACC
GTGCCCTCCAGCAGCTTGGGCACCCAGACCTACATCTGCAACGTGAATCACAA
GCCCAGCAACACCAAGGTGGACAAGAAAGTTGAGCCCAAATCTTGTGACAAA
ACTCACACATGCCCACCGTGCCCAGCACCTGAAGCCGCCGGGGACCGTCAGT
CTTCCTCTTCCCCCCAAAACCCAAGGACACCCTCATGATCTCCCGGACCCCTGA

```
GGTCACATGCGTGGTGGTGAGCGTGAGCCACGAAGACCCTGAGGTCAAGTTCA
ACTGGTACGTGGACGGCGTGGAGGTGCATAATGCCAAGACAAAGCCGCGGGA
GGAGCAGTACAACAGCACGTACCGTGTGGTCAGCGTCCTCACCGTCCTGCACC
AGGACTGGCTGAATGGCAAGGAGTACAAGTGCAAGGTCTCCAACAAAGCCCT
CCCAGCCCCCATCGAGAAAACCATCTCCAAAGCCAAAGGGCAGCCCCGAGAA
CCACAGGTGTACACCCTGCCCCCATCCCGGGAGGAGATGACCAAGAACCAGGT
CAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCT
GGACTCCGACGGCTCCTTCTTCCTCTACAGCAAGCTCACCGTGGACAAGAGCA
GATGGCAGCAGGGGAACGTCTTCTCATGCTCCGTGATGCATGAGGCTCTGCAC
AACCACTACACGCAGAAGAGCCTCTCCCTGTCTCCGGGTAAA

SEQ ID NO: 204-KL2B494 LC DNA
TCTTCTGAGCTGACTCAGCCACCCTCGGTGTCAGTGGCCCCAGGACAGACGGC
CAGGATTACCTGTGGGGGAAACAACATTGGAAGTAAAAGTGTGCACTGGTACC
AGCAGAAGCCAGGCCAGGCCCCTGTGCTGGTCGTCTATGATGATAGCGACCGG
CCCTCAGGGATCCCTGAGCGATTCTCTGGCTCCAACTCTGGGAACACGGCCAC
CCTGACCATCAGCAGGGTCGAAGCCGGGGATGAGGCCGACTATTACTGTCAGG
TGTGGGATAGTAGTAGTGATCATGTGGTATTCGGCGGAGGGACCAAGCTGACC
GTCCTAGGTCAGCCCAAGGCTGCACCCAGTGTCACTCTGTTCCCGCCCTCCTCT
GAGGAGCTTCAAGCCAACAAGGCCACACTGGTGTGTCTCATAAGTGACTTCTA
CCCGGGAGCCGTGACAGTGGCCTGGAAGGCCGATAGCAGCCCCGTCAAGGCG
GGAGTGGAGACCACCACACCCTCCAAACAAAGCAACAACAAGTACGCGGCCA
GCAGCTATCTGAGCCTGACGCCTGAGCAGTGGAAGTCCCACAGAAGCTACAGC
TGCCAGGTCACGCATGAAGGGAGCACCGTGGAGAAGACAGTGGCCCCTACAG
AATGTTCA

SEQ ID NO: 205-CAR (KL2B357 HL and KL2B357 LH)
QVQLQESGPGLVKPSQTLSLTCTVSGNSITSDYAWNWIRQFPGKGLEWIGYISYSG
STTYNPSLKSRVTISRDTSKNQFSLKLSSVTAADTAVYYCATGYYYGSGFWGQGT
LVTVSSGGSEGKSSGSGSESKSTGGSDIVLTQSPDSLAVSLGERATINCRASESVEY
FGTSLMHWYQQKPGQPPKLLIYAASNVESGVPDRFSGSGSGTDFTLTISSLQAEDV
AVYFCQQTRKVPYTFGGGTKVEIKTSTPAPRPPTPAPTIASQPLSLRPEACRPAAGG
AVHTRGLDFACDIYIWAPLAGTCGVLLLSLVITLYCKRGRKKLLYIFKQPFMRPVQ
TTQEEDGCSCRFPEEEEGGCELRVKFSRSADAPAYKQGQNQLYNELNLGRREEYD
VLDKRRGRDPEMGGKPRRKNPQEGLYNELQKDKMAEAYSEIGMKGERRRGKGH
DGLYQGLSTATKDTYDALHMQALPPR SEQ ID NO: 207-CAR (KL2B358 HL)
QVQLQESGPGLVKPSQTLSLTCTVSGNSITSDYAWNWIRQPPGKGLEWIGYISYSG
STTYNPSLKSRVTISRDTSKNQFSLKLSSVTAADTAVYYCATGYYYGSGFWGQGT
LVTVSSGGSEGKSSGSGSESKSTGGSEIVLTQSPATLSLSPGERATLSCRASESVEYF
GTSLMHWYQQKPGQPPRLLIYAASNVESGIPARFSGSGSGTDFTLTISSVEPEDFAV
YFCQQTRKVPYTFGGGTKVEIKTSTPAPRPPTPAPTIASQPLSLRPEACRPAAGGAV
HTRGLDFACDIYIWAPLAGTCGVLLLSLVITLYCKRGRKKLLYIFKQPFMRPVQTT
QEEDGCSCRFPEEEEGGCELRVKFSRSADAPAYKQGQNQLYNELNLGRREEYDVL
DKRRGRDPEMGGKPRRKNPQEGLYNELQKDKMAEAYSEIGMKGERRRGKGHDG
LYQGLSTATKDTYDALHMQALPPR SEQ ID NO: 208-CAR (KL2B358 LH)
EIVLTQSPATLSLSPGERATLSCRASESVEYFGTSLMHWYQQKPGQPPRLLIYAASN
VESGIPARFSGSGSGTDFTLTISSVEPEDFAVYFCQQTRKVPYTFGGGTKVEIKGGS
EGKSSGSGSESKSTGGSQVQLQESGPGLVKPSQTLSLTCTVSGNSITSDYAWNWIR
QPPGKGLEWIGYISYSGSTTYNPSLKSRVTISRDTSKNQFSLKLSSVTAADTAVYYC
ATGYYYGSGFWGQGTLVTVSSTSTPAPRPPTPAPTIASQPLSLRPEACRPAAGGAV
HTRGLDFACDIYIWAPLAGTCGVLLLSLVITLYCKRGRKKLLYIFKQPFMRPVQTT
QEEDGCSCRFPEEEEGGCELRVKFSRSADAPAYKQGQNQLYNELNLGRREEYDVL
DKRRGRDPEMGGKPRRKNPQEGLYNELQKDKMAEAYSEIGMKGERRRGKGHDG
LYQGLSTATKDTYDALHMQALPPR SEQ ID NO: 209-CAR (KL2B360 HL)
QVQLQESGPGLVKPSQTLSLTCTVSGNSITSDYAWNWIRQFPGKGLEWIGYISYSG
STTYNPSLKSRVTISRDTSKNQFSLKLSSVTAADTAVYYCATGYYYGSGFWGQGT
LVTVSSGGSEGKSSGSGSESKSTGGSEIVLTQSPATLSLSPGERATLSCRASESVEYF
GTSLMHWYQQKPGQPPRLLIYAASNVESGIPARFSGSGSGTDFTLTISSVEPEDFAV
YFCQQTRKVPYTFGGGTKVEIKTSTPAPRPPTPAPTIASQPLSLRPEACRPAAGGAV
HTRGLDFACDIYIWAPLAGTCGVLLLSLVITLYCKRGRKKLLYIFKQPFMRPVQTT
QEEDGCSCRFPEEEEGGCELRVKFSRSADAPAYKQGQNQLYNELNLGRREEYDVL
DKRRGRDPEMGGKPRRKNPQEGLYNELQKDKMAEAYSEIGMKGERRRGKGHDG
LYQGLSTATKDTYDALHMQALPPR SEQ ID NO: 210-CAR (KL2B360 LH)
EIVLTQSPATLSLSPGERATLSCRASESVEYFGTSLMHWYQQKPGQPPRLLIYAASN
VESGIPARFSGSGSGTDFTLTISSVEPEDFAVYFCQQTRKVPYTFGGGTKVEIKGGS
EGKSSGSGSESKSTGGSQVQLQESGPGLVKPSQTLSLTCTVSGNSITSDYAWNWIR
QPPGKGLEWIGYISYSGSTTYNPSLKSRVTISRDTSKNQFSLKLSSVTAADTAVYYC
ATGYYYGSGFWGQGTLVTVSSTSTPAPRPPTPAPTIASQPLSLRPEACRPAAGGAV
HTRGLDFACDIYIWAPLAGTCGVLLLSLVITLYCKRGRKKLLYIFKQPFMRPVQTT
```

QEEDGCSCRFPEEEEGGCELRVKFSRSADAPAYKQGQNQLYNELNLGRREEYDVL
DKRRGRDPEMGGKPRRKNPQEGLYNELQKDKMAEAYSEIGMKGERRRGKGHDG
LYQGLSTATKDTYDALHMQALPPR

SEQ ID NO: 211-CAR (KL2B30 HL)
QVQLQESGPGLVKPSETLSLTCTVSGGSISSYYWSWIRQPPGKGLEWIGYIYYSGST
NYNPSLKSRVTISVDTSKNQFSLKLSSVTAADTAVYYCAGTTIFGVVTPNFYYGM
DVWGQGTTVTVSSGGSEGKSSGSGSESKSTGGSDIQMTQSPSFLSASVGDRVTITC
RASQGISSYLAWYQQKPGKAPKFLIYAASTLQSGVPSRFSGSGSGTEFTLTISSLQP
EDFATYYCQQLNSYPLTFGGGTKVEIKTSTPAPRPPTPAPTIASQPLSLRPEACRPA
AGGAVHTRGLDFACDIYIWAPLAGTCGVLLLSLVITLYCKRGRKKLLYIFKQPFMR
PVQTTQEEDGCSCRFPEEEEGGCELRVKFSRSADAPAYKQGQNQLYNELNLGRRE
EYDVLDKRRGRDPEMGGKPRRKNPQEGLYNELQKDKMAEAYSEIGMKGERRRG
KGHDGLYQGLSTATKDTYDALHMQALPPR

SEQ ID NO: 212-CAR (KL2B30 LH)
DIQMTQSPSFLSASVGDRVTITCRASQGISSYLAWYQQKPGKAPKFLIYAASTLQS
GVPSRFSGSGSGTEFTLTISSLQPEDFATYYCQQLNSYPLTFGGGTKVEIKGGSEG
KSSGSGSESKSTGGSQVQLQESGPGLVKPSETLSLTCTVSGGSISSYYWSWIRQPPG
KGLEWIGYIYYSGSTNYNPSLKSRVTISVDTSKNQFSLKLSSVTAADTAVYYCAGT
TIFGVVTPNFYYGMDVWGQGTTVTVSSTSTPAPRPPTPAPTIASQPLSLRPEACRPA
AGGAVHTRGLDFACDIYIWAPLAGTCGVLLLSLVITLYCKRGRKKLLYIFKQPFMR
PVQTTQEEDGCSCRFPEEEEGGCELRVKFSRSADAPAYKQGQNQLYNELNLGRRE
EYDVLDKRRGRDPEMGGKPRRKNPQEGLYNELQKDKMAEAYSEIGMKGERRRG
KGHDGLYQGLSTATKDTYDALHMQALPPR

SEQ ID NO: 213-CAR (KL2B53 HL)
EVQLVESGGGVVQPGRSLRLSCVASGFTFSSYDIHWVRQAPGKGLEWVAIISYDG
SKKDYTDSVKGRFTISRDNSKNTLYLQMDSLRVEDSAVYSCARESGWSHYYYG
MDVWGQGTMVTVSSGGSEGKSSGSGSESKSTGGSDIVMTQSPSSLSASVGDRVTI
TCRASQDISNYLAWYQQKPGKVPKFLIYAASTLHSGVPSRFSGSGSGTDFTLTISSL
QPEDVATYYCQKYNSAPYTFGQGTRLEIKTSTPAPRPPTPAPTIASQPLSLRPEACR
PAAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYKQGQNQLYNELNLGR
REEYDVLDKRRGRDPEMGGKPRRKNPQEGLYNELQKDKMAEAYSEIGMKGERR
RGKGHDGLYQGLSTATKDTYDALHMQALPPR

SEQ ID NO: 214-CAR (KL2B53 LH)
DIVMTQSPSSLSASVGDRVTITCRASQDISNYLAWYQQKPGKVPKFLIYAASTLHS
GVPSRFSGSGSGTDFTLTISSLQPEDVATYYCQKYNSAPYTFGQGTRLEIKGGSEGK
SSGSGSESKSTGGSEVQLVESGGGVVQPGRSLRLSCVASGFTFSSYDIHWVRQAPG
KGLEWVAIISYDGSKKDYTDSVKGRFTISRDNSKNTLYLQMDSLRVEDSAVYSCA
RESGWSHYYYYGMDVWGQGTMVTVSSTSTPAPRPPTPAPTIASQPLSLRPEACRP
AAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYKQGQNQLYNELNLGR
REEYDVLDKRRGRDPEMGGKPRRKNPQEGLYNELQKDKMAEAYSEIGMKGERR
RGKGHDGLYQGLSTATKDTYDALHMQALPPR

SEQ ID NO: 215-CAR (KL2B242 HL)
QVQLQESGPGLVKPSETLSLTCTVSGGSISSYYWSWLRQPAGSGLEWIGRLYVSGF
TNYNPSLKSRVTLSLDPSRNQLSLKLSSVTAADTAVYYCAGDSGNYWGWFDPWG
QGTLVTVSSGGSEGKSSGSGSESKSTGGSSYELTQPPSVSVSPGETASITCSGDQLG
ENYACWYQQKPGQSPVLVIYQDSKRPSGIPERFSGSNSGNTATLTISGTQALDEAD
YYCQAWDNSIVVFGGGTKLTVLTSTPAPRPPTPAPTIASQPLSLRPEACRPAAGGA
VHTRGLDFACDIYIWAPLAGTCGVLLLSLVITLYCKRGRKKLLYIFKQPFMRPVQT
TQEEDGCSCRFPEEEEGGCELRVKFSRSADAPAYKQGQNQLYNELNLGRREEYDV
LDKRRGRDPEMGGKPRRKNPQEGLYNELQKDKMAEAYSEIGMKGERRRGKGHD
GLYQGLSTATKDTYDALHMQALPPR

SEQ ID NO: 216-CAR (KL2B242 LH)
SYELTQPPSVSVSPGETASITCSGDQLGENYACWYQQKPGQSPVLVIYQDSKRPSGI
PERFSGSNSGNTATLTISGTQALDEADYYCQAWDNSIVVFGGGTKLTVLGGSEGK
SSGSGSESKSTGGSQVQLQESGPGLVKPSETLSLTCTVSGGSISSYYWSWLRQPAG
SGLEWIGRLYVSGFTNYNPSLKSRVTLSLDPSRNQLSLKLSSVTAADTAVYYCAG
DSGNYWGWFDPWGQGTLVTVSSTSTPAPRPPTPAPTIASQPLSLRPEACRPAAGGA
VHTRGLDFACDIYIWAPLAGTCGVLLLSLVITLYCKRGRKKLLYIFKQPFMRPVQT
TQEEDGCSCRFPEEEEGGCELRVKFSRSADAPAYKQGQNQLYNELNLGRREEYDV
LDKRRGRDPEMGGKPRRKNPQEGLYNELQKDKMAEAYSEIGMKGERRRGKGHD
GLYQGLSTATKDTYDALHMQALPPR

SEQ ID NO: 217-CAR (KL2B467 HL)
QVQLVESGGGVVQPGRSLRLSCAASGFTFSYYGMHWVRQAPGKGLEWVAFISYD
GSNKYYADSVKGRFTISRDNSKNTLYLQMNSLRAEDTAVYYCAHLPYSGSYWAF
DYWGQGTQVTVSSGGSEGKSSGSGSESKSTGGSQSVLTQPPSVSVAPGQTASITCG
GDNIGSKSVHWYQQKPGQAPVLVVYDNSDRPSGIPERFSGSNSGTTATLTISRVEA
GDEADYYCQVWDSSSDHPVVFGGGTKVTVSTPAPRPPTPAPTIASQPLSLRPEAC
RPAAGGAVHTRGLDFACDIYIWAPLAGTCGVLLLSLVITLYCKRGRKKLLYIFKQP

FMRPVQTTQEEDGCSCRFPEEEEGGCELRVKFSRSADAPAYKQGQNQLYNELNLG
RREEYDVLDKRRGRDPEMGGKPRRKNPQEGLYNELQKDKMAEAYSEIGMKGER
RRGKGHDGLYQGLSTATKDTYDALHMQALPPR

SEQ ID NO: 218-CAR (KL2B467 LH)
QSVLTQPPSVSVAPGQTASITCGGDNIGSKSVHWYQQKPGQAPVLVVYDNSDRPS
GIPERFSGSNSGTTATLTISRVEAGDEADYYCQVWDSSSDHVVFGGGTKVTVGG
SEGKSSGSGSESKSTGGSQVQLVESGGGVVQPGRSLRLSCAASGFTFSYYGMHWV
RQAPGKGLEWVAFISYDGSNKYYADSVKGRFTISRDNSKNTLYLQMNSLRAEDT
AVYYCAHLPYSGSYWAFDYWGQGTQVTVSSTSTPAPRPPTPAPTIASQPLSLRPEA
CRPAAGGAVHTRGLDFACDIYIWAPLAGTCGVLLLSLVITLYCKRGRKKLLYIFKQ
PFMRPVQTTQEEDGCSCRFPEEEEGGCELRVKFSRSADAPAYKQGQNQLYNELNL
GRREEYDVLDKRRGRDPEMGGKPRRKNPQEGLYNELQKDKMAEAYSEIGMKGE
RRRGKGHDGLYQGLSTATKDTYDALHMQALPPR

SEQ ID NO: 219-CAR (KL2B494 HL)
QVQLVESGGGLVQPGGSLRLSCAASGFTFSHYAMSWVRQAPGKGLEWVSTIGGS
GGSTYYADSVKGRFTISRDNSKNTLYLQMNSLRAEDTAVYYCAKPHIVMVTALL
YDGMDVWGQGTMVTVSSGGSEGKSSGSGSESKSTGGSSSELTQPPSVSVAPGQTA
RITCGGNNIGSKSVHWYQQKPGQAPVLVVYDDSDRPSGIPERFSGSNSGNTATLTI
SRVEAGDEADYYCQVWDSSSDHVVFGGGTKLTVLTSTPAPRPPTPAPTIASQPLSL
RPEACRPAAGGAVHTRGLDFACDIYIWAPLAGTCGVLLLSLVITLYCKRGRKKLL
YIFKQPFMRPVQTTQEEDGCSCRFPEEEEGGCELRVKFSRSADAPAYKQGQNQLY
NELNLGRREEYDVLDKRRGRDPEMGGKPRRKNPQEGLYNELQKDKMAEAYSEIG
MKGERRRGKGHDGLYQGLSTATKDTYDALHMQALPPR

SEQ ID NO: 220-CAR (KL2B494 LH)
SSELTQPPSVSVAPGQTARITCGGNNIGSKSVHWYQQKPGQAPVLVVYDDSDRPS
GIPERFSGSNSGNTATLTISRVEAGDEADYYCQVWDSSSDHVVFGGGTKLTVLGG
SEGKSSGSGSESKSTGGSQVQLVESGGGLVQPGGSLRLSCAASGFTFSHYAMSWV
RQAPGKGLEWVSTIGGSGGSTYYADSVKGRFTISRDNSKNTLYLQMNSLRAEDTA
VYYCAKPHIVMVTALLYDGMDVWGQGTMVTVSSTSTPAPRPPTPAPTIASQPLSL
RPEACRPAAGGAVHTRGLDFACDIYIWAPLAGTCGVLLLSLVITLYCKRGRKKLL
YIFKQPFMRPVQTTQEEDGCSCRFPEEEEGGCELRVKFSRSADAPAYKQGQNQLY
NELNLGRREEYDVLDKRRGRDPEMGGKPRRKNPQEGLYNELQKDKMAEAYSEIG
MKGERRRGKGHDGLYQGLSTATKDTYDALHMQALPPR

SEQ ID NO: 221-Extracellular antigen-binding domain (KL2B357 HL)
QVQLQESGPGLVKPSQTLSLTCTVSGNSITSDYAWNWIRQFPGKGLEWIGYISYSG
STTYNPSLKSRVTISRDTSKNQFSLKLSSVTAADTAVYYCATGYYYGSGFWGQGT
LVTVSSGGSEGKSSGSGSESKSTGGSDIVLTQSPDSLAVSLGERATINCRASESVEY
FGTSLMHWYQQKPGQPPKLLIYAASNVESGVPDRFSGSGSGTDFTLTISSLQAEDV
AVYFCQQTRKVPYTFGGGTKVEIK SEQ ID NO: 222-Extracellular antigen-binding domain (KL2B357 LH)
DIVLTQSPDSLAVSLGERATINCRASESVEYFGTSLMHWYQQKPGQPPKLLIYAAS
NVESGVPDRFSGSGSGTDFTLTISSLQAEDVAVYFCQQTRKVPYTFGGGTKVEIKG
GSEGKSSGSGSESKSTGGSQVQLQESGPGLVKPSQTLSLTCTVSGNSITSDYAWNW
IRQFPGKGLEWIGYISYSGSTTYNPSLKSRVTISRDTSKNQFSLKLSSVTAADTAVY
YCATGYYYGSGFWGQGTLVTVSS SEQ ID NO: 223-Extracellular antigen-binding domain (KL2B358 HL)
QVQLQESGPGLVKPSQTLSLTCTVSGNSITSDYAWNWIRQPPGKGLEWIGYISYSG
STTYNPSLKSRVTISRDTSKNQFSLKLSSVTAADTAVYYCATGYYYGSGFWGQGT
LVTVSSGGSEGKSSGSGSESKSTGGSEIVLTQSPATLSLSPGERATLSCRASESVEYF
GTSLMHWYQQKPGQPPRLLIYAASNVESGIPARFSGSGSGTDFTLTISSVEPEDFAV
YFCQQTRKVPYTFGGGTKVEIK SEQ ID NO: 224-Extracellular antigen-binding domain (KL2B358 LH)
EIVLTQSPATLSLSPGERATLSCRASESVEYFGTSLMHWYQQKPGQPPRLLIYAASN
VESGIPARFSGSGSGTDFTLTISSVEPEDFAVYFCQQTRKVPYTFGGGTKVEIKGGS
EGKSSGSGSESKSTGGSQVQLQESGPGLVKPSQTLSLTCTVSGNSITSDYAWNWIR
QPPGKGLEWIGYISYSGSTTYNPSLKSRVTISRDTSKNQFSLKLSSVTAADTAVYYC
ATGYYYGSGFWGQGTLVTVSS SEQ ID NO: 225-Extracellular antigen-binding domain (KL2B360 HL)
QVQLQESGPGLVKPSQTLSLTCTVSGNSITSDYAWNWIRQFPGKGLEWIGYISYSG
STTYNPSLKSRVTISRDTSKNQFSLKLSSVTAADTAVYYCATGYYYGSGFWGQGT
LVTVSSGGSEGKSSGSGSESKSTGGSEIVLTQSPATLSLSPGERATLSCRASESVEYF
GTSLMHWYQQKPGQPPRLLIYAASNVESGIPARFSGSGSGTDFTLTISSVEPEDFAV
YFCQQTRKVPYTFGGGTKVEIK SEQ ID NO: 226-Extracellular antigen-binding domain (KL2B360 LH)
EIVLTQSPATLSLSPGERATLSCRASESVEYFGTSLMHWYQQKPGQPPRLLIYAASN
VESGIPARFSGSGSGTDFTLTISSVEPEDFAVYFCQQTRKVPYTFGGGTKVEIKGGS
EGKSSGSGSESKSTGGSQVQLQESGPGLVKPSQTLSLTCTVSGNSITSDYAWNWIR
QFPGKGLEWIGYISYSGSTTYNPSLKSRVTISRDTSKNQFSLKLSSVTAADTAVYYC
ATGYYYGSGFWGQGTLVTVSS SEQ ID NO: 227-Extracellular antigen-binding domain (KL2B30 HL)
QVQLQESGPGLVKPSETLSLTCTVSGGSISSYYWSWIRQPPGKGLEWIGYIYYSGST
NYNPSLKSRVTISVDTSKNQFSLKLSSVTAADTAVYYCAGTTIFGVVTPNFYYGM
DVWGQGTTVTVSSGGSEGKSSGSGSESKSTGGSDIQMTQSPSFLSASVGDRVTITC
RASQGISSYLAWYQQKPGKAPKFLIYAASTLQSGVPSRFSGSGSGTEFTLTISSLQP
EDFATYYCQQLNSYPLTFGGGTKVEIK SEQ ID NO: 228-Extracellular antigen-binding domain (KL2B30 LH)
DIQMTQSPSFLSASVGDRVTITCRASQGISSYLAWYQQKPGKAPKFLIYAASTLQS
GVPSRFSGSGSGTEFTLTISSLQPEDFATYYCQQLNSYPLTFGGGTKVEIKGGSEG
KSSGSGSESKSTGGSQVQLQESGPGLVKPSETLSLTCTVSGGSISSYYWSWIRQPPG
KGLEWIGYIYYSGSTNYNPSLKSRVTISVDTSKNQFSLKLSSVTAADTAVYYCAGT
TIFGVVTPNFYYGMDVWGQGTTVTVSS SEQ ID NO: 229-Extracellular antigen-binding domain (KL2B53 HL)
EVQLVESGGGVVQPGRSLRLSCVASGFTFSSYDIHWVRQAPGKGLEWVAIISYDG
SKKDYTDSVKGRFTISRDNSKNTLYLQMDSLRVEDSAVYSCARESGWSHYYYYG
MDVWGQGTMVTVSSGGSEGKSSGSGSESKSTGGSDIVMTQSPSSLSASVGDRVTI
TCRASQDISNYLAWYQQKPGKVPKFLIYAASTLHSGVPSRFSGSGSGTDFTLTISSL
QPEDVATYYCQKYNSAPYTFGQGTRLEIK SEQ ID NO: 230-Extracellular antigen-binding domain (KL2B53 LH)
DIVMTQSPSSLSASVGDRVTITCRASQDISNYLAWYQQKPGKVPKFLIYAASTLHS
GVPSRFSGSGSGTDFTLTISSLQPEDVATYYCQKYNSAPYTFGQGTRLEIKGGSEGK
SSGSGSESKSTGGSEVQLVESGGGVVQPGRSLRLSCVASGFTFSSYDIHWVRQAPG
KGLEWVAIISYDGSKKDYTDSVKGRFTISRDNSKNTLYLQMDSLRVEDSAVYSCA
RESGWSHYYYYGMDVWGQGTMVTVSS SEQ ID NO: 231-Extracellular antigen-binding domain (KL2B242 HL)
QVQLQESGPGLVKPSETLSLTCTVSGGSISSYYWSWLRQPAGSGLEWIGRLYVSGF
TNYNPSLKSRVTLSLDPSRNQLSLKLSSVTAADTAVYYCAGDSGNYWGWFDPWG
QGTLVTVSSGGSEGKSSGSGSESKSTGGSSYELTQPPSVSVSPGETASITCSGDQLG
ENYACWYQQKPGQSPVLVIYQDSKRPSGIPERFSGSNSGNTATLTISGTQALDEAD
YYCQAWDNSIVVFGGGTKLTVL SEQ ID NO: 232-Extracellular antigen-binding domain (KL2B242 LH)
SYELTQPPSVSVSPGETASITCSGDQLGENYACWYQQKPGQSPVLVIYQDSKRPSGI
PERFSGSNSGNTATLTISGTQALDEADYYCQAWDNSIVVFGGGTKLTVLGGSEGK
SSGSGSESKSTGGSQVQLQESGPGLVKPSETLSLTCTVSGGSISSYYWSWLRQPAG
SGLEWIGRLYVSGFTNYNPSLKSRVTLSLDPSRNQLSLKLSSVTAADTAVYYCAG
DSGNYWGWFDPWGQGTLVTVSS SEQ ID NO: 233-Extracellular antigen-binding domain (KL2B467 HL)
QVQLVESGGGVVQPGRSLRLSCAASGFTFSYYGMHWVRQAPGKGLEWVAFISYD
GSNKYYADSVKGRFTISRDNSKNTLYLQMNSLRAEDTAVYYCAHLPYSGSYWAF
DYWGQGTQVTVSSGGSEGKSSGSGSESKSTGGSQSVLTQPPSVSVAPGQTASITCG
GDNIGSKSVHWYQQKPGQAPVLVVYDNSDRPSGIPERFSGSNSGTTATLTISRVEA
GDEADYYCQVWDSSSDHPVVFGGGTKVTV SEQ ID NO: 234-Extracellular antigen-binding domain (KL2B467 LH)
QSVLTQPPSVSVAPGQTASITCGGDNIGSKSVHWYQQKPGQAPVLVVYDNSDRPS
GIPERFSGSNSGTTATLTISRVEAGDEADYYCQVWDSSSDHPVVFGGGTKVTVGG
SEGKSSGSGSESKSTGGSQVQLVESGGGVVQPGRSLRLSCAASGFTFSYYGMHWV
RQAPGKGLEWVAFISYDGSNKYYADSVKGRFTISRDNSKNTLYLQMNSLRAEDT
AVYYCAHLPYSGSYWAFDYWGQGTQVTVSS SEQ ID NO: 235-Extracellular antigen-binding domain (KL2B494 HL)
QVQLVESGGGLVQPGGSLRLSCAASGFTFSHYAMSWVRQAPGKGLEWVSTIGGS
GGSTYYADSVKGRFTISRDNSKNTLYLQMNSLRAEDTAVYYCAKPHIVMVTALL
YDGMDVWGQGTMVTVSSGGSEGKSSGSGSESKSTGGSSSELTQPPSVSVAPGQTA
RITCGGNNIGSKSVHWYQQKPGQAPVLVVYDDSDRPSGIPERFSGSNSGNTATLTI
SRVEAGDEADYYCQVWDSSSDHVVFGGGTKLTVL SEQ ID NO: 236-Extracellular antigen-binding domain (KL2B494 LH)
SSELTQPPSVSVAPGQTARITCGGNNIGSKSVHWYQQKPGQAPVLVVYDDSDRPS
GIPERFSGSNSGNTATLTISRVEAGDEADYYCQVWDSSSDHVVFGGGTKLTVLGG
SEGKSSGSGSESKSTGGSQVQLVESGGGLVQPGGSLRLSCAASGFTFSHYAMSWV
RQAPGKGLEWVSTIGGSGGSTYYADSVKGRFTISRDNSKNTLYLQMNSLRAEDTA
VYYCAKPHIVMVTALLYDGMDVWGQGTMVTVSS SEQ ID NO: 237-Linker sequence
GGGSGGGS SEQ ID NO: 238-Linker sequence
GGGSGGGSGGGS SEQ ID NO: 239-Linker sequence
GGGSGGGSGGGSGGGS SEQ ID NO: 240-Linker sequence
GGGSGGGSGGGSGGGSGGGS SEQ ID NO: 241-Linker sequence
GGGGSGGGGSGGGGS SEQ ID NO: 242-Linker sequence
GGGGSGGGGSGGGGSGGGGS SEQ ID NO: 243-Linker sequence
GGGGSGGGGSGGGGSGGGGSGGGGS SEQ ID NO: 244-Linker sequence
GSTSGSGKPGSGEGSTKG SEQ ID NO: 245-Linker sequence
IRPRAIGGSKPRVA SEQ ID NO: 246-Linker sequence
GKGGSGKGGSGKGGS SEQ ID NO: 247-Linker sequence
GGKGSGGKGSGGKGS SEQ ID NO: 248-Linker sequence
GGGKSGGGKSGGGKS SEQ ID NO: 249-Linker sequence
GKGKSGKGKSGKGKS SEQ ID NO: 250-Linker sequence
GGGKSGGKGSGKGGS SEQ ID NO: 251-Linker sequence
GKPGSGKPGSGKPGS SEQ ID NO: 252-Linker sequence
GKPGSGKPGSGKPGSGKPGS SEQ ID NO: 253-Linker sequence
GKGKSGKGKSGKGKSGKGKS SEQ ID NO: 254-Linker sequence
STAGDTHLGGEDFD SEQ ID NO: 255-Linker sequence
GEGGSGEGGSGEGGS SEQ ID NO: 256-Linker sequence
GGEGSGGEGSGGEGS SEQ ID NO: 257-Linker sequence
GEGESGEGESGEGES SEQ ID NO: 258-Linker sequence
GGGESGGEGSGEGGS SEQ ID NO: 259-Linker sequence
GEGESGEGESGEGESGEGES SEQ ID NO: 260-Linker sequence
GSTSGSGKPGSGEGSTKG SEQ ID NO: 261-Linker sequence
PRGASKSGSASQTGSAPGS SEQ ID NO: 262-Linker sequence
GTAAAGAGAAGGAAAGAAG SEQ ID NO: 263-Linker sequence
GTSGSSGSGSGGSGSGGGG SEQ ID NO: 264-Linker sequence
GKPGSGKPGSGKPGSGKPGS SEQ ID NO: 265-Linker sequence
GSGS SEQ ID NO: 266-Linker sequence
APAPAPAPAP SEQ ID NO: 267-Linker sequence
APAPAPAPAPAPAPAPAP SEQ ID NO: 268-Linker sequence
AEAAAKEAAAKEAAAAKEAAAAKEAAAAKAAA SEQ ID NO: 269-CAR hinge sequence
EPKSCDKTHTCPPCP SEQ ID NO: 270-CAR hinge sequence
ERKCCVECPPCP SEQ ID NO: 271-CAR hinge sequence
ELKTPLGDTTHTCPRCP(EPKSCDTPPPCPRCP)3

SEQ ID NO: 272-CAR hinge sequence
ESKYGPPCPSCP

SEQ ID NO: 273-Extracellular antigen-binding domain 1
(HL_HCG5_LCD6_20AA) with signal peptide
MAWVWTLLFLMAAAQSIQAQVQLQESGPGLVKPSDTLSLTCAVSGNSITSDYAW
NWIRQFPGKGLEWMGYISYSGSTTYNPSLKSRVTISRDTSKNQFSLKLSSVTPVDT
AVYYCATGYYYGSGFWGQGTLVTVSSGGSEGKSSGSGSESKSTGGSDIVLTQSPD
SLAVSLGERATINCKASESVEYFGTSLMHWYQQKPGQPPKLLIYAASNRESGVPD
RFSGSGSGTDFTLTIQSVQAEDVSVYFCQQTRKVPYTFGQGTKLEIK SEQ ID NO: 274-Extracellular antigen-binding domain 2
(HL_HCG5_LCHumanized_20AA) with signal peptide
MAWVWTLLFLMAAAQSIQAQVQLQESGPGLVKPSDTLSLTCAVSGNSITSDYAW
NWIRQFPGKGLEWMGYISYSGSTTYNPSLKSRVTISRDTSKNQFSLKLSSVTPVDT
AVYYCATGYYYGSGFWGQGTLVTVSSGGSEGKSSGSGSESKSTGGSDIVLTQSPD
SLAVSLGERATINCKASESVEYFGTSLMHWYQQKPGQPPKLLIYAASNRESGVPD
RFSGSGSGTDFTLTISSLQAEDVAVYYCQQTRKVPYTFGQGTKLEIK SEQ ID NO: 275-Extracellular antigen-binding domain 3 (HL_HCF3_LCB7_20AA)
with signal peptide
MAWVWTLLFLMAAAQSIQAQVQLQESGPGLVKPSDTLSLTCAVSGNSITSDYAW
NWIRQFPGKGLEWIGYISYSGSTTYNPSLKSRVTISRDTSKNQFSLKLSSVTPVDTA
VYYCATGYYYGSGFWGQGTLVTVSSGGSEGKSSGSGSESKSTGGSDIVLTQSPDS
LAVSLGERATINCKASESVEYFGTSLMHWYQQKPGQPPKLLIYAASNRESGVPDR
FSGSGSGTDFTLTISSVQAEDVAVYYCQQTRKVPYTFGQGTKLEIK SEQ ID NO: 276-Extracellular antigen-binding domain 4
(HL_HCG5_LCB7_20AA) with signal peptide
MAWVWTLLFLMAAAQSIQAQVQLQESGPGLVKPSDTLSLTCAVSGNSITSDYAW
NWIRQFPGKGLEWMGYISYSGSTTYNPSLKSRVTISRDTSKNQFSLKLSSVTPVDT
AVYYCATGYYYGSGFWGQGTLVTVSSGGSEGKSSGSGSESKSTGGSDIVLTQSPD
SLAVSLGERATINCKASESVEYFGTSLMHWYQQKPGQPPKLLIYAASNRESGVPD
RFSGSGSGTDFTLTISSVQAEDVAVYYCQQTRKVPYTFGQGTKLEIK SEQ ID NO: 277-Extracellular antigen-binding domain 5
(LH_LCD6_HCG5_20AA) with signal peptide
MAWVWTLLFLMAAAQSIQADIVLTQSPDSLAVSLGERATINCKASESVEYFGTSL
MHWYQQKPGQPPKLLIYAASNRESGVPDRFSGSGSGTDFTLTIQSVQAEDVSVYF
CQQTRKVPYTFGQGTKLEIKGGSEGKSSGSGSESKSTGGSQVQLQESGPGLVKPSD
TLSLTCAVSGNSITSDYAWNWIRQFPGKGLEWMGYISYSGSTTYNPSLKSRVTISR
DTSKNQFSLKLSSVTPVDTAVYYCATGYYYGSGFWGQGTLVTVSS SEQ ID NO: 278-Extracellular antigen-binding domain 6
(LH_LCHumanized_HCF3_20AA) with signal peptide
MAWVWTLLFLMAAAQSIQADIVLTQSPDSLAVSLGERATINCKASESVEYFGTSL
MHWYQQKPGQPPKLLIYAASNRESGVPDRFSGSGSGTDFTLTISSLQAEDVAVYY
CQQTRKVPYTFGQGTKLEIKGGSEGKSSGSGSESKSTGGSQVQLQESGPGLVKPSD
TLSLTCAVSGNSITSDYAWNWIRQFPGKGLEWIGYISYSGSTTYNPSLKSRVTISRD
TSKNQFSLKLSSVTPVDTAVYYCATGYYYGSGFWGQGTLVTVSS SEQ ID NO: 279-Extracellular antigen-binding domain 7
(LH_LCHumanized_HCG5_20AA) with signal peptide
MAWVWTLLFLMAAAQSIQADIVLTQSPDSLAVSLGERATINCKASESVEYFGTSL
MHWYQQKPGQPPKLLIYAASNRESGVPDRFSGSGSGTDFTLTISSLQAEDVAVYY
CQQTRKVPYTFGQGTKLEIKGGSEGKSSGSGSESKSTGGSQVQLQESGPGLVKPSD
TLSLTCAVSGNSITSDYAWNWIRQFPGKGLEWMGYISYSGSTTYNPSLKSRVTISR
DTSKNQFSLKLSSVTPVDTAVYYCATGYYYGSGFWGQGTLVTVSS SEQ ID NO: 280-Extracellular antigen-binding domain 8 (LH_LCB7_HCF3_20AA) with signal peptide
MAWVWTLLFLMAAAQSIQADIVLTQSPDSLAVSLGERATINCKASESVEYFGTSL
MHWYQQKPGQPPKLLIYAASNRESGVPDRFSGSGSGTDFTLTISSVQAEDVAVYY
CQQTRKVPYTFGQGTKLEIKGGSEGKSSGSGSESKSTGGSQVQLQESGPGLVKPSD
TLSLTCAVSGNSITSDYAWNWIRQFPGKGLEWIGYISYSGSTTYNPSLKSRVTISRD
TSKNQFSLKLSSVTPVDTAVYYCATGYYYGSGFWGQGTLVTVSS SEQ ID NO: 281-Extracellular antigen-binding domain 9 (LH_LCB7_HCG5_20AA) with signal peptide
MAWVWTLLFLMAAAQSIQADIVLTQSPDSLAVSLGERATINCKASESVEYFGTSL
MHWYQQKPGQPPKLLIYAASNRESGVPDRFSGSGSGTDFTLTISSVQAEDVAVYY
CQQTRKVPYTFGQGTKLEIKGGSEGKSSGSGSESKSTGGSQVQLQESGPGLVKPSD
TLSLTCAVSGNSITSDYAWNWIRQFPGKGLEWMGYISYSGSTTYNPSLKSRVTISR
DTSKNQFSLKLSSVTPVDTAVYYCATGYYYGSGFWGQGTLVTVSS SEQ ID NO: 282-Extracellular antigen-binding domain 10 (LH_LCD6_HCF3_20AA) with signal peptide
MAWVWTLLFLMAAAQSIQADIVLTQSPDSLAVSLGERATINCKASESVEYFGTSL
MHWYQQKPGQPPKLLIYAASNRESGVPDRFSGSGSGTDFTLTIQSVQAEDVSVYF
CQQTRKVPYTFGQGTKLEIKGGSEGKSSGSGSESKSTGGSQVQLQESGPGLVKPSD
TLSLTCAVSGNSITSDYAWNWIRQFPGKGLEWIGYISYSGSTTYNPSLKSRVTISRD
TSKNQFSLKLSSVTPVDTAVYYCATGYYYGSGFWGQGTLVTVSS SEQ ID NO: 283-Extracellular antigen-binding domain 11 (HL_HCHumanized_LCB7_20AA) with signal peptide
MAWVWTLLFLMAAAQSIQAVQLQESGPGLVKPSDTLSLTCAVSGNSITSDYAW
NWIRQPPGKGLEWIGYISYSGSTTYNPSLKSRVTMSRDTSKNQFSLKLSSVTAVDT
AVYYCATGYYYGSGFWGQGTLVTVSSGGSEGKSSGSGSESKSTGGSDIVLTQSPD
SLAVSLGERATINCKASESVEYFGTSLMHWYQQKPGQPPKLLIYAASNRESGVPD
RFSGSGSGTDFTLTISSVQAEDVAVYYCQQTRKVPYTFGQGTKLEIK SEQ ID NO: 284-Extracellular antigen-binding domain 12 (HL_HCHumanized_LCD6_20AA) with signal peptide
MAWVWTLLFLMAAAQSIQAVQLQESGPGLVKPSDTLSLTCAVSGNSITSDYAW
NWIRQPPGKGLEWIGYISYSGSTTYNPSLKSRVTMSRDTSKNQFSLKLSSVTAVDT
AVYYCATGYYYGSGFWGQGTLVTVSSGGSEGKSSGSGSESKSTGGSDIVLTQSPD
SLAVSLGERATINCKASESVEYFGTSLMHWYQQKPGQPPKLLIYAASNRESGVPD
RFSGSGSGTDFTLTIQSVQAEDVSVYFCQQTRKVPYTFGQGTKLEIK SEQ ID NO: 285-Extracellular antigen-binding domain 13 (HL_HCHumanized_LCHumanized_20AA) with signal peptide
MAWVWTLLFLMAAAQSIQAVQLQESGPGLVKPSDTLSLTCAVSGNSITSDYAW
NWIRQPPGKGLEWIGYISYSGSTTYNPSLKSRVTMSRDTSKNQFSLKLSSVTAVDT
AVYYCATGYYYGSGFWGQGTLVTVSSGGSEGKSSGSGSESKSTGGSDIVLTQSPD
SLAVSLGERATINCKASESVEYFGTSLMHWYQQKPGQPPKLLIYAASNRESGVPD
RFSGSGSGTDFTLTISSLQAEDVAVYYCQQTRKVPYTFGQGTKLEIK SEQ ID NO: 286-Extracellular antigen-binding domain 14 (LH_LCD6_HCHumanized_20AA) with signal peptide
MAWVWTLLFLMAAAQSIQADIVLTQSPDSLAVSLGERATINCKASESVEYFGTSL
MHWYQQKPGQPPKLLIYAASNRESGVPDRFSGSGSGTDFTLTIQSVQAEDVSVYF
CQQTRKVPYTFGQGTKLEIKGGSEGKSSGSGSESKSTGGSQVQLQESGPGLVKPSD
TLSLTCAVSGNSITSDYAWNWIRQPPGKGLEWIGYISYSGSTTYNPSLKSRVTMSR
DTSKNQFSLKLSSVTAVDTAVYYCATGYYYGSGFWGQGTLVTVSS SEQ ID NO: 287-Extracellular antigen-binding domain 15 (LH_LCHumanized_HCHumanized_20AA) with signal peptide
MAWVWTLLFLMAAAQSIQADIVLTQSPDSLAVSLGERATINCKASESVEYFGTSL
MHWYQQKPGQPPKLLIYAASNRESGVPDRFSGSGSGTDFTLTISSLQAEDVAVYY
CQQTRKVPYTFGQGTKLEIKGGSEGKSSGSGSESKSTGGSQVQLQESGPGLVKPSD
TLSLTCAVSGNSITSDYAWNWIRQPPGKGLEWIGYISYSGSTTYNPSLKSRVTMSR
DTSKNQFSLKLSSVTAVDTAVYYCATGYYYGSGFWGQGTLVTVSS SEQ ID NO: 288-Extracellular antigen-binding domain 16 (LH_LCB7_HCHumanized_20AA) with signal peptide
MAWVWTLLFLMAAAQSIQADIVLTQSPDSLAVSLGERATINCKASESVEYFGTSL
MHWYQQKPGQPPKLLIYAASNRESGVPDRFSGSGSGTDFTLTISSVQAEDVAVYY
CQQTRKVPYTFGQGTKLEIKGGSEGKSSGSGSESKSTGGSQVQLQESGPGLVKPSD
TLSLTCAVSGNSITSDYAWNWIRQPPGKGLEWIGYISYSGSTTYNPSLKSRVTMSR
DTSKNQFSLKLSSVTAVDTAVYYCATGYYYGSGFWGQGTLVTVSS SEQ ID NO: 289-Extracellular antigen-binding domain 17 (KL2B413_HL) with signal peptide
MAWVWTLLFLMAAAQSIQAEVQLVESGGGLVQPGGSLRLSCAASGFTFSSYWMT
WVRQAPGKGLEWVANIKQDGSERYYVDSVKGRFTISRDNAKNSLYLQMNSLRAE
DTAVYYCARDQNYDILTGHYGMDVWGQGTTVTVSSGGSEGKSSGSGSESKSTGG
SEIVLTQSPSFLSASVGDRVTITCRASQGISSYLSWYQQKPGKAPKLLIYATSTLQSG
VPSRFSGSGSGTEFTLTISSLQPEDFATYYCQQLNSYPRTFGQGTKVEIK SEQ ID NO: 290-Extracellular antigen-binding domain 18 (KL2B413 LH) with signal peptide
MAWVWTLLFLMAAAQSIQAEIVLTQSPSFLSASVGDRVTITCRASQGISSYLSWYQ
QKPGKAPKLLIYATSTLQSGVPSRFSGSGSGTEFTLTISSLQPEDFATYYCQQLNSY
PRTFGQGTKVEIKGGSEGKSSGSGSESKSTGGSEVQLVESGGGLVQPGGSLRLSCA
ASGFTFSSYWMTWVRQAPGKGLEWVANIKQDGSERYYVDSVKGRFTISRDNAKN
SLYLQMNSLRAEDTAVYYCARDQNYDILTGHYGMDVWGQGTTVTVSS SEQ ID NO: 291-Extracellular antigen-binding domain 19 (KL2B359-HL) with signal peptide
MAWVWTLLFLMAAAQSIQAQVQLQESGPGLVKPSQTLSLTCTVSGNSITSDYAW
NWIRQFPGKRLEWIGYISYSGSTTYNPSLKSRVTISRDTSKNQFSLKLSSVTAADTA
VYYCATGYYYGSGFWGQGTLVTVSSGGSEGKSSGSGSESKSTGGSEIVLTQSPATL
SLSPGERATLSCRASESVEYFGTSLMHWYQQKPGQPPRLLIYAASNVESGIPARFS
GSGSGTDFTLTISSVEPEDFAVYFCQQTRKVPYTFGGGTKVEIK SEQ ID NO: 292-Extracellular antigen-binding domain 20 (KL2B359-LH) with signal peptide
MAWVWTLLFLMAAAQSIQAEIVLTQSPATLSLSPGERATLSCRASESVEYFGTSLM
HWYQQKPGQPPRLLIYAASNVESGIPARFSGSGSGTDFTLTISSVEPEDFAVYFCQQ
TRKVPYTFGGGTKVEIKGGSEGKSSGSGSESKSTGGSQVQLQESGPGLVKPSQTLS
LTCTVSGNSITSDYAWNWIRQFPGKRLEWIGYISYSGSTTYNPSLKSRVTISRDTSK
NQFSLKLSSVTAADTAVYYCATGYYYGSGFWGQGTLVTVSS SEQ ID NO: 293-Extracellular antigen-binding domain (KL2B357 HL) with signal peptide
MAWVWTLLFLMAAAQSIQAQVQLQESGPGLVKPSQTLSLTCTVSGNSITSDYAW
NWIRQFPGKGLEWIGYISYSGSTTYNPSLKSRVTISRDTSKNQFSLKLSSVTAADTA
VYYCATGYYYGSGFWGQGTLVTVSSGGSEGKSSGSGSESKSTGGSDIVLTQSPDS
LAVSLGERATINCRASESVEYFGTSLMHWYQQKPGQPPKLLIYAASNVESGVPDR
FSGSGSGTDFTLTISSLQAEDVAVYFCQQTRKVPYTFGGGTKVEIK SEQ ID NO: 294-Extracellular antigen-binding domain (KL2B357 LH) with signal peptide
MAWVWTLLFLMAAAQSIQADIVLTQSPDSLAVSLGERATINCRASESVEYFGTSL
MHWYQQKPGQPPKLLIYAASNVESGVPDRFSGSGSGTDFTLTISSLQAEDVAVYF
CQQTRKVPYTFGGGTKVEIKGGSEGKSSGSGSESKSTGGSQVQLQESGPGLVKPSQ
TLSLTCTVSGNSITSDYAWNWIRQFPGKGLEWIGYISYSGSTTYNPSLKSRVTISRD
TSKNQFSLKLSSVTAADTAVYYCATGYYYGSGFWGQGTLVTVSS SEQ ID NO: 295-Extracellular antigen-binding domain (KL2B358 HL) with signal peptide
MAWVWTLLFLMAAAQSIQAQVQLQESGPGLVKPSQTLSLTCTVSGNSITSDYAW
NWIRQPPGKGLEWIGYISYSGSTTYNPSLKSRVTISRDTSKNQFSLKLSSVTAADTA
VYYCATGYYYGSGFWGQGTLVTVSSGGSEGKSSGSGSESKSTGGSEIVLTQSPATL
SLSPGERATLSCRASESVEYFGTSLMHWYQQKPGQPPRLLIYAASNVESGIPARFS
GSGSGTDFTLTISSVEPEDFAVYFCQQTRKVPYTFGGGTKVEIK SEQ ID NO: 296-Extracellular antigen-binding domain (KL2B358 LH) with signal peptide
MAWVWTLLFLMAAAQSIQAEIVLTQSPATLSLSPGERATLSCRASESVEYFGTSLM
HWYQQKPGQPPRLLIYAASNVESGIPARFSGSGSGTDFTLTISSVEPEDFAVYFCQQ
TRKVPYTFGGGTKVEIKGGSEGKSSGSGSESKSTGGSQVQLQESGPGLVKPSQTLS
LTCTVSGNSITSDYAWNWIRQPPGKGLEWIGYISYSGSTTYNPSLKSRVTISRDTSK
NQFSLKLSSVTAADTAVYYCATGYYYGSGFWGQGTLVTVSS SEQ ID NO: 297-Extracellular antigen-binding domain (KL2B360 HL) with signal peptide
MAWVWTLLFLMAAAQSIQAQVQLQESGPGLVKPSQTLSLTCTVSGNSITSDYAW
NWIRQFPGKGLEWIGYISYSGSTTYNPSLKSRVTISRDTSKNQFSLKLSSVTAADTA
VYYCATGYYYGSGFWGQGTLVTVSSGGSEGKSSGSGSESKSTGGSEIVLTQSPATL
SLSPGERATLSCRASESVEYFGTSLMHWYQQKPGQPPRLLIYAASNVESGIPARFS
GSGSGTDFTLTISSVEPEDFAVYFCQQTRKVPYTFGGGTKVEIK SEQ ID NO: 298-Extracellular antigen-binding domain (KL2B360 LH) with signal peptide
MAWVWTLLFLMAAAQSIQAEIVLTQSPATLSLSPGERATLSCRASESVEYFGTSLM
HWYQQKPGQPPRLLIYAASNVESGIPARFSGSGSGTDFTLTISSVEPEDFAVYFCQQ
TRKVPYTFGGGTKVEIKGGSEGKSSGSGSESKSTGGSQVQLQESGPGLVKPSQTLS
LTCTVSGNSITSDYAWNWIRQFPGKGLEWIGYISYSGSTTYNPSLKSRVTISRDTSK
NQFSLKLSSVTAADTAVYYCATGYYYGSGFWGQGTLVTVSS SEQ ID NO: 299-Extracellular antigen-binding domain (KL2B30 HL) with signal peptide
MAWVWTLLFLMAAAQSIQAQVQLQESGPGLVKPSETLSLTCTVSGGSISSYYWS
WIRQPPGKGLEWIGYIYYSGSTNYNPSLKSRVTISVDTSKNQFSLKLSSVTAADTA
VYYCAGTTIFGVVTPNFYYGMDVWGQGTTVTVSSGGSEGKSSGSGSESKSTGGSD

```
IQMTQSPSFLSASVGDRVTITCRASQGISSYLAWYQQKPGKAPKFLIYAASTLQSG
VPSRFSGSGSGTEFTLTISSLQPEDFATYYCQQLNSYPLTFGGGTKVEIK

SEQ ID NO: 300-Extracellular antigen-binding domain (KL2B30 LH) with signal
peptide
MAWVWTLLFLMAAAQSIQADIQMTQSPSFLSASVGDRVTITCRASQGISSYLAWY
QQKPGKAPKFLIYAASTLQSGVPSRFSGSGSGTEFTLTISSLQPEDFATYYCQQLNS
YPLTFGGGTKVEIKGGSEGKSSGSGSESKSTGGSQVQLQESGPGLVKPSETLSLTCT
VSGGSISSYYWSWIRQPPGKGLEWIGYIYYSGSTNYNPSLKSRVTISVDTSKNQFSL
KLSSVTAADTAVYYCAGTTIFGVVTPNFYYGMDVWGQGTTVTVSS SEQ ID NO: 301-Extracellular antigen-binding domain (KL2B53 HL) with signal
peptide
MAWVWTLLFLMAAAQSIQAEVQLVESGGGVVQPGRSLRLSCVASGFTFSSYDIH
WVRQAPGKGLEWVAIISYDGSKKDYTDSVKGRFTISRDNSKNTLYLQMDSLRVE
DSAVYSCARESGWSHYYYYGMDVWGQGTMVTVSSGGSEGKSSGSGSESKSTGG
SDIVMTQSPSSLSASVGDRVTITCRASQDISNYLAWYQQKPGKVPKFLIYAASTLH
SGVPSRFSGSGSGTDFTLTISSLQPEDVATYYCQKYNSAPYTFGQGTRLEIK SEQ ID NO: 302-Extracellular antigen-binding domain (KL2B53 LH) with signal
peptide
MAWVWTLLFLMAAAQSIQADIVMTQSPSSLSASVGDRVTITCRASQDISNYLAWY
QQKPGKVPKFLIYAASTLHSGVPSRFSGSGSGTDFTLTISSLQPEDVATYYCQKYNS
APYTFGQGTRLEIKGGSEGKSSGSGSESKSTGGSEVQLVESGGGVVQPGRSLRLSC
VASGFTFSSYDIHWVRQAPGKGLEWVAIISYDGSKKDYTDSVKGRFTISRDNSKNT
LYLQMDSLRVEDSAVYSCARESGWSHYYYYGMDVWGQGTMVTVSS SEQ ID NO: 303-Extracellular antigen-binding domain (KL2B242 HL) with signal
peptide
MAWVWTLLFLMAAAQSIQAQVQLQESGPGLVKPSETLSLTCTVSGGSISSYYWS
WLRQPAGSGLEWIGRLYVSGFTNYNPSLKSRVTLSLDPSRNQLSLKLSSVTAADTA
VYYCAGDSGNYWGWFDPWGQGTLVTVSSGGSEGKSSGSGSESKSTGGSSYELTQ
PPSVSVSPGETASITCSGDQLGENYACWYQQKPGQSPVLVIYQDSKRPSGIPERFSG
SNSGNTATLTISGTQALDEADYYCQAWDNSIVVFGGGTKLTVL SEQ ID NO: 304-Extracellular antigen-binding domain (KL2B242 LH) with signal
peptide
MAWVWTLLFLMAAAQSIQASYELTQPPSVSVSPGETASITCSGDQLGENYACWY
QQKPGQSPVLVIYQDSKRPSGIPERFSGSNSGNTATLTISGTQALDEADYYCQAWD
NSIVVFGGGTKLTVLGGSEGKSSGSGSESKSTGGSQVQLQESGPGLVKPSETLSLTC
TVSGGSISSYYWSWLRQPAGSGLEWIGRLYVSGFTNYNPSLKSRVTLSLDPSRNQL
SLKLSSVTAADTAVYYCAGDSGNYWGWFDPWGQGTLVTVSS SEQ ID NO: 305-Extracellular antigen-binding domain (KL2B467 HL) with signal
peptide
MAWVWTLLFLMAAAQSIQAQVQLVESGGGVVQPGRSLRLSCAASGFTFSYYGM
HWVRQAPGKGLEWVAFISYDGSNKYYADSVKGRFTISRDNSKNTLYLQMNSLRA
EDTAVYYCAHLPYSGSYWAFDYWGQGTQVTVSSGGSEGKSSGSGSESKSTGGSQ
SVLTQPPSVSVAPGQTASITCGGDNIGSKSVHWYQQKPGQAPVLVVYDNSDRPSGI
PERFSGSNSGTTATLTISRVEAGDEADYYCQVWDSSSDHPVVFGGGTKVTV SEQ ID NO: 306-Extracellular antigen-binding domain (KL2B467 LH) with signal
peptide
MAWVWTLLFLMAAAQSIQAQSVLTQPPSVSVAPGQTASITCGGDNIGSKSVHWY
QQKPGQAPVLVVYDNSDRPSGIPERFSGSNSGTTATLTISRVEAGDEADYYCQVW
DSSSDHPVVFGGGTKVTVGGSEGKSSGSGSESKSTGGSQVQLVESGGGVVQPGRS
LRLSCAASGFTFSYYGMHWVRQAPGKGLEWVAFISYDGSNKYYADSVKGRFTIS
RDNSKNTLYLQMNSLRAEDTAVYYCAHLPYSGSYWAFDYWGQGTQVTVSS SEQ ID NO: 307-Extracellular antigen-binding domain (KL2B494 HL) with signal
peptide
MAWVWTLLFLMAAAQSIQAQVQLVESGGGLVQPGGSLRLSCAASGFTFSHYAMS
WVRQAPGKGLEWVSTIGGSGGSTYYADSVKGRFTISRDNSKNTLYLQMNSLRAE
DTAVYYCAKPHIVMVTALLYDGMDVWGQGTMVTVSSGGSEGKSSGSGSESKST
GGSSSELTQPPSVSVAPGQTARITCGGNNIGSKSVHWYQQKPGQAPVLVVYDDSD
RPSGIPERFSGSNSGNTATLTISRVEAGDEADYYCQVWDSSSDHVVFGGGTKLTVL SEQ ID NO: 308-Extracellular antigen-binding domain (KL2B494 LH) with signal
peptide
MAWVWTLLFLMAAAQSIQASSELTQPPSVSVAPGQTARITCGGNNIGSKSVHWY
QQKPGQAPVLVVYDDSDRPSGIPERFSGSNSGNTATLTISRVEAGDEADYYCQVW
DSSSDHVVFGGGTKLTVLGGSEGKSSGSGSESKSTGGSQVQLVESGGGLVQPGGS
LRLSCAASGFTFSHYAMSWVRQAPGKGLEWVSTIGGSGGSTYYADSVKGRFTISR
DNSKNTLYLQMNSLRAEDTAVYYCAKPHIVMVTALLYDGMDVWGQGTMVTVS
S
```

SEQ ID NO: 309-heavy chain CDR1 sequence
GFTFSSYWMT

SEQ ID NO: 310-heavy chain CDR2 sequence
NIKQDGSERY

SEQ ID NO: 311-heavy chain CDR3 sequence
DQNYDILTGHYGMDV

SEQ ID NO: 312-light chain CDR1 sequence
RASQGISSYLS

SEQ ID NO: 313-light chain CDR2 sequence
ATSTLQS

SEQ ID NO: 314-heavy chain CDR1 sequence
SYWMT

SEQ ID NO: 315-heavy chain CDR2 sequence
NIKQDGSERYYVDSVKG

SEQ ID NO: 316-heavy chain CDR2 sequence
YISYSGSTTYSPSLKS

SEQ ID NO: 317-VH (m11B6)
DVQLQESGPGLVKPSQSLSLTCTVTGNSITSDYAWNWIRQFPGNRLEWMGYISYSG
STTYSPSLKSRFSITRDTSKNQFFLQLNSVTPEDTATYFCATGYYYGSGFWGQGTLV
TVSS

SEQ ID NO: 318-VL (m11B6)
DIVLTQSPASLAVSLGQRATISCRASESVEYFGTSLMHWYRQKPGQPPKLLIYAASN
VESGVPARFSGSGSGTDFSLNIQPVEEDDFSMYFCQQTRKVPYTFGGGTKLEIK

SEQ ID NO: 319-human Kallikrein-2 6-His protein
VPLIEGRIVGGWECEKHSQPWQVAVYSHGWAHCGGVLVHPQWVLTAAHCLKKN
SQVWLGRHNLFEPEDTGQRVPVSHSFPHPLYNMSLLKHQSLRPDEDSSHDLMLLR
LSEPAKITDVVKVLGLPTQEPALGTTCYASGWGSIEPEEFLRPRSLQCVSLHYSEKV
TEFMLCAGLWTGGKDTCGGDSGGPLVCNGVLQGITSWGPEPCALPEKPAVYTKV
VHYRKWIKDTIAANPHHHHHH SEQ ID NO: 320-VH cDNA (m11B6)
GATGTGCAGCTTCAGGAGTCTGGACCCGGACTTGTTAAACCAAGTCAGTCTCTG
TCCCTGACCTGTACCGTCACCGGCAACAGCATCACAAGCGATTACGCATGGAA
CTGGATCAGGCAGTTCCCTGGAAATCGACTCGAATGGATGGGCTACATTTCATA
CTCCGGTTCAACCACTTACTCTCCATCCTTGAAATCTAGGTTCAGCATCACCCG
TGATACCTCAAAGAACCAATTTTTTCTGCAACTGAATAGCGTAACTCCAGAGGA
CACAGCCACATATTTCTGCGCACTGGGTATTACTATGGCTCAGGTTTCTGGGG
TCAGGGCACTCTCGTCACCGTCAGCAGC SEQ ID NO: 321-VH cDNA (hu11B6)
CAGGTCCAACTGCAAGAGAGCGGACCCGGGCCTGGTAAAGCCATCCGACACATT
GTCCCTGACGTGTGCGGTAAGTGGAAACTCTATCACTAGCGACTATGCGTGGA
ATTGGATAAGACAACCGCCGGGCAAGGGGCTGGAATGGATAGGATATATCAGC
TATTCCGGTTCTACGACATACAATCCTTCCCTGAAAAGCAGAGTCACTATGTCA
CGCGACACGTCCAAGAATCAGTTCTCATTGAAATTGTCATCCGTAACGGCCGTT
GACACTGCGGTTTATTATTGCGCAACCGGATATTACTACGGCTCTGGTTTTTGG
GGACAGGGAACACTTGTTACTGTTAGTTCA SEQ ID NO: 322-VH cDNA (HCF3-LCD6)
CAGGTGCAGCTGCAGGAGAGCGGCCCAGGCCTGGTGAAGCCAAGCGACACCCT
GAGCCTGACCTGCGCCGTGAGCGGCAACAGCATCACCAGCGACTACGCCTGGA
ACTGGATCCGCCAGTTCCCAGGCAAGGGCCTGGAGTGGATCGGCTACATCAGC
TACAGCGGCAGCACCACCTACAACCCAAGCCTGAAGAGCCGCGTCACCATCAG
CCGCGACACCAGCAAGAACCAGTTCAGCCTGAAGCTGAGCAGCGTGACCCCTG
TGGACACCGCCGTGTACTACTGCGCCACCGGCTACTACTACGGCAGCGGCTTCT
GGGGCCAGGGCACCCTGGTGACCGTGAGCAGC SEQ ID NO: 323-VH cDNA (HCG5-LCB7)
CAGGTGCAGCTGCAGGAGAGCGGCCCAGGCCTGGTGAAGCCAAGCGACACCCT
GAGCCTGACCTGCGCCGTGAGCGGCAACAGCATCACCAGCGACTACGCCTGGA
ACTGGATCCGCCAGTTCCCAGGCAAGGGCCTGGAGTGGATGGGCTACATCAGC
TACAGCGGCAGCACCACCTACAACCCAAGCCTGAAGAGCCGCGTCACCATCAG
CCGCGACACCAGCAAGAACCAGTTCAGCCTGAAGCTGAGCAGCGTGACCCCTG
TGGACACCGCCGTGTACTACTGCGCCACCGGCTACTACTACGGCAGCGGCTTCT
GGGGCCAGGGCACCCTGGTGACCGTGAGCAGC SEQ ID NO: 324-VH cDNA (KL2B359)
CAGGTTCAGCTGCAAGAGTCTGGACCAGGCCTGGTCAAGCCCTCTCAGACCCT
GTCTCTGACCTGTACCGTGTCCGGCAACTCCATCACCTCTGACTACGCCTGGAA -continued CTGGATTCGGCAGTTCCCTGGCAAGCGCCTTGAGTGGATCGGCTACATCTCCTA
CTCCGGTTCCACCACCTACAACCCCAGCCTGAAGTCCCGGGTCACCATCTCCCG
CGACACCTCCAAGAACCAGTTCTCCCTGAAGCTGTCCTCCGTGACCGCTGCTGA
TACCGCCGTGTACTACTGTGCCACCGGCTACTACTACGGCTCCGGCTTTTGGGG
ACAGGGCACACTGGTTACCGTGTCTAGT SEQ ID NO: 325-VH cDNA (KL2B413)
GAGGTGCAACTTGTGGAGAGCGGCGGAGGTCTGGTCCAACCCGGAGGAAGTCT
CCGTCTCTCCTGTGCTGCTAGTGGCTTCACTTTCAGCTCATATTGGATGACATGG
GTGAGACAAGCCCCAGGAAGGGGCTCGAGTGGGTAGCTAACATTAAACAGG
ACGGCTCCAACGGTACTATGTTGATTCTGTGAAGGGACGGTTCACTATATCCA
GGGATAATGCAAAAAATTCACTCTATCTTCAAATGAACTCACTCAGAGCAGAG
GACACTGCCGTGTATTATTGCGCCAGGGATCAAAATTATGACATACTGACCGGT
CATTATGGAATGGATGTTTGGGGCCAGGGAACAACCGTTACCGTCTCAAGT SEQ ID NO: 326-VL cDNA (m11B6)
GACATTGTGCTGACACAGAGTCCAGCATCCTTGGCAGTATCTTTGGGGCAGCG
GGCAACAATTTCATGCCGTGCATCTGAAAGTGTGGAGTATTTTGGAACTTCTCT
TATGCACTGGTATCGCCAGAAGCCTGGGCAGCCTCCCAAACTCCTTATATATGC
CGCTTCCAACGTGGAGTCCGGAGTACCAGCACGCTTTTCCGGCTCTGGGTCCGG
CACAGACTTTTCCCTCAATATCCAACCTGTTGAAGAAGACGATTTTTCCATGTA
TTTTTGCCAACAGACACGCAAGGTTCCATATACATTCGGCGGCGGCACTAAACT
TGAGATCAAA SEQ ID NO: 327-VL cDNA (hu11B6)
GACATAGTCTTGACTCAGAGCCCGGATTCCCTTGCTGTGTCTCTGGGAGAACGA
GCTACGATCAACTGCAAGGCAAGTGAATCCGTAGAATACTTCGGGACACATT
GATGCATTGGTATCAACAGAAACCGGGGCAACCGCCCAAATTGCTGATATATG
CGGCTAGTAATAGAGAATCAGGAGTACCGGATAGGTTTAGTGGTTCAGGATCA
GGTACAGATTTCACCCTGACAATAAGTAGCTTGCAAGCCGAAGACGTAGCAGT
GTATTACTGCCAACAAACCCGAAAGGTGCCATATACGTTTGGACAGGGTACAA
AGTTGGAAATCAAA SEQ ID NO: 328-VL cDNA (HCF3-LCD6)
GACATCGTGCTGACCCAGAGCCCAGACAGCCTGGCCGTGAGCCTGGGCGAGCG
CGCCACCATCAACTGCAAGGCCAGCGAGAGCGTGGAGTACTTCGGCACCAGCC
TGATGCACTGGTACCAGCAGAAGCCAGGCCAGCCACCAAAGCTGCTGATCTAC
GCTGCCAGCAACCGCGAGAGCGGCGTGCCAGACCGCTTCAGCGGCAGCGGCAG
CGGCACCGACTTCACCCTGACCATCCAGAGCGTGCAGGCCGAGGACGTCTCCG
TGTACTTCTGCCAGCAGACCCGCAAGGTGCCATACACCTTCGGCCAGGGCACC
AAGCTGGAGATCAAG SEQ ID NO: 329-VL cDNA (HCG5-LCB7)
GACATCGTGCTGACCCAGAGCCCAGACAGCCTGGCCGTGAGCCTGGGCGAGCG
CGCCACCATCAACTGCAAGGCCAGCGAGAGCGTGGAGTACTTCGGCACCAGCC
TGATGCACTGGTACCAGCAGAAGCCAGGCCAGCCACCAAAGCTGCTGATCTAC
GCTGCCAGCAACCGCGAGAGCGGCGTGCCAGACCGCTTCAGCGGCAGCGGCAG
CGGCACCGACTTCACCCTGACCATCAGCAGCGTGCAGGCCGAGGACGTCGCCG
TGTACTACTGCCAGCAGACCCGCAAGGTGCCATACACCTTCGGCCAGGGCACC
AAGCTGGAGATCAAG SEQ ID NO: 330-VL cDNA (KL2B359)
GAGATCGTGCTGACCCAGTCTCCTGCCACACTGTCACTGTCTCCAGGCGAGAGA
GCCACCCTCTCTTGTAGAGCCTCCGAGTCCGTGGAATACTTCGGCACCTCTCTG
ATGCACTGGTACCAGCAGAAGCCCGGCCAGCCTCCTAGACTGCTGATCTACGC
CGCCTCCAACGTCGAATCTGGCATCCCCGCTAGATTCTCCGGCTCTGGCTCTGG
CACAGACTTTACCCTGACCATCCTCCGTGGAACCCGAGGATTTCGCTGTGTA
CTTTTGCCAGCAGACCCGGAAGGTGCCCTACACATTTGGCGGCGGAACAAAGG
TGGAAATCAAG SEQ ID NO: 331-VL cDNA (KL2B413)
GAAATCGTACTGACCCAGTCCCCTTCTTTCTTGAGTGCATCAGTTGGGGATAGA
GTGACCATTACTTGTAGAGCATCTCAAGGTATTTCTTCATACTTGTCTTGGTATC
AACAAAAACCTGGCAAGGCACCCAAACTCTTGATCTACGCCACCTCTACATTG
CAAAGTGGGGTTCCTTCTAGGTTTTCAGGCTCCGGCTCTGGTACCGAGTTCACC
CTCACTATAAGCAGTCTCCAACCTGAAGATTTCGCTACTTATTATTGTCAGCAG
CTTAATTCTTATCCCCGAACCTTTGGTCAAGGAACTAAGGTCGAGATCAAA SEQ ID NO: 332-m11B6 HC IgG4
DVQLQESGPGLVKPSQSLSLTCTVTGNSITSDYAWNWIRQFPGNRLEWMGYISYSG
STTYSPSLKSRFSITRDTSKNQFFLQLNSVTPEDTATYFCATGYYYGSGFWGQGTLV
TVSSAKTTAPSVYPLAPVCGDTTGSSVTLGCLVKGYFPEPVTLTWNSGSLSSGVHT
FPAVLQSDLYTLSSSVTVTSSTWPSQSITCNVAHPASSTKVDKKIEPRGPTIKPCPPC
KCPAPNLLGGPSVFIFPPKIKDVLMISLSPIVTCVVVDVSEDDPDVQISWFVNNVEV
HTAQTQTHREDYNSTLRVVSALPIQHQDWMSGKEFKCKVNNKDLPAPIERTISKPK
GSVRAPQVYVLPPPEEEMTKKQVTLTCMVTDFMPEDIYVEWTNNGKTELNYKNT
EPVLDSDGSYFMYSKLRVEKKNWVERNSYSCSVVHEGLHNHHTTKSFSRTPGK

```
SEQ ID NO: 333-m11B6 LC IgG4
DIVLTQSPASLAVSLGQRATISCRASESVEYFGTSLMHWYRQKPGQPPKLLIYAASN
VESGVPARFSGSGSGTDFSLNIQPVEEDDFSMYFCQQTRKVPYTFGGGTKLEIKRA
DAAPTVSIFPPSSEQLTSGGASVVCFLNNFYPKDINVKWKIDGSERQNGVLNSWTD
QDSKDSTYSMSSTLTLTKDEYERHNSYTCEATHKTSTSPIVKSFNRNEC

SEQ ID NO: 334-h11B6 HC IgG4
QVQLQESGPGLVKPSDTLSLTCAVSGNSITSDYAWNWIRQPPGKGLEWIGYISYSG
STTYNPSLKSRVTMSRDTSKNQFSLKLSSVTAVDTAVYYCATGYYYGSGFWGQGT
LVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKT
HTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSLS
PGK

SEQ ID NO: 335-h11B6 LC IgG4
DIVLTQSPDSLAVSLGERATINCKASESVEYFGTSLMHWYQQKPGQPPKLLIYAAS
NRESGVPDRFSGSGSGTDFTLTISSLQAEDVAVYYCQQTRKVPYTFGQGTKLEIKRT
VAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC

SEQ ID NO: 336-m11B6 HC DNA
GATGTGCAGCTTCAGGAGTCTGGACCCGGACTTGTTAAACCAAGTCAGTCTCTG
TCCCTGACCTGTACCGTCACCGGCAACAGCATCACAAGCGATTACGCATGGAA
CTGGATCAGGCAGTTCCCTGGAAATCGACTCGAATGGATGGGCTACATTTCATA
CTCCGGTTCAACCACTTACTCTCCATCCTTGAAATCTAGGTTCAGCATCACCCG
TGATACCTCAAAGAACCAATTTTTTCTGCAACTGAATAGCGTAACTCCAGAGGA
CACAGCCACATATTTCTGCGCCACTGGGTATTACTATGGCTCAGGTTTCTGGGG
TCAGGGCACTCTCGTCACCGTCAGCAGCGCCAAAACAACAGCACCAAGTGTCT
ATCCACTGGCCCCTGTGTGTGGAGATACAACTGGCTCCTCGGTGACTCTAGGAT
GCCTGGTCAAGGGTTATTTCCCTGAGCCAGTGACCTTGACCTGGAACTCTGGAT
CCCTGTCCAGTGGTGTGCACACCTTCCCAGCTGTCCTGCAGTCTGACCTCTACA
CCCTCAGCAGCTCAGTGACTGTAACCTCGAGCACCTGGCCCAGCCAGTCCATCA
CCTGCAATGTGGCCCACCCGGCAAGCAGCACCAAGGTGGACAAGAAAATTGAG
CCCAGAGGGCCCACAATCAAGCCCTGTCCTCCATGCAAATGCCCAGCACCTAA
CCTCTTGGGTGGACCATCCGTCTTCATCTTCCCTCCAAAGATCAAGGATGTACT
CATGATCTCCCTGAGCCCCATAGTCACATGTGTGGTGGTGGATGTGAGCGAGG
ATGACCCAGATGTCCAGATCAGCTGGTTTGTGAACAACGTGGAAGTACACACA
GCTCAGACACAAACCCATAGAGAGGATTACAACAGTACTCTCCGGGTGGTCAG
TGCCCTCCCCATCCAGCACCAGGACTGGATGAGTGGCAAGGAGTTCAAATGCA
AGGTCAACAACAAAGACCTCCCAGCGCCCATCGAGAGAACCATCTCAAAACCC
AAAGGGTCAGTAAGAGCTCCACAGGTATATGTCTTGCCTCCACCAGAAGAAGA
GATGACTAAGAAACAGGTCACTCTGACCTGCATGGTCACCGACTTCATGCCTG
AAGACATTTACGTGGAGTGGACCAACAACGGGAAAACAGAGCTAAACTACAA
GAACACTGAACCAGTCCTGGACTCTGATGGTTCTTACTTCATGTACAGCAAGCT
GAGAGTGGAAAAGAAGAACTGGGTGGAAAGAAATAGCTACTCCTGTTCAGTG
GTCCACGAGGGTCTGCACAATCACCACACGACTAAGAGCTTCTCCCGGACTCC
GGGTAAA

SEQ ID NO: 337-mu11B6 LC DNA
GACATTGTGCTGACACAGAGTCCAGCATCCTTGGCAGTATCTTTGGGGCAGCG
GGCAACAATTTCATGCCGTGCATCTGAAAGTGTGGAGTATTTTGGAACTTCTCT
TATGCACTGGTATCGCCAGAAGCCTGGGCAGCCTCCCAAACTCCTTATATATGC
CGCTTCCAACGTGGAGTCCGGAGTACCAGCACGCTTTTCCGGCTCTGGGTCCGG
CACAGACTTTTCCCTCAATATCCAACCTGTTGAAGAAGACGATTTTTCCATGTA
TTTTTGCCAACAGACACGCAAGGTTCCATATACATTCGGCGGCGGCACTAAACT
TGAGATCAAACGGGCTGATGCTGCACCGACTGTGTCCATCTTCCCACCATCCAG
TGAGCAGTTAACATCTGGAGGTGCCTCAGTCGTGTGCTTCTTGAACAACTTCTA
CCCCAAAGACATCAATGTCAAGTGGAAGATTGATGGCAGTGAACGACAAAATG
GCGTCCTGAACAGTTGGACTGATCAGGACAGCAAAGACAGCACCTACAGCATG
AGCAGCACCCTCACGTTGACCAAGGACGAGTATGAACGACATAACAGCTATAC
CTGTGAGGCCACTCACAAGACATCAACTTCACCCATTGTCAAGAGCTTCAACA
GGAATGAGTGT

SEQ ID NO: 338-hu11B6 HC DNA
CAGGTCCAACTGCAAGAGAGCGGACCGGGCCTGGTAAAGCCATCCGACACATT
GTCCCTGACGTGTGCGGTAAGTGGAAACTCTATCACTAGCGACTATGCGTGGA
ATTGGATAAGACAACCGCCGGGCAAGGGGCTGGAATGGATAGGATATATCAGC
TATTCCGGTTCTACGACATACAATCCTTCCCTGAAAAGCAGAGTCACTATGTCA
CGCGACACGTCCAAGAATCAGTTCTCATTGAAATTGTCATCCGTAACGGCCGTT
GACACTGCGGTTTATTATTGCGCAACCGGATATTACTACGGCTCTGGTTTTTGG
GGACAGGGAACACTTGTTACTGTTAGTTCAGCCTCCACCAAGGGCCCATCGGTC
TTCCCCCTGGCACCCTCCTCCAAGAGCACCTCTGGGGGCACAGCGGCCCTGGGC
TGCCTGGTCAAGGACTACTTCCCCGAACCGGTGACGGTGTCGTGGAACTCAGG
CGCCCTGACCAGCGGCGTGCACACCTTCCCGGCTGTCCTACAGTCCTCAGGACT
CTACTCCCTCAGCAGCGTGGTGACCGTGCCCTCCAGCAGCTTGGGCACCCAGAC
CTACATCTGCAACGTGAATCACAAGCCCAGCAACACCAAGGTGGACAAGAAAG
```

```
TTGAGCCCAAATCTTGTGACAAAACTCACACATGCCCACCGTGCCCAGCACCTG
AACTCCTGGGGGGACCGTCAGTCTTCCTCTTCCCCCCAAAACCCAAGGACACCC
TCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAA
TGCCAAGACAAAGCCGCGGGAGGAGCAGTACAACAGCACGTACCGTGTGGTC
AGCGTCCTCACCGTCCTGCACCAGGACTGGCTGAATGGCAAGGAGTACAAGTG
CAAGGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGGGAG
GAGATGACCAAGAACCAGGTCAGCCTGACCTGCCTGGTCAAAGGCTTCTATCC
CAGCGACATCGCCGTGGAGTGGGAGAGCAATGGGCAGCCGGAGAACAACTAC
AAGACCACGCCTCCCGTGCTGGACTCCGACGGCTCCTTCTTCCTCTACAGCAAG
CTCACCGTGGACAAGAGCAGATGGCAGCAGGGGAACGTCTTCTCATGCTCCGT
GATGCATGAGGCTCTGCACAACCACTACACGCAGAAGAGCCTCTCCCTGTCTCC
GGGTAAA

SEQ ID NO: 339-hu11B6 LC DNA
GACATAGTCTTGACTCAGAGCCCGGATTCCCTTGCTGTGTCTCTGGGAGAACGA
GCTACGATCAACTGCAAGGCAAGTGAATCCGTAGAATACTTCGGGACATCATT
GATGCATTGGTATCAACAGAAACCGGGGCAACCGCCCAAATTGCTGATATATG
CGGCTAGTAATAGAGAATCAGGAGTACCGGATAGGTTTAGTGGTTCAGGATCA
GGTACAGATTTCACCCTGACAATAAGTAGCTTGCAAGCCGAAGACGTAGCAGT
GTATTACTGCCAACAAACCCGAAAGGTGCCATATACGTTTGGACAGGGTACAA
AGTTGGAAATCAAACGTACGGTGGCTGCACCATCTGTCTTCATCTTCCCGCCAT
CTGATGAGCAGTTGAAATCTGGAACTGCCTCTGTTGTGTGCCTGCTGAATAACT
TCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACA
GCCTCAGCAGCACCCTGACGCTGAGCAAAGCAGACTACGAGAAACACAAAGTC
TACGCCTGCGAAGTCACCCATCAGGGCCTGAGCTCGCCCGTCACAAAGAGCTT
CAACAGGGGAGAGTGT

SEQ ID NO: 340-scFv 17 (KL2B413 HL)
EVQLVESGGGLVQPGGSLRLSCAASGFTFSSYWMTWVRQAPGKGLEWVANIKQD
GSERYYVDSVKGRFTISRDNAKNSLYLQMNSLRAEDTAVYYCARDQNYDILTGHY
GMDVWGQGTTVTVSSGGSEGKSSGSGSESKSTGGSEIVLTQSPSFLSASVGDRVTIT
CRASQGISSYLSWYQQKPGKAPKLLIYATSTLQSGVPSRFSGSGSGTEFTLTISSLQP
EDFATYYCQQLNSYPRTFGQGTKVEIK

SEQ ID NO: 341-scFv 18 (KL2B413 LH)
EIVLTQSPSFLSASVGDRVTITCRASQGISSYLSWYQQKPGKAPKLLIYATSTLQSGV
PSRFSGSGSGTEFTLTISSLQPEDFATYYCQQLNSYPRTFGQGTKVEIKGGSEGKSSG
SGSESKSTGGSEVQLVESGGGLVQPGGSLRLSCAASGFTFSSYWMTWVRQAPGKG
LEWVANIKQDGSERYYVDSVKGRFTISRDNAKNSLYLQMNSLRAEDTAVYYCAR
DQNYDILTGHYGMDVWGQGTTVTVSS

SEQ ID NO: 342-scFv 19 (KL2B359 HL)
QVQLQESGPGLVKPSQTLSLTCTVSGNSITSDYAWNWIRQFPGKRLEWIGYISYSGS
TTYNPSLKSRVTISRDTSKNQFSLKLSSVTAADTAVYYCATGYYYGSFWGQGTL
VTVSSGGSEGKSSGSGSESKSTGGSEIVLTQSPATLSLSPGERATLSCRASESVEYFG
TSLMHWYQQKPGQPPRLLIYAASNVESGIPARFSGSGSGTDFTLTISSVEPEDFAVY
FCQQTRKVPYTFGGGTKVEIK

SEQ ID NO: 343-scFv 20 (KL2B359 LH)
EIVLTQSPATLSLSPGERATLSCRASESVEYFGTSLMHWYQQKPGQPPRLLIYAASN
VESGIPARFSGSGSGTDFTLTISSVEPEDFAVYFCQQTRKVPYTFGGGTKVEIKGGSE
GKSSGSGSESKSTGGSQVQLQESGPGLVKPSQTLSLTCTVSGNSITSDYAWNWIRQF
PGKRLEWIGYISYSGSTTYNPSLKSRVTISRDTSKNQFSLKLSSVTAADTAVYYCAT
GYYYGSFWGQGTLVTVSS

SEQ ID NO: 344 VH consensus sequence
QVQLQESGPGLVKPSX₁TLSLTCX₂VSGNSITSDYAWNWIRQX₃PGKGLEWX₄GYIS
YSGSTTYNPSLKSRVTMSRDTSKNQFSLKLSSVTX₅X₆DTAVYYCATGYYYGSGF
WGQGTLVTVSS
X1 is D or Q; X2 is A or T; X3 is P or F; X4 is I or M; X5 is A or P; or X6 is V
or A.
HCDR residues are underlined.

SEQ ID NO: 345 VL consensus sequence
X₁IVLTQSPX₂X₃LX₄X₅SX₆GERATX₆X₈CX₉ASESVEYFGTSLMHWYQQKPGQPPX₁₀
LLIYAASNX₁₁ESGX₁₂PX₁₃RFSGSGSGTDFTLTIX₁₄SLQX₁₅EDX₁₆AVYX₁₇CQQTRKV
PYTFGX₁₈GTKX19EIK
X1 is D or E; X2 is D or A; X3 is S or T; X4 is A or S; X5 is V or L; X6 is L or
P; X7 is I or L; X8 is N or S; X9 is R or K; X10 is K or R; X11 is V or R; X12
is V or I; X13 is A or D; X14 is Q or S; X15 is P or A; X16 is F or V; X17 is Y
or F; X18 is Q or G; and X19 is L or V. LCDR residues are underlined.

SEQ ID NO: 346-epitope
KVTEF
```

-continued

SEQ ID NO: 347-epitope
HYRKW

SEQ ID NO: 348-epitope
SHGWAH

SEQ ID NO: 349-epitope
RHNLFEPEDTGQRVP

SEQ ID NO: 350-epitope
GWGSIEPEE

What is claimed is:

1. A chimeric antigen receptor (CAR) comprising:
   (a) an extracellular domain that specifically binds to the human Kallikrein-2 (hK2) antigen, wherein the extracellular antigen-binding domain comprises:

a heavy chain complementarity determining region 1 (CDR1) having the amino acid sequence of SEQ ID NO: 63, a heavy chain CDR2 having the amino acid sequence of SEQ ID NO: 64, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 68, a light chain CDR2 having the amino acid sequence of SEQ ID NO: 70, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 69, a light chain CDR3 having the amino acid sequence of SEQ ID NO: 71;

a heavy chain complementarity determining region 1 (CDR1) having the amino acid sequence of SEQ ID NO: 63, a heavy chain CDR2 having the amino acid sequence of SEQ ID NO: 65, a heavy chain CDR3 having the amino acid sequence of SEQ ID NO: 66, and a light chain complementarity determining region 1 (CDR1) having the amino acid sequence of SEQ ID NO: 67, a light chain CDR2 having the amino acid sequence of SEQ ID NO: 126, a light chain CDR3 having the amino acid sequence of SEQ ID NO: 71;

a heavy chain complementarity determining region 1 (CDR1) having the amino acid sequence of SEQ ID NO: 314, a heavy chain CDR2 having the amino acid sequence of SEQ ID NO: 315, a heavy chain CDR3 having the amino acid sequence of SEQ ID NO: 311, and a light chain complementarity determining region 1 (CDR1) having the amino acid sequence of SEQ ID NO: 312, a light chain CDR2 having the amino acid sequence of SEQ ID NO: 313, a light chain CDR3 having the amino acid sequence of SEQ ID NO: 91;

a heavy chain complementarity determining region 1 (CDR1) having the amino acid sequence of SEQ ID NO: 102, a heavy chain CDR2 having the amino acid sequence of SEQ ID NO: 103, a heavy chain CDR3 having the amino acid sequence of SEQ ID NO: 104, and a light chain complementarity determining region 1 (CDR1) having the amino acid sequence of SEQ ID NO: 128, a light chain CDR2 having the amino acid sequence of SEQ ID NO: 129, a light chain CDR3 having the amino acid sequence of SEQ ID NO: 130;

a heavy chain complementarity determining region 1 (CDR1) having the amino acid sequence of SEQ ID NO: 107, a heavy chain CDR2 having the amino acid sequence of SEQ ID NO: 108, a heavy chain CDR3 having the amino acid sequence of SEQ ID NO: 109, and a light chain complementarity determining region 1 (CDR1) having the amino acid sequence of SEQ ID NO: 125, a light chain CDR2 having the amino acid sequence of SEQ ID NO: 131, a light chain CDR3 having the amino acid sequence of SEQ ID NO: 132;

a heavy chain complementarity determining region 1 (CDR1) having the amino acid sequence of SEQ ID NO: 102, a heavy chain CDR2 having the amino acid sequence of SEQ ID NO: 112, a heavy chain CDR3 having the amino acid sequence of SEQ ID NO: 113, and a light chain complementarity determining region 1 (CDR1) having the amino acid sequence of SEQ ID NO: 133, a light chain CDR2 having the amino acid sequence of SEQ ID NO: 134, a light chain CDR3 having the amino acid sequence of SEQ ID NO: 135;

a heavy chain complementarity determining region 1 (CDR1) having the amino acid sequence of SEQ ID NO: 115, a heavy chain CDR2 having the amino acid sequence of SEQ ID NO: 116, a heavy chain CDR3 having the amino acid sequence of SEQ ID NO: 117, and a light chain complementarity determining region 1 (CDR1) having the amino acid sequence of SEQ ID NO: 136, a light chain CDR2 having the amino acid sequence of SEQ ID NO: 137, a light chain CDR3 having the amino acid sequence of SEQ ID NO: 138; or a heavy chain complementarity determining region 1 (CDR1) having the amino acid sequence of SEQ ID NO: 120, a heavy chain CDR2 having the amino acid sequence of SEQ ID NO: 121, a heavy chain CDR3 having the amino acid sequence of SEQ ID NO: 122, and a light chain complementarity determining region 1 (CDR1) having the amino acid sequence of SEQ ID NO: 97, a light chain CDR2 having the amino acid sequence of SEQ ID NO: 127, a light chain CDR3 having the amino acid sequence of SEQ ID NO: 138;

(b) a transmembrane domain, wherein the transmembrane domain comprises a CD8a transmembrane region (CD8a-TM) polypeptide, and (c) an intracellular signaling domain optionally comprising at least one co-stimulatory domain comprising a TNF receptor superfamily member 9 (CD137) component and a primary signaling domain comprising a T-cell surface glycoprotein CD3 zeta chain (CD3z) component.

2. The CAR of claim 1, wherein
the CD8a-hinge region comprises an amino acid sequence that is at least 90% identical to SEQ ID NO: 25, 269, 270, 271, or 272;
the transmembrane domain comprises an amino acid sequence that is at least 90% identical to SEQ ID NO: 26; and/or
the intracellular signaling domain comprises a co-stimulatory domain having an amino acid sequence that is at least 90% identical to SEQ ID NO: 27, and a primary signaling domain having an amino acid sequence that is at least 90% identical to SEQ ID NO: 28.

3. The CAR according to claim 1, wherein the extracellular antigen-binding domain comprises: a heavy chain complementarity determining region 1 (CDR1) having the amino acid sequence of SEQ ID NO: 86, a heavy chain CDR2 having the amino acid sequence of SEQ ID NO: 87, a heavy chain CDR3 having the amino acid sequence of SEQ ID NO: 88, and a light chain complementarity determining region 1 (CDR1) having the amino acid sequence of SEQ ID NO: 89, a light chain CDR2 having the amino acid sequence of SEQ ID NO: 90, a light chain CDR3 having the amino acid sequence of SEQ ID NO: 91.

4. The CAR according to claim 1, comprising an extracellular antigen-binding domain, a transmembrane domain and an intracellular signaling domain, wherein the extracellular antigen-binding domain comprises:
a light chain variable domain (VL) comprising an amino acid sequence selected from SEQ ID NOS: 1, 2, 3, 74, 75, 147, 148, 149, 150, 151, 152 and 318; and/or
a heavy chain variable domain (VH) comprising an amino acid sequence selected from SEQ ID NOS: 4, 5, 6, 76, 77, 140, 141, 142, 143, 144, 145, 146 and 317;
wherein the extracellular antigen-binding domain binds the human Kallikrein-2 (hK2) antigen.

5. The CAR of claim 4, wherein the extracellular antigen-binding domain comprises:
a light chain variable region comprising an amino acid sequence of SEQ ID NO: 1 and a heavy chain variable region comprising an amino acid sequence of SEQ ID NO: 4;
a light chain variable region comprising an amino acid sequence of SEQ ID NO: 2 and a heavy chain variable region comprising an amino acid sequence of SEQ ID NO: 4;
a light chain variable region comprising an amino acid sequence of SEQ ID NO: 3 and a heavy chain variable region comprising an amino acid sequence of SEQ ID NO: 6;
a light chain variable region comprising an amino acid sequence of SEQ ID NO: 3 and a heavy chain variable region comprising an amino acid sequence of SEQ ID NO: 4;
a light chain variable region comprising an amino acid sequence of SEQ ID NO: 2 and a heavy chain variable region comprising an amino acid sequence of SEQ ID NO: 6;

a light chain variable region comprising an amino acid sequence of SEQ ID NO: 3 and a heavy chain variable region comprising an amino acid sequence of SEQ ID NO: 4;

a light chain variable region comprising an amino acid sequence of SEQ ID NO: 1 and a heavy chain variable region comprising an amino acid sequence of SEQ ID NO: 6;

a light chain variable region comprising an amino acid sequence of SEQ ID NO: 3 and a heavy chain variable region comprising an amino acid sequence of SEQ ID NO: 5;

a light chain variable region comprising an amino acid sequence of SEQ ID NO: 1 and a heavy chain variable region comprising an amino acid sequence of SEQ ID NO: 5;

a light chain variable region comprising an amino acid sequence of SEQ ID NO: 2 and a heavy chain variable region comprising an amino acid sequence of SEQ ID NO: 5;

a light chain variable region comprising an amino acid sequence of SEQ ID NO: 3 and a heavy chain variable region comprising an amino acid sequence of SEQ ID NO: 5;

a light chain variable region comprising an amino acid sequence of SEQ ID NO: 74 and a heavy chain variable region comprising an amino acid sequence of SEQ ID NO: 76;

a light chain variable region comprising an amino acid sequence of SEQ ID NO: 75 and a heavy chain variable region comprising an amino acid sequence of SEQ ID NO: 77;

a light chain variable region comprising an amino acid sequence of SEQ ID NO: 147 and a heavy chain variable region comprising an amino acid sequence of SEQ ID NO: 140;

a light chain variable region comprising an amino acid sequence of SEQ ID NO: 75 and a heavy chain variable region comprising an amino acid sequence of SEQ ID NO: 141;

a light chain variable region comprising an amino acid sequence of SEQ ID NO: 75 and a heavy chain variable region comprising an amino acid sequence of SEQ ID NO: 140;

a light chain variable region comprising an amino acid sequence of SEQ ID NO: 148 and a heavy chain variable region comprising an amino acid sequence of SEQ ID NO: 142;

a light chain variable region comprising an amino acid sequence of SEQ ID NO: 149 and a heavy chain variable region comprising an amino acid sequence of SEQ ID NO: 143;

a light chain variable region comprising an amino acid sequence of SEQ ID NO: 150 and a heavy chain variable region comprising an amino acid sequence of SEQ ID NO: 144;

a light chain variable region comprising an amino acid sequence of SEQ ID NO: 151 and a heavy chain variable region comprising an amino acid sequence of SEQ ID NO: 145;

a light chain variable region comprising an amino acid sequence of SEQ ID NO: 152 and a heavy chain variable region comprising an amino acid sequence of SEQ ID NO: 146;

a light chain variable region comprising an amino acid sequence of SEQ ID NO: 318 and a heavy chain variable region comprising an amino acid sequence of SEQ ID NO: 317.

6. The CAR of claim 1, wherein the extracellular antigen-binding domain comprises a single-chain variable fragment (scFv), the scFv comprising a light chain variable region (VL) and a heavy chain variable region (VH).

7. The CAR of claim 6, wherein the scFv comprises a linker polypeptide between the light chain variable region (VL) and the heavy chain variable region (VH).

8. The CAR of claim 7, wherein the linker polypeptide comprises an amino acid sequence of SEQ ID NO: 7.

9. The CAR of claim 6, wherein the scFv comprises an amino acid sequence selected from the group consisting of SEQ ID NOS: 8-23, 169-184 and 340-343.

10. The CAR of claim 1, wherein the extracellular antigen-binding domain comprises a signal polypeptide.

11. The CAR of claim 10, wherein the signal polypeptide comprises an amino acid sequence of SEQ ID NO: 24.

12. The CAR of claim 1, wherein the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member component, and a combination thereof.

13. The CAR of claim 12, wherein the CD137 component comprises an amino acid sequence of SEQ ID NO: 27.

14. The CAR of claim 12 or claim 13, wherein the CD3z component comprises an amino acid sequence of SEQ ID NO: 28.

15. The CAR of claim 12, wherein the intracellular signaling domain comprises an amino acid sequence of SEQ ID NO: 45, or, optionally, the intracellular signaling domain comprises a co-stimulatory domain comprising an amino acid sequence of SEQ ID NO: 27, and a primary signaling domain comprising an amino acid sequence of SEQ ID NO: 28.

16. The CAR of claim 1, wherein the transmembrane domain comprises a CD8a transmembrane region (CD8a-TM) polypeptide.

17. The CAR of claim 16, wherein the CD8a-TM polypeptide comprises an amino acid sequence of SEQ ID NO: 26.

18. The CAR of claim 1, further comprising a hinge region linking the transmembrane domain to the extracellular antigen-binding domain.

19. The CAR of claim 18, wherein the hinge region is a CD8a-hinge region.

20. The CAR of claim 19, wherein the CD8a-hinge region comprises an amino acid sequence of SEQ ID NO: 25, 269, 270, 271, or 272.

21. The CAR of claim 1, wherein the extracellular antigen-binding domain comprises an amino acid sequence selected from the group consisting of SEQ ID NOS: 29-44, 78-81, 221-236, and 273-308.

22. The CAR of claim 1, wherein the CAR comprises an amino acid sequence selected from the group consisting of SEQ ID NOS: 46-61, 82-85 and 205-220.

23. An isolated nucleic acid molecule encoding the CAR of claim 1.

24. A vector comprising the nucleic acid molecule of claim 23.

25. A cell expressing the nucleic acid molecule of claim 23 wherein the cell is a T cell or an NK cell.

26. An isolated lymphocyte expressing the CAR of claim 1.

27. The isolated lymphocyte of claim 26, wherein the lymphocyte is a T lymphocyte.

28. The isolated lymphocyte of claim 26, wherein the lymphocyte is a natural killer (NK) cell.

29. A pharmaceutical composition, comprising an effective amount of the lymphocyte of claim 26.

30. A pharmaceutical composition, comprising an effective amount of the lymphocyte of claim 26 and a pharmaceutically acceptable excipient.

31. A method of detecting the presence of cancer in a subject, comprising:
contacting a cell sample obtained from the subject with the CAR of claim 1, thereby forming a CAR-cell complex, and
detecting the complex, wherein detection of the complex is indicative of the presence of cancer in the subject.

32. A method of targeted killing of a cancer cell, the method comprising:
contacting the cancer cell with the lymphocyte of claim 1, whereby the lymphocyte induces killing of the cancer cell.

33. The method of claim 32, wherein the cancer cell is a prostate cancer cell or androgen receptor-expressing breast cancer cell.

34. A method of treating a subject having cancer, the method comprising:
administering a therapeutically effective amount of the lymphocyte of claim 1 to a subject in need thereof, whereby the lymphocyte induces killing of cancer cells in the subject.

35. The method of claim 34, wherein the cancer is prostate cancer or androgen receptor-expressing breast cancer.

* * * * *

SEQUENCE LISTING

<160> NUMBER OF SEQ ID NOS: 351

<210> SEQ ID NO 1
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
                20                  25                  30

Gly Thr Ser Leu Met His Trp Tyr Gln Gln Lys Pro Gly Gln Pro Pro
            35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Gln
65                  70                  75                  80

Ser Val Gln Ala Glu Asp Val Ser Val Tyr Phe Cys Gln Gln Thr Arg
                85                  90                  95

Lys Val Pro Tyr Thr Phe Gly Gln Gly Thr Lys Leu Glu Ile Lys
                100                 105                 110

<210> SEQ ID NO 2
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
                20                  25                  30

Gly Thr Ser Leu Met His Trp Tyr Gln Gln Lys Pro Gly Gln Pro Pro
            35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Arg
                85                  90                  95

```
Lys Val Pro Tyr Thr Phe Gly Gln Gly Thr Lys Leu Glu Ile Lys
                100                 105                 110

<210> SEQ ID NO 3
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys
                100                 105                 110

<210> SEQ ID NO 4
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Pro Val Asp Thr Ala Val Tyr Tyr Cys
                85                  90                  95

Ala Thr Gly Tyr Tyr Tyr Gly Ser Gly Phe Trp Gly Gln Gly Thr Leu
                100                 105                 110

Val Thr Val Ser Ser
            115

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 5

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Met Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser
            115
```

<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Pro Val Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser
            115
```

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Gly Gly Ser Glu Gly Lys Ser Ser Gly Ser Gly Ser Glu Ser Lys Ser
1               5                   10                  15

Thr Gly Gly Ser
            20
```

```
<210> SEQ ID NO 8
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Pro Val Asp Thr Ala Val Tyr Tyr Cys
                85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Gln Ser Val Gln Ala Glu Asp Val
    210                 215                 220

Ser Val Tyr Phe Cys Gln Gln Thr Arg Lys Val Pro Tyr Thr Phe Gly
225                 230                 235                 240

Gln Gly Thr Lys Leu Glu Ile Lys
                245

<210> SEQ ID NO 9
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45
```

Met Gly Tyr Ile Ser Tyr Ser Gly Ser Thr Thr Tyr Asn Pro Ser Leu
            50                  55                  60

Lys Ser Arg Val Thr Ile Ser Arg Asp Thr Ser Lys Asn Gln Phe Ser
 65                  70                  75                  80

Leu Lys Leu Ser Ser Val Thr Pro Val Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
            115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
            195                 200                 205

Gly Thr Asp Phe Thr Leu Thr Ile Ser Ser Leu Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys
                245

<210> SEQ ID NO 10
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Pro Gly Leu Val Lys Pro Ser Asp
 1               5                  10                  15

Thr Leu Ser Leu Thr Cys Ala Val Ser Gly Asn Ser Ile Thr Ser Asp
                20                  25                  30

Tyr Ala Trp Asn Trp Ile Arg Gln Phe Pro Gly Lys Gly Leu Glu Trp
            35                  40                  45

Ile Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
 65                  70                  75                  80

Leu Lys Leu Ser Ser Val Thr Pro Val Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
            115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

```
Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Ser Ser Val Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys
                245

<210> SEQ ID NO 11
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Pro Val Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Ser Ser Val Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys
                245
```

```
<210> SEQ ID NO 12
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Gln
65                  70                  75                  80

Ser Val Gln Ala Glu Asp Val Ser Val Tyr Phe Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Met Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
                245

<210> SEQ ID NO 13
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
```

```
                    50                  55                  60
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Thr Arg
                    85                  90                  95

Lys Val Pro Tyr Thr Phe Gly Gln Gly Thr Lys Leu Glu Ile Lys Gly
                100                 105                 110

Gly Ser Glu Gly Lys Ser Ser Gly Ser Gly Ser Glu Ser Lys Ser Thr
                115                 120                 125

Gly Gly Ser Gln Val Gln Leu Gln Glu Ser Gly Pro Gly Leu Val Lys
            130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Ile Gly Tyr Ile Ser Tyr Ser Gly Ser Thr Thr Tyr Asn
                180                 185                 190

Pro Ser Leu Lys Ser Arg Val Thr Ile Ser Arg Asp Thr Ser Lys Asn
                195                 200                 205

Gln Phe Ser Leu Lys Leu Ser Ser Val Thr Pro Val Asp Thr Ala Val
            210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
                245
```

<210> SEQ ID NO 14
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Asp Ile Val Leu Thr Gln Ser Pro Asp Ser Leu Ala Val Ser Leu Gly
 1               5                  10                  15

Glu Arg Ala Thr Ile Asn Cys Lys Ala Ser Glu Ser Val Glu Tyr Phe
                20                  25                  30

Gly Thr Ser Leu Met His Trp Tyr Gln Gln Lys Pro Gly Gln Pro Pro
            35                  40                  45

Lys Leu Leu Ile Tyr Ala Ala Ser Asn Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Thr Arg
                    85                  90                  95

Lys Val Pro Tyr Thr Phe Gly Gln Gly Thr Lys Leu Glu Ile Lys Gly
                100                 105                 110

Gly Ser Glu Gly Lys Ser Ser Gly Ser Gly Ser Glu Ser Lys Ser Thr
                115                 120                 125

Gly Gly Ser Gln Val Gln Leu Gln Glu Ser Gly Pro Gly Leu Val Lys
            130                 135                 140

Pro Ser Asp Thr Leu Ser Leu Thr Cys Ala Val Ser Gly Asn Ser Ile
145                 150                 155                 160
```

```
Thr Ser Asp Tyr Ala Trp Asn Trp Ile Arg Gln Phe Pro Gly Lys Gly
                165                 170                 175

Leu Glu Trp Met Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
    210                 215                 220

Tyr Tyr Cys Ala Thr Gly Tyr Tyr Tyr Gly Ser Gly Phe Trp Gly Gln
225                 230                 235                 240

Gly Thr Leu Val Thr Val Ser Ser
                245
```

<210> SEQ ID NO 15
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
    210                 215                 220

Tyr Tyr Cys Ala Thr Gly Tyr Tyr Tyr Gly Ser Gly Phe Trp Gly Gln
225                 230                 235                 240

Gly Thr Leu Val Thr Val Ser Ser
                245
```

<210> SEQ ID NO 16

```
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Met Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
                245

<210> SEQ ID NO 17
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60
```

```
Arg Phe Ser Gly Ser Gly Ser Gly Thr Asp Phe Thr Leu Thr Ile Gln
 65                  70                  75                  80

Ser Val Gln Ala Glu Asp Val Ser Val Tyr Phe Cys Gln Gln Thr Arg
                 85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
            115                 120                 125

Gly Gly Ser Gln Val Gln Leu Gln Glu Ser Gly Pro Gly Leu Val Lys
        130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
                245

<210> SEQ ID NO 18
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Met Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
```

```
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Ser Ser Val Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys
                245

<210> SEQ ID NO 19
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Met Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Gln Ser Val Gln Ala Glu Asp Val
    210                 215                 220

Ser Val Tyr Phe Cys Gln Gln Thr Arg Lys Val Pro Tyr Thr Phe Gly
225                 230                 235                 240

Gln Gly Thr Lys Leu Glu Ile Lys
                245

<210> SEQ ID NO 20
<211> LENGTH: 248
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Met Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
            115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys
                245

<210> SEQ ID NO 21
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

```
Arg Phe Ser Gly Ser Gly Ser Gly Thr Asp Phe Thr Leu Thr Ile Gln
 65                  70                  75                  80

Ser Val Gln Ala Glu Asp Val Ser Val Tyr Phe Cys Gln Gln Thr Arg
                 85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
            115                 120                 125

Gly Gly Ser Gln Val Gln Leu Gln Glu Ser Gly Pro Gly Leu Val Lys
        130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Pro Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Met Ser Arg Asp Thr Ser Lys Asn
        195                 200                 205

Gln Phe Ser Leu Lys Leu Ser Ser Val Thr Ala Val Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
                245

<210> SEQ ID NO 22
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Val Leu Thr Gln Ser Pro Asp Ser Leu Ala Val Ser Leu Gly
  1               5                  10                  15

Glu Arg Ala Thr Ile Asn Cys Lys Ala Ser Glu Ser Val Glu Tyr Phe
             20                  25                  30

Gly Thr Ser Leu Met His Trp Tyr Gln Gln Lys Pro Gly Gln Pro Pro
         35                  40                  45

Lys Leu Leu Ile Tyr Ala Ala Ser Asn Arg Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Thr Arg
                 85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
            115                 120                 125

Gly Gly Ser Gln Val Gln Leu Gln Glu Ser Gly Pro Gly Leu Val Lys
        130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Pro Pro Gly Lys Gly
                165                 170                 175
```

```
Leu Glu Trp Ile Gly Tyr Ile Ser Tyr Ser Gly Ser Thr Thr Tyr Asn
            180                 185                 190

Pro Ser Leu Lys Ser Arg Val Thr Met Ser Arg Asp Thr Ser Lys Asn
        195                 200                 205

Gln Phe Ser Leu Lys Leu Ser Ser Val Thr Ala Val Asp Thr Ala Val
    210                 215                 220

Tyr Tyr Cys Ala Thr Gly Tyr Tyr Gly Ser Gly Phe Trp Gly Gln
225             230                 235                 240

Gly Thr Leu Val Thr Val Ser Ser
                245

<210> SEQ ID NO 23
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Pro Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Met Ser Arg Asp Thr Ser Lys Asn
        195                 200                 205

Gln Phe Ser Leu Lys Leu Ser Ser Val Thr Ala Val Asp Thr Ala Val
    210                 215                 220

Tyr Tyr Cys Ala Thr Gly Tyr Tyr Gly Ser Gly Phe Trp Gly Gln
225             230                 235                 240

Gly Thr Leu Val Thr Val Ser Ser
                245

<210> SEQ ID NO 24
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 24

Met Ala Trp Val Trp Thr Leu Leu Phe Leu Met Ala Ala Ala Gln Ser
1               5                   10                  15

Ile Gln Ala

<210> SEQ ID NO 25
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Thr Ser Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 27
<211> LENGTH: 42
<212> TYPE: PRT
<213> ORGANISM: Homo sapiens

<400> SEQUENCE: 27

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Arg Val Lys Phe Ser Arg Ser Ala Asp Ala Pro Ala Tyr Lys Gln Gly
1               5                   10                  15
```

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 29
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
                20                  25                  30

Tyr Ala Trp Asn Trp Ile Arg Gln Phe Pro Gly Lys Gly Leu Glu Trp
            35                  40                  45

Met Gly Tyr Ile Ser Tyr Ser Gly Ser Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Pro Val Asp Thr Ala Val Tyr Tyr Cys
                85                  90                  95

Ala Thr Gly Tyr Tyr Gly Ser Gly Phe Trp Gly Gln Gly Thr Leu
                100                 105                 110

Val Thr Val Ser Ser Gly Gly Ser Glu Gly Lys Ser Ser Gly Ser Gly
            115                 120                 125

Ser Glu Ser Lys Ser Thr Gly Gly Ser Asp Ile Val Leu Thr Gln Ser
        130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Gln Ser Val Gln Ala Glu Asp Val
    210                 215                 220

Ser Val Tyr Phe Cys Gln Gln Thr Arg Lys Val Pro Tyr Thr Phe Gly
225                 230                 235                 240

Gln Gly Thr Lys Leu Glu Ile Lys
                245

```
<210> SEQ ID NO 30
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Pro Val Asp Thr Ala Val Tyr Tyr Cys
                85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
            115                 120                 125

Ser Glu Ser Lys Ser Thr Gly Gly Ser Asp Ile Val Leu Thr Gln Ser
130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys
                245

<210> SEQ ID NO 31
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Ile Gly Tyr Ile Ser Tyr Ser Gly Ser Thr Thr Tyr Asn Pro Ser Leu
```

```
            50                  55                  60
Lys Ser Arg Val Thr Ile Ser Arg Asp Thr Ser Lys Asn Gln Phe Ser
 65                  70                  75                  80

Leu Lys Leu Ser Ser Val Thr Pro Val Asp Thr Ala Val Tyr Tyr Cys
                 85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Ser Ser Val Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys
                245

<210> SEQ ID NO 32
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Gln Glu Ser Gly Pro Gly Leu Val Lys Pro Ser Asp
  1               5                  10                  15

Thr Leu Ser Leu Thr Cys Ala Val Ser Gly Asn Ser Ile Thr Ser Asp
             20                  25                  30

Tyr Ala Trp Asn Trp Ile Arg Gln Phe Pro Gly Lys Gly Leu Glu Trp
         35                  40                  45

Met Gly Tyr Ile Ser Tyr Ser Gly Ser Thr Thr Tyr Asn Pro Ser Leu
     50                  55                  60

Lys Ser Arg Val Thr Ile Ser Arg Asp Thr Ser Lys Asn Gln Phe Ser
 65                  70                  75                  80

Leu Lys Leu Ser Ser Val Thr Pro Val Asp Thr Ala Val Tyr Tyr Cys
                 85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160
```

Lys Ala Ser Glu Ser Val Glu Tyr Phe Gly Thr Ser Leu Met His Trp
            165                 170                 175

Tyr Gln Gln Lys Pro Gly Gln Pro Pro Lys Leu Leu Ile Tyr Ala Ala
        180                 185                 190

Ser Asn Arg Glu Ser Gly Val Pro Asp Arg Phe Ser Gly Ser Gly Ser
    195                 200                 205

Gly Thr Asp Phe Thr Leu Thr Ile Ser Ser Val Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys
            245

<210> SEQ ID NO 33
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Gln
65                  70                  75                  80

Ser Val Gln Ala Glu Asp Val Ser Val Tyr Phe Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Met Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
            245

<210> SEQ ID NO 34

<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
                245
```

<210> SEQ ID NO 35
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60
```

```
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Thr Arg
                 85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
            115                 120                 125

Gly Gly Ser Gln Val Gln Leu Gln Glu Ser Gly Pro Gly Leu Val Lys
        130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Met Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
                245

<210> SEQ ID NO 36
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Val Leu Thr Gln Ser Pro Asp Ser Leu Ala Val Ser Leu Gly
  1               5                  10                  15

Glu Arg Ala Thr Ile Asn Cys Lys Ala Ser Glu Ser Val Glu Tyr Phe
             20                  25                  30

Gly Thr Ser Leu Met His Trp Tyr Gln Gln Lys Pro Gly Gln Pro Pro
         35                  40                  45

Lys Leu Leu Ile Tyr Ala Ala Ser Asn Arg Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Val Gln Ala Glu Asp Val Ala Val Tyr Tyr Cys Gln Gln Thr Arg
                 85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
            115                 120                 125

Gly Gly Ser Gln Val Gln Leu Gln Glu Ser Gly Pro Gly Leu Val Lys
        130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
```

```
                        165                 170                 175
Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
                245

<210> SEQ ID NO 37
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Met Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
                245

<210> SEQ ID NO 38
<211> LENGTH: 248
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Asp Ile Val Leu Thr Gln Ser Pro Asp Ser Leu Ala Val Ser Leu Gly
1               5                   10                  15
Glu Arg Ala Thr Ile Asn Cys Lys Ala Ser Glu Ser Val Glu Tyr Phe
            20                  25                  30
Gly Thr Ser Leu Met His Trp Tyr Gln Gln Lys Pro Gly Gln Pro Pro
        35                  40                  45
Lys Leu Leu Ile Tyr Ala Ala Ser Asn Arg Glu Ser Gly Val Pro Asp
    50                  55                  60
Arg Phe Ser Gly Ser Gly Ser Gly Thr Asp Phe Thr Leu Thr Ile Gln
65                  70                  75                  80
Ser Val Gln Ala Glu Asp Val Ser Val Tyr Phe Cys Gln Gln Thr Arg
                85                  90                  95
Lys Val Pro Tyr Thr Phe Gly Gln Gly Thr Lys Leu Glu Ile Lys Gly
            100                 105                 110
Gly Ser Glu Gly Lys Ser Ser Gly Ser Gly Ser Glu Ser Lys Ser Thr
        115                 120                 125
Gly Gly Ser Gln Val Gln Leu Gln Glu Ser Gly Pro Gly Leu Val Lys
    130                 135                 140
Pro Ser Asp Thr Leu Ser Leu Thr Cys Ala Val Ser Gly Asn Ser Ile
145                 150                 155                 160
Thr Ser Asp Tyr Ala Trp Asn Trp Ile Arg Gln Phe Pro Gly Lys Gly
                165                 170                 175
Leu Glu Trp Ile Gly Tyr Ile Ser Tyr Ser Gly Ser Thr Thr Tyr Asn
            180                 185                 190
Pro Ser Leu Lys Ser Arg Val Thr Ile Ser Arg Asp Thr Ser Lys Asn
        195                 200                 205
Gln Phe Ser Leu Lys Leu Ser Ser Val Thr Pro Val Asp Thr Ala Val
    210                 215                 220
Tyr Tyr Cys Ala Thr Gly Tyr Tyr Gly Ser Gly Phe Trp Gly Gln
225                 230                 235                 240
Gly Thr Leu Val Thr Val Ser Ser
                245
```

<210> SEQ ID NO 39
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Gln Val Gln Leu Gln Glu Ser Gly Pro Gly Leu Val Lys Pro Ser Asp
1               5                   10                  15
Thr Leu Ser Leu Thr Cys Ala Val Ser Gly Asn Ser Ile Thr Ser Asp
            20                  25                  30
Tyr Ala Trp Asn Trp Ile Arg Gln Pro Pro Gly Lys Gly Leu Glu Trp
        35                  40                  45
Ile Gly Tyr Ile Ser Tyr Ser Gly Ser Thr Thr Tyr Asn Pro Ser Leu
    50                  55                  60
```

```
Lys Ser Arg Val Thr Met Ser Arg Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Ser Ser Val Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys
                245
```

<210> SEQ ID NO 40
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Gln Val Gln Leu Gln Glu Ser Gly Pro Gly Leu Val Lys Pro Ser Asp
  1               5                  10                  15

Thr Leu Ser Leu Thr Cys Ala Val Ser Gly Asn Ser Ile Thr Ser Asp
             20                  25                  30

Tyr Ala Trp Asn Trp Ile Arg Gln Pro Pro Gly Lys Gly Leu Glu Trp
         35                  40                  45

Ile Gly Tyr Ile Ser Tyr Ser Gly Ser Thr Thr Tyr Asn Pro Ser Leu
 50                  55                  60

Lys Ser Arg Val Thr Met Ser Arg Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175
```

Tyr Gln Gln Lys Pro Gly Gln Pro Pro Lys Leu Leu Ile Tyr Ala Ala
                180                 185                 190

Ser Asn Arg Glu Ser Gly Val Pro Asp Arg Phe Ser Gly Ser Gly Ser
            195                 200                 205

Gly Thr Asp Phe Thr Leu Thr Ile Gln Ser Val Gln Ala Glu Asp Val
        210                 215                 220

Ser Val Tyr Phe Cys Gln Gln Thr Arg Lys Val Pro Tyr Thr Phe Gly
225                 230                 235                 240

Gln Gly Thr Lys Leu Glu Ile Lys
                245

<210> SEQ ID NO 41
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Tyr Tyr Asn Pro Ser Leu
    50                  55                  60

Lys Ser Arg Val Thr Met Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys
                245

<210> SEQ ID NO 42
<211> LENGTH: 248
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 42

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Gln
65                  70                  75                  80

Ser Val Gln Ala Glu Asp Val Ser Val Tyr Phe Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Pro Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Met Ser Arg Asp Thr Ser Lys Asn
        195                 200                 205

Gln Phe Ser Leu Lys Leu Ser Ser Val Thr Ala Val Asp Thr Ala Val
    210                 215                 220

Tyr Tyr Cys Ala Thr Gly Tyr Tyr Tyr Gly Ser Gly Phe Trp Gly Gln
225                 230                 235                 240

Gly Thr Leu Val Thr Val Ser Ser
                245

<210> SEQ ID NO 43
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser

```
                65                  70                  75                  80
Ser Leu Gln Ala Glu Asp Val Ala Val Tyr Tyr Cys Gln Gln Thr Arg
                    85                  90                  95

Lys Val Pro Tyr Thr Phe Gly Gln Gly Thr Lys Leu Glu Ile Lys Gly
                100                 105                 110

Gly Ser Glu Gly Lys Ser Ser Gly Ser Gly Ser Glu Ser Lys Ser Thr
                115                 120                 125

Gly Gly Ser Gln Val Gln Leu Gln Glu Ser Gly Pro Gly Leu Val Lys
            130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Pro Pro Gly Lys Gly
                165                 170                 175

Leu Glu Trp Ile Gly Tyr Ile Ser Tyr Ser Gly Ser Thr Thr Tyr Asn
                180                 185                 190

Pro Ser Leu Lys Ser Arg Val Thr Met Ser Arg Asp Thr Ser Lys Asn
                195                 200                 205

Gln Phe Ser Leu Lys Leu Ser Ser Val Thr Ala Val Asp Thr Ala Val
            210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
                245

<210> SEQ ID NO 44
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
                20                  25                  30

Gly Thr Ser Leu Met His Trp Tyr Gln Gln Lys Pro Gly Gln Pro Pro
            35                  40                  45

Lys Leu Leu Ile Tyr Ala Ala Ser Asn Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Thr Arg
                    85                  90                  95

Lys Val Pro Tyr Thr Phe Gly Gln Gly Thr Lys Leu Glu Ile Lys Gly
                100                 105                 110

Gly Ser Glu Gly Lys Ser Ser Gly Ser Gly Ser Glu Ser Lys Ser Thr
                115                 120                 125

Gly Gly Ser Gln Val Gln Leu Gln Glu Ser Gly Pro Gly Leu Val Lys
            130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Pro Pro Gly Lys Gly
                165                 170                 175
```

```
Leu Glu Trp Ile Gly Tyr Ile Ser Tyr Ser Gly Ser Thr Thr Tyr Asn
            180                 185                 190

Pro Ser Leu Lys Ser Arg Val Thr Met Ser Arg Asp Thr Ser Lys Asn
        195                 200                 205

Gln Phe Ser Leu Lys Leu Ser Ser Val Thr Ala Val Asp Thr Ala Val
    210                 215                 220

Tyr Tyr Cys Ala Thr Gly Tyr Tyr Gly Ser Gly Phe Trp Gly Gln
225             230                 235                 240

Gly Thr Leu Val Thr Val Ser Ser
                245

<210> SEQ ID NO 45
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys Phe Ser Arg
        35                  40                  45

Ser Ala Asp Ala Pro Ala Tyr Lys Gln Gly Gln Asn Gln Leu Tyr Asn
    50                  55                  60

Glu Leu Asn Leu Gly Arg Arg Glu Glu Tyr Asp Val Leu Asp Lys Arg
65                  70                  75                  80

Arg Gly Arg Asp Pro Glu Met Gly Gly Lys Pro Arg Arg Lys Asn Pro
                85                  90                  95

Gln Glu Gly Leu Tyr Asn Glu Leu Gln Lys Asp Lys Met Ala Glu Ala
            100                 105                 110

Tyr Ser Glu Ile Gly Met Lys Gly Glu Arg Arg Arg Gly Lys Gly His
        115                 120                 125

Asp Gly Leu Tyr Gln Gly Leu Ser Thr Ala Thr Lys Asp Thr Tyr Asp
    130                 135                 140

Ala Leu His Met Gln Ala Leu Pro Pro Arg
145                 150

<210> SEQ ID NO 46
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Thr Tyr Asn Pro Ser Leu
    50                  55                  60
```

```
Lys Ser Arg Val Thr Ile Ser Arg Asp Thr Ser Lys Asn Gln Phe Ser
 65                  70                  75                  80

Leu Lys Leu Ser Ser Val Thr Pro Val Asp Thr Ala Val Tyr Tyr Cys
                 85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
                180                 185                 190

Ser Asn Arg Glu Ser Gly Val Pro Asp Arg Phe Ser Gly Ser Gly Ser
            195                 200                 205

Gly Thr Asp Phe Thr Leu Thr Ile Gln Ser Val Gln Ala Glu Asp Val
    210                 215                 220

Ser Val Tyr Phe Cys Gln Gln Thr Arg Lys Val Pro Tyr Thr Phe Gly
225                 230                 235                 240

Gln Gly Thr Lys Leu Glu Ile Lys Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470
```

```
<210> SEQ ID NO 47
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Pro Val Asp Thr Ala Val Tyr Tyr Cys
                85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365
```

```
Ala Pro Ala Tyr Lys Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
450                 455                 460

Met Gln Ala Leu Pro Pro Arg
465                 470

<210> SEQ ID NO 48
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
                20                  25                  30

Tyr Ala Trp Asn Trp Ile Arg Gln Phe Pro Gly Lys Gly Leu Glu Trp
                35                  40                  45

Ile Gly Tyr Ile Ser Tyr Ser Gly Ser Thr Thr Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Pro Val Asp Thr Ala Val Tyr Tyr Cys
                85                  90                  95

Ala Thr Gly Tyr Tyr Gly Ser Gly Phe Trp Gly Gln Gly Thr Leu
                100                 105                 110

Val Thr Val Ser Ser Gly Gly Ser Glu Gly Lys Ser Ser Gly Ser Gly
            115                 120                 125

Ser Glu Ser Lys Ser Thr Gly Gly Ser Asp Ile Val Leu Thr Gln Ser
        130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
                180                 185                 190

Ser Asn Arg Glu Ser Gly Val Pro Asp Arg Phe Ser Gly Ser Gly Ser
            195                 200                 205

Gly Thr Asp Phe Thr Leu Thr Ile Ser Ser Val Gln Ala Glu Asp Val
        210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys Thr Ser Thr Pro Ala Pro Arg Pro
                245                 250                 255
```

Pro Thr Pro Ala Pro Thr Ile Ala Ser Gln Pro Leu Ser Leu Arg Pro
            260                 265                 270

Glu Ala Cys Arg Pro Ala Ala Gly Ala Val His Thr Arg Gly Leu
        275                 280                 285

Asp Phe Ala Cys Asp Ile Tyr Ile Trp Ala Pro Leu Ala Gly Thr Cys
290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
450                 455                 460

Met Gln Ala Leu Pro Pro Arg
465                 470

<210> SEQ ID NO 49
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Pro Val Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser

```
                130                 135                 140
Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
                180                 185                 190

Ser Asn Arg Glu Ser Gly Val Pro Asp Arg Phe Ser Gly Ser Gly Ser
                195                 200                 205

Gly Thr Asp Phe Thr Leu Thr Ile Ser Ser Val Gln Ala Glu Asp Val
                210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys Thr Ser Thr Pro Ala Pro Arg Pro
                245                 250                 255

Pro Thr Pro Ala Pro Thr Ile Ala Ser Gln Pro Leu Ser Leu Arg Pro
                260                 265                 270

Glu Ala Cys Arg Pro Ala Ala Gly Gly Ala Val His Thr Arg Gly Leu
                275                 280                 285

Asp Phe Ala Cys Asp Ile Tyr Ile Trp Ala Pro Leu Ala Gly Thr Cys
                290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
                340                 345                 350

Glu Glu Gly Gly Cys Glu Leu Arg Val Lys Phe Ser Arg Ser Ala Asp
                355                 360                 365

Ala Pro Ala Tyr Lys Gln Gly Gln Asn Gln Leu Tyr Asn Glu Leu Asn
                370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
                435                 440                 445

Tyr Gln Gly Leu Ser Thr Ala Thr Lys Asp Thr Tyr Asp Ala Leu His
                450                 455                 460

Met Gln Ala Leu Pro Pro Arg
465                 470

<210> SEQ ID NO 50
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Val Leu Thr Gln Ser Pro Asp Ser Leu Ala Val Ser Leu Gly
1               5                   10                  15
```

-continued

Glu Arg Ala Thr Ile Asn Cys Lys Ala Ser Gln Ser Val Glu Tyr Phe
                20                  25                  30

Gly Thr Ser Leu Met His Trp Tyr Gln Gln Lys Pro Gly Gln Pro Pro
            35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Gln
65                  70                  75                  80

Ser Val Gln Ala Glu Asp Val Ser Val Tyr Phe Cys Gln Gln Thr Arg
                85                  90                  95

Lys Val Pro Tyr Thr Phe Gly Gln Gly Thr Lys Leu Glu Ile Lys Gly
                100                 105                 110

Gly Ser Glu Gly Lys Ser Ser Gly Ser Gly Ser Glu Ser Lys Ser Thr
            115                 120                 125

Gly Gly Ser Gln Val Gln Leu Gln Glu Ser Gly Pro Gly Leu Val Lys
        130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Met Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu

```
                    435                 440                 445
Tyr Gln Gly Leu Ser Thr Ala Thr Lys Asp Thr Tyr Asp Ala Leu His
    450                 455                 460
Met Gln Ala Leu Pro Pro Arg
465                 470

<210> SEQ ID NO 51
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320
```

```
Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470

<210> SEQ ID NO 52
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Met Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205
```

```
Gln Phe Ser Leu Lys Leu Ser Ser Val Thr Pro Val Asp Thr Ala Val
    210                 215                 220

Tyr Tyr Cys Ala Thr Gly Tyr Tyr Tyr Gly Ser Gly Phe Trp Gly Gln
225                 230                 235                 240

Gly Thr Leu Val Thr Val Ser Ser Thr Ser Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470

<210> SEQ ID NO 53
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
                20                  25                  30

Gly Thr Ser Leu Met His Trp Tyr Gln Gln Lys Pro Gly Gln Pro Pro
            35                  40                  45

Lys Leu Leu Ile Tyr Ala Ala Ser Asn Arg Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Thr Arg
```

```
                85                  90                  95
Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
            115                 120                 125

Gly Gly Ser Gln Val Gln Leu Gln Glu Ser Gly Pro Gly Leu Val Lys
130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
            165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
            195                 200                 205

Gln Phe Ser Leu Lys Leu Ser Ser Val Thr Pro Val Asp Thr Ala Val
            210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser Thr Ser Thr Pro Ala Pro Arg Pro
            245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
            275                 280                 285

Asp Phe Ala Cys Asp Ile Tyr Ile Trp Ala Pro Leu Ala Gly Thr Cys
            290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
            325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
            355                 360                 365

Ala Pro Ala Tyr Lys Gln Gly Gln Asn Gln Leu Tyr Asn Glu Leu Asn
            370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
            405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
            450                 455                 460

Met Gln Ala Leu Pro Pro Arg
465                 470

<210> SEQ ID NO 54
<211> LENGTH: 471
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 54

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Met Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Pro Val Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
```

```
385                 390                 395                 400
Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
                435                 440                 445

Tyr Gln Gly Leu Ser Thr Ala Thr Lys Asp Thr Tyr Asp Ala Leu His
450                 455                 460

Met Gln Ala Leu Pro Pro Arg
465                 470

<210> SEQ ID NO 55
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
                20                  25                  30

Gly Thr Ser Leu Met His Trp Tyr Gln Gln Lys Pro Gly Gln Pro Pro
            35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Gln
65                  70                  75                  80

Ser Val Gln Ala Glu Asp Val Ser Val Tyr Phe Cys Gln Gln Thr Arg
                85                  90                  95

Lys Val Pro Tyr Thr Phe Gly Gln Gly Thr Lys Leu Glu Ile Lys Gly
                100                 105                 110

Gly Ser Glu Gly Lys Ser Ser Gly Ser Gly Ser Glu Ser Lys Ser Thr
            115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
    195                 200                 205

Gln Phe Ser Leu Lys Leu Ser Ser Val Thr Pro Val Asp Thr Ala Val
210                 215                 220

Tyr Tyr Cys Ala Thr Gly Tyr Tyr Tyr Gly Ser Gly Phe Trp Gly Gln
225                 230                 235                 240

Gly Thr Leu Val Thr Val Ser Thr Ser Thr Pro Ala Pro Arg Pro
                245                 250                 255

Pro Thr Pro Ala Pro Thr Ile Ala Ser Gln Pro Leu Ser Leu Arg Pro
                260                 265                 270
```

Glu Ala Cys Arg Pro Ala Ala Gly Gly Ala Val His Thr Arg Gly Leu
            275                 280                 285

Asp Phe Ala Cys Asp Ile Tyr Ile Trp Ala Pro Leu Ala Gly Thr Cys
        290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470

<210> SEQ ID NO 56
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Met Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Ser Ser Val Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470

<210> SEQ ID NO 57
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp

```
            35                  40                  45
Ile Gly Tyr Ile Ser Tyr Ser Gly Ser Thr Thr Tyr Asn Pro Ser Leu
 50                  55                  60

Lys Ser Arg Val Thr Met Ser Arg Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Thr Gly Tyr Tyr Gly Ser Gly Phe Trp Gly Gln Gly Thr Leu
                100                 105                 110

Val Thr Val Ser Ser Gly Gly Ser Glu Gly Lys Ser Ser Gly Ser Gly
                115                 120                 125

Ser Glu Ser Lys Ser Thr Gly Gly Ser Asp Ile Val Leu Thr Gln Ser
        130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
                180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Gln Ser Val Gln Ala Glu Asp Val
210                 215                 220

Ser Val Tyr Phe Cys Gln Gln Thr Arg Lys Val Pro Tyr Thr Phe Gly
225                 230                 235                 240

Gln Gly Thr Lys Leu Glu Ile Lys Thr Ser Thr Pro Ala Pro Arg Pro
                245                 250                 255

Pro Thr Pro Ala Pro Thr Ile Ala Ser Gln Pro Leu Ser Leu Arg Pro
                260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
                340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
        370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
        450                 455                 460
```

```
Met Gln Ala Leu Pro Pro Arg
465                 470

<210> SEQ ID NO 58
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Met Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
            115                 120                 125

Ser Glu Ser Lys Ser Thr Gly Gly Ser Asp Ile Val Leu Thr Gln Ser
130                 135                 140

Pro Asp Ser Leu Ala Val Ser Leu Gly Glu Arg Ala Thr Ile Asn Cys
145                 150                 155                 160

Lys Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Arg Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Tyr Cys Gln Gln Thr Arg Lys Val Pro Tyr Thr Phe Gly
225                 230                 235                 240

Gln Gly Thr Lys Leu Glu Ile Lys Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
```

```
            340                 345                 350
Glu Glu Gly Gly Cys Glu Leu Arg Val Lys Phe Ser Arg Ser Ala Asp
            355                 360                 365

Ala Pro Ala Tyr Lys Gln Gly Gln Asn Gln Leu Tyr Asn Glu Leu Asn
        370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
                435                 440                 445

Tyr Gln Gly Leu Ser Thr Ala Thr Lys Asp Thr Tyr Asp Ala Leu His
        450                 455                 460

Met Gln Ala Leu Pro Pro Arg
465                 470

<210> SEQ ID NO 59
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Gln
65                  70                  75                  80

Ser Val Gln Ala Glu Asp Val Ser Val Tyr Phe Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Pro Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Met Ser Arg Asp Thr Ser Lys Asn
        195                 200                 205

Gln Phe Ser Leu Lys Leu Ser Ser Val Thr Ala Val Asp Thr Ala Val
    210                 215                 220
```

Tyr Tyr Cys Ala Thr Gly Tyr Tyr Gly Ser Gly Phe Trp Gly Gln
225                 230                 235                 240

Gly Thr Leu Val Thr Val Ser Ser Thr Ser Pro Ala Pro Arg Pro
            245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
            275                 280                 285

Asp Phe Ala Cys Asp Ile Tyr Ile Trp Ala Pro Leu Ala Gly Thr Cys
            290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
                340                 345                 350

Glu Glu Gly Gly Cys Glu Leu Arg Val Lys Phe Ser Arg Ser Ala Asp
            355                 360                 365

Ala Pro Ala Tyr Lys Gln Gly Gln Asn Gln Leu Tyr Asn Glu Leu Asn
            370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
            450                 455                 460

Met Gln Ala Leu Pro Pro Arg
465                 470

<210> SEQ ID NO 60
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Gly
            100                 105                 110

```
Gly Ser Glu Gly Lys Ser Ser Gly Ser Glu Ser Lys Ser Thr
            115                 120                 125
Gly Gly Ser Gln Val Gln Leu Gln Glu Ser Gly Pro Gly Leu Val Lys
130                 135                 140
Pro Ser Asp Thr Leu Ser Leu Thr Cys Ala Val Ser Gly Asn Ser Ile
145                 150                 155                 160
Thr Ser Asp Tyr Ala Trp Asn Trp Ile Arg Gln Pro Pro Gly Lys Gly
                165                 170                 175
Leu Glu Trp Ile Gly Tyr Ile Ser Tyr Ser Gly Ser Thr Thr Tyr Asn
                180                 185                 190
Pro Ser Leu Lys Ser Arg Val Thr Met Ser Arg Asp Thr Ser Lys Asn
                195                 200                 205
Gln Phe Ser Leu Lys Leu Ser Ser Val Thr Ala Val Asp Thr Ala Val
    210                 215                 220
Tyr Tyr Cys Ala Thr Gly Tyr Tyr Gly Ser Gly Phe Trp Gly Gln
225                 230                 235                 240
Gly Thr Leu Val Thr Val Ser Ser Thr Ser Thr Pro Ala Pro Arg Pro
                245                 250                 255
Pro Thr Pro Ala Pro Thr Ile Ala Ser Gln Pro Leu Ser Leu Arg Pro
                260                 265                 270
Glu Ala Cys Arg Pro Ala Ala Gly Gly Ala Val His Thr Arg Gly Leu
            275                 280                 285
Asp Phe Ala Cys Asp Ile Tyr Ile Trp Ala Pro Leu Ala Gly Thr Cys
        290                 295                 300
Gly Val Leu Leu Leu Ser Leu Val Ile Thr Leu Tyr Cys Lys Arg Gly
305                 310                 315                 320
Arg Lys Lys Leu Leu Tyr Ile Phe Lys Gln Pro Phe Met Arg Pro Val
                325                 330                 335
Gln Thr Thr Gln Glu Glu Asp Gly Cys Ser Cys Arg Phe Pro Glu Glu
                340                 345                 350
Glu Glu Gly Gly Cys Glu Leu Arg Val Lys Phe Ser Arg Ser Ala Asp
            355                 360                 365
Ala Pro Ala Tyr Lys Gln Gly Gln Asn Gln Leu Tyr Asn Glu Leu Asn
        370                 375                 380
Leu Gly Arg Arg Glu Glu Tyr Asp Val Leu Asp Lys Arg Arg Gly Arg
385                 390                 395                 400
Asp Pro Glu Met Gly Gly Lys Pro Arg Arg Lys Asn Pro Gln Glu Gly
                405                 410                 415
Leu Tyr Asn Glu Leu Gln Lys Asp Lys Met Ala Glu Ala Tyr Ser Glu
                420                 425                 430
Ile Gly Met Lys Gly Glu Arg Arg Arg Gly Lys Gly His Asp Gly Leu
            435                 440                 445
Tyr Gln Gly Leu Ser Thr Ala Thr Lys Asp Thr Tyr Asp Ala Leu His
    450                 455                 460
Met Gln Ala Leu Pro Pro Arg
465                 470

<210> SEQ ID NO 61
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 61

```
Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Asp Thr Leu Ser Leu Thr Cys Ala Val Ser Gly Asn Ser Ile
145                 150                 155                 160

Thr Ser Asp Tyr Ala Trp Asn Trp Ile Arg Gln Pro Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Met Ser Arg Asp Thr Ser Lys Asn
        195                 200                 205

Gln Phe Ser Leu Lys Leu Ser Ser Val Thr Ala Val Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415
```

```
Leu Tyr Asn Glu Leu Gln Lys Asp Lys Met Ala Glu Ala Tyr Ser Glu
            420                 425                 430

Ile Gly Met Lys Gly Glu Arg Arg Gly Lys Gly His Asp Gly Leu
            435                 440                 445

Tyr Gln Gly Leu Ser Thr Ala Thr Lys Asp Thr Tyr Asp Ala Leu His
            450                 455                 460

Met Gln Ala Leu Pro Pro Arg
465                 470

<210> SEQ ID NO 62
<211> LENGTH: 261
<212> TYPE: PRT
<213> ORGANISM: Homo sapiens

<400> SEQUENCE: 62

Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys Gly Gly Val Leu Val His Pro Gln Trp Val Leu Thr Ala Ala
    50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205

Cys Gly Gly Asp Ser Gly Gly Pro Leu Val Cys Asn Gly Val Leu Gln
    210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
                245                 250                 255

Ile Ala Ala Asn Pro
            260

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                                 peptide

<400> SEQUENCE: 63

Ser Asp Tyr Ala Trp Asn
1               5

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Tyr Ile Ser Tyr Ser Gly Ser Thr Thr Tyr Ser Pro Ser Leu Lys Ser
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Ile Ser Tyr Ser Gly Ser Thr Thr Tyr Asn Pro Ser Leu Lys Ser
1               5                   10                  15

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Tyr Tyr Tyr Gly Ser Gly Phe
1               5

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Ala Ser Glu Ser Val Glu Tyr Phe Gly Thr Ser Leu Met His
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Ala Ser Glu Ser Val Glu Tyr Phe Gly Thr Ser Leu Met His
1               5                   10                  15

<210> SEQ ID NO 69
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Ala Ser Asn Val Glu Ser
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Ala Ser Asn Arg Glu Ser
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gln Thr Arg Lys Val Pro Tyr Thr
1               5

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Asn Ser Ile Thr Ser Asp Tyr Ala Trp Asn
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Ile Ser Tyr Ser Gly Ser Thr Thr
1               5

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74
```

```
Glu Ile Val Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ser Trp Tyr Gln Gln Lys Pro Gly Lys Ala Pro Lys Leu Leu Ile
        35                  40                  45

Tyr Ala Thr Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys
            100                 105
```

<210> SEQ ID NO 75
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Arg Leu Leu Ile Tyr Ala Ala Ser Asn Val Glu Ser Gly Ile Pro Ala
50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Val Tyr Phe Cys Gln Gln Thr Arg
                85                  90                  95

Lys Val Pro Tyr Thr Phe Gly Gly Gly Thr Lys Val Glu Ile Lys
            100                 105                 110
```

<210> SEQ ID NO 76
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Arg Tyr Tyr Val Asp Ser Val
50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Gln Asn Tyr Asp Ile Leu Thr Gly His Tyr Gly Met Asp
            100                 105                 110

Val Trp Gly Gln Gly Thr Thr Val Thr Val Ser Ser
        115                 120
```

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Phe Pro Gly Lys Arg Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser
        115
```

<210> SEQ ID NO 78
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Asn Tyr Asp Ile Leu Thr Gly His Tyr Gly Met Asp
            100                 105                 110

Val Trp Gly Gln Gly Thr Thr Val Thr Val Ser Ser Gly Gly Ser Glu
        115                 120                 125
```

Gly Lys Ser Ser Gly Ser Gly Ser Glu Ser Lys Ser Thr Gly Gly Ser
        130                 135                 140

Glu Ile Val Leu Thr Gln Ser Pro Ser Phe Leu Ser Ala Ser Val Gly
145                 150                 155                 160

Asp Arg Val Thr Ile Thr Cys Arg Ala Ser Gln Gly Ile Ser Ser Tyr
                165                 170                 175

Leu Ser Trp Tyr Gln Gln Lys Pro Gly Lys Ala Pro Lys Leu Leu Ile
            180                 185                 190

Tyr Ala Thr Ser Thr Leu Gln Ser Gly Val Pro Ser Arg Phe Ser Gly
        195                 200                 205

Ser Gly Ser Gly Thr Glu Phe Thr Leu Thr Ile Ser Ser Leu Gln Pro
210                 215                 220

Glu Asp Phe Ala Thr Tyr Tyr Cys Gln Gln Leu Asn Ser Tyr Pro Arg
225                 230                 235                 240

Thr Phe Gly Gln Gly Thr Lys Val Glu Ile Lys
                245                 250

<210> SEQ ID NO 79
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Ile Val Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ser Trp Tyr Gln Gln Lys Pro Gly Lys Ala Pro Lys Leu Leu Ile
            35                  40                  45

Tyr Ala Thr Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys Gly Gly Ser Glu Gly
            100                 105                 110

Lys Ser Ser Gly Ser Gly Ser Glu Ser Lys Ser Thr Gly Gly Ser Glu
        115                 120                 125

Val Gln Leu Val Glu Ser Gly Gly Gly Leu Val Gln Pro Gly Gly Ser
130                 135                 140

Leu Arg Leu Ser Cys Ala Ala Ser Gly Phe Thr Phe Ser Ser Tyr Trp
145                 150                 155                 160

Met Thr Trp Val Arg Gln Ala Pro Gly Lys Gly Leu Glu Trp Val Ala
                165                 170                 175

Asn Ile Lys Gln Asp Gly Ser Glu Arg Tyr Tyr Val Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
210                 215                 220

Arg Asp Gln Asn Tyr Asp Ile Leu Thr Gly His Tyr Gly Met Asp Val
225                 230                 235                 240

```
Trp Gly Gln Gly Thr Thr Val Thr Val Ser Ser
                245                 250

<210> SEQ ID NO 80
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Phe Pro Gly Lys Arg Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
            115                 120                 125

Ser Glu Ser Lys Ser Thr Gly Gly Ser Glu Ile Val Leu Thr Gln Ser
        130                 135                 140

Pro Ala Thr Leu Ser Leu Ser Pro Gly Glu Arg Ala Thr Leu Ser Cys
145                 150                 155                 160

Arg Ala Ser Glu Ser Val Glu Tyr Phe Gly Thr Ser Leu Met His Trp
                165                 170                 175

Tyr Gln Gln Lys Pro Gly Gln Pro Pro Arg Leu Leu Ile Tyr Ala Ala
            180                 185                 190

Ser Asn Val Glu Ser Gly Ile Pro Ala Arg Phe Ser Gly Ser Gly Ser
        195                 200                 205

Gly Thr Asp Phe Thr Leu Thr Ile Ser Ser Val Glu Pro Glu Asp Phe
    210                 215                 220

Ala Val Tyr Phe Cys Gln Gln Thr Arg Lys Val Pro Tyr Thr Phe Gly
225                 230                 235                 240

Gly Gly Thr Lys Val Glu Ile Lys
                245

<210> SEQ ID NO 81
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Phe
            20                  25                  30
```

Gly Thr Ser Leu Met His Trp Tyr Gln Gln Lys Pro Gly Gln Pro
            35                  40                  45

Arg Leu Leu Ile Tyr Ala Ala Ser Asn Val Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Val Tyr Phe Cys Gln Gln Thr Arg
                85                  90                  95

Lys Val Pro Tyr Thr Phe Gly Gly Thr Lys Val Glu Ile Lys Gly
            100                 105                 110

Gly Ser Glu Gly Lys Ser Ser Gly Ser Glu Ser Lys Ser Thr
            115                 120                 125

Gly Gly Ser Gln Val Gln Leu Gln Glu Ser Gly Pro Gly Leu Val Lys
            130                 135                 140

Pro Ser Gln Thr Leu Ser Leu Thr Cys Thr Val Ser Gly Asn Ser Ile
145                 150                 155                 160

Thr Ser Asp Tyr Ala Trp Asn Trp Ile Arg Gln Phe Pro Gly Lys Arg
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
            195                 200                 205

Gln Phe Ser Leu Lys Leu Ser Ser Val Thr Ala Ala Asp Thr Ala Val
    210                 215                 220

Tyr Tyr Cys Ala Thr Gly Tyr Tyr Tyr Gly Ser Gly Phe Trp Gly Gln
225                 230                 235                 240

Gly Thr Leu Val Thr Val Ser Ser
            245

<210> SEQ ID NO 82
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
            35                  40                  45

Ala Asn Ile Lys Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Asn Tyr Asp Ile Leu Thr Gly His Tyr Gly Met Asp
            100                 105                 110

Val Trp Gly Gln Gly Thr Thr Val Thr Val Ser Ser Gly Gly Ser Glu
            115                 120                 125

Gly Lys Ser Ser Gly Ser Gly Ser Glu Ser Lys Ser Thr Gly Gly Ser

```
            130                 135                 140
Glu Ile Val Leu Thr Gln Ser Pro Ser Phe Leu Ser Ala Ser Val Gly
145                 150                 155                 160

Asp Arg Val Thr Ile Thr Cys Arg Ala Ser Gln Gly Ile Ser Ser Tyr
                165                 170                 175

Leu Ser Trp Tyr Gln Gln Lys Pro Gly Lys Ala Pro Lys Leu Leu Ile
            180                 185                 190

Tyr Ala Thr Ser Thr Leu Gln Ser Gly Val Pro Ser Arg Phe Ser Gly
            195                 200                 205

Ser Gly Ser Gly Thr Glu Phe Thr Leu Thr Ile Ser Ser Leu Gln Pro
210                 215                 220

Glu Asp Phe Ala Thr Tyr Tyr Cys Gln Gln Leu Asn Ser Tyr Pro Arg
225                 230                 235                 240

Thr Phe Gly Gln Gly Thr Lys Val Glu Ile Lys Thr Ser Thr Pro Ala
                245                 250                 255

Pro Arg Pro Pro Thr Pro Ala Pro Thr Ile Ala Ser Gln Pro Leu Ser
                260                 265                 270

Leu Arg Pro Glu Ala Cys Arg Pro Ala Ala Gly Gly Ala Val His Thr
            275                 280                 285

Arg Gly Leu Asp Phe Ala Cys Asp Ile Tyr Ile Trp Ala Pro Leu Ala
            290                 295                 300

Gly Thr Cys Gly Val Leu Leu Leu Ser Leu Val Ile Thr Leu Tyr Cys
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
                340                 345                 350

Pro Glu Glu Glu Glu Gly Gly Cys Glu Leu Arg Val Lys Phe Ser Arg
            355                 360                 365

Ser Ala Asp Ala Pro Ala Tyr Lys Gln Gly Gln Asn Gln Leu Tyr Asn
370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
            435                 440                 445

Asp Gly Leu Tyr Gln Gly Leu Ser Thr Ala Thr Lys Asp Thr Tyr Asp
450                 455                 460

Ala Leu His Met Gln Ala Leu Pro Pro Arg
465                 470

<210> SEQ ID NO 83
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Ile Val Leu Thr Gln Ser Pro Ser Phe Leu Ser Ala Ser Val Gly
1               5                   10                  15
```

```
Asp Arg Val Thr Ile Thr Cys Arg Ala Ser Gln Gly Ile Ser Ser Tyr
             20                  25                  30

Leu Ser Trp Tyr Gln Gln Lys Pro Gly Lys Ala Pro Lys Leu Leu Ile
         35                  40                  45

Tyr Ala Thr Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Arg
                 85                  90                  95

Thr Phe Gly Gln Gly Thr Lys Val Glu Ile Lys Gly Gly Ser Glu Gly
             100                 105                 110

Lys Ser Ser Gly Ser Gly Ser Glu Ser Lys Ser Thr Gly Gly Ser Glu
         115                 120                 125

Val Gln Leu Val Glu Ser Gly Gly Leu Val Gln Pro Gly Gly Ser
     130                 135                 140

Leu Arg Leu Ser Cys Ala Ala Ser Gly Phe Thr Phe Ser Ser Tyr Trp
145                 150                 155                 160

Met Thr Trp Val Arg Gln Ala Pro Gly Lys Gly Leu Glu Trp Val Ala
             165                 170                 175

Asn Ile Lys Gln Asp Gly Ser Glu Arg Tyr Tyr Val Asp Ser Val Lys
             180                 185                 190

Gly Arg Phe Thr Ile Ser Arg Asp Asn Ala Lys Asn Ser Leu Tyr Leu
         195                 200                 205

Gln Met Asn Ser Leu Arg Ala Glu Asp Thr Ala Val Tyr Tyr Cys Ala
210                 215                 220

Arg Asp Gln Asn Tyr Asp Ile Leu Thr Gly His Tyr Gly Met Asp Val
225                 230                 235                 240

Trp Gly Gln Gly Thr Thr Val Thr Val Ser Ser Thr Ser Thr Pro Ala
             245                 250                 255

Pro Arg Pro Pro Thr Pro Ala Pro Thr Ile Ala Ser Gln Pro Leu Ser
         260                 265                 270

Leu Arg Pro Glu Ala Cys Arg Pro Ala Ala Gly Gly Ala Val His Thr
         275                 280                 285

Arg Gly Leu Asp Phe Ala Cys Asp Ile Tyr Ile Trp Ala Pro Leu Ala
290                 295                 300

Gly Thr Cys Gly Val Leu Leu Leu Ser Leu Val Ile Thr Leu Tyr Cys
305                 310                 315                 320

Lys Arg Gly Arg Lys Lys Leu Leu Tyr Ile Phe Lys Gln Pro Phe Met
             325                 330                 335

Arg Pro Val Gln Thr Thr Gln Glu Glu Asp Gly Cys Ser Cys Arg Phe
             340                 345                 350

Pro Glu Glu Glu Glu Gly Gly Cys Glu Leu Arg Val Lys Phe Ser Arg
         355                 360                 365

Ser Ala Asp Ala Pro Ala Tyr Lys Gln Gly Gln Asn Gln Leu Tyr Asn
     370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                 405                 410                 415

Gln Glu Gly Leu Tyr Asn Glu Leu Gln Lys Asp Lys Met Ala Glu Ala
             420                 425                 430

Tyr Ser Glu Ile Gly Met Lys Gly Glu Arg Arg Arg Gly Lys Gly His
```

-continued

```
                435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470

<210> SEQ ID NO 84
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Phe Pro Gly Lys Arg Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Glu Ile Val Leu Thr Gln Ser
130                 135                 140

Pro Ala Thr Leu Ser Leu Ser Pro Gly Glu Arg Ala Thr Leu Ser Cys
145                 150                 155                 160

Arg Ala Ser Glu Ser Val Glu Tyr Phe Gly Thr Ser Leu Met His Trp
                165                 170                 175

Tyr Gln Gln Lys Pro Gly Gln Pro Pro Arg Leu Leu Ile Tyr Ala Ala
            180                 185                 190

Ser Asn Val Glu Ser Gly Ile Pro Ala Arg Phe Ser Gly Ser Gly Ser
        195                 200                 205

Gly Thr Asp Phe Thr Leu Thr Ile Ser Ser Val Glu Pro Glu Asp Phe
    210                 215                 220

Ala Val Tyr Phe Cys Gln Gln Thr Arg Lys Val Pro Tyr Thr Phe Gly
225                 230                 235                 240

Gly Gly Thr Lys Val Glu Ile Lys Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320
```

```
Arg Lys Lys Leu Leu Tyr Ile Phe Lys Gln Pro Phe Met Arg Pro Val
            325                 330                 335

Gln Thr Thr Gln Glu Glu Asp Gly Cys Ser Cys Arg Phe Pro Glu Glu
        340                 345                 350

Glu Glu Gly Gly Cys Glu Leu Arg Val Lys Phe Ser Arg Ser Ala Asp
            355                 360                 365

Ala Pro Ala Tyr Lys Gln Gly Gln Asn Gln Leu Tyr Asn Glu Leu Asn
        370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
            405                 410                 415

Leu Tyr Asn Glu Leu Gln Lys Asp Lys Met Ala Glu Ala Tyr Ser Glu
        420                 425                 430

Ile Gly Met Lys Gly Glu Arg Arg Gly Lys Gly His Asp Gly Leu
            435                 440                 445

Tyr Gln Gly Leu Ser Thr Ala Thr Lys Asp Thr Tyr Asp Ala Leu His
        450                 455                 460

Met Gln Ala Leu Pro Pro Arg
465                 470

<210> SEQ ID NO 85
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Arg Leu Leu Ile Tyr Ala Ala Ser Asn Val Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Val Tyr Phe Cys Gln Gln Thr Arg
                85                  90                  95

Lys Val Pro Tyr Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Gln Thr Leu Ser Leu Thr Cys Thr Val Ser Gly Asn Ser Ile
145                 150                 155                 160

Thr Ser Asp Tyr Ala Trp Asn Trp Ile Arg Gln Phe Pro Gly Lys Arg
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205
```

```
Gln Phe Ser Leu Lys Leu Ser Ser Val Thr Ala Ala Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser Thr Ser Pro Ala Pro Arg Pro
                245                 250                 255

Pro Thr Pro Ala Pro Thr Ile Ala Ser Gln Pro Leu Ser Leu Arg Pro
                260                 265                 270

Glu Ala Cys Arg Pro Ala Ala Gly Gly Ala Val His Thr Arg Gly Leu
            275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
                340                 345                 350

Glu Glu Gly Gly Cys Glu Leu Arg Val Lys Phe Ser Arg Ser Ala Asp
            355                 360                 365

Ala Pro Ala Tyr Lys Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Phe Thr Phe Ser Ser Tyr Trp
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ile Lys Gln Asp Gly Ser Glu Arg
1               5
```

```
<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Arg Asp Gln Asn Tyr Asp Ile Leu Thr Gly His Tyr Gly Met Asp
1               5                   10                  15
Val

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Gly Ile Ser Ser Tyr
1               5

<210> SEQ ID NO 90
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Thr Ser
1

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Gln Leu Asn Ser Tyr Pro Arg Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Asn Ser Ile Thr Ser Asp Tyr Ala
1               5

<210> SEQ ID NO 93
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 93

Ile Ser Tyr Ser Gly Ser Thr
1               5

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Thr Gly Tyr Tyr Tyr Gly Ser Gly Phe
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Glu Ser Val Glu Tyr Phe Gly Thr Ser Leu
1               5                   10

<210> SEQ ID NO 96
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Ala Ser
1

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Asn Asn Ile Gly Ser Lys Ser Val His
1               5                   10

<210> SEQ ID NO 98
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Thr Ser Gly Ser Ser Gly Ser Gly Ser Gly Gly Ser Gly Ser Gly
1               5                   10                  15

Gly Gly Gly

```
<210> SEQ ID NO 99
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Lys Pro Gly Ser Gly Lys Pro Gly Ser Gly Lys Pro Gly Ser Gly
1               5                   10                  15

Lys Pro Gly Ser
            20

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Tyr Ile Ser Tyr Ser Gly Ser Thr Thr Tyr Asn Pro Ser Leu Lys Ser
1               5                   10                  15

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Asn Ser Ile Thr Ser Asp Tyr Ala Trp Asn
1               5                   10

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Tyr Tyr Trp Ser
1               5

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Ile Tyr Tyr Ser Gly Ser Thr Asn Tyr Asn Pro Ser Leu Lys Ser
1               5                   10                  15

<210> SEQ ID NO 104
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 104

Thr Thr Ile Phe Gly Val Val Thr Pro Asn Phe Tyr Tyr Gly Met Asp
1               5                   10                  15

Val

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Gly Ser Ile Ser Ser Tyr Tyr Trp Ser
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr Ile Tyr Tyr Ser Gly Ser Thr Asn
1               5

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Tyr Asp Ile His
1               5

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Ile Ser Tyr Asp Gly Ser Lys Lys Asp Tyr Thr Asp Ser Val Lys
1               5                   10                  15

Gly

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109
```

```
Glu Ser Gly Trp Ser His Tyr Tyr Tyr Gly Met Asp Val
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Phe Thr Phe Ser Ser Tyr Asp Ile His
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ile Ile Ser Tyr Asp Gly Ser Lys Lys Asp
1               5                   10

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Leu Tyr Val Ser Gly Phe Thr Asn Tyr Asn Pro Ser Leu Lys Ser
1               5                   10                  15

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Ser Gly Asn Tyr Trp Gly Trp Phe Asp Pro
1               5                   10

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Leu Tyr Val Ser Gly Phe Thr Asn
1               5

<210> SEQ ID NO 115
<211> LENGTH: 5
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 115

Tyr Tyr Gly Met His
1               5

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Phe Ile Ser Tyr Asp Gly Ser Asn Lys Tyr Tyr Ala Asp Ser Val Lys
1               5                   10                  15

Gly

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Leu Pro Tyr Ser Gly Ser Tyr Trp Ala Phe Asp Tyr
1               5                   10

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Phe Thr Phe Ser Tyr Tyr
1               5

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Phe Ile Ser Tyr Asp Gly Ser Asn Lys Tyr
1               5                   10

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

His Tyr Ala Met Ser

```
1               5

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Thr Ile Gly Gly Ser Gly Gly Ser Thr Tyr Tyr Ala Asp Ser Val Lys
1               5                   10                  15

Gly

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Pro His Ile Val Met Val Thr Ala Leu Leu Tyr Asp Gly Met Asp Val
1               5                   10                  15

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Phe Thr Phe Ser His Tyr Ala Met Ser
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Ile Gly Gly Ser Gly Gly Ser Thr Tyr Tyr
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Ala Ser Gln Asp Ile Ser Asn Tyr Leu Ala
1               5                   10

<210> SEQ ID NO 126
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 126

Ala Ala Ser Asn Val Glu Ser
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asp Asp Ser Asp Arg Pro Ser
1               5

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Ala Ser Gln Gly Ile Ser Ser Tyr Leu Ala
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Ala Ser Thr Leu Gln Ser
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Gln Leu Asn Ser Tyr Pro Leu Thr
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Ala Ser Thr Leu His Ser
1               5
```

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Lys Tyr Asn Ser Ala Pro Tyr Thr
1               5

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Gly Asp Gln Leu Gly Glu Asn Tyr Ala Cys
1               5                   10

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Asp Ser Lys Arg Pro Ser
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Ala Trp Asp Asn Ser Ile Val Val
1               5

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Gly Asp Asn Ile Gly Ser Lys Ser Val His
1               5                   10

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 137

Asp Asn Ser Asp Arg Pro Ser
1               5

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gln Val Trp Asp Ser Ser Ser Asp His Pro Val Val
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gln Val Trp Asp Ser Ser Ser Asp His Val Val
1               5                   10

<210> SEQ ID NO 140
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser
        115

<210> SEQ ID NO 141
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Thr Tyr Asn Pro Ser Leu
50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser
            115

<210> SEQ ID NO 142
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly Thr Thr Ile Phe Gly Val Val Thr Pro Asn Phe Tyr Tyr Gly Met
            100                 105                 110

Asp Val Trp Gly Gln Gly Thr Thr Val Thr Val Ser Ser
            115                 120                 125

<210> SEQ ID NO 143
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Asp Ile His Trp Val Arg Gln Ala Pro Gly Lys Gly Leu Glu Trp Val
        35                  40                  45

Ala Ile Ile Ser Tyr Asp Gly Ser Lys Lys Asp Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Val Glu Asp Ser Ala Val Tyr Ser Cys
                85                  90                  95

Ala Arg Glu Ser Gly Trp Ser His Tyr Tyr Tyr Gly Met Asp Val
                100                 105                 110

Trp Gly Gln Gly Thr Met Val Thr Val Ser Ser
            115                 120

<210> SEQ ID NO 144
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Leu Arg Gln Pro Ala Gly Ser Gly Leu Glu Trp Ile
            35                  40                  45

Gly Arg Leu Tyr Val Ser Gly Phe Thr Asn Tyr Asn Pro Ser Leu Lys
        50                  55                  60

Ser Arg Val Thr Leu Ser Leu Asp Pro Ser Arg Asn Gln Leu Ser Leu
65                  70                  75                  80

Lys Leu Ser Ser Val Thr Ala Ala Asp Thr Ala Val Tyr Tyr Cys Ala
                85                  90                  95

Gly Asp Ser Gly Asn Tyr Trp Gly Trp Phe Asp Pro Trp Gly Gln Gly
                100                 105                 110

Thr Leu Val Thr Val Ser Ser
            115

<210> SEQ ID NO 145
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
                20                  25                  30

Gly Met His Trp Val Arg Gln Ala Pro Gly Lys Gly Leu Glu Trp Val
            35                  40                  45

Ala Phe Ile Ser Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala His Leu Pro Tyr Ser Gly Ser Tyr Trp Ala Phe Asp Tyr Trp Gly
            100                 105                 110

Gln Gly Thr Gln Val Thr Val Ser Ser
        115                 120

<210> SEQ ID NO 146
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ala Met Ser Trp Val Arg Gln Ala Pro Gly Lys Gly Leu Glu Trp Val
        35                  40                  45

Ser Thr Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Ile Val Met Val Thr Ala Leu Leu Tyr Asp Gly Met
            100                 105                 110

Asp Val Trp Gly Gln Gly Thr Met Val Thr Val Ser Ser
        115                 120                 125

<210> SEQ ID NO 147
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Thr Arg
                85                  90                  95

Lys Val Pro Tyr Thr Phe Gly Gly Gly Thr Lys Val Glu Ile Lys
            100                 105                 110

<210> SEQ ID NO 148
<211> LENGTH: 107
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 148

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Phe Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 149
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Val Pro Lys Phe Leu Ile
        35                  40                  45

Tyr Ala Ala Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Arg Leu Glu Ile Lys
            100                 105

<210> SEQ ID NO 150
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ser Tyr Glu Leu Thr Gln Pro Pro Ser Val Ser Val Ser Pro Gly Glu
1               5                   10                  15

Thr Ala Ser Ile Thr Cys Ser Gly Asp Gln Leu Gly Glu Asn Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser

```
                        50                  55                  60

Asn Ser Gly Asn Thr Ala Thr Leu Thr Ile Ser Gly Thr Gln Ala Leu
 65                  70                  75                  80

Asp Glu Ala Asp Tyr Tyr Cys Gln Ala Trp Asp Asn Ser Ile Val Val
                 85                  90                  95

Phe Gly Gly Gly Thr Lys Leu Thr Val Leu
                100                 105

<210> SEQ ID NO 151
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Ser Val Leu Thr Gln Pro Pro Ser Val Ser Val Ala Pro Gly Gln
 1               5                  10                  15

Thr Ala Ser Ile Thr Cys Gly Gly Asp Asn Ile Gly Ser Lys Ser Val
                20                  25                  30

His Trp Tyr Gln Gln Lys Pro Gly Gln Ala Pro Val Leu Val Val Tyr
             35                  40                  45

Asp Asn Ser Asp Arg Pro Ser Gly Ile Pro Glu Arg Phe Ser Gly Ser
         50                  55                  60

Asn Ser Gly Thr Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Pro Val Val Phe Gly Gly Gly Thr Lys Val Thr Val
                100                 105

<210> SEQ ID NO 152
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Ser Ser Glu Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
             35                  40                  45

Asp Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu
                100                 105

<210> SEQ ID NO 153
<211> LENGTH: 351
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 153

```
caggttcagc tgcaagagtc tggaccaggc ctggtcaagc cctctcagac cctgtctctg    60
acctgtaccg tgtccggcaa ctccatcacc tctgactacg cctggaactg gattcggcag   120
ttccctggca agggccttga gtggatcggc tacatctcct actccggttc caccacctac   180
aaccccagcc tgaagtcccg ggtcaccatc tcccgcgaca cctccaagaa ccagttctcc   240
ctgaagctgt cctccgtgac cgctgctgat accgccgtgt actactgtgc caccggctac   300
tactacggct ccggcttttg gggacagggc acactggtta ccgtgtctag t            351
```

<210> SEQ ID NO 154
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 154

```
caggttcagc tgcaagagtc tggaccaggc ctggtcaagc cctctcagac cctgtctctg    60
acctgtaccg tgtccggcaa ctccatcacc tctgactacg cctggaactg gattcggcag   120
ccacctggca agggccttga gtggatcggc tacatctcct actccggttc caccacctac   180
aaccccagcc tgaagtcccg ggtcaccatc tcccgcgaca cctccaagaa ccagttctcc   240
ctgaagctgt cctccgtgac cgctgctgat accgccgtgt actactgtgc caccggctac   300
tactacggct ccggcttttg gggacagggc acactggtta ccgtgtctag t            351
```

<210> SEQ ID NO 155
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155

```
caggttcagc tgcaagagtc tggaccaggc ctggtcaagc cctctcagac cctgtctctg    60
acctgtaccg tgtccggcaa ctccatcacc tctgactacg cctggaactg gattcggcag   120
ttccctggca agggccttga gtggatcggc tacatctcct actccggttc caccacctac   180
aaccccagcc tgaagtcccg ggtcaccatc tcccgcgaca cctccaagaa ccagttctcc   240
ctgaagctgt cctccgtgac cgctgctgat accgccgtgt actactgtgc caccggctac   300
tactacggct ccggcttttg gggacagggc acactggtta ccgtgtctag t            351
```

<210> SEQ ID NO 156
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 156

```
caggtgcagc tgcaggagtc gggcccagga ctggtgaagc cttcggagac cctgtccctc    60
acctgcactg tctctggtgg ctccatcagt agttactact ggagctggat ccggcagccc   120
```
ccagggaagg gactggagtg gattggatat atctattaca gtgggagcac caactacaac        180
ccctccctca agagtcgagt caccatatca gtagacacgt ccaagaacca gttctccctg        240
aagctgagct ctgtgaccgc tgcggacacg gccgtgtatt actgtgcggg gactacgatt        300
tttggagtgg ttaccccaa cttctactac ggtatggacg tctggggcca agggaccacg         360
gtcaccgtct cctca        375

<210> SEQ ID NO 157
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
gaggtgcagc tggtggagtc tgggggaggc gtggtccagc ctgggaggtc cctgagactc        60
tcctgtgtag cctctggatt caccttcagt agttatgaca tacactgggt ccgccaggct        120
ccaggcaagg ggctggagtg ggtggcaatt atttcatatg atggaagtaa aaaagactat        180
acagactccg tgaagggccg attcaccatc tccagagaca attccaagaa cacgctgtat        240
ctgcaaatgg acagcctgag agttgaggac tcggctgtgt attcctgtgc gagagaaagt        300
ggctggtccc actactacta ttacggtatg gacgtctggg gccaagggac aatggtcacc        360
gtctcttca        369

<210> SEQ ID NO 158
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158
caggtgcagc tgcaggagtc gggcccagga ctggtgaagc cttcggagac cctgtccctc        60
acctgcactg tctctggtgg ctccatcagt agttactatt ggagctggct ccggcagccc        120
gccgggtcgg gactggagtg gattgggcgt ttatatgtca gtgggttcac caactacaac        180
ccctccctca agagtcgagt caccttgtca ctagacccgt ccaggaacca gttgtccctg        240
aaactgagtt ctgtgaccgc cgcggacacg gccgtatatt attgtgcggg agatagtggg        300
aactactggg gttggttcga cccctggggc cagggaaccc tggtcaccgt ctcctca        357

<210> SEQ ID NO 159
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159
caggtgcagc tggtggagtc tgggggaggc gtggtccagc ctgggaggtc cctgagactc        60
tcctgtgcag cctctggatt caccttcagt tactatggca tgcactgggt ccgccaggct        120
ccaggcaagg ggctggagtg ggtggcattt atatcatatg atggaagtaa taaatactat        180
gcagactccg tgaagggccg attcaccatc tccagagaca attccaagaa cacgctgtat        240
ctgcaaatga acagcctgag agctgaggac acggctgtgt attactgtgc ccacctccct        300

```
tatagtggga gctactgggc ctttgactac tggggccagg gaacccaggt caccgtctct    360
tca                                                                  363

<210> SEQ ID NO 160
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
caggtgcagc tggtggagtc tgggggaggc ttggtacagc ctggggggtc cctgagactc    60
tcctgtgcag cctctggatt cacctttagt cattatgcca tgagctgggt ccgccaggct    120
ccagggaagg ggctggagtg ggtctcaact attggtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaacctcat    300
attgtaatgg tgactgctct tctctacgac ggtatggacg tctggggcca agggacaatg    360
gtcaccgtct cctca                                                     375

<210> SEQ ID NO 161
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
gacatcgtgc tgacccagtc tccagactct ctggctgtgt ctctgggcga gagagccacc    60
atcaactgca gagcctccga gtccgtggaa tacttcggca cctctctgat gcactggtac    120
cagcagaagc ccggccagcc tcctaagctg ctgatctacg ccgcctccaa cgtggaatct    180
ggcgtgcccg atagattttc cggctctggc tctggcaccg actttaccct gaccatcagc    240
tctctgcagg ccgaggatgt ggccgtgtac ttctgtcagc agacccggaa ggtgccctac    300
acatttggcg gcggaacaaa ggtggaaatc aag                                 333

<210> SEQ ID NO 162
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162
gagatcgtgc tgacccagtc tcctgccaca ctgtcactgt ctccaggcga gagagccacc    60
ctctcttgta gagcctccga gtccgtggaa tacttcggca cctctctgat gcactggtac    120
cagcagaagc ccggccagcc tcctagactg ctgatctacg ccgcctccaa cgtcgaatct    180 ggcatcccccg ctagattctc cggctctggc tctggcacag actttaccct gaccatctcc    240
tccgtggaac ccgaggattt cgctgtgtac ttttgccagc agacccggaa ggtgccctac    300
acatttggcg gcggaacaaa ggtggaaatc aag                                 333

<210> SEQ ID NO 163
<211> LENGTH: 333
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163
gagatcgtgc tgacccagtc tcctgccaca ctgtcactgt ctccaggcga gagagccacc    60
ctctcttgta gagcctccga gtccgtggaa tacttcggca cctctctgat gcactggtac   120
cagcagaagc ccggccagcc tcctagactg ctgatctacg ccgcctccaa cgtcgaatct   180
ggcatccccg ctagattctc cggctctggc tctggcacag actttaccct gaccatctcc   240
tccgtggaac ccgaggattt cgctgtgtac ttttgccagc agacccggaa ggtgccctat   300
acatttggcg gcggaacaaa ggtggaaatc aag                                333

<210> SEQ ID NO 164
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164
gacatccaga tgacccagtc tccttccttc ctgtctgcat ctgtaggaga cagagtcacc    60
atcacttgcc gggccagtca gggcattagc agttatttag cctggtatca gcaaaaacca   120
gggaaagccc ctaagttcct gatctatgct gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatagtt accctctcac tttcggcgga   300
gggaccaagg tggaaatcaa a                                             321

<210> SEQ ID NO 165
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
gacatcgtga tgacccagtc tccatcctcc ctgtctgcat ctgtaggaga cagagtcacc    60
atcacttgcc gggcgagtca ggacattagc aattatttag cctggtatca gcagaaacca   120
gggaaagttc ctaagttcct gatctatgct gcatccactt tgcactctgg ggtcccatct   180
cggttcagtg gcagtggatc tgggacagat ttcactctca ccatcagcag cctgcagcct   240
gaagatgttg caacttatta ctgtcaaaag tataacagtg ccccgtacac ttttggccaa   300
gggacacgac tggagattaa a                                             321

<210> SEQ ID NO 166
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166
tcctatgagc tgactcagcc accctcagtg tccgtgtccc caggagagac agccagcatc    60
```

```
acctgctctg gagatcaatt gggggaaaat tatgcttgct ggtatcagca gaagccaggc      120
cagtcccctg tgttggtcat ctatcaagat agtaagcggc cctcagggat ccctgagcga      180
ttctctggct ccaactctgg gaacacagcc actctgacca tcagcgggac ccaggctctg      240
gatgaggctg actattactg tcaggcgtgg gacaacagta ttgtggtatt cggcggaggg      300
accaagctga ccgtccta                                                   318

<210> SEQ ID NO 167
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167
cagtctgtgc tgactcagcc accctcggtg tcagtggccc ccgggcagac ggccagtatt      60
acctgtgggg gagacaacat tggaagtaaa agtgtgcact ggtaccagca gaagccaggc      120
caggcccctg tgctggtcgt ctatgataat agcgaccggc cctcagggat ccctgagcga      180
ttctctggct ccaactctgg gaccacggcc accctgacca tcagcagggt cgaagccggg      240
gatgaggccg actattactg tcaggtgtgg gatagtagta gtgatcatcc tgtggtattc      300
ggcggaggga ccaaggtcac cgtccta                                         327

<210> SEQ ID NO 168
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 168
tcttctgagc tgactcagcc accctcggtg tcagtggccc caggacagac ggccaggatt      60
acctgtgggg gaaacaacat tggaagtaaa agtgtgcact ggtaccagca gaagccaggc      120
caggcccctg tgctggtcgt ctatgatgat agcgaccggc cctcagggat ccctgagcga      180
ttctctggct ccaactctgg gaacacggcc accctgacca tcagcagggt cgaagccggg      240
gatgaggccg actattactg tcaggtgtgg gatagtagta gtgatcatgt ggtattcggc      300
ggagggacca agctgaccgt ccta                                            324

<210> SEQ ID NO 169
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60
```

```
Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Arg Ala Ser Glu Ser Val Glu Tyr Phe Gly Thr Ser Leu Met His Trp
                165                 170                 175

Tyr Gln Gln Lys Pro Gly Gln Pro Lys Leu Leu Ile Tyr Ala Ala
            180                 185                 190

Ser Asn Val Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220

Ala Val Tyr Phe Cys Gln Gln Thr Arg Lys Val Pro Tyr Thr Phe Gly
225                 230                 235                 240

Gly Gly Thr Lys Val Glu Ile Lys
                245

<210> SEQ ID NO 170
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Thr Arg
                85                  90                  95

Lys Val Pro Tyr Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Gln Thr Leu Ser Leu Thr Cys Thr Val Ser Gly Asn Ser Ile
145                 150                 155                 160

Thr Ser Asp Tyr Ala Trp Asn Trp Ile Arg Gln Phe Pro Gly Lys Gly
                165                 170                 175
```

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
            195                 200                 205

Gln Phe Ser Leu Lys Leu Ser Ser Val Thr Ala Ala Asp Thr Ala Val
210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
            245

<210> SEQ ID NO 171
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Pro Pro Gly Lys Gly Leu Glu Trp
            35                  40                  45

Ile Gly Tyr Ile Ser Tyr Ser Gly Ser Thr Thr Tyr Asn Pro Ser Leu
50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
            115                 120                 125

Ser Glu Ser Lys Ser Thr Gly Gly Ser Glu Ile Val Leu Thr Gln Ser
130                 135                 140

Pro Ala Thr Leu Ser Leu Ser Pro Gly Glu Arg Ala Thr Leu Ser Cys
145                 150                 155                 160

Arg Ala Ser Glu Ser Val Glu Tyr Phe Gly Thr Ser Leu Met His Trp
            165                 170                 175

Tyr Gln Gln Lys Pro Gly Gln Pro Pro Arg Leu Leu Ile Tyr Ala Ala
            180                 185                 190

Ser Asn Val Glu Ser Gly Ile Pro Ala Arg Phe Ser Gly Ser Gly Ser
            195                 200                 205

Gly Thr Asp Phe Thr Leu Thr Ile Ser Ser Val Glu Pro Glu Asp Phe
            210                 215                 220

Ala Val Tyr Phe Cys Gln Gln Thr Arg Lys Val Pro Tyr Thr Phe Gly
225                 230                 235                 240

Gly Gly Thr Lys Val Glu Ile Lys
            245

<210> SEQ ID NO 172
<211> LENGTH: 248
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 172

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Glu Ser Val Glu Tyr Phe
            20                  25                  30
Gly Thr Ser Leu Met His Trp Tyr Gln Gln Lys Pro Gly Gln Pro Pro
        35                  40                  45
Arg Leu Leu Ile Tyr Ala Ala Ser Asn Val Glu Ser Gly Ile Pro Ala
    50                  55                  60
Arg Phe Ser Gly Ser Gly Ser Gly Thr Asp Phe Thr Leu Thr Ile Ser
65                  70                  75                  80
Ser Val Glu Pro Glu Asp Phe Ala Val Tyr Phe Cys Gln Gln Thr Arg
                85                  90                  95
Lys Val Pro Tyr Thr Phe Gly Gly Gly Thr Lys Val Glu Ile Lys Gly
            100                 105                 110
Gly Ser Glu Gly Lys Ser Ser Gly Ser Gly Ser Glu Ser Lys Ser Thr
        115                 120                 125
Gly Gly Ser Gln Val Gln Leu Gln Glu Ser Gly Pro Gly Leu Val Lys
    130                 135                 140
Pro Ser Gln Thr Leu Ser Leu Thr Cys Thr Val Ser Gly Asn Ser Ile
145                 150                 155                 160
Thr Ser Asp Tyr Ala Trp Asn Trp Ile Arg Gln Pro Pro Gly Lys Gly
                165                 170                 175
Leu Glu Trp Ile Gly Tyr Ile Ser Tyr Ser Gly Ser Thr Thr Tyr Asn
            180                 185                 190
Pro Ser Leu Lys Ser Arg Val Thr Ile Ser Arg Asp Thr Ser Lys Asn
        195                 200                 205
Gln Phe Ser Leu Lys Leu Ser Ser Val Thr Ala Ala Asp Thr Ala Val
    210                 215                 220
Tyr Tyr Cys Ala Thr Gly Tyr Tyr Tyr Gly Ser Gly Phe Trp Gly Gln
225                 230                 235                 240
Gly Thr Leu Val Thr Val Ser Ser
                245
```

<210> SEQ ID NO 173
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 173

```
Gln Val Gln Leu Gln Glu Ser Gly Pro Gly Leu Val Lys Pro Ser Gln
1               5                   10                  15
Thr Leu Ser Leu Thr Cys Thr Val Ser Gly Asn Ser Ile Thr Ser Asp
            20                  25                  30
Tyr Ala Trp Asn Trp Ile Arg Gln Phe Pro Gly Lys Gly Leu Glu Trp
        35                  40                  45
Ile Gly Tyr Ile Ser Tyr Ser Gly Ser Thr Thr Tyr Asn Pro Ser Leu
    50                  55                  60
Lys Ser Arg Val Thr Ile Ser Arg Asp Thr Ser Lys Asn Gln Phe Ser
```

```
                65                  70                  75                  80
Leu Lys Leu Ser Ser Val Thr Ala Ala Asp Thr Ala Val Tyr Tyr Cys
                    85                  90                  95

Ala Thr Gly Tyr Tyr Tyr Gly Ser Gly Phe Trp Gly Gln Gly Thr Leu
                    100                 105                 110

Val Thr Val Ser Ser Gly Gly Ser Glu Gly Lys Ser Gly Ser Gly
                    115                 120                 125

Ser Glu Ser Lys Ser Thr Gly Gly Ser Glu Ile Val Leu Thr Gln Ser
            130                 135                 140

Pro Ala Thr Leu Ser Leu Ser Pro Gly Glu Arg Ala Thr Leu Ser Cys
145                 150                 155                 160

Arg Ala Ser Glu Ser Val Glu Tyr Phe Gly Thr Ser Leu Met His Trp
                    165                 170                 175

Tyr Gln Gln Lys Pro Gly Gln Pro Pro Arg Leu Leu Ile Tyr Ala Ala
                    180                 185                 190

Ser Asn Val Glu Ser Gly Ile Pro Ala Arg Phe Ser Gly Ser Gly Ser
                    195                 200                 205

Gly Thr Asp Phe Thr Leu Thr Ile Ser Ser Val Glu Pro Glu Asp Phe
            210                 215                 220

Ala Val Tyr Phe Cys Gln Gln Thr Arg Lys Val Pro Tyr Thr Phe Gly
225                 230                 235                 240

Gly Gly Thr Lys Val Glu Ile Lys
                    245

<210> SEQ ID NO 174
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Phe
                20                  25                  30

Gly Thr Ser Leu Met His Trp Tyr Gln Gln Lys Pro Gly Gln Pro Pro
            35                  40                  45

Arg Leu Leu Ile Tyr Ala Ala Ser Asn Val Glu Ser Gly Ile Pro Ala
        50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Val Tyr Phe Cys Gln Gln Thr Arg
                85                  90                  95

Lys Val Pro Tyr Thr Phe Gly Gly Gly Thr Lys Val Glu Ile Lys Gly
                    100                 105                 110

Gly Ser Glu Gly Lys Ser Ser Gly Ser Gly Ser Glu Ser Lys Ser Thr
            115                 120                 125

Gly Gly Ser Gln Val Gln Leu Gln Glu Ser Gly Pro Gly Leu Val Lys
        130                 135                 140

Pro Ser Gln Thr Leu Ser Leu Thr Cys Thr Val Ser Gly Asn Ser Ile
145                 150                 155                 160

Thr Ser Asp Tyr Ala Trp Asn Trp Ile Arg Gln Phe Pro Gly Lys Gly
                    165                 170                 175
```

```
Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Ala Ala Asp Thr Ala Val
    210                 215                 220

Tyr Tyr Cys Ala Thr Gly Tyr Tyr Gly Ser Gly Phe Trp Gly Gln
225             230                 235                 240

Gly Thr Leu Val Thr Val Ser Ser
            245

<210> SEQ ID NO 175
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly Thr Thr Ile Phe Gly Val Val Thr Pro Asn Phe Tyr Tyr Gly Met
            100                 105                 110

Asp Val Trp Gly Gln Gly Thr Thr Val Thr Val Ser Ser Gly Gly Ser
        115                 120                 125

Glu Gly Lys Ser Ser Gly Ser Gly Ser Glu Ser Lys Ser Thr Gly Gly
    130                 135                 140

Ser Asp Ile Gln Met Thr Gln Ser Pro Ser Phe Leu Ser Ala Ser Val
145                 150                 155                 160

Gly Asp Arg Val Thr Ile Thr Cys Arg Ala Ser Gln Gly Ile Ser Ser
                165                 170                 175

Tyr Leu Ala Trp Tyr Gln Gln Lys Pro Gly Lys Ala Pro Lys Phe Leu
            180                 185                 190

Ile Tyr Ala Ala Ser Thr Leu Gln Ser Gly Val Pro Ser Arg Phe Ser
        195                 200                 205

Gly Ser Gly Ser Gly Thr Glu Phe Thr Leu Thr Ile Ser Ser Leu Gln
    210                 215                 220

Pro Glu Asp Phe Ala Thr Tyr Tyr Cys Gln Gln Leu Asn Ser Tyr Pro
225                 230                 235                 240

Leu Thr Phe Gly Gly Gly Thr Lys Val Glu Ile Lys
            245                 250

<210> SEQ ID NO 176
<211> LENGTH: 252
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 176

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Phe Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys Gly Gly Ser Glu Gly
            100                 105                 110

Lys Ser Ser Gly Ser Gly Ser Glu Ser Lys Ser Thr Gly Gly Ser Gln
        115                 120                 125

Val Gln Leu Gln Glu Ser Gly Pro Gly Leu Val Lys Pro Ser Glu Thr
130                 135                 140

Leu Ser Leu Thr Cys Thr Val Ser Gly Gly Ser Ile Ser Ser Tyr Tyr
145                 150                 155                 160

Trp Ser Trp Ile Arg Gln Pro Pro Gly Lys Gly Leu Glu Trp Ile Gly
                165                 170                 175

Tyr Ile Tyr Tyr Ser Gly Ser Thr Asn Tyr Asn Pro Ser Leu Lys Ser
            180                 185                 190

Arg Val Thr Ile Ser Val Asp Thr Ser Lys Asn Gln Phe Ser Leu Lys
        195                 200                 205

Leu Ser Ser Val Thr Ala Ala Asp Thr Ala Val Tyr Tyr Cys Ala Gly
    210                 215                 220

Thr Thr Ile Phe Gly Val Val Thr Pro Asn Phe Tyr Tyr Gly Met Asp
225                 230                 235                 240

Val Trp Gly Gln Gly Thr Thr Val Thr Val Ser Ser
                245                 250

<210> SEQ ID NO 177
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Asp Ile His Trp Val Arg Gln Ala Pro Gly Lys Gly Leu Glu Trp Val
        35                  40                  45

Ala Ile Ile Ser Tyr Asp Gly Ser Lys Lys Asp Tyr Thr Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asp Ser Leu Arg Val Glu Asp Ser Ala Val Tyr Ser Cys
                85                  90                  95

Ala Arg Glu Ser Gly Trp Ser His Tyr Tyr Tyr Gly Met Asp Val
            100                 105                 110

Trp Gly Gln Gly Thr Met Val Thr Val Ser Ser Gly Gly Ser Glu Gly
        115                 120                 125

Lys Ser Gly Ser Gly Ser Glu Ser Lys Ser Thr Gly Gly Ser Asp
130                 135                 140

Ile Val Met Thr Gln Ser Pro Ser Ser Leu Ser Ala Ser Val Gly Asp
145                 150                 155                 160

Arg Val Thr Ile Thr Cys Arg Ala Ser Gln Asp Ile Ser Asn Tyr Leu
                165                 170                 175

Ala Trp Tyr Gln Gln Lys Pro Gly Lys Val Pro Lys Phe Leu Ile Tyr
            180                 185                 190

Ala Ala Ser Thr Leu His Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Val Ala Thr Tyr Tyr Cys Gln Lys Tyr Asn Ser Ala Pro Tyr Thr
225                 230                 235                 240

Phe Gly Gln Gly Thr Arg Leu Glu Ile Lys
                245                 250

<210> SEQ ID NO 178
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Val Pro Lys Phe Leu Ile
        35                  40                  45

Tyr Ala Ala Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Arg Leu Glu Ile Lys Gly Ser Glu Gly
            100                 105                 110

Lys Ser Gly Ser Gly Ser Glu Ser Lys Ser Thr Gly Gly Ser Glu
        115                 120                 125

Val Gln Leu Val Glu Ser Gly Gly Val Val Gln Pro Gly Arg Ser
130                 135                 140

Leu Arg Leu Ser Cys Val Ala Ser Gly Phe Thr Phe Ser Ser Tyr Asp
145                 150                 155                 160

Ile His Trp Val Arg Gln Ala Pro Gly Lys Gly Leu Glu Trp Val Ala
                165                 170                 175

Ile Ile Ser Tyr Asp Gly Ser Lys Lys Asp Tyr Thr Asp Ser Val Lys
```

```
                    180                 185                 190
Gly Arg Phe Thr Ile Ser Arg Asp Asn Ser Lys Asn Thr Leu Tyr Leu
            195                 200                 205

Gln Met Asp Ser Leu Arg Val Glu Asp Ser Ala Val Tyr Ser Cys Ala
        210                 215                 220

Arg Glu Ser Gly Trp Ser His Tyr Tyr Tyr Gly Met Asp Val Trp
225                 230                 235                 240

Gly Gln Gly Thr Met Val Thr Val Ser Ser
                245                 250

<210> SEQ ID NO 179
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Leu Arg Gln Pro Ala Gly Ser Gly Leu Glu Trp Ile
        35                  40                  45

Gly Arg Leu Tyr Val Ser Gly Phe Thr Asn Tyr Asn Pro Ser Leu Lys
    50                  55                  60

Ser Arg Val Thr Leu Ser Leu Asp Pro Ser Arg Asn Gln Leu Ser Leu
65                  70                  75                  80

Lys Leu Ser Ser Val Thr Ala Ala Asp Thr Ala Val Tyr Tyr Cys Ala
                85                  90                  95

Gly Asp Ser Gly Asn Tyr Trp Gly Trp Phe Asp Pro Trp Gly Gln Gly
            100                 105                 110

Thr Leu Val Thr Val Ser Ser Gly Gly Ser Glu Gly Lys Ser Ser Gly
        115                 120                 125

Ser Gly Ser Glu Ser Lys Ser Thr Gly Gly Ser Ser Tyr Glu Leu Thr
    130                 135                 140

Gln Pro Pro Ser Val Ser Val Ser Pro Gly Glu Thr Ala Ser Ile Thr
145                 150                 155                 160

Cys Ser Gly Asp Gln Leu Gly Glu Asn Tyr Ala Cys Trp Tyr Gln Gln
                165                 170                 175

Lys Pro Gly Gln Ser Pro Val Leu Val Ile Tyr Gln Asp Ser Lys Arg
            180                 185                 190

Pro Ser Gly Ile Pro Glu Arg Phe Ser Gly Ser Asn Ser Gly Asn Thr
        195                 200                 205

Ala Thr Leu Thr Ile Ser Gly Thr Gln Ala Leu Asp Glu Ala Asp Tyr
    210                 215                 220

Tyr Cys Gln Ala Trp Asp Asn Ser Ile Val Val Phe Gly Gly Gly Thr
225                 230                 235                 240

Lys Leu Thr Val Leu
                245

<210> SEQ ID NO 180
<211> LENGTH: 245
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 180

Ser Tyr Glu Leu Thr Gln Pro Pro Ser Val Ser Val Ser Pro Gly Glu
1               5                   10                  15

Thr Ala Ser Ile Thr Cys Ser Gly Asp Gln Leu Gly Glu Asn Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Asn Ser Ile Val Val
                85                  90                  95

Phe Gly Gly Gly Thr Lys Leu Thr Val Leu Gly Gly Ser Glu Gly Lys
            100                 105                 110

Ser Ser Gly Ser Gly Ser Glu Ser Lys Ser Thr Gly Gly Ser Gln Val
        115                 120                 125

Gln Leu Gln Glu Ser Gly Pro Gly Leu Val Lys Pro Ser Glu Thr Leu
    130                 135                 140

Ser Leu Thr Cys Thr Val Ser Gly Gly Ser Ile Ser Ser Tyr Tyr Trp
145                 150                 155                 160

Ser Trp Leu Arg Gln Pro Ala Gly Ser Gly Leu Glu Trp Ile Gly Arg
                165                 170                 175

Leu Tyr Val Ser Gly Phe Thr Asn Tyr Asn Pro Ser Leu Lys Ser Arg
            180                 185                 190

Val Thr Leu Ser Leu Asp Pro Ser Arg Asn Gln Leu Ser Leu Lys Leu
        195                 200                 205

Ser Ser Val Thr Ala Ala Asp Thr Ala Val Tyr Tyr Cys Ala Gly Asp
    210                 215                 220

Ser Gly Asn Tyr Trp Gly Trp Phe Asp Pro Trp Gly Gln Gly Thr Leu
225                 230                 235                 240

Val Thr Val Ser Ser
                245

<210> SEQ ID NO 181
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ala Phe Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                    85                  90                  95

Ala His Leu Pro Tyr Ser Gly Ser Tyr Trp Ala Phe Asp Tyr Trp Gly
            100                 105                 110

Gln Gly Thr Gln Val Thr Val Ser Ser Gly Gly Ser Glu Gly Lys Ser
            115                 120                 125

Ser Gly Ser Gly Ser Glu Ser Lys Ser Thr Gly Gly Ser Gln Ser Val
130                 135                 140

Leu Thr Gln Pro Pro Ser Val Ser Val Ala Pro Gly Gln Thr Ala Ser
145                 150                 155                 160

Ile Thr Cys Gly Gly Asp Asn Ile Gly Ser Lys Ser Val His Trp Tyr
                    165                 170                 175

Gln Gln Lys Pro Gly Gln Ala Pro Val Leu Val Val Tyr Asp Asn Ser
            180                 185                 190

Asp Arg Pro Ser Gly Ile Pro Glu Arg Phe Ser Gly Ser Asn Ser Gly
            195                 200                 205

Thr Thr Ala Thr Leu Thr Ile Ser Arg Val Glu Ala Gly Asp Glu Ala
            210                 215                 220

Asp Tyr Tyr Cys Gln Val Trp Asp Ser Ser Ser Asp His Pro Val Val
225                 230                 235                 240

Phe Gly Gly Gly Thr Lys Val Thr Val
                    245

<210> SEQ ID NO 182
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gln Ser Val Leu Thr Gln Pro Pro Ser Val Ser Val Ala Pro Gly Gln
1               5                   10                  15

Thr Ala Ser Ile Thr Cys Gly Gly Asp Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asn Ser Asp Arg Pro Ser Gly Ile Pro Glu Arg Phe Ser Gly Ser
        50                  55                  60

Asn Ser Gly Thr Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Val Val Phe Gly Gly Gly Thr Lys Val Thr Val Gly Gly Ser Glu
            100                 105                 110

Gly Lys Ser Ser Gly Ser Gly Ser Glu Ser Lys Ser Thr Gly Gly Ser
            115                 120                 125

Gln Val Gln Leu Val Glu Ser Gly Gly Val Val Gln Pro Gly Arg
130                 135                 140

Ser Leu Arg Leu Ser Cys Ala Ala Ser Gly Phe Thr Phe Ser Tyr Tyr
145                 150                 155                 160

Gly Met His Trp Val Arg Gln Ala Pro Gly Lys Gly Leu Glu Trp Val
                    165                 170                 175

Ala Phe Ile Ser Tyr Asp Gly Ser Asn Lys Tyr Tyr Ala Asp Ser Val
            180                 185                 190
```

```
Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala His Leu Pro Tyr Ser Gly Ser Tyr Trp Ala Phe Asp Tyr Trp Gly
225                 230                 235                 240

Gln Gly Thr Gln Val Thr Val Ser Ser
                245

<210> SEQ ID NO 183
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ala Met Ser Trp Val Arg Gln Ala Pro Gly Lys Gly Leu Glu Trp Val
        35                  40                  45

Ser Thr Ile Gly Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Ile Val Met Val Thr Ala Leu Leu Tyr Asp Gly Met
            100                 105                 110

Asp Val Trp Gly Gln Gly Thr Met Val Thr Val Ser Ser Gly Gly Ser
        115                 120                 125

Glu Gly Lys Ser Ser Gly Ser Gly Ser Glu Ser Lys Ser Thr Gly Gly
    130                 135                 140

Ser Ser Ser Glu Leu Thr Gln Pro Pro Ser Val Ser Val Ala Pro Gly
145                 150                 155                 160

Gln Thr Ala Arg Ile Thr Cys Gly Gly Asn Asn Ile Gly Ser Lys Ser
                165                 170                 175

Val His Trp Tyr Gln Gln Lys Pro Gly Gln Ala Pro Val Leu Val Val
            180                 185                 190

Tyr Asp Asp Ser Asp Arg Pro Ser Gly Ile Pro Glu Arg Phe Ser Gly
        195                 200                 205

Ser Asn Ser Gly Asn Thr Ala Thr Leu Thr Ile Ser Arg Val Glu Ala
    210                 215                 220

Gly Asp Glu Ala Asp Tyr Tyr Cys Gln Val Trp Asp Ser Ser Ser Asp
225                 230                 235                 240

His Val Val Phe Gly Gly Gly Thr Lys Leu Thr Val Leu
                245                 250

<210> SEQ ID NO 184
<211> LENGTH: 253
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 184

```
Ser Ser Glu Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Ser Glu
            100                 105                 110

Gly Lys Ser Ser Gly Ser Gly Ser Glu Ser Lys Ser Thr Gly Gly Ser
        115                 120                 125

Gln Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Ser His Tyr
145                 150                 155                 160

Ala Met Ser Trp Val Arg Gln Ala Pro Gly Lys Gly Leu Glu Trp Val
                165                 170                 175

Ser Thr Ile Gly Gly Ser Gly Gly Ser Thr Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Lys Pro His Ile Val Met Val Thr Ala Leu Leu Tyr Asp Gly Met
225                 230                 235                 240

Asp Val Trp Gly Gln Gly Thr Met Val Thr Val Ser Ser
                245                 250
```

<210> SEQ ID NO 185
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

```
                 85                  90                  95
Gly Thr Thr Ile Phe Gly Val Val Thr Pro Asn Phe Tyr Tyr Gly Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
            210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 186
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 186

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Phe Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 187
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Glu Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Asp Ile His Trp Val Arg Gln Ala Pro Gly Lys Gly Leu Glu Trp Val
        35                  40                  45

Ala Ile Ile Ser Tyr Asp Gly Ser Lys Lys Asp Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Val Glu Asp Ser Ala Val Tyr Ser Cys
                85                  90                  95

Ala Arg Glu Ser Gly Trp Ser His Tyr Tyr Tyr Tyr Gly Met Asp Val
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 188
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr

```
            20                  25                  30
Leu Ala Trp Tyr Gln Gln Lys Pro Gly Lys Val Pro Lys Phe Leu Ile
        35                  40                  45

Tyr Ala Ala Ser Thr Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Tyr
                 85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 189
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Leu Arg Gln Pro Ala Gly Ser Gly Leu Glu Trp Ile
        35                  40                  45

Gly Arg Leu Tyr Val Ser Gly Phe Thr Asn Tyr Asn Pro Ser Leu Lys
    50                  55                  60

Ser Arg Val Thr Leu Ser Leu Asp Pro Ser Arg Asn Gln Leu Ser Leu
 65                  70                  75                  80

Lys Leu Ser Ser Val Thr Ala Ala Asp Thr Ala Val Tyr Tyr Cys Ala
                85                  90                  95

Gly Asp Ser Gly Asn Tyr Trp Gly Trp Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Lys Thr Tyr Thr Cys Asn Val Asp His Lys Pro
    195                 200                 205

Ser Asn Thr Lys Val Asp Lys Arg Val Glu Ser Lys Tyr Gly Pro Pro
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 190
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Ser Tyr Glu Leu Thr Gln Pro Pro Ser Val Ser Val Ser Pro Gly Glu
1               5                   10                  15

Thr Ala Ser Ile Thr Cys Ser Gly Asp Gln Leu Gly Glu Asn Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Leu
65                  70                  75                  80
```

Asp Glu Ala Asp Tyr Tyr Cys Gln Ala Trp Asp Asn Ser Ile Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210

<210> SEQ ID NO 191
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ala Phe Ile Ser Tyr Asp Gly Ser Asn Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala His Leu Pro Tyr Ser Gly Ser Tyr Trp Ala Phe Asp Tyr Trp Gly
            100                 105                 110

Gln Gly Thr Gln Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys

```
                210                 215                 220
Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 192
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Gln Ser Val Leu Thr Gln Pro Pro Ser Val Ser Val Ala Pro Gly Gln
1               5                   10                  15

Thr Ala Ser Ile Thr Cys Gly Gly Asp Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asn Ser Asp Arg Pro Ser Gly Ile Pro Glu Arg Phe Ser Gly Ser
    50                  55                  60

Asn Ser Gly Thr Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Val Val Phe Gly Gly Gly Thr Lys Val Thr Val Leu Gly Gln Pro
            100                 105                 110
```

```
Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
    195                 200                 205

Val Ala Pro Thr Glu Cys Ser
    210                 215

<210> SEQ ID NO 193
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ala Met Ser Trp Val Arg Gln Ala Pro Gly Lys Gly Leu Glu Trp Val
        35                  40                  45

Ser Thr Ile Gly Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Pro His Ile Val Met Val Thr Ala Leu Leu Tyr Asp Gly Met
                100                 105                 110

Asp Val Trp Gly Gln Gly Thr Met Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
    195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255
```

```
Asp Thr Leu Met Ile Ser Arg Thr Pro Glu Val Thr Cys Val Val Val
                260                 265                 270

Ser Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 194
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Ser Ser Glu Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
```

145                 150                 155                 160
Val Glu Thr Thr Thr Pro Ser Lys Gln Ser Asn Asn Lys Tyr Ala Ala
                    165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
                195                 200                 205

Ala Pro Thr Glu Cys Ser
            210

<210> SEQ ID NO 195
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
caggtgcagc tgcaggagtc gggcccagga ctggtgaagc cttcggagac cctgtccctc        60
acctgcactg tctctggtgg ctccatcagt agttactact ggagctggat ccggcagccc       120
ccagggaagg gactggagtg gattggatat atctattaca gtgggagcac caactacaac       180
ccctccctca gagtcgagt caccatatca gtagacacgt ccaagaacca gttccctg          240 aagctgagct ctgtgaccgc tgcggacacg gccgtgtatt actgtgcggg gactacgatt       300
tttggagtgg ttaccccaa cttctactac ggtatggacg tctggggcca agggaccacg        360
gtcaccgtct cctcagcttc caccaagggc ccatccgtct tccccctggc gccctgctcc       420
aggagcacct ccgagagcac agccgccctg ggctgcctgg tcaaggacta cttccccgaa       480
ccggtgacgg tgtcgtggaa ctcaggcgcc ctgaccagcg gcgtgcacac cttcccggct       540
gtcctacagt cctcaggact ctactccctc agcagcgtgg tgaccgtgcc ctccagcagc       600
ttgggcacga aacctacac ttgcaacgta gatcacaagc ccagcaacac caaggtggac        660
aagagagttg agtccaaata tggtccccca tgcccaccat gcccagcacc tgaggccgcc       720
gggggaccat cagtcttcct gttccccca aaacccaagg acactctcat gatctcccgg        780 accctgagg tcacgtgcgt ggtggtggac gtgagccagg aagaccccga ggtccagttc        840
aactggtacg tggatggcgt ggaggtgcat aatgccaaga caaagccgcg ggaggagcag       900
ttcaacagca cgtaccgtgt ggtcagcgtc ctcaccgtcc tgcaccagga ctggctgaac       960
ggcaaggagt acaagtgcaa ggtctccaac aaaggcctcc cgtcctccat cgagaaaacc      1020
atctccaaag ccaaagggca gccccgagag ccacaggtgt acaccctgcc cccatcccag      1080
gaggagatga ccaagaacca ggtcagcctg acctgcctgg tcaaaggctt ctaccccagc      1140
gacatcgccg tggagtggga gagcaatggg cagccggaga caactacaa gaccacgcct       1200 cccgtgctgg actccgacgg ctccttcttc ctctacagca ggctaaccgt ggacaagagc      1260
agatggcagg aggggaatgt cttctcatgc tccgtgatgc atgaggctct gcacaaccac      1320
tacacacaga gagcctctc cctgtctctg ggtaaa                                 1356

<210> SEQ ID NO 196
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196

```
gacatccaga tgacccagtc tccttccttc ctgtctgcat ctgtaggaga cagagtcacc    60
atcacttgcc gggccagtca gggcattagc agttatttag cctggtatca gcaaaaacca   120
gggaaagccc ctaagttcct gatctatgct gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatagtt accctctcac tttcggcgga   300
gggaccaagg tggaaatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga aaacacaaa gtctacgcct gcgaagtcac ccatcagggc   600
ctgagctcgc ccgtcacaaa gagcttcaac aggggagagt gt                     642
```

<210> SEQ ID NO 197
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 197

```
gaggtgcagc tggtggagtc tgggggaggc gtggtccagc ctgggaggtc cctgagactc    60
tcctgtgtag cctctggatt caccttcagt agttatgaca tacactgggt ccgccaggct   120
ccaggcaagg ggctggagtg gtggcaatt atttcatatg atggaagtaa aaaagactat   180
acagactccg tgaagggccg attcaccatc tccagagaca attccaagaa cacgctgtat   240
ctgcaaatgg acagcctgag agttgaggac tcggctgtgt attcctgtgc gagagaaagt   300
ggctggtccc actactacta ttacggtatg gacgtctggg gccaagggac aatggtcacc   360
gtctcttcag cttccaccaa gggcccatcc gtcttccccc tggcgccctg ctccaggagc   420
acctccgaga gcacagccgc cctgggctgc ctggtcaagg actacttccc cgaaccggtg   480
acggtgtcgt ggaactcagg cgccctgacc agcggcgtgc acaccttccc ggctgtccta   540
cagtcctcag gactctactc cctcagcagc gtggtgaccg tgccctccag cagcttgggc   600
acgaaaacct acacttgcaa cgtagatcac aagcccagca acaccaaggt ggacaagaga   660
gttgagtcca atatggtcc cccatgccca ccatgcccag cacctgaggc cgccggggga   720
ccatcagtct tcctgttccc cccaaaaccc aaggacactc tcatgatctc ccggaccct   780
gaggtcacgt gcgtggtggt ggacgtgagc caggaagacc ccgaggtcca gttcaactgg   840
tacgtggatg gcgtggaggt gcataatgcc aagacaaagc cgcgggagga gcagttcaac   900
agcacgtacc gtgtggtcag cgtcctcacc gtcctgcacc aggactggct gaacggcaag   960
gagtacaagt gcaaggtctc caacaaaggc ctcccgtcct ccatcgagaa aaccatctcc  1020
aaagccaaag gcagccccg agagccacag gtgtacaccc tgcccccatc ccaggaggag  1080
atgaccaaga accaggtcag cctgacctgc ctggtcaaag gcttctaccc cagcgacatc  1140
gccgtggagt gggagagcaa tgggcagccg gagaacaact acaagaccac gcctcccgtg  1200
ctggactccg acggctcctt cttcctctac agcaggctaa ccgtggacaa gagcagatgg  1260
caggagggga atgtcttctc atgctccgtg atgcatgagg ctctgcacaa ccactacaca  1320
```
cagaagagcc tctccctgtc tctgggtaaa                                    1350

<210> SEQ ID NO 198
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198
gacatcgtga tgacccagtc tccatcctcc ctgtctgcat ctgtaggaga cagagtcacc      60
atcacttgcc gggcgagtca ggacattagc aattatttag cctggtatca gcagaaacca    120
gggaaagttc ctaagttcct gatctatgct gcatccactt tgcactctgg ggtcccatct    180
cggttcagtg gcagtggatc tgggacagat ttcactctca ccatcagcag cctgcagcct    240
gaagatgttg caacttatta ctgtcaaaag tataacagtg ccccgtacac ttttggccaa    300
gggacacgac tggagattaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga aaacacaaa gtctacgcct gcgaagtcac ccatcagggc     600
ctgagctcgc ccgtcacaaa gagcttcaac aggggagagt gt                       642

<210> SEQ ID NO 199
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 199
caggtgcagc tgcaggagtc gggcccagga ctggtgaagc cttcggagac cctgtccctc      60
acctgcactg tctctggtgg ctccatcagt agttactatt ggagctggct ccggcagccc    120
gccgggtcgg gactggagtg gattgggcgt ttatatgtca gtgggttcac caactacaac    180
ccctccctca gagtcgagt caccttgtca ctagacccgt ccaggaacca gttgtccctg     240
aaactgagtt ctgtgaccgc cgcggacacg gccgtatatt attgtgcggg agatagtggg    300
aactactggg gttggttcga cccctggggc cagggaaccc tggtcaccgt ctcctcagct    360
tccaccaagg gcccatccgt cttccccctg gcgccctgct ccaggagcac ctccgagagc    420
acagccgccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac gaaaacctac    600
acttgcaacg tagatcacaa gcccagcaac accaaggtgg acaagagagt tgagtccaaa    660
tatggtcccc catgcccacc atgcccagca cctgaggccg ccggggggacc atcagtcttc    720 ctgttccccc caaaacccaa ggacactctc atgatctccc ggacccctga ggtcacgtgc    780
gtggtggtgg acgtgagcca ggaagacccc gaggtccagt tcaactggta cgtggatggc    840
gtggaggtgc ataatgccaa gacaaagccg cgggaggagc agttcaacag cacgtaccgt    900
gtggtcagcg tcctcaccgt cctgcaccag gactggctga acggcaagga gtacaagtgc    960

```
aaggtctcca acaaaggcct cccgtcctcc atcgagaaaa ccatctccaa agccaaaggg   1020 cagcccgag  agccacaggt gtacaccctg cccccatccc aggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacgc ctcccgtgct ggactccgac   1200
ggctccttct tcctctacag caggctaacc gtggacaaga gcagatggca ggaggggaat   1260
gtcttctcat gctccgtgat gcatgaggct ctgcacaacc actacacaca gaagagcctc   1320
tccctgtctc tgggtaaa                                                 1338
```

<210> SEQ ID NO 200
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200

```
tcctatgagc tgactcagcc accctcagtg tccgtgtccc caggagagac agccagcatc    60
acctgctctg gagatcaatt gggggaaaat tatgcttgct ggtatcagca gaagccaggc   120
cagtcccctg tgttggtcat ctatcaagat agtaagcggc cctcagggat ccctgagcga   180
ttctctggct ccaactctgg gaacacagcc actctgacca tcagcgggac ccaggctctg   240
gatgaggctg actattactg tcaggcgtgg gacaacagta ttgtggtatt cggcggaggg   300
accaagctga ccgtcctagg tcagcccaag gctgcaccca gtgtcactct gttcccgccc   360
tcctctgagg agcttcaagc caacaaggcc acactggtgt gtctcataag tgacttctac   420
ccgggagccg tgacagtggc ctggaaggca gatagcagcc ccgtcaaggc gggagtggag   480
accaccacac cctccaaaca aagcaacaac aagtacgcgg ccagcagcta tctgagcctg   540
acgcctgagc agtggaagtc ccacagaagc tacagctgcc aggtcacgca tgaagggagc   600
accgtggaga agacagtggc ccctacagaa tgttca                             636
```

<210> SEQ ID NO 201
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201

```
caggtgcagc tggtggagtc tgggggaggc gtggtccagc ctggaggtc  cctgagactc    60 tcctgtgcag cctctggatt caccttcagt actatggca  tgcactgggt ccgccaggct   120
ccaggcaagg ggctggagtg ggtggcattt atatcatatg atggaagtaa taatactat    180 gcagactccg tgaagggccg attcaccatc tccagagaca attccaagaa cacgctgtat   240
ctgcaaatga acagcctgag agctgaggac acggctgtgt attactgtgc ccacctccct   300
tatagtggga gctactgggc ctttgactac tggggccagg gaacccaggt caccgtctct   360
tcagcctcca ccaagggccc atcggtcttc cccctggcac cctcctccaa gagcacctct   420
gggggcacag cggccctggg ctgcctggtc aaggactact ccccgaacc  ggtgacggtg   480 tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gaaagttgag   660
```

```
cccaaatcttgtgacaaaactcacacatgcccaccgtgcccagcacctgaagccgccggg     720 ggaccgtcagtcttcctcttccccccaaaacccaaggacaccctcatgatctcccggacc     780 cctgaggtcacatgcgtggtggtgagcgtgagccacgaagaccctgaggtcaagttcaac     840 tggtacgtggacggcgtggaggtgcataatgccaagacaagccgcgggaggagcagtac     900 aacagcacgtaccgtgtggtcagcgtcctcaccgtcctgccaccaggactggctgaatggc     960 aaggagtacaagtgcaaggtctccaacaaagcccctcccagccccatcgagaaaaccatc   1020 tccaaagccaaagggcagccccgagaaccacaggtgtacaccctgcccccatcccgggag   1080 gagatgaccaagaaccaggtcagcctgacctgcctggtcaaaggcttctatcccagcgac   1140 atcgccgtggagtgggagagcaatgggcagccggagaacaactacaagaccacgcctccc   1200 gtgctggactccgacggctccttcttcctctacagcaagctcaccgtggacaagagcaga   1260 tggcagcagggaacgtcttctcatgctccgtgatgcatgaggctctgcacaaccactac   1320 acgcagaagagcctctccctgtctccgggtaaa                                1353
```

<210> SEQ ID NO 202
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 202

```
cagtctgtgctgactcagccaccctcggtgtcagtggcccccgggcagacggccagtatt     60 acctgtggggagacaacatggaagtaaaagtgtgcactggtaccagcagaagccaggc    120 caggcccctgtgctggtcgtctatgataatagcgaccggccctcagggatccctgagcga    180 ttctctggctccaactctggggaccacggccaccctgaccatcagcagggtcgaagccggg    240 gatgaggccgactattactgtcaggtgtgggatagtagtagtgatcatcctgtggtattc    300 ggcggagggaccaaggtcaccgtcctaggtcagcccaaggctgcacccagtgtcactctg    360 ttcccgccctcctctgaggagcttcaagccaacaaggccacactggtgtgtctcataagt    420 gacttctaccgggagccgtgacagtggcctggaaggccgatagcagccccgtcaaggcg    480 ggagtggagaccaccacacctccaaacaaagcaacaacagtacgcggccagcagctat    540 ctgagcctgacgcctgagcagtggaagtccacagaagctacagctgccaggtcacgcat    600 gaagggagcaccgtggagaagacagtggccctacagaatgttca                      645
```

<210> SEQ ID NO 203
<211> LENGTH: 1365
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 203

```
caggtgcagctggtggagtctggggaggcttggtacagcctgggggtccctgagactc      60 tcctgtgcagcctctggattcacctttagtcattatgccatgagctgggtccgccaggct    120 ccagggaaggggctggagtgggtctcaactattggtggtagtggtggtaggcacatactac    180 gcagactccgtgaagggccggttcaccatctccagagacaattccaagaacacgctgtat    240 ctgcaaatgaacagcctgagagccgaggacacggccgtattactgtgcgaaacctcat    300
```

```
attgtaatgg tgactgctct tctctacgac ggtatggacg tctggggcca agggacaatg    360
gtcaccgtct cctcagcctc caccaagggc ccatcggtct tccccctggc accctcctcc    420
aagagcacct ctggggggcac agcggccctg ggctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aatcacaagc ccagcaacac caaggtggac    660
aagaaagttg agcccaaatc ttgtgacaaa actcacacat gcccaccgtg cccagcacct    720
gaagccgccg ggggaccgtc agtcttcctc ttccccccaa acccaaggga caccctcatg    780
atctcccgga cccctgaggt cacatgcgtg gtggtgagcg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctccc agcccccatc    1020
gagaaaacca tctccaaagc caagggccag ccccgagaac acaggtgta caccctgccc    1080 ccatcccggg aggagatgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaa               1365

<210> SEQ ID NO 204
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
tcttctgagc tgactcagcc accctcggtg tcagtggccc caggacagac ggccaggatt    60
acctgtgggg gaaacaacat tggaagtaaa agtgtgcact ggtaccagca gaagccaggc    120
caggcccctg tgctggtcgt ctatgatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcatgt ggtattcggc    300
ggagggacca agctgaccgt cctaggtcag cccaaggctg cacccagtgt cactctgttc    360
ccgcccctcc tgaggagct tcaagccaac aaggccacac tggtgtgtct cataagtgac    420
ttctacccgg gagccgtgac agtggcctgg aaggccgata gcagccccgt caaggcggga    480
gtggagacca ccacacccctc caaacaaagc aacaacaagt acgcggccag cagctatctg    540
agcctgacgc ctgagcagtg gaagtccaca gaagctaca gctgccaggt cacgcatgaa    600
gggagcaccg tggagaagac agtggccccct acagaatgtt ca                   642

<210> SEQ ID NO 205
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205
```

-continued

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Phe Pro Gly Lys Gly Leu Glu Trp
            35                  40                  45

Ile Gly Tyr Ile Ser Tyr Ser Gly Ser Thr Thr Tyr Asn Pro Ser Leu
50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
            115                 120                 125

Ser Glu Ser Lys Ser Thr Gly Gly Ser Asp Ile Val Leu Thr Gln Ser
            130                 135                 140

Pro Asp Ser Leu Ala Val Ser Leu Gly Glu Arg Ala Thr Ile Asn Cys
145                 150                 155                 160

Arg Ala Ser Glu Ser Val Glu Tyr Phe Gly Thr Ser Leu Met His Trp
            165                 170                 175

Tyr Gln Gln Lys Pro Gly Gln Pro Pro Lys Leu Leu Ile Tyr Ala Ala
            180                 185                 190

Ser Asn Val Glu Ser Gly Val Pro Asp Arg Phe Ser Gly Ser Gly Ser
            195                 200                 205

Gly Thr Asp Phe Thr Leu Thr Ile Ser Ser Leu Gln Ala Glu Asp Val
            210                 215                 220

Ala Val Tyr Phe Cys Gln Gln Thr Arg Lys Val Pro Tyr Thr Phe Gly
225                 230                 235                 240

Gly Gly Thr Lys Val Glu Ile Lys Thr Ser Thr Pro Ala Pro Arg Pro
            245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
            275                 280                 285

Asp Phe Ala Cys Asp Ile Tyr Ile Trp Ala Pro Leu Ala Gly Thr Cys
            290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
            325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
            355                 360                 365

Ala Pro Ala Tyr Lys Gln Gly Gln Asn Gln Leu Tyr Asn Glu Leu Asn
            370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
            405                 410                 415
```

```
Leu Tyr Asn Glu Leu Gln Lys Asp Lys Met Ala Glu Ala Tyr Ser Glu
            420                 425                 430

Ile Gly Met Lys Gly Glu Arg Arg Gly Lys Gly His Asp Gly Leu
        435                 440                 445

Tyr Gln Gly Leu Ser Thr Ala Thr Lys Asp Thr Tyr Asp Ala Leu His
450                 455                 460

Met Gln Ala Leu Pro Pro Arg
465                 470

<210> SEQ ID NO 206
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Thr Arg
                85                  90                  95

Lys Val Pro Tyr Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Gln Thr Leu Ser Leu Thr Cys Thr Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Ala Ala Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300
```

```
Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
            325                 330                 335

Gln Thr Thr Gln Glu Glu Asp Gly Cys Ser Cys Arg Phe Pro Glu Glu
        340                 345                 350

Glu Glu Gly Gly Cys Glu Leu Arg Val Lys Phe Ser Arg Ser Ala Asp
    355                 360                 365

Ala Pro Ala Tyr Lys Gln Gly Gln Asn Gln Leu Tyr Asn Glu Leu Asn
370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
        450                 455                 460

Met Gln Ala Leu Pro Pro Arg
465                 470

<210> SEQ ID NO 207
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Glu Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Glu Ser Val Glu Tyr Phe Gly Thr Ser Leu Met His Trp
                165                 170                 175

Tyr Gln Gln Lys Pro Gly Gln Pro Pro Arg Leu Leu Ile Tyr Ala Ala
```

```
            180                 185                 190
Ser Asn Val Glu Ser Gly Ile Pro Ala Arg Phe Ser Gly Ser Gly Ser
            195                 200                 205

Gly Thr Asp Phe Thr Leu Thr Ile Ser Ser Val Glu Pro Glu Asp Phe
            210                 215                 220

Ala Val Tyr Phe Cys Gln Gln Thr Arg Lys Val Pro Tyr Thr Phe Gly
225                 230                 235                 240

Gly Gly Thr Lys Val Glu Ile Lys Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
            275                 280                 285

Asp Phe Ala Cys Asp Ile Tyr Ile Trp Ala Pro Leu Ala Gly Thr Cys
            290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
            355                 360                 365

Ala Pro Ala Tyr Lys Gln Gly Gln Asn Gln Leu Tyr Asn Glu Leu Asn
370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
450                 455                 460

Met Gln Ala Leu Pro Pro Arg
465                 470

<210> SEQ ID NO 208
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Arg Leu Leu Ile Tyr Ala Ala Ser Asn Val Glu Ser Gly Ile Pro Ala
    50                  55                  60
```

-continued

```
Arg Phe Ser Gly Ser Gly Ser Gly Thr Asp Phe Thr Leu Thr Ile Ser
 65                  70                  75                  80

Ser Val Glu Pro Glu Asp Phe Ala Val Tyr Phe Cys Gln Gln Thr Arg
             85                  90                  95

Lys Val Pro Tyr Thr Phe Gly Gly Thr Lys Val Glu Ile Lys Gly
            100                 105                 110

Gly Ser Glu Gly Lys Ser Ser Gly Ser Gly Ser Glu Ser Lys Ser Thr
            115                 120                 125

Gly Gly Ser Gln Val Gln Leu Gln Glu Ser Gly Pro Gly Leu Val Lys
        130                 135                 140

Pro Ser Gln Thr Leu Ser Leu Thr Cys Thr Val Ser Gly Asn Ser Ile
145                 150                 155                 160

Thr Ser Asp Tyr Ala Trp Asn Trp Ile Arg Gln Pro Pro Gly Lys Gly
            165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
            195                 200                 205

Gln Phe Ser Leu Lys Leu Ser Ser Val Thr Ala Ala Asp Thr Ala Val
210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser Thr Ser Thr Pro Ala Pro Arg Pro
            245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
            275                 280                 285

Asp Phe Ala Cys Asp Ile Tyr Ile Trp Ala Pro Leu Ala Gly Thr Cys
        290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
            325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
            405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
        450                 455                 460

Met Gln Ala Leu Pro Pro Arg
465                 470
```

<210> SEQ ID NO 209
<211> LENGTH: 471
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 209

Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Gly Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Glu Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Glu Ser Val Glu Tyr Phe Gly Thr Ser Leu Met His Trp
                165                 170                 175

Tyr Gln Gln Lys Pro Gly Gln Pro Pro Arg Leu Leu Ile Tyr Ala Ala
            180                 185                 190

Ser Asn Val Glu Ser Gly Ile Pro Ala Arg Phe Ser Gly Ser Gly Ser
        195                 200                 205

Gly Thr Asp Phe Thr Leu Thr Ile Ser Ser Val Glu Pro Glu Asp Phe
    210                 215                 220

Ala Val Tyr Phe Cys Gln Gln Thr Arg Lys Val Pro Tyr Thr Phe Gly
225                 230                 235                 240

Gly Gly Thr Lys Val Glu Ile Lys Thr Ser Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Lys Gln Gly Gln Asn Gln Leu Tyr Asn Glu Leu Asn
370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
                435                 440                 445

Tyr Gln Gly Leu Ser Thr Ala Thr Lys Asp Thr Tyr Asp Ala Leu His
450                 455                 460

Met Gln Ala Leu Pro Pro Arg
465                 470

<210> SEQ ID NO 210
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Phe
                20                  25                  30

Gly Thr Ser Leu Met His Trp Tyr Gln Gln Lys Pro Gly Gln Pro Pro
            35                  40                  45

Arg Leu Leu Ile Tyr Ala Ala Ser Asn Val Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Val Tyr Phe Cys Gln Gln Thr Arg
                85                  90                  95

Lys Val Pro Tyr Thr Phe Gly Gly Gly Thr Lys Val Glu Ile Lys Gly
                100                 105                 110

Gly Ser Glu Gly Lys Ser Ser Gly Ser Gly Ser Glu Ser Lys Ser Thr
            115                 120                 125

Gly Gly Ser Gln Val Gln Leu Gln Glu Ser Gly Pro Gly Leu Val Lys
130                 135                 140

Pro Ser Gln Thr Leu Ser Leu Thr Cys Thr Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Ile Gly Tyr Ile Ser Tyr Ser Gly Ser Thr Thr Tyr Asn
                180                 185                 190

Pro Ser Leu Lys Ser Arg Val Thr Ile Ser Arg Asp Thr Ser Lys Asn
            195                 200                 205

Gln Phe Ser Leu Lys Leu Ser Ser Val Thr Ala Ala Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser Thr Ser Thr Pro Ala Pro Arg Pro
                245                 250                 255

```
Pro Thr Pro Ala Pro Thr Ile Ala Ser Gln Pro Leu Ser Leu Arg Pro
            260                 265                 270

Glu Ala Cys Arg Pro Ala Ala Gly Ala Val His Thr Arg Gly Leu
            275                 280                 285

Asp Phe Ala Cys Asp Ile Tyr Ile Trp Ala Pro Leu Ala Gly Thr Cys
290                 295                 300

Gly Val Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
            355                 360                 365

Ala Pro Ala Tyr Lys Gln Gly Gln Asn Gln Leu Tyr Asn Glu Leu Asn
370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
450                 455                 460

Met Gln Ala Leu Pro Pro Arg
465                 470

<210> SEQ ID NO 211
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly Thr Thr Ile Phe Gly Val Val Thr Pro Asn Phe Tyr Tyr Gly Met
            100                 105                 110

Asp Val Trp Gly Gln Gly Thr Thr Val Thr Val Ser Ser Gly Gly Ser
        115                 120                 125

Glu Gly Lys Ser Ser Gly Ser Gly Ser Glu Ser Lys Ser Thr Gly Gly
```

```
            130                 135                 140
Ser Asp Ile Gln Met Thr Gln Ser Pro Ser Phe Leu Ser Ala Ser Val
145                 150                 155                 160

Gly Asp Arg Val Thr Ile Thr Cys Arg Ala Ser Gln Gly Ile Ser Ser
                165                 170                 175

Tyr Leu Ala Trp Tyr Gln Gln Lys Pro Gly Lys Ala Pro Lys Phe Leu
            180                 185                 190

Ile Tyr Ala Ala Ser Thr Leu Gln Ser Gly Val Pro Ser Arg Phe Ser
        195                 200                 205

Gly Ser Gly Ser Gly Thr Glu Phe Thr Leu Thr Ile Ser Ser Leu Gln
    210                 215                 220

Pro Glu Asp Phe Ala Thr Tyr Tyr Cys Gln Gln Leu Asn Ser Tyr Pro
225                 230                 235                 240

Leu Thr Phe Gly Gly Gly Thr Lys Val Glu Ile Lys Thr Ser Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
    290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
                325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu Arg Val Lys Phe Ser
        355                 360                 365

Arg Ser Ala Asp Ala Pro Ala Tyr Lys Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475

<210> SEQ ID NO 212
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Asp Ile Gln Met Thr Gln Ser Pro Ser Phe Leu Ser Ala Ser Val Gly
1               5                   10                  15
```

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Phe Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Leu
             85                  90                  95

Thr Phe Gly Gly Gly Thr Lys Val Glu Ile Lys Gly Gly Ser Glu Gly
            100                 105                 110

Lys Ser Ser Gly Ser Gly Ser Glu Ser Lys Ser Thr Gly Gly Ser Gln
        115                 120                 125

Val Gln Leu Gln Glu Ser Gly Pro Gly Leu Val Lys Pro Ser Glu Thr
130                 135                 140

Leu Ser Leu Thr Cys Thr Val Ser Gly Gly Ser Ile Ser Ser Tyr Tyr
145                 150                 155                 160

Trp Ser Trp Ile Arg Gln Pro Pro Gly Lys Gly Leu Glu Trp Ile Gly
                165                 170                 175

Tyr Ile Tyr Tyr Ser Gly Ser Thr Asn Tyr Asn Pro Ser Leu Lys Ser
            180                 185                 190

Arg Val Thr Ile Ser Val Asp Thr Ser Lys Asn Gln Phe Ser Leu Lys
        195                 200                 205

Leu Ser Ser Val Thr Ala Ala Asp Thr Ala Val Tyr Tyr Cys Ala Gly
210                 215                 220

Thr Thr Ile Phe Gly Val Val Thr Pro Asn Phe Tyr Tyr Gly Met Asp
225                 230                 235                 240

Val Trp Gly Gln Gly Thr Thr Val Thr Val Ser Ser Thr Ser Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
                325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu Arg Val Lys Phe Ser
        355                 360                 365

Arg Ser Ala Asp Ala Pro Ala Tyr Lys Gln Gly Gln Asn Gln Leu Tyr
370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly

```
                435                 440                 445
His Asp Gly Leu Tyr Gln Gly Leu Ser Thr Ala Thr Lys Asp Thr Tyr
            450                 455                 460

Asp Ala Leu His Met Gln Ala Leu Pro Pro Arg
465                 470                 475

<210> SEQ ID NO 213
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Asp Ile His Trp Val Arg Gln Ala Pro Gly Lys Gly Leu Glu Trp Val
        35                  40                  45

Ala Ile Ile Ser Tyr Asp Gly Ser Lys Lys Asp Tyr Thr Asp Ser Val
50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Val Glu Asp Ser Ala Val Tyr Ser Cys
                85                  90                  95

Ala Arg Glu Ser Gly Trp Ser His Tyr Tyr Tyr Gly Met Asp Val
            100                 105                 110

Trp Gly Gln Gly Thr Met Val Thr Val Ser Ser Gly Gly Ser Glu Gly
        115                 120                 125

Lys Ser Ser Gly Ser Gly Ser Glu Ser Lys Ser Thr Gly Gly Ser Asp
130                 135                 140

Ile Val Met Thr Gln Ser Pro Ser Ser Leu Ser Ala Ser Val Gly Asp
145                 150                 155                 160

Arg Val Thr Ile Thr Cys Arg Ala Ser Gln Asp Ile Ser Asn Tyr Leu
                165                 170                 175

Ala Trp Tyr Gln Gln Lys Pro Gly Lys Val Pro Lys Phe Leu Ile Tyr
            180                 185                 190

Ala Ala Ser Thr Leu His Ser Gly Val Pro Ser Arg Phe Ser Gly Ser
        195                 200                 205

Gly Ser Gly Thr Asp Phe Thr Leu Thr Ile Ser Ser Leu Gln Pro Glu
210                 215                 220

Asp Val Ala Thr Tyr Tyr Cys Gln Lys Tyr Asn Ser Ala Pro Tyr Thr
225                 230                 235                 240

Phe Gly Gln Gly Thr Arg Leu Glu Ile Lys Thr Ser Thr Pro Ala Pro
                245                 250                 255

Arg Pro Pro Thr Pro Ala Pro Thr Ile Ala Ser Gln Pro Leu Ser Leu
            260                 265                 270

Arg Pro Glu Ala Cys Arg Pro Ala Ala Gly Gly Ala Val His Thr Arg
        275                 280                 285

Gly Leu Asp Phe Ala Cys Asp Ile Tyr Ile Trp Ala Pro Leu Ala Gly
    290                 295                 300

Thr Cys Gly Val Leu Leu Leu Ser Leu Val Ile Thr Leu Tyr Cys Lys
305                 310                 315                 320
```

```
Arg Gly Arg Lys Lys Leu Leu Tyr Ile Phe Lys Gln Pro Phe Met Arg
                325                 330                 335

Pro Val Gln Thr Thr Gln Glu Glu Asp Gly Cys Ser Cys Arg Phe Pro
            340                 345                 350

Glu Glu Glu Glu Gly Gly Cys Glu Leu Arg Val Lys Phe Ser Arg Ser
        355                 360                 365

Ala Asp Ala Pro Ala Tyr Lys Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470

<210> SEQ ID NO 214
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Val Pro Lys Phe Leu Ile
        35                  40                  45

Tyr Ala Ala Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Arg Leu Glu Ile Lys Gly Gly Ser Glu Gly
            100                 105                 110

Lys Ser Ser Gly Ser Gly Ser Glu Ser Lys Ser Thr Gly Gly Ser Glu
        115                 120                 125

Val Gln Leu Val Glu Ser Gly Gly Gly Val Gln Pro Gly Arg Ser
    130                 135                 140

Leu Arg Leu Ser Cys Val Ala Ser Gly Phe Thr Phe Ser Ser Tyr Asp
145                 150                 155                 160

Ile His Trp Val Arg Gln Ala Pro Gly Lys Gly Leu Glu Trp Val Ala
                165                 170                 175

Ile Ile Ser Tyr Asp Gly Ser Lys Lys Asp Tyr Thr Asp Ser Val Lys
            180                 185                 190

Gly Arg Phe Thr Ile Ser Arg Asp Asn Ser Lys Asn Thr Leu Tyr Leu
        195                 200                 205
```

Gln Met Asp Ser Leu Arg Val Glu Asp Ser Ala Val Tyr Ser Cys Ala
            210                 215                 220

Arg Glu Ser Gly Trp Ser His Tyr Tyr Tyr Gly Met Asp Val Trp
225                 230                 235                 240

Gly Gln Gly Thr Met Val Thr Val Ser Ser Thr Ser Thr Pro Ala Pro
                245                 250                 255

Arg Pro Pro Thr Pro Ala Pro Thr Ile Ala Ser Gln Pro Leu Ser Leu
            260                 265                 270

Arg Pro Glu Ala Cys Arg Pro Ala Ala Gly Gly Ala Val His Thr Arg
            275                 280                 285

Gly Leu Asp Phe Ala Cys Asp Ile Tyr Ile Trp Ala Pro Leu Ala Gly
            290                 295                 300

Thr Cys Gly Val Leu Leu Leu Ser Leu Val Ile Thr Leu Tyr Cys Lys
305                 310                 315                 320

Arg Gly Arg Lys Lys Leu Leu Tyr Ile Phe Lys Gln Pro Phe Met Arg
                325                 330                 335

Pro Val Gln Thr Thr Gln Glu Glu Asp Gly Cys Ser Cys Arg Phe Pro
            340                 345                 350

Glu Glu Glu Glu Gly Gly Cys Glu Leu Arg Val Lys Phe Ser Arg Ser
            355                 360                 365

Ala Asp Ala Pro Ala Tyr Lys Gln Gly Gln Asn Gln Leu Tyr Asn Glu
            370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
            435                 440                 445

Gly Leu Tyr Gln Gly Leu Ser Thr Ala Thr Lys Asp Thr Tyr Asp Ala
            450                 455                 460

Leu His Met Gln Ala Leu Pro Pro Arg
465                 470

<210> SEQ ID NO 215
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Leu Arg Gln Pro Ala Gly Ser Gly Leu Glu Trp Ile
        35                  40                  45

Gly Arg Leu Tyr Val Ser Gly Phe Thr Asn Tyr Asn Pro Ser Leu Lys
    50                  55                  60

Ser Arg Val Thr Leu Ser Leu Asp Pro Ser Arg Asn Gln Leu Ser Leu
65                  70                  75                  80

Lys Leu Ser Ser Val Thr Ala Ala Asp Thr Ala Val Tyr Tyr Cys Ala

```
                  85                  90                  95
Gly Asp Ser Gly Asn Tyr Trp Gly Trp Phe Asp Pro Trp Gly Gln Gly
                100                 105                 110

Thr Leu Val Thr Val Ser Ser Gly Gly Ser Glu Gly Lys Ser Ser Gly
            115                 120                 125

Ser Gly Ser Glu Ser Lys Ser Thr Gly Gly Ser Ser Tyr Glu Leu Thr
        130                 135                 140

Gln Pro Pro Ser Val Ser Val Ser Pro Gly Glu Thr Ala Ser Ile Thr
145                 150                 155                 160

Cys Ser Gly Asp Gln Leu Gly Glu Asn Tyr Ala Cys Trp Tyr Gln Gln
                165                 170                 175

Lys Pro Gly Gln Ser Pro Val Leu Val Ile Tyr Gln Asp Ser Lys Arg
            180                 185                 190

Pro Ser Gly Ile Pro Glu Arg Phe Ser Gly Ser Asn Ser Gly Asn Thr
        195                 200                 205

Ala Thr Leu Thr Ile Ser Gly Thr Gln Ala Leu Asp Glu Ala Asp Tyr
    210                 215                 220

Tyr Cys Gln Ala Trp Asp Asn Ser Ile Val Val Phe Gly Gly Gly Thr
225                 230                 235                 240

Lys Leu Thr Val Leu Thr Ser Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
        275                 280                 285

Cys Asp Ile Tyr Ile Trp Ala Pro Leu Ala Gly Thr Cys Gly Val Leu
    290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
        355                 360                 365

Tyr Lys Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg
465

<210> SEQ ID NO 216
<211> LENGTH: 468
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 216

```
Ser Tyr Glu Leu Thr Gln Pro Pro Ser Val Ser Val Ser Pro Gly Glu
1               5                   10                  15

Thr Ala Ser Ile Thr Cys Ser Gly Asp Gln Leu Gly Glu Asn Tyr Ala
                20                  25                  30

Cys Trp Tyr Gln Gln Lys Pro Gly Gln Ser Pro Val Leu Val Ile Tyr
                35                  40                  45

Gln Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Asn Ser Ile Val Val
                85                  90                  95

Phe Gly Gly Gly Thr Lys Leu Thr Val Leu Gly Gly Ser Glu Gly Lys
                100                 105                 110

Ser Ser Gly Ser Gly Ser Glu Ser Lys Ser Thr Gly Gly Ser Gln Val
            115                 120                 125

Gln Leu Gln Glu Ser Gly Pro Gly Leu Val Lys Pro Ser Glu Thr Leu
130                 135                 140

Ser Leu Thr Cys Thr Val Ser Gly Gly Ser Ile Ser Ser Tyr Tyr Trp
145                 150                 155                 160

Ser Trp Leu Arg Gln Pro Ala Gly Ser Gly Leu Glu Trp Ile Gly Arg
                165                 170                 175

Leu Tyr Val Ser Gly Phe Thr Asn Tyr Asn Pro Ser Leu Lys Ser Arg
            180                 185                 190

Val Thr Leu Ser Leu Asp Pro Ser Arg Asn Gln Leu Ser Leu Lys Leu
            195                 200                 205

Ser Ser Val Thr Ala Ala Asp Thr Ala Val Tyr Tyr Cys Ala Gly Asp
            210                 215                 220

Ser Gly Asn Tyr Trp Gly Trp Phe Asp Pro Trp Gly Gln Gly Thr Leu
225                 230                 235                 240

Val Thr Val Ser Ser Thr Ser Thr Pro Ala Pro Arg Pro Pro Thr Pro
                245                 250                 255

Ala Pro Thr Ile Ala Ser Gln Pro Leu Ser Leu Arg Pro Glu Ala Cys
                260                 265                 270

Arg Pro Ala Ala Gly Gly Ala Val His Thr Arg Gly Leu Asp Phe Ala
                275                 280                 285

Cys Asp Ile Tyr Ile Trp Ala Pro Leu Ala Gly Thr Cys Gly Val Leu
                290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
            355                 360                 365

Tyr Lys Gln Gly Gln Asn Gln Leu Tyr Asn Glu Leu Asn Leu Gly Arg
370                 375                 380

Arg Glu Glu Tyr Asp Val Leu Asp Lys Arg Arg Gly Arg Asp Pro Glu
```

```
                385                 390                 395                 400
Met Gly Gly Lys Pro Arg Arg Lys Asn Pro Gln Glu Gly Leu Tyr Asn
                    405                 410                 415

Glu Leu Gln Lys Asp Lys Met Ala Glu Ala Tyr Ser Glu Ile Gly Met
                420                 425                 430

Lys Gly Glu Arg Arg Arg Gly Lys Gly His Asp Gly Leu Tyr Gln Gly
                435                 440                 445

Leu Ser Thr Ala Thr Lys Asp Thr Tyr Asp Ala Leu His Met Gln Ala
450                 455                 460

Leu Pro Pro Arg
465

<210> SEQ ID NO 217
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
                20                  25                  30

Gly Met His Trp Val Arg Gln Ala Pro Gly Lys Gly Leu Glu Trp Val
            35                  40                  45

Ala Phe Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala His Leu Pro Tyr Ser Gly Ser Tyr Trp Ala Phe Asp Tyr Trp Gly
                100                 105                 110

Gln Gly Thr Gln Val Thr Val Ser Ser Gly Ser Glu Gly Lys Ser
            115                 120                 125

Ser Gly Ser Gly Ser Glu Ser Lys Ser Thr Gly Gly Ser Gln Ser Val
            130                 135                 140

Leu Thr Gln Pro Pro Ser Val Ser Val Ala Pro Gly Gln Thr Ala Ser
145                 150                 155                 160

Ile Thr Cys Gly Gly Asp Asn Ile Gly Ser Lys Ser Val His Trp Tyr
                165                 170                 175

Gln Gln Lys Pro Gly Gln Ala Pro Val Leu Val Val Tyr Asp Asn Ser
                180                 185                 190

Asp Arg Pro Ser Gly Ile Pro Glu Arg Phe Ser Gly Ser Asn Ser Gly
            195                 200                 205

Thr Thr Ala Thr Leu Thr Ile Ser Arg Val Glu Ala Gly Asp Glu Ala
    210                 215                 220

Asp Tyr Tyr Cys Gln Val Trp Asp Ser Ser Ser Asp His Pro Val Val
225                 230                 235                 240

Phe Gly Gly Gly Thr Lys Val Thr Val Thr Ser Thr Pro Ala Pro Arg
                245                 250                 255

Pro Pro Thr Pro Ala Pro Thr Ile Ala Ser Gln Pro Leu Ser Leu Arg
            260                 265                 270
```

```
Pro Glu Ala Cys Arg Pro Ala Gly Gly Ala Val His Thr Arg Gly
            275                 280                 285

Leu Asp Phe Ala Cys Asp Ile Tyr Ile Trp Ala Pro Leu Ala Gly Thr
290                 295                 300

Cys Gly Val Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Arg Val Lys Phe Ser Arg Ser Ala
            355                 360                 365

Asp Ala Pro Ala Tyr Lys Gln Gly Gln Asn Gln Leu Tyr Asn Glu Leu
370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
            435                 440                 445

Leu Tyr Gln Gly Leu Ser Thr Ala Thr Lys Asp Thr Tyr Asp Ala Leu
450                 455                 460

His Met Gln Ala Leu Pro Pro Arg
465                 470

<210> SEQ ID NO 218
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Gln Ser Val Leu Thr Gln Pro Pro Ser Val Ser Val Ala Pro Gly Gln
1               5                   10                  15

Thr Ala Ser Ile Thr Cys Gly Gly Asp Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asn Ser Asp Arg Pro Ser Gly Ile Pro Glu Arg Phe Ser Gly Ser
50                  55                  60

Asn Ser Gly Thr Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Val Val Phe Gly Gly Gly Thr Lys Val Thr Val Gly Gly Ser Glu
            100                 105                 110

Gly Lys Ser Ser Gly Ser Gly Ser Glu Ser Lys Ser Thr Gly Gly Ser
        115                 120                 125

Gln Val Gln Leu Val Glu Ser Gly Gly Val Val Gln Pro Gly Arg
    130                 135                 140

Ser Leu Arg Leu Ser Cys Ala Ala Ser Gly Phe Thr Phe Ser Tyr Tyr
145                 150                 155                 160
```

Gly Met His Trp Val Arg Gln Ala Pro Gly Lys Gly Leu Glu Trp Val
                165                 170                 175

Ala Phe Ile Ser Tyr Asp Gly Ser Asn Lys Tyr Tyr Ala Asp Ser Val
                180                 185                 190

Lys Gly Arg Phe Thr Ile Ser Arg Asp Asn Ser Lys Asn Thr Leu Tyr
                195                 200                 205

Leu Gln Met Asn Ser Leu Arg Ala Glu Asp Thr Ala Val Tyr Tyr Cys
                210                 215                 220

Ala His Leu Pro Tyr Ser Gly Ser Tyr Trp Ala Phe Asp Tyr Trp Gly
225                 230                 235                 240

Gln Gly Thr Gln Val Thr Val Ser Ser Thr Ser Pro Ala Pro Arg
                245                 250                 255

Pro Pro Thr Pro Ala Pro Thr Ile Ala Ser Gln Pro Leu Ser Leu Arg
                260                 265                 270

Pro Glu Ala Cys Arg Pro Ala Ala Gly Gly Ala Val His Thr Arg Gly
                275                 280                 285

Leu Asp Phe Ala Cys Asp Ile Tyr Ile Trp Ala Pro Leu Ala Gly Thr
                290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
                340                 345                 350

Glu Glu Glu Gly Gly Cys Glu Leu Arg Val Lys Phe Ser Arg Ser Ala
                355                 360                 365

Asp Ala Pro Ala Tyr Lys Gln Gly Gln Asn Gln Leu Tyr Asn Glu Leu
                370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
                420                 425                 430

Glu Ile Gly Met Lys Gly Glu Arg Arg Arg Gly Lys Gly His Asp Gly
                435                 440                 445

Leu Tyr Gln Gly Leu Ser Thr Ala Thr Lys Asp Thr Tyr Asp Ala Leu
                450                 455                 460

His Met Gln Ala Leu Pro Pro Arg
465                 470

<210> SEQ ID NO 219
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
                20                  25                  30

Ala Met Ser Trp Val Arg Gln Ala Pro Gly Lys Gly Leu Glu Trp Val

```
            35                  40                  45
Ser Thr Ile Gly Gly Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Pro His Ile Val Met Val Thr Ala Leu Leu Tyr Asp Gly Met
                100                 105                 110
Asp Val Trp Gly Gln Gly Thr Met Val Thr Val Ser Ser Gly Gly Ser
            115                 120                 125
Glu Gly Lys Ser Ser Gly Ser Gly Ser Glu Ser Lys Ser Thr Gly Gly
            130                 135                 140
Ser Ser Ser Glu Leu Thr Gln Pro Pro Ser Val Ser Val Ala Pro Gly
145                 150                 155                 160
Gln Thr Ala Arg Ile Thr Cys Gly Gly Asn Asn Ile Gly Ser Lys Ser
                165                 170                 175
Val His Trp Tyr Gln Gln Lys Pro Gly Gln Ala Pro Val Leu Val Val
            180                 185                 190
Tyr Asp Asp Ser Asp Arg Pro Ser Gly Ile Pro Glu Arg Phe Ser Gly
            195                 200                 205
Ser Asn Ser Gly Asn Thr Ala Thr Leu Thr Ile Ser Arg Val Glu Ala
210                 215                 220
Gly Asp Glu Ala Asp Tyr Tyr Cys Gln Val Trp Asp Ser Ser Ser Asp
225                 230                 235                 240
His Val Val Phe Gly Gly Gly Thr Lys Leu Thr Val Leu Thr Ser Thr
                245                 250                 255
Pro Ala Pro Arg Pro Pro Thr Pro Ala Pro Thr Ile Ala Ser Gln Pro
            260                 265                 270
Leu Ser Leu Arg Pro Glu Ala Cys Arg Pro Ala Ala Gly Gly Ala Val
            275                 280                 285
His Thr Arg Gly Leu Asp Phe Ala Cys Asp Ile Tyr Ile Trp Ala Pro
            290                 295                 300
Leu Ala Gly Thr Cys Gly Val Leu Leu Leu Ser Leu Val Ile Thr Leu
305                 310                 315                 320
Tyr Cys Lys Arg Gly Arg Lys Lys Leu Leu Tyr Ile Phe Lys Gln Pro
                325                 330                 335
Phe Met Arg Pro Val Gln Thr Thr Gln Glu Glu Asp Gly Cys Ser Cys
                340                 345                 350
Arg Phe Pro Glu Glu Glu Glu Gly Gly Cys Glu Leu Arg Val Lys Phe
            355                 360                 365
Ser Arg Ser Ala Asp Ala Pro Ala Tyr Lys Gln Gly Gln Asn Gln Leu
            370                 375                 380
Tyr Asn Glu Leu Asn Leu Gly Arg Arg Glu Glu Tyr Asp Val Leu Asp
385                 390                 395                 400
Lys Arg Arg Gly Arg Asp Pro Glu Met Gly Gly Lys Pro Arg Arg Lys
                405                 410                 415
Asn Pro Gln Glu Gly Leu Tyr Asn Glu Leu Gln Lys Asp Lys Met Ala
                420                 425                 430
Glu Ala Tyr Ser Glu Ile Gly Met Lys Gly Glu Arg Arg Arg Gly Lys
            435                 440                 445
Gly His Asp Gly Leu Tyr Gln Gly Leu Ser Thr Ala Thr Lys Asp Thr
            450                 455                 460
```

```
Tyr Asp Ala Leu His Met Gln Ala Leu Pro Pro Arg
465                 470                 475

<210> SEQ ID NO 220
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Ser Ser Glu Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Thr Lys Leu Thr Val Leu Gly Gly Ser Glu
            100                 105                 110

Gly Lys Ser Ser Gly Ser Gly Ser Glu Ser Lys Ser Thr Gly Gly Ser
            115                 120                 125

Gln Val Gln Leu Val Glu Ser Gly Gly Gly Leu Val Gln Pro Gly Gly
        130                 135                 140

Ser Leu Arg Leu Ser Cys Ala Ala Ser Gly Phe Thr Phe Ser His Tyr
145                 150                 155                 160

Ala Met Ser Trp Val Arg Gln Ala Pro Gly Lys Gly Leu Glu Trp Val
                165                 170                 175

Ser Thr Ile Gly Gly Ser Gly Gly Ser Thr Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Lys Pro His Ile Val Met Val Thr Ala Leu Leu Tyr Asp Gly Met
225                 230                 235                 240

Asp Val Trp Gly Gln Gly Thr Met Val Thr Val Ser Ser Thr Ser Thr
                245                 250                 255

Pro Ala Pro Arg Pro Pro Thr Pro Ala Pro Thr Ile Ala Ser Gln Pro
            260                 265                 270

Leu Ser Leu Arg Pro Glu Ala Cys Arg Pro Ala Ala Gly Gly Ala Val
        275                 280                 285

His Thr Arg Gly Leu Asp Phe Ala Cys Asp Ile Tyr Ile Trp Ala Pro
    290                 295                 300

Leu Ala Gly Thr Cys Gly Val Leu Leu Leu Ser Leu Val Ile Thr Leu
305                 310                 315                 320

Tyr Cys Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
```

```
                340                 345                 350
Arg Phe Pro Glu Glu Glu Gly Gly Cys Glu Leu Arg Val Lys Phe
        355                 360                 365

Ser Arg Ser Ala Asp Ala Pro Ala Tyr Lys Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
        435                 440                 445

Gly His Asp Gly Leu Tyr Gln Gly Leu Ser Thr Ala Thr Lys Asp Thr
    450                 455                 460

Tyr Asp Ala Leu His Met Gln Ala Leu Pro Pro Arg
465                 470                 475

<210> SEQ ID NO 221
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Asp Ile Val Leu Thr Gln Ser
    130                 135                 140

Pro Asp Ser Leu Ala Val Ser Leu Gly Glu Arg Ala Thr Ile Asn Cys
145                 150                 155                 160

Arg Ala Ser Glu Ser Val Glu Tyr Phe Gly Thr Ser Leu Met His Trp
                165                 170                 175

Tyr Gln Gln Lys Pro Gly Gln Pro Pro Lys Leu Leu Ile Tyr Ala Ala
            180                 185                 190

Ser Asn Val Glu Ser Gly Val Pro Asp Arg Phe Ser Gly Ser Gly Ser
        195                 200                 205

Gly Thr Asp Phe Thr Leu Thr Ile Ser Ser Leu Gln Ala Glu Asp Val
    210                 215                 220
```

```
Ala Val Tyr Phe Cys Gln Gln Thr Arg Lys Val Pro Tyr Thr Phe Gly
225                 230                 235                 240

Gly Gly Thr Lys Val Glu Ile Lys
            245

<210> SEQ ID NO 222
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Thr Arg
                85                  90                  95

Lys Val Pro Tyr Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Gln Thr Leu Ser Leu Thr Cys Thr Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Ala Ala Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
            245

<210> SEQ ID NO 223
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
        115                 120                 125

Ser Glu Ser Lys Ser Thr Gly Gly Ser Glu Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Glu Ser Val Glu Tyr Phe Gly Thr Ser Leu Met His Trp
                165                 170                 175

Tyr Gln Gln Lys Pro Gly Gln Pro Pro Arg Leu Leu Ile Tyr Ala Ala
            180                 185                 190

Ser Asn Val Glu Ser Gly Ile Pro Ala Arg Phe Ser Gly Ser Gly Ser
        195                 200                 205

Gly Thr Asp Phe Thr Leu Thr Ile Ser Ser Val Glu Pro Glu Asp Phe
    210                 215                 220

Ala Val Tyr Phe Cys Gln Gln Thr Arg Lys Val Pro Tyr Thr Phe Gly
225                 230                 235                 240

Gly Gly Thr Lys Val Glu Ile Lys
                245

<210> SEQ ID NO 224
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Arg Leu Leu Ile Tyr Ala Ala Ser Asn Val Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Val Tyr Phe Cys Gln Gln Thr Arg
                85                  90                  95

Lys Val Pro Tyr Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125
```

Gly Gly Ser Gln Val Gln Leu Gln Glu Ser Gly Pro Gly Leu Val Lys
            130                 135                 140

Pro Ser Gln Thr Leu Ser Leu Thr Cys Thr Val Ser Gly Asn Ser Ile
145                 150                 155                 160

Thr Ser Asp Tyr Ala Trp Asn Trp Ile Arg Gln Pro Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
            195                 200                 205

Gln Phe Ser Leu Lys Leu Ser Ser Val Thr Ala Ala Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
                245

<210> SEQ ID NO 225
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gln Val Gln Leu Gln Glu Ser Gly Pro Gly Leu Val Lys Pro Ser Gln
1               5                   10                  15

Thr Leu Ser Leu Thr Cys Thr Val Ser Gly Asn Ser Ile Thr Ser Asp
            20                  25                  30

Tyr Ala Trp Asn Trp Ile Arg Gln Phe Pro Gly Lys Gly Leu Glu Trp
        35                  40                  45

Ile Gly Tyr Ile Ser Tyr Ser Gly Ser Thr Thr Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Gly Tyr Tyr Gly Ser Gly Phe Trp Gly Gln Gly Thr Leu
            100                 105                 110

Val Thr Val Ser Ser Gly Gly Glu Gly Lys Ser Ser Gly Ser Gly
            115                 120                 125

Ser Glu Ser Lys Ser Thr Gly Gly Ser Glu Ile Val Leu Thr Gln Ser
130                 135                 140

Pro Ala Thr Leu Ser Leu Ser Pro Gly Glu Arg Ala Thr Leu Ser Cys
145                 150                 155                 160

Arg Ala Ser Glu Ser Val Glu Tyr Phe Gly Thr Ser Leu Met His Trp
                165                 170                 175

Tyr Gln Gln Lys Pro Gly Gln Pro Arg Leu Leu Ile Tyr Ala Ala
            180                 185                 190

Ser Asn Val Glu Ser Gly Ile Pro Ala Arg Phe Ser Gly Ser Gly Ser
            195                 200                 205

Gly Thr Asp Phe Thr Leu Thr Ile Ser Ser Val Glu Pro Glu Asp Phe
    210                 215                 220

Ala Val Tyr Phe Cys Gln Gln Thr Arg Lys Val Pro Tyr Thr Phe Gly

```
                225                 230                 235                 240
Gly Gly Thr Lys Val Glu Ile Lys
                245

<210> SEQ ID NO 226
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Arg Leu Leu Ile Tyr Ala Ala Ser Asn Val Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Val Tyr Phe Cys Gln Gln Thr Arg
                85                  90                  95

Lys Val Pro Tyr Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Gln Thr Leu Ser Leu Thr Cys Thr Val Ser Gly Asn Ser Ile
145                 150                 155                 160

Thr Ser Asp Tyr Ala Trp Asn Trp Ile Arg Gln Phe Pro Gly Lys Gly
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Ala Ala Asp Thr Ala Val
    210                 215                 220

Tyr Tyr Cys Ala Thr Gly Tyr Tyr Tyr Gly Ser Gly Phe Trp Gly Gln
225                 230                 235                 240

Gly Thr Leu Val Thr Val Ser Ser
                245

<210> SEQ ID NO 227
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
```

```
                    20                  25                  30
Tyr Trp Ser Trp Ile Arg Gln Pro Pro Gly Lys Gly Leu Glu Trp Ile
            35                  40                  45
Gly Tyr Ile Tyr Tyr Ser Gly Ser Thr Asn Tyr Asn Pro Ser Leu Lys
        50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Gly Thr Thr Ile Phe Gly Val Val Thr Pro Asn Phe Tyr Tyr Gly Met
            100                 105                 110
Asp Val Trp Gly Gln Gly Thr Thr Val Thr Val Ser Ser Gly Gly Ser
        115                 120                 125
Glu Gly Lys Ser Ser Gly Ser Gly Ser Glu Ser Lys Ser Thr Gly Gly
        130                 135                 140
Ser Asp Ile Gln Met Thr Gln Ser Pro Ser Phe Leu Ser Ala Ser Val
145                 150                 155                 160
Gly Asp Arg Val Thr Ile Thr Cys Arg Ala Ser Gln Gly Ile Ser Ser
                165                 170                 175
Tyr Leu Ala Trp Tyr Gln Gln Lys Pro Gly Lys Ala Pro Lys Phe Leu
            180                 185                 190
Ile Tyr Ala Ala Ser Thr Leu Gln Ser Gly Val Pro Ser Arg Phe Ser
        195                 200                 205
Gly Ser Gly Ser Gly Thr Glu Phe Thr Leu Thr Ile Ser Ser Leu Gln
        210                 215                 220
Pro Glu Asp Phe Ala Thr Tyr Tyr Cys Gln Gln Leu Asn Ser Tyr Pro
225                 230                 235                 240
Leu Thr Phe Gly Gly Gly Thr Lys Val Glu Ile Lys
                245                 250

<210> SEQ ID NO 228
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Asp Ile Gln Met Thr Gln Ser Pro Ser Phe Leu Ser Ala Ser Val Gly
1               5                   10                  15
Asp Arg Val Thr Ile Thr Cys Arg Ala Ser Gln Gly Ile Ser Ser Tyr
            20                  25                  30
Leu Ala Trp Tyr Gln Gln Lys Pro Gly Lys Ala Pro Lys Phe Leu Ile
        35                  40                  45
Tyr Ala Ala Ser Thr Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Leu Asn Ser Tyr Pro Leu
                85                  90                  95
Thr Phe Gly Gly Gly Thr Lys Val Glu Ile Lys Gly Gly Ser Glu Gly
            100                 105                 110
Lys Ser Ser Gly Ser Gly Ser Glu Ser Lys Ser Thr Gly Gly Ser Gln
        115                 120                 125
```

```
Val Gln Leu Gln Glu Ser Gly Pro Gly Leu Val Lys Pro Ser Glu Thr
130                 135                 140

Leu Ser Leu Thr Cys Thr Val Ser Gly Gly Ser Ile Ser Ser Tyr Tyr
145                 150                 155                 160

Trp Ser Trp Ile Arg Gln Pro Pro Gly Lys Gly Leu Glu Trp Ile Gly
                165                 170                 175

Tyr Ile Tyr Tyr Ser Gly Ser Thr Asn Tyr Asn Pro Ser Leu Lys Ser
                180                 185                 190

Arg Val Thr Ile Ser Val Asp Thr Ser Lys Asn Gln Phe Ser Leu Lys
                195                 200                 205

Leu Ser Ser Val Thr Ala Ala Asp Thr Ala Val Tyr Tyr Cys Ala Gly
210                 215                 220

Thr Thr Ile Phe Gly Val Val Thr Pro Asn Phe Tyr Tyr Gly Met Asp
225                 230                 235                 240

Val Trp Gly Gln Gly Thr Thr Val Thr Val Ser Ser
                245                 250

<210> SEQ ID NO 229
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Glu Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
                20                  25                  30

Asp Ile His Trp Val Arg Gln Ala Pro Gly Lys Gly Leu Glu Trp Val
            35                  40                  45

Ala Ile Ile Ser Tyr Asp Gly Ser Lys Lys Asp Tyr Thr Asp Ser Val
50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Val Glu Asp Ser Ala Val Tyr Ser Cys
                85                  90                  95

Ala Arg Glu Ser Gly Trp Ser His Tyr Tyr Tyr Gly Met Asp Val
                100                 105                 110

Trp Gly Gln Gly Thr Met Val Thr Val Ser Ser Gly Gly Ser Glu Gly
            115                 120                 125

Lys Ser Ser Gly Ser Gly Ser Glu Ser Lys Ser Thr Gly Gly Ser Asp
130                 135                 140

Ile Val Met Thr Gln Ser Pro Ser Ser Leu Ala Ser Val Gly Asp
145                 150                 155                 160

Arg Val Thr Ile Thr Cys Arg Ala Ser Gln Asp Ile Ser Asn Tyr Leu
                165                 170                 175

Ala Trp Tyr Gln Gln Lys Pro Gly Lys Val Pro Lys Phe Leu Ile Tyr
                180                 185                 190

Ala Ala Ser Thr Leu His Ser Gly Val Pro Ser Arg Phe Ser Gly Ser
                195                 200                 205

Gly Ser Gly Thr Asp Phe Thr Leu Thr Ile Ser Ser Leu Gln Pro Glu
210                 215                 220

Asp Val Ala Thr Tyr Tyr Cys Gln Lys Tyr Asn Ser Ala Pro Tyr Thr
225                 230                 235                 240
```

Phe Gly Gln Gly Thr Arg Leu Glu Ile Lys
                245                 250

<210> SEQ ID NO 230
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Val Pro Lys Phe Leu Ile
        35                  40                  45

Tyr Ala Ala Ser Thr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Arg Leu Glu Ile Lys Gly Ser Gly Glu Gly
            100                 105                 110

Lys Ser Ser Gly Ser Gly Ser Glu Ser Lys Ser Thr Gly Gly Ser Glu
        115                 120                 125

Val Gln Leu Val Glu Ser Gly Gly Val Val Gln Pro Gly Arg Ser
    130                 135                 140

Leu Arg Leu Ser Cys Val Ala Ser Gly Phe Thr Phe Ser Ser Tyr Asp
145                 150                 155                 160

Ile His Trp Val Arg Gln Ala Pro Gly Lys Gly Leu Glu Trp Val Ala
                165                 170                 175

Ile Ile Ser Tyr Asp Gly Ser Lys Lys Asp Tyr Thr Asp Ser Val Lys
            180                 185                 190

Gly Arg Phe Thr Ile Ser Arg Asp Asn Ser Lys Asn Thr Leu Tyr Leu
        195                 200                 205

Gln Met Asp Ser Leu Arg Val Glu Asp Ser Ala Val Tyr Ser Cys Ala
    210                 215                 220

Arg Glu Ser Gly Trp Ser His Tyr Tyr Tyr Gly Met Asp Val Trp
225                 230                 235                 240

Gly Gln Gly Thr Met Val Thr Val Ser Ser
                245                 250

<210> SEQ ID NO 231
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

```
Tyr Trp Ser Trp Leu Arg Gln Pro Ala Gly Ser Gly Leu Glu Trp Ile
            35                  40                  45

Gly Arg Leu Tyr Val Ser Gly Phe Thr Asn Tyr Asn Pro Ser Leu Lys
 50                  55                  60

Ser Arg Val Thr Leu Ser Leu Asp Pro Ser Arg Asn Gln Leu Ser Leu
 65                  70                  75                  80

Lys Leu Ser Ser Val Thr Ala Ala Asp Thr Ala Val Tyr Tyr Cys Ala
                85                  90                  95

Gly Asp Ser Gly Asn Tyr Trp Gly Trp Phe Asp Pro Trp Gly Gln Gly
                100                 105                 110

Thr Leu Val Thr Val Ser Gly Gly Ser Glu Gly Lys Ser Ser Gly
            115                 120                 125

Ser Gly Ser Glu Ser Lys Ser Thr Gly Gly Ser Ser Tyr Glu Leu Thr
130                 135                 140

Gln Pro Pro Ser Val Ser Val Ser Pro Gly Glu Thr Ala Ser Ile Thr
145                 150                 155                 160

Cys Ser Gly Asp Gln Leu Gly Glu Asn Tyr Ala Cys Trp Tyr Gln Gln
                165                 170                 175

Lys Pro Gly Gln Ser Pro Val Leu Val Ile Tyr Gln Asp Ser Lys Arg
                180                 185                 190

Pro Ser Gly Ile Pro Glu Arg Phe Ser Gly Ser Asn Ser Gly Asn Thr
                195                 200                 205

Ala Thr Leu Thr Ile Ser Gly Thr Gln Ala Leu Asp Glu Ala Asp Tyr
            210                 215                 220

Tyr Cys Gln Ala Trp Asp Asn Ser Ile Val Val Phe Gly Gly Gly Thr
225                 230                 235                 240

Lys Leu Thr Val Leu
                245

<210> SEQ ID NO 232
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Ser Tyr Glu Leu Thr Gln Pro Pro Ser Val Ser Val Ser Pro Gly Glu
 1               5                  10                  15

Thr Ala Ser Ile Thr Cys Ser Gly Asp Gln Leu Gly Glu Asn Tyr Ala
                20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Leu
 65                  70                  75                  80

Asp Glu Ala Asp Tyr Tyr Cys Gln Ala Trp Asp Asn Ser Ile Val Val
                85                  90                  95

Phe Gly Gly Gly Thr Lys Leu Thr Val Leu Gly Ser Glu Gly Lys
                100                 105                 110

Ser Ser Gly Ser Gly Ser Glu Ser Lys Ser Thr Gly Gly Ser Gln Val
            115                 120                 125

Gln Leu Gln Glu Ser Gly Pro Gly Leu Val Lys Pro Ser Glu Thr Leu
```

```
                130                 135                 140
Ser Leu Thr Cys Thr Val Ser Gly Gly Ser Ile Ser Ser Tyr Tyr Trp
145                 150                 155                 160

Ser Trp Leu Arg Gln Pro Ala Gly Ser Gly Leu Glu Trp Ile Gly Arg
                165                 170                 175

Leu Tyr Val Ser Gly Phe Thr Asn Tyr Asn Pro Ser Leu Lys Ser Arg
            180                 185                 190

Val Thr Leu Ser Leu Asp Pro Ser Arg Asn Gln Leu Ser Leu Lys Leu
        195                 200                 205

Ser Ser Val Thr Ala Ala Asp Thr Ala Val Tyr Tyr Cys Ala Gly Asp
    210                 215                 220

Ser Gly Asn Tyr Trp Gly Trp Phe Asp Pro Trp Gly Gln Gly Thr Leu
225                 230                 235                 240

Val Thr Val Ser Ser
                245

<210> SEQ ID NO 233
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ala Phe Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala His Leu Pro Tyr Ser Gly Ser Tyr Trp Ala Phe Asp Tyr Trp Gly
            100                 105                 110

Gln Gly Thr Gln Val Thr Val Ser Ser Gly Ser Glu Gly Lys Ser Ser
        115                 120                 125

Ser Gly Ser Gly Ser Glu Ser Lys Ser Thr Gly Gly Ser Gln Ser Val
    130                 135                 140

Leu Thr Gln Pro Pro Ser Val Ser Val Ala Pro Gly Gln Thr Ala Ser
145                 150                 155                 160

Ile Thr Cys Gly Gly Asp Asn Ile Gly Ser Lys Ser Val His Trp Tyr
            165                 170                 175

Gln Gln Lys Pro Gly Gln Ala Pro Val Leu Val Val Tyr Asp Asn Ser
        180                 185                 190

Asp Arg Pro Ser Gly Ile Pro Glu Arg Phe Ser Gly Ser Asn Ser Gly
    195                 200                 205

Thr Thr Ala Thr Leu Thr Ile Ser Arg Val Glu Ala Gly Asp Glu Ala
    210                 215                 220

Asp Tyr Tyr Cys Gln Val Trp Asp Ser Ser Ser Asp His Pro Val Val
225                 230                 235                 240
```

```
Phe Gly Gly Gly Thr Lys Val Thr Val
                245

<210> SEQ ID NO 234
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gln Ser Val Leu Thr Gln Pro Pro Ser Val Ser Val Ala Pro Gly Gln
1               5                   10                  15

Thr Ala Ser Ile Thr Cys Gly Gly Asp Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asn Ser Asp Arg Pro Ser Gly Ile Pro Glu Arg Phe Ser Gly Ser
    50                  55                  60

Asn Ser Gly Thr Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Val Val Phe Gly Gly Gly Thr Lys Val Thr Val Gly Gly Ser Glu
            100                 105                 110

Gly Lys Ser Ser Gly Ser Gly Ser Glu Ser Lys Ser Thr Gly Gly Ser
        115                 120                 125

Gln Val Gln Leu Val Glu Ser Gly Gly Val Val Gln Pro Gly Arg
    130                 135                 140

Ser Leu Arg Leu Ser Cys Ala Ala Ser Gly Phe Thr Phe Ser Tyr Tyr
145                 150                 155                 160

Gly Met His Trp Val Arg Gln Ala Pro Gly Lys Gly Leu Glu Trp Val
                165                 170                 175

Ala Phe Ile Ser Tyr Asp Gly Ser Asn Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala His Leu Pro Tyr Ser Gly Ser Tyr Trp Ala Phe Asp Tyr Trp Gly
225                 230                 235                 240

Gln Gly Thr Gln Val Thr Val Ser Ser
                245

<210> SEQ ID NO 235
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30
```

```
Ala Met Ser Trp Val Arg Gln Ala Pro Gly Lys Gly Leu Glu Trp Val
            35                  40                  45

Ser Thr Ile Gly Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro His Ile Val Met Val Thr Ala Leu Leu Tyr Asp Gly Met
                100                 105                 110

Asp Val Trp Gly Gln Gly Thr Met Val Thr Val Ser Ser Gly Gly Ser
            115                 120                 125

Glu Gly Lys Ser Ser Gly Ser Gly Ser Glu Ser Lys Ser Thr Gly Gly
130                 135                 140

Ser Ser Ser Glu Leu Thr Gln Pro Pro Ser Val Ser Val Ala Pro Gly
145                 150                 155                 160

Gln Thr Ala Arg Ile Thr Cys Gly Gly Asn Asn Ile Gly Ser Lys Ser
                165                 170                 175

Val His Trp Tyr Gln Gln Lys Pro Gly Gln Ala Pro Val Leu Val Val
            180                 185                 190

Tyr Asp Asp Ser Asp Arg Pro Ser Gly Ile Pro Glu Arg Phe Ser Gly
            195                 200                 205

Ser Asn Ser Gly Asn Thr Ala Thr Leu Thr Ile Ser Arg Val Glu Ala
        210                 215                 220

Gly Asp Glu Ala Asp Tyr Tyr Cys Gln Val Trp Asp Ser Ser Ser Asp
225                 230                 235                 240

His Val Val Phe Gly Gly Gly Thr Lys Leu Thr Val Leu
                245                 250

<210> SEQ ID NO 236
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Ser Ser Glu Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu Gly Gly Ser Glu
            100                 105                 110

Gly Lys Ser Ser Gly Ser Gly Ser Glu Ser Lys Ser Thr Gly Gly Ser
        115                 120                 125

Gln Val Gln Leu Val Glu Ser Gly Gly Gly Leu Val Gln Pro Gly Gly
    130                 135                 140
```

Ser Leu Arg Leu Ser Cys Ala Ala Ser Gly Phe Thr Phe Ser His Tyr
145                 150                 155                 160

Ala Met Ser Trp Val Arg Gln Ala Pro Gly Lys Gly Leu Glu Trp Val
                165                 170                 175

Ser Thr Ile Gly Gly Ser Gly Gly Ser Thr Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Lys Pro His Ile Val Met Val Thr Ala Leu Leu Tyr Asp Gly Met
225                 230                 235                 240

Asp Val Trp Gly Gln Gly Thr Met Val Thr Val Ser Ser
                245                 250

<210> SEQ ID NO 237
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Gly Gly Ser Gly Gly Gly Ser
1               5

<210> SEQ ID NO 238
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Gly Gly Ser Gly Gly Gly Ser Gly Gly Gly Ser
1               5                   10

<210> SEQ ID NO 239
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Gly Gly Ser Gly Gly Gly Ser Gly Gly Gly Ser Gly Gly Gly Ser
1               5                   10                  15

<210> SEQ ID NO 240
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Gly Gly Ser Gly Gly Gly Ser Gly Gly Gly Ser Gly Gly Gly Ser
1               5                   10                  15

Gly Gly Gly Ser

20

<210> SEQ ID NO 241
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Gly Gly Gly Ser Gly Gly Gly Ser Gly Gly Gly Gly Ser
1               5                   10                  15

<210> SEQ ID NO 242
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Gly Gly Gly Ser Gly Gly Gly Gly Ser Gly Gly Gly Gly Ser Gly
1               5                   10                  15

Gly Gly Gly Ser
            20

<210> SEQ ID NO 243
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 244
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Ser Thr Ser Gly Ser Gly Lys Pro Gly Ser Gly Glu Gly Ser Thr
1               5                   10                  15

Lys Gly

<210> SEQ ID NO 245
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ile Arg Pro Arg Ala Ile Gly Gly Ser Lys Pro Arg Val Ala
1               5                   10

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Lys Gly Gly Ser Gly Lys Gly Gly Ser Gly Lys Gly Gly Ser
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gly Gly Lys Gly Ser Gly Gly Lys Gly Ser Gly Gly Lys Gly Ser
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gly Gly Gly Lys Ser Gly Gly Gly Lys Ser Gly Gly Gly Lys Ser
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gly Lys Gly Lys Ser Gly Lys Gly Lys Ser Gly Lys Gly Lys Ser
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gly Gly Gly Lys Ser Gly Gly Lys Gly Ser Gly Lys Gly Gly Ser
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 251

Gly Lys Pro Gly Ser Gly Lys Pro Gly Ser Gly Lys Pro Gly Ser
1               5                   10                  15

<210> SEQ ID NO 252
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Lys Pro Gly Ser Gly Lys Pro Gly Ser Gly Lys Pro Gly Ser Gly
1               5                   10                  15

Lys Pro Gly Ser
            20

<210> SEQ ID NO 253
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gly Lys Gly Lys Ser Gly Lys Gly Lys Ser Gly Lys Gly Lys Ser Gly
1               5                   10                  15

Lys Gly Lys Ser
            20

<210> SEQ ID NO 254
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ser Thr Ala Gly Asp Thr His Leu Gly Gly Glu Asp Phe Asp
1               5                   10

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gly Glu Gly Gly Ser Gly Glu Gly Gly Ser Gly Glu Gly Gly Ser
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256
```

```
Gly Gly Glu Gly Ser Gly Gly Glu Gly Ser Gly Gly Glu Gly Ser
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gly Glu Gly Glu Ser Gly Glu Gly Glu Ser Gly Glu Gly Glu Ser
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gly Gly Gly Glu Ser Gly Gly Glu Gly Ser Gly Glu Gly Gly Ser
1               5                   10                  15

<210> SEQ ID NO 259
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gly Glu Gly Glu Ser Gly Glu Gly Glu Ser Gly Glu Gly Glu Ser Gly
1               5                   10                  15

Glu Gly Glu Ser
            20

<210> SEQ ID NO 260
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gly Ser Thr Ser Gly Ser Gly Lys Pro Gly Ser Gly Glu Gly Ser Thr
1               5                   10                  15

Lys Gly

<210> SEQ ID NO 261
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Pro Arg Gly Ala Ser Lys Ser Gly Ser Ala Ser Gln Thr Gly Ser Ala
1               5                   10                  15

Pro Gly Ser
```

<210> SEQ ID NO 262
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Thr Ala Ala Ala Gly Ala Gly Ala Ala Gly Gly Ala Ala Ala Gly
1               5                   10                  15

Ala Ala Gly

<210> SEQ ID NO 263
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gly Thr Ser Gly Ser Ser Gly Ser Gly Ser Gly Gly Ser Gly Ser Gly
1               5                   10                  15

Gly Gly Gly

<210> SEQ ID NO 264
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gly Lys Pro Gly Ser Gly Lys Pro Gly Ser Gly Lys Pro Gly Ser Gly
1               5                   10                  15

Lys Pro Gly Ser
            20

<210> SEQ ID NO 265
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Ser Gly Ser
1

<210> SEQ ID NO 266
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ala Pro Ala Pro Ala Pro Ala Pro Ala Pro
1               5                   10

```
<210> SEQ ID NO 267
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ala Pro Ala Pro Ala Pro Ala Pro Ala Pro Ala Pro Ala Pro Ala Pro
1               5                   10                  15

Ala Pro Ala Pro
            20

<210> SEQ ID NO 268
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Ala Glu Ala Ala Ala Lys Glu Ala Ala Ala Lys Glu Ala Ala Ala Ala
1               5                   10                  15

Lys Glu Ala Ala Ala Ala Lys Glu Ala Ala Ala Lys Ala Ala Ala
            20                  25                  30

<210> SEQ ID NO 269
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Glu Pro Lys Ser Cys Asp Lys Thr His Thr Cys Pro Pro Cys Pro
1               5                   10                  15

<210> SEQ ID NO 270
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Glu Arg Lys Cys Cys Val Glu Cys Pro Pro Cys Pro
1               5                   10

<210> SEQ ID NO 271
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
```

```
                35                  40                  45
Pro Lys Ser Cys Asp Thr Pro Pro Cys Pro Arg Cys Pro
    50                  55                  60

<210> SEQ ID NO 272
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Glu Ser Lys Tyr Gly Pro Pro Cys Pro Ser Cys Pro
1               5                  10

<210> SEQ ID NO 273
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Met Ala Trp Val Trp Thr Leu Leu Phe Leu Met Ala Ala Ala Gln Ser
1               5                  10                  15

Ile Gln Ala Gln Val Gln Leu Gln Glu Ser Gly Pro Gly Leu Val Lys
            20                  25                  30

Pro Ser Asp Thr Leu Ser Leu Thr Cys Ala Val Ser Gly Asn Ser Ile
        35                  40                  45

Thr Ser Asp Tyr Ala Trp Asn Trp Ile Arg Gln Phe Pro Gly Lys Gly
    50                  55                  60

Leu Glu Trp Met Gly Tyr Ile Ser Tyr Ser Gly Ser Thr Thr Tyr Asn
65                  70                  75                  80

Pro Ser Leu Lys Ser Arg Val Thr Ile Ser Arg Asp Thr Ser Lys Asn
                85                  90                  95

Gln Phe Ser Leu Lys Leu Ser Ser Val Thr Pro Val Asp Thr Ala Val
            100                 105                 110

Tyr Tyr Cys Ala Thr Gly Tyr Tyr Gly Ser Gly Phe Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Glu Ser Val Glu Tyr Phe Gly Thr Ser Leu
            180                 185                 190

Met His Trp Tyr Gln Gln Lys Pro Gly Gln Pro Pro Lys Leu Leu Ile
        195                 200                 205

Tyr Ala Ala Ser Asn Arg Glu Ser Gly Val Pro Asp Arg Phe Ser Gly
    210                 215                 220

Ser Gly Ser Gly Thr Asp Phe Thr Leu Thr Ile Gln Ser Val Gln Ala
225                 230                 235                 240

Glu Asp Val Ser Val Tyr Phe Cys Gln Gln Thr Arg Lys Val Pro Tyr
                245                 250                 255

Thr Phe Gly Gln Gly Thr Lys Leu Glu Ile Lys
```

<210> SEQ ID NO 274
<211> LENGTH: 267
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 274

Met Ala Trp Val Trp Thr Leu Leu Phe Leu Met Ala Ala Ala Gln Ser
1               5                   10                  15

Ile Gln Ala Gln Val Gln Leu Gln Glu Ser Gly Pro Gly Leu Val Lys
            20                  25                  30

Pro Ser Asp Thr Leu Ser Leu Thr Cys Ala Val Ser Gly Asn Ser Ile
        35                  40                  45

Thr Ser Asp Tyr Ala Trp Asn Trp Ile Arg Gln Phe Pro Gly Lys Gly
    50                  55                  60

Leu Glu Trp Met Gly Tyr Ile Ser Tyr Ser Gly Ser Thr Thr Tyr Asn
65                  70                  75                  80

Pro Ser Leu Lys Ser Arg Val Thr Ile Ser Arg Asp Thr Ser Lys Asn
                85                  90                  95

Gln Phe Ser Leu Lys Leu Ser Ser Val Thr Pro Val Asp Thr Ala Val
            100                 105                 110

Tyr Tyr Cys Ala Thr Gly Tyr Tyr Gly Ser Gly Phe Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Glu Ser Val Glu Tyr Phe Gly Thr Ser Leu
            180                 185                 190

Met His Trp Tyr Gln Gln Lys Pro Gly Gln Pro Pro Lys Leu Leu Ile
        195                 200                 205

Tyr Ala Ala Ser Asn Arg Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Gln Gln Thr Arg Lys Val Pro Tyr
                245                 250                 255

Thr Phe Gly Gln Gly Thr Lys Leu Glu Ile Lys
            260                 265

<210> SEQ ID NO 275
<211> LENGTH: 267
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 275

Met Ala Trp Val Trp Thr Leu Leu Phe Leu Met Ala Ala Ala Gln Ser
1               5                   10                  15

Ile Gln Ala Gln Val Gln Leu Gln Glu Ser Gly Pro Gly Leu Val Lys

```
                20                  25                  30
Pro Ser Asp Thr Leu Ser Leu Thr Cys Ala Val Ser Gly Asn Ser Ile
            35                  40                  45

Thr Ser Asp Tyr Ala Trp Asn Trp Ile Arg Gln Phe Pro Gly Lys Gly
        50                  55                  60

Leu Glu Trp Ile Gly Tyr Ile Ser Tyr Ser Gly Ser Thr Thr Tyr Asn
65                  70                  75                  80

Pro Ser Leu Lys Ser Arg Val Thr Ile Ser Arg Asp Thr Ser Lys Asn
                85                  90                  95

Gln Phe Ser Leu Lys Leu Ser Ser Val Thr Pro Val Asp Thr Ala Val
            100                 105                 110

Tyr Tyr Cys Ala Thr Gly Tyr Tyr Gly Ser Gly Phe Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Glu Ser Val Glu Tyr Phe Gly Thr Ser Leu
            180                 185                 190

Met His Trp Tyr Gln Gln Lys Pro Gly Gln Pro Pro Lys Leu Leu Ile
        195                 200                 205

Tyr Ala Ala Ser Asn Arg Glu Ser Gly Val Pro Asp Arg Phe Ser Gly
    210                 215                 220

Ser Gly Ser Gly Thr Asp Phe Thr Leu Thr Ile Ser Ser Val Gln Ala
225                 230                 235                 240

Glu Asp Val Ala Val Tyr Tyr Cys Gln Gln Thr Arg Lys Val Pro Tyr
                245                 250                 255

Thr Phe Gly Gln Gly Thr Lys Leu Glu Ile Lys
            260                 265

<210> SEQ ID NO 276
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Met Ala Trp Val Trp Thr Leu Leu Phe Leu Met Ala Ala Ala Gln Ser
1               5                   10                  15

Ile Gln Ala Gln Val Gln Leu Gln Glu Ser Gly Pro Gly Leu Val Lys
            20                  25                  30

Pro Ser Asp Thr Leu Ser Leu Thr Cys Ala Val Ser Gly Asn Ser Ile
        35                  40                  45

Thr Ser Asp Tyr Ala Trp Asn Trp Ile Arg Gln Phe Pro Gly Lys Gly
    50                  55                  60

Leu Glu Trp Met Gly Tyr Ile Ser Tyr Ser Gly Ser Thr Thr Tyr Asn
65                  70                  75                  80

Pro Ser Leu Lys Ser Arg Val Thr Ile Ser Arg Asp Thr Ser Lys Asn
                85                  90                  95

Gln Phe Ser Leu Lys Leu Ser Ser Val Thr Pro Val Asp Thr Ala Val
            100                 105                 110
```

```
Tyr Tyr Cys Ala Thr Gly Tyr Tyr Gly Ser Gly Phe Trp Gly Gln
            115                 120                 125

Gly Thr Leu Val Thr Val Ser Ser Gly Gly Ser Glu Gly Lys Ser Ser
130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Glu Ser Val Glu Tyr Phe Gly Thr Ser Leu
            180                 185                 190

Met His Trp Tyr Gln Gln Lys Pro Gly Gln Pro Pro Lys Leu Leu Ile
            195                 200                 205

Tyr Ala Ala Ser Asn Arg Glu Ser Gly Val Pro Asp Arg Phe Ser Gly
            210                 215                 220

Ser Gly Ser Gly Thr Asp Phe Thr Leu Thr Ile Ser Ser Val Gln Ala
225                 230                 235                 240

Glu Asp Val Ala Val Tyr Tyr Cys Gln Gln Thr Arg Lys Val Pro Tyr
                245                 250                 255

Thr Phe Gly Gln Gly Thr Lys Leu Glu Ile Lys
            260                 265

<210> SEQ ID NO 277
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Glu Ser Val
        35                  40                  45

Glu Tyr Phe Gly Thr Ser Leu Met His Trp Tyr Gln Gln Lys Pro Gly
    50                  55                  60

Gln Pro Pro Lys Leu Leu Ile Tyr Ala Ala Ser Asn Arg Glu Ser Gly
65                  70                  75                  80

Val Pro Asp Arg Phe Ser Gly Ser Gly Ser Gly Thr Asp Phe Thr Leu
                85                  90                  95

Thr Ile Gln Ser Val Gln Ala Glu Asp Val Ser Val Tyr Phe Cys Gln
            100                 105                 110

Gln Thr Arg Lys Val Pro Tyr Thr Phe Gly Gln Gly Thr Lys Leu Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Gln Glu Ser Gly Pro Gly
145                 150                 155                 160

Leu Val Lys Pro Ser Asp Thr Leu Ser Leu Thr Cys Ala Val Ser Gly
                165                 170                 175

Asn Ser Ile Thr Ser Asp Tyr Ala Trp Asn Trp Ile Arg Gln Phe Pro
            180                 185                 190

Gly Lys Gly Leu Glu Trp Met Gly Tyr Ile Ser Tyr Ser Gly Ser Thr
        195                 200                 205
```

Thr Tyr Asn Pro Ser Leu Lys Ser Arg Val Thr Ile Ser Arg Asp Thr
    210                 215                 220

Ser Lys Asn Gln Phe Ser Leu Lys Leu Ser Ser Val Thr Pro Val Asp
225                 230                 235                 240

Thr Ala Val Tyr Tyr Cys Ala Thr Gly Tyr Tyr Tyr Gly Ser Gly Phe
                245                 250                 255

Trp Gly Gln Gly Thr Leu Val Thr Val Ser Ser
            260                 265

<210> SEQ ID NO 278
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Glu Ser Val
        35                  40                  45

Glu Tyr Phe Gly Thr Ser Leu Met His Trp Tyr Gln Gln Lys Pro Gly
    50                  55                  60

Gln Pro Pro Lys Leu Leu Ile Tyr Ala Ala Ser Asn Arg Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Thr Arg Lys Val Pro Tyr Thr Phe Gly Gln Gly Thr Lys Leu Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Gln Glu Ser Gly Pro Gly
145                 150                 155                 160

Leu Val Lys Pro Ser Asp Thr Leu Ser Leu Thr Cys Ala Val Ser Gly
                165                 170                 175

Asn Ser Ile Thr Ser Asp Tyr Ala Trp Asn Trp Ile Arg Gln Phe Pro
            180                 185                 190

Gly Lys Gly Leu Glu Trp Ile Gly Tyr Ile Ser Tyr Ser Gly Ser Thr
        195                 200                 205

Thr Tyr Asn Pro Ser Leu Lys Ser Arg Val Thr Ile Ser Arg Asp Thr
    210                 215                 220

Ser Lys Asn Gln Phe Ser Leu Lys Leu Ser Ser Val Thr Pro Val Asp
225                 230                 235                 240

Thr Ala Val Tyr Tyr Cys Ala Thr Gly Tyr Tyr Tyr Gly Ser Gly Phe
                245                 250                 255

Trp Gly Gln Gly Thr Leu Val Thr Val Ser Ser
            260                 265

<210> SEQ ID NO 279
<211> LENGTH: 267
<212> TYPE: PRT

<213> ORGANISM: Artificial Sequence
<220> FEATURE:
<223> OTHER INFORMATION: Description of Artificial Sequence: Synthetic
       polypeptide

<400> SEQUENCE: 279

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Glu Ser Val
        35                  40                  45

Glu Tyr Phe Gly Thr Ser Leu Met His Trp Tyr Gln Gln Lys Pro Gly
    50                  55                  60

Gln Pro Pro Lys Leu Leu Ile Tyr Ala Ala Ser Asn Arg Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Thr Arg Lys Val Pro Tyr Thr Phe Gly Gly Gly Thr Lys Leu Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Gln Ser Gly Pro Gly
145                 150                 155                 160

Leu Val Lys Pro Ser Asp Thr Leu Ser Leu Thr Cys Ala Val Ser Gly
                165                 170                 175

Asn Ser Ile Thr Ser Asp Tyr Ala Trp Asn Trp Ile Arg Gln Phe Pro
            180                 185                 190

Gly Lys Gly Leu Glu Trp Met Gly Tyr Ile Ser Tyr Ser Gly Ser Thr
        195                 200                 205

Thr Tyr Asn Pro Ser Leu Lys Ser Arg Val Thr Ile Ser Arg Asp Thr
    210                 215                 220

Ser Lys Asn Gln Phe Ser Leu Lys Leu Ser Ser Val Thr Pro Val Asp
225                 230                 235                 240

Thr Ala Val Tyr Tyr Cys Ala Thr Gly Tyr Tyr Tyr Gly Ser Gly Phe
                245                 250                 255

Trp Gly Gln Gly Thr Leu Val Thr Val Ser Ser
            260                 265

<210> SEQ ID NO 280
<211> LENGTH: 267
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 280

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Glu Ser Val
        35                  40                  45

Glu Tyr Phe Gly Thr Ser Leu Met His Trp Tyr Gln Gln Lys Pro Gly

```
            50                  55                  60

Gln Pro Pro Lys Leu Leu Ile Tyr Ala Ala Ser Asn Arg Glu Ser Gly
 65                  70                  75                  80

Val Pro Asp Arg Phe Ser Gly Ser Gly Ser Gly Thr Asp Phe Thr Leu
                     85                  90                  95

Thr Ile Ser Ser Val Gln Ala Glu Asp Val Ala Val Tyr Tyr Cys Gln
                100                 105                 110

Gln Thr Arg Lys Val Pro Tyr Thr Phe Gly Gln Gly Thr Lys Leu Glu
            115                 120                 125

Ile Lys Gly Gly Ser Glu Gly Lys Ser Ser Gly Ser Gly Ser Glu Ser
130                 135                 140

Lys Ser Thr Gly Gly Ser Gln Val Gln Leu Gln Glu Ser Gly Pro Gly
145                 150                 155                 160

Leu Val Lys Pro Ser Asp Thr Leu Ser Leu Thr Cys Ala Val Ser Gly
                165                 170                 175

Asn Ser Ile Thr Ser Asp Tyr Ala Trp Asn Trp Ile Arg Gln Phe Pro
                180                 185                 190

Gly Lys Gly Leu Glu Trp Ile Gly Tyr Ile Ser Tyr Ser Gly Ser Thr
            195                 200                 205

Thr Tyr Asn Pro Ser Leu Lys Ser Arg Val Thr Ile Ser Arg Asp Thr
210                 215                 220

Ser Lys Asn Gln Phe Ser Leu Lys Leu Ser Ser Val Thr Pro Val Asp
225                 230                 235                 240

Thr Ala Val Tyr Tyr Cys Ala Thr Gly Tyr Tyr Tyr Gly Ser Gly Phe
                245                 250                 255

Trp Gly Gln Gly Thr Leu Val Thr Val Ser Ser
            260                 265

<210> SEQ ID NO 281
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Met Ala Trp Val Trp Thr Leu Leu Phe Leu Met Ala Ala Ala Gln Ser
 1               5                  10                  15

Ile Gln Ala Asp Ile Val Leu Thr Gln Ser Pro Asp Ser Leu Ala Val
                20                  25                  30

Ser Leu Gly Glu Arg Ala Thr Ile Asn Cys Lys Ala Ser Glu Ser Val
            35                  40                  45

Glu Tyr Phe Gly Thr Ser Leu Met His Trp Tyr Gln Gln Lys Pro Gly
 50                  55                  60

Gln Pro Pro Lys Leu Leu Ile Tyr Ala Ala Ser Asn Arg Glu Ser Gly
 65                  70                  75                  80

Val Pro Asp Arg Phe Ser Gly Ser Gly Ser Gly Thr Asp Phe Thr Leu
                     85                  90                  95

Thr Ile Ser Ser Val Gln Ala Glu Asp Val Ala Val Tyr Tyr Cys Gln
                100                 105                 110

Gln Thr Arg Lys Val Pro Tyr Thr Phe Gly Gln Gly Thr Lys Leu Glu
            115                 120                 125

Ile Lys Gly Gly Ser Glu Gly Lys Ser Ser Gly Ser Gly Ser Glu Ser
130                 135                 140
```

```
Lys Ser Thr Gly Gly Ser Gln Val Gln Leu Gln Glu Ser Gly Pro Gly
145                 150                 155                 160

Leu Val Lys Pro Ser Asp Thr Leu Ser Leu Thr Cys Ala Val Ser Gly
                165                 170                 175

Asn Ser Ile Thr Ser Asp Tyr Ala Trp Asn Trp Ile Arg Gln Phe Pro
            180                 185                 190

Gly Lys Gly Leu Glu Trp Met Gly Tyr Ile Ser Tyr Ser Gly Ser Thr
        195                 200                 205

Thr Tyr Asn Pro Ser Leu Lys Ser Arg Val Thr Ile Ser Arg Asp Thr
    210                 215                 220

Ser Lys Asn Gln Phe Ser Leu Lys Leu Ser Ser Val Thr Pro Val Asp
225                 230                 235                 240

Thr Ala Val Tyr Tyr Cys Ala Thr Gly Tyr Tyr Tyr Gly Ser Gly Phe
                245                 250                 255

Trp Gly Gln Gly Thr Leu Val Thr Val Ser Ser
                260                 265
```

<210> SEQ ID NO 282
<211> LENGTH: 267
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 282

```
Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Glu Ser Val
        35                  40                  45

Glu Tyr Phe Gly Thr Ser Leu Met His Trp Tyr Gln Gln Lys Pro Gly
    50                  55                  60

Gln Pro Pro Lys Leu Leu Ile Tyr Ala Ala Ser Asn Arg Glu Ser Gly
65                  70                  75                  80

Val Pro Asp Arg Phe Ser Gly Ser Gly Ser Gly Thr Asp Phe Thr Leu
                85                  90                  95

Thr Ile Gln Ser Val Gln Ala Glu Asp Val Ser Val Tyr Phe Cys Gln
            100                 105                 110

Gln Thr Arg Lys Val Pro Tyr Thr Phe Gly Gln Gly Thr Lys Leu Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Gln Glu Ser Gly Pro Gly
145                 150                 155                 160

Leu Val Lys Pro Ser Asp Thr Leu Ser Leu Thr Cys Ala Val Ser Gly
                165                 170                 175

Asn Ser Ile Thr Ser Asp Tyr Ala Trp Asn Trp Ile Arg Gln Phe Pro
            180                 185                 190

Gly Lys Gly Leu Glu Trp Ile Gly Tyr Ile Ser Tyr Ser Gly Ser Thr
        195                 200                 205

Thr Tyr Asn Pro Ser Leu Lys Ser Arg Val Thr Ile Ser Arg Asp Thr
    210                 215                 220

Ser Lys Asn Gln Phe Ser Leu Lys Leu Ser Ser Val Thr Pro Val Asp
225                 230                 235                 240
```

```
Thr Ala Val Tyr Tyr Cys Ala Thr Gly Tyr Tyr Gly Ser Gly Phe
            245                 250                 255

Trp Gly Gln Gly Thr Leu Val Thr Val Ser Ser
            260                 265
```

<210> SEQ ID NO 283
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

```
Met Ala Trp Val Trp Thr Leu Leu Phe Leu Met Ala Ala Ala Gln Ser
1               5                   10                  15

Ile Gln Ala Gln Val Gln Leu Gln Glu Ser Gly Pro Gly Leu Val Lys
            20                  25                  30

Pro Ser Asp Thr Leu Ser Leu Thr Cys Ala Val Ser Gly Asn Ser Ile
        35                  40                  45

Thr Ser Asp Tyr Ala Trp Asn Trp Ile Arg Gln Pro Pro Gly Lys Gly
    50                  55                  60

Leu Glu Trp Ile Gly Tyr Ile Ser Tyr Ser Gly Ser Thr Thr Tyr Asn
65                  70                  75                  80

Pro Ser Leu Lys Ser Arg Val Thr Met Ser Arg Asp Thr Ser Lys Asn
                85                  90                  95

Gln Phe Ser Leu Lys Leu Ser Ser Val Thr Ala Val Asp Thr Ala Val
            100                 105                 110

Tyr Tyr Cys Ala Thr Gly Tyr Tyr Gly Ser Gly Phe Trp Gly Gln
        115                 120                 125

Gly Thr Leu Val Thr Val Ser Ser Gly Gly Ser Glu Gly Lys Ser Ser
    130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Glu Ser Val Glu Tyr Phe Gly Thr Ser Leu
            180                 185                 190

Met His Trp Tyr Gln Gln Lys Pro Gly Gln Pro Lys Leu Leu Ile
        195                 200                 205

Tyr Ala Ala Ser Asn Arg Glu Ser Gly Val Pro Asp Arg Phe Ser Gly
    210                 215                 220

Ser Gly Ser Gly Thr Asp Phe Thr Leu Thr Ile Ser Ser Val Gln Ala
225                 230                 235                 240

Glu Asp Val Ala Val Tyr Tyr Cys Gln Gln Thr Arg Lys Val Pro Tyr
                245                 250                 255

Thr Phe Gly Gln Gly Thr Lys Leu Glu Ile Lys
            260                 265
```

<210> SEQ ID NO 284
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

```
Met Ala Trp Val Trp Thr Leu Leu Phe Leu Met Ala Ala Gln Ser
1               5                   10                  15

Ile Gln Ala Gln Val Gln Leu Gln Glu Ser Gly Pro Gly Leu Val Lys
            20                  25                  30

Pro Ser Asp Thr Leu Ser Leu Thr Cys Ala Val Ser Gly Asn Ser Ile
            35                  40                  45

Thr Ser Asp Tyr Ala Trp Asn Trp Ile Arg Gln Pro Pro Gly Lys Gly
        50                  55                  60

Leu Glu Trp Ile Gly Tyr Ile Ser Tyr Ser Gly Ser Thr Thr Tyr Asn
65                  70                  75                  80

Pro Ser Leu Lys Ser Arg Val Thr Met Ser Arg Asp Thr Ser Lys Asn
                85                  90                  95

Gln Phe Ser Leu Lys Leu Ser Ser Val Thr Ala Val Asp Thr Ala Val
            100                 105                 110

Tyr Tyr Cys Ala Thr Gly Tyr Tyr Gly Ser Gly Phe Trp Gly Gln
            115                 120                 125

Gly Thr Leu Val Thr Val Ser Ser Gly Gly Ser Glu Gly Lys Ser Ser
        130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Glu Ser Val Glu Tyr Phe Gly Thr Ser Leu
            180                 185                 190

Met His Trp Tyr Gln Gln Lys Pro Gly Gln Pro Pro Lys Leu Leu Ile
            195                 200                 205

Tyr Ala Ala Ser Asn Arg Glu Ser Gly Val Pro Asp Arg Phe Ser Gly
210                 215                 220

Ser Gly Ser Gly Thr Asp Phe Thr Leu Thr Ile Gln Ser Val Gln Ala
225                 230                 235                 240

Glu Asp Val Ser Val Tyr Phe Cys Gln Gln Thr Arg Lys Val Pro Tyr
                245                 250                 255

Thr Phe Gly Gln Gly Thr Lys Leu Glu Ile Lys
            260                 265

<210> SEQ ID NO 285
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Met Ala Trp Val Trp Thr Leu Leu Phe Leu Met Ala Ala Gln Ser
1               5                   10                  15

Ile Gln Ala Gln Val Gln Leu Gln Glu Ser Gly Pro Gly Leu Val Lys
            20                  25                  30

Pro Ser Asp Thr Leu Ser Leu Thr Cys Ala Val Ser Gly Asn Ser Ile
            35                  40                  45

Thr Ser Asp Tyr Ala Trp Asn Trp Ile Arg Gln Pro Pro Gly Lys Gly
        50                  55                  60

Leu Glu Trp Ile Gly Tyr Ile Ser Tyr Ser Gly Ser Thr Thr Tyr Asn
65                  70                  75                  80

Pro Ser Leu Lys Ser Arg Val Thr Met Ser Arg Asp Thr Ser Lys Asn
```

```
                    85                  90                  95

Gln Phe Ser Leu Lys Leu Ser Ser Val Thr Ala Val Asp Thr Ala Val
            100                 105                 110

Tyr Tyr Cys Ala Thr Gly Tyr Tyr Gly Ser Gly Phe Trp Gly Gln
            115                 120                 125

Gly Thr Leu Val Thr Val Ser Ser Gly Gly Ser Glu Gly Lys Ser Ser
130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Lys Ala Ser Glu Ser Val Glu Tyr Phe Gly Thr Ser Leu
            180                 185                 190

Met His Trp Tyr Gln Gln Lys Pro Gly Gln Pro Pro Lys Leu Leu Ile
            195                 200                 205

Tyr Ala Ala Ser Asn Arg Glu Ser Gly Val Pro Asp Arg Phe Ser Gly
            210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Gln Gln Thr Arg Lys Val Pro Tyr
                245                 250                 255

Thr Phe Gly Gln Gly Thr Lys Leu Glu Ile Lys
            260                 265

<210> SEQ ID NO 286
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Glu Ser Val
        35                  40                  45

Glu Tyr Phe Gly Thr Ser Leu Met His Trp Tyr Gln Gln Lys Pro Gly
    50                  55                  60

Gln Pro Pro Lys Leu Leu Ile Tyr Ala Ala Ser Asn Arg Glu Ser Gly
65                  70                  75                  80

Val Pro Asp Arg Phe Ser Gly Ser Gly Ser Gly Thr Asp Phe Thr Leu
                85                  90                  95

Thr Ile Gln Ser Val Gln Ala Glu Asp Val Ser Val Tyr Phe Cys Gln
            100                 105                 110

Gln Thr Arg Lys Val Pro Tyr Thr Phe Gly Gln Gly Thr Lys Leu Glu
            115                 120                 125

Ile Lys Gly Gly Ser Glu Gly Lys Ser Ser Gly Ser Gly Ser Glu Ser
            130                 135                 140

Lys Ser Thr Gly Gly Ser Gln Val Gln Leu Gln Glu Ser Gly Pro Gly
145                 150                 155                 160

Leu Val Lys Pro Ser Asp Thr Leu Ser Leu Thr Cys Ala Val Ser Gly
                165                 170                 175
```

```
Asn Ser Ile Thr Ser Asp Tyr Ala Trp Asn Trp Ile Arg Gln Pro Pro
            180                 185                 190

Gly Lys Gly Leu Glu Trp Ile Gly Tyr Ile Ser Tyr Ser Gly Ser Thr
        195                 200                 205

Thr Tyr Asn Pro Ser Leu Lys Ser Arg Val Thr Met Ser Arg Asp Thr
    210                 215                 220

Ser Lys Asn Gln Phe Ser Leu Lys Leu Ser Ser Val Thr Ala Val Asp
225                 230                 235                 240

Thr Ala Val Tyr Tyr Cys Ala Thr Gly Tyr Tyr Tyr Gly Ser Gly Phe
                245                 250                 255

Trp Gly Gln Gly Thr Leu Val Thr Val Ser Ser
            260                 265
```

<210> SEQ ID NO 287
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

```
Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Glu Ser Val
        35                  40                  45

Glu Tyr Phe Gly Thr Ser Leu Met His Trp Tyr Gln Gln Lys Pro Gly
    50                  55                  60

Gln Pro Pro Lys Leu Leu Ile Tyr Ala Ala Ser Asn Arg Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Leu Gln Ala Glu Asp Val Ala Val Tyr Tyr Cys Gln
            100                 105                 110

Gln Thr Arg Lys Val Pro Tyr Thr Phe Gly Gln Gly Thr Lys Leu Glu
        115                 120                 125

Ile Lys Gly Gly Ser Glu Gly Lys Ser Ser Gly Ser Gly Ser Glu Ser
    130                 135                 140

Lys Ser Thr Gly Gly Ser Gln Val Gln Leu Gln Glu Ser Gly Pro Gly
145                 150                 155                 160

Leu Val Lys Pro Ser Asp Thr Leu Ser Leu Thr Cys Ala Val Ser Gly
                165                 170                 175

Asn Ser Ile Thr Ser Asp Tyr Ala Trp Asn Trp Ile Arg Gln Pro Pro
            180                 185                 190

Gly Lys Gly Leu Glu Trp Ile Gly Tyr Ile Ser Tyr Ser Gly Ser Thr
        195                 200                 205

Thr Tyr Asn Pro Ser Leu Lys Ser Arg Val Thr Met Ser Arg Asp Thr
    210                 215                 220

Ser Lys Asn Gln Phe Ser Leu Lys Leu Ser Ser Val Thr Ala Val Asp
225                 230                 235                 240

Thr Ala Val Tyr Tyr Cys Ala Thr Gly Tyr Tyr Tyr Gly Ser Gly Phe
                245                 250                 255

Trp Gly Gln Gly Thr Leu Val Thr Val Ser Ser
            260                 265
```

<210> SEQ ID NO 288
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Lys Ala Ser Glu Ser Val
        35                  40                  45

Glu Tyr Phe Gly Thr Ser Leu Met His Trp Tyr Gln Gln Lys Pro Gly
    50                  55                  60

Gln Pro Pro Lys Leu Leu Ile Tyr Ala Ala Ser Asn Arg Glu Ser Gly
65                  70                  75                  80

Val Pro Asp Arg Phe Ser Gly Ser Gly Ser Gly Thr Asp Phe Thr Leu
                85                  90                  95

Thr Ile Ser Ser Val Gln Ala Glu Asp Val Ala Val Tyr Tyr Cys Gln
            100                 105                 110

Gln Thr Arg Lys Val Pro Tyr Thr Phe Gly Gln Gly Thr Lys Leu Glu
        115                 120                 125

Ile Lys Gly Gly Ser Glu Gly Lys Ser Ser Gly Ser Gly Ser Glu Ser
130                 135                 140

Lys Ser Thr Gly Gly Ser Gln Val Gln Leu Gln Glu Ser Gly Pro Gly
145                 150                 155                 160

Leu Val Lys Pro Ser Asp Thr Leu Ser Leu Thr Cys Ala Val Ser Gly
                165                 170                 175

Asn Ser Ile Thr Ser Asp Tyr Ala Trp Asn Trp Ile Arg Gln Pro Pro
            180                 185                 190

Gly Lys Gly Leu Glu Trp Ile Gly Tyr Ile Ser Tyr Ser Gly Ser Thr
        195                 200                 205

Thr Tyr Asn Pro Ser Leu Lys Ser Arg Val Thr Met Ser Arg Asp Thr
    210                 215                 220

Ser Lys Asn Gln Phe Ser Leu Lys Leu Ser Ser Val Thr Ala Val Asp
225                 230                 235                 240

Thr Ala Val Tyr Tyr Cys Ala Thr Gly Tyr Tyr Tyr Gly Ser Gly Phe
                245                 250                 255

Trp Gly Gln Gly Thr Leu Val Thr Val Ser Ser
            260                 265

<210> SEQ ID NO 289
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Met Ala Trp Val Trp Thr Leu Leu Phe Leu Met Ala Ala Ala Gln Ser
1               5                   10                  15

Ile Gln Ala Glu Val Gln Leu Val Glu Ser Gly Gly Gly Leu Val Gln
            20                  25                  30

```
Pro Gly Gly Ser Leu Arg Leu Ser Cys Ala Ala Ser Gly Phe Thr Phe
            35                  40                  45

Ser Ser Tyr Trp Met Thr Trp Val Arg Gln Ala Pro Gly Lys Gly Leu
 50                  55                  60

Glu Trp Val Ala Asn Ile Lys Gln Asp Gly Ser Glu Arg Tyr Tyr Val
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
                100                 105                 110

Tyr Tyr Cys Ala Arg Asp Gln Asn Tyr Asp Ile Leu Thr Gly His Tyr
                115                 120                 125

Gly Met Asp Val Trp Gly Gln Gly Thr Thr Val Thr Val Ser Ser Gly
        130                 135                 140

Gly Ser Glu Gly Lys Ser Ser Gly Ser Gly Ser Glu Ser Lys Ser Thr
145                 150                 155                 160

Gly Gly Ser Glu Ile Val Leu Thr Gln Ser Pro Ser Phe Leu Ser Ala
                165                 170                 175

Ser Val Gly Asp Arg Val Thr Ile Thr Cys Arg Ala Ser Gln Gly Ile
                180                 185                 190

Ser Ser Tyr Leu Ser Trp Tyr Gln Gln Lys Pro Gly Lys Ala Pro Lys
                195                 200                 205

Leu Leu Ile Tyr Ala Thr Ser Thr Leu Gln Ser Gly Val Pro Ser Arg
        210                 215                 220

Phe Ser Gly Ser Gly Ser Gly Thr Glu Phe Thr Leu Thr Ile Ser Ser
225                 230                 235                 240

Leu Gln Pro Glu Asp Phe Ala Thr Tyr Tyr Cys Gln Gln Leu Asn Ser
                245                 250                 255

Tyr Pro Arg Thr Phe Gly Gln Gly Thr Lys Val Glu Ile Lys
                260                 265                 270

<210> SEQ ID NO 290
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Met Ala Trp Val Trp Thr Leu Leu Phe Leu Met Ala Ala Ala Gln Ser
 1               5                  10                  15

Ile Gln Ala Glu Ile Val Leu Thr Gln Ser Pro Ser Phe Leu Ser Ala
                20                  25                  30

Ser Val Gly Asp Arg Val Thr Ile Thr Cys Arg Ala Ser Gln Gly Ile
        35                  40                  45

Ser Ser Tyr Leu Ser Trp Tyr Gln Gln Lys Pro Gly Lys Ala Pro Lys
        50                  55                  60

Leu Leu Ile Tyr Ala Thr Ser Thr Leu Gln Ser Gly Val Pro Ser Arg
 65                  70                  75                  80

Phe Ser Gly Ser Gly Ser Gly Thr Glu Phe Thr Leu Thr Ile Ser Ser
                 85                  90                  95

Leu Gln Pro Glu Asp Phe Ala Thr Tyr Tyr Cys Gln Gln Leu Asn Ser
                100                 105                 110

Tyr Pro Arg Thr Phe Gly Gln Gly Thr Lys Val Glu Ile Lys Gly Gly
```

```
              115                 120                 125
Ser Glu Gly Lys Ser Gly Ser Gly Ser Glu Ser Lys Ser Thr Gly
        130                 135                 140

Gly Ser Glu Val Gln Leu Val Glu Ser Gly Gly Leu Val Gln Pro
145                 150                 155                 160

Gly Gly Ser Leu Arg Leu Ser Cys Ala Ala Ser Gly Phe Thr Phe Ser
                165                 170                 175

Ser Tyr Trp Met Thr Trp Val Arg Gln Ala Pro Gly Lys Gly Leu Glu
            180                 185                 190

Trp Val Ala Asn Ile Lys Gln Asp Gly Ser Glu Arg Tyr Tyr Val Asp
                195                 200                 205

Ser Val Lys Gly Arg Phe Thr Ile Ser Arg Asp Asn Ala Lys Asn Ser
        210                 215                 220

Leu Tyr Leu Gln Met Asn Ser Leu Arg Ala Glu Asp Thr Ala Val Tyr
225                 230                 235                 240

Tyr Cys Ala Arg Asp Gln Asn Tyr Asp Ile Leu Thr Gly His Tyr Gly
                245                 250                 255

Met Asp Val Trp Gly Gln Gly Thr Thr Val Thr Val Ser Ser
            260                 265                 270

<210> SEQ ID NO 291
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Met Ala Trp Val Trp Thr Leu Leu Phe Leu Met Ala Ala Ala Gln Ser
1               5                   10                  15

Ile Gln Ala Gln Val Gln Leu Gln Glu Ser Gly Pro Gly Leu Val Lys
                20                  25                  30

Pro Ser Gln Thr Leu Ser Leu Thr Cys Thr Val Ser Gly Asn Ser Ile
            35                  40                  45

Thr Ser Asp Tyr Ala Trp Asn Trp Ile Arg Gln Phe Pro Gly Lys Arg
        50                  55                  60

Leu Glu Trp Ile Gly Tyr Ile Ser Tyr Ser Gly Ser Thr Thr Tyr Asn
65                  70                  75                  80

Pro Ser Leu Lys Ser Arg Val Thr Ile Ser Arg Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Thr Gly Tyr Tyr Tyr Gly Ser Gly Phe Trp Gly Gln
        115                 120                 125

Gly Thr Leu Val Thr Val Ser Ser Gly Gly Ser Glu Gly Lys Ser Ser
        130                 135                 140

Gly Ser Gly Ser Glu Ser Lys Ser Thr Gly Gly Ser Glu Ile Val Leu
145                 150                 155                 160

Thr Gln Ser Pro Ala Thr Leu Ser Leu Ser Pro Gly Glu Arg Ala Thr
                165                 170                 175

Leu Ser Cys Arg Ala Ser Glu Ser Val Glu Tyr Phe Gly Thr Ser Leu
            180                 185                 190

Met His Trp Tyr Gln Gln Lys Pro Gly Gln Pro Pro Arg Leu Leu Ile
        195                 200                 205
```

```
Tyr Ala Ala Ser Asn Val Glu Ser Gly Ile Pro Ala Arg Phe Ser Gly
    210                 215                 220

Ser Gly Ser Gly Thr Asp Phe Thr Leu Thr Ile Ser Ser Val Glu Pro
225                 230                 235                 240

Glu Asp Phe Ala Val Tyr Phe Cys Gln Gln Thr Arg Lys Val Pro Tyr
                245                 250                 255

Thr Phe Gly Gly Gly Thr Lys Val Glu Ile Lys
                260                 265

<210> SEQ ID NO 292
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Met Ala Trp Val Trp Thr Leu Leu Phe Leu Met Ala Ala Ala Gln Ser
1               5                   10                  15

Ile Gln Ala Glu Ile Val Leu Thr Gln Ser Pro Ala Thr Leu Ser Leu
                20                  25                  30

Ser Pro Gly Glu Arg Ala Thr Leu Ser Cys Arg Ala Ser Glu Ser Val
            35                  40                  45

Glu Tyr Phe Gly Thr Ser Leu Met His Trp Tyr Gln Gln Lys Pro Gly
    50                  55                  60

Gln Pro Pro Arg Leu Leu Ile Tyr Ala Ala Ser Asn Val Glu Ser Gly
65                  70                  75                  80

Ile Pro Ala Arg Phe Ser Gly Ser Gly Ser Gly Thr Asp Phe Thr Leu
                85                  90                  95

Thr Ile Ser Ser Val Glu Pro Glu Asp Phe Ala Val Tyr Phe Cys Gln
                100                 105                 110

Gln Thr Arg Lys Val Pro Tyr Thr Phe Gly Gly Gly Thr Lys Val Glu
            115                 120                 125

Ile Lys Gly Gly Ser Glu Gly Lys Ser Ser Gly Ser Gly Ser Glu Ser
130                 135                 140

Lys Ser Thr Gly Gly Ser Gln Val Gln Leu Gln Glu Ser Gly Pro Gly
145                 150                 155                 160

Leu Val Lys Pro Ser Gln Thr Leu Ser Leu Thr Cys Thr Val Ser Gly
                165                 170                 175

Asn Ser Ile Thr Ser Asp Tyr Ala Trp Asn Trp Ile Arg Gln Phe Pro
            180                 185                 190

Gly Lys Arg Leu Glu Trp Ile Gly Tyr Ile Ser Tyr Ser Gly Ser Thr
    195                 200                 205

Thr Tyr Asn Pro Ser Leu Lys Ser Arg Val Thr Ile Ser Arg Asp Thr
    210                 215                 220

Ser Lys Asn Gln Phe Ser Leu Lys Leu Ser Ser Val Thr Ala Ala Asp
225                 230                 235                 240

Thr Ala Val Tyr Tyr Cys Ala Thr Gly Tyr Tyr Gly Ser Gly Phe
                245                 250                 255

Trp Gly Gln Gly Thr Leu Val Thr Val Ser Ser
                260                 265

<210> SEQ ID NO 293
<211> LENGTH: 267
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 293

Met Ala Trp Val Trp Thr Leu Leu Phe Leu Met Ala Ala Ala Gln Ser
1               5                   10                  15

Ile Gln Ala Gln Val Gln Leu Gln Glu Ser Gly Pro Gly Leu Val Lys
            20                  25                  30

Pro Ser Gln Thr Leu Ser Leu Thr Cys Thr Val Ser Gly Asn Ser Ile
        35                  40                  45

Thr Ser Asp Tyr Ala Trp Asn Trp Ile Arg Gln Phe Pro Gly Lys Gly
    50                  55                  60

Leu Glu Trp Ile Gly Tyr Ile Ser Tyr Ser Gly Ser Thr Thr Tyr Asn
65                  70                  75                  80

Pro Ser Leu Lys Ser Arg Val Thr Ile Ser Arg Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Thr Gly Tyr Tyr Gly Ser Gly Phe Trp Gly Gln
        115                 120                 125

Gly Thr Leu Val Thr Val Ser Ser Gly Gly Ser Glu Gly Lys Ser Ser
130                 135                 140

Gly Ser Gly Ser Glu Ser Lys Ser Thr Gly Gly Ser Asp Ile Val Leu
145                 150                 155                 160

Thr Gln Ser Pro Asp Ser Leu Ala Val Ser Leu Gly Glu Arg Ala Thr
                165                 170                 175

Ile Asn Cys Arg Ala Ser Glu Ser Val Glu Tyr Phe Gly Thr Ser Leu
            180                 185                 190

Met His Trp Tyr Gln Gln Lys Pro Gly Gln Pro Pro Lys Leu Leu Ile
        195                 200                 205

Tyr Ala Ala Ser Asn Val Glu Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Phe Cys Gln Gln Thr Arg Lys Val Pro Tyr
                245                 250                 255

Thr Phe Gly Gly Gly Thr Lys Val Glu Ile Lys
            260                 265

<210> SEQ ID NO 294
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Met Ala Trp Val Trp Thr Leu Leu Phe Leu Met Ala Ala Ala Gln Ser
1               5                   10                  15

Ile Gln Ala Asp Ile Val Leu Thr Gln Ser Pro Asp Ser Leu Ala Val
            20                  25                  30

Ser Leu Gly Glu Arg Ala Thr Ile Asn Cys Arg Ala Ser Glu Ser Val
        35                  40                  45

Glu Tyr Phe Gly Thr Ser Leu Met His Trp Tyr Gln Gln Lys Pro Gly
    50                  55                  60
```

-continued

```
Gln Pro Pro Lys Leu Leu Ile Tyr Ala Ala Ser Asn Val Glu Ser Gly
 65                  70                  75                  80

Val Pro Asp Arg Phe Ser Gly Ser Gly Ser Gly Thr Asp Phe Thr Leu
                 85                  90                  95

Thr Ile Ser Ser Leu Gln Ala Glu Asp Val Ala Val Tyr Phe Cys Gln
            100                 105                 110

Gln Thr Arg Lys Val Pro Tyr Thr Phe Gly Gly Gly Thr Lys Val Glu
        115                 120                 125

Ile Lys Gly Gly Ser Glu Gly Lys Ser Ser Gly Ser Gly Ser Glu Ser
130                 135                 140

Lys Ser Thr Gly Gly Ser Gln Val Gln Leu Gln Glu Ser Gly Pro Gly
145                 150                 155                 160

Leu Val Lys Pro Ser Gln Thr Leu Ser Leu Thr Cys Thr Val Ser Gly
                165                 170                 175

Asn Ser Ile Thr Ser Asp Tyr Ala Trp Asn Trp Ile Arg Gln Phe Pro
            180                 185                 190

Gly Lys Gly Leu Glu Trp Ile Gly Tyr Ile Ser Tyr Ser Gly Ser Thr
        195                 200                 205

Thr Tyr Asn Pro Ser Leu Lys Ser Arg Val Thr Ile Ser Arg Asp Thr
    210                 215                 220

Ser Lys Asn Gln Phe Ser Leu Lys Leu Ser Ser Val Thr Ala Ala Asp
225                 230                 235                 240

Thr Ala Val Tyr Tyr Cys Ala Thr Gly Tyr Tyr Gly Ser Gly Phe
                245                 250                 255

Trp Gly Gln Gly Thr Leu Val Thr Val Ser Ser
            260                 265
```

<210> SEQ ID NO 295
<211> LENGTH: 267
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 295

```
Met Ala Trp Val Trp Thr Leu Leu Phe Leu Met Ala Ala Ala Gln Ser
  1               5                  10                  15

Ile Gln Ala Gln Val Gln Leu Gln Glu Ser Gly Pro Gly Leu Val Lys
             20                  25                  30

Pro Ser Gln Thr Leu Ser Leu Thr Cys Thr Val Ser Gly Asn Ser Ile
         35                  40                  45

Thr Ser Asp Tyr Ala Trp Asn Trp Ile Arg Gln Pro Pro Gly Lys Gly
     50                  55                  60

Leu Glu Trp Ile Gly Tyr Ile Ser Tyr Ser Gly Ser Thr Thr Tyr Asn
 65                  70                  75                  80

Pro Ser Leu Lys Ser Arg Val Thr Ile Ser Arg Asp Thr Ser Lys Asn
                 85                  90                  95

Gln Phe Ser Leu Lys Leu Ser Ser Val Thr Ala Ala Asp Thr Ala Val
            100                 105                 110

Tyr Tyr Cys Ala Thr Gly Tyr Tyr Gly Ser Gly Phe Trp Gly Gln
        115                 120                 125

Gly Thr Leu Val Thr Val Ser Ser Gly Gly Ser Glu Gly Lys Ser Ser
130                 135                 140

Gly Ser Gly Ser Glu Ser Lys Ser Thr Gly Gly Ser Glu Ile Val Leu
```

```
            145                 150                 155                 160
Thr Gln Ser Pro Ala Thr Leu Ser Leu Ser Pro Gly Glu Arg Ala Thr
                165                 170                 175

Leu Ser Cys Arg Ala Ser Glu Ser Val Glu Tyr Phe Gly Thr Ser Leu
            180                 185                 190

Met His Trp Tyr Gln Gln Lys Pro Gly Gln Pro Pro Arg Leu Leu Ile
        195                 200                 205

Tyr Ala Ala Ser Asn Val Glu Ser Gly Ile Pro Ala Arg Phe Ser Gly
    210                 215                 220

Ser Gly Ser Gly Thr Asp Phe Thr Leu Thr Ile Ser Ser Val Glu Pro
225                 230                 235                 240

Glu Asp Phe Ala Val Tyr Phe Cys Gln Gln Thr Arg Lys Val Pro Tyr
                245                 250                 255

Thr Phe Gly Gly Gly Thr Lys Val Glu Ile Lys
            260                 265

<210> SEQ ID NO 296
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Met Ala Trp Val Trp Thr Leu Leu Phe Leu Met Ala Ala Ala Gln Ser
1               5                   10                  15

Ile Gln Ala Glu Ile Val Leu Thr Gln Ser Pro Ala Thr Leu Ser Leu
            20                  25                  30

Ser Pro Gly Glu Arg Ala Thr Leu Ser Cys Arg Ala Ser Glu Ser Val
        35                  40                  45

Glu Tyr Phe Gly Thr Ser Leu Met His Trp Tyr Gln Gln Lys Pro Gly
    50                  55                  60

Gln Pro Pro Arg Leu Leu Ile Tyr Ala Ala Ser Asn Val Glu Ser Gly
65                  70                  75                  80

Ile Pro Ala Arg Phe Ser Gly Ser Gly Ser Gly Thr Asp Phe Thr Leu
                85                  90                  95

Thr Ile Ser Ser Val Glu Pro Glu Asp Phe Ala Val Tyr Phe Cys Gln
            100                 105                 110

Gln Thr Arg Lys Val Pro Tyr Thr Phe Gly Gly Gly Thr Lys Val Glu
        115                 120                 125

Ile Lys Gly Gly Ser Glu Gly Lys Ser Ser Gly Ser Gly Ser Glu Ser
    130                 135                 140

Lys Ser Thr Gly Ser Gln Val Gln Leu Gln Glu Ser Gly Pro Gly
145                 150                 155                 160

Leu Val Lys Pro Ser Gln Thr Leu Ser Leu Thr Cys Thr Val Ser Gly
                165                 170                 175

Asn Ser Ile Thr Ser Asp Tyr Ala Trp Asn Trp Ile Arg Gln Pro Pro
            180                 185                 190

Gly Lys Gly Leu Glu Trp Ile Gly Tyr Ile Ser Tyr Ser Gly Ser Thr
        195                 200                 205

Thr Tyr Asn Pro Ser Leu Lys Ser Arg Val Thr Ile Ser Arg Asp Thr
    210                 215                 220

Ser Lys Asn Gln Phe Ser Leu Lys Leu Ser Ser Val Thr Ala Ala Asp
225                 230                 235                 240
```

Thr Ala Val Tyr Tyr Cys Ala Thr Gly Tyr Tyr Gly Ser Gly Phe
            245                 250                 255

Trp Gly Gln Gly Thr Leu Val Thr Val Ser Ser
            260                 265

<210> SEQ ID NO 297
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Met Ala Trp Val Trp Thr Leu Leu Phe Leu Met Ala Ala Gln Ser
1               5                   10                  15

Ile Gln Ala Gln Val Gln Leu Gln Glu Ser Gly Pro Gly Leu Val Lys
            20                  25                  30

Pro Ser Gln Thr Leu Ser Leu Thr Cys Thr Val Ser Gly Asn Ser Ile
            35                  40                  45

Thr Ser Asp Tyr Ala Trp Asn Trp Ile Arg Gln Phe Pro Gly Lys Gly
50                  55                  60

Leu Glu Trp Ile Gly Tyr Ile Ser Tyr Ser Gly Ser Thr Thr Tyr Asn
65                  70                  75                  80

Pro Ser Leu Lys Ser Arg Val Thr Ile Ser Arg Asp Thr Ser Lys Asn
            85                  90                  95

Gln Phe Ser Leu Lys Leu Ser Ser Val Thr Ala Ala Asp Thr Ala Val
            100                 105                 110

Tyr Tyr Cys Ala Thr Gly Tyr Tyr Gly Ser Gly Phe Trp Gly Gln
            115                 120                 125

Gly Thr Leu Val Thr Val Ser Ser Gly Gly Ser Glu Gly Lys Ser Ser
            130                 135                 140

Gly Ser Gly Ser Glu Ser Lys Ser Thr Gly Gly Ser Glu Ile Val Leu
145                 150                 155                 160

Thr Gln Ser Pro Ala Thr Leu Ser Leu Ser Pro Gly Glu Arg Ala Thr
            165                 170                 175

Leu Ser Cys Arg Ala Ser Glu Ser Val Glu Tyr Phe Gly Thr Ser Leu
            180                 185                 190

Met His Trp Tyr Gln Gln Lys Pro Gly Gln Pro Pro Arg Leu Leu Ile
            195                 200                 205

Tyr Ala Ala Ser Asn Val Glu Ser Gly Ile Pro Ala Arg Phe Ser Gly
            210                 215                 220

Ser Gly Ser Gly Thr Asp Phe Thr Leu Thr Ile Ser Ser Val Glu Pro
225                 230                 235                 240

Glu Asp Phe Ala Val Tyr Phe Cys Gln Gln Thr Arg Lys Val Pro Tyr
            245                 250                 255

Thr Phe Gly Gly Gly Thr Lys Val Glu Ile Lys
            260                 265

<210> SEQ ID NO 298
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

-continued

```
Met Ala Trp Val Trp Thr Leu Leu Phe Leu Met Ala Ala Ala Gln Ser
1               5                   10                  15

Ile Gln Ala Glu Ile Val Leu Thr Gln Ser Pro Ala Thr Leu Ser Leu
                20                  25                  30

Ser Pro Gly Glu Arg Ala Thr Leu Ser Cys Arg Ala Ser Glu Ser Val
            35                  40                  45

Glu Tyr Phe Gly Thr Ser Leu Met His Trp Tyr Gln Gln Lys Pro Gly
        50                  55                  60

Gln Pro Pro Arg Leu Leu Ile Tyr Ala Ala Ser Asn Val Glu Ser Gly
65                  70                  75                  80

Ile Pro Ala Arg Phe Ser Gly Ser Gly Ser Gly Thr Asp Phe Thr Leu
                85                  90                  95

Thr Ile Ser Ser Val Glu Pro Glu Asp Phe Ala Val Tyr Phe Cys Gln
            100                 105                 110

Gln Thr Arg Lys Val Pro Tyr Thr Phe Gly Gly Gly Thr Lys Val Glu
        115                 120                 125

Ile Lys Gly Gly Ser Glu Gly Lys Ser Ser Gly Ser Gly Ser Glu Ser
130                 135                 140

Lys Ser Thr Gly Gly Ser Gln Val Gln Leu Gln Glu Ser Gly Pro Gly
145                 150                 155                 160

Leu Val Lys Pro Ser Gln Thr Leu Ser Leu Thr Cys Thr Val Ser Gly
                165                 170                 175

Asn Ser Ile Thr Ser Asp Tyr Ala Trp Asn Trp Ile Arg Gln Phe Pro
            180                 185                 190

Gly Lys Gly Leu Glu Trp Ile Gly Tyr Ile Ser Tyr Ser Gly Ser Thr
        195                 200                 205

Thr Tyr Asn Pro Ser Leu Lys Ser Arg Val Thr Ile Ser Arg Asp Thr
    210                 215                 220

Ser Lys Asn Gln Phe Ser Leu Lys Leu Ser Ser Val Thr Ala Ala Asp
225                 230                 235                 240

Thr Ala Val Tyr Tyr Cys Ala Thr Gly Tyr Tyr Gly Ser Gly Phe
                245                 250                 255

Trp Gly Gln Gly Thr Leu Val Thr Val Ser Ser
        260                 265
```

<210> SEQ ID NO 299
<211> LENGTH: 271
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 299

```
Met Ala Trp Val Trp Thr Leu Leu Phe Leu Met Ala Ala Ala Gln Ser
1               5                   10                  15

Ile Gln Ala Gln Val Gln Leu Gln Glu Ser Gly Pro Gly Leu Val Lys
                20                  25                  30

Pro Ser Glu Thr Leu Ser Leu Thr Cys Thr Val Ser Gly Gly Ser Ile
            35                  40                  45

Ser Ser Tyr Tyr Trp Ser Trp Ile Arg Gln Pro Pro Gly Lys Gly Leu
        50                  55                  60

Glu Trp Ile Gly Tyr Ile Tyr Tyr Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95
```

Phe Ser Leu Lys Leu Ser Ser Val Thr Ala Ala Asp Thr Ala Val Tyr
            100                 105                 110

Tyr Cys Ala Gly Thr Thr Ile Phe Gly Val Val Thr Pro Asn Phe Tyr
        115                 120                 125

Tyr Gly Met Asp Val Trp Gly Gln Gly Thr Thr Val Thr Val Ser Ser
130                 135                 140

Gly Gly Ser Glu Gly Lys Ser Ser Gly Ser Gly Ser Glu Ser Lys Ser
145                 150                 155                 160

Thr Gly Gly Ser Asp Ile Gln Met Thr Gln Ser Pro Ser Phe Leu Ser
                165                 170                 175

Ala Ser Val Gly Asp Arg Val Thr Ile Thr Cys Arg Ala Ser Gln Gly
            180                 185                 190

Ile Ser Ser Tyr Leu Ala Trp Tyr Gln Gln Lys Pro Gly Lys Ala Pro
        195                 200                 205

Lys Phe Leu Ile Tyr Ala Ala Ser Thr Leu Gln Ser Gly Val Pro Ser
    210                 215                 220

Arg Phe Ser Gly Ser Gly Ser Gly Thr Glu Phe Thr Leu Thr Ile Ser
225                 230                 235                 240

Ser Leu Gln Pro Glu Asp Phe Ala Thr Tyr Tyr Cys Gln Gln Leu Asn
                245                 250                 255

Ser Tyr Pro Leu Thr Phe Gly Gly Gly Thr Lys Val Glu Ile Lys
            260                 265                 270

<210> SEQ ID NO 300
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Met Ala Trp Val Trp Thr Leu Leu Phe Leu Met Ala Ala Ala Gln Ser
1               5                   10                  15

Ile Gln Ala Asp Ile Gln Met Thr Gln Ser Pro Ser Phe Leu Ser Ala
            20                  25                  30

Ser Val Gly Asp Arg Val Thr Ile Thr Cys Arg Ala Ser Gln Gly Ile
        35                  40                  45

Ser Ser Tyr Leu Ala Trp Tyr Gln Gln Lys Pro Gly Lys Ala Pro Lys
    50                  55                  60

Phe Leu Ile Tyr Ala Ala Ser Thr Leu Gln Ser Gly Val Pro Ser Arg
65                  70                  75                  80

Phe Ser Gly Ser Gly Ser Gly Thr Glu Phe Thr Leu Thr Ile Ser Ser
                85                  90                  95

Leu Gln Pro Glu Asp Phe Ala Thr Tyr Tyr Cys Gln Gln Leu Asn Ser
            100                 105                 110

Tyr Pro Leu Thr Phe Gly Gly Gly Thr Lys Val Glu Ile Lys Gly Gly
        115                 120                 125

Ser Glu Gly Lys Ser Ser Gly Ser Gly Ser Glu Ser Lys Ser Thr Gly
    130                 135                 140

Gly Ser Gln Val Gln Leu Gln Glu Ser Gly Pro Gly Leu Val Lys Pro
145                 150                 155                 160

Ser Glu Thr Leu Ser Leu Thr Cys Thr Val Ser Gly Ser Ile Ser
                165                 170                 175

Ser Tyr Tyr Trp Ser Trp Ile Arg Gln Pro Pro Gly Lys Gly Leu Glu

```
                    180                 185                 190
Trp Ile Gly Tyr Ile Tyr Tyr Ser Gly Ser Thr Asn Tyr Asn Pro Ser
                195                 200                 205
Leu Lys Ser Arg Val Thr Ile Ser Val Asp Thr Ser Lys Asn Gln Phe
            210                 215                 220
Ser Leu Lys Leu Ser Ser Val Thr Ala Ala Asp Thr Ala Val Tyr Tyr
225                 230                 235                 240
Cys Ala Gly Thr Thr Ile Phe Gly Val Val Thr Pro Asn Phe Tyr Tyr
                245                 250                 255
Gly Met Asp Val Trp Gly Gln Gly Thr Thr Val Thr Val Ser Ser
                260                 265                 270

<210> SEQ ID NO 301
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Met Ala Trp Val Trp Thr Leu Leu Phe Leu Met Ala Ala Ala Gln Ser
1               5                   10                  15
Ile Gln Ala Glu Val Gln Leu Val Glu Ser Gly Gly Gly Val Val Gln
            20                  25                  30
Pro Gly Arg Ser Leu Arg Leu Ser Cys Val Ala Ser Gly Phe Thr Phe
        35                  40                  45
Ser Ser Tyr Asp Ile His Trp Val Arg Gln Ala Pro Gly Lys Gly Leu
    50                  55                  60
Glu Trp Val Ala Ile Ile Ser Tyr Asp Gly Ser Lys Lys Asp Tyr Thr
65                  70                  75                  80
Asp Ser Val Lys Gly Arg Phe Thr Ile Ser Arg Asp Asn Ser Lys Asn
                85                  90                  95
Thr Leu Tyr Leu Gln Met Asp Ser Leu Arg Val Glu Asp Ser Ala Val
            100                 105                 110
Tyr Ser Cys Ala Arg Glu Ser Gly Trp Ser His Tyr Tyr Tyr Tyr Gly
        115                 120                 125
Met Asp Val Trp Gly Gln Gly Thr Met Val Thr Val Ser Ser Gly Gly
    130                 135                 140
Ser Glu Gly Lys Ser Ser Gly Ser Gly Ser Glu Ser Lys Ser Thr Gly
145                 150                 155                 160
Gly Ser Asp Ile Val Met Thr Gln Ser Pro Ser Ser Leu Ser Ala Ser
                165                 170                 175
Val Gly Asp Arg Val Thr Ile Thr Cys Arg Ala Ser Gln Asp Ile Ser
            180                 185                 190
Asn Tyr Leu Ala Trp Tyr Gln Gln Lys Pro Gly Lys Val Pro Lys Phe
        195                 200                 205
Leu Ile Tyr Ala Ala Ser Thr Leu His Ser Gly Val Pro Ser Arg Phe
    210                 215                 220
Ser Gly Ser Gly Ser Gly Thr Asp Phe Thr Leu Thr Ile Ser Ser Leu
225                 230                 235                 240
Gln Pro Glu Asp Val Ala Thr Tyr Tyr Cys Gln Lys Tyr Asn Ser Ala
                245                 250                 255
Pro Tyr Thr Phe Gly Gln Gly Thr Arg Leu Glu Ile Lys
            260                 265
```

<210> SEQ ID NO 302
<211> LENGTH: 269
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 302

Met Ala Trp Val Trp Thr Leu Leu Phe Leu Met Ala Ala Gln Ser
1               5                   10                  15

Ile Gln Ala Asp Ile Val Met Thr Gln Ser Pro Ser Ser Leu Ser Ala
            20                  25                  30

Ser Val Gly Asp Arg Val Thr Ile Thr Cys Arg Ala Ser Gln Asp Ile
        35                  40                  45

Ser Asn Tyr Leu Ala Trp Tyr Gln Gln Lys Pro Gly Lys Val Pro Lys
    50                  55                  60

Phe Leu Ile Tyr Ala Ala Ser Thr Leu His Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Val Ala Thr Tyr Tyr Cys Gln Lys Tyr Asn Ser
            100                 105                 110

Ala Pro Tyr Thr Phe Gly Gln Gly Thr Arg Leu Glu Ile Lys Gly Gly
        115                 120                 125

Ser Glu Gly Lys Ser Ser Gly Ser Gly Ser Glu Ser Lys Ser Thr Gly
    130                 135                 140

Gly Ser Glu Val Gln Leu Val Glu Ser Gly Gly Val Val Gln Pro
145                 150                 155                 160

Gly Arg Ser Leu Arg Leu Ser Cys Val Ala Ser Gly Phe Thr Phe Ser
                165                 170                 175

Ser Tyr Asp Ile His Trp Val Arg Gln Ala Pro Gly Lys Gly Leu Glu
            180                 185                 190

Trp Val Ala Ile Ile Ser Tyr Asp Gly Ser Lys Lys Asp Tyr Thr Asp
        195                 200                 205

Ser Val Lys Gly Arg Phe Thr Ile Ser Arg Asp Asn Ser Lys Asn Thr
    210                 215                 220

Leu Tyr Leu Gln Met Asp Ser Leu Arg Val Glu Asp Ser Ala Val Tyr
225                 230                 235                 240

Ser Cys Ala Arg Glu Ser Gly Trp Ser His Tyr Tyr Tyr Gly Met
                245                 250                 255

Asp Val Trp Gly Gln Gly Thr Met Val Thr Val Ser Ser
            260                 265

<210> SEQ ID NO 303
<211> LENGTH: 264
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 303

Met Ala Trp Val Trp Thr Leu Leu Phe Leu Met Ala Ala Gln Ser
1               5                   10                  15

Ile Gln Ala Gln Val Gln Leu Gln Glu Ser Gly Pro Gly Leu Val Lys
            20                  25                  30

Pro Ser Glu Thr Leu Ser Leu Thr Cys Thr Val Ser Gly Ser Ile
            35                  40                  45

Ser Ser Tyr Tyr Trp Ser Trp Leu Arg Gln Pro Ala Gly Ser Gly Leu
 50                  55                  60

Glu Trp Ile Gly Arg Leu Tyr Val Ser Gly Phe Thr Asn Tyr Asn Pro
 65                  70                  75                  80

Ser Leu Lys Ser Arg Val Thr Leu Ser Leu Asp Pro Ser Arg Asn Gln
            85                  90                  95

Leu Ser Leu Lys Leu Ser Ser Val Thr Ala Ala Asp Thr Ala Val Tyr
            100                 105                 110

Tyr Cys Ala Gly Asp Ser Gly Asn Tyr Trp Gly Trp Phe Asp Pro Trp
            115                 120                 125

Gly Gln Gly Thr Leu Val Thr Val Ser Ser Gly Gly Ser Glu Gly Lys
 130                 135                 140

Ser Ser Gly Ser Gly Ser Glu Ser Lys Ser Thr Gly Gly Ser Ser Tyr
 145                 150                 155                 160

Glu Leu Thr Gln Pro Pro Ser Val Ser Val Ser Pro Gly Glu Thr Ala
            165                 170                 175

Ser Ile Thr Cys Ser Gly Asp Gln Leu Gly Glu Asn Tyr Ala Cys Trp
            180                 185                 190

Tyr Gln Gln Lys Pro Gly Gln Ser Pro Val Leu Val Ile Tyr Gln Asp
            195                 200                 205

Ser Lys Arg Pro Ser Gly Ile Pro Glu Arg Phe Ser Gly Ser Asn Ser
            210                 215                 220

Gly Asn Thr Ala Thr Leu Thr Ile Ser Gly Thr Gln Ala Leu Asp Glu
225                 230                 235                 240

Ala Asp Tyr Tyr Cys Gln Ala Trp Asp Asn Ser Ile Val Val Phe Gly
            245                 250                 255

Gly Gly Thr Lys Leu Thr Val Leu
            260

<210> SEQ ID NO 304
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Met Ala Trp Val Trp Thr Leu Leu Phe Leu Met Ala Ala Ala Gln Ser
 1               5                  10                  15

Ile Gln Ala Ser Tyr Glu Leu Thr Gln Pro Pro Ser Val Ser Val Ser
            20                  25                  30

Pro Gly Glu Thr Ala Ser Ile Thr Cys Ser Gly Asp Gln Leu Gly Glu
            35                  40                  45

Asn Tyr Ala Cys Trp Tyr Gln Gln Lys Pro Gly Gln Ser Pro Val Leu
 50                  55                  60

Val Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
            85                  90                  95

Gln Ala Leu Asp Glu Ala Asp Tyr Tyr Cys Gln Ala Trp Asp Asn Ser
            100                 105                 110

Ile Val Val Phe Gly Gly Gly Thr Lys Leu Thr Val Leu Gly Gly Ser
            115                 120                 125

```
Glu Gly Lys Ser Ser Gly Ser Gly Ser Glu Ser Lys Ser Thr Gly Gly
            130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Gly Ser Ile Ser Ser
                165                 170                 175

Tyr Tyr Trp Ser Trp Leu Arg Gln Pro Ala Gly Ser Gly Leu Glu Trp
            180                 185                 190

Ile Gly Arg Leu Tyr Val Ser Gly Phe Thr Asn Tyr Asn Pro Ser Leu
            195                 200                 205

Lys Ser Arg Val Thr Leu Ser Leu Asp Pro Ser Arg Asn Gln Leu Ser
            210                 215                 220

Leu Lys Leu Ser Ser Val Thr Ala Ala Asp Thr Ala Val Tyr Tyr Cys
225                 230                 235                 240

Ala Gly Asp Ser Gly Asn Tyr Trp Gly Trp Phe Asp Pro Trp Gly Gln
                245                 250                 255

Gly Thr Leu Val Thr Val Ser Ser
            260

<210> SEQ ID NO 305
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Met Ala Trp Val Trp Thr Leu Leu Phe Leu Met Ala Ala Ala Gln Ser
1               5                   10                  15

Ile Gln Ala Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Tyr Tyr Gly Met His Trp Val Arg Gln Ala Pro Gly Lys Gly Leu
    50                  55                  60

Glu Trp Val Ala Phe Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala His Leu Pro Tyr Ser Gly Ser Tyr Trp Ala Phe Asp
        115                 120                 125

Tyr Trp Gly Gln Gly Thr Gln Val Thr Val Ser Ser Gly Gly Ser Glu
130                 135                 140

Gly Lys Ser Ser Gly Ser Gly Ser Glu Ser Lys Ser Thr Gly Gly Ser
145                 150                 155                 160

Gln Ser Val Leu Thr Gln Pro Pro Ser Val Ser Val Ala Pro Gly Gln
                165                 170                 175

Thr Ala Ser Ile Thr Cys Gly Gly Asp Asn Ile Gly Ser Lys Ser Val
            180                 185                 190

His Trp Tyr Gln Gln Lys Pro Gly Gln Ala Pro Val Leu Val Val Tyr
        195                 200                 205

Asp Asn Ser Asp Arg Pro Ser Gly Ile Pro Glu Arg Phe Ser Gly Ser
```

210                 215                 220
Asn Ser Gly Thr Thr Ala Thr Leu Thr Ile Ser Arg Val Glu Ala Gly
225                 230                 235                 240

Asp Glu Ala Asp Tyr Tyr Cys Gln Val Trp Asp Ser Ser Asp His
                245                 250                 255

Pro Val Val Phe Gly Gly Gly Thr Lys Val Thr Val
                260                 265

<210> SEQ ID NO 306
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Met Ala Trp Val Trp Thr Leu Leu Phe Leu Met Ala Ala Ala Gln Ser
1               5                   10                  15

Ile Gln Ala Gln Ser Val Leu Thr Gln Pro Ser Val Ser Val Ala
            20                  25                  30

Pro Gly Gln Thr Ala Ser Ile Thr Cys Gly Gly Asp Asn Ile Gly Ser
        35                  40                  45

Lys Ser Val His Trp Tyr Gln Gln Lys Pro Gly Gln Ala Pro Val Leu
    50                  55                  60

Val Val Tyr Asp Asn Ser Asp Arg Pro Ser Gly Ile Pro Glu Arg Phe
65              70                  75                  80

Ser Gly Ser Asn Ser Gly Thr Thr Ala Thr Leu Thr Ile Ser Arg Val
                85                  90                  95

Glu Ala Gly Asp Glu Ala Asp Tyr Tyr Cys Gln Val Trp Asp Ser Ser
            100                 105                 110

Ser Asp His Pro Val Val Phe Gly Gly Gly Thr Lys Val Thr Val Gly
        115                 120                 125

Gly Ser Glu Gly Lys Ser Ser Gly Ser Gly Ser Glu Ser Lys Ser Thr
    130                 135                 140

Gly Gly Ser Gln Val Gln Leu Val Glu Ser Gly Gly Val Val Gln
145                 150                 155                 160

Pro Gly Arg Ser Leu Arg Leu Ser Cys Ala Ala Ser Gly Phe Thr Phe
                165                 170                 175

Ser Tyr Tyr Gly Met His Trp Val Arg Gln Ala Pro Gly Lys Gly Leu
            180                 185                 190

Glu Trp Val Ala Phe Ile Ser Tyr Asp Gly Ser Asn Lys Tyr Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala His Leu Pro Tyr Ser Gly Ser Tyr Trp Ala Phe Asp
                245                 250                 255

Tyr Trp Gly Gln Gly Thr Gln Val Thr Val Ser Ser
            260                 265

<210> SEQ ID NO 307
<211> LENGTH: 272
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 307

Met Ala Trp Val Trp Thr Leu Leu Phe Leu Met Ala Ala Gln Ser
1               5                   10                  15

Ile Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser His Tyr Ala Met Ser Trp Val Arg Gln Ala Pro Gly Lys Gly Leu
    50                  55                  60

Glu Trp Val Ser Thr Ile Gly Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Pro His Ile Val Met Val Thr Ala Leu Leu Tyr
        115                 120                 125

Asp Gly Met Asp Val Trp Gly Gln Gly Thr Met Val Thr Val Ser Ser
    130                 135                 140

Gly Gly Ser Glu Gly Lys Ser Ser Gly Ser Gly Ser Glu Ser Lys Ser
145                 150                 155                 160

Thr Gly Gly Ser Ser Glu Leu Thr Gln Pro Pro Ser Val Ser Val
                165                 170                 175

Ala Pro Gly Gln Thr Ala Arg Ile Thr Cys Gly Gly Asn Asn Ile Gly
            180                 185                 190

Ser Lys Ser Val His Trp Tyr Gln Gln Lys Pro Gly Gln Ala Pro Val
        195                 200                 205

Leu Val Val Tyr Asp Asp Ser Asp Arg Pro Ser Gly Ile Pro Glu Arg
    210                 215                 220

Phe Ser Gly Ser Asn Ser Gly Asn Thr Ala Thr Leu Thr Ile Ser Arg
225                 230                 235                 240

Val Glu Ala Gly Asp Glu Ala Asp Tyr Tyr Cys Gln Val Trp Asp Ser
                245                 250                 255

Ser Ser Asp His Val Val Phe Gly Gly Gly Thr Lys Leu Thr Val Leu
            260                 265                 270

<210> SEQ ID NO 308
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Met Ala Trp Val Trp Thr Leu Leu Phe Leu Met Ala Ala Gln Ser
1               5                   10                  15

Ile Gln Ala Ser Ser Glu Leu Thr Gln Pro Pro Ser Val Ser Val Ala
            20                  25                  30

Pro Gly Gln Thr Ala Arg Ile Thr Cys Gly Gly Asn Asn Ile Gly Ser
        35                  40                  45

Lys Ser Val His Trp Tyr Gln Gln Lys Pro Gly Gln Ala Pro Val Leu
    50                  55                  60

-continued

```
Val Val Tyr Asp Asp Ser Asp Arg Pro Ser Gly Ile Pro Glu Arg Phe
 65                  70                  75                  80

Ser Gly Ser Asn Ser Gly Asn Thr Ala Thr Leu Thr Ile Ser Arg Val
                 85                  90                  95

Glu Ala Gly Asp Glu Ala Asp Tyr Tyr Cys Gln Val Trp Asp Ser Ser
            100                 105                 110

Ser Asp His Val Val Phe Gly Gly Gly Thr Lys Leu Thr Val Leu Gly
        115                 120                 125

Gly Ser Glu Gly Lys Ser Ser Gly Ser Gly Ser Glu Ser Lys Ser Thr
130                 135                 140

Gly Gly Ser Gln Val Gln Leu Val Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser His Tyr Ala Met Ser Trp Val Arg Gln Ala Pro Gly Lys Gly Leu
            180                 185                 190

Glu Trp Val Ser Thr Ile Gly Gly Ser Gly Gly Ser Thr Tyr Tyr Ala
        195                 200                 205

Asp Ser Val Lys Gly Arg Phe Thr Ile Ser Arg Asp Asn Ser Lys Asn
210                 215                 220

Thr Leu Tyr Leu Gln Met Asn Ser Leu Arg Ala Glu Asp Thr Ala Val
225                 230                 235                 240

Tyr Tyr Cys Ala Lys Pro His Ile Val Met Val Thr Ala Leu Leu Tyr
                245                 250                 255

Asp Gly Met Asp Val Trp Gly Gln Gly Thr Met Val Thr Val Ser Ser
            260                 265                 270

<210> SEQ ID NO 309
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gly Phe Thr Phe Ser Ser Tyr Trp Met Thr
1               5                   10

<210> SEQ ID NO 310
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Asn Ile Lys Gln Asp Gly Ser Glu Arg Tyr
1               5                   10

<210> SEQ ID NO 311
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Asp Gln Asn Tyr Asp Ile Leu Thr Gly His Tyr Gly Met Asp Val
```

```
<210> SEQ ID NO 312
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Arg Ala Ser Gln Gly Ile Ser Ser Tyr Leu Ser
1               5                   10

<210> SEQ ID NO 313
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Ala Thr Ser Thr Leu Gln Ser
1               5

<210> SEQ ID NO 314
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ser Tyr Trp Met Thr
1               5

<210> SEQ ID NO 315
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Asn Ile Lys Gln Asp Gly Ser Glu Arg Tyr Tyr Val Asp Ser Val Lys
1               5                   10                  15

Gly

<210> SEQ ID NO 316
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Tyr Ile Ser Tyr Ser Gly Ser Thr Thr Tyr Ser Pro Ser Leu Lys Ser
1               5                   10                  15

<210> SEQ ID NO 317
<211> LENGTH: 117
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 317

Asp Val Gln Leu Gln Glu Ser Gly Pro Gly Leu Val Lys Pro Ser Gln
1               5                   10                  15

Ser Leu Ser Leu Thr Cys Thr Val Thr Gly Asn Ser Ile Thr Ser Asp
            20                  25                  30

Tyr Ala Trp Asn Trp Ile Arg Gln Phe Pro Gly Asn Arg Leu Glu Trp
        35                  40                  45

Met Gly Tyr Ile Ser Tyr Ser Gly Ser Thr Thr Tyr Ser Pro Ser Leu
50                  55                  60

Lys Ser Arg Phe Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Phe Cys
                85                  90                  95

Ala Thr Gly Tyr Tyr Tyr Gly Ser Gly Phe Trp Gly Gln Gly Thr Leu
            100                 105                 110

Val Thr Val Ser Ser
        115

<210> SEQ ID NO 318
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Phe
            20                  25                  30

Gly Thr Ser Leu Met His Trp Tyr Arg Gln Lys Pro Gly Gln Pro Pro
        35                  40                  45

Lys Leu Leu Ile Tyr Ala Ala Ser Asn Val Glu Ser Gly Val Pro Ala
50                  55                  60

Arg Phe Ser Gly Ser Gly Ser Gly Thr Asp Phe Ser Leu Asn Ile Gln
65                  70                  75                  80

Pro Val Glu Glu Asp Asp Phe Ser Met Tyr Phe Cys Gln Gln Thr Arg
                85                  90                  95

Lys Val Pro Tyr Thr Phe Gly Gly Gly Thr Lys Leu Glu Ile Lys
            100                 105                 110

<210> SEQ ID NO 319
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Val Pro Leu Ile Glu Gly Arg Ile Val Gly Gly Trp Glu Cys Glu Lys
1               5                   10                  15

His Ser Gln Pro Trp Gln Val Ala Val Tyr Ser His Gly Trp Ala His
            20                  25                  30
```

```
Cys Gly Gly Val Leu Val His Pro Gln Trp Val Leu Thr Ala Ala His
         35                  40                  45

Cys Leu Lys Lys Asn Ser Gln Val Trp Leu Gly Arg His Asn Leu Phe
 50                  55                  60

Glu Pro Glu Asp Thr Gly Gln Arg Val Pro Val Ser His Ser Phe Pro
 65                  70                  75                  80

His Pro Leu Tyr Asn Met Ser Leu Leu Lys His Gln Ser Leu Arg Pro
                 85                  90                  95

Asp Glu Asp Ser Ser His Asp Leu Met Leu Leu Arg Leu Ser Glu Pro
            100                 105                 110

Ala Lys Ile Thr Asp Val Val Lys Val Leu Gly Leu Pro Thr Gln Glu
        115                 120                 125

Pro Ala Leu Gly Thr Thr Cys Tyr Ala Ser Gly Trp Gly Ser Ile Glu
    130                 135                 140

Pro Glu Glu Phe Leu Arg Pro Arg Ser Leu Gln Cys Val Ser Leu His
145                 150                 155                 160

Tyr Ser Glu Lys Val Thr Glu Phe Met Leu Cys Ala Gly Leu Trp Thr
                165                 170                 175

Gly Gly Lys Asp Thr Cys Gly Gly Asp Ser Gly Gly Pro Leu Val Cys
            180                 185                 190

Asn Gly Val Leu Gln Gly Ile Thr Ser Trp Gly Pro Glu Pro Cys Ala
        195                 200                 205

Leu Pro Glu Lys Pro Ala Val Tyr Thr Lys Val Val His Tyr Arg Lys
    210                 215                 220

Trp Ile Lys Asp Thr Ile Ala Ala Asn Pro His His His His His His
225                 230                 235                 240

<210> SEQ ID NO 320
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 320
gatgtgcagc ttcaggagtc tggacccgga cttgttaaac caagtcagtc tctgtccctg      60
acctgtaccg tcaccggcaa cagcatcaca agcgattacg catggaactg gatcaggcag     120
ttccctggaa atcgactcga atggatgggc tacatttcat actccggttc aaccacttac     180
tctccatcct tgaaatctag gttcagcatc acccgtgata cctcaaagaa ccaattttt     240 ctgcaactga atagcgtaac tccagaggac acagccacat atttctgcgc cactgggtat     300
tactatggct caggtttctg gggtcagggc actctcgtca ccgtcagcag c               351

<210> SEQ ID NO 321
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 321
caggtccaac tgcaagagag cggaccgggc ctggtaaagc catccgacac attgtccctg      60
acgtgtgcgg taagtggaaa ctctatcact agcgactatg cgtggaattg gataagacaa     120
ccgccgggca aggggctgga atggatagga tatatcagct attccggttc tacgacatac     180
```

```
aatccttccc tgaaaagcag agtcactatg tcacgcgaca cgtccaagaa tcagttctca    240
ttgaaattgt catccgtaac ggccgttgac actgcggttt attattgcgc aaccggatat    300
tactacggct ctggtttttg gggacaggga acacttgtta ctgttagttc a             351
```

<210> SEQ ID NO 322
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 322

```
caggtgcagc tgcaggagag cggcccaggc ctggtgaagc caagcgacac cctgagcctg     60
acctgcgccg tgagcggcaa cagcatcacc agcgactacg cctggaactg gatccgccag    120
ttcccaggca agggcctgga gtggatcggc tacatcagct acagcggcag caccacctac    180
aacccaagcc tgaagagccg cgtcaccatc agccgcgaca ccagcaagaa ccagttcagc    240
ctgaagctga gcagcgtgac ccctgtggac accgccgtgt actactgcgc caccggctac    300
tactacggca gcggcttctg gggccagggc accctggtga ccgtgagcag c             351
```

<210> SEQ ID NO 323
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 323

```
caggtgcagc tgcaggagag cggcccaggc ctggtgaagc caagcgacac cctgagcctg     60
acctgcgccg tgagcggcaa cagcatcacc agcgactacg cctggaactg gatccgccag    120
ttcccaggca agggcctgga gtggatgggc tacatcagct acagcggcag caccacctac    180
aacccaagcc tgaagagccg cgtcaccatc agccgcgaca ccagcaagaa ccagttcagc    240
ctgaagctga gcagcgtgac ccctgtggac accgccgtgt actactgcgc caccggctac    300
tactacggca gcggcttctg gggccagggc accctggtga ccgtgagcag c             351
```

<210> SEQ ID NO 324
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 324

```
caggttcagc tgcaagagtc tggaccaggc ctggtcaagc cctctcagac cctgtctctg     60
acctgtaccg tgtccggcaa ctccatcacc tctgactacg cctggaactg gattcggcag    120
ttccctggca agcgccttga gtggatcggc tacatctcct actccggttc caccacctac    180
aaccccagcc tgaagtcccg ggtcaccatc tcccgcgaca cctccaagaa ccagttctcc    240
ctgaagctgt cctccgtgac cgctgctgat accgccgtgt actactgtgc caccggctac    300
tactacggct ccggcttttg gggacagggc acactggtta ccgtgtctag t             351
```

<210> SEQ ID NO 325
<211> LENGTH: 372
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 325

```
gaggtgcaac ttgtggagag cggcggaggt ctggtccaac ccggaggaag tctccgtctc    60
tcctgtgctg ctagtggctt cactttcagc tcatattgga tgacatgggt gagacaagcc   120
ccaggaaagg ggctcgagtg ggtagctaac attaaacagg acggctccga acggtactat   180
gttgattctg tgaagggacg gttcactata tccagggata atgcaaaaaa ttcactctat   240
cttcaaatga actcactcag agcagaggac actgccgtgt attattgcgc cagggatcaa   300
aattatgaca tactgaccgg tcattatgga atggatgttt ggggccaggg aacaaccgtt   360
accgtctcaa gt                                                       372
```

<210> SEQ ID NO 326
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 326

```
gacattgtgc tgacacagag tccagcatcc ttggcagtat ctttggggca gcgggcaaca    60
atttcatgcc gtgcatctga aagtgtggag tattttggaa cttctcttat gcactggtat   120
cgccagaagc ctgggcagcc tcccaaactc cttatatatg ccgcttccaa cgtggagtcc   180
ggagtaccag cacgcttttc cggctctggg tccggcacag acttttccct caatatccaa   240
cctgttgaag aagacgattt ttccatgtat ttttgccaac agacacgcaa ggttccatat   300
acattcggcg gcggcactaa acttgagatc aaa                                333
```

<210> SEQ ID NO 327
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 327

```
gacatagtct tgactcagag cccggattcc cttgctgtgt ctctgggaga acgagctacg    60
atcaactgca aggcaagtga atccgtagaa tacttcggga catcattgat gcattggtat   120
caacagaaac cggggcaacc gcccaaattg ctgatatatg cggctagtaa tagagaatca   180
ggagtaccgg ataggtttag tggttcagga tcaggtacag atttcaccct gacaataagt   240
agcttgcaag ccgaagacgt agcagtgtat tactgccaac aaacccgaaa ggtgccatat   300
acgtttggac agggtacaaa gttggaaatc aaa                                333
```

<210> SEQ ID NO 328
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 328

```
gacatcgtgc tgacccagag cccagacagc ctggccgtga gcctgggcga gcgcgccacc    60
```

```
atcaactgca aggccagcga gagcgtggag tacttcggca ccagcctgat gcactggtac    120
cagcagaagc caggccagcc accaaagctg ctgatctacg ctgccagcaa ccgcgagagc    180
ggcgtgccag accgcttcag cggcagcggc agcggcaccg acttcaccct gaccatccag    240
agcgtgcagg ccgaggacgt ctccgtgtac ttctgccagc agacccgcaa ggtgccatac    300
accttcggcc agggcaccaa gctggagatc aag                                333
```

<210> SEQ ID NO 329
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 329

```
gacatcgtgc tgacccagag cccagacagc ctggccgtga gcctgggcga gcgcgccacc    60
atcaactgca aggccagcga gagcgtggag tacttcggca ccagcctgat gcactggtac    120
cagcagaagc caggccagcc accaaagctg ctgatctacg ctgccagcaa ccgcgagagc    180
ggcgtgccag accgcttcag cggcagcggc agcggcaccg acttcaccct gaccatcagc    240
agcgtgcagg ccgaggacgt cgccgtgtac tactgccagc agacccgcaa ggtgccatac    300
accttcggcc agggcaccaa gctggagatc aag                                333
```

<210> SEQ ID NO 330
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 330

```
gagatcgtgc tgacccagtc tcctgccaca ctgtcactgt ctccaggcga gagagccacc    60
ctctcttgta gagcctccga gtccgtggaa tacttcggca cctctctgat gcactggtac    120
cagcagaagc ccggccagcc tcctagactg ctgatctacg ccgcctccaa cgtcgaatct    180
ggcatccccg ctagattctc cggctctggc tctggcacag actttaccct gaccatctcc    240
tccgtggaac ccgaggattt cgctgtgtac ttttgccagc agacccggaa ggtgccctac    300
acatttggcg gcggaacaaa ggtggaaatc aag                                333
```

<210> SEQ ID NO 331
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 331

```
gaaatcgtac tgacccagtc cccttctttc ttgagtgcat cagttgggga tagagtgacc    60
attacttgta gagcatctca aggtatttct tcatacttgt cttggtatca acaaaaacct    120
ggcaaggcac ccaaactctt gatctacgcc acctctacat tgcaaagtgg ggttccttct    180
aggttttcag gctccggctc tggtaccgag ttcaccctca ctataagcag tctccaacct    240
gaagatttcg ctacttatta ttgtcagcag cttaattctt atccccgaac ctttggtcaa    300
ggaactaagg tcgagatcaa a                                             321
```

<210> SEQ ID NO 332
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Asn Ser Ile Thr Ser Asp
            20                  25                  30

Tyr Ala Trp Asn Trp Ile Arg Gln Phe Pro Gly Asn Arg Leu Glu Trp
        35                  40                  45

Met Gly Tyr Ile Ser Tyr Ser Gly Ser Thr Thr Tyr Ser Pro Ser Leu
    50                  55                  60

Lys Ser Arg Phe Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Phe Cys
                85                  90                  95

Ala Thr Gly Tyr Tyr Tyr Gly Ser Gly Phe Trp Gly Gln Gly Thr Leu
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
```

```
            355                 360                 365
Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                    405                 410                 415

Trp Val Glu Arg Asn Ser Tyr Ser Cys Ser Val Val His Glu Gly Leu
                420                 425                 430

His Asn His His Thr Thr Lys Ser Phe Ser Arg Thr Pro Gly Lys
            435                 440                 445

<210> SEQ ID NO 333
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Phe
            20                  25                  30

Gly Thr Ser Leu Met His Trp Tyr Arg Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile Gln
65                  70                  75                  80

Pro Val Glu Glu Asp Asp Phe Ser Met Tyr Phe Cys Gln Gln Thr Arg
                85                  90                  95

Lys Val Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 334
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 334

```
Gln Val Gln Leu Gln Glu Ser Gly Pro Gly Leu Val Lys Pro Ser Asp
1               5                   10                  15
Thr Leu Ser Leu Thr Cys Ala Val Ser Gly Asn Ser Ile Thr Ser Asp
            20                  25                  30
Tyr Ala Trp Asn Trp Ile Arg Gln Pro Pro Gly Lys Gly Leu Glu Trp
        35                  40                  45
Ile Gly Tyr Ile Ser Tyr Ser Gly Ser Thr Thr Tyr Asn Pro Ser Leu
    50                  55                  60
Lys Ser Arg Val Thr Met Ser Arg Asp Thr Ser Lys Asn Gln Phe Ser
65                  70                  75                  80
Leu Lys Leu Ser Ser Val Thr Ala Val Asp Thr Ala Val Tyr Tyr Cys
                85                  90                  95
Ala Thr Gly Tyr Tyr Gly Ser Gly Phe Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Lys Thr His
210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
            290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
```

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 335
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 336
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 336
gatgtgcagc ttcaggagtc tggacccgga cttgttaaac caagtcagtc tctgtccctg      60
acctgtaccg tcaccggcaa cagcatcaca agcgattacg catggaactg gatcaggcag     120
ttccctggaa atcgactcga atggatgggc tacatttcat actccggttc aaccacttac     180
tctccatcct tgaaatctag gttcagcatc accegtgata cctcaaagaa ccaattttt      240

| | |
|---|---|
| ctgcaactga atagcgtaac tccagaggac acagccacat atttctgcgc cactgggtat | 300 |
| tactatggct caggtttctg ggtcagggc actctcgtca ccgtcagcag cgccaaaaca | 360 |
| acagcaccaa gtgtctatcc actggcccct gtgtgtggag atacaactgg ctcctcggtg | 420 |
| actctaggat gcctggtcaa gggttatttc cctgagccag tgaccttgac ctggaactct | 480 |
| ggatccctgt ccagtggtgt gcacaccttc ccagctgtcc tgcagtctga cctctacacc | 540 |
| ctcagcagct cagtgactgt aacctcgagc acctggccca gccagtccat cacctgcaat | 600 |
| gtggcccacc cggcaagcag caccaaggtg gacaagaaaa ttgagcccag agggcccaca | 660 |
| atcaagccct gtcctccatg caaatgccca gcacctaacc tcttgggtgg accatccgtc | 720 |
| ttcatcttcc ctccaaagat caaggatgta ctcatgatct ccctgagccc catagtcaca | 780 |
| tgtgtggtgg tggatgtgag cgaggatgac ccagatgtcc agatcagctg gtttgtgaac | 840 |
| aacgtggaag tacacacagc tcagacacaa acccatagag aggattacaa cagtactctc | 900 |
| cgggtggtca gtgccctccc catccagcac caggactgga tgagtggcaa ggagttcaaa | 960 |
| tgcaaggtca caacaaaga cctcccagcg cccatcgaga gaaccatctc aaaacccaaa | 1020 |
| gggtcagtaa gagctccaca ggtatatgtc ttgcctccac cagaagaaga gatgactaag | 1080 |
| aaacaggtca ctctgacctg catggtcacc gacttcatgc ctgaagacat ttacgtggag | 1140 |
| tggaccaaca cgggaaaac agagctaaac tacaagaaca ctgaaccagt cctggactct | 1200 |
| gatggttctt acttcatgta cagcaagctg agagtgaaa agaagaactg ggtggaaaga | 1260 |
| aatagctact cctgttcagt ggtccacgag ggtctgcaca atcaccacac gactaagagc | 1320 |
| ttctcccgga ctccgggtaa a | 1341 |

<210> SEQ ID NO 337
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 337

| | |
|---|---|
| gacattgtgc tgacacagag tccagcatcc ttggcagtat ctttgggca gcgggcaaca | 60 |
| atttcatgcc gtgcatctga aagtgtggag tatttggaa cttctcttat gcactggtat | 120 |
| cgccagaagc ctgggcagcc tcccaaactc cttatatatg ccgcttccaa cgtggagtcc | 180 |
| ggagtaccag cacgcttttc cggctctggg tccggcacag acttttccct caatatccaa | 240 |
| cctgttgaag aagacgattt ttccatgtat ttttgccaac agacacgcaa ggttccatat | 300 |
| acattcggcg gcggcactaa acttgagatc aaacggctg atgctgcacc gactgtgtcc | 360 |
| atcttcccac catccagtga gcagttaaca tctggaggtg cctcagtcgt gtgcttcttg | 420 |
| aacaacttct accccaaaga catcaatgtc aagtggaaga ttgatggcag tgaacgacaa | 480 |
| aatggcgtcc tgaacagttg gactgatcag gacagcaaag acagcaccta cagcatgagc | 540 |
| agcaccctca cgttgaccaa ggacgagtat gaacgacata cagctatac ctgtgaggcc | 600 |
| actcacaaga catcaacttc acccattgtc aagagcttca caggaatga gtgt | 654 |

<210> SEQ ID NO 338
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 338

```
caggtccaac tgcaagagag cggaccgggc ctggtaaagc catccgacac attgtccctg      60
acgtgtgcgg taagtggaaa ctctatcact agcgactatg cgtggaattg gataagacaa     120
ccgccgggca aggggctgga atggatagga tatatcagct attccggttc tacgacatac     180
aatccttccc tgaaaagcag agtcactatg tcacgcgaca cgtccaagaa tcagttctca     240
ttgaaattgt catccgtaac ggccgttgac actgcggttt attattgcgc aaccggatat     300
tactacggct ctggtttttg gggacaggga acacttgtta ctgttagttc agcctccacc     360
aagggcccat cggtcttccc cctggcaccc tcctccaaga gcacctctgg ggcacagcg      420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcagatg gcagcagggg    1260
aacgtcttct catgctccgt gatgcatgag gctctgcaca accactacac gcagaagagc    1320
ctctccctgt ctccgggtaa a                                              1341
```

<210> SEQ ID NO 339
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 339

```
gacatagtct tgactcagag cccggattcc cttgctgtgt ctctgggaga acgagctacg      60
atcaactgca aggcaagtga atccgtagaa tacttcggga tcattgat gcattggtat      120
caacagaaac cggggcaacc gcccaaattg ctgatatatg cggctagtaa tagagaatca     180
ggagtaccgg ataggtttag tggttcagga tcaggtacag atttcaccct gacaataagt     240
agcttgcaag ccgaagacgt agcagtgtat tactgccaac aaacccgaaa ggtgccatat     300
acgtttggac agggtacaaa gttggaaatc aaacgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca aagtctacgc ctgcgaagtc     600
```
acccatcagg gcctgagctc gcccgtcaca aagagcttca acaggggaga gtgt    654

<210> SEQ ID NO 340
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Asn Tyr Asp Ile Leu Thr Gly His Tyr Gly Met Asp
            100                 105                 110

Val Trp Gly Gln Gly Thr Thr Val Thr Val Ser Ser Gly Gly Ser Glu
        115                 120                 125

Gly Lys Ser Ser Gly Ser Gly Ser Glu Ser Lys Ser Thr Gly Gly Ser
    130                 135                 140

Glu Ile Val Leu Thr Gln Ser Pro Ser Phe Leu Ser Ala Ser Val Gly
145                 150                 155                 160

Asp Arg Val Thr Ile Thr Cys Arg Ala Ser Gln Gly Ile Ser Ser Tyr
                165                 170                 175

Leu Ser Trp Tyr Gln Gln Lys Pro Gly Lys Ala Pro Lys Leu Leu Ile
            180                 185                 190

Tyr Ala Thr Ser Thr Leu Gln Ser Gly Val Pro Ser Arg Phe Ser Gly
        195                 200                 205

Ser Gly Ser Gly Thr Glu Phe Thr Leu Thr Ile Ser Ser Leu Gln Pro
    210                 215                 220

Glu Asp Phe Ala Thr Tyr Tyr Cys Gln Gln Leu Asn Ser Tyr Pro Arg
225                 230                 235                 240

Thr Phe Gly Gln Gly Thr Lys Val Glu Ile Lys
                245                 250
```

<210> SEQ ID NO 341
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

```
Glu Ile Val Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30
```

```
Leu Ser Trp Tyr Gln Gln Lys Pro Gly Lys Ala Pro Lys Leu Leu Ile
            35                  40                  45

Tyr Ala Thr Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Arg
                 85                  90                  95

Thr Phe Gly Gln Gly Thr Lys Val Glu Ile Lys Gly Gly Ser Glu Gly
            100                 105                 110

Lys Ser Ser Gly Ser Gly Ser Glu Ser Lys Ser Thr Gly Gly Ser Glu
            115                 120                 125

Val Gln Leu Val Glu Ser Gly Gly Gly Leu Val Gln Pro Gly Gly Ser
130                 135                 140

Leu Arg Leu Ser Cys Ala Ala Ser Gly Phe Thr Phe Ser Ser Tyr Trp
145                 150                 155                 160

Met Thr Trp Val Arg Gln Ala Pro Gly Lys Gly Leu Glu Trp Val Ala
                165                 170                 175

Asn Ile Lys Gln Asp Gly Ser Glu Arg Tyr Tyr Val Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
    210                 215                 220

Arg Asp Gln Asn Tyr Asp Ile Leu Thr Gly His Tyr Gly Met Asp Val
225                 230                 235                 240

Trp Gly Gln Gly Thr Thr Val Thr Val Ser Ser
                245                 250

<210> SEQ ID NO 342
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Gln Val Gln Leu Gln Glu Ser Gly Pro Gly Leu Val Lys Pro Ser Gln
 1               5                  10                  15

Thr Leu Ser Leu Thr Cys Thr Val Ser Gly Asn Ser Ile Thr Ser Asp
            20                  25                  30

Tyr Ala Trp Asn Trp Ile Arg Gln Phe Pro Gly Lys Arg Leu Glu Trp
            35                  40                  45

Ile Gly Tyr Ile Ser Tyr Ser Gly Ser Thr Thr Tyr Asn Pro Ser Leu
 50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Thr Gly Tyr Tyr Tyr Gly Ser Gly Phe Trp Gly Gln Gly Thr Leu
            100                 105                 110

Val Thr Val Ser Ser Gly Gly Ser Glu Gly Lys Ser Ser Gly Ser Gly
            115                 120                 125

Ser Glu Ser Lys Ser Thr Gly Gly Ser Glu Ile Val Leu Thr Gln Ser
130                 135                 140
```

```
Pro Ala Thr Leu Ser Leu Ser Pro Gly Glu Arg Ala Thr Leu Ser Cys
145                 150                 155                 160

Arg Ala Ser Glu Ser Val Glu Tyr Phe Gly Thr Ser Leu Met His Trp
                165                 170                 175

Tyr Gln Gln Lys Pro Gly Gln Pro Pro Arg Leu Leu Ile Tyr Ala Ala
            180                 185                 190

Ser Asn Val Glu Ser Gly Ile Pro Ala Arg Phe Ser Gly Ser Gly Ser
        195                 200                 205

Gly Thr Asp Phe Thr Leu Thr Ile Ser Ser Val Glu Pro Glu Asp Phe
    210                 215                 220

Ala Val Tyr Phe Cys Gln Gln Thr Arg Lys Val Pro Tyr Thr Phe Gly
225                 230                 235                 240

Gly Gly Thr Lys Val Glu Ile Lys
                245
```

<210> SEQ ID NO 343
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Arg Leu Leu Ile Tyr Ala Ala Ser Asn Val Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Val Tyr Phe Cys Gln Gln Thr Arg
                85                  90                  95

Lys Val Pro Tyr Thr Phe Gly Gly Gly Thr Lys Val Glu Ile Lys Gly
            100                 105                 110

Gly Ser Glu Gly Lys Ser Ser Gly Ser Gly Ser Glu Ser Lys Ser Thr
        115                 120                 125

Gly Gly Ser Gln Val Gln Leu Gln Glu Ser Gly Pro Gly Leu Val Lys
    130                 135                 140

Pro Ser Gln Thr Leu Ser Leu Thr Cys Thr Val Ser Gly Asn Ser Ile
145                 150                 155                 160

Thr Ser Asp Tyr Ala Trp Asn Trp Ile Arg Gln Phe Pro Gly Lys Arg
                165                 170                 175

Leu Glu Trp Ile Gly Tyr Ile Ser Tyr Ser Gly Ser Thr Thr Tyr Asn
            180                 185                 190

Pro Ser Leu Lys Ser Arg Val Thr Ile Ser Arg Asp Thr Ser Lys Asn
        195                 200                 205

Gln Phe Ser Leu Lys Leu Ser Ser Val Thr Ala Ala Asp Thr Ala Val
    210                 215                 220

Tyr Tyr Cys Ala Thr Gly Tyr Tyr Gly Ser Gly Phe Trp Gly Gln
225                 230                 235                 240

Gly Thr Leu Val Thr Val Ser Ser
```

245

<210> SEQ ID NO 344
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D or Q
<220> FEATURE:
<221> NAME/KEY: MOD_RES
<222> LOCATION: (23)..(23)
<223> OTHER INFORMATION: A or T
<220> FEATURE:
<221> NAME/KEY: MOD_RES
<222> LOCATION: (41)..(41)
<223> OTHER INFORMATION: P or F
<220> FEATURE:
<221> NAME/KEY: MOD_RES
<222> LOCATION: (49)..(49)
<223> OTHER INFORMATION: I or M
<220> FEATURE:
<221> NAME/KEY: MOD_RES
<222> LOCATION: (88)..(88)
<223> OTHER INFORMATION: A or P
<220> FEATURE:
<221> NAME/KEY: MOD_RES
<222> LOCATION: (89)..(89)
<223> OTHER INFORMATION: V or A

<400> SEQUENCE: 344

Gln Val Gln Leu Gln Glu Ser Gly Pro Gly Leu Val Lys Pro Ser Xaa
1               5                   10                  15

Thr Leu Ser Leu Thr Cys Xaa Val Ser Gly Asn Ser Ile Thr Ser Asp
            20                  25                  30

Tyr Ala Trp Asn Trp Ile Arg Gln Xaa Pro Gly Lys Gly Leu Glu Trp
        35                  40                  45

Xaa Gly Tyr Ile Ser Tyr Ser Gly Ser Thr Thr Tyr Asn Pro Ser Leu
    50                  55                  60

Lys Ser Arg Val Thr Met Ser Arg Asp Thr Ser Lys Asn Gln Phe Ser
65                  70                  75                  80

Leu Lys Leu Ser Ser Val Thr Xaa Xaa Asp Thr Ala Val Tyr Tyr Cys
                85                  90                  95

Ala Thr Gly Tyr Tyr Tyr Gly Ser Gly Phe Trp Gly Gln Gly Thr Leu
            100                 105                 110

Val Thr Val Ser Ser
        115

<210> SEQ ID NO 345
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: D or E
<220> FEATURE:
<221> NAME/KEY: MOD_RES
<222> LOCATION: (9)..(9)
<223> OTHER INFORMATION: D or A
<220> FEATURE:
<221> NAME/KEY: MOD_RES

```
<222> LOCATION: (10)..(10)
<223> OTHER INFORMATION: S or T
<220> FEATURE:
<221> NAME/KEY: MOD_RES
<222> LOCATION: (12)..(12)
<223> OTHER INFORMATION: A or S
<220> FEATURE:
<221> NAME/KEY: MOD_RES
<222> LOCATION: (13)..(13)
<223> OTHER INFORMATION: V or L
<220> FEATURE:
<221> NAME/KEY: MOD_RES
<222> LOCATION: (15)..(15)
<223> OTHER INFORMATION: L or P
<220> FEATURE:
<221> NAME/KEY: MOD_RES
<222> LOCATION: (21)..(21)
<223> OTHER INFORMATION: I or L
<220> FEATURE:
<221> NAME/KEY: MOD_RES
<222> LOCATION: (22)..(22)
<223> OTHER INFORMATION: N or S
<220> FEATURE:
<221> NAME/KEY: MOD_RES
<222> LOCATION: (24)..(24)
<223> OTHER INFORMATION: R or K
<220> FEATURE:
<221> NAME/KEY: MOD_RES
<222> LOCATION: (49)..(49)
<223> OTHER INFORMATION: K or R
<220> FEATURE:
<221> NAME/KEY: MOD_RES
<222> LOCATION: (58)..(58)
<223> OTHER INFORMATION: V or R
<220> FEATURE:
<221> NAME/KEY: MOD_RES
<222> LOCATION: (62)..(62)
<223> OTHER INFORMATION: V or I
<220> FEATURE:
<221> NAME/KEY: MOD_RES
<222> LOCATION: (64)..(64)
<223> OTHER INFORMATION: A or D
<220> FEATURE:
<221> NAME/KEY: MOD_RES
<222> LOCATION: (80)..(80)
<223> OTHER INFORMATION: Q or S
<220> FEATURE:
<221> NAME/KEY: MOD_RES
<222> LOCATION: (84)..(84)
<223> OTHER INFORMATION: P or A
<220> FEATURE:
<221> NAME/KEY: MOD_RES
<222> LOCATION: (87)..(87)
<223> OTHER INFORMATION: F or V
<220> FEATURE:
<221> NAME/KEY: MOD_RES
<222> LOCATION: (91)..(91)
<223> OTHER INFORMATION: Y or F
<220> FEATURE:
<221> NAME/KEY: MOD_RES
<222> LOCATION: (104)..(104)
<223> OTHER INFORMATION: Q or G
<220> FEATURE:
<221> NAME/KEY: MOD_RES
<222> LOCATION: (108)..(108)
<223> OTHER INFORMATION: L or V

<400> SEQUENCE: 345

Xaa Ile Val Leu Thr Gln Ser Pro Xaa Xaa Leu Xaa Xaa Ser Xaa Gly
1               5                   10                  15

Glu Arg Ala Thr Xaa Xaa Cys Xaa Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Xaa Leu Leu Ile Tyr Ala Ala Ser Asn Xaa Glu Ser Gly Xaa Pro Xaa
```

```
                50             55             60
Arg Phe Ser Gly Ser Gly Ser Gly Thr Asp Phe Thr Leu Thr Ile Xaa
 65                 70                  75                  80

Ser Leu Gln Xaa Glu Asp Xaa Ala Val Tyr Xaa Cys Gln Gln Thr Arg
                 85                  90                  95

Lys Val Pro Tyr Thr Phe Gly Xaa Gly Thr Lys Xaa Glu Ile Lys
            100                 105                 110

<210> SEQ ID NO 346
<211> LENGTH: 5
<212> TYPE: PRT
<213> ORGANISM: Homo sapiens

<400> SEQUENCE: 346

Lys Val Thr Glu Phe
 1                5

<210> SEQ ID NO 347
<211> LENGTH: 5
<212> TYPE: PRT
<213> ORGANISM: Homo sapiens

<400> SEQUENCE: 347

His Tyr Arg Lys Trp
 1                5

<210> SEQ ID NO 348
<211> LENGTH: 6
<212> TYPE: PRT
<213> ORGANISM: Homo sapiens

<400> SEQUENCE: 348

Ser His Gly Trp Ala His
 1                5

<210> SEQ ID NO 349
<211> LENGTH: 15
<212> TYPE: PRT
<213> ORGANISM: Homo sapiens

<400> SEQUENCE: 349

Arg His Asn Leu Phe Glu Pro Glu Asp Thr Gly Gln Arg Val Pro
 1                5                  10                  15

<210> SEQ ID NO 350
<211> LENGTH: 9
<212> TYPE: PRT
<213> ORGANISM: Homo sapiens

<400> SEQUENCE: 350

Gly Trp Gly Ser Ile Glu Pro Glu Glu
 1                5

<210> SEQ ID NO 351
<211> LENGTH: 244
<212> TYPE: PRT
<213> ORGANISM: Homo sapiens

<400> SEQUENCE: 351

Val Pro Leu Ile Glu Gly Arg Ile Val Gly Gly Trp Glu Cys Glu Lys
 1                5                  10                  15

His Ser Gln Pro Trp Gln Val Ala Val Tyr Ser His Gly Trp Ala His
                 20                  25                  30
```

```
Cys Gly Gly Val Leu Val His Pro Gln Trp Val Leu Thr Ala Ala His
        35                  40                  45
Cys Leu Lys Lys Asn Ser Gln Val Trp Leu Gly Arg His Asn Leu Phe
    50                  55                  60
Glu Pro Glu Asp Thr Gly Gln Arg Val Pro Val Ser His Ser Phe Pro
65                  70                  75                  80
His Pro Leu Tyr Asn Met Ser Leu Leu Lys His Gln Ser Leu Arg Pro
                85                  90                  95
Asp Glu Asp Ser Ser His Asp Leu Met Leu Leu Arg Leu Ser Glu Pro
                100                 105                 110
Ala Lys Ile Thr Asp Val Val Lys Val Leu Gly Leu Pro Thr Gln Glu
                115                 120                 125
Pro Ala Leu Gly Thr Thr Cys Tyr Ala Ser Gly Trp Gly Ser Ile Glu
                130                 135                 140
Pro Glu Glu Phe Leu Arg Pro Arg Ser Leu Gln Cys Val Ser Leu His
145                 150                 155                 160
Leu Leu Ser Asn Asp Met Cys Ala Arg Ala Tyr Ser Glu Lys Val Thr
                165                 170                 175
Glu Phe Met Leu Cys Ala Gly Leu Trp Thr Gly Gly Lys Asp Thr Cys
                180                 185                 190
Gly Gly Asp Ser Gly Gly Pro Leu Val Cys Asn Gly Val Leu Gln Gly
                195                 200                 205
Ile Thr Ser Trp Gly Pro Glu Pro Cys Ala Leu Pro Glu Lys Pro Ala
                210                 215                 220
Val Tyr Thr Lys Val Val His Tyr Arg Lys Trp Ile Lys Asp Thr Ile
225                 230                 235                 240

Ala Ala Asn Pro
```